United States Patent
Chatterjee et al.

(10) Patent No.: US 11,708,348 B2
(45) Date of Patent: Jul. 25, 2023

(54) PROTEASE INHIBITORS FOR TREATMENT OF CORONAVIRUS INFECTIONS

(71) Applicant: The Scripps Research Institute, La Jolla, CA (US)

(72) Inventors: Arnab K. Chatterjee, San Diego, CA (US); Jian Jeffrey Chen, San Diego, CA (US); Elshan Nakath, La Jolla, CA (US); Alireza Rahimi, La Jolla, CA (US); Anil Kumar Gupta, San Diego, CA (US); Gennadii Grabovyi, La Jolla, CA (US); Katy Wilson, La Jolla, CA (US); Sourav Ghorai, La Jolla, CA (US); Armen Nazarian, La Jolla, CA (US); James Pedroarena, La Jolla, CA (US); Wrickban Mazumdar, La Jolla, CA (US); Frank Weiss, La Jolla, CA (US); Lirui Song, San Diego, CA (US); Malina A. Bakowski, La Jolla, CA (US); Laura Riva, San Diego, CA (US); Karen Wolff, Encinitas, CA (US); Case W. McNamara, San Marcos, CA (US); Thomas F. Rogers, Del Mar, CA (US); Jacqueline Malvin, San Diego, CA (US); Shuangwei Li, San Diego, CA (US); Sean Joseph, San Diego, CA (US); Ashley Woods, San Diego, CA (US); Yuyin Liu, San Diego, CA (US); Neechi Okwor, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 17/837,814

(22) Filed: Jun. 10, 2022

(65) Prior Publication Data

US 2023/0024012 A1 Jan. 26, 2023

Related U.S. Application Data

(60) Provisional application No. 63/266,234, filed on Dec. 30, 2021, provisional application No. 63/209,862, filed on Jun. 11, 2021.

(51) Int. Cl.
| | | |
|---|---|---|
| C07D 401/12 | (2006.01) |
| A61K 38/55 | (2006.01) |
| C07D 207/267 | (2006.01) |
| C07D 211/76 | (2006.01) |
| C07D 403/12 | (2006.01) |
| C07D 405/10 | (2006.01) |
| C07D 405/12 | (2006.01) |
| C07D 413/12 | (2006.01) |
| C07D 413/14 | (2006.01) |
| C07D 471/04 | (2006.01) |
| C07D 493/04 | (2006.01) |

(52) U.S. Cl.
CPC ............ *C07D 401/12* (2013.01); *A61K 38/55* (2013.01); *C07D 207/267* (2013.01); *C07D 211/76* (2013.01); *C07D 403/12* (2013.01); *C07D 405/10* (2013.01); *C07D 405/12* (2013.01); *C07D 413/12* (2013.01); *C07D 413/14* (2013.01); *C07D 471/04* (2013.01); *C07D 493/04* (2013.01)

(58) Field of Classification Search
None
See application file for complete search history.

(56) References Cited

FOREIGN PATENT DOCUMENTS

| | | |
|---|---|---|
| EP | 0272671 A2 | 6/1988 |
| WO | 2005113580 A1 | 12/2005 |
| WO | 2017053864 A1 | 3/2017 |
| WO | 2020181165 A1 | 9/2020 |
| WO | 2020191348 A1 | 9/2020 |
| WO | 2022066776 A1 | 3/2022 |

OTHER PUBLICATIONS

Chen et al., Emerging Coronaviruses: Genome Structure, Replication, and Pathogenesis, Journal of Medical Virology, 2020, 92(10):2249 and 92(4):418-423.

Dai et al., Structure-Based Design of Antiviral Drug Candidates Targeting the SARS-CoV-2 Main Protease, Science, 2020, 368(6497):1331-1335.

Dragovich et al., Structure-Based Design, Synthesis, and Biological Evaluation of Irreversible Human Rhinovirus 3C Protease Inhibitors. 4. Incorporation of P1 Lactam Moieties as L-Glutamine Replacements, Journal of Medicinal Chemistry, 1999, 42(7):1213-1224.

Hilgenfeld, From SARS to MERS: Crystallographic Studies on Coronaviral Proteases Enable Antiviral Drug Design, FEBS Journal, 2014, 281(18):4085-4096.

Hoffman et al., Discovery of Ketone-Based Covalent Inhibitors of Coronavirus 3CL Proteases for the Potential Therapeutic Treatment of COVID-19. Journal of Medicinal Chemistry, 2020, 63(21):12725-12747.

(Continued)

*Primary Examiner* — Zinna Northington Davis
(74) *Attorney, Agent, or Firm* — Jennifer Kisko; Wei Yan

(57) ABSTRACT

Provided herein are compounds of Formula (I), their pharmaceutically acceptable salts, and their pharmaceutical compositions:

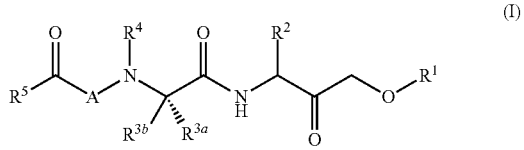

wherein $R^1$, $R^2$, $R^{3a}$, $R^{3b}$, $R^4$, $R^5$, and A are defined in the present disclosure. The compounds are potent inhibitors of the main protease ($M^{pro}$) of severe acute respiratory syndrome Coronavirus-2 (SARS-CoV-2), and they are useful in treating or preventing COVID-19 in a subject.

4 Claims, No Drawings

(56) References Cited

OTHER PUBLICATIONS

Kulkarni et al., Three-Dimensional Quantitative Structure—Activity Relationship of Interieukin 1-β Converting Enzyme Inhibitors: A Comparative Molecular Field Analysis Study, Journal of Medicinal Chemistry, 1999, 42(3):373-380.

Linton, Caspase Inhibitors: A Pharmaceutical Industry Perspective, Current Topics in Medicinal Chemistry, 2005, 5(16):1697-1717.

Linton et al., First-in-Class Pan Caspase Inhibitor Developed for the Treatment of Liver Disease, Journal of Medicinal Chemistry, 2005, 48(22):6779-6782.

Qiao et al., SARS-CoV-2 Mpro Inhibitors with Antiviral Activity in a Transgenic Mouse Model, Science, 2021, 371(6536):1374-1378.

Sanman et al., Disruption of Glycolytic Flux is a Signal for Inflammasome Signaling and Pyroptotic Cell Death, eLIFE, 2016, 5:e13663, pp. 1-32.

Smith et al., New Inhibitors of Cysteine Proteinases. Peptidyl Acyloxymethyl Ketones and the quiescent Nucleofuge Strategy, Journal of the American Chemical Society, 1988, 110(13):4429-4431.

Van de Plassche et al., Peptidyl Acyloxymethyl Ketones as Activity-Based Probes for the Main Protease of SARS-CoV-2, ChemBioChem, 2020, 21(23):3383-3388.

Yip et al., Discovery of a Novel Bicycloproline P2 Bearing Peptidyl α-ketoamide LY514962 as HCV Protease Inhibitor, Bioorganic & Medicinal Chemistry Letters, 2004, 14(1):251-256.

Zhang et al., α-Ketoamides as Broad-Spectrum Inhibitors of Coronavirus and Enterovirus Replication: Structure-Based Design, Synthesis, and Activity Assessment, Journal of Medicinal Chemistry, 2020, 63(9):4562-4578.

PCT International Search Report and Written Opinion, PCT/US2022/033069, dated Sep. 30, 2022, 27 pages.

PROTEASE INHIBITORS FOR TREATMENT OF CORONAVIRUS INFECTIONS

CROSS-REFERENCE TO RELATED APPLICATIONS

This application claims the benefit of priority of U.S. Provisional Patent Application Ser. No. 63/209,862, filed Jun. 11, 2021, and U.S. Provisional Patent Application Ser. No. 63/266,234, filed Dec. 30, 2021, the contents of which are incorporated by reference in its entirety.

BACKGROUND

In early December of 2019, the severe acute respiratory syndrome coronavirus 2 (SARS-CoV-2) was identified as the cause of rapidly increasing numbers of severe pneumonia-like symptoms termed COVID-19. Since then, SARS-CoV-2 has rightfully been given its pandemic status by the World Health Organization (WHO). As of May 7, 2021, SARS-CoV-2 has spread throughout the world causing more than 155,000,000 confirmed infections and more than 3,250,000 reported deaths in 223 different countries. Development of several effective anti-SARS-CoV-2 vaccines could contribute to the control of the pandemic; however, emergence of SARS-CoV-2 strains with escape mutations that render some of the vaccines less effective and overall limited global supply of COVID-19 vaccines make a case for continued effort to identify therapeutic interventions. Yet, despite an extensive effort by the research community, antiviral treatment options for COVID-19 remain limited. These include corticosteroids such as dexamethasone and the intravenously-delivered antiviral remdesivir for treatment of patients with severe or critical COVID-19.

Remdesivir, a nucleotide analog prodrug and an RNA-dependent RNA polymerase (RdRp) inhibitor with broad antiviral activity, demonstrated positive clinical endpoints in a Phase III Adaptive COVID-19 Treatment Trial (median time to recovery shortened from 15 to 11 days) that justified its emergency use authorization by the US Food & Drug Administration for treatment of hospitalized COVID-19 patients. However, Remdesivir, together with hydroxychloroquine, lopinavir and interferon regimens, has recently failed to reduce mortality of hospitalized COVID-19 patients in a large multi-center WHO SOLIDARITY trial[9]. Remdesivir's modest efficacy and intravenous delivery should invigorate the discovery of new or supplemental therapies that produce greater clinical improvements and that can be administered outside of a hospital setting (i.e. orally).

Beyond RdRp, other high-value drug targets have been identified in SARS-CoV-2. Belonging to the genus betacoronavirus, this virus encodes two large overlapping polyprotein precursors (pp1a and pp1ab), four structural proteins (spike, envelope, membrane, and nucleocapsid), and several accessory proteins. The two polyproteins (pp1a/pp1ab) must be cleaved into its individual, nonstructural proteins for successful viral replication (Y. Chen et al. *J Med Virol.* 2020; 92(10):2249.). Two viral proteases are essential and responsible for processing the polyproteins: the main protease ($M^{pro}$ or 3CL protease) and a papain-like protease (Hilgenfeld R. From SARS to MERS: crystallographic studies on coronaviral proteases enable antiviral drug design. FEBS J. 2014; 281(18):4085-96). Importantly, $M^{pro}$ cleaves polypeptides after a glutamine residue in the P1 position of the substrate, which is a unique activity not observed in other human proteases and suggests that this viral protease can be specifically and selectively inhibited by a small molecule inhibitor (Zhang L et al. α-Ketoamides as Broad-Spectrum Inhibitors of Coronavirus and Enterovirus Replication: Structure-Based Design, Synthesis, and Activity Assessment. J Med Chem. 2020; 63(9):4562-4578).

Examination of the active site of $M^{pro}$ reveals four sites (S1', S1, S2, and S4), which, in turn, can accommodate four corresponding fragments of the substrate (P1', P1, P2, and P3, respectively). Because polypeptides are the natural substrate, then peptidomimetic inhibitors are a rationale choice for high-affinity small molecules for proteases. Affinity of a peptidomimetic inhibitor can be further enhanced by introducing a warhead in P1 to form a covalent bond with the catalytic site Cys145, which is an essential residue for the antiviral activity (Dai W et al. Structure-based design of antiviral drug candidates targeting the SARS-CoV-2 main protease. Science. 2020; 368(6497):1331-1335). In addition, it is well established that a glutamine derivative (γ-lactam) is highly preferred to occupy the S1 site of cysteine proteases, which not only mimics the native P1 glutamine of the substrates but also increases the activity of inhibitors (Dragovich P S et al. Structure-based design, synthesis, and biological evaluation of irreversible human rhinovirus 3C protease inhibitors. 4. Incorporation of P1 lactam moieties as L-glutamine replacements. J Med Chem. 1999; 42(7):1213-24). In addition, a bicycloproline moiety, either (1R,2S,5S)-6,6-dimethyl-3-aza-bicyclo[3.1.0]hexane-2-formamide (P2 of boceprevir) or (1S,3aR,6aS)-octahydrocyclopenta[c]pyrrole-1-formamide (P2 of telaprevir), as a P2 fragment, suitably occupy the S2 pocket of $M^{pro}$ (Qiao J et al. SARS-CoV-2 Mpro inhibitors with antiviral activity in a transgenic mouse model. Science. 2021; 371(6536):1374-1378). As previously reported, the rigid and hydrophobic bicycloproline can increase exposure of an orally administered compound (Yip Y et al. Discovery of a novel bicycloproline P2 bearing peptidyl alpha-ketoamide LY514962 as HCV protease inhibitor. Bioorg Med Chem Lett. 2004; 14(1):251-6). Thus, the modifications to the molecule representing the P3 fragment and the specific warhead, are important for imparting favorable biological activity and pharmacokinetic properties for an optimal drug candidate.

Finally, a compound designated as PF-00835231, is a potent COVID-2 $M^{pro}$ protease inhibitor, and it was recently advanced into clinical trial for COVID-2 through IV infusion of its phosphate prodrug. The corresponding methyl ether of PF-00835231 is 3-5 fold less active in cell and enzyme assays (Hoffman, R. L. et al., *J Med. Chem.* (2020) 63, 12725-12747).

SUMMARY

The present disclosure provides a surprisingly potent inhibitor of COVID-2 $M^{pro}$ as a compound of Formula (I) or its pharmaceutically acceptable salt:

wherein
R$^1$ is selected from the group consisting of
C$_1$-C$_6$-alkyl, C$_3$-C$_{10}$-cycloalkyl, C$_6$-C$_{10}$-aryl, and 5- to 10-membered heteroaryl (wherein 1-4 heteroaryl members are independently selected from N, O, and S), wherein any alkyl, cycloalkyl, aryl, and heteroaryl is mono- to perhalogenated, optionally wherein any alkyl, cycloalkyl, aryl, and heteroaryl is mono- to perfluorinated, or wherein any cycloalkyl, aryl, and heteroaryl is substituted with one to three $C_1$-$C_6$-haloalkyl; and $P(O)(R^{1a})_2$, wherein each $R^{1a}$ is independently selected from the group consisting of $C_6$-$C_{10}$-aryl, 5- to 10-membered heteroaryl (wherein 1-4 heteroaryl members are independently selected from N, O, and S), and $C_1$-$C_6$-alkyl optionally interrupted by one or more heteroatoms selected from —NH—, O, and S;

$R^2$ is selected from the group consisting of

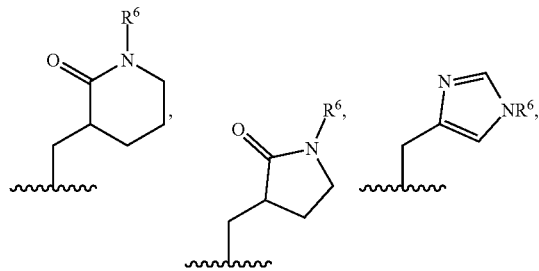

$C_1$-$C_6$-alkyl, —($C_1$-$C_6$-alkyl)($C_3$-$C_{10}$-cycloalkyl), —($C_1$-$C_6$-alkyl)(3- to 6-membered heterocycloalkyl) (wherein 1-4 ring members are independently selected from C(O), N, O, and S), —($C_1$-$C_6$-alkyl)(5- to 10-membered heteroaryl) (wherein 1-4 heteroaryl members are independently selected from N, O, and S), —($C_1$-$C_6$-alkyl)$NR^6R^7$, $C_1$-$C_6$-alkyl (optionally interrupted by one or more heteroatoms selected from —NH—, O, and $S(O)_{0-2}$), —($C_1$-$C_6$-alkyl)N(H)CN(H)$NH_2$, and —($C_1$-$C_6$-alkyl)C(O)$NR^6R^7$, wherein $R^6$ and $R^7$ are independently selected from H and $C_1$-$C_6$-alkyl;

$R^{3a}$, $R^{3b}$ and each instance of $R^4$ are independently selected from H, $C_1$-$C_8$-alkyl, $C_2$-$C_8$-alkenyl, $C_3$-$C_{10}$-cycloalkyl, —($C_1$-$C_6$-alkyl)($C_3$-$C_{10}$-cycloalkyl), —($C_1$-$C_6$-alkyl)($C_6$-$C_{10}$-aryl), —($C_1$-$C_6$-alkyl)(3- to 6-membered heterocycloalkyl) (wherein 1-4 ring members are independently selected from N, O, and S), and —($C_1$-$C_6$-alkyl)(5- to 10-membered heteroaryl) (wherein 1-4 heteroaryl members are independently selected from N, O, and S), wherein $R^{3a}$, $R^{3b}$ and $R^4$ are optionally and independently substituted with 1 to 5 substituents independently selected from the group consisting of halo, OH, $NH_2$, $C_1$-$C_6$-alkyl optionally substituted with $NH_2$, $C_1$-$C_6$-haloalkyl, $C_1$-$C_6$-alkoxy, $C_3$-$C_8$-cycloalkyl (optionally substituted with 1-3 substituents independently selected from halo and $NH_2$), CN, and $CONR^6R^7$;

or $R^{3a}$ and $R^4$, $R^{3b}$ and $R^4$, or $R^{3a}$ and $R^{3b}$ together with the atoms to which they are bound form mono- or bicyclic ring having 3-10 ring members selected from C, N, O, and S and that, if bicyclic, is optionally fused, bridged, or spiro-fused, wherein the mono- or bicyclic ring is optionally substituted with halo, OH, $C_2$-$C_6$-alkenyl, $C_1$-$C_6$-haloalkyl, $C_1$-$C_6$-alkoxy, $C_3$-$C_8$-cycloalkyl (optionally and independently substituted with 1-3 substituents selected from halo and $NH_2$), $C_6$-$C_{10}$-aryl, $C_1$-$C_6$-alkyl optionally substituted with $NH_2$, ($C_1$-$C_6$-alkyl)-($C_3$-$C_8$-cycloalkyl), 3- to 6-membered heterocycloalkyl (wherein 1-4 ring members are independently selected from N, O, and S), CN, and $CONR^6R^7$;

A is a bond or a moiety of formula (II):

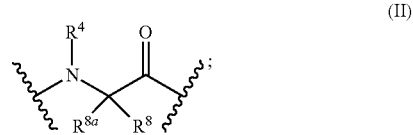

$R^8$ and $R^{8a}$ are independently selected from H, $C_1$-$C_8$-alkyl, $C_3$-$C_{10}$-cycloalkyl, $C_6$-$C_{10}$-aryl, 3- to 6-membered heterocycloalkyl (wherein 1-4 ring members are independently selected from N, O, and S), 5- to 10-membered heteroaryl (wherein 1-4 heteroaryl members are independently selected from N, O, and S), —($C_1$-$C_6$-alkyl)($C_3$-$C_{10}$-cycloalkyl), —($C_1$-$C_6$-alkyl)($C_6$-$C_{10}$-aryl), —($C_1$-$C_6$-alkyl)(3- to 6-membered heterocycloalkyl (wherein 1-4 ring members are independently selected from N, O, and S), and —($C_1$-$C_6$-alkyl)(5- to 10-membered heteroaryl) (wherein 1-4 heteroaryl members are independently selected from N, O, and S);

wherein $R^8$ and $R^{8a}$ are optionally and independently substituted with 1 to 5 substituents independently selected from the group consisting of halo, OH, $C_1$-$C_6$-alkoxy, $C_3$-$C_8$-cycloalkyl (optionally substituted with 1-3 substituents independently selected from halo and $NH_2$), $NH_2$, $C_1$-$C_6$-alkyl optionally substituted with $NH_2$, CN, and $CONR^6R^7$, or $R^4$ and $R^8$ or $R^8$ and $R^{8a}$, together with the atoms to which they are bound, form a mono- or bicyclic ring having 3-10 ring members selected from C, N, O, and S and that, if bicyclic, is optionally fused, bridged, or spiro-fused, wherein the mono- or bicyclic ring is optionally substituted with halo, OH, $C_1$-$C_6$-haloalkyl, $C_1$-$C_6$-alkoxy, $C_3$-$C_8$-cycloalkyl (optionally and independently substituted with 1-3 substituents selected from halo and $NH_2$), $C_1$-$C_6$-alkyl optionally substituted with $NH_2$, 3- to 6-membered heterocycloalkyl (wherein 1-4 ring members are independently selected from N, O, and S), CN, $CONR^6R^7$;

$R^5$ is selected from the group consisting of $C_1$-$C_{20}$-alkyl (optionally interrupted by one or more heteroatoms selected from —NH—, O, and S), $C_2$-$C_6$-alkenyl, $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —O—($C_1$-$C_6$-alkyl)($C_6$-$C_{10}$-aryl), —O—($C_3$-$C_8$-cycloalkyl), —O—($C_1$-$C_6$-alkyl)($C_3$-$C_8$-cycloalkyl), —($C_1$-$C_6$-alkyl)-O—($C_6$-$C_{10}$-aryl), —($C_1$-$C_6$-alkyl)-NH—($C_6$-$C_{10}$-aryl), —($C_1$-$C_6$-alkyl)-NHC(O)—($C_6$-$C_{10}$-aryl), —($C_2$-$C_6$-alkenyl)($C_6$-$C_{10}$-aryl), —($C_1$-$C_6$-alkyl)(3- to 6-membered heterocycloalkyl) (wherein 1-4 ring members are independently selected from N, O, and $S(O)_{0-2}$), $C_3$-$C_8$-cycloalkyl, —($C_1$-$C_6$-alkyl)-NH—($C_3$-$C_8$-cycloalkyl), —($C_1$-$C_6$-alkyl)-($C_3$-$C_8$-cycloalkyl), 3- to 14-membered heterocycloalkyl (wherein 1-4 ring members are independently selected from N, O, and S), —O-(3- to 8-membered heterocycloalkyl (wherein 1-4 ring members are independently selected from N, O, and S)), —($C_1$-$C_6$-alkyl)-(5- to 10-membered heteroaryl (wherein 1-4 heteroaryl members are independently selected from N, O, and S)), —C(O)—($C_1$-$C_6$-alkyl), —C(O)($C_6$-$C_{10}$-aryl), —($C_1$-$C_6$-alkyl)-NH-(5- to 10-membered heteroaryl (wherein 1-4 heteroaryl members are independently selected from N, O, and S)), —CHN(OH), —($C_1$-$C_6$-alkyl)-NH—S(O)$_2$—NR$^9$R$^{10}$), —O—($C_2$-$C_6$-alkenyl)-($C_6$-$C_{10}$-aryl), —C(O)OR$^9$, —($C_1$-$C_6$-alkyl)-C(O)OR$^9$, —($C_1$-$C_6$-alkyl)-S(O)$_2$—NH$_2$, and —NH—$C_6$-$C_{10}$-aryl, wherein R$^5$ is optionally substituted with one to three substituents selected from the group consisting of halo, $C_1$-$C_6$-alkyl, $C_1$-$C_6$-haloalkyl, oxo, —$C_1$-$C_6$-alkyl-NH$_2$, —$C_6$-$C_{10}$-aryl (optionally substituted with 1-3 halo), —($C_1$-$C_6$-alkyl)($C_6$-$C_{10}$-aryl), 5- to 10-membered heteroaryl (wherein 1-4 heteroaryl members are independently selected from N, O, and S), CN, OCF$_3$, COR$^9$, —OC(O)R$^9$, CONR$^9$R$^{10}$, —OCONR$^9$R$^{10}$, NR$^9$R$^{10}$, —NR$^9$C(O)NR$^9$R$^{10}$, —NR$^9$C(O)OR$^{10}$, —NR$^9$S(O)$_2$R$^{10}$, OR$^9$, SR$^9$, SO$_2$R$^9$, —N(H)C(O)(3- to 6-membered heterocycloalkyl), —N═O, and —N(H)C(O)CF$_3$, and wherein two substituents together with the carbon atom to which they are bound optionally form a mono- or bicyclic ring having 3-10 ring members selected from C, N, O, and S;

R$^9$ and R$^{10}$ are independently selected from H, $C_1$-$C_6$-alkyl, $C_3$-$C_8$-cycloalkyl, $C_6$-$C_{10}$-aryl, and —($C_1$-$C_6$-alkyl)($C_6$-$C_{10}$-aryl);

or R$^5$ is

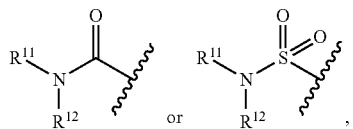

wherein R$^{11}$ and R$^{12}$ are independently selected from H, $C_1$-$C_8$ alkyl, $C_3$-$C_8$-cycloalkyl, —($C_1$-$C_6$-alkyl)-$C_3$-$C_8$-cycloalkyl, —($C_3$-$C_8$-cycloalkyl)($C_6$-$C_{10}$-aryl), —($C_3$-$C_8$-cycloalkyl)-($C_1$-$C_6$-alkyl), $C_6$-$C_{10}$-aryl, —($C_1$-$C_6$-alkyl)($C_6$-$C_{10}$-aryl), 5- to 10-membered heteroaryl (wherein 1-4 heteroaryl members are independently selected from N, O, and S), —($C_1$-$C_6$-alkyl)(5- to 10-membered heteroaryl (wherein 1-4 heteroaryl members are independently selected from N, O, and S)), 3- to 6-membered heterocycloalkyl (wherein 1-4 ring members are independently selected from N, O, and S(O)$_{0-2}$), —($C_1$-$C_6$-alkyl)(3- to 8-membered heterocycloalkyl (wherein 1-4 ring members are independently selected from N, O, and S)), and —S(O)$_2$—N(H)($C_6$-$C_{10}$-aryl), wherein R$^{11}$ and R$^{12}$ are optionally substituted with one to three substituents independently selected from the group consisting of halo, OH, NH$_2$, $C_1$-$C_6$-haloalkyl, $C_1$-$C_6$-alkyl (optionally and independently substituted with 1-3 substituents selected from halo and NH$_2$, or optionally interrupted by one or more heteroatoms selected from —NH—, O, and S), $C_1$-$C_6$-alkoxy (optionally substituted with 1-3 halo), $C_3$-$C_8$-cycloalkyl (optionally and independently substituted with 1-3 substituents selected from halo and NH$_2$), CN, —($C_1$-$C_6$-alkyl)($C_6$-$C_{10}$-aryl), and CONR$^6$R$^7$;

or R$^{11}$ and R$^{12}$, together with the nitrogen atom to which they are bound, form a mono- or bicyclic ring having 4-10 ring members selected from C, N, O, and S and that, if bicyclic, is optionally fused, bridged, or spiro-fused, wherein the mono- or bicyclic ring is optionally substituted with one to three substituents selected from halo, OH, $C_1$-$C_6$-haloalkyl, C(O)R$^9$, $C_1$-$C_6$-alkoxy, $C_3$-$C_8$-cycloalkyl (optionally and independently substituted with 1-3 substituents selected from halo and NH$_2$), $C_1$-$C_6$-alkyl optionally substituted with NH$_2$, 3- to 6-membered heterocycloalkyl (wherein 1-4 ring members are independently selected from N, O, and S), CN, and CONR$^6$R$^7$;

or a pharmaceutically acceptable salt thereof.

In some embodiments, in Formula (I), R$^1$ is selected from the group consisting of:

$C_1$-$C_6$-alkyl, $C_3$-$C_{10}$-cycloalkyl, $C_6$-$C_{10}$-aryl, and 5- to 10-membered heteroaryl (wherein 1-4 heteroaryl members are independently selected from N, O, and S), wherein any alkyl, cycloalkyl, aryl, and heteroaryl is mono- to perfluorinated; and P(O)(R$^{1a}$)$_2$, wherein each R$^{1a}$ is independently selected from the group consisting of $C_6$-$C_{10}$-aryl, 5- to 10-membered heteroaryl (wherein 1-4 heteroaryl members are independently selected from N, O, and S), and $C_1$-$C_6$-alkyl optionally interrupted by one or more heteroatoms selected from —NH—, O, and S.

In some embodiments, R$^2$ is selected from the group consisting of

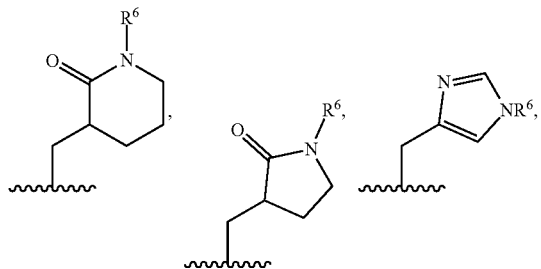

—($C_1$-$C_6$-alkyl)($C_3$-$C_{10}$-cycloalkyl), and —($C_1$-$C_6$-alkyl)N(H)CN(H)NH$_2$, and —($C_1$-$C_6$-alkyl)C(O)NR$^6$R$^7$ wherein R$^6$ and R$^7$ are independently selected from H and $C_1$-$C_6$-alkyl.

In some embodiments, R$^{3a}$, R$^{3b}$ and each instance of R$^4$ are independently selected from H, $C_1$-$C_8$-alkyl, $C_2$-$C_8$-alkenyl, $C_3$-$C_{10}$-cycloalkyl, —($C_1$-$C_6$-alkyl)($C_3$-$C_{10}$-cycloalkyl), —($C_1$-$C_6$-alkyl)($C_6$-$C_{10}$-aryl), —($C_1$-$C_6$-alkyl)(3- to 6-membered heterocycloalkyl (wherein 1-4 ring members are independently selected from N, O, and S), and —($C_1$-$C_6$-alkyl)(5- to 10-membered heteroaryl) (wherein 1-4 heteroaryl members are independently selected from N, O, and S).

In various embodiments, R$^{3a}$, R$^{3b}$ and R$^4$ are optionally and independently substituted with 1 to 5 substituents independently selected from the group consisting of halo, OH, NH$_2$, $C_1$-$C_6$-alkyl optionally substituted with NH$_2$, $C_1$-$C_6$-haloalkyl, $C_1$-$C_6$-alkoxy, $C_3$-$C_8$-cycloalkyl (optionally substituted with 1-3 substituents independently selected from halo and NH$_2$), CN, CONR$^6$R$^7$.

In some embodiments, R$^{3a}$ and R$^4$, R$^{3b}$ and R$^4$, or R$^{3a}$ and R$^{3b}$ together with the atoms to which they are bound form mono- or bicyclic ring having 3-10 ring members selected from C, N, O, and S and that, if bicyclic, is optionally fused, bridged, or spiro-fused, wherein the mono- or bicyclic ring is optionally substituted with halo, OH, $C_2$-$C_6$-alkenyl, $C_1$-$C_6$-haloalkyl, $C_1$-$C_6$-alkoxy, $C_3$-$C_8$-cycloalkyl (optionally and independently substituted with 1-3 substituents selected from halo and $NH_2$), $C_1$-$C_6$-alkyl optionally substituted with $NH_2$, 3- to 6-membered heterocycloalkyl (wherein 1-4 ring members are independently selected from N, O, and S), CN, and $CONR^6R^7$.

In some embodiments, A is a bond or a moiety of formula (II):

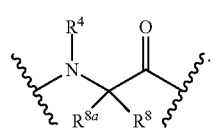

$R^8$ and $R^{8a}$ are independently selected from H, $C_1$-$C_8$-alkyl, $C_3$-$C_{10}$-cycloalkyl, $C_6$-$C_{10}$-aryl, 3- to 6-membered heterocycloalkyl (wherein 1-4 ring members are independently selected from N, O, and S), 5- to 10-membered heteroaryl (wherein 1-4 heteroaryl members are independently selected from N, O, and S), —($C_1$-$C_6$-alkyl)($C_3$-$C_{10}$-cycloalkyl), —($C_1$-$C_6$-alkyl)($C_6$-$C_{10}$-aryl), —($C_1$-$C_6$-alkyl)(3- to 6-membered heterocycloalkyl (wherein 1-4 ring members are independently selected from N, O, and S), and —($C_1$-$C_6$-alkyl)(5- to 10-membered heteroaryl) (wherein 1-4 heteroaryl members are independently selected from N, O, and S).

In some embodiments, $R^8$ and $R^{8a}$ are optionally and independently substituted with 1 to 5 substituents independently selected from the group consisting of halo, OH, $C_1$-$C_6$-alkoxy, $C_3$-$C_8$-cycloalkyl (optionally substituted with 1-3 substituents independently selected from halo and $NH_2$), $NH_2$, $C_1$-$C_6$-alkyl optionally substituted with $NH_2$, CN, and $CONR^6R^7$.

In embodiments, $R^4$ and $R^8$ or $R^8$ and $R^{8a}$, together with the atoms to which they are bound, form a mono- or bicyclic ring having 3-10 ring members selected from C, N, O, and S and that, if bicyclic, is optionally fused, bridged, or spiro-fused, wherein the mono- or bicyclic ring is optionally substituted with halo, OH, $C_1$-$C_6$-haloalkyl, $C_1$-$C_6$-alkoxy, $C_3$-$C_8$-cycloalkyl (optionally and independently substituted with 1-3 substituents selected from halo and $NH_2$), $C_1$-$C_6$-alkyl optionally substituted with $NH_2$, 3- to 6-membered heterocycloalkyl (wherein 1-4 ring members are independently selected from N, O, and S), CN, and $CONR^6R^7$.

In some embodiments, $R^5$ is selected from the group consisting of $C_1$-$C_{20}$-alkyl, such as $C_1$-$C_6$-alkyl (optionally interrupted by one or more heteroatoms selected from —NH—, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —O—($C_1$-$C_6$-alkyl)($C_6$-$C_{10}$-aryl), —O—($C_3$-$C_8$-cycloalkyl), —O—($C_1$-$C_6$-alkyl)($C_3$-$C_8$-cycloalkyl), —($C_1$-$C_6$-alkyl)-O—($C_6$-$C_{10}$-aryl), —($C_1$-$C_6$-alkyl)-NH—($C_6$-$C_{10}$-aryl), —($C_1$-$C_6$-alkyl)-NHC(O)—($C_6$-$C_{10}$-aryl), —($C_2$-$C_6$-alkenyl)($C_6$-$C_{10}$-aryl), —($C_1$-$C_6$-alkyl)(3- to 6-membered heterocycloalkyl) (wherein 1-4 ring members are independently selected from N, O, and $S(O)_{0-2}$), $C_3$-$C_8$-cycloalkyl, 3- to -14-membered, such as 3- to 6-membered heterocycloalkyl (wherein 1-4 ring members are independently selected from N, O, and S), —O-(3- to 6-membered heterocycloalkyl (wherein 1-4 ring members are independently selected from N, O, and S)), —($C_1$-$C_6$-alkyl)-(5- to 10-membered heteroaryl (wherein 1-4 heteroaryl members are independently selected from N, O, and S)), and —($C_1$-$C_6$-alkyl)-NH-(5- to 10-membered heteroaryl (wherein 1-4 heteroaryl members are independently selected from N, O, and S)).

In various embodiments, $R^5$ is optionally substituted with one to three substituents selected from the group consisting of halo, $C_1$-$C_6$-alkyl, $C_1$-$C_6$-haloalkyl, —$C_1$-$C_6$-alkyl-$NH_2$, —$C_6$-$C_{10}$-aryl, —($C_1$-$C_6$-alkyl)($C_6$-$C_{10}$-aryl), CN, $COR^9$, —$OC(O)R^9$, $CONR^9R^{10}$, —$OCONR^9R^{10}$, $NR^9R^{10}$, —$NR^9C(O)NR^9R^{10}$, —$NR^9C(O)OR^{10}$, $OR^9$, $SR^9$, $SO_2R^9$, —N(H)C(O)(3- to 6-membered heterocycloalkyl), and —N(H)C(O)$CF_3$, and wherein two substituents together with the carbon atom to which they are bound optionally form a mono- or bicyclic ring having 3-10 ring members selected from C, N, O, and S.

$R^9$ and $R^{10}$ are independently selected from H, $C_1$-$C_6$-alkyl, $C_3$-$C_8$-cycloalkyl, $C_6$-$C_{10}$-aryl, and —($C_1$-$C_6$-alkyl)($C_6$-$C_{10}$-aryl).

In some embodiments, $R^5$ is

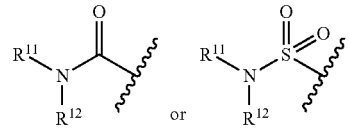

wherein $R^{11}$ and $R^{12}$ are independently selected from H, $C_1$-$C_8$ alkyl, $C_3$-$C_8$-cycloalkyl, —($C_1$-$C_6$-alkyl)-$C_3$-$C_8$-cycloalkyl, $C_6$-$C_{10}$-aryl, —($C_1$-$C_6$-alkyl)($C_6$-$C_{10}$-aryl), 5- to 10-membered heteroaryl (wherein 1-4 heteroaryl members are independently selected from N, O, and S), —($C_1$-$C_6$-alkyl)(5- to 10-membered heteroaryl (wherein 1-4 heteroaryl members are independently selected from N, O, and S)), 3- to 6-membered heterocycloalkyl (wherein 1-4 ring members are independently selected from N, O, and S), —($C_1$-$C_6$-alkyl)(3- to 6-membered heterocycloalkyl (wherein 1-4 ring members are independently selected from N, O, and S)), and —$S(O)_2$—N(H)($C_6$-$C_{10}$-aryl).

$R^{11}$ and $R^{12}$ are optionally substituted with one to three substituents independently selected from the group consisting of halo, OH, $NH_2$, $C_1$-$C_6$-alkyl (optionally and independently substituted with 1-3 substituents selected from halo and $NH_2$), $C_1$-$C_6$-alkoxy, $C_3$-$C_8$-cycloalkyl (optionally and independently substituted with 1-3 substituents selected from halo and $NH_2$), CN, —($C_1$-$C_6$-alkyl)($C_6$-$C_{10}$-aryl), and $CONR^6R^7$.

In some embodiments, $R^{11}$ and $R^{12}$, together with the nitrogen atom to which they are bound, form a mono- or bicyclic ring having 4-10 ring members selected from C, N, O, and S and that, if bicyclic, is optionally fused, bridged, or spiro-fused. The mono- or bicyclic ring is optionally substituted with one to three substituents selected from halo, OH, $C_1$-$C_6$-haloalkyl, $C_1$-$C_6$-alkoxy, $C_3$-$C_8$-cycloalkyl (optionally and independently substituted with 1-3 substituents selected from halo and $NH_2$), $C_1$-$C_6$-alkyl optionally substituted with $NH_2$, 3- to 6-membered heterocycloalkyl (wherein 1-4 ring members are independently selected from N, O, and S), CN, and $CONR^6R^7$.

The present disclosure also provides in embodiments a pharmaceutical composition comprising a compound or a pharmaceutically acceptable salt thereof as described herein and a pharmaceutically acceptable carrier.

In another embodiment, the present disclosure provides a method for inhibiting the main protease ($M^{pro}$) of severe acute respiratory syndrome Coronavirus-2 (SARS-CoV-2). The method comprises contacting $M^{pro}$ with a compound or pharmaceutically acceptable thereof as described herein.

Another embodiment is a method for treating COVID-19 in a subject suffering therefrom, or for preventing COVID-19 in a subject. The method comprises contacting $M^{pro}$ with a compound or pharmaceutically acceptable thereof as described herein.

The present disclosure also provides, in an embodiment, a compound or pharmaceutically acceptable salt thereof as described herein for inhibiting the main protease ($M^{pro}$) of severe acute respiratory syndrome Coronavirus-2 (SARS-CoV-2) in a subject.

The present disclosure provides in another embodiment a compound or pharmaceutically acceptable salt thereof as described herein for treating COVID-19 in a subject suffering therefrom, or for preventing COVID-19 in a subject.

DETAILED DESCRIPTION

Compounds of the present disclosure are potent inhibitors of $M^{pro}$, exhibit significant metabolic stability, and are useful in oral dosing to patients for treatment of COVID-19 and for prophylaxis against COVID-19. Limited evidence to date on the known $M^{pro}$ inhibitor PF-00835231 indicates that its methyl ether is 3-5 fold less active in cell and enzyme assays (RL Hoffman, 2020). In contrast, formula (I) compounds of the present disclosure, including fluorinated phenyl and alkyl ethers, show unexpected and dramatic improvements in antiviral activities, e.g., high cellular potencies ($EC_{50}$ less than about 5 nM) as illustrated by the examples herein.

Definitions

"Alkyl" refers to straight or branched chain hydrocarbyl including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH($CH_3$)$_2$, —CH($CH_3$)($CH_2CH_3$), —CH($CH_2CH_3$)$_2$, —C($CH_3$)$_3$, —C($CH_2CH_3$)$_3$, —CH$_2$CH($CH_3$)$_2$, —CH$_2$CH($CH_3$) ($CH_2$CH$_3$), —CH$_2$CH($CH_2$CH$_3$)$_2$, —CH$_2$C($CH_3$)$_3$, —CH$_2$C($CH_2$CH$_3$)$_3$, —CH($CH_3$)CH($CH_3$)($CH_2$CH$_3$), —CH$_2$CH$_2$CH($CH_3$)$_2$, —CH$_2$CH$_2$CH($CH_3$)($CH_2$CH$_3$), —CH$_2$CH$_2$CH($CH_2$CH$_3$)$_2$, —CH$_2$CH$_2$C($CH_3$)$_3$, —CH$_2$CH$_2$C($CH_2$CH$_3$)$_3$, —CH($CH_3$)CH$_2$CH($CH_3$)$_2$, —CH ($CH_3$)CH($CH_3$)CH($CH_3$)$_2$, and the like. Thus, alkyl groups include primary alkyl groups, secondary alkyl groups, and tertiary alkyl groups. An alkyl group can be unsubstituted or optionally substituted with one or more substituents as described herein.

Each of the terms "halogen," "halide," and "halo" refers to —F or fluoro, —Cl or chloro, —Br or bromo, or —I or iodo.

The term "alkenyl" refers to straight or branched chain hydrocarbyl groups including from 2 to about 20 carbon atoms having 1-3, 1-2, or at least one carbon to carbon double bond. An alkenyl group can be unsubstituted or optionally substituted with one or more substituents as described herein.

"Alkyne or "alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein.

The term "alkoxy" or "alkoxyl" refers to an —O-alkyl group having the indicated number of carbon atoms. For example, a ($C_1$-$C_6$)-alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O— hexyl, —O-isohexyl, and —O-neohexyl.

The term "cycloalkyl" refers to a saturated monocyclic, bicyclic, tricyclic, or polycyclic, 3- to 14-membered ring system, such as a $C_3$-$C_8$-cycloalkyl. The cycloalkyl may be attached via any atom. Representative examples of cycloalkyl include, but are not limited to cyclopropyl, cyclobutyl, cyclopentyl, and cyclohexyl. Polycyclic cycloalkyl includes rings that can be fused, bridged, and/or spiro-fused. A cycloalkyl group can be unsubstituted or optionally substituted with one or more substituents as described herein.

"Aryl" when used alone or as part of another term means a carbocyclic aromatic group whether or not fused having the number of carbon atoms designated or if no number is designated, up to 14 carbon atoms, such as a $C_6$-$C_{10}$-aryl or $C_6$-$C_{14}$-aryl. Examples of aryl groups include phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). "Aryl" also contemplates an aryl ring that is part of a fused polycyclic system, such as aryl fused to cycloalkyl as defined herein. An exemplary aryl is phenyl. An aryl group can be unsubstituted or optionally substituted with one or more substituents as described herein.

The term "heteroatom" refers to N, O, and S. Compounds of the present disclosure that contain N or S atoms can be optionally oxidized to the corresponding N-oxide, sulfoxide, or sulfone compounds.

"Heteroaryl," alone or in combination with any other moiety described herein, is a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A heteroaryl group can be unsubstituted or optionally substituted with one or more substituents as described herein.

"Heterocycloalkyl" is a saturated or partially unsaturated non-aromatic monocyclic, bicyclic, tricyclic or polycyclic ring system that has from 3 to 14, such as 3 to 6, atoms in which 1 to 3 carbon atoms in the ring are replaced by heteroatoms of O, S or N. Polycyclic heterocycloalkyl includes rings that can be fused, bridged, and/or spiro-fused. In addition, a heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A heterocycloalkyl group can be unsubstituted or optionally substituted with one or more substituents as described herein.

The term "nitrile" or "cyano" can be used interchangeably and refers to a —CN group.

The term "oxo" refers to a =O atom bound to an atom that is part of a saturated or unsaturated moiety. Thus, the =O atom can be bound to a carbon, sulfur, or nitrogen atom that is part of a cyclic or acyclic moiety.

A "hydroxyl" or "hydroxy" refers to an —OH group.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified to the contrary, the term "compound" is inclusive in that it encompasses a compound or a pharmaceutically acceptable salt, stereoisomer, and/or tautomer thereof. Thus, for instance, a compound of Formula I includes a pharmaceutically acceptable salt of a tautomer of the compound.

In this disclosure, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The present disclosure includes all pharmaceutically acceptable isotopically-labelled compounds of Formula (I), wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, F, $^{15}$O and $^{13}$N, can be useful in Positron Emission Topography (PET) studies for examining substrate receptor occupancy. Isotopically-labeled compounds of Formula (I) may generally be prepared by conventional techniques known to those skilled in the art or by processes analogous to those described in the accompanying Examples using an appropriate isotopically-labeled reagents in place of the non-labeled reagent previously employed.

Site specific substitution of atoms having the same atomic number but an atomic mass or mass number different from the atomic mass or mass number that predominates in nature can be regarded as a substituent of a compound of the present disclosure. A sample of a compound having such an isotope as a substituent has at least 50% isotope incorporation at the labelled position(s). The concentration of such isotopes, e.g., deuterium, may be defined by the isotopic enrichment factor. The term "isotopic enrichment factor" as used herein means the ratio between the isotopic abundance and the natural abundance of a specified isotope. For example, if a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

The terms "treat", "treating" and "treatment" refer to the amelioration or eradication of a disease or symptoms associated with a disease. In various embodiments, the terms refer to minimizing or slowing the spread, progression, or worsening of the disease resulting from the administration of one or more prophylactic or therapeutic compounds described herein to a patient with such a disease.

The terms "prevent," "preventing," and "prevention" refer to the prevention of the onset, recurrence, or spread of the disease in a patient resulting from the administration of a compound described herein.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or is synergistic with another therapeutic agent.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult. In the present disclosure, the terms "patient" and "subject" are used interchangeably.

COMPOUNDS

The M$^{pro}$ inhibitor compound of the present disclosure conforms in various embodiments to Formula (I):

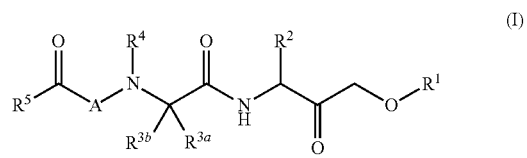

wherein R$^1$, R$^2$, R$^{3a}$, R$^{3b}$, R$^4$, R$^5$, and A are defined in summary hereinabove.

In some embodiments, R$^1$ is a mono- to perfluorinated. In some embodiments, R$^1$ is a mono- to perfluorinated C$_1$-C$_6$-alkyl or C$_6$-C$_{10}$-aryl. The degree of fluorination is limited only by the number of possible sites for substitution on the alkyl or aryl. Thus, in some embodiments, R$^1$ is a mono- to perfluorinated C$_1$-C$_6$-alkyl, such as illustrative examples that include —CHF$_2$ and —CF$_3$. In accordance with an embodiment, R$^1$ is —CF$_3$. In other embodiments, R$^1$ is a mono- to perfluorinated C$_6$-C$_{10}$-aryl, such as fluorophenyl, difluorophenyl, trifluorophenyl, tetrafluorophenyl, and pentafluorophenyl. In an illustrative embodiment, R$^1$ is 2,3,5,6-tetrafluorophenyl:

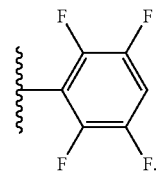

In additional embodiment, optionally in combination with any other embodiment, R$^2$ is

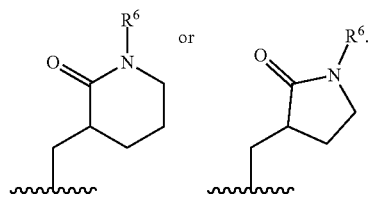

Thus, in an embodiment, $R^2$ is

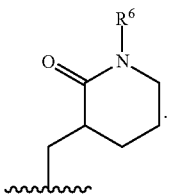

In another embodiment, $R^2$ is

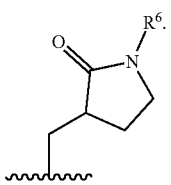

In exemplary embodiments, optionally in combination with these, $R^6$ is H.

The present disclosure also provides a Formula (I) compound, per various embodiments, wherein $R^{3a}$ is H and $R^{3b}$ is selected from the group consisting of optionally substituted $C_1$-$C_8$-alkyl and —($C_1$-$C_6$-alkyl)($C_3$-$C_{10}$-cycloalkyl). For example, $R^{3a}$ is H and $R^{3b}$ is optionally substituted $C_1$-$C_8$-alkyl. An illustrative $C_1$-$C_8$-alkyl, among others described herein, is

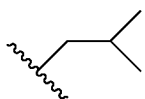 [SMILES: *CC(C)C]

(iso-butyl).

In still other embodiments, the moiety

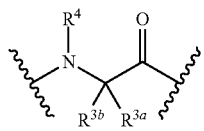

in Formula (I) is selected from those wherein $R^{3a}$ is H, and $R^{3b}$ and $R^4$ together with the atoms to which they are bound form an optionally substituted 3-10 membered mono- or bicyclic ring, such as any ring described herein. Where the ring is bicyclic, it is optionally fused, bridged, or spiro-fused to another component ring. Thus, in exemplary embodiment, the moiety

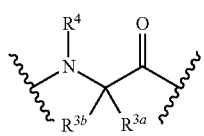

is selected from the group consisting of:

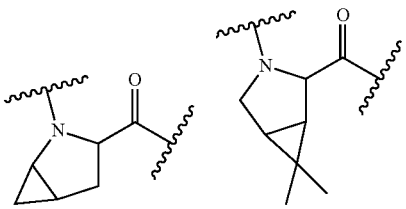

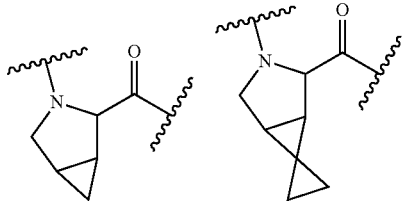

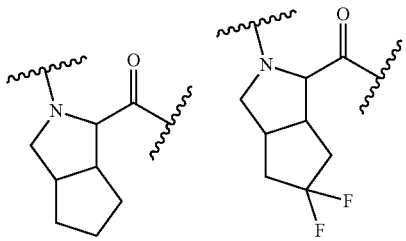

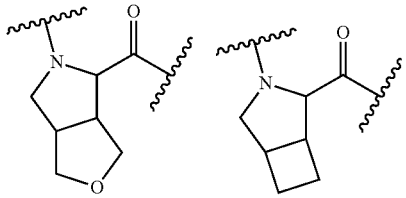

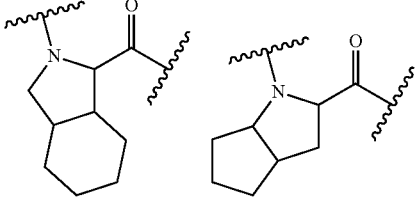

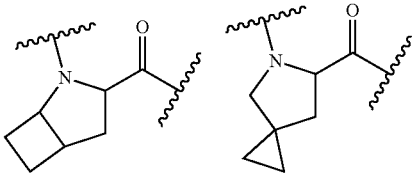

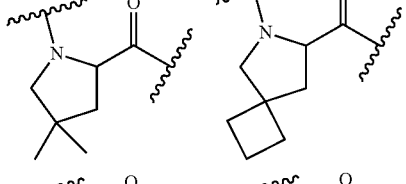

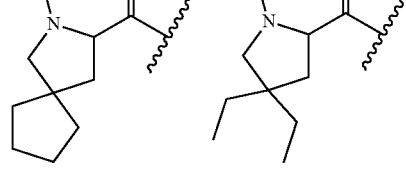

-continued

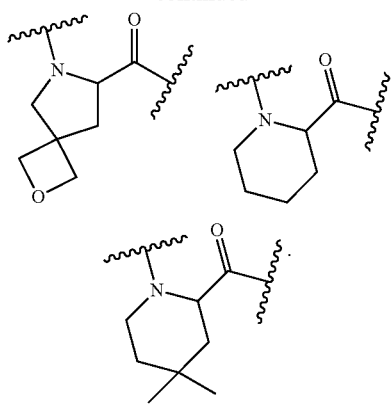

In some Formula (I) compounds, according to embodiments optionally in combination with any other embodiment, A is a bond.

In one embodiment, R⁵ is

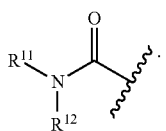

Various and all combinations of $R^{11}$ and $R^{12}$ are contemplated. In illustrative embodiments, $R^{11}$ is H. In still additional embodiments, $R^5$ is selected from the group consisting of:

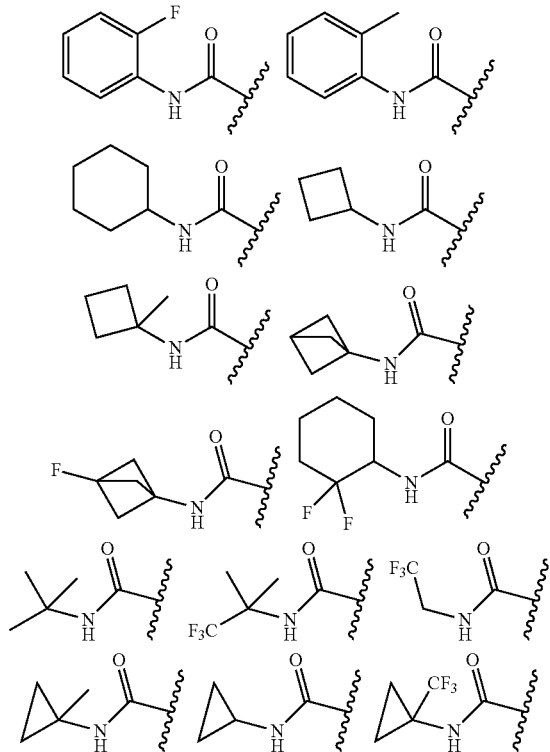

-continued

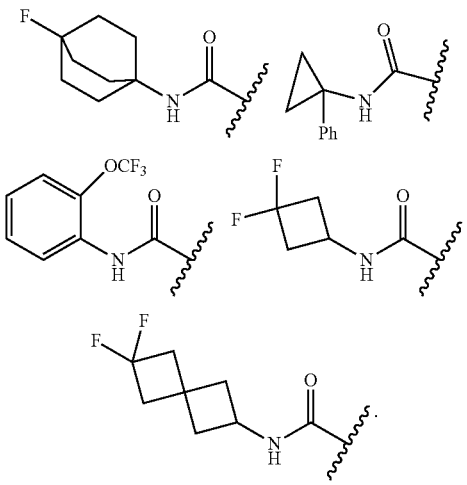

In still other embodiments, $R^5$ is selected from the group consisting of:

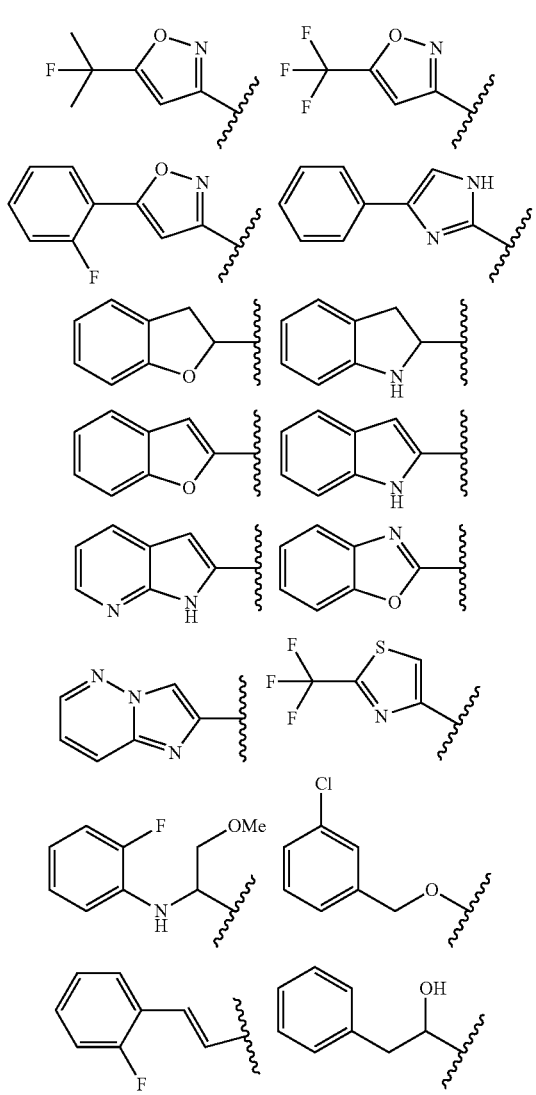

-continued

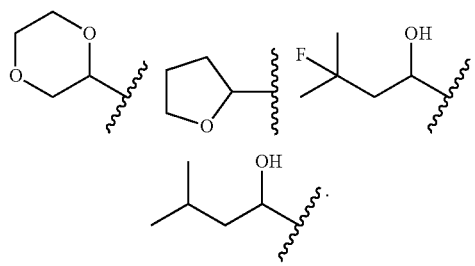

In another embodiment, A is a moiety of formula (II):

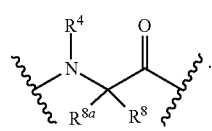 (II)

All combinations of $R^{8a}$ and $R^8$ are contemplated. Thus, in an embodiment, $R^{8a}$ is H. Optionally in combination these embodiments, $R^4$ and $R^8$ together with the atoms to which they are bound, form an optionally substituted mono- or bicyclic ring having 3-10 ring members selected from C, N, O, and S. If the ring is bicyclic, then it can optionally fused, bridged, or spiro-fused. For example, formula (II) moieties include those selected from the group consisting of:

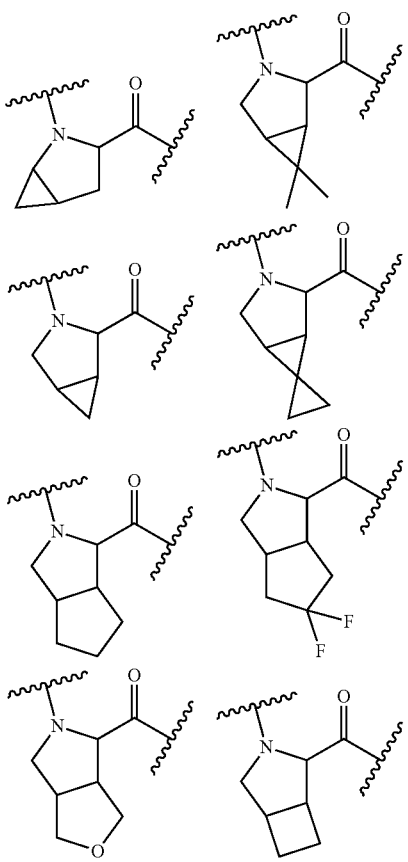

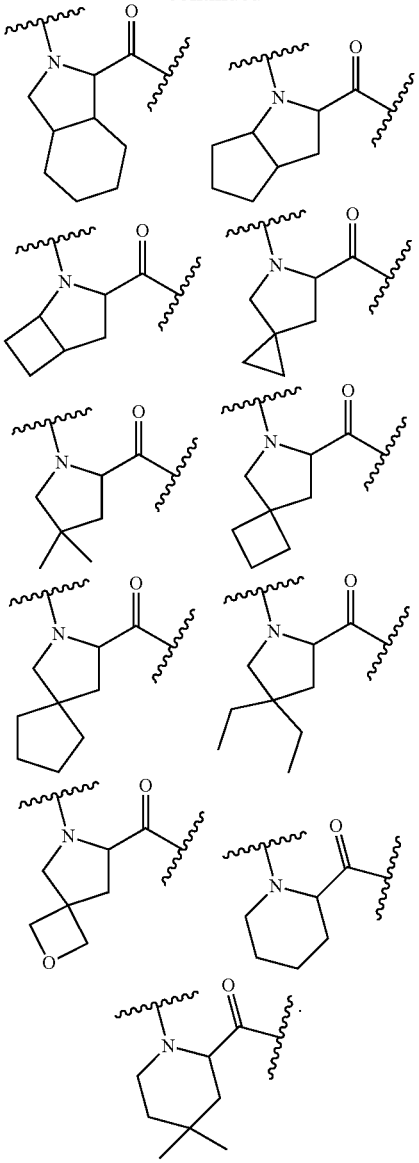

In some embodiments, disclosed is a compound of Formula (I), or a pharmaceutically acceptable salt thereof, wherein:

$R^1$ is a mono- to perfluorinated $C_1$-$C_6$-alkyl or $C_6$-$C_{10}$-aryl;

$R^2$ is

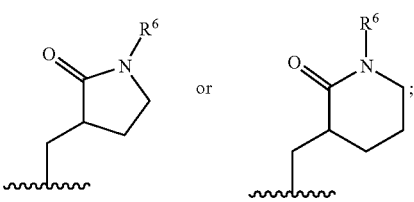

$R^{3a}$, $R^{3b}$, and $R^4$ are independently selected from H, $C_1$-$C_8$-alkyl, —($C_1$-$C_6$-alkyl)($C_3$-$C_{10}$-cycloalkyl), —($C_1$-$C_6$-alkyl)($C_6$-$C_{10}$-aryl), and —($C_1$-$C_6$-alkyl)(3- to 6-membered heterocycloalkyl) (wherein 1-4 ring members are independently selected from N, O, and S), wherein $R^{3b}$ is optionally substituted with 1 to 5 halo; or $R^{3a}$ and $R^4$, $R^{3b}$ and $R^4$, or $R^{3a}$ and $R^{3b}$ together with the atoms to which they are bound form mono- or bicyclic ring having 3-10 ring members selected from C, N, O, and S, and that, if bicyclic, is optionally fused, bridged, or spiro-fused, wherein the mono- or bicyclic ring is optionally substituted with $C_1$-$C_6$-alkyl, $C_1$-$C_6$-haloalkyl, and $C_6$-$C_{10}$-aryl;

A is a bond; and $R^5$ is selected from the group consisting of $C_1$-$C_{20}$-alkyl (optionally interrupted by one or more heteroatoms selected from —NH—, O, and S), 5- to 10-membered heteroaryl (wherein 1-4 heteroaryl members are independently selected from N, O, and S), —O—($C_1$-$C_6$-alkyl)($C_6$-$C_{10}$-aryl), $C_6$-$C_{10}$-aryl, $C_3$-$C_8$-cycloalkyl, 3- to 14-membered heterocycloalkyl (wherein 1-4 ring members are independently selected from N, O, and S), —($C_1$-$C_6$-alkyl)($C_6$-$C_{10}$-aryl), —($C_1$-$C_6$-alkyl)-($C_3$-$C_8$-cycloalkyl), —C(O)—($C_1$-$C_6$-alkyl), and $C_2$-$C_6$-alkenyl;

wherein $R^5$ is optionally substituted with one to three substituents selected from the group consisting of halo, —$C_6$-$C_{10}$-aryl (optionally substituted with 1-3 substituents selected from halo), $C_1$-$C_6$-haloalkyl, $OR^9$, $C_1$-$C_6$-alkyl, $OCF_3$, —$OC(O)R^9$, —$OCONR^9R^{10}$, and —$NR^9C(O)OR^{10}$;

$R^9$ and $R^{10}$ are independently selected from the group consisting of H, $C_1$-$C_6$-alkyl, $C_3$-$C_8$-cycloalkyl, and —($C_1$-$C_6$-alkyl)($C_6$-$C_{10}$-aryl);

or $R^5$ is

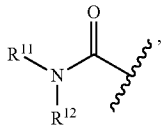

wherein $R^{11}$ and $R^{12}$ are independently selected from the group consisting of H, $C_1$-$C_8$ alkyl, $C_6$-$C_{10}$-aryl, and $C_3$-$C_8$-cycloalkyl, wherein $R^{11}$ and $R^{12}$ are optionally substituted with one to three substituents independently selected from the group consisting of halo, $C_1$-$C_6$-haloalkyl, 3- to 6-membered heterocycloalkyl (wherein 1-4 ring members are independently selected from N, O, and $S(O)_{0-2}$), $C_1$-$C_6$-alkyl (optionally and independently substituted with 1-3 substituents selected from halo and $NH_2$, or optionally interrupted by one or more heteroatoms selected from —NH—, O, and S), and $C_1$-$C_6$-alkoxy (optionally substituted with 1-3 halo).

In some embodiments, disclosed is a compound of Formula (I), or a pharmaceutically acceptable salt thereof, wherein:

$R^1$ is trifluoromethyl or tri- to perfluorinated phenyl;

$R^2$ is or

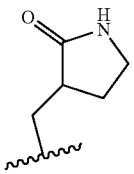 or 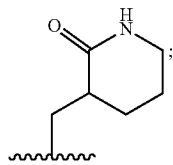

$R^{3a}$ is H, $R^4$ is H, and $R^{3b}$ is —$CH_2$-cyclopropyl, —$CH_2$-cyclobutyl, —$CH_2$-cyclohexyl, isobutyl, neopentyl optionally substituted with 1 to 3 fluoro, benzyl, or —$CH_2$-tetrahydropyranyl, or $R^{3a}$ is H, and $R^{3b}$ and $R^4$ together with the atoms to which they are bound form mono- or bicyclic ring having 5-8 ring members selected from C and N, and that, if bicyclic, is fused or spiro-fused, wherein the mono- or bicyclic ring is optionally substituted with methyl, trifluoromethyl, or phenyl;

A is a bond; and $R^5$ is selected from the group consisting of methyl, n-Pr, i-Pr, iso-butyl, n-butyl, perdeuterated n-butyl, sec-butyl, iso-pentyl, tert-pentyl, neo-heptyl, 2-methylpentyl, 2,4-dimethylpentyl, 1-methoxy-3-methylbutyl, indolyl, thiazolyl, benzyloxy, 1,3-benzodioxolyl, isoxazolyl, 1,2-benzisoxazolyl, benzoxazolyl, imidazo[1,2-b]pyridazinyl, 1,4-dioxanyl, tetrahydrofuranyl, 2-oxabicyclo[2.1.1]hexanyl, 7-oxabicyclo[2.2.1]heptanyl, benzyl, —$(CH_2)_2$-cyclopropyl, cyclopropyl, —$CH_2$-cyclobutyl, cyclobutyl, cyclopentyl, cyclohexyl, —C(O)-(iso-butyl), —C(O)-(iso-pentyl), and 3-methylbut-1-enyl;

wherein $R^5$ is optionally substituted with one to three substituents selected from the group consisting of fluoro, chloro, phenyl (optionally substituted with 1-3 fluoro), monofluoro-i-Pr, difluoro-i-Pr, trifluoromethyl, methyl, tert-butyl, hydroxy, methoxy, $OCF_3$, —$OC(O)NR^9R^{10}$, —$OC(O)R^9$, and —$NR^9C(O)OR^{10}$;

$R^9$ and $R^{10}$ are independently selected from the group consisting of H, ethyl, i-Pr, tert-butyl, cyclohexyl, and benzyl;

or $R^5$ is

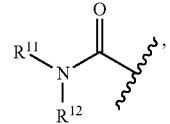

wherein $R^{11}$ and $R^{12}$ are independently selected from the group consisting of H, methyl, tert-butyl, phenyl, cyclopropyl, cyclobutyl, cyclohexyl, and bicyclo[1.1.1]pentanyl, wherein $R^{11}$ and $R^{12}$ are optionally substituted with one to three substituents independently selected from the group consisting of fluoro, chloro, monofluoromethyl, trifluoromethyl, tetrahydropyranyl, methyl, and methoxy.

In some embodiments, disclosed is a compound of Formula (I), or a pharmaceutically acceptable salt thereof, wherein:

$R^1$ is a mono- to perfluorinated $C_1$-$C_6$-alkyl or $C_6$-$C_{10}$-aryl;

$R^2$ is

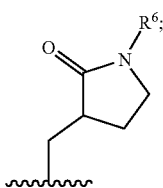

$R^{3a}$, $R^{3b}$, and $R^4$ are independently selected from H, $C_1$-$C_8$-alkyl;

or $R^{3a}$ and $R^4$, $R^{3b}$ and $R^4$, or $R^{3a}$ and $R^{3b}$ together with the atoms to which they are bound form mono- or bicyclic ring having 3-10 ring members selected from C, N, O, and S, and that, if bicyclic, is fused or spiro-fused, wherein the mono- or bicyclic ring is optionally substituted with $C_1$-$C_6$-alkyl or $C_1$-$C_6$-haloalkyl;

A is a bond; and $R^5$ is selected from the group consisting of $C_1$-$C_{20}$-alkyl (optionally interrupted by one or more heteroatoms selected from —NH—, O, and S), 5- to 10-membered heteroaryl (wherein 1-4 heteroaryl members are independently selected from N, O, and S), $C_3$-$C_8$-cycloalkyl, 3- to 14-membered heterocycloalkyl (wherein 1-4 ring members are independently selected from N, O, and S), and —($C_1$-$C_6$-alkyl)($C_6$-$C_{10}$-aryl);

wherein $R^5$ is optionally substituted with one to three substituents selected from the group consisting of halo, $C_1$-$C_6$-haloalkyl, and OH;

or $R^5$ is

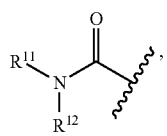

wherein $R^{11}$ and $R^{12}$ are independently selected from the group consisting of H, $C_1$-$C_8$ alkyl, $C_6$-$C_{10}$-aryl, and $C_3$-$C_8$-cycloalkyl, wherein $R^{11}$ and $R^{12}$ are optionally substituted with one to three substituents independently selected from the group consisting of halo, $C_1$-$C_6$-haloalkyl, and $C_1$-$C_6$-alkyl (optionally and independently substituted with 1-3 substituents selected from halo and NH$_2$, or optionally interrupted by one or more heteroatoms selected from —NH—, O, and S).

In some embodiments, disclosed is a compound of Formula (I), or a pharmaceutically acceptable salt thereof, wherein:

$R^1$ is trifluoromethyl or tetra-fluorinated phenyl;

$R^2$ is

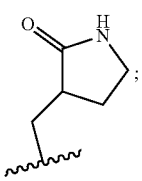

$R^{3a}$ is H, $R^4$ is H, and $R^{3b}$ is isobutyl or neopentyl, or $R^{3a}$ is H, and $R^{3b}$ and $R^4$ together with the atoms to which they are bound form mono- or bicyclic ring having 5-8 ring members selected from C and N, and that, if bicyclic, is fused or spiro-fused, wherein the mono- or bicyclic ring is optionally substituted with methyl or trifluoromethyl;

A is a bond; and $R^5$ is selected from the group consisting of methyl, iso-pentyl, indolyl, isoxazolyl, tetrahydrofuranyl, 2-oxabicyclo[2.1.1]hexanyl, and benzyl;

wherein $R^5$ is optionally substituted with one to three substituents selected from the group consisting of fluoro, monofluoro-i-Pr, trifluoromethyl, and hydroxy;

or $R^5$ is

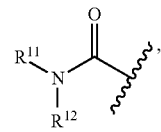

wherein $R^{11}$ and $R^{12}$ are independently selected from the group consisting of H, methyl, tert-butyl, phenyl, cyclopropyl, cyclohexyl, and bicyclo[1.1.1]pentanyl, wherein $R^{11}$ and $R^{12}$ are optionally substituted with one to three substituents independently selected from the group consisting of fluoro, trifluoromethyl, and methyl.

In some embodiments, $R^5$ is selected from the group consisting of:

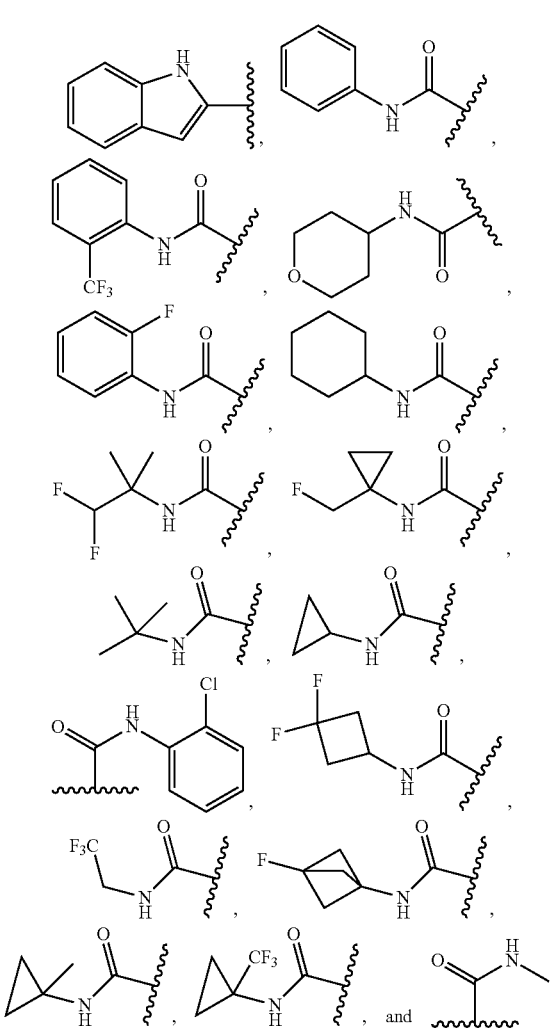

In some embodiments, $R^5$ is selected from the group consisting of:

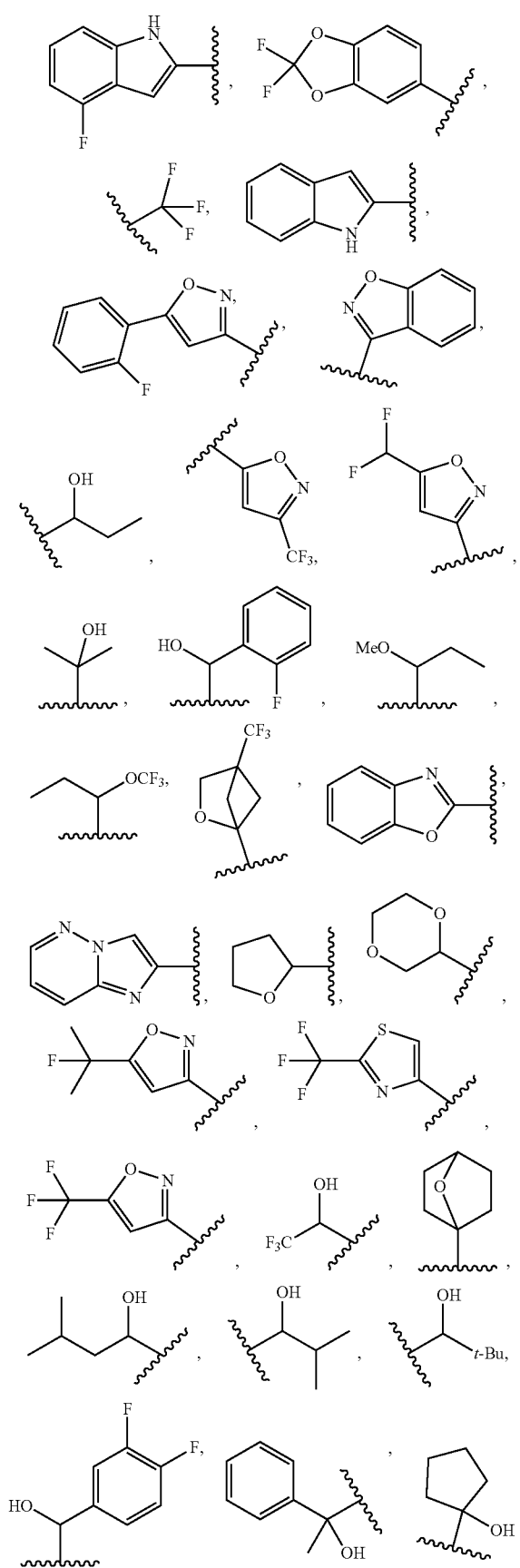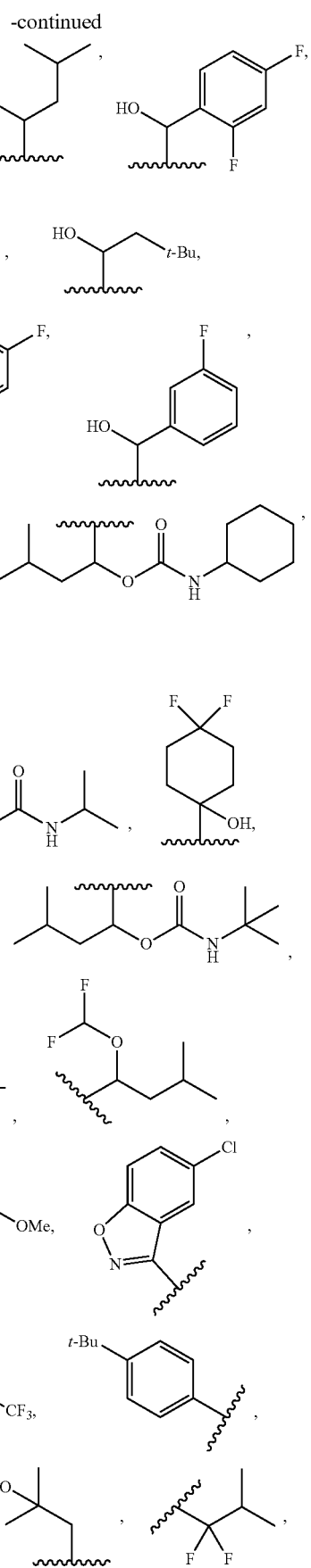

-continued

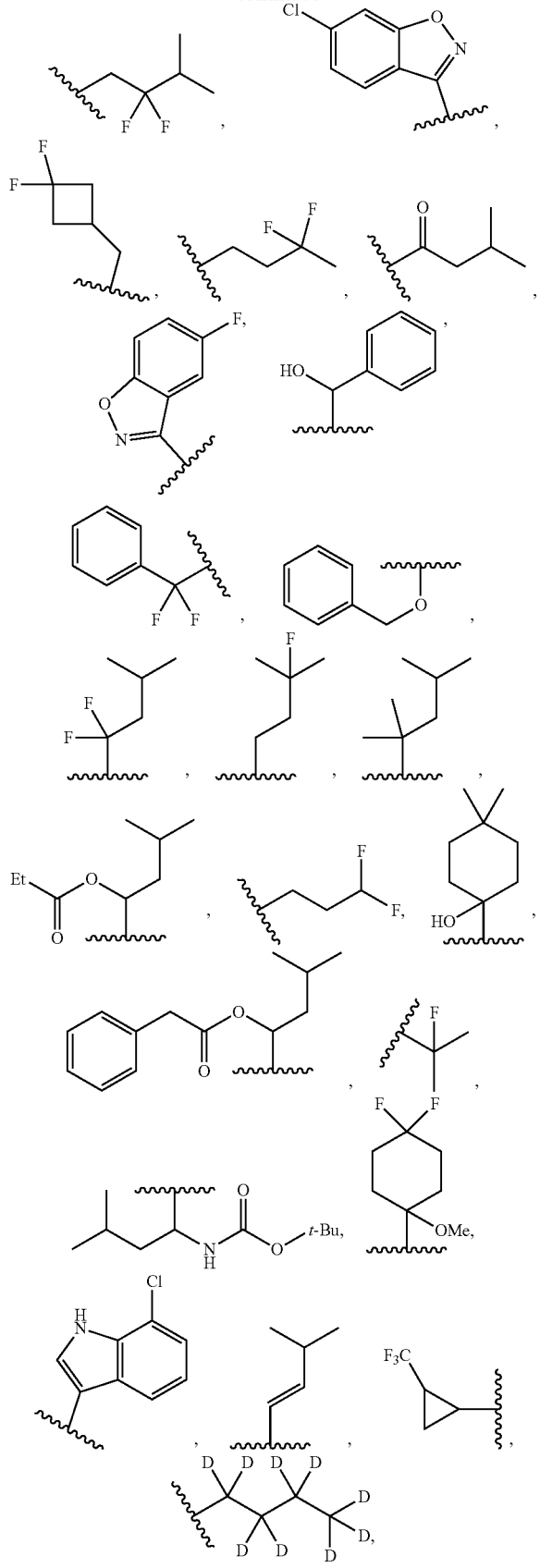

Me, Et, i-Pr, n-pentyl, and f-flu.

In some embodiments, R⁵ is selected from the group consisting of

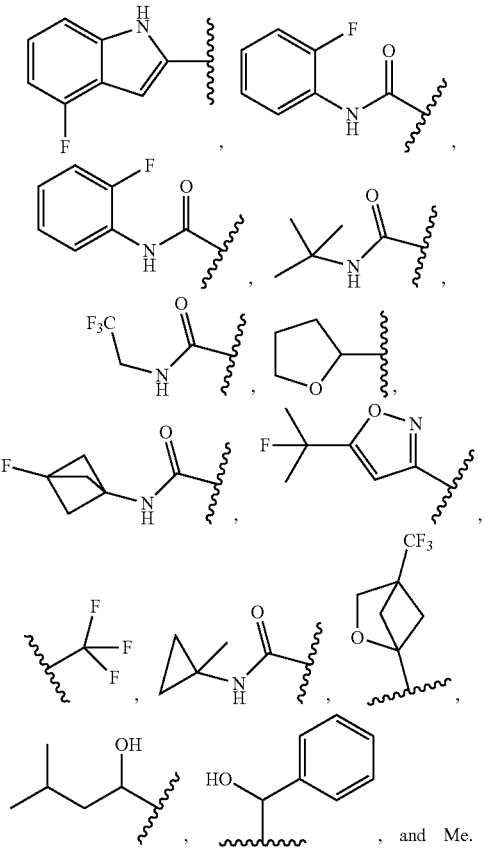

, and Me.

In various embodiments, the present disclosure provides a compound of formula (I), or a pharmaceutically acceptable salt thereof, wherein:

$R^1$ is a mono- to perfluorinated $C_1$-$C_6$-alkyl;

$R^2$ is

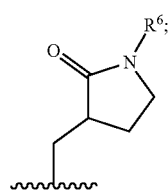

the moiety

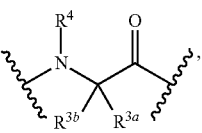

$R^{3a}$ is H, and $R^{3b}$ and $R^4$ together with the atoms to which they are bound form an optionally substituted 3-10 membered mono- or bicyclic ring that, if bicyclic, is optionally fused, bridged, or spiro-fused;

A is a bond; and $R^5$ is $C_1$-$C_6$-alkyl (optionally interrupted by one or more heteroatoms selected from —NH—, O, and S), optionally substituted with one to three substituents selected from the group consisting of halo, $C_1$-$C_6$-alkyl, $C_1$-$C_6$-haloalkyl, and $OR^9$.

In another aspect, disclosed is a compound of Formula (III),

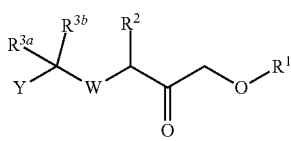
(III)

wherein

W is —C(O)—NH— or

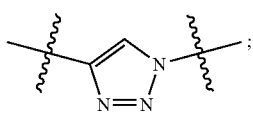 [SMILES: *c1cn(*)nn1]
;

Y is $R^A$—C($R^{4a}$)($R^{4b}$)—, $R^A$—C(O)—N($R^4$)—,

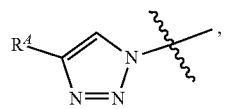
, or ($R^B$)($R^4$)N—;

provided that when W is —C(O)—NH—, Y is not $R^A$—C(O)—N($R^4$)—;

$R^1$ is selected from the group consisting of: $C_1$-$C_6$-alkyl or $C_6$-$C_{10}$-aryl, wherein the alkyl and aryl are mono- to perfluorinated;

$R^2$ is selected from the group consisting of

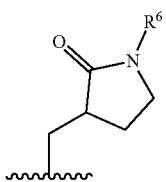

wherein $R^6$ is H or $C_1$-$C_6$-alkyl;

$R^{3a}$, $R^{3b}$, $R^{4a}$, $R^{4b}$, and $R^4$ are each independently selected from H or $C_1$-$C_8$-alkyl, or $R^{3a}$ and $R^4$, $R^{3b}$ and $R^4$, $R^{3a}$ and $R^{3b}$, or $R^{3a}$ and $R^{4a}$ together with the atoms to which they are bound form mono- or bicyclic ring having 3-10 ring members selected from C, N, O, and S and that, if bicyclic, is optionally fused, bridged, or spiro-fused;

$R^A$ is

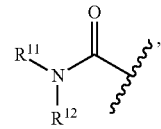
, wherein $R^{11}$ is H or $C_1$-$C_8$ alkyl;

$R^{12}$ are independently selected from H, $C_1$-$C_8$ alkyl, $C_6$-$C_{10}$-aryl, —($C_1$-$C_6$-alkyl)($C_6$-$C_{10}$-aryl);

wherein $R^{11}$ and $R^{12}$ are optionally substituted with one to three substituents independently selected from the group consisting of halo and $C_1$-$C_6$-haloalkyl;

$R^B$ is $R^{13}$ or —S(O)$_2$—$R^{13}$, wherein $R^{13}$ is selected from the group consisting of $C_6$-$C_{10}$-aryl, 5- to 10-membered heteroaryl (wherein 1-4 heteroaryl members are independently selected from N, O, and S), wherein $R^{13}$ is optionally substituted with one to three substituents selected from the group consisting of halo and $C_1$-$C_6$-alkyl, or a pharmaceutically acceptable salt thereof.

In some embodiments, the compound of Formula (III) X, or a pharmaceutically acceptable salt thereof, has a structure of Formula (III-a), Formula (III-b), Formula (III-c), or Formula (III-d):

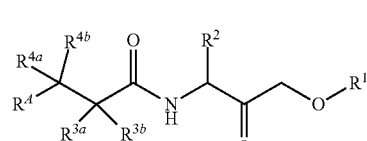
(III-a)

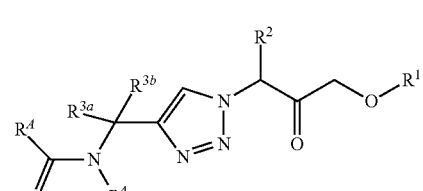
(III-b)

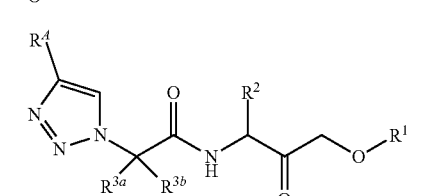
(III-c)

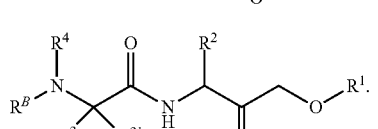
(III-d)

In some embodiments, the compound of Formula (III), or a pharmaceutically acceptable salt thereof, has a structure of formula (III-a), wherein $R^A$ is selected from the group consisting of —C(O)NH—($C_1$-$C_6$-alkyl), —C(O)NH—($C_6$-$C_{10}$-aryl), and —C(O)NH—($C_1$-$C_6$-alkyl)($C_6$-$C_{10}$-aryl), wherein $R^A$ is optionally substituted with one to three halo.

In some embodiments, the compound of Formula (III), or a pharmaceutically acceptable salt thereof, has a structure of formula (III-b), wherein $R^A$ is-C(O)NH—($C_6$-$C_{10}$-aryl); wherein $R^A$ is optionally substituted with one to three halo.

In some embodiments, the compound of Formula (III), or a pharmaceutically acceptable salt thereof, has a structure of formula (III-c), wherein $R^A$ is selected from the group consisting of —C(O)NH—($C_1$-$C_6$-alkyl) and —C(O)NH—($C_6$-$C_{10}$-aryl), wherein the $C_6$-$C_{10}$-aryl is optionally substituted with one to three $C_1$-$C_6$-alkyl In some embodiments, the compound of Formula (III), or a pharmaceutically acceptable salt thereof, has a structure of formula (III-d), wherein $R^B$ is 5- to 10-membered heteroaryl (wherein 1-4 heteroaryl members are independently selected from N, O, and S) or —S(O)$_2$-(5- to 10-membered heteroaryl (wherein 1-4 heteroaryl members are independently selected from N, O, and S)), wherein $R^B$ is optionally substituted with one to three $C_1$-$C_6$-alkyl.

Specific examples of Formula (I) compounds or their pharmaceutically acceptable salts constitute additional embodiments of the disclosure. Some of these are illustrated throughout the examples and shown in Table 1 below. In some embodiments, the compound of Formula (I) is selected from the group consisting of:

4-methoxy-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

N—((S)-1-(((S)-4-(2,6-difluorophenoxy)-3-oxo-1-((S)-2-oxopyrrolidin-3-yl)butan-2-yl)amino)-4-methyl-1-oxopentan-2-yl)-4-methoxy-1H-indole-2-carboxamide;

(S)-3-((S)-2-(4-methoxy-1H-indole-2-carboxamido)-4-methylpentanamido)-2-oxo-4-((S)-2-oxopyrrolidin-3-yl)butyl 2,6-dichlorobenzoate;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

N—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-1H-indole-2-carboxamide;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

N—((S)-1-(((S)-4-(2,6-difluorophenoxy)-3-oxo-1-((S)-2-oxopyrrolidin-3-yl)butan-2-yl)amino)-4-methyl-1-oxopentan-2-yl)-4-methoxy-1H-indole-2-carboxamide;

(S)-3-((S)-2-(4-methoxy-1H-indole-2-carboxamido)-4-methylpentanamido)-2-oxo-4-((S)-2-oxopyrrolidin-3-yl)butyl 2,6-dichlorobenzoate;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)benzamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-phenyloxalamide;

5-fluoro-N—((S)-5-methyl-1-oxo-1-(((S)-3-oxo-1-((S)-2-oxopyrrolidin-3-yl)-4-(2,3,5,6-tetrafluorophenoxy)butan-2-yl)amino)hexan-2-yl)-1H-indole-2-carboxamide;

5-fluoro-N—((S)-1-oxo-1-(((S)-3-oxo-1-((S)-2-oxopyrrolidin-3-yl)-4-(2,3,5,6-tetrafluorophenoxy)butan-2-yl)amino)-4-phenylbutan-2-yl)-1H-indole-2-carboxamide;

N—((S)-4,4-dimethyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-5-fluoro-1H-indole-2-carboxamide;

5-fluoro-N—((S)-1-oxo-1-(((S)-3-oxo-1-((S)-2-oxopyrrolidin-3-yl)-4-(2,3,5,6-tetrafluorophenoxy)butan-2-yl)amino)-3-phenylpropan-2-yl)-1H-indole-2-carboxamide;

benzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

5-fluoro-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

5-fluoro-N—((S)-1-oxo-1-(((S)-3-oxo-1-((S)-2-oxopyrrolidin-3-yl)-4-(2,3,5,6-tetrafluorophenoxy)butan-2-yl)amino)-3-(4-(trifluoromethyl)phenyl)propan-2-yl)-1H-indole-2-carboxamide;

5-fluoro-N—((S)-4-fluoro-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

5-fluoro-N-((2S)-3-(4-methoxyphenyl)-1-oxo-1-(((2S)-3-oxo-1-(2-oxopyrrolidin-3-yl)-4-(2,3,5,6-tetrafluorophenoxy)butan-2-yl)amino)propan-2-yl)-1H-indole-2-carboxamide;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)quinoline-2-carboxamide;

cyclopentyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

3-chlorobenzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

4-fluorobenzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)benzo[d][1,3]dioxole-5-carboxamide;

1-(cyclopentanecarbonyl)-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)piperidine-4-carboxamide;

(R)—N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)tetrahydrofuran-2-carboxamide;

1-(cyclopentanecarbonyl)-N—((S)-3-oxo-1-((S)-2-oxopyrrolidin-3-yl)-4-(2,3,5,6-tetrafluorophenoxy)butan-2-yl)piperidine-4-carboxamide;

$N^1$-(2-fluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-pyrrolo[3,2-c]pyridine-2-carboxamide;

$N^1$—((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-phenyloxalamide;

$N^1$—((S)-3-cyclobutyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-phenyloxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(2-(trifluoromethyl)phenyl)oxalamide;

$N^1$-(2-(tert-butyl)phenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(naphthalen-2-yl)oxalamide;

$N^1$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-phenyloxalamide;

$N^1$—((S)-5-methyl-1-oxo-1-(((S)-3-oxo-1-((S)-2-oxopyrrolidin-3-yl)-4-(2,3,5,6-tetrafluorophenoxy)butan-2-yl)amino)hexan-2-yl)-$N^2$-phenyloxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(o-tolyl)oxalamide;

$N^1$-(4-fluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(4-chlorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-4-methyl-N—((S)-3-oxo-1-((S)-2-oxopyrrolidin-3-yl)-4-(2,3,5,6-tetrafluorophenoxy)butan-2-yl)-2-(2-(phenylamino)acetamido)pentanamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-phenethyloxalamide;

$N^1$-benzyl-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(3-fluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-3-cyclopentyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-phenyloxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(pyridin-2-yl)oxalamide;

$N^1$-(2-chlorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide $N^1$-(2,6-difluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(2-(trifluoromethyl)pyridin-3-yl)oxalamide;

$N^1$-((2S)-1-(((2S)-3-hydroxy-1-((S)-2-oxopyrrolidin-3-yl)-4-(2,3,5,6-tetrafluorophenoxy)butan-2-yl)amino)-4-methyl-1-oxopentan-2-yl)-$N^2$-phenyloxalamide;

(S)-3-((S)-2-(5-fluoro-1H-indole-2-carboxamido)-4-methylpentanamido)-2-oxo-4-((S)-2-oxopyrrolidin-3-yl)butyl diphenylphosphinate;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(naphthalen-1-yl)oxalamide;

$N^1$-(3-chlorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(3,4-difluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(R)—$N^4$-(2-fluorobenzyl)-2-isobutyl-$N^1$—((S)-3-oxo-1-((S)-2-oxopyrrolidin-3-yl)-4-(2,3,5,6-tetrafluorophenoxy)butan-2-yl)succinimide;

(R)—$N^4$-(2,6-difluorobenzyl)-2-isobutyl-$N^1$—((S)-3-oxo-1-((S)-2-oxopyrrolidin-3-yl)-4-(2,3,5,6-tetrafluorophenoxy)butan-2-yl)succinimide;

$N^1$-(2-bromophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-benzylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-1-oxo-1-(((S)-3-oxo-1-((S)-2-oxopyrrolidin-3-yl)-4-(2,3,5,6-tetrafluorophenoxy)butan-2-yl)amino)pent-4-en-2-yl)-$N^2$-phenyloxalamide;

$N^1$-(2,5-dichlorobenzyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-2-((E)-3-(2-fluorophenyl)acrylamido)-4-methyl-N—((S)-3-oxo-1-((S)-2-oxopyrrolidin-3-yl)-4-(2,3,5,6-tetrafluorophenoxy)butan-2-yl)pentanamide;

$N^1$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-(2-fluorophenyl)oxalamide;

$N^1$-(2-(difluoromethoxy)phenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-ethylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2,6-dimethylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2,3-dimethylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-2-cinnamamido-4-methyl-N—((S)-3-oxo-1-((S)-2-oxopyrrolidin-3-yl)-4-(2,3,5,6-tetrafluorophenoxy)butan-2-yl)pentanamide;

5-(2-fluorophenyl)-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)isoxazole-3-carboxamide;

$N^1$-(2-fluoro-4-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-cyclohexyl-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N—(S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-5-phenylisoxazole-3-carboxamide;

$N^1$-(2,3-difluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2,5-difluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-3-((S)-4-methyl-2-(2-oxo-2-(phenylamino)acetamido)pentanamido)-2-oxo-4-((S)-2-oxopyrrolidin-3-yl)butyl diphenylphosphinate;

$N^1$-(4-fluoro-2-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-cyanophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(3,3-difluoro-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(2-fluorophenyl)oxalamide;

$N^1$-(4-chloro-2-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(2,4-difluorophenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(5-fluoro-2-methoxyphenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$—((S)-1-(((S)-1-cyclohexyl-3-oxo-4-(2,3,5,6-tetrafluorophenoxy)butan-2-yl)amino)-4-methyl-1-oxopentan-2-yl)-N$^2$-(2-fluorophenyl)oxalamide;

N$^1$-(cyclopentylmethyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(2-fluoro-6-methylphenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(5-fluoro-2-methylphenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-2-(3-(2-fluorophenyl)ureido)-4-methyl-N—((S)-3-oxo-1-((S)-2-oxopyrrolidin-3-yl)-4-(2,3,5,6-tetrafluorophenoxy)butan-2-yl)pentanamide;

N$^1$-(2-fluorophenyl)-N$^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N$^1$-(2-isopropylphenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(4-bromo-3,5-difluorophenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(2-chlorophenyl)-N$^2$—((S)-3-(4,4-difluorocyclohexyl)-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide;

N$^1$-(3-fluoro-2-methylphenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(2-fluorophenyl)-N$^2$—((S)-3-methyl-1-oxo-1-(((S)-3-oxo-1-((S)-2-oxopyrrolidin-3-yl)-4-(2,3,5,6-tetrafluorophenoxy)butan-2-yl)amino)butan-2-yl)oxalamide;

(S)-1-(2-((2-fluorophenyl)amino)-2-oxoacetyl)-N—((S)-3-oxo-1-((S)-2-oxopyrrolidin-3-yl)-4-(2,3,5,6-tetrafluorophenoxy)butan-2-yl)pyrrolidine-2-carboxamide;

N$^1$-(2-chlorophenyl)-N$^2$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide;

N$^1$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N$^2$-(o-tolyl)oxalamide;

N$^1$-(3,3-difluorocyclohexyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(R)-1-(2-((2-fluorophenyl)amino)-2-oxoacetyl)-N—((S)-3-oxo-1-((S)-2-oxopyrrolidin-3-yl)-4-(2,3,5,6-tetrafluorophenoxy)butan-2-yl)piperidine-3-carboxamide;

N$^1$-(4-bromo-2-fluorophenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(2S)-4-methyl-N—((S)-3-oxo-1-((S)-2-oxopyrrolidin-3-yl)-4-(2,3,5,6-tetrafluorophenoxy)butan-2-yl)-2-(3,3,3-trifluoro-2-((2-fluorophenyl)amino)propanamido)pentanamide;

N$^1$-cyclopropyl-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$-(1-methylcyclopropyl)oxalamide;

N$^1$-(tert-butyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$-(tetrahydro-2H-pyran-4-yl)oxalamide;

N$^1$-cyclopentyl-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$-((S)-tetrahydro-2H-pyran-3-yl)oxalamide;

(S)-2-(2-(4-acetylpiperazin-1-yl)-2-oxoacetamido)-4-methyl-N—((S)-3-oxo-1-((S)-2-oxopyrrolidin-3-yl)-4-(2,3,5,6-tetrafluorophenoxy)butan-2-yl)pentanamide;

N$^1$-methyl-N$^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$-(o-tolyl)oxalamide;

N$^1$—((S)-1-oxo-1-(((S)-3-oxo-1-((S)-2-oxopyrrolidin-3-yl)-4-(2,3,5,6-tetrafluorophenoxy)butan-2-yl)amino)-3-phenylpropan-2-yl)-N$^2$-(o-tolyl)oxalamide;

N$^1$-methyl-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^1$-(o-tolyl)oxalamide;

N$^1$—((S)-4-cyclohexyl-1-oxo-1-(((S)-3-oxo-1-((S)-2-oxopyrrolidin-3-yl)-4-(2,3,5,6-tetrafluorophenoxy)butan-2-yl)amino)butan-2-yl)-N$^2$-(2-fluorophenyl)oxalamide;

N$^1$—((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N$^2$-(2-fluorophenyl)oxalamide;

N—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-5-(2-fluorophenyl)isoxazole-3-carboxamide;

N$^1$-(2-benzylphenyl)-N$^2$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide;

N$^1$-(2-methoxyphenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$-(2-(trifluoromethoxy)phenyl)oxalamide;

5-methyl-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)isoxazole-3-carboxamide;

5-methyl-N—((S)-3-methyl-1-(((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)amino)-1-oxobutan-2-yl)isoxazole-3-carboxamide;

N$^1$—((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N$^2$-(o-tolyl)oxalamide;

N$^1$-(2-(tert-butyl)phenyl)-N$^2$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide;

N—((S)-3,3-dimethyl-1-(((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)amino)-1-oxobutan-2-yl)-5-methylisoxazole-3-carboxamide;

N$^1$—((S)-3,3-dimethyl-1-oxo-1-(((S)-3-oxo-1-((S)-2-oxopyrrolidin-3-yl)-4-(2,3,5,6-tetrafluorophenoxy)butan-2-yl)amino)butan-2-yl)-N$^2$-(2-fluorophenyl)oxalamide;

N$^1$-(3-methoxyphenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(4-methoxyphenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-N$^2$-phenyloxalamide;

N$^1$—((S)-1-(((S)-6-(dimethylamino)-2,6-dioxo-1-(2,3,5,6-tetrafluorophenoxy)hexan-3-yl)amino)-4-methyl-1-oxopentan-2-yl)-N$^2$-(2-fluorophenyl)oxalamide;

N$^1$-cyclobutyl-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-3-((S)-2-(2-((2-fluorophenyl)amino)-2-oxoacetamido)-4-methylpentanamido)-2-oxo-4-((S)-2-oxopyrrolidin-3-yl)butyl diphenylphosphinate;

(R)-tetrahydrofuran-3-yl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

(S)-tetrahydrofuran-3-yl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

3-(3-chlorophenyl)propyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

N$^1$-(2-fluorophenyl)-N$^2$—((S)-4-methyl-1-oxo-1-(((S)-3-oxo-1-((S)-2-oxopiperidin-3-yl)-4-(2,3,5,6-tetrafluorophenoxy)butan-2-yl)amino)pentan-2-yl)oxalamide;

N$^1$—((S)-4,4-dimethyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$-(2-fluorophenyl)oxalamide;

N$^1$-(2-fluorophenyl)-N$^2$—((S)-4-methyl-1-oxo-1-(((S)-3-oxo-1-((S)-2-oxopyrrolidin-3-yl)-4-(2,4,6-trifluorophenoxy)butan-2-yl)amino)pentan-2-yl)oxalamide;

N$^1$-(2-fluorophenyl)-N$^2$—((S)-4-methyl-1-oxo-1-(((S)-3-oxo-1-((S)-2-oxopyrrolidin-3-yl)-4-(2,3,6-trifluorophenoxy)butan-2-yl)amino)pentan-2-yl)oxalamide;

N$^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$-((R)-tetrahydro-2H-pyran-3-yl)oxalamide;

N$^1$-(2-chlorophenyl)-N$^2$-(1-oxo-1-(((S)-3-oxo-1-((S)-2-oxopyrrolidin-3-yl)-4-(2,3,5,6-tetrafluorophenoxy)butan-2-yl)amino)-3-(tetrahydro-2H-pyran-4-yl)propan-2-yl)oxalamide;

N$^1$—((S)-1-(((S)-1-(1H-imidazol-5-yl)-3-oxo-4-(2,3,5,6-tetrafluorophenoxy)butan-2-yl)amino)-4-methyl-1-oxopentan-2-yl)-N$^2$-(2-fluorophenyl)oxalamide;

N$^1$—((S)-1-(((R)-1-(1H-imidazol-5-yl)-3-oxo-4-(2,3,5,6-tetrafluorophenoxy)butan-2-yl)amino)-4-methyl-1-oxopentan-2-yl)-N$^2$-(2-fluorophenyl)oxalamide;

cyclopentylmethyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

3-chlorophenethyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

(E)-3-(3-chlorophenyl)allyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

N$^1$-(1-acetylpiperidin-4-yl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(2-fluorophenyl)-N$^2$—((S)-4-methyl-1-oxo-1-(((S)-3-oxo-1-((S)-2-oxopyrrolidin-3-yl)-4-((5-(trifluoromethyl)isoxazol-3-yl)oxy)butan-2-yl)amino)pentan-2-yl)oxalamide;

N$^1$—((S)-1-(((S)-7-amino-2-oxo-1-(2,3,5,6-tetrafluorophenoxy)heptan-3-yl)amino)-4-methyl-1-oxopentan-2-yl)-N$^2$-(2-fluorophenyl)oxalamide;

N$^1$-(2-(methoxymethyl)phenyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-2-(2-(3-chlorophenyl)acetamido)-4-methyl-N—((S)-3-oxo-1-((S)-2-oxopyrrolidin-3-yl)-4-(2,3,5,6-tetrafluorophenoxy)butan-2-yl)pentanamide;

N$^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$—((S)-1,2,3,4-tetrahydronaphthalen-1-yl)oxalamide;

(S)-2-((R)-2-(3-chlorophenyl)-2-hydroxyacetamido)-4-methyl-N—((S)-3-oxo-1-((S)-2-oxopyrrolidin-3-yl)-4-(2,3,5,6-tetrafluorophenoxy)butan-2-yl)pentanamide;

N$^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N$^2$—((R)-1,2,3,4-tetrahydronaphthalen-1-yl)oxalamide;

N$^1$—((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl)propan-2-yl)-N$^2$-(o-tolyl)oxalamide;

(S)-2-(2-(3,4-dihydroquinolin-1(2H)-yl)-2-oxoacetamido)-4-methyl-N—((S)-3-oxo-1-((S)-2-oxopyrrolidin-3-yl)-4-(2,3,5,6-tetrafluorophenoxy)butan-2-yl)pentanamide;

(3R,3aS,6aR)-hexahydrofuro[2,3-b]furan-3-yl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

N$^1$-(4,4-difluorocyclohexyl)-N$^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N$^1$-(2,6-dimethylphenyl)-N$^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

2,2-difluoro-N—((S)-4-methyl-1-oxo-1-(((S)-3-oxo-1-((S)-2-oxopyrrolidin-3-yl)-4-(trifluoromethoxy)butan-2-yl)amino)pentan-2-yl)benzo[d][1,3]dioxole-5-carboxamide;

(S)-2-(2-(5-acetyl-2-methoxyphenyl)acetamido)-4-methyl-N—((S)-3-oxo-1-((S)-2-oxopyrrolidin-3-yl)-4-(2,3,5,6-tetrafluorophenoxy)butan-2-yl)pentanamide;

N$^1$—((S)-1-oxo-1-(((S)-3-oxo-1-((S)-2-oxopyrrolidin-3-yl)-4-(trifluoromethoxy)butan-2-yl)amino)-3-(pyridin-2-yl)propan-2-yl)-N$^2$-(o-tolyl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-benzo[d]imidazole-2-carboxamide;

N—((S)-1-(((S)-4-((1,1,1,3,3,3-hexafluoropropan-2-yl)oxy)-3-oxo-1-((S)-2-oxopyrrolidin-3-yl)butan-2-yl)amino)-4-methyl-1-oxopentan-2-yl)-4-methoxy-1H-indole-2-carboxamide;

4-methoxy-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-indole-2-carboxamide;

$N^1$-(2,6-diisopropylphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(2-fluorophenyl)isoxazole-3-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-fluoro-1H-indole-2-carboxamide;

4-methoxy-N—((S)-4-methyl-1-oxo-1-(((S)-3-oxo-1-((S)-2-oxopyrrolidin-3-yl)-4-(2,2,2-trifluoroethoxy)butan-2-yl)amino)pentan-2-yl)-1H-indole-2-carboxamide;

$N^1$-cyclohexyl-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2,6-dimethoxyphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2-methoxy-6-methylphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2-fluoro-6-methoxyphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2,6-diethylphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)benzo[d][1,3]dioxole-5-carboxamide;

$N^1$-(2,2-difluorocyclohexyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2,6-diisopropoxyphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

5-(2-fluorophenyl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)isoxazole-3-carboxamide;

$N^1$-(tert-butyl)-$N^2$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2-(tert-butyl)phenyl)-$N^2$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-cyclopropyl-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2-fluorophenyl)-$N^2$—((S)-4-methyl-1-oxo-1-(((S)-3-oxo-1-((S)-2-oxopyrrolidin-3-yl)-4-((1,1,3,3-tetrafluoropropan-2-yl)oxy)butan-2-yl)amino)pentan-2-yl)oxalamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(3,3-difluorocyclobutyl)oxalamide;

$N^1$-(2-(methoxymethyl)phenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

4-methoxy-N—((S)-4-methyl-1-oxo-1-(((S)-3-oxo-1-((S)-2-oxopyrrolidin-3-yl)-4-((1,1,3,3-tetrafluoropropan-2-yl)oxy)butan-2-yl)amino)pentan-2-yl)-1H-indole-2-carboxamide;

$N^1$-(3,3-difluorocyclobutyl)-$N^2$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(tert-butyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(tert-butyl)-$N^2$-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)oxalamide;

$N^1$-(3,3-difluorocyclobutyl)-$N^2$—((S)-1-oxo-1-(((S)-3-oxo-1-((S)-2-oxopyrrolidin-3-yl)-4-(trifluoromethoxy)butan-2-yl)amino)-3-phenylpropan-2-yl)oxalamide;

5-(2-fluorophenyl)-N-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)isoxazole-3-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(4-fluorophenyl)-1,3,4-oxadiazole-2-carboxamide;

$N^1$-(2,6-dicyclopropylphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(1-(p-tolyl)cyclopropyl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-c]pyridine-2-carboxamide;

$N^1$-(3-methoxyphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(2,2,2-trifluoroethyl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-2-oxopiperidine-3-carboxamide;

$N^1$-(bicyclo[1.1.1]pentan-1-yl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-3-phenyl-1H-pyrazole-5-carboxamide;

$N^1$-(1-methoxy-2-methylpropan-2-yl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-b]pyridine-2-carboxamide;

(3S)-3-((S)-2-(4-methoxy-1H-indole-2-carboxamido)-4-methylpentanamido)-2-oxo-4-(2-oxopyrrolidin-3-yl)butyl diphenylphosphinate;

(2S)-2-(2-(3,4-dihydroquinolin-1(2H)-yl)-2-oxoacetamido)-4-methyl-N-((2S)-3-oxo-1-(2-oxopyrrolidin-3-yl)-4-(trifluoromethoxy)butan-2-yl)pentanamide;

$N^1$-(2-fluorophenyl)-$N^2$—((S)-3-methyl-1-(1-((S)-3-oxo-1-((S)-2-oxopyrrolidin-3-yl)-4-(2,3,5,6-tetrafluorophenoxy)butan-2-yl)-1H-1,2,3-triazol-4-yl)butyl)oxalamide;

N—((S)-1-(((S)-4-(difluoromethoxy)-3-oxo-1-((S)-2-oxopyrrolidin-3-yl)butan-2-yl)amino)-4-methyl-1-oxopentan-2-yl)-4-methoxy-1H-indole-2-carboxamide;

3-chlorobenzyl ((S)-4-methyl-1-oxo-1-(((S)-3-oxo-1-((S)-2-oxopyrrolidin-3-yl)-4-(trifluoromethoxy)butan-2-yl)amino)pentan-2-yl)carbamate;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[3,2-c]pyridine-2-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)benzo[d]oxazole-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)imidazo[1,2-a]pyridine-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)imidazo[1,2-b]pyridazine-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)indoline-2-carboxamide;

$N^1$-(3,3-difluorocyclobutyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(o-tolyl)oxalamide;

(S)-2-((R)-2-hydroxy-3-phenylpropanamido)-4-methyl-N—((S)-3-oxo-1-((S)-2-oxopyrrolidin-3-yl)-4-(trifluoromethoxy)butan-2-yl)pentanamide;

N—((S)-6-amino-1-(((S)-4-methyl-1-oxo-1-(((S)-3-oxo-1-((S)-2-oxopyrrolidin-3-yl)-4-(trifluoromethoxy)butan-2-yl)amino)pentan-2-yl)amino)-1-oxohexan-2-yl)-2-fluorobenzamide;

5-(3-fluorophenyl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-imidazole-2-carboxamide;

5-(2-methoxyphenyl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-imidazole-2-carboxamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(1,1,1-trifluoro-2-methylpropan-2-yl)oxalamide;

$N^1$—((S)-3-cyclohexyl-1-oxo-1-(((S)-3-oxo-1-((S)-2-oxopyrrolidin-3-yl)-4-(trifluoromethoxy)butan-2-yl)amino)propan-2-yl)-$N^2$-(1,1,1-trifluoro-2-methylpropan-2-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-5-oxotetrahydrofuran-2-carboxamide;

2-methyl-N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;

$N^1$—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-$N^2$-(1-methylcyclopropyl)oxalamide $N^1$-(1-(2-fluorophenyl)cyclopropyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(1-methylcyclopropyl)oxalamide;

$N^1$-(2-fluorophenyl)-$N^2$-((2S)-1-oxo-1-(((S)-3-oxo-1-((S)-2-oxopyrrolidin-3-yl)-4-(trifluoromethoxy)butan-2-yl)amino)-3-(2-oxopyrrolidin-3-yl)propan-2-yl)oxalamide;

$N^1$-(2-fluorophenyl)-$N^2$—((S)-4-methyl-1-oxo-1-(((S)-3-oxo-1-((S)-2-oxopiperidin-3-yl)-4-(trifluoromethoxy)butan-2-yl)amino)pentan-2-yl)oxalamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(3,3-difluoro-1-methylcyclobutyl)oxalamide;

$N^1$-cyclobutyl-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(4-methyltetrahydro-2H-pyran-4-yl)oxalamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-phenyl-1H-imidazole-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-5-phenyl-1H-imidazole-2-carboxamide;

(R)—N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;

$N^1$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-$N^2$-(3-fluorobicyclo[1.1.1]pentan-1-yl)oxalamide;

$N^1$-((2S)-3-(2,2-difluorocyclopentyl)-1-oxo-1-(((S)-3-oxo-1-((S)-2-oxopyrrolidin-3-yl)-4-(trifluoromethoxy)butan-2-yl)amino)propan-2-yl)-$N^2$-(2-fluorophenyl)oxalamide;

$N^1$-(2-fluorophenyl)-$N^2$—((S)-1-(((S)-6-guanidino-2-oxo-1-(2,3,5,6-tetrafluorophenoxy)hexan-3-yl)amino)-4-methyl-1-oxopentan-2-yl)oxalamide;

4-methoxy-N—((S)-4-methyl-1-oxo-1-(((S)-3-oxo-1-((S)-2-oxopiperidin-3-yl)-4-(trifluoromethoxy)butan-2-yl)amino)pentan-2-yl)-1H-indole-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-3-carboxamide;

$N^1$-(1-(hydroxymethyl)cyclopropyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(piperidin-4-yl)oxalamide;

4-methoxy-N—((S)-1-oxo-1-(((S)-3-oxo-1-((S)-2-oxopyrrolidin-3-yl)-4-(trifluoromethoxy)butan-2-yl)amino)-5-phenylpentan-2-yl)-1H-indole-2-carboxamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(1,1-dioxidothietan-3-yl)oxalamide;

(S)-2-((R)-2-((2-fluorophenyl)amino)-3-methoxypropanamido)-4-methyl-N—((S)-3-oxo-1-((S)-2-oxopyrrolidin-3-yl)-4-(trifluoromethoxy)butan-2-yl)pentanamide;

(S)-2-((S)-2-((2-fluorophenyl)amino)-3-methoxypropanamido)-4-methyl-N—((S)-3-oxo-1-((S)-2-oxopyrrolidin-3-yl)-4-(trifluoromethoxy)butan-2-yl)pentanamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(1-(trifluoromethyl)cyclopropyl)oxalamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(3-(methoxymethyl)oxetan-3-yl)oxalamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(2-oxaspiro[3.3]heptan-6-yl)oxalamide;

N¹-(6,6-difluorospiro[3.3]heptan-2-yl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-N²-(3-methoxyphenyl)oxalamide;

N¹-(2-fluorophenyl)-N²—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)oxalamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(oxetan-3-yl)oxalamide;

N¹—((S)-4-methyl-1-oxo-1-(((S)-3-oxo-1-((S)-2-oxopiperidin-3-yl)-4-(trifluoromethoxy)butan-2-yl)amino)pentan-2-yl)-N²-(1-methylcyclopropyl)oxalamide;

N¹-(1,1-difluoro-2-methylpropan-2-yl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—(S)-4-methyl-1-oxo-1-(((S)-3-oxo-1-((S)-2-oxopyrrolidin-3-yl)-4-(trifluoromethoxy)butan-2-yl)amino)pentan-2-yl)-1,4-dioxane-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[3,2-b]pyridine-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-b]pyridine-3-carboxamide;

N¹—((S)-3-(4-fluorophenyl)-1-oxo-1-(((S)-3-oxo-1-((S)-2-oxopyrrolidin-3-yl)-4-(trifluoromethoxy)butan-2-yl)amino)propan-2-yl)-N²-(1-methylcyclopropyl)oxalamide;

N¹-(4-fluorobicyclo[2.2.2]octan-1-yl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(3-methylpyrrolidin-3-yl)oxalamide;

5-(2-fluoropropan-2-yl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)isoxazole-3-carboxamide;

N¹-(1-(fluoromethyl)cyclopropyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

7-methoxy-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-2,3-dihydrobenzofuran-2-carboxamide;

(1S,3aR,6aS)-2-(2-((2-fluorophenyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

N¹-(2-fluorophenyl)-N²-(4-(((S)-3-oxo-1-((S)-2-oxopyrrolidin-3-yl)-4-(trifluoromethoxy)butan-2-yl)carbamoyl)tetrahydro-2H-pyran-4-yl)oxalamide;

(2S,4R)-1-(2-((2-fluorophenyl)amino)-2-oxoacetyl)-4-methoxy-N—((S)-3-oxo-1-((S)-2-oxopyrrolidin-3-yl)-4-(trifluoromethoxy)butan-2-yl)pyrrolidine-2-carboxamide;

5-fluoro-N-((1R,2S)-1-(((S)-3-oxo-1-((S)-2-oxopyrrolidin-3-yl)-4-(trifluoromethoxy)butan-2-yl)carbamoyl)-2-vinylcyclopropyl)-1H-indole-2-carboxamide;

(1S,3aR,6aS)-2-(2-(tert-butylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

N-((1R,2R)-2-ethyl-1-(((S)-3-oxo-1-((S)-2-oxopyrrolidin-3-yl)-4-(trifluoromethoxy)butan-2-yl)carbamoyl)cyclopropyl)-5-fluoro-1H-indole-2-carboxamide;

N¹-(1-(methoxymethyl)cyclopropyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[3,2-b]pyridine-3-carboxamide;

(1R,2S,5S)-3-((S)-3,3-dimethyl-2-(2,2,2-trifluoroacetamido)butanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,3S,5R)-2-(2-((2-fluorophenyl)amino)-2-oxoacetyl)-N—((S)-3-oxo-1-((S)-2-oxopyrrolidin-3-yl)-4-(trifluoromethoxy)butan-2-yl)-2-azabicyclo[3.1.0]hexane-3-carboxamide;

(1S,3aR,6aS)-2-((S)-3,3-dimethyl-2-(2,2,2-trifluoroacetamido)butanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

N¹-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)-N²-(2,2,2-trifluoroethyl)oxalamide;

(2S,4R)-1-(2-((2-fluorophenyl)amino)-2-oxoacetyl)-N—((S)-3-oxo-1-((S)-2-oxopyrrolidin-3-yl)-4-(trifluoromethoxy)butan-2-yl)-4-(trifluoromethyl)pyrrolidine-2-carboxamide;

(3aS,4S,6aR)-5-((S)-3,3-dimethyl-2-(2,2,2-trifluoroacetamido)butanoyl)-N—((S)-3-oxo-1-((S)-2-oxopyrrolidin-3-yl)-4-(trifluoromethoxy)butan-2-yl)hexahydro-1H-furo[3,4-c]pyrrole-4-carboxamide;

(1S,3aR,6aS)-N—((S)-3-oxo-1-((S)-2-oxopyrrolidin-3-yl)-4-(trifluoromethoxy)butan-2-yl)-2-(1-(2,2,2-trifluoroacetamido)cyclopropane-1-carbonyl)octahydrocyclopenta[c]pyrrole-1-carboxamide;

(1S,3aR,6aS)-N—((S)-3-oxo-1-((S)-2-oxopyrrolidin-3-yl)-4-(trifluoromethoxy)butan-2-yl)-2-(1-(2,2,2-trifluoroacetamido)cyclobutane-1-carbonyl)octahydrocyclopenta[c]pyrrole-1-carboxamide;

(1S,3aR,6aS)-2-((1S,2R)-2-methyl-1-(2,2,2-trifluoroacetamido)cyclopropane-1-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-((S)-3,3-dimethyl-2-(2,2,2-trifluoroacetamido)butanoyl)-N—((S)-3-oxo-1-((S)-2-oxopyrrolidin-3-yl)-4-(trifluoromethoxy)butan-2-yl)-3-azaspiro[bicyclo[3.1.0]hexane-6,1'-cyclopropane]-2-carboxamide;

(1S,3aR,7aS)-N—((S)-3-oxo-1-((S)-2-oxopyrrolidin-3-yl)-4-(trifluoromethoxy)butan-2-yl)-2-(2-(trifluoromethyl)thiazole-4-carbonyl)octahydro-1H-isoindole-1-carboxamide;

(1S,3aR,7aS)-N—((S)-3-oxo-1-((S)-2-oxopyrrolidin-3-yl)-4-(trifluoromethoxy)butan-2-yl)-2-(5-(trifluoromethyl)isoxazole-3-carbonyl)octahydro-1H-isoindole-1-carboxamide;

(2S,3aS,7aS)-N—((S)-3-oxo-1-((S)-2-oxopyrrolidin-3-yl)-4-(trifluoromethoxy)butan-2-yl)-1-(2-oxo-2-((1,1,1-trifluoro-2-methylpropan-2-yl)amino)acetyl)octahydro-1H-indole-2-carboxamide;

(1R,2S,5S)-3-((N-(2-fluorophenyl)sulfamoyl)carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(N-(2-fluorophenyl)sulfamoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,2R,5S)-6,6-dimethyl-N—((S)-3-oxo-1-((S)-2-oxopyrrolidin-3-yl)-4-(trifluoromethoxy)butan-2-yl)-3-(N-(2,2,2-trifluoroacetyl)-O-(trifluoromethyl)-L-threonyl)bicyclo[3.1.0]hexane-2-carboxamide;

(1R,2S,5S)-3-(O-(difluoromethyl)-N-(2,2,2-trifluoroacetyl)-L-seryl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,2R,5S)-3-(O-(difluoromethyl)-N-(2,2,2-trifluoroacetyl)-L-threonyl)-6,6-dimethyl-N—((S)-3-oxo-1-((S)-2-oxopyrrolidin-3-yl)-4-(trifluoromethoxy)butan-2-yl)bicyclo[3.1.0]hexane-2-carboxamide;

(1R,2S,5S)-3-((S)-3-(3,3-difluoroazetidin-1-yl)-2-(2,2,2-trifluoroacetamido)propanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(3-(2,2,2-trifluoroacetamido)cyclobutane-1-carbonyl)-3-azabicyclo[3.1.0]hexane-2-carboxamide;

(1R,2S,5S)-3-((S)-3,3-dimethyl-2-((R)-tetrahydrofuran-2-carboxamido)butanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-6,6-dimethyl-N—((S)-3-oxo-1-((S)-2-oxopyrrolidin-3-yl)-4-(trifluoromethoxy)butan-2-yl)-3-((R)-tetrahydrofuran-2-carbonyl)-3-azabicyclo[3.1.0]hexane-2-carboxamide;

(1R,2S,5S)-6,6-dimethyl-N-((2S)-3-oxo-1-(2-oxopyrrolidin-3-yl)-4-(trifluoromethoxy)butan-2-yl)-3-((R)-4,4,4-trifluoro-2-hydroxybutanoyl)-3-azabicyclo[3.1.0]hexane-2-carboxamide;

N—((S)-1-oxo-1-(((S)-3-oxo-1-((S)-2-oxopyrrolidin-3-yl)-4-(trifluoromethoxy)butan-2-yl)amino)butan-2-yl)-5-oxaspiro[2.4]heptane-6-carboxamide;

(1S,3aR,6aS)-N—((S)-3-oxo-1-((S)-2-oxopyrrolidin-3-yl)-4-(trifluoromethoxy)butan-2-yl)-2-(5-oxaspiro[2.4]heptane-6-carbonyl)octahydrocyclopenta[c]pyrrole-1-carboxamide;

(2R)—N-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)tetrahydrofuran-2-carboxamide;

(1S,3aR,6aS)-N—((S)-3-oxo-1-((S)-2-oxopyrrolidin-3-yl)-4-(trifluoromethoxy)butan-2-yl)-2-((R)-tetrahydrofuran-2-carbonyl)octahydrocyclopenta[c]pyrrole-1-carboxamide;

(R)—N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)tetrahydrofuran-2-carboxamide;

(R)—N—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;

(S)—N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;

(1R,3S,5R)—N—((S)-3-oxo-1-((S)-2-oxopyrrolidin-3-yl)-4-(trifluoromethoxy)butan-2-yl)-2-((R)-tetrahydrofuran-2-carbonyl)-2-azabicyclo[3.1.0]hexane-3-carboxamide;

(1R,3S,5R)—N-(3-oxo-1-((S)-2-oxopyrrolidin-3-yl)-4-(trifluoromethoxy)butan-2-yl)-2-((S)-tetrahydrofuran-2-carbonyl)-2-azabicyclo[3.1.0]hexane-3-carboxamide;

(S)—N—((S)-3-oxo-1-((S)-2-oxopyrrolidin-3-yl)-4-(trifluoromethoxy)butan-2-yl)-5-((R)-tetrahydrofuran-2-carbonyl)-5-azaspiro[2.4]heptane-6-carboxamide;

(1R,2S,5S)-3-((R)-1,4-dioxane-2-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-((S)-1,4-dioxane-2-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-(7-oxabicyclo[2.2.1]heptane-1-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-7-oxabicyclo[2.2.1]heptane-1-carboxamide;

(1S,3aR,6aS)-2-(2-methyltetrahydrofuran-2-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(6S)-5-(2-methyltetrahydrofuran-2-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(4-methyl-2-oxabicyclo[2.1.1]hexane-1-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

4-methyl-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-2-oxabicyclo[2.1.1]hexane-1-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-4-(2,2,2-trifluoroacetamido)-2-oxabicyclo[2.1.1]hexane-1-carboxamide;

(1S,3aR,6aS)-N—((S)-3-oxo-1-((S)-2-oxopyrrolidin-3-yl)-4-(trifluoromethoxy)butan-2-yl)-2-(4-(trifluoromethyl)-2-oxabicyclo[2.1.1]hexane-1-carbonyl)octahydrocyclopenta[c]pyrrole-1-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-4-(trifluoromethyl)-2-oxabicyclo[2.1.1]hexane-1-carboxamide;

(S)—N—((S)-3-oxo-1-((S)-2-oxopyrrolidin-3-yl)-4-(trifluoromethoxy)butan-2-yl)-5-(4-(trifluoromethyl)-2-oxabicyclo[2.1.1]hexane-1-carbonyl)-5-azaspiro[2.4]heptane-6-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(4-(trifluoromethyl)-2-oxabicyclo[2.1.1]hexane-1-carbonyl)-3-azabicyclo[3.1.0]hexane-2-carboxamide;

4-(difluoromethyl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-2-oxabicyclo[2.1.1]hexane-1-carboxamide;

(S)-5-(4-(difluoromethyl)-2-oxabicyclo[2.1.1]hexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(4-(difluoromethyl)-2-oxabicyclo[2.1.1]hexane-1-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-(4-(difluoromethyl)-2-oxabicyclo[2.1.1]hexane-1-carbonyl)-6,6-dimethyl-N—((S)-3-oxo-1-((S)-

2-oxopyrrolidin-3-yl)-4-(trifluoromethoxy)butan-2-yl)-3-azabicyclo[3.1.0]hexane-2-carboxamide;
(1S,3aR,6aS)-2-(3,3-difluorotetrahydrofuran-2-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;
3,3-difluoro-N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;
(1R,3S,5R)—N-(3-oxo-1-((S)-2-oxopyrrolidin-3-yl)-4-(trifluoromethoxy)butan-2-yl)-2-((S)-tetrahydrofuran-2-carbonyl)-2-azabicyclo[3.1.0]hexane-3-carboxamide;
(R)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl tert-butylcarbamate;
(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl tert-butylcarbamate;
(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl isopropylcarbamate;
(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl cyclohexylcarbamate;
(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl phenylcarbamate;
(R)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl ethylcarbamate;
(S)-5-((R)-2-(difluoromethoxy)-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(S)-5-((R)-2-(2-hydroxy-2-methylpropoxy)-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1R,2S,5S)-6,6-dimethyl-N—((S)-3-oxo-1-((S)-2-oxopyrrolidin-3-yl)-4-(trifluoromethoxy)butan-2-yl)-3-((R)-2-(trifluoromethoxy)butanoyl)-3-azabicyclo[3.1.0]hexane-2-carboxamide;
(1R,2S,5S)-3-((R)-2-methoxybutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;
(S)-2-((R)-2-methoxybutanamido)-4-methyl-N—((S)-3-oxo-1-((S)-2-oxopyrrolidin-3-yl)-4-(trifluoromethoxy)butan-2-yl)pentanamide;
(6S)-5-(2-methoxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(S)-5-((S)-2-methoxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(S)-5-(2,2-dimethoxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;
(S)-2-((R)-2-hydroxy-3,3-dimethylbutanamido)-4-methyl-N—((S)-3-oxo-1-((S)-2-oxopyrrolidin-3-yl)-4-(trifluoromethoxy)butan-2-yl)pentanamide;
(S)-5-((R)-2-hydroxy-3,3-dimethylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1R,2S,5S)-3-((R)-2-hydroxy-3,3-dimethylbutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;
(S)-5-((S)-2-hydroxy-3,3-dimethylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1R,2S,5S)-3-((S)-2-hydroxy-3,3-dimethylbutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;
(6S)-5-(2-hydroxy-4,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1R,2S,5S)-3-(2-hydroxy-4,4-dimethylpentanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;
(1S,3aR,6aS)-2-(2-hydroxy-4,4-dimethylpentanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;
(S)-5-((S)-2-hydroxy-4,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(S)-5-((S)-4-fluoro-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1R,2S,5S)-3-(2-hydroxy-2-methylpropanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;
(1S,3aR,6aS)-2-(2-hydroxy-2-methylpropanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;
(S)-2-(2-hydroxy-2-methylpropanamido)-4-methyl-N—((S)-3-oxo-1-((S)-2-oxopyrrolidin-3-yl)-4-(trifluoromethoxy)butan-2-yl)pentanamide;
(S)-5-(2-hydroxy-2-methylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(S)-2-((R)-2-hydroxy-3-methylbutanamido)-4-methyl-N—((S)-3-oxo-1-((S)-2-oxopyrrolidin-3-yl)-4-(trifluoromethoxy)butan-2-yl)pentanamide;
(S)-5-((R)-2-hydroxy-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1R,2S,5S)-3-((R)-2-hydroxy-3-methylbutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;
(S)-5-((S)-2-hydroxy-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1S,3aR,6aS)-2-((R)-2-hydroxy-3-methylbutanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;
(6S)-5-(2-hydroxy-2,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-4-methylpentanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((R)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-2-hydroxy-4-methylpentanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((S)-2-hydroxy-2-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-2-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxy-3,3-dimethylcyclobutane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((S)-2-hydroxy-2-methylbutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-((R)-2-hydroxybutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-2-((R)-2-hydroxybutanamido)-4-methyl-N—((S)-3-oxo-1-((S)-2-oxopyrrolidin-3-yl)-4-(trifluoromethoxy)butan-2-yl)pentanamide;

(1R,2S,5S)-3-((S)-2-hydroxybutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((R)-2-hydroxybutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(2R)-2-hydroxy-N-(3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)butanamide;

(2S,3aS,7aS)-1-((R)-2-hydroxybutanoyl)-N—((S)-3-oxo-1-((S)-2-oxopyrrolidin-3-yl)-4-(trifluoromethoxy)butan-2-yl)octahydro-1H-indole-2-carboxamide;

(2S,3aS,6aS)-1-((R)-2-hydroxybutanoyl)-N—((S)-3-oxo-1-((S)-2-oxopyrrolidin-3-yl)-4-(trifluoromethoxy)butan-2-yl)octahydrocyclopenta[b]pyrrole-2-carboxamide;

(R)-2-hydroxy-N-((R)-3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)butanamide;

(R)-2-hydroxy-N—((S)-3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)butanamide;

(1S,3aR,6aS)-2-((R)-2-hydroxybutanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-((R)-2-hydroxypentanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-((2R,3R)-2-hydroxy-3-methylpentanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((2R,3R)-2-hydroxy-3-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-methoxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-2-(2-methoxyphenyl)acetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(6S)-5-(2-hydroxy-2-(1-methyl-1H-imidazol-5-yl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-4-methyl-N—((S)-3-oxo-1-((S)-2-oxopyrrolidin-3-yl)-4-(trifluoromethoxy)butan-2-yl)-2-((S)-3,3,3-trifluoro-2-hydroxypropanamido)pentanamide;

(S)—N—((S)-3-oxo-1-((S)-2-oxopyrrolidin-3-yl)-4-(trifluoromethoxy)butan-2-yl)-5-((S)-3,3,3-trifluoro-2-hydroxypropanoyl)-5-azaspiro[2.4]heptane-6-carboxamide;

(1R,2S,5S)-6,6-dimethyl-N—((S)-3-oxo-1-((S)-2-oxopyrrolidin-3-yl)-4-(trifluoromethoxy)butan-2-yl)-3-((S)-3,3,3-trifluoro-2-hydroxypropanoyl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-5-((R)-3,3,3-trifluoro-2-hydroxypropanoyl)-5-azaspiro[2.4]heptane-6-carboxamide;

(6S)-5-(2-(1,1-dioxidotetrahydro-2H-thiopyran-4-yl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)—N—((S)-3-oxo-1-((S)-2-oxopyrrolidin-3-yl)-4-(trifluoromethoxy)butan-2-yl)-5-(5,5,5-trifluoro-2-hydroxy-4-(trifluoromethyl)pentanoyl)-5-azaspiro[2.4]heptane-6-carboxamide;

(6S)—N—((S)-3-oxo-1-((S)-2-oxopyrrolidin-3-yl)-4-(trifluoromethoxy)butan-2-yl)-5-(4,4,4-trifluoro-2-hydroxybutanoyl)-5-azaspiro[2.4]heptane-6-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(4,4,4-trifluoro-2-hydroxybutanoyl)-3-azabicyclo[3.1.0]hexane-2-carboxamide;

(S)-5-((R)-3-cyclopropyl-2-hydroxypropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-3-cyclopropyl-2-hydroxypropanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-((S)-3-cyclopropyl-2-hydroxypropanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(6S)—N—((S)-3-oxo-1-((S)-2-oxopyrrolidin-3-yl)-4-(trifluoromethoxy)butan-2-yl)-5-(5,5,5-trifluoro-2-hydroxypentanoyl)-5-azaspiro[2.4]heptane-6-carboxamide;

(S)-2-((S)-3-fluoro-2-hydroxypropanamido)-4-methyl-N—((S)-3-oxo-1-((S)-2-oxopyrrolidin-3-yl)-4-(trifluoromethoxy)butan-2-yl)pentanamide;

(S)-5-((S)-3-fluoro-2-hydroxypropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-3-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-hydroxy-2-(3,4,5-trifluorophenyl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-(3,4-difluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-(2-(3,4-difluorophenyl)-2-hydroxyacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(6S)-5-(2-(2,4-difluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-(4-fluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-2-(4-fluorophenyl)-2-hydroxyacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(6S)-5-(2-(3-fluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-hydroxy-2-(2-(trifluoromethyl)phenyl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-(2-fluorophenyl)-2-hydroxyacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-2-((R)-2-(2-fluorophenyl)-2-hydroxyacetamido)-4-methyl-N—((S)-3-oxo-1-((S)-2-oxopyrrolidin-3-yl)-4-(trifluoromethoxy)butan-2-yl)pentanamide;

(1S,3aR,6aS)-2-((R)-2-(2-fluorophenyl)-2-hydroxyacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((R)-2-(2-fluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((S)-2-(2-fluorophenyl)-2-hydroxyacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((R)-2-hydroxy-2-phenylacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-2-phenylacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-((R)-2-hydroxy-2-phenylacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((S)-2-hydroxy-2-phenylacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((S)-2-hydroxy-2-phenylacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-((S)-2-hydroxy-2-phenylacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(6S)-5-(2-hydroxy-2-(pyridin-2-yl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-hydroxy-2-(pyridin-2-yl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxycyclopropane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4,4-difluoro-1-hydroxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxycyclobutane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxycyclopentane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-2-hydroxypentanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)—N—((S)-3-oxo-1-((S)-2-oxopyrrolidin-3-yl)-4-(trifluoromethoxy)butan-2-yl)-5-((2R,4R)-5,5,5-trifluoro-2-hydroxy-4-methylpentanoyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((2R,4S)-5,5,5-trifluoro-2-hydroxy-4-methylpentanoyl)-5-azaspiro[2.4]heptane-6-carboxamide;

(S)-5-(4-methyl-2-oxopentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-3-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-3-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

methyl ((S)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl)carbamate;

(S)-4-methyl-N—((S)-3-oxo-1-((S)-2-oxopyrrolidin-3-yl)-4-(trifluoromethoxy)butan-2-yl)-2-(2-((1-(trifluoromethyl)cyclopropyl)amino)acetamido)pentanamide;

(S)-5-((methylcarbamoyl)-D-leucyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-2-acetamido-3,3-dimethylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((2-fluorobenzoyl)glycyl)-N—((S)-3-oxo-1-((S)-2-oxopyrrolidin-3-yl)-4-(trifluoromethoxy)butan-2-yl)-5-azaspiro[2.4]heptane-6-carboxamide;

tert-butyl ((R)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-1-oxobutan-2-yl)carbamate;

(1R,2S,5S)-3-((R)-2-aminobutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-(methylprolyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((S)-3,3-dimethyl-2-(2,2,2-trifluoroacetamido)butanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-(3-(4,4-difluoropiperidin-1-yl)-2-(2,2,2-trifluoroacetamido)propanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((S)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(2-(2-chlorophenyl)-2-hydroxyacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

cyclopropyl ((S)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-3,3-dimethyl-1-oxobutan-2-yl)carbamate;

(S)-5-(2-ethylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,3S,5R)-2-((R)-2-hydroxy-4-methylpentanoyl)-5-methyl-N—((S)-3-oxo-1-((S)-2-oxopyrrolidin-3-yl)-4-(trifluoromethoxy)butan-2-yl)-2-azabicyclo[3.1.0]hexane-3-carboxamide;

(S)-5-((R)-4,4-difluoro-2-hydroxybutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-4,4-difluoro-2-hydroxybutanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,3S,5R)-2-((R)-2-hydroxy-3-methylbutanoyl)-5-methyl-N—((S)-3-oxo-1-((S)-2-oxopyrrolidin-3-yl)-4-(trifluoromethoxy)butan-2-yl)-2-azabicyclo[3.1.0]hexane-3-carboxamide;

(S)-5-(4-(tert-butyl)benzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-4,4-dimethylpentanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-(2-(3-(tert-butyl)phenyl)-2-methylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-methyl-2-(3-(trifluoromethyl)phenyl)propanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(3-(trifluoromethyl)benzoyl)-5-azaspiro[2.4]heptane-6-carboxamide;

(S)-5-(3-(tert-butyl)benzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

5-(2-fluorophenyl)-N—((S)-1-oxo-1-(((S)-3-oxo-1-((S)-2-oxopyrrolidin-3-yl)-4-(trifluoromethoxy)butan-2-yl)amino)-3-phenylpropan-2-yl)isoxazole-3-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(phenylamino)-1,3,4-oxadiazole-2-carboxamide;

5-benzyl-N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)isoxazole-3-carboxamide;

(S)-4-methyl-2-((1-methyl-1H-indole)-5-sulfonamido)-N—((S)-3-oxo-1-((S)-2-oxopyrrolidin-3-yl)-4-(trifluoromethoxy)butan-2-yl)pentanamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-5-(pyridin-2-yl)isoxazole-3-carboxamide;

(S)-4-methyl-2-((2-oxo-1,2-dihydroquinolin-3-yl)amino)-N—((S)-3-oxo-1-((S)-2-oxopyrrolidin-3-yl)-4-(trifluoromethoxy)butan-2-yl)pentanamide;

7-methoxy-N—((S)-4-methyl-1-oxo-1-(((S)-3-oxo-1-((S)-2-oxopyrrolidin-3-yl)-4-(trifluoromethoxy)butan-2-yl)amino)pentan-2-yl)benzofuran-2-carboxamide;

(1S,3aR,6aS)-2-(2-(cyclohexylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(2-(trifluoromethyl)thiazole-4-carbonyl)-3-azabicyclo[3.1.0]hexane-2-carboxamide;

(1R,2S,5S)-6,6-dimethyl-3-(2-((1-methylcyclopropyl)amino)-2-oxoacetyl)-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(2-(cyclohexylamino)-2-oxoacetyl)-6,6-dimethyl-N—((S)-3-oxo-1-((S)-2-oxopiperidin-3-yl)-4-(trifluoromethoxy)butan-2-yl)-3-azabicyclo[3.1.0]hexane-2-carboxamide;

(1R,2S,5S)-3-(2-(tert-butylamino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-2-(2-oxo-2-(((1,1,1-trifluoro-2-methylpropan-2-yl)amino)acetyl)-1,2,3,4-tetrahydroisoquinoline-3-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(2-oxo-2-(o-tolylamino)acetyl)-3-azabicyclo[3.1.0]hexane-2-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(5-(trifluoromethyl)isoxazole-3-carbonyl)-3-azabicyclo[3.1.0]hexane-2-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(2-oxo-2-((1-(trifluoromethyl)cyclopropyl)amino)acetyl)-3-azabicyclo[3.1.0]hexane-2-carboxamide;

(1S,3aR,6aS)-N—((S)-3-oxo-1-((S)-2-oxopyrrolidin-3-yl)-4-(trifluoromethoxy)butan-2-yl)-2-(2-(trifluoromethyl)thiazole-4-carbonyl)octahydrocyclopenta[c]pyrrole-1-carboxamide;

(1R,2S,5S)-3-(2-((3,3-difluorocyclobutyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(5-(2-fluoropropan-2-yl)isoxazole-3-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-(2-((2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

$N^1$-(2-fluorophenyl)-$N^2$-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)oxalamide;

N-((2S)-4-methyl-1-oxo-1-(((2S)-3-oxo-1-(2-oxopyrrolidin-3-yl)-4-(trifluoromethoxy)butan-2-yl)amino)pentan-2-yl)-2-(trifluoromethyl)thiazole-4-carboxamide;

(6S)-1,1-difluoro-5-(2-((2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-N—((S)-3-oxo-1-((S)-2-oxopyrrolidin-3-yl)-4-(trifluoromethoxy)butan-2-yl)-2-(5-(trifluoromethyl)isoxazole-3-carbonyl)octahydrocyclopenta[c]pyrrole-1-carboxamide;

(1R,2S,5S)-3-(2-((2,2-difluoropropyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(3S,4S)-4-methyl-N—((S)-3-oxo-1-((S)-2-oxopyrrolidin-3-yl)-4-(trifluoromethoxy)butan-2-yl)-1-(2-oxo-2-((1,1,1-trifluoro-2-methylpropan-2-yl)amino)acetyl)pyrrolidine-3-carboxamide;

(1R,2S,5S)-3-(2-((3-fluorobicyclo[1.1.1]pentan-1-yl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(3S,4aS,8aS)-N—((S)-3-oxo-1-((S)-2-oxopyrrolidin-3-yl)-4-(trifluoromethoxy)butan-2-yl)-2-(2-oxo-2-((1,1,1-trifluoro-2-methylpropan-2-yl)amino)acetyl)decahydroisoquinoline-3-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(3-(trifluoromethyl)isoxazole-5-carbonyl)-3-azabicyclo[3.1.0]hexane-2-carboxamide;

(1R,2S,5S)-3-(2-((2-fluorophenyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(2-fluoropropan-2-yl)isoxazole-3-carboxamide;

(1S,3aR,6aS)-2-(5-(2-fluoropropan-2-yl)isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-6,6-dimethyl-N—((R)-3-oxo-1-((S)-2-oxopyrrolidin-3-yl)-4-(trifluoromethoxy)butan-2-yl)-3-(3-(trifluoromethyl)isoxazole-5-carbonyl)-3-azabicyclo[3.1.0]hexane-2-carboxamide;

(1S,2S,5R)-3-(2-(tert-butylamino)-2-oxoacetyl)-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-(2-((1-methylcyclopropyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-((1-methylcyclopropyl)amino)-2-oxoacetyl)-N—((R)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-(tert-butylamino)-2-oxoacetyl)-N—((R)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-(cyclopropylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(2S,3aS,7aS)-1-(2-(tert-butylamino)-2-oxoacetyl)-N—((S)-3-oxo-1-((S)-2-oxopyrrolidin-3-yl)-4-(trifluoromethoxy)butan-2-yl)octahydro-1H-indole-2-carboxamide;

5-(2-fluoropropan-2-yl)-N-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)isoxazole-3-carboxamide;

(1S,3aR,6aS)-2-(5-(difluoromethyl)isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,2S)-3-(5-(2-fluoropropan-2-yl)isoxazole-3-carbonyl)-N—((S)-3-oxo-1-((S)-2-oxopyrrolidin-3-yl)-4-(trifluoromethoxy)butan-2-yl)-3-azabicyclo[3.1.0]hex-4-ene-2-carboxamide;

(S)-5-(2-(tert-butylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

$N^1$-(tert-butyl)-$N^2$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)oxalamide;

$N^1$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-$N^2$-(o-tolyl)oxalamide;

$N^1$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-$N^2$-(2,2,2-trifluoroethyl)oxalamide;

$N^1$-(3-fluorobicyclo[1.1.1]pentan-1-yl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(o-tolyl)oxalamide;

6-(2-(tert-butylamino)-2-oxoacetyl)-2,2-difluoro-N—((S)-3-oxo-1-((S)-2-oxopyrrolidin-3-yl)-4-(trifluoromethoxy)butan-2-yl)-6-azaspiro[3.4]octane-7-carboxamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(3-fluorobicyclo[1.1.1]pentan-1-yl)oxalamide;

$N^1$-(3-fluorobicyclo[1.1.1]pentan-1-yl)-$N^2$-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)oxalamide;

6-(2-(tert-butylamino)-2-oxoacetyl)-N—((S)-3-oxo-1-((S)-2-oxopyrrolidin-3-yl)-4-(trifluoromethoxy)butan-2-yl)-6-azaspiro[3.4]octane-7-carboxamide;

N¹—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N²-(1-(trifluoromethyl)cyclopropyl)oxalamide;

(1S,3aR,6aS)-N—((S)-3-oxo-1-((S)-2-oxopyrrolidin-3-yl)-4-(trifluoromethoxy)butan-2-yl)-2-(2-oxo-2-(o-tolylamino)acetyl)octahydrocyclopenta[c]pyrrole-1-carboxamide;

(R)-6-(2-(tert-butylamino)-2-oxoacetyl)-N—((S)-3-oxo-1-((S)-2-oxopyrrolidin-3-yl)-4-(trifluoromethoxy)butan-2-yl)-2-oxa-6-azaspiro[3.4]octane-7-carboxamide;

(S)-6-(2-(tert-butylamino)-2-oxoacetyl)-N—((S)-3-oxo-1-((S)-2-oxopyrrolidin-3-yl)-4-(trifluoromethoxy)butan-2-yl)-2-oxa-6-azaspiro[3.4]octane-7-carboxamide;

(1R,2S,5S)-3-(2-((2,2-difluoroethyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

N¹—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N²-(2,2,2-trifluoroethyl)oxalamide;

(3R,6S)-5-(2-(tert-butylamino)-2-oxoacetyl)-1,1-difluoro-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(2-((2,2-difluoroethyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-(tert-butylamino)-2-oxoacetyl)-5,5-difluoro-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,3S,5R)-2-2-(tert-butylamino)-2-oxoacetyl)-N—((S)-3-oxo-1-((S)-2-oxopyrrolidin-3-yl)-4-(trifluoromethoxy)butan-2-yl)-2-azabicyclo[3.1.0]hexane-3-carboxamide;

2-(2-(tert-butylamino)-2-oxoacetyl)-N—((S)-3-oxo-1-((S)-2-oxopyrrolidin-3-yl)-4-(trifluoromethoxy)butan-2-yl)-8-oxa-2-azaspiro[4.5]decane-3-carboxamide;

(1S,3aR,6aS)-2-(2-((3,3-difluorocyclobutyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

N¹-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)-N²-(o-tolyl)oxalamide;

(1S,3aR,6aS)-2-(2-((3-fluorobicyclo[1.1.1]pentan-1-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-N—((S)-3-oxo-1-((S)-2-oxopyrrolidin-3-yl)-4-(trifluoromethoxy)butan-2-yl)-2-(2-oxo-2-((1,1,1-trifluoro-2-methylpropan-2-yl)amino)acetyl)octahydrocyclopenta[c]pyrrole-1-carboxamide;

(S)—N—((S)-3-oxo-1-((S)-2-oxopyrrolidin-3-yl)-4-(trifluoromethoxy)butan-2-yl)-5-(2-oxo-2-(o-tolylamino)acetyl)-5-azaspiro[2.4]heptane-6-carboxamide;

N¹—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-N²-(2-fluorophenyl)oxalamide;

N¹-(tert-butyl)-N²—((S)-1-cyclopentyl-2-oxo-2-(((S)-3-oxo-1-((S)-2-oxopyrrolidin-3-yl)-4-(trifluoromethoxy)butan-2-yl)amino)ethyl)-N²-methyloxalamide;

2-(2-((2-fluorophenyl)amino)-2-oxoacetyl)-N—((S)-3-oxo-1-((S)-2-oxopyrrolidin-3-yl)-4-(trifluoromethoxy)butan-2-yl)-8-oxa-2-azaspiro[4.5]decane-3-carboxamide;

2-(2-(tert-butylamino)-2-oxoacetyl)-N—((S)-3-oxo-1-((S)-2-oxopyrrolidin-3-yl)-4-(trifluoromethoxy)butan-2-yl)-2-azaspiro[4.5]decane-3-carboxamide;

5-(difluoromethyl)-N—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)isoxazole-3-carboxamide;

(1S,3aR,6aS)-2-(1-methyl-1H-pyrazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-((1-methyl-1H-pyrazol-3-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-6,6-dimethyl-3-(2-((1-methyl-1H-pyrazol-3-yl)amino)-2-oxoacetyl)-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(2-((3,3-difluorocyclobutyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(2S,4R)-1-(2-(tert-butylamino)-2-oxoacetyl)-4-methoxy-N—((S)-3-oxo-1-((S)-2-oxopyrrolidin-3-yl)-4-(trifluoromethoxy)butan-2-yl)pyrrolidine-2-carboxamide;

N—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-2-(trifluoromethyl)thiazole-5-carboxamide;

(1S,3S,5S)-2-(2-((2-fluorophenyl)amino)-2-oxoacetyl)-N—((S)-3-oxo-1-((S)-2-oxopyrrolidin-3-yl)-4-(trifluoromethoxy)butan-2-yl)-2-azabicyclo[3.1.0]hexane-3-carboxamide;

(S)-4,4-dimethyl-1-(2-((1-methylcyclopropyl)amino)-2-oxoacetyl)-N—((S)-3-oxo-1-((S)-2-oxopyrrolidin-3-yl)-4-(trifluoromethoxy)butan-2-yl)pyrrolidine-2-carboxamide;

(S)-4-(2-((1-methylcyclopropyl)amino)-2-oxoacetyl)-N—((S)-3-oxo-1-((S)-2-oxopyrrolidin-3-yl)-4-(trifluoromethoxy)butan-2-yl)-4-azaspiro[2.4]heptane-5-carboxamide;

(1R,3S,4S)—N—((S)-3-oxo-1-((S)-2-oxopyrrolidin-3-yl)-4-(trifluoromethoxy)butan-2-yl)-2-(2-oxo-2-((2,2,2-trifluoroethyl)amino)acetyl)-2-azabicyclo[2.2.1]heptane-3-carboxamide;

(S)-1-(2-((3,3-difluorocyclobutyl)amino)-2-oxoacetyl)-4,4-dimethyl-N—((S)-3-oxo-1-((S)-2-oxopyrrolidin-3-yl)-4-(trifluoromethoxy)butan-2-yl)pyrrolidine-2-carboxamide;

(1S,3aR,6aS)-2-(2-morpholino-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(5-methylisoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3S,4R)-2-(2-((1-methylcyclopropyl)amino)-2-oxoacetyl)-N—((S)-3-oxo-1-((S)-2-oxopyrrolidin-3-yl)-4-(trifluoromethoxy)butan-2-yl)-2-azabicyclo[2.2.1]heptane-3-carboxamide;

(2R,3aS,5R,6aS)-4-(2-(tert-butylamino)-2-oxoacetyl)-2-methyl-N—((S)-3-oxo-1-((S)-2-oxopyrrolidin-3-yl)-4-(trifluoromethoxy)butan-2-yl)hexahydro-2H-furo[3,2-b]pyrrole-5-carboxamide;

(1S,3aR,6aS)-2-(2-(((1R,5S,6r)-3-oxabicyclo[3.1.0]hexan-6-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(6,7-dihydro-4H-pyrano[3,4-d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-((3-methylpyridin-2-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(2R,3aS,5S,6aS)-4-(2-(tert-butylamino)-2-oxoacetyl)-2-methyl-N—((S)-3-oxo-1-((S)-2-oxopyrrolidin-3-yl)-4-(trifluoromethoxy)butan-2-yl)hexahydro-2H-furo[3,2-b]pyrrole-5-carboxamide;

1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N-(o-tolyl)-1H-1,2,3-triazole-4-carboxamide;

(1R,2S,5S)-3-(2-(tert-butylamino)-2-oxoacetyl)-N—((S)-3-oxo-1-((S)-2-oxopyrrolidin-3-yl)-4-(trifluoromethoxy)butan-2-yl)-3-azaspiro[bicyclo[3.1.0]hexane-6,1'-cyclopropane]-2-carboxamide;

(1S,3aR,6aS)-2-(2-(((1,1-difluoro-2-methylpropan-2-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-(2-(((1,1-difluoro-2-methylpropan-2-yl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-N—((S)-3-oxo-1-((S)-2-oxopyrrolidin-3-yl)-4-(trifluoromethoxy)butan-2-yl)-2-(4,5,6,7-tetrahydroisoxazolo[4,5-c]pyridine-3-carbonyl)octahydrocyclopenta[c]pyrrole-1-carboxamide;

(1S,3aR,6aS)-2-(benzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-6-(2-(((1-methylcyclopropyl)amino)-2-oxoacetyl)-N—((S)-3-oxo-1-((S)-2-oxopyrrolidin-3-yl)-4-(trifluoromethoxy)butan-2-yl)-6-azaspiro[3.4]octane-7-carboxamide;

tetrahydrofuran-3-yl (1S,3aR,6aS)-1-(((S)-3-oxo-1-((S)-2-oxopyrrolidin-3-yl)-4-(trifluoromethoxy)butan-2-yl)carbamoyl)hexahydrocyclopenta[c]pyrrole-2(1H)-carboxylate;

(1s,4R)-2-(2-(tert-butylamino)-2-oxoacetyl)-N—((S)-3-oxo-1-((S)-2-oxopyrrolidin-3-yl)-4-(trifluoromethoxy)butan-2-yl)-2-azabicyclo[2.1.1]hexane-1-carboxamide;

(1S,2S,5R)-3-(2-(tert-butylamino)-2-oxoacetyl)-N—((S)-3-oxo-1-((S)-2-oxopyrrolidin-3-yl)-4-(trifluoromethoxy)butan-2-yl)-3-azabicyclo[3.2.0]heptane-2-carboxamide;

(1s,4R)-2-(2-((2-fluorophenyl)amino)-2-oxoacetyl)-N—((S)-3-oxo-1-((S)-2-oxopyrrolidin-3-yl)-4-(trifluoromethoxy)butan-2-yl)-2-azabicyclo[2.1.1]hexane-1-carboxamide;

(1S,2S,5R)-3-(2-((2-fluorophenyl)amino)-2-oxoacetyl)-N—((S)-3-oxo-1-((S)-2-oxopyrrolidin-3-yl)-4-(trifluoromethoxy)butan-2-yl)-3-azabicyclo[3.2.0]heptane-2-carboxamide;

$N^1$—((S)-5,5-difluoro-4,4-dimethyl-1-oxo-1-(((S)-3-oxo-1-((S)-2-oxopyrrolidin-3-yl)-4-(trifluoromethoxy)butan-2-yl)amino)pentan-2-yl)-$N^2$-(3-fluorobicyclo[1.1.1]pentan-1-yl)oxalamide;

$N^1$—((S)-3-cyclobutyl-1-oxo-1-(((S)-3-oxo-1-((S)-2-oxopyrrolidin-3-yl)-4-(trifluoromethoxy)butan-2-yl)amino)propan-2-yl)-$N^2$-(3-fluorobicyclo[1.1.1]pentan-1-yl)oxalamide;

(1S,3aR,6aS)-2-(2-((2-cyanopropan-2-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(R)-1-(2-(tert-butylamino)-2-oxoacetyl)-2-(cyclopropylmethyl)-N—((S)-3-oxo-1-((S)-2-oxopyrrolidin-3-yl)-4-(trifluoromethoxy)butan-2-yl)pyrrolidine-2-carboxamide;

(S)-5-(5,5-dimethyl-4,5,6,7-tetrahydrobenzo[d]isoxazole-3-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

methyl 2-oxo-2-((1S,3aR,6aS)-1-(((S)-3-oxo-1-((S)-2-oxopyrrolidin-3-yl)-4-(trifluoromethoxy)butan-2-yl)carbamoyl)hexahydrocyclopenta[c]pyrrol-2(1H)-yl)acetate;

(S)—N—((S)-3-oxo-1-((S)-2-oxopyrrolidin-3-yl)-4-(trifluoromethoxy)butan-2-yl)-5-(2-oxo-2-((2,2,2-trifluoroethyl)amino)acetyl)-5-azaspiro[2.4]heptane-6-carboxamide;

(S)-5-(2-(((1-methylcyclopropyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(5-(difluoromethyl)isoxazole-3-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

$N^1$-(3-fluorobicyclo[1.1.1]pentan-1-yl)-$N^2$—((S)-3-(1-methylcyclobutyl)-1-oxo-1-(((S)-3-oxo-1-((S)-2-oxopyrrolidin-3-yl)-4-(trifluoromethoxy)butan-2-yl)amino)propan-2-yl)oxalamide;

(1S,3aR,6aS)-2-(2-(tert-butylamino)-2-oxoacetyl)-N—((S)-3-oxo-1-(2-oxo-1,2-dihydropyridin-3-yl)-4-(trifluoromethoxy)butan-2-yl)octahydrocyclopenta[c]pyrrole-1-carboxamide;

(S)-5-(2-(((2-methoxyphenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2-oxo-2-((2-(trifluoromethyl)phenyl)amino)acetyl)-5-azaspiro[2.4]heptane-6-carboxamide;

$N^1$-(1-methylcyclopropyl)-$N^2$-(3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)oxalamide;

$N^1$-cyclopropyl-$N^2$-(3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)oxalamide;

$N^1$-(3-fluorobicyclo[1.1.1]pentan-1-yl)-$N^2$-((1S,2R)-2-(((S)-3-oxo-1-((S)-2-oxopyrrolidin-3-yl)-4-(trifluoromethoxy)butan-2-yl)carbamoyl)-[1,1'-bi(cyclopropan)]-2-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1,2,4-oxadiazole-3-carboxamide;

(1R,3S,5R)-2-(2-((2-fluorophenyl)amino)-2-oxoacetyl)-5-methyl-N—((S)-3-oxo-1-((S)-2-oxopyrrolidin-3-yl)-4-(trifluoromethoxy)butan-2-yl)-2-azabicyclo[3.1.0]hexane-3-carboxamide;

$N^1$-(3-fluorobicyclo[1.1.1]pentan-1-yl)-$N^2$—((S)-3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)oxalamide;

(S)-1-(2-((2-fluorophenyl)amino)-2-oxoacetyl)-N—((S)-3-oxo-1-((S)-2-oxopyrrolidin-3-yl)-4-(trifluoromethoxy)butan-2-yl)azetidine-2-carboxamide;

(S)-1-(2-((2-fluorophenyl)amino)-2-oxoacetyl)-N—((S)-3-oxo-1-((S)-2-oxopyrrolidin-3-yl)-4-(trifluoromethoxy)butan-2-yl)azepane-2-carboxamide;

N¹—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N²-(1-methylcyclopropyl)oxalamide;

N¹-cyclopropyl-N²—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)oxalamide;

(R)-5-(2-((2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((3,3-difluorocyclobutyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

N¹—((S)-3-(3,4-difluorophenyl)-1-oxo-1-(((S)-3-oxo-1-((S)-2-oxopyrrolidin-3-yl)-4-(trifluoromethoxy)butan-2-yl)amino)propan-2-yl)-N²-(2-fluorophenyl)oxalamide;

(S)—N—((S)-3-oxo-1-((S)-2-oxopyrrolidin-3-yl)-4-(trifluoromethoxy)butan-2-yl)-5-(2-oxo-2-((1,1,1-trifluoro-2-methylpropan-2-yl)amino)acetyl)-5-azaspiro[2.4]heptane-6-carboxamide;

(S)-5-(2-((4-chloro-2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

N-(tert-butyl)-1-(4-methyl-1-oxo-1-(((S)-3-oxo-1-((S)-2-oxopyrrolidin-3-yl)-4-(trifluoromethoxy)butan-2-yl)amino)pentan-2-yl)-1H-1,2,3-triazole-4-carboxamide;

(S)-5-(3-fluoropicolinoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-(3,5-difluoro-2-hydroxybenzoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((S)-3-hydroxy-2-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(3-(trifluoromethyl)bicyclo[1.1.1]pentan-1-yl)oxalamide;

(S)-5-(2-((2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-4,4,6-d³-6-carboxamide;

(S)-5-(2-((2,3-difluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((2-fluoro-3-methoxyphenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((2-fluoro-3-(trifluoromethoxy)phenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(2-(tert-butylamino)-2-oxoacetyl)-4-fluoro-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(2-((2,5-difluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((2-chloro-6-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(5-fluoro-1H-indole-2-carbonyl)-N—((R)-3-oxo-1-((S)-2-oxopyrrolidin-3-yl)-4-(trifluoromethoxy)butan-2-yl)octahydrocyclopenta[c]pyrrole-1-carboxamide;

(S)-5-(4-methoxy-1H-indole-2-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((2-chlorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((3-chlorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(4-methoxy-1H-indole-2-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(6-chlorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)—N—((S)-3-oxo-1-((S)-2-oxopyrrolidin-3-yl)-4-(trifluoromethoxy)butan-2-yl)-5-(2-oxo-2-((2-(trifluoromethoxy)phenyl)amino)acetyl)-5-azaspiro[2.4]heptane-6-carboxamide;

(1S,3aR,6aS)-2-(6-fluorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-(tert-butylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1,3,3-d3-1-carboxamide;

(S)-5-(2-((2-(tert-butyl)phenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(5-fluorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-((2-(tert-butyl)phenyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(2,2-difluoro-2-phenylacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(L-leucyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-pentanoyl-5-azaspiro[2.4]heptane-6-carboxamide;

(S)-5-(2-methyl-2-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

benzyl ((S)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-3,3-dimethyl-1-oxobutan-2-yl)carbamate;

(1S,3aR,6aS)-2-(2-(6-chloropyrazin-2-yl)-2-methoxy-acetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(R)-1-(2-fluorophenyl)-2-oxo-2-((1S,3aR,6aS)-1-(((S)-3-oxo-1-((S)-2-oxopyrrolidin-3-yl)-4-(trifluoromethoxy)butan-2-yl)carbamoyl)hexahydrocyclopenta[c]pyrrol-2(1H)-yl)ethyl 2-phenylacetate;

(S)-5-(2,2-difluoro-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4-fluoro-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2,2,4-trimethylpentanoyl)-5-azaspiro[2.4]heptane-6-carboxamide;

(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl propionate;

(S)-5-(3-fluorobicyclo[1.1.1]pentane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((S)-2-phenylpropanoyl)-5-azaspiro[2.4]heptane-6-carboxamide;

(1R,2S,5S)-6,6-dimethyl-N—((S)-3-oxo-1-((S)-2-oxopyrrolidin-3-yl)-4-(trifluoromethoxy)butan-2-yl)-3-((S)-2-phenylpropanoyl)-3-azabicyclo[3.1.0]hexane-2-carboxamide;

(1R,2S,5S)-3-(4,4-difluoro-1-hydroxycyclohexane-1-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl isobutyrate;

(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl 2-phenylacetate;

(S)-5-(1-hydroxy-4,4-dimethylcyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((S)-2-(3-cyclopropylureido)-3,3-dimethylbutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-(2,2-difluoroacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-1-((R)-2-hydroxy-4-methylpentanoyl)-N—((S)-3-oxo-1-((S)-2-oxopyrrolidin-3-yl)-4-(trifluoromethoxy)butan-2-yl)piperidine-2-carboxamide;

(2S,4R)-4-(tert-butyl)-1-((R)-2-hydroxy-4-methylpentanoyl)-N—((S)-3-oxo-1-((S)-2-oxopyrrolidin-3-yl)-4-(trifluoromethoxy)butan-2-yl)piperidine-2-carboxamide;

(1R,2S,5S)-3-((R)-2-hydroxy-4-methylpentanoyl)-N—((S)-3-oxo-1-((S)-2-oxopyrrolidin-3-yl)-4-(trifluoromethoxy)butan-2-yl)-3-azabicyclo[3.2.1]octane-2-carboxamide;

(S)-1-((R)-2-hydroxy-4-methylpentanoyl)-N—((S)-3-oxo-1-((S)-2-oxopyrrolidin-3-yl)-4-(trifluoromethoxy)butan-2-yl)azepane-2-carboxamide;

(S)-6-((R)-2-hydroxy-4-methylpentanoyl)-N—((S)-3-oxo-1-((S)-2-oxopyrrolidin-3-yl)-4-(trifluoromethoxy)butan-2-yl)-6-azaspiro[2.5]octane-5-carboxamide;

(S)-1-((R)-2-hydroxy-4-methylpentanoyl)-4,4-dimethyl-N—((S)-3-oxo-1-((S)-2-oxopyrrolidin-3-yl)-4-(trifluoromethoxy)butan-2-yl)piperidine-2-carboxamide;

(S)-2-((R)-2-hydroxy-4-methylpentanoyl)-N—((S)-3-oxo-1-((S)-2-oxopyrrolidin-3-yl)-4-(trifluoromethoxy)butan-2-yl)-2-azabicyclo[2.2.2]octane-3-carboxamide;

tert-butyl ((R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl)carbamate;

(S)-5-(D-leucyl)-N—((S)-3-oxo-1-((S)-2-oxopyrrolidin-3-yl)-4-(trifluoromethoxy)butan-2-yl)-5-azaspiro[2.4]heptane-6-carboxamide;

tert-butyl methyl((R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl)carbamate;

(S)-5-(4,4-difluoro-1-methoxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-isopropoxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2-phenylacetyl)-5-azaspiro[2.4]heptane-6-carboxamide;

(S)-5-(1-hydroxy-4-(trifluoromethyl)cyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-3-((S)-2-(2-((2-fluorophenyl)amino)-2-oxoacetamido)-4-methylpentanamido)-2-oxo-4-((S)-2-oxopyrrolidin-3-yl)butyl methyl(phenyl)phosphinate;

4-fluoro-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

(S)-3-((S)-4-methyl-2-(2-oxo-2-(phenylamino)acetamido)pentanamido)-2-oxo-4-((S)-2-oxopyrrolidin-3-yl)butyl methyl(phenyl)phosphinate;

$N^1$-(2-fluorophenyl)-$N^2$—((S)-4-methyl-1-(((S)-5-(methylthio)-2-oxo-1-(2,3,5,6-tetrafluorophenoxy)pentan-3-yl)amino)-1-oxopentan-2-yl)oxalamide $N^1$-(2-fluorophenyl)-$N^2$—((S)-4-methyl-1-(((S)-5-(methylsulfonyl)-2-oxo-1-(2,3,5,6-tetrafluorophenoxy)pentan-3-yl)amino)-1-oxopentan-2-yl)oxalamide;

(1R,2S,5S)-3-(5-(2-fluoropropan-2-yl)isoxazole-3-carbonyl)-6,6-dimethyl-N—((S)-3-oxo-1-((S)-2-oxopyrrolidin-3-yl)-4-(2,3,5,6-tetrafluorophenoxy)butan-2-yl)-3-azabicyclo[3.1.0]hexane-2-carboxamide;

(1S,3aR,6aS)-N—((S)-3-oxo-1-((S)-2-oxopyrrolidin-3-yl)-4-(trifluoromethoxy)butan-2-yl)-2-(2-oxo-2-((1-(trifluoromethyl)cyclopropyl)amino)acetyl)octahydrocyclopenta[c]pyrrole-1-carboxamide;

2-(2-(tert-butylamino)-2-oxoacetyl)-N—((S)-3-oxo-1-((S)-2-oxopyrrolidin-3-yl)-4-(trifluoromethoxy)butan-2-yl)-2-azaspiro[4.4]nonane-3-carboxamide;

(1S,3aR,6aS)-N—((S)-3-oxo-1-((S)-2-oxopyrrolidin-3-yl)-4-(trifluoromethoxy)butan-2-yl)-2-((1r,4S)-4-(trifluoromethyl)-2-oxabicyclo[2.1.1]hexane-1-carbonyl)octahydrocyclopenta[c]pyrrole-1-carboxamide;

(S)-5-((R)-2-hydroxy-4,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(5-chlorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(methyl-D-leucyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4,4-difluorocyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxypent-4-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(7-chloro-1H-indole-2-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-acetyl-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-pivaloyl-5-azaspiro[2.4]heptane-6-carboxamide;

(S)-5-((R,E)-2-hydroxy-5-(4-methoxyphenyl)pent-4-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R,E)-5-(4-fluorophenyl)-2-hydroxypent-4-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-4-methylpentanoyl)-N—((R)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((N-phenylsulfamoyl)glycyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(3-((N-phenylsulfamoyl)amino)propanoyl)-5-azaspiro[2.4]heptane-6-carboxamide;

(R)—N—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-2-hydroxy-4-methylpentanamide;

(S)—N—((S)-3-oxo-1-((S)-2-oxopyrrolidin-3-yl)-4-(trifluoromethoxy)butan-2-yl)-5-((2,2,2-trifluoroethyl)glycyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2-(2,2,2-trifluoroethoxy)acetyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2-oxo-2-phenylacetyl)-5-azaspiro[2.4]heptane-6-carboxamide;

(S)-5-((R,E)-2-hydroxy-6-(methylsulfonamido)hex-4-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(methylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

N$^1$—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-N$^2$-methyloxalamide;

(S)-5-(4,4-difluoropentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((S)-tetrahydrofuran-2-carbonyl)-5-azaspiro[2.4]heptane-6-carboxamide;

(S)-5-(4,4-difluoro-1-(2,2,2-trifluoroacetamido)cyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)—N—((S)-3-oxo-1-((S)-2-oxopyrrolidin-3-yl)-4-(trifluoromethoxy)butan-2-yl)-5-(3,3,3-trifluoro-2-hydroxy-2-phenylpropanoyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(tetrahydro-2H-pyran-4-carbonyl)-5-azaspiro[2.4]heptane-6-carboxamide;

(S)-5-(4,4-difluorobutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(3,3,4,4-tetrafluorobutanoyl)-5-azaspiro[2.4]heptane-6-carboxamide;

(2S,4R)-1-((R)-2-hydroxy-4-methylpentanoyl)-N—((S)-3-oxo-1-((S)-2-oxopyrrolidin-3-yl)-4-(trifluoromethoxy)butan-2-yl)-4-(trifluoromethyl)pyrrolidine-2-carboxamide;

(S)—N—((S)-3-oxo-1-((S)-2-oxopyrrolidin-3-yl)-4-(trifluoromethoxy)butan-2-yl)-5-(2-(trifluoromethyl)benzoyl)-5-azaspiro[2.4]heptane-6-carboxamide;

(S)-5-(2,2-difluorobenzo[d][1,3]dioxole-5-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-propionyl-5-azaspiro[2.4]heptane-6-carboxamide;

(S)-5-(but-3-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(pent-4-enoyl)-5-azaspiro[2.4]heptane-6-carboxamide;

(S)-5-((N-methylsulfamoyl)glycyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((N,N-dimethylsulfamoyl)glycyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(N-(N,N-dimethylsulfamoyl)-N-methylglycyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-benzoyl-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-isobutyl-1H-1,2,3-triazole-4-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(5)-1-((R)-2-hydroxy-4-methylpentanoyl)-N—((S)-3-oxo-1-((S)-2-oxopyrrolidin-3-yl)-4-(trifluoromethoxy)butan-2-yl)pyrrolidine-2-carboxamide;

(5)-5-((R)-2-hydroxypropanoyl)-N—((S)-3-oxo-1-((5)-2-oxopyrrolidin-3-yl)-4-(trifluoromethoxy)butan-2-yl)-5-azaspiro[2.4]heptane-6-carboxamide;

(5)-5-(2-hydroxyacetyl)-N-((5)-3-oxo-1-((5)-2-oxopyrrolidin-3-yl)-4-(trifluoromethoxy)butan-2-yl)-5-azaspiro[2.4]heptane-6-carboxamide;

(S)-5-(3,5-difluorobenzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((S)-3,3,3-trifluoro-2-hydroxy-2-methylpropanoyl)-5-azaspiro[2.4]heptane-6-carboxamide;

(S)-5-(2-(3,3-difluorocyclobutyl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4-chloro-2-fluorobenzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2,2,2-trifluoroacetyl)-5-azaspiro[2.4]heptane-6-carboxamide;

(S)-5-isobutyryl-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-butyryl-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-4-(methyl-$^{13}$C)pentanoyl-1,2,3,4,5-$^{13}C_5$)—N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-hexanoyl-N—((S)-3-oxo-1-((S)-2-oxopyrrolidin-3-yl)-4-(trifluoromethoxy)butan-2-yl)-5-azaspiro[2.4]heptane-6-carboxamide;

(S)-2-acetamido-4-methyl-N—((S)-3-oxo-1-((S)-2-oxopyrrolidin-3-yl)-4-(trifluoromethoxy)butan-2-yl)pentanamide;

(S)-5-(2,4-difluorobenzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(1-methylcyclopentyl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3,3-difluoro-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(3,3,4,4-tetrafluoropentanoyl)-5-azaspiro[2.4]heptane-6-carboxamide;

(S)-5-(2,2-difluoro-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-2-phenylacetyl)-6,6-dimethyl-N—((R)-3-oxo-1-((S)-2-oxopyrrolidin-3-yl)-4-(trifluoromethoxy)butan-2-yl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-5-((R)-2-(trifluoromethoxy)butanoyl)-5-azaspiro[2.4]heptane-6-carboxamide;

(S)-5-(3-hydroxy-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((1R,2R)-2-(trifluoromethyl)cyclopropane-1-carbonyl)-5-azaspiro[2.4]heptane-6-carboxamide;

(S)-2-hydroxy-4-methyl-N—((S)-3-oxo-1-((S)-2-oxopyrrolidin-3-yl)-4-(trifluoromethoxy)butan-2-yl)pentanamide;

(6S)-5-(3,3-difluorocyclopentane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3,3-difluorocyclobutane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((R)-3,3,3-trifluoro-2-hydroxy-2-methylpropanoyl)-5-azaspiro[2.4]heptane-6-carboxamide;

(S)-5-(cyclopentanecarbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4R)-1-acetyl-N—((S)-3-oxo-1-((S)-2-oxopyrrolidin-3-yl)-4-(trifluoromethoxy)butan-2-yl)-4-(trifluoromethyl)pyrrolidine-2-carboxamide;

(S)-5-((E)-4-methylpent-2-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((2R,3S)-2,3-dihydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-4-methylpentanoyl)-N—((R)-3-oxo-1-((R)-2-oxopyrrolidin-3-yl)-4-(trifluoromethoxy)butan-2-yl)-5-azaspiro[2.4]heptane-6-carboxamide;

(S)-5-((R)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-2-hydroxy-4-methylpentanoyl)-N—((R)-3-oxo-1-((R)-2-oxopyrrolidin-3-yl)-4-(trifluoromethoxy)butan-2-yl)-5-azaspiro[2.4]heptane-6-carboxamide;

(S)-5-((S)-2-hydroxy-4-methylpentanoyl)-N—((R)-3-oxo-1-((R)-2-oxopyrrolidin-3-yl)-4-(trifluoromethoxy)butan-2-yl)-5-azaspiro[2.4]heptane-6-carboxamide;

(S)-5-((S)-2-hydroxy-4-methylpentanoyl)-N—((S)-3-oxo-1-((R)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(pentanoyl-d9)-5-azaspiro[2.4]heptane-6-carboxamide;

(S)-5-(hexanoyl-d$_{11}$)—N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4-(methyl-d3)pentanoyl-2,2,3,3,4,5,5,5-d$_8$)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-fluoro-2-methylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(butanoyl-d7)—N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3-(methyl-d3)butanoyl-2,2,3,4,4,4-d6)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-methylpropanoyl-2-d)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(methyl-d3)propanoyl-3,3,3-d$^3$)—N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(hexanoyl-2,2-d2)—N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-(2-fluoro-3-methoxyphenyl)-2-hydroxyacetyl)-6,6-dimethyl-N—((S)-3-oxo-1-((S)-2- oxopyrrolidin-3-yl)-4-(trifluoromethoxy)butan-2-yl)-3-azabicyclo[3.1.0]hexane-2-carboxamide;

$N^1$—((S)-1-(((S)-4-hydroxy-3-oxo-1-((S)-2-oxopiperidin-3-yl)butan-2-yl)amino)-4,4-dimethyl-1-oxopentan-2-yl)-$N^2$-(6-(trifluoromethyl)pyridin-2-yl)oxalamide;

(S)—N—((S)-3-oxo-1-((S)-2-oxopyrrolidin-3-yl)-4-(trifluoromethoxy)butan-2-yl)-5-(5,5,5-trifluoro-2-oxo-4-(trifluoromethyl)pentanoyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((R)-5,5,5-trifluoro-2-hydroxy-4-(trifluoromethyl)pentanoyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((S)-5,5,5-trifluoro-2-hydroxy-4-(trifluoromethyl)pentanoyl)-5-azaspiro[2.4]heptane-6-carboxamide;

(S)-5-(2-(cyclopropylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(isopropylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-2,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(ethylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(R)-5-(4,4-difluoropentanoyl)-N—((R)-3-oxo-1-((S)-2-oxopyrrolidin-3-yl)-4-(trifluoromethoxy)butan-2-yl)-5-azaspiro[2.4]heptane-6-carboxamide;

(S)-4,4-difluoro-1-((R)-2-hydroxy-4-methylpentanoyl)-N—((S)-3-oxo-1-((S)-2-oxopyrrolidin-3-yl)-4-(trifluoromethoxy)butan-2-yl)pyrrolidine-2-carboxamide;

(S)-5-((R)-2,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4R)-1-((R)-2-hydroxy-4-methylpentanoyl)-4-methyl-N—((S)-3-oxo-1-((S)-2-oxopyrrolidin-3-yl)-4-(trifluoromethoxy)butan-2-yl)pyrrolidine-2-carboxamide;

(S)-5-((R)-4-fluoro-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(hexanoyl-5,5,6,6,6-d5)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2,2-difluoro-3-hydroxybutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(hexanoyl-6,6,6-d$^3$)—N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-methoxybutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(acetyl-d$^3$)—N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-cyclobutyl-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4S)-1-((R)-2-hydroxy-4-methylpentanoyl)-N—((S)-3-oxo-1-((S)-2-oxopyrrolidin-3-yl)-4-(trifluoromethoxy)butan-2-yl)-4-phenylpyrrolidine-2-carboxamide;

(6S)-5-(3-fluoro-2-hydroxy-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(pentanoyl-5,5,5-d3)-5-azaspiro[2.4]heptane-6-carboxamide;

(S)-5-(butanoyl-4,4,4-d3)-N—((S)-3-oxo-1-((S)-2-oxopyrrolidin-3-yl)-4-(trifluoromethoxy)butan-2-yl)-5-azaspiro[2.4]heptane-6-carboxamide;

(S)-4-methyl-2-((1-methyl-1H-indole)-5-sulfonamido)-N—((S)-3-oxo-1-((S)-2-oxopyrrolidin-3-yl)-4-(2,3,5,6-tetrafluorophenoxy)butan-2-yl)pentanamide;

(S)-5-((R)-2-hydroxypentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(R)-2-hydroxy-4-methyl-N—((S)-4-methyl-1-oxo-1-(((S)-3-oxo-1-((S)-2-oxopyrrolidin-3-yl)-4-(trifluoromethoxy)butan-2-yl)amino)pentan-2-yl)pentanamide;

1-((S)-2-hydroxy-2-phenylacetyl)-N—((S)-3-oxo-1-((S)-2-oxopyrrolidin-3-yl)-4-(trifluoromethoxy)butan-2-yl)azepane-2-carboxamide;

1-((S)-2-hydroxy-2-phenylacetyl)-N—((S)-3-oxo-1-((S)-2-oxopyrrolidin-3-yl)-4-(trifluoromethoxy)butan-2-yl)piperidine-2-carboxamide;

6-((R)-2-hydroxy-4-methylpentanoyl)-N—((S)-3-oxo-1-((S)-2-oxopyrrolidin-3-yl)-4-(trifluoromethoxy)butan-2-yl)-6-azaspiro[3.4]octane-7-carboxamide;

(2S)-4-(bicyclo[1.1.1]pentan-2-yl)-1-((R)-2-hydroxy-4-methylpentanoyl)-N—((S)-3-oxo-1-((S)-2-oxopyrrolidin-3-yl)-4-(trifluoromethoxy)butan-2-yl)pyrrolidine-2-carboxamide;

(2S,4S)-4-(cyclobutylmethyl)-1-((R)-2-hydroxy-4-methylpentanoyl)-N—((S)-3-oxo-1-((S)-2-oxopyrrolidin-3-yl)-4-(trifluoromethoxy)butan-2-yl)pyrrolidine-2-carboxamide;

(S)—N—((S)-3-oxo-1-((S)-2-oxopyrrolidin-3-yl)-4-(trifluoromethoxy)butan-2-yl)-5-(2-(4-(trifluoromethoxy)phenoxy)acetyl)-5-azaspiro[2.4]heptane-6-carboxamide;

(6S)-5-(4-methyl-2-nitrosopentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4R)-1-(2-(tert-butylamino)-2-oxoacetyl)-N—((S)-3-oxo-1-((S)-2-oxopyrrolidin-3-yl)-4-(trifluoromethoxy)butan-2-yl)-4-(trifluoromethyl)pyrrolidine-2-carboxamide;

(S)—N—((S)-3-oxo-1-((S)-2-oxopyrrolidin-3-yl)-4-(trifluoromethoxy)butan-2-yl)-5-(1H-pyrrolo[2,3-b]pyridine-2-carbonyl)-5-azaspiro[2.4]heptane-6-carboxamide;

2-((4-fluorophenyl)amino)-N—((S)-3-oxo-1-((S)-2-oxopyrrolidin-3-yl)-4-(trifluoromethoxy)butan-2-yl)acetamide;

(2S,4S)-1-(2-fluoro-2-methylpropanoyl)-N—((S)-3-oxo-1-((S)-2-oxopyrrolidin-3-yl)-4-(trifluoromethoxy)butan-2-yl)-4-phenylpyrrolidine-2-carboxamide;

(S)-5-((R)-2-hydroxy-4-methylpentanoyl)-N—((S)-3-oxo-1-((S)-2-oxopiperidin-3-yl)-4-(perfluorophenoxy)butan-2-yl)-5-azaspiro[2.4]heptane-6-carboxamide;

(2S,4S)-1-((S)-2-hydroxy-2-phenylacetyl)-N—((S)-3-oxo-1-((S)-2-oxopyrrolidin-3-yl)-4-(trifluoromethoxy)butan-2-yl)-4-phenylpyrrolidine-2-carboxamide;

(S)-5-((R)-2-hydroxy-4-methylpentanoyl)-N—((S)-3-oxo-1-((S)-2-oxopiperidin-3-yl)-4-(2,3,5,6-tetrafluorophenoxy)butan-2-yl)-5-azaspiro[2.4]heptane-6-carboxamide;

(S)-5-((R)-2-hydroxy-4-methylpentanoyl)-N—((S)-3-oxo-1-((S)-2-oxopiperidin-3-yl)-4-(2,3,6-trifluorophenoxy)butan-2-yl)-5-azaspiro[2.4]heptane-6-carboxamide;

(1S,3aR,6aS)-2-(6-chlorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

4-fluoro-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

(2S,4R)-1-((S)-2-hydroxy-2-phenylacetyl)-N—((S)-3-oxo-1-((S)-2-oxopyrrolidin-3-yl)-4-(trifluoromethoxy)butan-2-yl)-4-(trifluoromethyl)pyrrolidine-2-carboxamide;

(2S,4S)-1-((R)-2-hydroxy-2-phenylacetyl)-N—((S)-3-oxo-1-((S)-2-oxopyrrolidin-3-yl)-4-(trifluoromethoxy)butan-2-yl)-4-phenylpyrrolidine-2-carboxamide;

(S)-1-((R)-2-hydroxy-4-methylpentanoyl)-5,5-dimethyl-N—((S)-3-oxo-1-((S)-2-oxopyrrolidin-3-yl)-4-(trifluoromethoxy)butan-2-yl)pyrrolidine-2-carboxamide;

$N^1$-(2-fluorophenyl)-$N^2$—((S)-4-methyl-1-oxo-1-(((S)-3-oxo-1-((S)-2-oxopyrrolidin-3-yl)-4-((2-(trifluoromethyl)pyrimidin-4-yl)oxy)butan-2-yl)amino)pentan-2-yl)oxalamide; and N—((S)-4-methyl-1-oxo-1-(((S)-3-oxo-1-((S)-2-oxopyrrolidin-3-yl)-4-(trifluoromethoxy)butan-2-yl)amino)pentan-2-yl)-5-oxaspiro[2.4]heptane-6-carboxamide, or a pharmaceutically acceptable salt thereof.

Specific examples of Formula (III) compounds or their pharmaceutically acceptable salts constitute additional embodiments of the disclosure. In some embodiments, the compound of Formula (III) is selected from the group consisting of:

(R)—$N^4$-(2-fluorobenzyl)-2-isobutyl-$N^1$—((S)-3-oxo-1-((S)-2-oxopyrrolidin-3-yl)-4-(2,3,5,6-tetrafluorophenoxy)butan-2-yl)succinimide;

(R)—$N^4$-(2,6-difluorobenzyl)-2-isobutyl-$N^1$—((S)-3-oxo-1-((S)-2-oxopyrrolidin-3-yl)-4-(2,3,5,6-tetrafluorophenoxy)butan-2-yl)succinimide;

(R)-2-isobutyl-$N^1$—((S)-3-oxo-1-((S)-2-oxopyrrolidin-3-yl)-4-(2,3,5,6-tetrafluorophenoxy)butan-2-yl)-$N^4$-phenylsuccinamide;

(5R,6R)-N5-isobutyl-$N^6$—((S)-3-oxo-1-((S)-2-oxopyrrolidin-3-yl)-4-(trifluoromethoxy)butan-2-yl)spiro[2.4]heptane-5,6-dicarboxamide;

$N^1$-(2-fluorophenyl)-$N^2$—((S)-3-methyl-1-(1-((S)-3-oxo-1-((S)-2-oxopyrrolidin-3-yl)-4-(2,3,5,6-tetrafluorophenoxy)butan-2-yl)-1H-1,2,3-triazol-4-yl)butyl)oxalamide;

1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N-(o-tolyl)-1H-1,2,3-triazole-4-carboxamide;

N-(tert-butyl)-1-(4-methyl-1-oxo-1-(((S)-3-oxo-1-((S)-2-oxopyrrolidin-3-yl)-4-(trifluoromethoxy)butan-2-yl)amino)pentan-2-yl)-1H-1,2,3-triazole-4-carboxamide;

(S)-4-methyl-2-((1-methyl-1H-indole)-5-sulfonamido)-N—((S)-3-oxo-1-((S)-2-oxopyrrolidin-3-yl)-4-(trifluoromethoxy)butan-2-yl)pentanamide;

(S)-4-methyl-2-((2-oxo-1,2-dihydroquinolin-3-yl)amino)-N—((S)-3-oxo-1-((S)-2-oxopyrrolidin-3-yl)-4-(trifluoromethoxy)butan-2-yl)pentanamide;

(S)-4-methyl-2-((1-methyl-1H-indole)-5-sulfonamido)-N—((S)-3-oxo-1-((S)-2-oxopyrrolidin-3-yl)-4-(2,3,5,6-tetrafluorophenoxy)butan-2-yl)pentanamide; and 2-((4-fluorophenyl)amino)-N—((S)-3-oxo-1-((S)-2-oxopyrrolidin-3-yl)-4-(trifluoromethoxy)butan-2-yl)acetamide, or a pharmaceutically acceptable salt thereof.

In some embodiments, the compound or pharmaceutically acceptable salt thereof may demonstrate an EC50 value (e.g., in Hela cells) of less than 0.05 µM. For example, the compound may be selected from the group consisting of:

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-phenyloxalamide;

$N^1$-(2-fluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-pyrrolo[3,2-c]pyridine-2-carboxamide;

$N^1$—((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-phenyloxalamide;

$N^1$—((S)-3-cyclobutyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-phenyloxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(2-(trifluoromethyl)phenyl)oxalamide;

$N^1$-(2-(tert-butyl)phenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-phenyloxalamide;

$N^1$—((S)-5-methyl-1-oxo-1-(((S)-3-oxo-1-((S)-2-oxopyrrolidin-3-yl)-4-(2,3,5,6-tetrafluorophenoxy)butan-2-yl)amino)hexan-2-yl)-$N^2$-phenyloxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(o-tolyl)oxalamide;

$N^1$-(4-fluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-4-methyl-N—((S)-3-oxo-1-((S)-2-oxopyrrolidin-3-yl)-4-(2,3,5,6-tetrafluorophenoxy)butan-2-yl)-2-(2-(phenylamino)acetamido)pentanamide;

$N^1$—((S)-3-cyclopentyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-phenyloxalamide;

$N^1$-(2-chlorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2,6-difluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(2-(trifluoromethyl)pyridin-3-yl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(naphthalen-1-yl)oxalamide;

$N^1$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-(2-fluorophenyl)oxalamide;

$N^1$-(2-(difluoromethoxy)phenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-ethylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2,6-dimethylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2,3-dimethylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-fluoro-4-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(4-chloro-2-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2,4-difluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-fluoro-6-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(5-fluoro-2-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-fluorophenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2-isopropylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(3-fluoro-2-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-chlorophenyl)-$N^2$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide;

$N^1$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-(o-tolyl)oxalamide;

$N^1$—((S)-1-oxo-1-(((S)-3-oxo-1-((S)-2-oxopyrrolidin-3-yl)-4-(2,3,5,6-tetrafluorophenoxy)butan-2-yl)amino)-3-phenylpropan-2-yl)-$N^2$-(o-tolyl)oxalamide;

$N^1$—((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-(2-fluorophenyl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(2-(trifluoromethoxy)phenyl)oxalamide;

$N^1$—((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-$N^2$-(o-tolyl)oxalamide;

$N^1$-(2-(tert-butyl)phenyl)-$N^2$—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide;

$N^1$-(3-methoxyphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(4-methoxyphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-phenyloxalamide;

(S)-3-((S)-2-(2-((2-fluorophenyl)amino)-2-oxoacetamido)-4-methylpentanamido)-2-oxo-4-((S)-2-oxopyrrolidin-3-yl)butyl diphenylphosphinate;

$N^1$-(2-fluorophenyl)-$N^2$—((S)-4-methyl-1-oxo-1-(((S)-3-oxo-1-((S)-2-oxopiperidin-3-yl)-4-(2,3,5,6-tetrafluorophenoxy)butan-2-yl)amino)pentan-2-yl)oxalamide;

$N^1$—((S)-4,4-dimethyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(2-fluorophenyl)oxalamide;

$N^1$-(2-chlorophenyl)-$N^2$-(1-oxo-1-(((S)-3-oxo-1-((S)-2-oxopyrrolidin-3-yl)-4-(2,3,5,6-tetrafluorophenoxy)butan-2-yl)amino)-3-(tetrahydro-2H-pyran-4-yl)propan-2-yl)oxalamide;

$N^1$—((S)-1-(((S)-7-amino-2-oxo-1-(2,3,5,6-tetrafluorophenoxy)heptan-3-yl)amino)-4-methyl-1-oxopentan-2-yl)-$N^2$-(2-fluorophenyl)oxalamide;

$N^1$-(2,6-dimethylphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

2,2-difluoro-N—((S)-4-methyl-1-oxo-1-(((S)-3-oxo-1-((S)-2-oxopyrrolidin-3-yl)-4-(trifluoromethoxy)butan-2-yl)amino)pentan-2-yl)benzo[d][1,3]dioxole-5-carboxamide;

(S)-2-(2-(5-acetyl-2-methoxyphenyl)acetamido)-4-methyl-N—((S)-3-oxo-1-((S)-2-oxopyrrolidin-3-yl)-4-(2,3,5,6-tetrafluorophenoxy)butan-2-yl)pentanamide;

$N^1$—((S)-1-oxo-1-(((S)-3-oxo-1-((S)-2-oxopyrrolidin-3-yl)-4-(trifluoromethoxy)butan-2-yl)amino)-3-(pyridin-2-yl)propan-2-yl)-$N^2$-(o-tolyl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-benzo[d]imidazole-2-carboxamide;

4-methoxy-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-indole-2-carboxamide;

$N^1$-(2,6-diisopropylphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(2-fluorophenyl)isoxazole-3-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-fluoro-1H-indole-2-carboxamide;

$N^1$-cyclohexyl-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2,6-dimethoxyphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2-methoxy-6-methylphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$-(2-fluoro-6-methoxyphenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-(2,6-diethylphenyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-(2,2-difluorocyclohexyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-(2,6-diisopropoxyphenyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

5-(2-fluorophenyl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)isoxazole-3-carboxamide;

N¹-(tert-butyl)-N²—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-(2-(tert-butyl)phenyl)-N²—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-cyclopropyl-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N²-(3,3-difluorocyclobutyl)oxalamide;

N¹-(2-(methoxymethyl)phenyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-(3,3-difluorocyclobutyl)-N²—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-(tert-butyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-(3,3-difluorocyclobutyl)-N²—((S)-1-oxo-1-(((S)-3-oxo-1-((S)-2-oxopyrrolidin-3-yl)-4-(trifluoromethoxy)butan-2-yl)amino)-3-phenylpropan-2-yl)oxalamide;

5-(2-fluorophenyl)-N-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)isoxazole-3-carboxamide;

N¹-(2,6-dicyclopropylphenyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(1-(p-tolyl)cyclopropyl)oxalamide;

N¹-(3-methoxyphenyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(2,2,2-trifluoroethyl)oxalamide;

N¹-(bicyclo[1.1.1]pentan-1-yl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹-(1-methoxy-2-methylpropan-2-yl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-b]pyridine-2-carboxamide;

(2S)-2-(2-(3,4-dihydroquinolin-1(2H)-yl)-2-oxoacetamido)-4-methyl-N-((2S)-3-oxo-1-(2-oxopyrrolidin-3-yl)-4-(trifluoromethoxy)butan-2-yl)pentanamide;

3-chlorobenzyl ((S)-4-methyl-1-oxo-1-(((S)-3-oxo-1-((S)-2-oxopyrrolidin-3-yl)-4-(trifluoromethoxy)butan-2-yl)amino)pentan-2-yl)carbamate;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)benzo[d]oxazole-2-carboxamide;

N¹-(3,3-difluorocyclobutyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(o-tolyl)oxalamide;

(S)-2-((R)-2-hydroxy-3-phenylpropanamido)-4-methyl-N—((S)-3-oxo-1-((S)-2-oxopyrrolidin-3-yl)-4-(trifluoromethoxy)butan-2-yl)pentanamide;

5-(3-fluorophenyl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-imidazole-2-carboxamide;

5-(2-methoxyphenyl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-imidazole-2-carboxamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(1,1,1-trifluoro-2-methylpropan-2-yl)oxalamide;

N¹—((S)-3-cyclohexyl-1-oxo-1-(((S)-3-oxo-1-((S)-2-oxopyrrolidin-3-yl)-4-(trifluoromethoxy)butan-2-yl)amino)propan-2-yl)-N²-(1,1,1-trifluoro-2-methylpropan-2-yl)oxalamide;

N¹—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-N²-(1-methylcyclopropyl)oxalamide;

N¹-(1-(2-fluorophenyl)cyclopropyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(1-methylcyclopropyl)oxalamide;

N¹-(2-fluorophenyl)-N²—((S)-4-methyl-1-oxo-1-(((S)-3-oxo-1-((S)-2-oxopiperidin-3-yl)-4-(trifluoromethoxy)butan-2-yl)amino)pentan-2-yl)oxalamide;

N¹—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N²-(3,3-difluoro-1-methylcyclobutyl)oxalamide;

N¹-cyclobutyl-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-phenyl-1H-imidazole-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-5-phenyl-1H-imidazole-2-carboxamide;

N¹—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-N²-(3-fluorobicyclo[1.1.1]pentan-1-yl)oxalamide;

N¹-((2S)-3-(2,2-difluorocyclopentyl)-1-oxo-1-(((S)-3-oxo-1-((S)-2-oxopyrrolidin-3-yl)-4-(trifluoromethoxy)butan-2-yl)amino)propan-2-yl)-N²-(2-fluorophenyl)oxalamide;

4-methoxy-N—((S)-4-methyl-1-oxo-1-(((S)-3-oxo-1-((S)-2-oxopiperidin-3-yl)-4-(trifluoromethoxy)butan-2-yl)amino)pentan-2-yl)-1H-indole-2-carboxamide;

(S)-2-((R)-2-((2-fluorophenyl)amino)-3-methoxypropanamido)-4-methyl-N—((S)-3-oxo-1-((S)-2-oxopyrrolidin-3-yl)-4-(trifluoromethoxy)butan-2-yl)pentanamide;
(S)-2-((S)-2-((2-fluorophenyl)amino)-3-methoxypropanamido)-4-methyl-N—((S)-3-oxo-1-((S)-2-oxopyrrolidin-3-yl)-4-(trifluoromethoxy)butan-2-yl)pentanamide;
$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(1-(trifluoromethyl)cyclopropyl)oxalamide;
$N^1$-(6,6-difluorospiro[3.3]heptan-2-yl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;
$N^1$—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-$N^2$-(3-methoxyphenyl)oxalamide;
$N^1$-(2-fluorophenyl)-$N^2$—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)oxalamide;
$N^1$—((S)-4-methyl-1-oxo-1-(((S)-3-oxo-1-((S)-2-oxopiperidin-3-yl)-4-(trifluoromethoxy)butan-2-yl)amino)pentan-2-yl)-$N^2$-(1-methylcyclopropyl)oxalamide;
$N^1$-(1,1-difluoro-2-methylpropan-2-yl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;
$N^1$—((S)-3-(4-fluorophenyl)-1-oxo-1-(((S)-3-oxo-1-((S)-2-oxopyrrolidin-3-yl)-4-(trifluoromethoxy)butan-2-yl)amino)propan-2-yl)-$N^2$-(1-methylcyclopropyl)oxalamide;
$N^1$-(4-fluorobicyclo[2.2.2]octan-1-yl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;
5-(2-fluoropropan-2-yl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)isoxazole-3-carboxamide;
$N^1$-(1-(fluoromethyl)cyclopropyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;
7-methoxy-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-2,3-dihydrobenzofuran-2-carboxamide;
(1S,3aR,6aS)-2-(2-((2-fluorophenyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;
(1S,3aR,6aS)-2-(2-(tert-butylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;
(1R,2S,5S)-3-((S)-3,3-dimethyl-2-(2,2,2-trifluoroacetamido)butanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;
(1S,3aR,6aS)-2-((S)-3,3-dimethyl-2-(2,2,2-trifluoroacetamido)butanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;
(S)-5-(2-((2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;
$N^1$-(2-fluorophenyl)-$N^2$-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)oxalamide;
N-((2S)-4-methyl-1-oxo-1-(((2S)-3-oxo-1-(2-oxopyrrolidin-3-yl)-4-(trifluoromethoxy)butan-2-yl)amino)pentan-2-yl)-2-(trifluoromethyl)thiazole-4-carboxamide;
(1R,2S,5S)-6,6-dimethyl-N—((S)-3-oxo-1-((S)-2-oxopyrrolidin-3-yl)-4-(trifluoromethoxy)butan-2-yl)-3-(5-(trifluoromethyl)isoxazole-3-carbonyl)-3-azabicyclo[3.1.0]hexane-2-carboxamide;
N—((S)-1-oxo-1-(((S)-3-oxo-1-((S)-2-oxopyrrolidin-3-yl)-4-(trifluoromethoxy)butan-2-yl)amino)butan-2-yl)-5-oxaspiro[2.4]heptane-6-carboxamide;
(R)—N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)tetrahydrofuran-2-carboxamide;
(R)—N—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;
N—((S)-4-methyl-1-oxo-1-(((S)-3-oxo-1-((S)-2-oxopyrrolidin-3-yl)-4-(trifluoromethoxy)butan-2-yl)amino)pentan-2-yl)-7-oxabicyclo[2.2.1]heptane-1-carboxamide;
(1S,3aR,6aS)-N—((S)-3-oxo-1-((S)-2-oxopyrrolidin-3-yl)-4-(trifluoromethoxy)butan-2-yl)-2-(4-(trifluoromethyl)-2-oxabicyclo[2.1.1]hexane-1-carbonyl)octahydrocyclopenta[c]pyrrole-1-carboxamide;
N—((S)-4-methyl-1-oxo-1-(((S)-3-oxo-1-((S)-2-oxopyrrolidin-3-yl)-4-(trifluoromethoxy)butan-2-yl)amino)pentan-2-yl)-4-(trifluoromethyl)-2-oxabicyclo[2.1.1]hexane-1-carboxamide;
(S)—N—((S)-3-oxo-1-((S)-2-oxopyrrolidin-3-yl)-4-(trifluoromethoxy)butan-2-yl)-5-(4-(trifluoromethyl)-2-oxabicyclo[2.1.1]hexane-1-carbonyl)-5-azaspiro[2.4]heptane-6-carboxamide;
4-(difluoromethyl)-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-2-oxabicyclo[2.1.1]hexane-1-carboxamide;
(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl tert-butylcarbamate;
(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl isopropylcarbamate;
(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl cyclohexylcarbamate;
(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl phenylcarbamate;
(S)-5-((R)-2-(difluoromethoxy)-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1R,2S,5S)-6,6-dimethyl-N—((S)-3-oxo-1-((S)-2-oxopyrrolidin-3-yl)-4-(trifluoromethoxy)butan-2-yl)-3-((R)-2-(trifluoromethoxy)butanoyl)-3-azabicyclo[3.1.0]hexane-2-carboxamide;
(6S)-5-(2-methoxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(S)-5-((S)-2-hydroxy-3,3-dimethylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;
(1R,2S,5S)-3-((S)-2-hydroxy-3,3-dimethylbutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(6S)-5-(2-hydroxy-4,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-(2-hydroxy-4,4-dimethylpentanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-(2-hydroxy-4,4-dimethylpentanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((S)-2-hydroxy-4,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-hydroxy-2,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-4-methylpentanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((R)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-2-hydroxy-4-methylpentanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((S)-2-hydroxy-2-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-2-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxy-3,3-dimethylcyclobutane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxypentanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-((2R,3R)-2-hydroxy-3-methylpentanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((R)-2-methoxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-2-(2-methoxyphenyl)acetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(6S)—N—((S)-3-oxo-1-((S)-2-oxopyrrolidin-3-yl)-4-(trifluoromethoxy)butan-2-yl)-5-(5,5,5-trifluoro-2-hydroxy-4-(trifluoromethyl)pentanoyl)-5-azaspiro[2.4]heptane-6-carboxamide;

(1S,3aR,6aS)-2-((R)-3-cyclopropyl-2-hydroxypropanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-((S)-3-cyclopropyl-2-hydroxypropanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(2-(3,4-difluorophenyl)-2-hydroxyacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(6S)-5-(2-(2,4-difluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-2-(4-fluorophenyl)-2-hydroxyacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-((R)-2-(2-fluorophenyl)-2-hydroxyacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-2-((R)-2-(2-fluorophenyl)-2-hydroxyacetamido)-4-methyl-N—((S)-3-oxo-1-((S)-2-oxopyrrolidin-3-yl)-4-(trifluoromethoxy)butan-2-yl)pentanamide;

(1S,3aR,6aS)-2-((R)-2-(2-fluorophenyl)-2-hydroxyacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-((S)-2-(2-fluorophenyl)-2-hydroxyacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-((R)-2-hydroxy-2-phenylacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-((R)-2-hydroxy-2-phenylacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-((S)-2-hydroxy-2-phenylacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-((S)-2-hydroxy-2-phenylacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(4,4-difluoro-1-hydroxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((2R,4R)-5,5,5-trifluoro-2-hydroxy-4-methylpentanoyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((2R,4S)-5,5,5-trifluoro-2-hydroxy-4-methylpentanoyl)-5-azaspiro[2.4]heptane-6-carboxamide;

(S)-5-(4-methyl-2-oxopentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-4-methyl-N—((S)-3-oxo-1-((S)-2-oxopyrrolidin-3-yl)-4-(trifluoromethoxy)butan-2-yl)-2-(2-((1-(trifluoromethyl)cyclopropyl)amino)acetamido)pentanamide;

tert-butyl ((R)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-1-oxobutan-2-yl)carbamate;

(S)-5-((S)-3,3-dimethyl-2-(2,2,2-trifluoroacetamido)butanoyl)-N—((S)-3-oxo-1-((S)-2-oxopyrrolidin-3-yl)-4-(trifluoromethoxy)butan-2-yl)-5-azaspiro[2.4]heptane-6-carboxamide;

cyclopropyl ((S)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-3,3-dimethyl-1-oxobutan-2-yl)carbamate;

(S)-5-(4-(tert-butyl)benzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-4,4-dimethylpentanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-(2-methyl-2-(3-(trifluoromethyl)phenyl)propanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(3-(trifluoromethyl)benzoyl)-5-azaspiro[2.4]heptane-6-carboxamide;

(S)-5-(3-(tert-butyl)benzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

5-(2-fluorophenyl)-N—((S)-1-oxo-1-(((S)-3-oxo-1-((S)-2-oxopyrrolidin-3-yl)-4-(trifluoromethoxy)butan-2-yl)amino)-3-phenylpropan-2-yl)isoxazole-3-carboxamide;

5-benzyl-N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)isoxazole-3-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-5-(pyridin-2-yl)isoxazole-3-carboxamide;

7-methoxy-N—((S)-4-methyl-1-oxo-1-(((S)-3-oxo-1-((S)-2-oxopyrrolidin-3-yl)-4-(trifluoromethoxy)butan-2-yl)amino)pentan-2-yl)benzofuran-2-carboxamide;

(1R,2S,5S)-3-(2-(cyclohexylamino)-2-oxoacetyl)-6,6-dimethyl-N—((S)-3-oxo-1-((S)-2-oxopiperidin-3-yl)-4-(trifluoromethoxy)butan-2-yl)-3-azabicyclo[3.1.0]hexane-2-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(2-oxo-2-(o-tolylamino)acetyl)-3-azabicyclo[3.1.0]hexane-2-carboxamide;

(1S,3aR,6aS)-N—((S)-3-oxo-1-((S)-2-oxopyrrolidin-3-yl)-4-(trifluoromethoxy)butan-2-yl)-2-(2-(trifluoromethyl)thiazole-4-carbonyl)octahydrocyclopenta[c]pyrrole-1-carboxamide;

(1R,2S,5S)-3-(5-(2-fluoropropan-2-yl)isoxazole-3-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(2-((fluorophenyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(2-fluoropropan-2-yl)isoxazole-3-carboxamide;

(1S,3aR,6aS)-2-(5-(2-fluoropropan-2-yl)isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(5-(difluoromethyl)isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(2-(tert-butylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

$N^1$-(tert-butyl)-$N^2$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)oxalamide;

$N^1$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-$N^2$-(o-tolyl)oxalamide;

$N^1$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-$N^2$-(2,2,2-trifluoroethyl)oxalamide;

$N^1$-(3-fluorobicyclo[1.1.1]pentan-1-yl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(o-tolyl)oxalamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(3-fluorobicyclo[1.1.1]pentan-1-yl)oxalamide;

(1S,3aR,6aS)-N—((S)-3-oxo-1-((S)-2-oxopyrrolidin-3-yl)-4-(trifluoromethoxy)butan-2-yl)-2-(2-oxo-2-(o-tolylamino)acetyl)octahydrocyclopenta[c]pyrrole-1-carboxamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(2,2,2-trifluoroethyl)oxalamide;

(1S,3aR,6aS)-2-(2-((3,3-difluorocyclobutyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

$N^1$-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)-$N^2$-(o-tolyl)oxalamide;

(1S,3aR,6aS)-2-(2-((3-fluorobicyclo[1.1.1]pentan-1-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-N—((S)-3-oxo-1-((S)-2-oxopyrrolidin-3-yl)-4-(trifluoromethoxy)butan-2-yl)-2-(2-oxo-2-((1,1,1-trifluoro-2-methylpropan-2-yl)amino)acetyl)octahydrocyclopenta[c]pyrrole-1-carboxamide;

(S)—N—((S)-3-oxo-1-((S)-2-oxopyrrolidin-3-yl)-4-(trifluoromethoxy)butan-2-yl)-5-(2-oxo-2-(o-tolylamino)acetyl)-5-azaspiro[2.4]heptane-6-carboxamide;

$N^1$—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-$N^2$-(2-fluorophenyl)oxalamide;

2-(2-(tert-butylamino)-2-oxoacetyl)-N—((S)-3-oxo-1-((S)-2-oxopyrrolidin-3-yl)-4-(trifluoromethoxy)butan-2-yl)-2-azaspiro[4.5]decane-3-carboxamide;

5-(difluoromethyl)-N—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)isoxazole-3-carboxamide;

N—((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-2-(trifluoromethyl)thiazole-5-carboxamide;

1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N-(o-tolyl)-1H-1,2,3-triazole-4-carboxamide;

(1R,2S,5S)-3-(2-((1,1-difluoro-2-methylpropan-2-yl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-(benzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

$N^1$—((S)-5,5-difluoro-4,4-dimethyl-1-oxo-1-(((S)-3-oxo-1-((S)-2-oxopyrrolidin-3-yl)-4-(trifluoromethoxy)butan-2-yl)amino)pentan-2-yl)-$N^2$-(3-fluorobicyclo[1.1.1]pentan-1-yl)oxalamide;

$N^1$—((S)-3-cyclobutyl-1-oxo-1-(((S)-3-oxo-1-((S)-2-oxopyrrolidin-3-yl)-4-(trifluoromethoxy)butan-2-yl)amino)propan-2-yl)-$N^2$-(3-fluorobicyclo[1.1.1]pentan-1-yl)oxalamide;

(S)-5-(5-(difluoromethyl)isoxazole-3-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

$N^1$-(3-fluorobicyclo[1.1.1]pentan-1-yl)-$N^2$—((S)-3-(1-methylcyclobutyl)-1-oxo-1-(((S)-3-oxo-1-((S)-2-oxopyrrolidin-3-yl)-4-(trifluoromethoxy)butan-2-yl)amino)propan-2-yl)oxalamide;

(S)—N—((S)-3-oxo-1-((S)-2-oxopyrrolidin-3-yl)-4-(trifluoromethoxy)butan-2-yl)-5-(2-oxo-2-((2-(trifluoromethyl)phenyl)amino)acetyl)-5-azaspiro[2.4]heptane-6-carboxamide;

$N^1$-(1-methylcyclopropyl)-$N^2$-(3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)oxalamide;

$N^1$-cyclopropyl-$N^2$-(3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)oxalamide;

$N^1$-(3-fluorobicyclo[1.1.1]pentan-1-yl)-$N^2$—((S)-3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)oxalamide;

(S)-1-(2-((2-fluorophenyl)amino)-2-oxoacetyl)-N—((S)-3-oxo-1-((S)-2-oxopyrrolidin-3-yl)-4-(trifluoromethoxy)butan-2-yl)azepane-2-carboxamide;

$N^1$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-$N^2$-(1-methylcyclopropyl)oxalamide;

$N^1$-cyclopropyl-$N^2$—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)oxalamide;

(S)-5-(2-((4-chloro-2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

$N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(3-(trifluoromethyl)bicyclo[1.1.1]pentan-1-yl)oxalamide;

(S)-5-(2-((2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-4,4,6-d3-6-carboxamide;

(S)-5-(2-((2,3-difluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((2-fluoro-3-methoxyphenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((2-fluoro-3-(trifluoromethoxy)phenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((2,5-difluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(5-fluoro-1H-indole-2-carbonyl)-N—((R)-3-oxo-1-((S)-2-oxopyrrolidin-3-yl)-4-(trifluoromethoxy)butan-2-yl)octahydrocyclopenta[c]pyrrole-1-carboxamide;

(S)-5-(4-methoxy-1H-indole-2-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((2-chlorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-((3-chlorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(4-methoxy-1H-indole-2-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(6-chlorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)—N—((S)-3-oxo-1-((S)-2-oxopyrrolidin-3-yl)-4-(trifluoromethoxy)butan-2-yl)-5-(2-oxo-2-((2-(trifluoromethoxy)phenyl)amino)acetyl)-5-azaspiro[2.4]heptane-6-carboxamide;

(1S,3aR,6aS)-2-(6-fluorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-(tert-butylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1,3,3-d3-1-carboxamide;

(S)-5-(2-((2-(tert-butyl)phenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(5-fluorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-((2-(tert-butyl)phenyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(2,2-difluoro-2-phenylacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-methyl-2-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

benzyl ((S)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-3,3-dimethyl-1-oxobutan-2-yl)carbamate;

(S)-5-(2,2-difluoro-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2,2,4-trimethylpentanoyl)-5-azaspiro[2.4]heptane-6-carboxamide;

(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl propionate;

(1R,2S,5S)-6,6-dimethyl-N—((S)-3-oxo-1-((S)-2-oxopyrrolidin-3-yl)-4-(trifluoromethoxy)butan-2-yl)-3-((S)-2-phenylpropanoyl)-3-azabicyclo[3.1.0]hexane-2-carboxamide;

(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl 2-phenylacetate;

(S)-5-(1-hydroxy-4,4-dimethylcyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4R)-4-(tert-butyl)-1-((R)-2-hydroxy-4-methylpentanoyl)-N—((S)-3-oxo-1-((S)-2-oxopyrrolidin-3-yl)-4-(trifluoromethoxy)butan-2-yl)piperidine-2-carboxamide;

(S)-1-((R)-2-hydroxy-4-methylpentanoyl)-N—((S)-3-oxo-1-((S)-2-oxopyrrolidin-3-yl)-4-(trifluoromethoxy)butan-2-yl)azepane-2-carboxamide;

(S)-1-((R)-2-hydroxy-4-methylpentanoyl)-4,4-dimethyl-N—((S)-3-oxo-1-((S)-2-oxopyrrolidin-3-yl)-4-(trifluoromethoxy)butan-2-yl)piperidine-2-carboxamide;

(S)-2-((R)-2-hydroxy-4-methylpentanoyl)-N—((S)-3-oxo-1-((S)-2-oxopyrrolidin-3-yl)-4-(trifluoromethoxy)butan-2-yl)-2-azabicyclo[2.2.2]octane-3-carboxamide;

tert-butyl ((R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl)carbamate;

(S)-5-(4,4-difluoro-1-methoxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2-phenylacetyl)-5-azaspiro[2.4]heptane-6-carboxamide;

4-fluoro-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

2-(2-(tert-butylamino)-2-oxoacetyl)-N—((S)-3-oxo-1-((S)-2-oxopyrrolidin-3-yl)-4-(trifluoromethoxy)butan-2-yl)-2-azaspiro[4.4]nonane-3-carboxamide;

(S)-5-((R)-2-hydroxy-4,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(5-chlorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(7-chloro-1H-indole-2-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(R)—N—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-2-hydroxy-4-methylpentanamide;

$N^1$—((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-$N^2$-methyloxalamide;

(S)-5-(4,4-difluoropentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4R)-1-((R)-2-hydroxy-4-methylpentanoyl)-N—((S)-3-oxo-1-((S)-2-oxopyrrolidin-3-yl)-4-(trifluoromethoxy)butan-2-yl)-4-(trifluoromethyl)pyrrolidine-2-carboxamide;

(S)—N—((S)-3-oxo-1-((S)-2-oxopyrrolidin-3-yl)-4-(trifluoromethoxy)butan-2-yl)-5-(2-(trifluoromethyl)benzoyl)-5-azaspiro[2.4]heptane-6-carboxamide;

(S)-5-(2,2-difluorobenzo[d][1,3]dioxole-5-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(3,3-difluorocyclobutyl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-4-(methyl-13C)pentanoyl-1,2,3,4,5-13C5)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(1-methylcyclopentyl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3,3-difluoro-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2,2-difluoro-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((1R,2R)-2-(trifluoromethyl)cyclopropane-1-carbonyl)-5-azaspiro[2.4]heptane-6-carboxamide;

(6S)-5-(3,3-difluorocyclopentane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((E)-4-methylpent-2-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(pentanoyl-d9)-5-azaspiro[2.4]heptane-6-carboxamide;

(S)-5-(hexanoyl-d11)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4-(methyl-d3)pentanoyl-2,2,3,3,4,5,5,5-d8)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-fluoro-2-methylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(butanoyl-d7)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3-(methyl-d3)butanoyl-2,2,3,4,4,4-d6)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(hexanoyl-2,2-d2)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-(2-fluoro-3-methoxyphenyl)-2-hydroxyacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-5-(5,5,5-trifluoro-2-oxo-4-(trifluoromethyl)pentanoyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((R)-5,5,5-trifluoro-2-hydroxy-4-(trifluoromethyl)pentanoyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((S)-5,5,5-trifluoro-2-hydroxy-4-(trifluoromethyl)pentanoyl)-5-azaspiro[2.4]heptane-6-carboxamide;

(S)-5-(2-(isopropylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4R)-1-((R)-2-hydroxy-4-methylpentanoyl)-4-methyl-N—((S)-3-oxo-1-((S)-2-oxopyrrolidin-3-yl)-4-(trifluoromethoxy)butan-2-yl)pyrrolidine-2-carboxamide;

(S)-5-(hexanoyl-5,5,6,6,6-d5)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(hexanoyl-6,6,6-d3)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4S)-1-((R)-2-hydroxy-4-methylpentanoyl)-N—((S)-3-oxo-1-((S)-2-oxopyrrolidin-3-yl)-4-(trifluoromethoxy)butan-2-yl)-4-phenylpyrrolidine-2-carboxamide;

(S)—N—((S)-3-oxo-1-((S)-2-oxopyrrolidin-3-yl)-4-(trifluoromethoxy)butan-2-yl)-5-(pentanoyl-5,5,5-d3)-5-azaspiro[2.4]heptane-6-carboxamide;

(S)-4-methyl-2-((1-methyl-1H-indole)-5-sulfonamido)-N—((S)-3-oxo-1-((S)-2-oxopyrrolidin-3-yl)-4-(2,3,5,6-tetrafluorophenoxy)butan-2-yl)pentanamide;

1-((S)-2-hydroxy-2-phenylacetyl)-N—((S)-3-oxo-1-((S)-2-oxopyrrolidin-3-yl)-4-(trifluoromethoxy)butan-2-yl)piperidine-2-carboxamide;

(2S)-4-(bicyclo[1.1.1]pentan-2-yl)-1-((R)-2-hydroxy-4-methylpentanoyl)-N—((S)-3-oxo-1-((S)-2-oxopyrrolidin-3-yl)-4-(trifluoromethoxy)butan-2-yl)pyrrolidine-2-carboxamide;

(2S,4S)-4-(cyclobutylmethyl)-1-((R)-2-hydroxy-4-methylpentanoyl)-N—((S)-3-oxo-1-((S)-2-oxopyrrolidin-3-yl)-4-(trifluoromethoxy)butan-2-yl)pyrrolidine-2-carboxamide;

(S)—N—((S)-3-oxo-1-((S)-2-oxopyrrolidin-3-yl)-4-(trifluoromethoxy)butan-2-yl)-5-(2-(4-(trifluoromethoxy)phenoxy)acetyl)-5-azaspiro[2.4]heptane-6-carboxamide;

(S)-5-((R)-2-hydroxy-4-methylpentanoyl)-N—((S)-3-oxo-1-((S)-2-oxopiperidin-3-yl)-4-(perfluorophenoxy)butan-2-yl)-5-azaspiro[2.4]heptane-6-carboxamide;

(2S,4S)-1-((S)-2-hydroxy-2-phenylacetyl)-N—((S)-3-oxo-1-((S)-2-oxopiperidin-3-yl)-4-(trifluoromethoxy)butan-2-yl)-4-phenylpyrrolidine-2-carboxamide;

(S)-5-((R)-2-hydroxy-4-methylpentanoyl)-N—((S)-3-oxo-1-((S)-2-oxopiperidin-3-yl)-4-(2,3,5,6-tetrafluorophenoxy)butan-2-yl)-5-azaspiro[2.4]heptane-6-carboxamide;

(S)-5-((R)-2-hydroxy-4-methylpentanoyl)-N—((S)-3-oxo-1-((S)-2-oxopiperidin-3-yl)-4-(2,3,6-trifluorophenoxy)butan-2-yl)-5-azaspiro[2.4]heptane-6-carboxamide;

(1S,3aR,6aS)-2-(6-chlorobenzo[d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

4-fluoro-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide; and N—((S)-4-methyl-1-oxo-1-(((S)-3-oxo-1-((S)-2-oxopyrrolidin-3-yl)-4-(trifluoromethoxy)butan-2-yl)amino)pentan-2-yl)-5-oxaspiro[2.4]heptane-6-carboxamide, or a pharmaceutically acceptable salt thereof.

In some embodiments, the compound or pharmaceutically acceptable salt thereof may demonstrate an EC50 value (e.g., in Hela cells) of from 0.05 μM to less than 0.2 μM. For example, the compound may be selected from the group consisting of:

4-methoxy-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

N—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-1H-indole-2-carboxamide;

(S)-3-((S)-2-(4-methoxy-1H-indole-2-carboxamido)-4-methylpentanamido)-2-oxo-4-((S)-2-oxopyrrolidin-3-yl)butyl 2,6-dichlorobenzoate;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)benzamide;

5-fluoro-N—((S)-1-oxo-1-(((S)-3-oxo-1-((S)-2-oxopyrrolidin-3-yl)-4-(2,3,5,6-tetrafluorophenoxy)butan-2-yl)amino)-3-phenylpropan-2-yl)-1H-indole-2-carboxamide;

5-fluoro-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(naphthalen-2-yl)oxalamide;

$N^1$-(4-chlorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-phenethyloxalamide;

$N^1$-benzyl-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(3-fluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$-(pyridin-2-yl)oxalamide;

$N^1$-(3-chlorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(3,4-difluorophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$-(2-bromophenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-2-((E)-3-(2-fluorophenyl)acrylamido)-4-methyl-N—((S)-3-oxo-1-((S)-2-oxopyrrolidin-3-yl)-4-(2,3,5,6-tetrafluorophenoxy)butan-2-yl)pentanamide;

(S)-2-cinnamamido-4-methyl-N—((S)-3-oxo-1-((S)-2-oxopyrrolidin-3-yl)-4-(2,3,5,6-tetrafluorophenoxy)butan-2-yl)pentanamide;

$N^1$-cyclohexyl-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹-(2,3-difluorophenyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹-(2,5-difluorophenyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-3-((S)-4-methyl-2-(2-oxo-2-(phenylamino)acetamido)pentanamido)-2-oxo-4-((S)-2-oxopyrrolidin-3-yl)butyl diphenylphosphinate;

N¹-(2-cyanophenyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹-(3,3-difluoro-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N²-(2-fluorophenyl)oxalamide;

N¹-(5-fluoro-2-methoxyphenyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹-(cyclopentylmethyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-2-(3-(2-fluorophenyl)ureido)-4-methyl-N—(S)-3-oxo-1-((S)-2-oxopyrrolidin-3-yl)-4-(2,3,5,6-tetrafluorophenoxy)butan-2-yl)pentanamide;

N¹-(4-bromo-3,5-difluorophenyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹-(2-chlorophenyl)-N²—((S)-3-(4,4-difluorocyclohexyl)-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide;

N¹-(2-fluorophenyl)-N²—((S)-3-methyl-1-oxo-1-(((S)-3-oxo-1-((S)-2-oxopyrrolidin-3-yl)-4-(2,3,5,6-tetrafluorophenoxy)butan-2-yl)amino)butan-2-yl)oxalamide;

N¹-(3,3-difluorocyclohexyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹-(4-bromo-2-fluorophenyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹-cyclopropyl-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N²-(1-methylcyclopropyl)oxalamide;

N¹-(tert-butyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N²-(tetrahydro-2H-pyran-4-yl)oxalamide;

N¹-cyclopentyl-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N²-((S)-tetrahydro-2H-pyran-3-yl)oxalamide;

N¹-(2-benzylphenyl)-N²—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide;

N¹-(2-methoxyphenyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹—((S)-1-(((S)-6-(dimethylamino)-2,6-dioxo-1-(2,3,5,6-tetrafluorophenoxy)hexan-3-yl)amino)-4-methyl-1-oxopentan-2-yl)-N²-(2-fluorophenyl)oxalamide;

N¹-cyclobutyl-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N¹-(2-fluorophenyl)-N²—((S)-4-methyl-1-oxo-1-(((S)-3-oxo-1-((S)-2-oxopyrrolidin-3-yl)-4-(2,3,6-trifluorophenoxy)butan-2-yl)amino)pentan-2-yl)oxalamide;

N¹—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N²-((R)-tetrahydro-2H-pyran-3-yl)oxalamide;

N¹-(2-(methoxymethyl)phenyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(S)-2-((R)-2-(3-chlorophenyl)-2-hydroxyacetamido)-4-methyl-N—(S)-3-oxo-1-((S)-2-oxopyrrolidin-3-yl)-4-(2,3,5,6-tetrafluorophenoxy)butan-2-yl)pentanamide;

N¹—((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl)propan-2-yl)-N²-(o-tolyl)oxalamide;

(S)-2-(2-(3,4-dihydroquinolin-1(2H)-yl)-2-oxoacetamido)-4-methyl-N—(S)-3-oxo-1-((S)-2-oxopyrrolidin-3-yl)-4-(2,3,5,6-tetrafluorophenoxy)butan-2-yl)pentanamide;

N¹-(4,4-difluorocyclohexyl)-N²—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)benzo[d][1,3]dioxole-5-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(4-fluorophenyl)-1,3,4-oxadiazole-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-c]pyridine-2-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-3-phenyl-1H-pyrazole-5-carboxamide;

(3S)-3-((S)-2-(4-methoxy-1H-indole-2-carboxamido)-4-methylpentanamido)-2-oxo-4-(2-oxopyrrolidin-3-yl)butyl diphenylphosphinate;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)imidazo[1,2-a]pyridine-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)imidazo[1,2-b]pyridazine-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)indoline-2-carboxamide;

2-methyl-N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;

N¹—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N²-(4-methyltetrahydro-2H-pyran-4-yl)oxalamide;

(R)—N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;

4-methoxy-N—((S)-1-oxo-1-(((S)-3-oxo-1-((S)-2-oxopyrrolidin-3-yl)-4-(trifluoromethoxy)butan-2-yl)amino)-5-phenylpentan-2-yl)-1H-indole-2-carboxamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(2-oxaspiro[3.3]heptan-6-yl)oxalamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(oxetan-3-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1,4-dioxane-2-carboxamide;

N¹-(1-(methoxymethyl)cyclopropyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

(1R,3S,5R)-2-(2-((2-fluorophenyl)amino)-2-oxoacetyl)-N—((S)-3-oxo-1-((S)-2-oxopyrrolidin-3-yl)-4-(trifluoromethoxy)butan-2-yl)-2-azabicyclo[3.1.0]hexane-3-carboxamide;

(1S,3aR,6aS)-2-(2-((1-methylcyclopropyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-6,6-dimethyl-N—((S)-3-oxo-1-((S)-2-oxopyrrolidin-3-yl)-4-(trifluoromethoxy)butan-2-yl)-3-((R)-tetrahydrofuran-2-carbonyl)-3-azabicyclo[3.1.0]hexane-2-carboxamide;

(1S,3aR,6aS)-N—((S)-3-oxo-1-((S)-2-oxopyrrolidin-3-yl)-4-(trifluoromethoxy)butan-2-yl)-2-(5-oxaspiro[2.4]heptane-6-carbonyl)octahydrocyclopenta[c]pyrrole-1-carboxamide;

(1S,3aR,6aS)-N—((S)-3-oxo-1-((S)-2-oxopyrrolidin-3-yl)-4-(trifluoromethoxy)butan-2-yl)-2-((R)-tetrahydrofuran-2-carbonyl)octahydrocyclopenta[c]pyrrole-1-carboxamide;

(S)—N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;

(1R,2S,5S)-3-((R)-1,4-dioxane-2-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-(7-oxabicyclo[2.2.1]heptane-1-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(4-methyl-2-oxabicyclo[2.1.1]hexane-1-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

4-methyl-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-2-oxabicyclo[2.1.1]hexane-1-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(4-(trifluoromethyl)-2-oxabicyclo[2.1.1]hexane-1-carbonyl)-3-azabicyclo[3.1.0]hexane-2-carboxamide;

(1S,3aR,6aS)-2-(4-(difluoromethyl)-2-oxabicyclo[2.1.1]hexane-1-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-(4-(difluoromethyl)-2-oxabicyclo[2.1.1]hexane-1-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-(3,3-difluorotetrahydrofuran-2-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

3,3-difluoro-N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide;

(S)-5-((R)-2-(2-hydroxy-2-methylpropoxy)-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-methoxybutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-2-((R)-2-methoxybutanamido)-4-methyl-N—((S)-3-oxo-1-((S)-2-oxopyrrolidin-3-yl)-4-(trifluoromethoxy)butan-2-yl)pentanamide;

(S)-5-((S)-2-methoxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-2-((R)-2-hydroxy-3,3-dimethylbutanamido)-4-methyl-N—((S)-3-oxo-1-((S)-2-oxopyrrolidin-3-yl)-4-(trifluoromethoxy)butan-2-yl)pentanamide;

(S)-5-((R)-2-hydroxy-3,3-dimethylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-3,3-dimethylbutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((S)-4-fluoro-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-(2-hydroxy-2-methylpropanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3aR,6aS)-2-(2-hydroxy-2-methylpropanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-2-(2-hydroxy-2-methylpropanamido)-4-methyl-N—((S)-3-oxo-1-((S)-2-oxopyrrolidin-3-yl)-4-(trifluoromethoxy)butan-2-yl)pentanamide;

(S)-5-(2-hydroxy-2-methylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-2-((R)-2-hydroxy-3-methylbutanamido)-4-methyl-N—((S)-3-oxo-1-((S)-2-oxopyrrolidin-3-yl)-4-(trifluoromethoxy)butan-2-yl)pentanamide;

(S)-5-((R)-2-hydroxy-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-hydroxy-3-methylbutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((S)-2-hydroxy-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-2-hydroxy-3-methylbutanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-((R)-2-hydroxybutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-2-((R)-2-hydroxybutanamido)-4-methyl-N—((S)-3-oxo-1-((S)-2-oxopyrrolidin-3-yl)-4-(trifluoromethoxy)butan-2-yl)pentanamide;

(1R,2S,5S)-3-((S)-2-hydroxybutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((R)-2-hydroxybutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(R)-2-hydroxy-N—((R)-3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)butanamide;

(1S,3aR,6aS)-2-((R)-2-hydroxybutanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((2R,3R)-2-hydroxy-3-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-4-methyl-N—((S)-3-oxo-1-((S)-2-oxopyrrolidin-3-yl)-4-(trifluoromethoxy)butan-2-yl)-2-((S)-3,3,3-trifluoro-2-hydroxypropanamido)pentanamide;

(S)—N—((S)-3-oxo-1-((S)-2-oxopyrrolidin-3-yl)-4-(trifluoromethoxy)butan-2-yl)-5-((S)-3,3,3-trifluoro-2-hydroxypropanoyl)-5-azaspiro[2.4]heptane-6-carboxamide;

(1R,2S,5S)-6,6-dimethyl-N—((S)-3-oxo-1-((S)-2-oxopyrrolidin-3-yl)-4-(trifluoromethoxy)butan-2-yl)-3-((S)-3,3,3-trifluoro-2-hydroxypropanoyl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-5-((R)-3,3,3-trifluoro-2-hydroxypropanoyl)-5-azaspiro[2.4]heptane-6-carboxamide;

(6S)—N—((S)-3-oxo-1-((S)-2-oxopyrrolidin-3-yl)-4-(trifluoromethoxy)butan-2-yl)-5-(4,4,4-trifluoro-2-hydroxybutanoyl)-5-azaspiro[2.4]heptane-6-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(4,4,4-trifluoro-2-hydroxybutanoyl)-3-azabicyclo[3.1.0]hexane-2-carboxamide;

(S)-5-((R)-3-cyclopropyl-2-hydroxypropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)—N—((S)-3-oxo-1-((S)-2-oxopyrrolidin-3-yl)-4-(trifluoromethoxy)butan-2-yl)-5-(5,5,5-trifluoro-2-hydroxypentanoyl)-5-azaspiro[2.4]heptane-6-carboxamide;

(S)-5-((S)-3-fluoro-2-hydroxypropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-3-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-hydroxy-2-(3,4,5-trifluorophenyl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-(3,4-difluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-(4-fluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-(3-fluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-hydroxy-2-(2-(trifluoromethyl)phenyl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-(2-fluorophenyl)-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-2-phenylacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-2-hydroxy-2-phenylacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2-hydroxy-2-(pyridin-2-yl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxycyclopropane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxycyclobutane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxycyclopentane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-((R)-2-hydroxypentanoyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-((R)-3-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-3-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

methyl ((S)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl)carbamate;

(S)-5-((2-fluorobenzoyl)glycyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-ethylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,3S,5R)-2-((R)-2-hydroxy-4-methylpentanoyl)-5-methyl-N—((S)-3-oxo-1-((S)-2-oxopyrrolidin-3-yl)-4-(trifluoromethoxy)butan-2-yl)-2-azabicyclo[3.1.0]hexane-3-carboxamide;

(S)-5-((R)-4,4-difluoro-2-hydroxybutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,3S,5R)-2-((R)-2-hydroxy-3-methylbutanoyl)-5-methyl-N—((S)-3-oxo-1-((S)-2-oxopyrrolidin-3-yl)-4-(trifluoromethoxy)butan-2-yl)-2-azabicyclo[3.1.0]hexane-3-carboxamide;

(S)-5-(2-(3-(tert-butyl)phenyl)-2-methylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(2-(trifluoromethyl)thiazole-4-carbonyl)-3-azabicyclo[3.1.0]hexane-2-carboxamide;

(1R,2S,5S)-6,6-dimethyl-3-(2-((1-methylcyclopropyl)amino)-2-oxoacetyl)-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(2-(tert-butylamino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-2-(2-oxo-2-((1,1,1-trifluoro-2-methylpropan-2-yl)amino)acetyl)-1,2,3,4-tetrahydroisoquinoline-3-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(2-oxo-2-((1-(trifluoromethyl)cyclopropyl)amino)acetyl)-3-azabicyclo[3.1.0]hexane-2-carboxamide;

(1R,2S,5S)-3-(2-(((3,3-difluorocyclobutyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(6S)-1,1-difluoro-5-(2-((2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-N—((S)-3-oxo-1-((S)-2-oxopyrrolidin-3-yl)-4-(trifluoromethoxy)butan-2-yl)-2-(5-(trifluoromethyl)isoxazole-3-carbonyl)octahydrocyclopenta[c]pyrrole-1-carboxamide;

(1R,2S,5S)-3-(2-(((2,2-difluoropropyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(2-(((3-fluorobicyclo[1.1.1]pentan-1-yl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(3S,4aS,8aS)-N—((S)-3-oxo-1-((S)-2-oxopyrrolidin-3-yl)-4-(trifluoromethoxy)butan-2-yl)-2-(2-oxo-2-((1,1,1-trifluoro-2-methylpropan-2-yl)amino)acetyl)decahydroisoquinoline-3-carboxamide;

(1R,2S,5S)-6,6-dimethyl-N—((S)-3-oxo-1-((S)-2-oxopyrrolidin-3-yl)-4-(trifluoromethoxy)butan-2-yl)-3-(3-(trifluoromethyl)isoxazole-5-carbonyl)-3-azabicyclo[3.1.0]hexane-2-carboxamide;

(1R,2S,5S)-6,6-dimethyl-N—((R)-3-oxo-1-((S)-2-oxopyrrolidin-3-yl)-4-(trifluoromethoxy)butan-2-yl)-3-(3-(trifluoromethyl)isoxazole-5-carbonyl)-3-azabicyclo[3.1.0]hexane-2-carboxamide;

(1S,3aR,6aS)-2-(2-(tert-butylamino)-2-oxoacetyl)-N—((R)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-(cyclopropylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(2S,3aS,7aS)-1-(2-(tert-butylamino)-2-oxoacetyl)-N—((S)-3-oxo-1-((S)-2-oxopyrrolidin-3-yl)-4-(trifluoromethoxy)butan-2-yl)octahydro-1H-indole-2-carboxamide;

5-(2-fluoropropan-2-yl)-N-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)isoxazole-3-carboxamide;

6-(2-(tert-butylamino)-2-oxoacetyl)-2,2-difluoro-N—((S)-3-oxo-1-((S)-2-oxopyrrolidin-3-yl)-4-(trifluoromethoxy)butan-2-yl)-6-azaspiro[3.4]octane-7-carboxamide;

6-(2-(tert-butylamino)-2-oxoacetyl)-N—((S)-3-oxo-1-((S)-2-oxopyrrolidin-3-yl)-4-(trifluoromethoxy)butan-2-yl)-6-azaspiro[3.4]octane-7-carboxamide;

N¹—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N²-(1-(trifluoromethyl)cyclopropyl)oxalamide;

(1R,2S,5S)-3-(2-(((2,2-difluoroethyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(3R,6S)-5-(2-(tert-butylamino)-2-oxoacetyl)-1,1-difluoro-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(2-(tert-butylamino)-2-oxoacetyl)-5,5-difluoro-N—((S)-3-oxo-1-((S)-2-oxopyrrolidin-3-yl)-4-(trifluoromethoxy)butan-2-yl)octahydrocyclopenta[c]pyrrole-1-carboxamide;

N¹-(tert-butyl)-N²—((S)-1-cyclopentyl-2-oxo-2-(((S)-3-oxo-1-((S)-2-oxopyrrolidin-3-yl)-4-(trifluoromethoxy)butan-2-yl)amino)ethyl)-N²-methyloxalamide;

(1S,3aR,6aS)-2-(2-((1-methyl-1H-pyrazol-3-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-6,6-dimethyl-3-(2-((1-methyl-1H-pyrazol-3-yl)amino)-2-oxoacetyl)-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(2-(((3,3-difluorocyclobutyl)amino)-2-oxoacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1S,3S,5S)-2-(2-((2-fluorophenyl)amino)-2-oxoacetyl)-N—((S)-3-oxo-1-((S)-2-oxopyrrolidin-3-yl)-4-(trifluoromethoxy)butan-2-yl)-2-azabicyclo[3.1.0]hexane-3-carboxamide;

(1R,3S,4S)—N—((S)-3-oxo-1-((S)-2-oxopyrrolidin-3-yl)-4-(trifluoromethoxy)butan-2-yl)-2-(2-oxo-2-((2,2,2-trifluoroethyl)amino)acetyl)-2-azabicyclo[2.2.1]heptane-3-carboxamide;

(1S,3aR,6aS)-2-(5-methylisoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(6,7-dihydro-4H-pyrano[3,4-d]isoxazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,2S,5S)-3-(2-(tert-butylamino)-2-oxoacetyl)-N—((S)-3-oxo-1-((S)-2-oxopyrrolidin-3-yl)-4-(trifluoromethoxy)butan-2-yl)-3-azaspiro[bicyclo[3.1.0]hexane-6,1'-cyclopropane]-2-carboxamide;

(1S,3aR,6aS)-2-(2-((1,1-difluoro-2-methylpropan-2-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

tetrahydrofuran-3-yl (1S,3aR,6aS)-1-(((S)-3-oxo-1-((S)-2-oxopyrrolidin-3-yl)-4-(trifluoromethoxy)butan-2-yl)carbamoyl)hexahydrocyclopenta[c]pyrrole-2(1H)-carboxylate;

(1S,2S,5R)-3-(2-((2-fluorophenyl)amino)-2-oxoacetyl)-N—((S)-3-oxo-1-((S)-2-oxopyrrolidin-3-yl)-4-(trifluoromethoxy)butan-2-yl)-3-azabicyclo[3.2.0]heptane-2-carboxamide;

(1S,3aR,6aS)-2-(2-((2-cyanopropan-2-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(5,5-dimethyl-4,5,6,7-tetrahydrobenzo[d]isoxazole-3-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2-oxo-2-((2,2,2-trifluoroethyl)amino)acetyl)-5-azaspiro[2.4]heptane-6-carboxamide;

(S)-5-(2-((1-methylcyclopropyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-1-(2-((2-fluorophenyl)amino)-2-oxoacetyl)-N—((S)-3-oxo-1-((S)-2-oxopyrrolidin-3-yl)-4-(trifluoromethoxy)butan-2-yl)azetidine-2-carboxamide;

$N^1$—((S)-3-(3,4-difluorophenyl)-1-oxo-1-(((S)-3-oxo-1-((S)-2-oxopyrrolidin-3-yl)-4-(trifluoromethoxy)butan-2-yl)amino)propan-2-yl)-$N^2$-(2-fluorophenyl)oxalamide;

(S)—N—((S)-3-oxo-1-((S)-2-oxopyrrolidin-3-yl)-4-(trifluoromethoxy)butan-2-yl)-5-(2-oxo-2-((1,1,1-trifluoro-2-methylpropan-2-yl)amino)acetyl)-5-azaspiro[2.4]heptane-6-carboxamide;

N-(tert-butyl)-1-(4-methyl-1-oxo-1-(((S)-3-oxo-1-((S)-2-oxopyrrolidin-3-yl)-4-(trifluoromethoxy)butan-2-yl)amino)pentan-2-yl)-1H-1,2,3-triazole-4-carboxamide;

(1R,2S,5S)-3-(3,5-difluoro-2-hydroxybenzoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-((S)-3-hydroxy-2-phenylpropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(2-(tert-butylamino)-2-oxoacetyl)-4-fluoro-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-5-(2-((2-chloro-6-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-pentanoyl-5-azaspiro[2.4]heptane-6-carboxamide;

(1S,3aR,6aS)-2-(2-(6-chloropyrazin-2-yl)-2-methoxyacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(R)-1-(2-fluorophenyl)-2-oxo-2-((1S,3aR,6aS)-1-(((S)-3-oxo-1-((S)-2-oxopyrrolidin-3-yl)-4-(trifluoromethoxy)butan-2-yl)carbamoyl)hexahydrocyclopenta[c]pyrrol-2(1H)-yl)ethyl 2-phenylacetate;

(S)-5-(4-fluoro-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3-fluorobicyclo[1.1.1]pentane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((S)-2-phenylpropanoyl)-5-azaspiro[2.4]heptane-6-carboxamide;

(1R,2S,5S)-3-(4,4-difluoro-1-hydroxycyclohexane-1-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)-5-(2,2-difluoroacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-1-((R)-2-hydroxy-4-methylpentanoyl)-N—((S)-3-oxo-1-((S)-2-oxopyrrolidin-3-yl)-4-(trifluoromethoxy)butan-2-yl)piperidine-2-carboxamide;

(1R,2S,5S)-3-((R)-2-hydroxy-4-methylpentanoyl)-N—((S)-3-oxo-1-((S)-2-oxopyrrolidin-3-yl)-4-(trifluoromethoxy)butan-2-yl)-3-azabicyclo[3.2.1]octane-2-carboxamide;

(S)-6-((R)-2-hydroxy-4-methylpentanoyl)-N—((S)-3-oxo-1-((S)-2-oxopyrrolidin-3-yl)-4-(trifluoromethoxy)butan-2-yl)-6-azaspiro[2.5]octane-5-carboxamide;

tert-butyl methyl((R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl)carbamate;

(S)-5-(2-isopropoxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-hydroxy-4-(trifluoromethyl)cyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-3-((S)-2-(2-((2-fluorophenyl)amino)-2-oxoacetamido)-4-methylpentanamido)-2-oxo-4-((S)-2-oxopyrrolidin-3-yl)butyl methyl(phenyl)phosphinate;

(1S,3aR,6aS)-N—((S)-3-oxo-1-((S)-2-oxopyrrolidin-3-yl)-4-(trifluoromethoxy)butan-2-yl)-2-(2-oxo-2-((1-(trifluoromethyl)cyclopropyl)amino)acetyl)octahydrocyclopenta[c]pyrrole-1-carboxamide;

(S)-5-(methyl-D-leucyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(4,4-difluorocyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxypent-4-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-acetyl-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-pivaloyl-5-azaspiro[2.4]heptane-6-carboxamide;

(S)-5-((R,E)-2-hydroxy-5-(4-methoxyphenyl)pent-4-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R,E)-5-(4-fluorophenyl)-2-hydroxypent-4-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxy-4-methylpentanoyl)-N—((R)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((N-phenylsulfamoyl)glycyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((2,2,2-trifluoroethyl)glycyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2-(2,2,2-trifluoroethoxy)acetyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2-oxo-2-phenylacetyl)-5-azaspiro[2.4]heptane-6-carboxamide;

(S)-5-(2-(methylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)—N—((S)-3-oxo-1-((S)-2-oxopyrrolidin-3-yl)-4-(trifluoromethoxy)butan-2-yl)-5-(3,3,3-trifluoro-2-hydroxy-2-phenylpropanoyl)-5-azaspiro[2.4]heptane-6-carboxamide;

(S)-5-(4,4-difluorobutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(3,3,4,4-tetrafluorobutanoyl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-propionyl-5-azaspiro[2.4]heptane-6-carboxamide;

(S)-5-(but-3-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(pent-4-enoyl)-5-azaspiro[2.4]heptane-6-carboxamide;

(S)-5-benzoyl-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(1-isobutyl-1H-1,2,3-triazole-4-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-1-((R)-2-hydroxy-4-methylpentanoyl)-N—((S)-3-oxo-1-((S)-2-oxopyrrolidin-3-yl)-4-(trifluoromethoxy)butan-2-yl)pyrrolidine-2-carboxamide;

(S)-5-((R)-2-hydroxypropanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3,5-difluorobenzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((S)-3,3,3-trifluoro-2-hydroxy-2-methylpropanoyl)-5-azaspiro[2.4]heptane-6-carboxamide;

(S)-5-(4-chloro-2-fluorobenzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-isobutyryl-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-hexanoyl-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(3,3,4,4-tetrafluoropentanoyl)-5-azaspiro[2.4]heptane-6-carboxamide;

(1R,2S,5S)-3-((R)-2-hydroxy-2-phenylacetyl)-6,6-dimethyl-N—((R)-3-oxo-1-((S)-2-oxopyrrolidin-3-yl)-4-(trifluoromethoxy)butan-2-yl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-5-((R)-2-(trifluoromethoxy)butanoyl)-5-azaspiro[2.4]heptane-6-carboxamide;

(S)-5-(3-hydroxy-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3,3-difluorocyclobutane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((R)-3,3,3-trifluoro-2-hydroxy-2-methylpropanoyl)-5-azaspiro[2.4]heptane-6-carboxamide;

(S)-5-(cyclopentanecarbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(2S,4R)-1-acetyl-N—((S)-3-oxo-1-((S)-2-oxopyrrolidin-3-yl)-4-(trifluoromethoxy)butan-2-yl)-4-(trifluoromethyl)pyrrolidine-2-carboxamide;

(S)-5-((R)-2-hydroxy-4-methylpentanoyl)-N—((R)-3-oxo-1-((R)-2-oxopyrrolidin-3-yl)-4-(trifluoromethoxy)butan-2-yl)-5-azaspiro[2.4]heptane-6-carboxamide;

(S)-5-((R)-2-hydroxy-4-methylpentanoyl)-N—((R)-3-oxo-1-((R)-2-oxopyrrolidin-3-yl)-4-(trifluoromethoxy)butan-2-yl)-5-azaspiro[2.4]heptane-6-carboxamide;

(S)-5-((S)-2-hydroxy-4-methylpentanoyl)-N—((R)-3-oxo-1-((R)-2-oxopyrrolidin-3-yl)-4-(trifluoromethoxy)butan-2-yl)-5-azaspiro[2.4]heptane-6-carboxamide;

(S)-5-((S)-2-hydroxy-4-methylpentanoyl)-N—((S)-3-oxo-1-((R)-2-oxopyrrolidin-3-yl)-4-(trifluoromethoxy)butan-2-yl)-5-azaspiro[2.4]heptane-6-carboxamide;

(S)-5-(2-methylpropanoyl-2-d)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(methyl-d3)propanoyl-3,3,3-d3)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(cyclopropylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-2,4-dimethylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2-(ethylamino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(R)-5-(4,4-difluoropentanoyl)-N—((R)-3-oxo-1-((S)-2-oxopyrrolidin-3-yl)-4-(trifluoromethoxy)butan-2-yl)-5-azaspiro[2.4]heptane-6-carboxamide;

(S)-4,4-difluoro-1-((R)-2-hydroxy-4-methylpentanoyl)-N—((S)-3-oxo-1-((S)-2-oxopyrrolidin-3-yl)-4-(trifluoromethoxy)butan-2-yl)pyrrolidine-2-carboxamide;

(S)-5-((R)-4-fluoro-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(2,2-difluoro-3-hydroxybutanoyl)-N—((S)-3-oxo-1-((S)-2-oxopyrrolidin-3-yl)-4-(trifluoromethyl)butan-2-yl)-5-azaspiro[2.4]heptane-6-carboxamide;

(S)-5-((R)-2-cyclobutyl-2-hydroxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(6S)-5-(3-fluoro-2-hydroxy-3-methylbutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(butanoyl-4,4,4-d3)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((R)-2-hydroxypentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

1-((S)-2-hydroxy-2-phenylacetyl)-N—((S)-3-oxo-1-((S)-2-oxopyrrolidin-3-yl)-4-(trifluoromethoxy)butan-2-yl)azepane-2-carboxamide;

6-((R)-2-hydroxy-4-methylpentanoyl)-N—((S)-3-oxo-1-((S)-2-oxopyrrolidin-3-yl)-4-(trifluoromethoxy)butan-2-yl)-6-azaspiro[3.4]octane-7-carboxamide;

(2S,4R)-1-((S)-2-hydroxy-2-phenylacetyl)-N—((S)-3-oxo-1-((S)-2-oxopyrrolidin-3-yl)-4-(trifluoromethoxy)butan-2-yl)-4-(trifluoromethyl)pyrrolidine-2-carboxamide;

(2S,4S)-1-((R)-2-hydroxy-2-phenylacetyl)-N—((S)-3-oxo-1-((S)-2-oxopyrrolidin-3-yl)-4-(trifluoromethoxy)butan-2-yl)-4-phenylpyrrolidine-2-carboxamide;

(S)-1-((R)-2-hydroxy-4-methylpentanoyl)-5,5-dimethyl-N—((S)-3-oxo-1-((S)-2-oxopyrrolidin-3-yl)-4-(trifluoromethoxy)butan-2-yl)pyrrolidine-2-carboxamide, or a pharmaceutically acceptable salt thereof.

In some embodiments, the compound or pharmaceutically acceptable salt thereof may demonstrate an EC50 value (e.g., in Hela cells) of from 0.2 µM to less than 0.5 µM. For example, the compound may be selected from the group consisting of:

(S)-3-((S)-2-(4-methoxy-1H-indole-2-carboxamido)-4-methylpentanamido)-2-oxo-4-((S)-2-oxopyrrolidin-3-yl)butyl 2,6-dichlorobenzoate;

N—((S)-1-(((S)-4-(2,6-difluorophenoxy)-3-oxo-1-((S)-2-oxopyrrolidin-3-yl)butan-2-yl)amino)-4-methyl-1-oxopentan-2-yl)-4-methoxy-1H-indole-2-carboxamide;

5-fluoro-N—((S)-5-methyl-1-oxo-1-(((S)-3-oxo-1-((S)-2-oxopyrrolidin-3-yl)-4-(2,3,5,6-tetrafluorophenoxy)butan-2-yl)amino)hexan-2-yl)-1H-indole-2-carboxamide;

benzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

5-fluoro-N—((S)-1-oxo-1-(((S)-3-oxo-1-((S)-2-oxopyrrolidin-3-yl)-4-(2,3,5,6-tetrafluorophenoxy)butan-2-yl)amino)-3-(4-(trifluoromethyl)phenyl)propan-2-yl)-1H-indole-2-carboxamide;

5-fluoro-N-((2S)-3-(4-methoxyphenyl)-1-oxo-1-(((2S)-3-oxo-1-(2-oxopyrrolidin-3-yl)-4-(2,3,5,6-tetrafluorophenoxy)butan-2-yl)amino)propan-2-yl)-1H-indole-2-carboxamide;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)quinoline-2-carboxamide;

3-chlorobenzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

4-fluorobenzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)benzo[d][1,3]dioxole-5-carboxamide;

(R)—N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)tetrahydrofuran-2-carboxamide;

(S)-3-((S)-2-(5-fluoro-1H-indole-2-carboxamido)-4-methylpentanamido)-2-oxo-4-((S)-2-oxopyrrolidin-3-yl)butyl diphenylphosphinate;

$N^1$-(2-benzylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

$N^1$—((S)-1-oxo-1-(((S)-3-oxo-1-((S)-2-oxopyrrolidin-3-yl)-4-(2,3,5,6-tetrafluorophenoxy)butan-2-yl)amino)pent-4-en-2-yl)-$N^2$-phenyloxalamide;

$N^1$-(2,5-dichlorobenzyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

5-(2-fluorophenyl)-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)isoxazole-3-carboxamide;

N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-5-phenylisoxazole-3-carboxamide;

$N^1$-(4-fluoro-2-methylphenyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide;

(2S)-4-methyl-N—((S)-3-oxo-1-((S)-2-oxopyrrolidin-3-yl)-4-(2,3,5,6-tetrafluorophenoxy)butan-2-yl)-2-(3,3,3-trifluoro-2-((2-fluorophenyl)amino)propanamido)pentanamide;

$N^1$-methyl-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^1$-(o-tolyl)oxalamide;

$N^1$—((S)-4-cyclohexyl-1-oxo-1-(((S)-3-oxo-1-((S)-2-oxopyrrolidin-3-yl)-4-(2,3,5,6-tetrafluorophenoxy)butan-2-yl)amino)butan-2-yl)-$N^2$-(2-fluorophenyl)oxalamide;

N—((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-5-(2-fluorophenyl)isoxazole-3-carboxamide;

5-methyl-N—((S)-3-methyl-1-(((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)amino)-1-oxobutan-2-yl)isoxazole-3-carboxamide;

N—((S)-3,3-dimethyl-1-(((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)amino)-1-oxobutan-2-yl)-5-methylisoxazole-3-carboxamide;

$N^1$—((S)-3,3-dimethyl-1-oxo-1-(((S)-3-oxo-1-((S)-2-oxopyrrolidin-3-yl)-4-(2,3,5,6-tetrafluorophenoxy)butan-2-yl)amino)butan-2-yl)-$N^2$-(2-fluorophenyl)oxalamide;

$N^1$-(2-fluorophenyl)-$N^2$—(S)-4-methyl-1-oxo-1-(((S)-3-oxo-1-((S)-2-oxopyrrolidin-3-yl)-4-(2,4,6-trifluorophenoxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$—((S)-1,2,3,4-tetrahydronaphthalen-1-yl)oxalamide;

(3R,3aS,6aR)-hexahydrofuro[2,3-b]furan-3-yl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

N¹-(tert-butyl)-N²-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)oxalamide;

N—((S)-1-(((S)-4-(difluoromethoxy)-3-oxo-1-((S)-2-oxopyrrolidin-3-yl)butan-2-yl)amino)-4-methyl-1-oxopentan-2-yl)-4-methoxy-1H-indole-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[3,2-c]pyridine-2-carboxamide;

N¹-(2-fluorophenyl)-N²—((S)-1-(((S)-6-guanidino-2-oxo-1-(2,3,5,6-tetrafluorophenoxy)hexan-3-yl)amino)-4-methyl-1-oxopentan-2-yl)oxalamide;

N¹—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N²-(3-(methoxymethyl)oxetan-3-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[3,2-b]pyridine-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-b]pyridine-3-carboxamide;

N¹—((S)-4-methyl-1-oxo-1-(((S)-3-oxo-1-((S)-2-oxopyrrolidin-3-yl)-4-(trifluoromethoxy)butan-2-yl)amino)pentan-2-yl)-N²-(3-methylpyrrolidin-3-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[3,2-b]pyridine-3-carboxamide;

(1S,3aR,6aS)-N—((S)-3-oxo-1-((S)-2-oxopyrrolidin-3-yl)-4-(trifluoromethoxy)butan-2-yl)-2-(1-(2,2,2-trifluoroacetamido)cyclobutane-1-carbonyl)octahydrocyclopenta[c]pyrrole-1-carboxamide;

(1R,2S,5S)-3-((S)-3,3-dimethyl-2-((R)-tetrahydrofuran-2-carboxamido)butanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-5-((R)-tetrahydrofuran-2-carbonyl)-5-azaspiro[2.4]heptane-6-carboxamide;

(1R,2S,5S)-3-((S)-1,4-dioxane-2-carbonyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(6S)-5-(2-methyltetrahydrofuran-2-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-4-(2,2,2-trifluoroacetamido)-2-oxabicyclo[2.1.1]hexane-1-carboxamide;

(S)-5-(4-(difluoromethyl)-2-oxabicyclo[2.1.1]hexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(2,2-dimethoxyacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(2R)-2-hydroxy-N-(3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)butanamide;

(2S,3aS,7aS)-1-((R)-2-hydroxybutanoyl)-N—((S)-3-oxo-1-((S)-2-oxopyrrolidin-3-yl)-4-(trifluoromethoxy)butan-2-yl)octahydro-1H-indole-2-carboxamide;

(S)-2-((S)-3-fluoro-2-hydroxypropanamido)-4-methyl-N—((S)-3-oxo-1-((S)-2-oxopyrrolidin-3-yl)-4-(trifluoromethoxy)butan-2-yl)pentanamide;

(S)-5-(4-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((methylcarbamoyl)-D-leucyl)-N—((S)-3-oxo-1-((S)-2-oxopyrrolidin-3-yl)-4-(trifluoromethoxy)butan-2-yl)-5-azaspiro[2.4]heptane-6-carboxamide;

(1R,2S,5S)-3-((R)-2-aminobutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

(1R,2S,5S)-3-(3-(4,4-difluoropiperidin-1-yl)-2-(2,2,2-trifluoroacetamido)propanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide;

N—((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(phenylamino)-1,3,4-oxadiazole-2-carboxamide;

(S)-4-methyl-2-((1-methyl-1H-indole)-5-sulfonamido)-N—((S)-3-oxo-1-((S)-2-oxopyrrolidin-3-yl)-4-(trifluoromethoxy)butan-2-yl)pentanamide;

(S)-4-methyl-2-((2-oxo-1,2-dihydroquinolin-3-yl)amino)-N—((S)-3-oxo-1-((S)-2-oxopyrrolidin-3-yl)-4-(trifluoromethoxy)butan-2-yl)pentanamide;

(1S,2S,5R)-3-(2-(tert-butylamino)-2-oxoacetyl)-N—((S)-3-oxo-1-((S)-2-oxopyrrolidin-3-yl)-4-(trifluoromethoxy)butan-2-yl)-3-azabicyclo[3.1.0]hexane-2-carboxamide;

N¹-(3-fluorobicyclo[1.1.1]pentan-1-yl)-N²-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)oxalamide;

(1S,3aR,6aS)-2-(2-((2,2-difluoroethyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1R,3S,5R)-2-(2-(tert-butylamino)-2-oxoacetyl)-N—((S)-3-oxo-1-((S)-2-oxopyrrolidin-3-yl)-4-(trifluoromethoxy)butan-2-yl)-2-azabicyclo[3.1.0]hexane-3-carboxamide;

(1S,3S,4R)-2-(2-((1-methylcyclopropyl)amino)-2-oxoacetyl)-N—((S)-3-oxo-1-((S)-2-oxopyrrolidin-3-yl)-4-(trifluoromethoxy)butan-2-yl)-2-azabicyclo[2.2.1]heptane-3-carboxamide;

(1S,3aR,6aS)-2-(2-(((1R,5S,6r)-3-oxabicyclo[3.1.0]hexan-6-yl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,2S,5R)-3-(2-(tert-butylamino)-2-oxoacetyl)-N—((S)-3-oxo-1-((S)-2-oxopyrrolidin-3-yl)-4-(trifluoromethoxy)butan-2-yl)-3-azabicyclo[3.2.0]heptane-2-carboxamide;

(R)-1-(2-(tert-butylamino)-2-oxoacetyl)-2-(cyclopropylmethyl)-N—((S)-3-oxo-1-((S)-2-oxopyrrolidin-3-yl)-4-(trifluoromethoxy)butan-2-yl)pyrrolidine-2-carboxamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1,2,4-oxadiazole-3-carboxamide;

(S)-5-(2-(((3,3-difluorocyclobutyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(3-fluoropicolinoyl)-N—((S)-3-oxo-1-((S)-2-oxopyrrolidin-3-yl)-4-(trifluoromethoxy)butan-2-yl)-5-azaspiro[2.4]heptane-6-carboxamide;

(R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl isobutyrate;

(S)-5-(D-leucyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-3-((S)-4-methyl-2-(2-oxo-2-(phenylamino)acetamido)pentanamido)-2-oxo-4-((S)-2-oxopyrrolidin-3-yl)butyl methyl(phenyl)phosphinate;

(1R,2S,5S)-3-(5-(2-fluoropropan-2-yl)isoxazole-3-carbonyl)-6,6-dimethyl-N—((S)-3-oxo-1-((S)-2-oxopyrrolidin-3-yl)-4-(2,3,5,6-tetrafluorophenoxy)butan-2-yl)-3-azabicyclo[3.1.0]hexane-2-carboxamide;

(S)—N—((S)-3-oxo-1-((S)-2-oxopyrrolidin-3-yl)-4-(trifluoromethoxy)butan-2-yl)-5-(3-((N-phenylsulfamoyl)amino)propanoyl)-5-azaspiro[2.4]heptane-6-carboxamide;

(S)-5-((R,E)-2-hydroxy-6-(methylsulfonamido)hex-4-enoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-((S)-tetrahydrofuran-2-carbonyl)-5-azaspiro[2.4]heptane-6-carboxamide;

(S)-5-(4,4-difluoro-1-(2,2,2-trifluoroacetamido)cyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(tetrahydro-2H-pyran-4-carbonyl)-5-azaspiro[2.4]heptane-6-carboxamide;

(S)-5-((N,N-dimethylsulfamoyl)glycyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(N—(N,N-dimethylsulfamoyl)-N-methylglycyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)—N—((S)-3-oxo-1-((S)-2-oxopyrrolidin-3-yl)-4-(trifluoromethoxy)butan-2-yl)-5-(2,2,2-trifluoroacetyl)-5-azaspiro[2.4]heptane-6-carboxamide;

(S)-5-butyryl-N—((S)-3-oxo-1-((S)-2-oxopyrrolidin-3-yl)-4-(trifluoromethoxy)butan-2-yl)-5-azaspiro[2.4]heptane-6-carboxamide;

(S)-2-acetamido-4-methyl-N—((S)-3-oxo-1-((S)-2-oxopyrrolidin-3-yl)-4-(trifluoromethoxy)butan-2-yl)pentanamide;

(S)-5-(2,4-difluorobenzoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((2R,3S)-2,3-dihydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-((S)-2-hydroxy-4-methylpentanoyl)-N—((R)-3-oxo-1-((R)-2-oxopyrrolidin-3-yl)-4-(trifluoromethoxy)butan-2-yl)-5-azaspiro[2.4]heptane-6-carboxamide;

$N^1$—((S)-1-(((S)-4-hydroxy-3-oxo-1-((S)-2-oxopiperidin-3-yl)butan-2-yl)amino)-4,4-dimethyl-1-oxopentan-2-yl)-$N^2$-(6-(trifluoromethyl)pyridin-2-yl)oxalamide;

(6S)-5-(2-methoxybutanoyl)-N—((S)-3-oxo-1-((S)-2-oxopyrrolidin-3-yl)-4-(trifluoromethoxy)butan-2-yl)-5-azaspiro[2.4]heptane-6-carboxamide;

(S)-5-(acetyl-$d^3$)—N—((S)-3-oxo-1-((S)-2-oxopyrrolidin-3-yl)-4-(trifluoromethoxy)butan-2-yl)-5-azaspiro[2.4]heptane-6-carboxamide;

(R)-2-hydroxy-4-methyl-N—((S)-4-methyl-1-oxo-1-(((S)-3-oxo-1-((S)-2-oxopyrrolidin-3-yl)-4-(trifluoromethoxy)butan-2-yl)amino)pentan-2-yl)pentanamide; and $N^1$-(2-fluorophenyl)-$N^2$—((S)-4-methyl-1-oxo-1-(((S)-3-oxo-1-((S)-2-oxopyrrolidin-3-yl)-4-((2-(trifluoromethyl)pyrimidin-4-yl)oxy)butan-2-yl)amino)pentan-2-yl)oxalamide, or a pharmaceutically acceptable salt thereof.

In some embodiments, the compound or pharmaceutically acceptable salt thereof may demonstrate an EC50 value (e.g., in Hela cells) of from 0.5 μM to 1 μM. For example, the compound may be selected from the group consisting of:

N—((S)-1-(((S)-4-(2,6-difluorophenoxy)-3-oxo-1-((S)-2-oxopyrrolidin-3-yl)butan-2-yl)amino)-4-methyl-1-oxopentan-2-yl)-4-methoxy-1H-indole-2-carboxamide;

5-fluoro-N—((S)-1-oxo-1-(((S)-3-oxo-1-((S)-2-oxopyrrolidin-3-yl)-4-(2,3,5,6-tetrafluorophenoxy)butan-2-yl)amino)-4-phenylbutan-2-yl)-1H-indole-2-carboxamide;

N—((S)-4,4-dimethyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-5-fluoro-1H-indole-2-carboxamide;

5-fluoro-N—((S)-4-fluoro-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide;

1-(cyclopentanecarbonyl)-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)piperidine-4-carboxamide;

(S)-1-(2-((2-fluorophenyl)amino)-2-oxoacetyl)-N—((S)-3-oxo-1-((S)-2-oxopyrrolidin-3-yl)-4-(2,3,5,6-tetrafluorophenoxy)butan-2-yl)pyrrolidine-2-carboxamide;

5-methyl-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)isoxazole-3-carboxamide;

(S)-tetrahydrofuran-3-yl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

$N^1$—((S)-1-(((S)-1-(1H-imidazol-5-yl)-3-oxo-4-(2,3,5,6-tetrafluorophenoxy)butan-2-yl)amino)-4-methyl-1-oxopentan-2-yl)-$N^2$-(2-fluorophenyl)oxalamide;

$N^1$—((S)-1-(((R)-1-(1H-imidazol-5-yl)-3-oxo-4-(2,3,5,6-tetrafluorophenoxy)butan-2-yl)amino)-4-methyl-1-oxopentan-2-yl)-$N^2$-(2-fluorophenyl)oxalamide;

cyclopentylmethyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate;

$N^1$-(2-fluorophenyl)-$N^2$—((S)-4-methyl-1-oxo-1-(((S)-3-oxo-1-((S)-2-oxopyrrolidin-3-yl)-4-(5-(trifluoromethyl)isoxazol-3-yl)oxy)butan-2-yl)amino)pentan-2-yl)oxalamide;

$N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$—((R)-1,2,3,4-tetrahydronaphthalen-1-yl)oxalamide;

$N^1$-(2-fluorophenyl)-$N^2$—((S)-3-methyl-1-(1-((S)-3-oxo-1-((S)-2-oxopyrrolidin-3-yl)-4-(2,3,5,6-tetrafluorophenoxy)butan-2-yl)-1H-1,2,3-triazol-4-yl)butyl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)-5-oxotetrahydrofuran-2-carboxamide;

$N^1$-(2-fluorophenyl)-$N^2$-((2S)-1-oxo-1-(((S)-3-oxo-1-((S)-2-oxopyrrolidin-3-yl)-4-(trifluoromethoxy)butan-2-yl)amino)-3-(2-oxopyrrolidin-3-yl)propan-2-yl)oxalamide;

N—((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-3-carboxamide;

N¹-(1-(hydroxymethyl)cyclopropyl)-N²—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide;

N-((1R,2R)-2-ethyl-1-(((S)-3-oxo-1-((S)-2-oxopyrrolidin-3-yl)-4-(trifluoromethoxy)butan-2-yl)carbamoyl)cyclopropyl)-5-fluoro-1H-indole-2-carboxamide;

N¹-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)-N²-(2,2,2-trifluoroethyl)oxalamide;

(2R)—N-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)tetrahydrofuran-2-carboxamide;

(R)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl tert-butylcarbamate;

(R)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl ethylcarbamate;

(2S,3aS,6aS)-1-((R)-2-hydroxybutanoyl)-N—((S)-3-oxo-1-((S)-2-oxopyrrolidin-3-yl)-4-(trifluoromethoxy)butan-2-yl)octahydrocyclopenta[b]pyrrole-2-carboxamide;

(6S)-5-(2-hydroxy-2-(pyridin-3-yl)acetyl)-N—((S)-3-oxo-1-((S)-2-oxopyrrolidin-3-yl)-4-(trifluoromethoxy)butan-2-yl)-5-azaspiro[2.4]heptane-6-carboxamide;

(1S,3aR,6aS)-2-(methylprolyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-(cyclohexylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(R)-6-(2-(tert-butylamino)-2-oxoacetyl)-N—((S)-3-oxo-1-((S)-2-oxopyrrolidin-3-yl)-4-(trifluoromethoxy)butan-2-yl)-2-oxa-6-azaspiro[3.4]octane-7-carboxamide;

2-(2-(tert-butylamino)-2-oxoacetyl)-N—((S)-3-oxo-1-((S)-2-oxopyrrolidin-3-yl)-4-(trifluoromethoxy)butan-2-yl)-8-oxa-2-azaspiro[4.5]decane-3-carboxamide;

2-(2-((2-fluorophenyl)amino)-2-oxoacetyl)-N—((S)-3-oxo-1-((S)-2-oxopyrrolidin-3-yl)-4-(trifluoromethoxy)butan-2-yl)-8-oxa-2-azaspiro[4.5]decane-3-carboxamide;

(1S,3aR,6aS)-2-(1-methyl-1H-pyrazole-3-carbonyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(S)-1-(2-((3,3-difluorocyclobutyl)amino)-2-oxoacetyl)-4,4-dimethyl-N—((S)-3-oxo-1-((S)-2-oxopyrrolidin-3-yl)-4-(trifluoromethoxy)butan-2-yl)pyrrolidine-2-carboxamide;

(1S,3aR,6aS)-2-(2-morpholino-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide;

(1S,3aR,6aS)-2-(2-(tert-butylamino)-2-oxoacetyl)-N—((S)-3-oxo-1-(2-oxo-1,2-dihydropyridin-3-yl)-4-(trifluoromethoxy)butan-2-yl)octahydrocyclopenta[c]pyrrole-1-carboxamide;

(S)-5-(2-((2-methoxyphenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

(R)-5-(2-((2-fluorophenyl)amino)-2-oxoacetyl)-N—((S)-3-oxo-1-((S)-2-oxopyrrolidin-3-yl)-4-(trifluoromethoxy)butan-2-yl)-5-azaspiro[2.4]heptane-6-carboxamide;

N¹-(2-fluorophenyl)-N²—((S)-4-methyl-1-(((S)-5-(methylthio)-2-oxo-1-(2,3,5,6-tetrafluorophenoxy)pentan-3-yl)amino)-1-oxopentan-2-yl)oxalamide;

N¹-(2-fluorophenyl)-N²—((S)-4-methyl-1-(((S)-5-(methylsulfonyl)-2-oxo-1-(2,3,5,6-tetrafluorophenoxy)pentan-3-yl)amino)-1-oxopentan-2-yl)oxalamide;

(S)-5-((N-methylsulfamoyl)glycyl)-N—((S)-3-oxo-1-((S)-2-oxopyrrolidin-3-yl)-4-(trifluoromethoxy)butan-2-yl)-5-azaspiro[2.4]heptane-6-carboxamide; and (S)-2-hydroxy-4-methyl-N—((S)-3-oxo-1-((S)-2-oxopyrrolidin-3-yl)-4-(trifluoromethoxy)butan-2-yl)pentanamide, or a pharmaceutically acceptable salt thereof.

Pharmaceutical Composition and Utility Thereof

The disclosure also provides a pharmaceutical composition comprising a therapeutically effective amount of one or more compounds according to Formula I or a pharmaceutically acceptable salt, stereoisomer, and/or tautomer thereof in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in Table 1 or a pharmaceutically acceptable salt, stereoisomer, and/or tautomer thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The present disclosure, in providing Formula (I) compounds exhibiting high antiviral potencies, also provides a method for inhibiting the main protease ($M^{pro}$) of severe acute respiratory syndrome Coronavirus-2 (SARS-CoV-2), comprising contacting $M^{pro}$ with a Formula (I) compound or pharmaceutically acceptable thereof. The contacting can occur in vivo, such as a in a host organism, or it can occur in vitro or ex vivo. In an additional embodiment, a compound or pharmaceutically acceptable salt as described herein is useful in a method for treating COVID-19 in a subject by administering to the subject the compound or salt by any administration route described herein. In an embodiment, the administration is by oral dosing. The method also is useful in a prophylaxis regimen for preventing a subject from developing COVID-19, such as in compromised subject populations, where viral loads are high, or a combination thereof.

The following non-limiting examples illustrate additional embodiments of the present disclosure.

EXAMPLES

Abbreviations: ACN or MeCN for acetonitrile; AcOH or HOAc for acetic acid; aq. for aqueous; BnOH for benzyl alcohol; Boc for tert-butoxycarbonyl; BOP for (benzotriazol-1-yloxy)tris(dimethylamino)phosphonium hexafluorophosphate; Bu for butyl; dba for dibenzylideneacetone; CDI for 1,1'-carbonyldiimidazole; conc. for concentrated; DAST for diethylaminosulfur trifluoride; DCC for N,N-dicyclohexylcarbodiimide; DCM for dichloromethane or methylene chloride; DIC for N,N-diisopropylcarbodiimide; DIEA for N,N-diisopropylethylamine; DIPEA for diisopropylethylamine; DMF for N,N-dimethylformamide; DMSO for dimethyl sulfoxide; DMF for N,N-dimethylformamide; eq. or equiv. for equivalent or equivalents; EDCI for N-(3-dimethylaminopropyl)-N'-ethylcarbodiimide hydrochloride; Et for ethyl; Et$_2$O for diethyl ether; EtOAc for ethyl acetate; EtOH for ethanol; h for hour or hours; HATU for (1-[bis(dimethylamino)methylene]-1H-1,2,3-triazolo[4,5-b]pyridinium 3-oxide hexafluorophosphate; HBTU for N,N,N',N'-tetramethyl-O-(1H-benzotriazol-1-yl)uronium hexafluorophosphate; HOBt for 1-hydroxybenzotriazole; IPA for isopropyl alcohol; LCMS for liquid chromatography-mass spectrometry; MeOH for methanol; MS for mass spectrometry; NMI for 1-methylimidazole; NMM for N-methylmorpholine; NMR for nuclear magnetic resonance; min for minute or minutes; Py for pyridine; PyBOP for benzotriazole-1-yl-oxy-tris-pyrrolidino-phosphonium hexafluorophosphate; quant. for quantitative; R$_f$ for retention factor; rt or RT for room temperature (ambient temperature); sat. for saturated; SFC for supercritical fluid chromatography; soln. for solution; SPhos for 2-dicyclohexylphosphino-2',6'-dimethoxybiphenyl; t-Bu for tert-butyl; TCFH for chloro-N,N,N',N'-tetramethylformamidinium hexafluorophosphate; TEA for triethylamine; TFA for trifluoroacetic acid; TLC for thin-layer chromatography; TMSCF$_2$Br for (bromodifluoromethyl)trimethylsilane; TMSCN for trimethylsilyl cyanide; TMSCI for chlorotrimethylsilane; and THE for tetrahydrofuran.

General Synthetic Schemes

Compounds of Formula (I) are synthesized according to the following general schemes or its variations familiar to those skilled in the art, or by adaptation of, and as exemplified in the specific synthesis examples that follow:

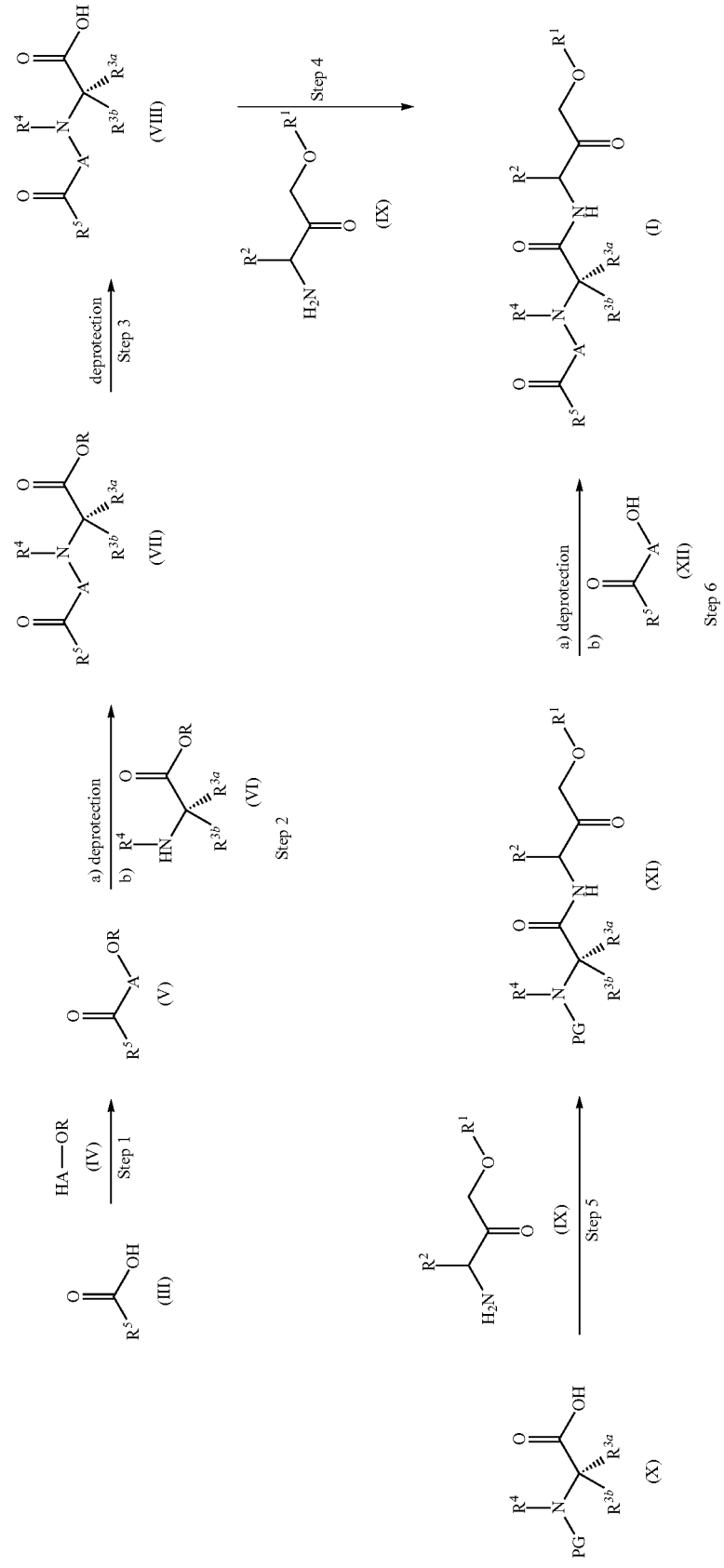
Scheme 1: Representative scheme for synthesis of exemplary compounds of the disclosure.

In Step 1, the acid (III) or its corresponding acid chloride or active ester, available either commercially or prepared from readily available starting materials according to steps familiar to those skilled in the art, is coupled with amino acid ester (IV) with standard peptide coupling agents such as HATU, EDCI, DCC, BOP, HBTU, and PyBOP. Step 1 is skipped in case A is a direct bond. Intermediate (V) is first deprotected depending upon the nature of R (e.g. base hydrolysis with R=Me, and hydrogenation with R=CH$_2$Ph) and then coupled with partially protected intermediate (VI) or its salt using standard peptide coupling conditions. The resulting intermediate (VII) is first deprotected (Step 3) and then coupled to intermediate (IX) or its salt in Step 4 to give the desired compound of formula (I).

Alternatively, protected acid (X), wherein PG is an amine protecting group, could be coupled in Step 5 with amine (IX) or its salt to give intermediate (XI). After deprotection of (XI), the resulting amine is coupled with acid (XII) to give the compound of formula (I).

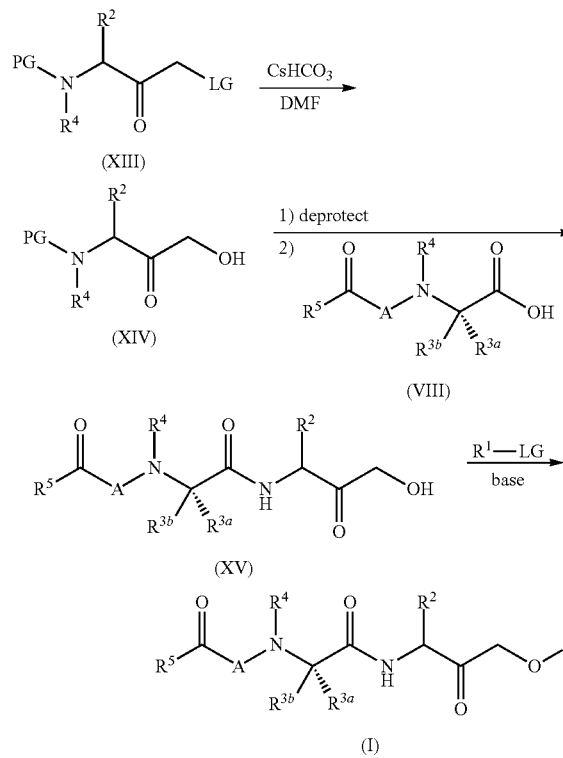

Scheme 2: Representative scheme for synthesis of exemplary compounds of the disclosure.

As shown in Scheme 2, compounds of formula (I) can be prepared starting with compounds of formula (XIII). Compounds of formula (XIII), wherein PG is an amine protecting group and LG is a leaving group, can be reacted with cesium bicarbonate in the DMF to give compounds of formula (XIV). Compounds of formula (XIV) can be deprotected and then coupled with compounds of formula (VIII) to give compounds of formula (XV). Treatment of compounds of formula (XV) with R$^1$-LG in the presence of an appropriate base supplies compounds of Formula (I).

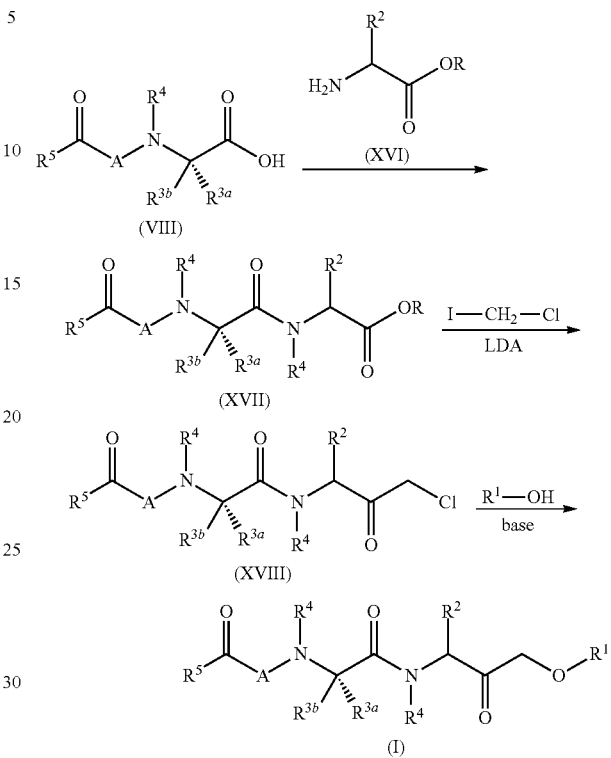

Scheme 3: Representative scheme for synthesis of exemplary compounds of the disclosure.

As shown in Scheme 3, compounds of formula (I) can be prepared from compounds of formula (VIII). Compounds of formula (VIII) can be coupled with amino esters of formula (XVI) to give compounds of formula (XVII). Compounds of formula (XVII) can be reacted with chloroiodomethane in the presence of lithium diisopropylamide and molecular sieves to give compounds of formula (XVIII). Compounds of formula (XVIII) can be reacted with alcohols or phenols, R$^1$—OH, in the presence of an appropriate base to give compounds of formula (I).

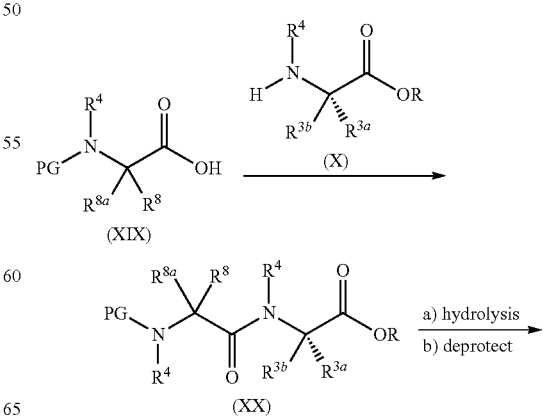

Scheme 4: Representative scheme for synthesis of exemplary compounds of the disclosure.

-continued

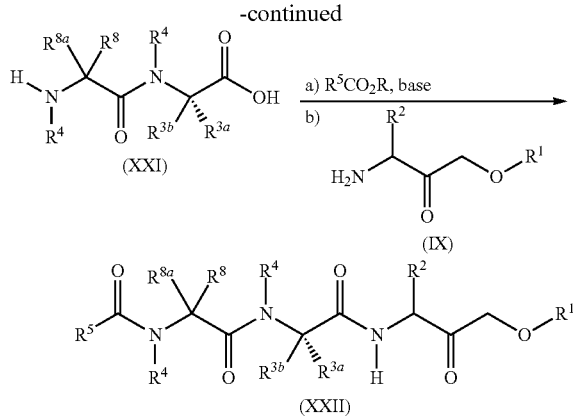

(XXI)

(IX)

(XXII)

As shown in Scheme 4, compounds of formula (XXII) can be prepared from compounds of formula (XIX). N-Protected amino acids of formula (XIX), wherein PG is an amine protecting group, can be coupled with amino esters of formula (X) to produce compounds of formula (XX). The esters of compounds of formula (XX) can be removed by hydrolysis followed by removal of the amine protecting group using conditions known to one of skill in the art and dependent upon the particular protecting group in use to give compounds of formula (XXI). Compounds of formula (XXI) can be reacted first at the amine moiety with an ester, $R^5CO_2R$, in the presence of a base. Subsequent coupling of the carboxylic acid moiety with amines of formula (IX) gives compounds of formula (XXII). Compounds of formula (XXII) are representative of compounds of formula (I).

Scheme 5: Representative scheme for synthesis of exemplary compounds of the disclosure.

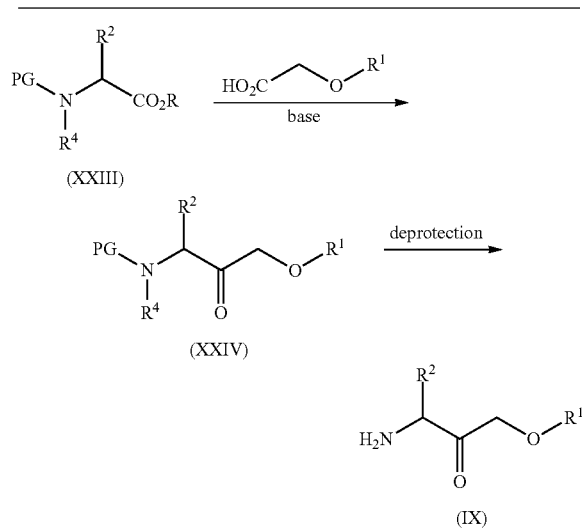

(XXIII)

(XXIV)

(IX)

As shown in Scheme 5, compounds of formula (IX) can be prepared from compounds of formula (XXIII). Compounds of formula (XXIII), wherein PG is an amine protecting group and R is a $C_1$-$C_4$-alkyl group, can be reacted with a carboxylic acid, $R^1O$—$CH_2CO_2H$, in the presence of a strong base such as but not limited to lithium bis(trimethylsilyl)amide first at cold temperatures (−78° C.) followed by warming to ambient temperature to give compounds of formula (XXIV). Compounds of formula (XXIV) can be deprotected to give compounds of formula (IX).

Scheme 6: Representative scheme for synthesis of exemplary compounds of the disclosure.

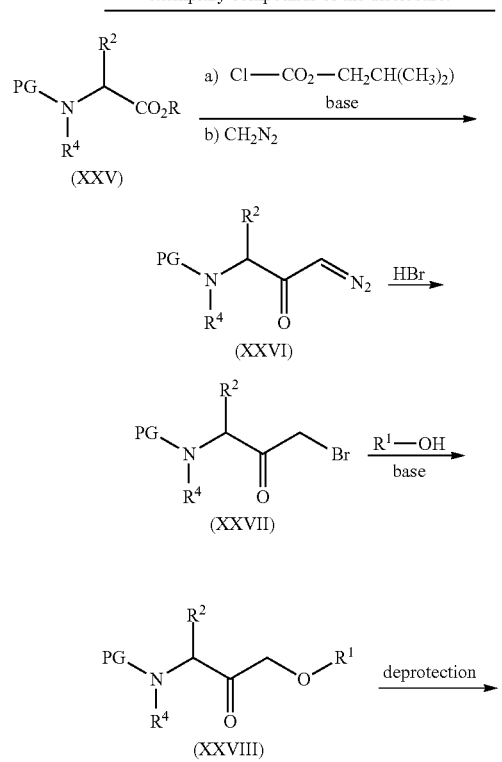

(XXV)

(XXVI)

(XXVII)

(XXVIII)

(IX)

As shown in Scheme 6, compounds of formula (IX) can also be prepared from compounds of formula (XXV). Compounds of formula (XXVV) can be reacted with isobutyl chloroformate in the presence of a tertiary amine base followed in a second reaction by treatment with diazomethane to give compounds of formula (XXVI). Compounds of formula (XXVI) can be treated with an acid, such as hydrobromic acid, to give compounds of formula (XXVII). Compounds of formula (XXVII) can be transformed by reacting with an alcohol or phenol, $R^1$—OH, in the presence of a base to give compounds of formula (XXVIII). Removal of the amine protecting group then supplies compounds of formula (IX).

Scheme 7: Representative scheme for synthesis of exemplary compounds of the disclosure.

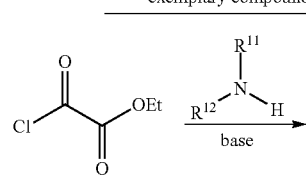

-continued

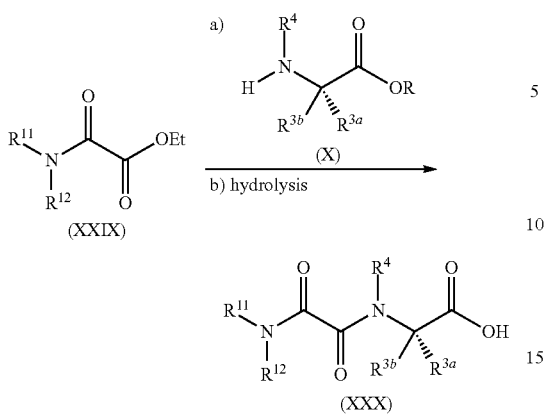

(XXIX)

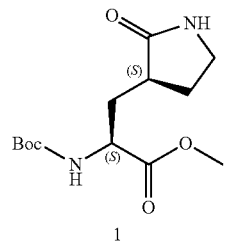

(XXX)

As shown in Scheme 7, compounds of formula (XXX) can be prepared from ethyl 2-chloro-2-oxoacetate. Ethyl 2-chloro-2-oxoacetate can be reacted with an amine, $R^{12}R^{11}NH$, in the presence of a tertiary amine base to give amides of formula (XXIX). Compounds of formula (XXIX) can first be coupled with amino esters of formula (X) and subsequently hydrolyzed to give compounds of formula (XXX). Compounds of formula (XXX) are representative of compounds of formula (VIII).

Preparation of Intermediate Compounds

Methyl (2S)-2-((tert-butoxycarbonyl)amino)-3-((S)-2-oxopyrrolidin-3-yl)propanoate (1)

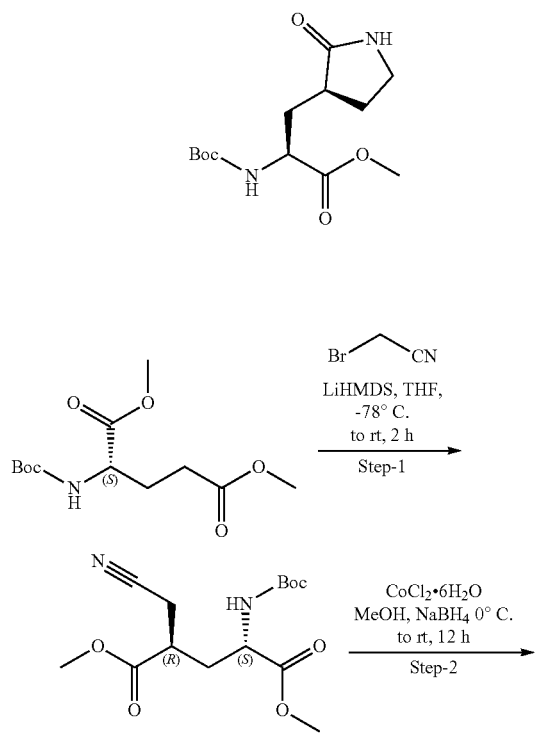

Step 1: Dimethyl (2S,4R)-2-((tert-butoxycarbonyl)amino)-4-(cyanomethyl)pentanedioate To the stirred solution of dimethyl (tert-butoxycarbonyl)-L-glutamate (100 g, 363.2 mol) in tetrahydrofuran (1000 mL), molecular sieves 4 Å (25 g) were added, and the resulting mixture was stirred at room temperature for 10 min. The reaction mixture was cooled to −78° C., lithium bis(trimethylsilyl)amide solution 1 M in THF (810 mL, 799 mol) was added and the resulting mixture was stirred at −78° C. for 1.5 h. Bromoacetonitrile (65.36 g, 544.09 mol) was added to the above solution at −78° C. dropwise over 1 h and the reaction mixture was stirred at −78° C. for 2 h. After completion of the reaction, the reaction mixture was quenched with methanol (50 mL) and stirred for 10 min at −78° C. The resulting solution was quenched with acetic acid (44 mL) in tetrahydrofuran (500 mL) and stirred for 10 min at −78° C. The cooling bath was removed and replaced with ice cold water bath and the reaction mixture was warmed up to 0-5° C. Brine solution (50 g NaCl in 500 mL water) was added. The organic layer was separated, and the aqueous part was extracted with tetrahydrofuran (2×500 mL). The combined organic layers were dried over anhydrous sodium sulfate and concentrated to give a dark brown oil. The crude compound was purified by silica-gel column chromatography using 15% ethyl acetate in hexane to afford dimethyl (2S,4R)-2-((tert-butoxycarbonyl)amino)-4-(cyanomethyl)pentanedioate (80 g) as a pale yellow oil. [TLC system: EtOAc:petroleum ether (4:6); Rf: 0.4].

Step 2: Methyl (2S)-2-((tert-butoxycarbonyl)amino)-3-((S)-2-oxopyrrolidin-3-yl)propanoate (1)

To a stirred solution dimethyl (2S,4R)-2-((tert-butoxycarbonyl)amino)-4-(cyanomethyl)pentanedioate (80.0 g, 254.5 mmol) in methanol (2000 mL), cobalt chloride (19.83 g, 152.7 mmol) was added at 0° C. Sodium borohydride (57.77 g, 1527 mmol) was added portion wise at 0° C. and the reaction mixture was stirred at room temperature for 24 h. It was quenched with saturated ammonium chloride solution (800 mL), filtered through a bed of diatomaceous earth and washed with methanol (500 mL). The filtrate was concentrated under reduced pressure to remove methanol and the resulting aqueous layer was extracted with ethyl acetate (3×500 mL). The combined organic layers were dried over anhydrous sodium sulfate, concentrated under reduced pressure and purified by silica gel column chromatography using 20% ethyl acetate in hexane to afford methyl (2S)-2-((tert-butoxycarbonyl)amino)-3-((S)-2-oxopyrrolidin-3-yl)propanoate (1) (45 g) as a pale yellow semi solid. [TLC system: EtOAc:petroleum ether (7:3); Rf: 0.2]. LCMS m/z 287.42 (M+1); $^1$H NMR (400 MHz, DMSO-$d_6$) δ ppm 5.86 (s, 1H), 5.49 (d, J=7.6 Hz, 1H), 4.32 (t, J=7.6 Hz, 1H), 3.74 (s, 3H), 3.37-3.33 (m, 2H), 2.47-2.46 (m, 2H), 2.17-2.11 (m, 1H), 1.87-1.68 (m, 2H). 1.44 (s, 9H).

Methyl (S)-2-((tert-butoxycarbonyl)amino)-3-((S)-2-oxopiperidin-3-yl)propanoate (2)

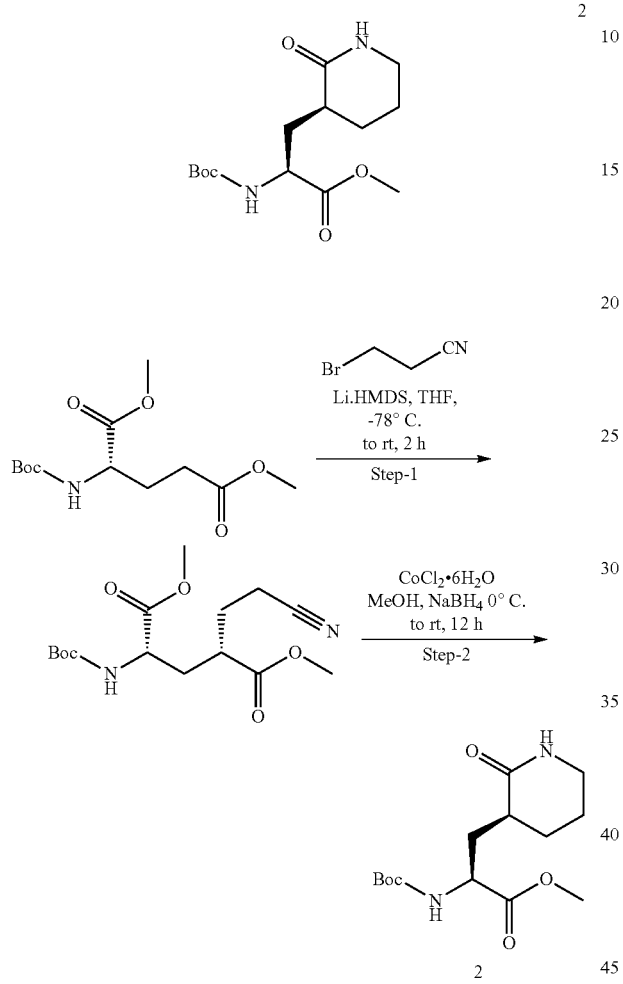

Step 1. Dimethyl (2S,4S)-2-((tert-butoxycarbonyl)amino)-4-(2-cyanoethyl)pentanedioate To the stirred solution of dimethyl (tert-butoxycarbonyl)-L-glutamate (25 g, 90.8 mol) in tetrahydrofuran (250 mL), molecular sieves 4 Å (10 g) were added, and the resulting mixture was stirred at room temperature for 10 min. The reaction mixture was cooled to −78° C. Lithium bis(trimethylsilyl)amide solution 1 M in THF (180 mL, 181.6 mol) was added and the resulting mixture was stirred at −78° C. for 1.5 h. 3-Bromopropanenitrile (14.59 g, 108.9 mol) was added to the above solution at −78° C. dropwise over 1 h and the reaction mixture was stirred at −78° C. for 2 h. After completion of the reaction, the reaction mixture was quenched with methanol (12.5 mL) and stirred for 10 min at −78° C. The resulting solution was quenched with acetic acid (11 mL) in tetrahydrofuran (125 mL) and stirred for 10 min at −78° C. The cooling bath was removed and replaced with an ice cold water bath and the reaction mixture was warmed to 0-5° C. Brine solution (12.5 g NaCl in 125 mL water) was added. The resulting mixture was filtered. The organic layer was separated, and the aqueous layer was extracted with tetrahydrofuran (3×125 mL). The combined organic layers were dried over anhydrous sodium sulfate and concentrated to give a dark brown oil. The crude compound was purified by silica gel column chromatography using 20% ethyl acetate in hexane to afford dimethyl (2S,4S)-2-((tert-butoxycarbonyl)amino)-4-(2-cyanoethyl)pentanedioate (14.0 g) as a pale yellow oil. [TLC system: EtOAc: petroleum ether (4:6); $R_f$: 0.4].

Step 2. Methyl (S)-2-((tert-butoxycarbonyl)amino)-3-((S)-2-oxopiperidin-3-yl)propanoate (2)

To a stirred solution dimethyl (2S,4S)-2-((tert-butoxycarbonyl)amino)-4-(2-cyanoethyl)pentanedioate (14.0 g, 42.6 mmol) in methanol (350 mL), cobalt chloride (3.32 g, 25.6 mmol) was added at 0° C. Sodium borohydride (9.67 g, 255.6 mmol) was added portionwise at 0° C. and the reaction mixture was stirred at room temperature for 24 h. After completion of the reaction, the reaction mixture was quenched with saturated ammonium chloride solution (140 mL), filtered through a bed of diatomaceous earth and washed with methanol (200 mL). The filtrate was concentrated under reduced pressure to remove methanol. The resulting aqueous layer was extracted with ethyl acetate (3×500 mL). The combined organic layers were dried over anhydrous sodium sulfate, concentrated and purified by silica gel column chromatography using 20% ethyl acetate in hexane to afford methyl (S)-2-((tert-butoxycarbonyl)amino)-3-((S)-2-oxopiperidin-3-yl)propanoate (2) (11.0 g) as a pale yellow semi solid. [TLC system: EtOAc:petroleum ether (7:3); $R_f$: 0.2]. LCMS m/z 245.27 (M−tBu); $^1$H NMR (400 MHz, DMSO-d$_6$) δ ppm 5.73 (s, 1H), 5.54 (d, J=8.4 Hz, 1H), 4.34-4.33 (m, 1H), 3.73 (s, 3H), 3.33-3.30 (m, 2H), 2.38-2.30 (m, 2H), 2.29-2.25 (m, 1H), 2.00-1.70 (m, 3H), 1.55-1.51 (m, 1H), 1.44 (s, 9H).

tert-Butyl ((S)-3-oxo-1-((S)-2-oxopyrrolidin-3-yl)-4-(trifluoromethoxy)butan-2-yl)carbamate (3)

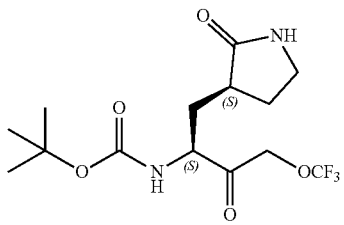

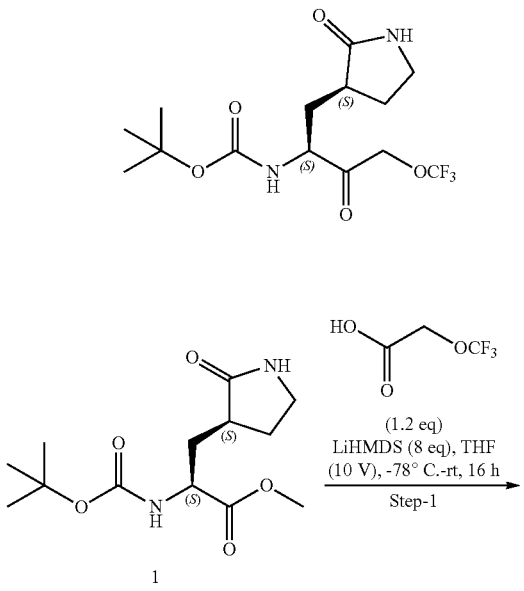

-continued

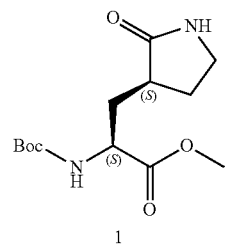

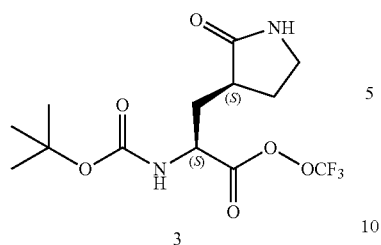

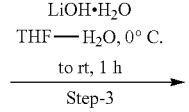

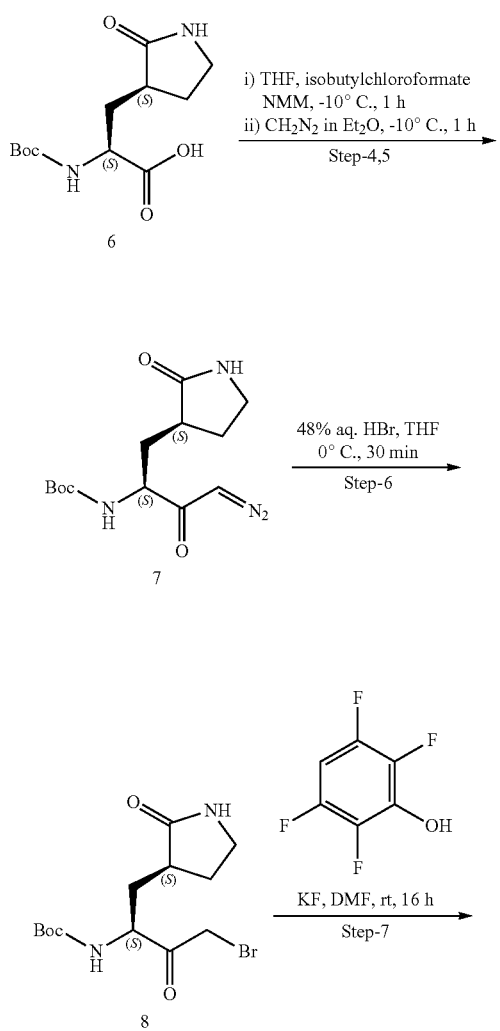

To a stirred solution of 2-(trifluoromethoxy)acetic acid (8.45 g, 58.67 mmol) in THF (90 mL), lithium bis(trimethylsilyl)amide solution (1 M in THF, 391.16 mL, 391.16 mmol) was added and the resulting mixture was stirred at −78° C. for 1 h. Methyl (S)-2-((tert-butoxycarbonyl)amino)-3-((S)-2-oxopyrrolidin-3-yl)propanoate (1) (14.0 g, 48.89 mmol) in THF (50 mL) was slowly added to the reaction mixture at −78° C. and the reaction mixture was stirred at −78° C. for 3 h and at room temperature for 16 h. After completion of the reaction, the reaction mixture was quenched with AcOH (28 mL) in THF (126 mL) at 0° C. and diluted with water (500 mL). The resulting mixture was filtered through diatomaceous earth washed with EtOAc (500 mL), and the filtrate was extracted with EtOAc (3×500 mL). The combined organic layers were dried over anhydrous $Na_2SO_4$, filtered, and concentrated under reduced pressure. The resulting crude compound was purified by a DAVISIL® grade silica gel column chromatography using 20% ethyl acetate in hexane as the eluent to afford tert-butyl ((S)-3-oxo-1-((S)-2-oxopyrrolidin-3-yl)-4-(trifluoromethoxy)butan-2-yl)carbamate (6.79 g, 39%) as pale brown solid. [TLC system: EtOAc:petroleum ether (7:3); $R_f$ value: 0.4]. LCMS m/z 355.37 (M+1) $^1$H NMR (400 MHz, DMSO-$d_6$) δ ppm 7.66 (s, 1H), 7.52 (dd, J=7.2 Hz, 18 Hz, 1H), 4.98 (s, 2H), 4.15-4.09 (m, 1H), 3.19-3.12 (m, 2H), 2.50-2.13 (m, 2H), 1.91-1.84 (m, 1H), 1.68-1.57 (m, 2H), 1.39 (s, 9H).

Similarly, tert-butyl ((S)-3-oxo-1-((S)-2-oxopiperidin-3-yl)-4-(trifluoromethoxy)butan-2-yl)carbamate (4) was prepared from methyl (S)-2-((tert-butoxycarbonyl)amino)-3-((S)-2-oxopiperidin-3-yl)propanoate (2).

tert-Butyl ((S)-3-oxo-1-((S)-2-oxopyrrolidin-3-yl)-4-(2,3,5,6-tetrafluorophenoxy) butan-2-yl)carbamate (5)

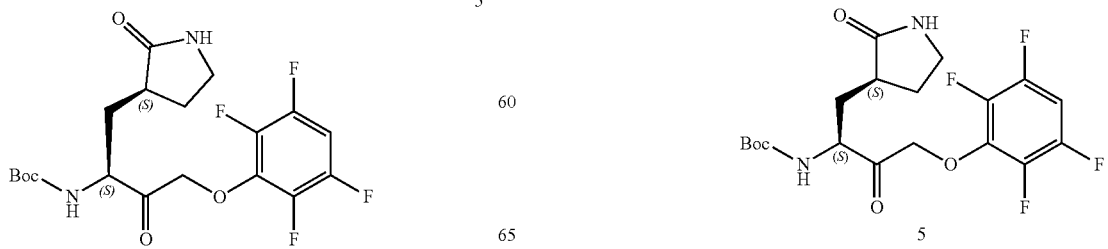

123

Step 1. (S)-2-((tert-Butoxycarbonyl)amino)-3-((S)-2-oxopyrrolidin-3-yl)propanoic acid (6)

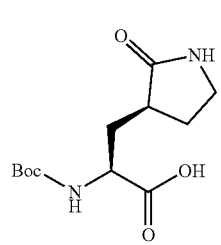

6

To a stirred solution of methyl (S)-2-((tert-butoxycarbonyl)amino)-3-((S)-2-oxopyrrolidin-3-yl)propanoate (1) (14.5 g, 50.64 mmol) in tetrahydrofuran (50 mL), lithium hydroxide monohydrate (2.55 g, 60.77 mmol) in water (10 mL) was added at 0° C. and the reaction mixture was stirred at 0° C. for 1 h. After completion, the reaction mixture was acidified with 2 N hydrochloric acid to pH-5 and extracted with ethyl acetate (3×300 mL). The combined organic layers were dried over anhydrous sodium sulfate and concentrated under reduced pressure to afford (S)-2-((tert-butoxycarbonyl)amino)-3-((S)-2-oxopyrrolidin-3-yl)propanoic acid (11.0 g) as a pale yellow gum. TLC system: EtOAc:petroleum ether (7:3); $R_f$: 0.1.

Step 2. tert-Butyl ((S)-4-diazo-3-oxo-1-((S)-2-oxopyrrolidin-3-yl)butan-2-yl)carbamate (7)

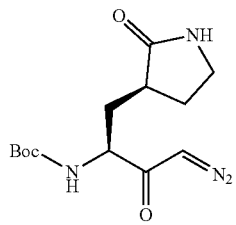

7

To a stirred solution of (S)-2-((tert-butoxycarbonyl)amino)-3-((S)-2-oxopyrrolidin-3-yl)propanoic acid (6) (11.0 g, 36.72 mmol) in tetrahydrofuran (300 mL), N-methylmorpholine (4.83 g, 47.74 mmol) and isobutyl chloroformate (10.18 g, 73.45 mmol) was sequentially added at −10° C. and the reaction mixture was stirred at −10° C. for 1 h. After completion, the reaction mixture was filtered and washed with tetrahydrofuran (50 mL). Freshly prepared diazomethane in diethyl ether (prepared from 5.0 mole equivalent of Diazald®) was added to the filtrate at −10° C. and the reaction mixture was stirred at room temperature for 1 h. After completion, the reaction mixture was diluted with water (100 mL) and extracted with ethyl acetate (3×300 mL). The combined organic layers were dried over anhydrous sodium sulfate and concentrated under reduced pressure to afford tert-butyl ((S)-4-diazo-3-oxo-1-((S)-2-oxopyrrolidin-3-yl)butan-2-yl)carbamate (10.8 g, crude) as a yellow liquid. TLC system: EtOAc:petroleum ether (7:3); $R_f$: 0.1.

124

Step 3. tert-Butyl ((S)-4-bromo-3-oxo-1-((S)-2-oxopyrrolidin-3-yl)butan-2-yl)carbamate (8)

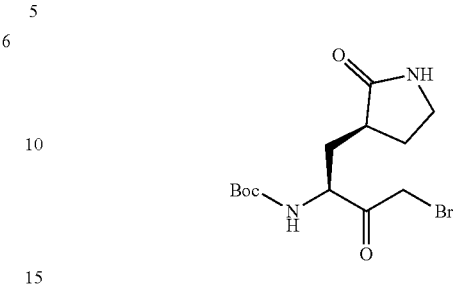

8

To a stirred solution of tert-butyl ((S)-4-diazo-3-oxo-1-((S)-2-oxopyrrolidin-3-yl)butan-2-yl)carbamate (7) (10.8 g, 36.44 mmol) in tetrahydrofuran (300 mL) was added 48% aqueous hydrobromic acid (6.87 g, 43.73 mmol) dropwise at 0° C. and the mixture was stirred at 0° C. for 30 min. After completion, the reaction mixture was basified with saturated sodium bicarbonate and extracted with ethyl acetate (3×150 mL). The combined organic layers were dried over anhydrous sodium sulfate and concentrated under reduced pressure to afford tert-butyl ((S)-4-bromo-3-oxo-1-((S)-2-oxopyrrolidin-3-yl)butan-2-yl)carbamate (12.5 g, crude) as a yellow liquid. TLC system: EtOAc:petroleum ether (7:3); $R_f$: 0.4.

Step 4. tert-Butyl ((S)-3-oxo-1-((S)-2-oxopyrrolidin-3-yl)-4-(2,3,5,6-tetrafluorophenoxy) butan-2-yl) carbamate (5)

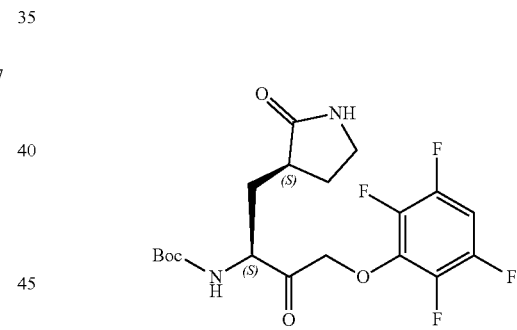

5

To the mixture of tert-butyl ((S)-4-bromo-3-oxo-1-((S)-2-oxopyrrolidin-3-yl)butan-2-yl)carbamate (12.5 g, 35.79 mmol) and 2,3,5,6-tetrafluorophenol (5.94 g, 35.79 mmol) in dimethylformamide (50 mL), potassium fluoride (6.47 g, 111.33 mmol) was added and the reaction mixture was stirred at room temperature for 24 h. After completion, the reaction mixture was diluted with water (100 mL) and extracted with ethyl acetate (3×300 mL). The combined organic layers were dried over anhydrous sodium sulfate and concentrated under reduced pressure. The crude residue was then purified by silica gel (230-400 mesh) column chromatography using 40-60% ethyl acetate in petroleum ether as a gradient to afford tert-butyl ((S)-3-oxo-1-((S)-2-oxopyrrolidin-3-yl)-4-(2,3,5,6-tetrafluorophenoxy)butan-2-yl)carbamate (7.1 g) as a brown solid. TLC system: EtOAc:petroleum ether (7:3); $R_f$: 0.5. LCMS m/z 435.22 (M+1); $^1$H NMR (400 MHz, DMSO-$d_6$) δ ppm 7.65-7.47 (m, 3H), 5.30-5.19 (m, 2H), 4.16-4.10 (m, 1H), 3.16-3.12 (m, 2H), 2.25-2.10 (m, 2H), 1.92-1.85 (m, 1H), 1.67-1.56 (m, 2H), 1.39 (s, 9H).

125 tert-Butyl ((S)-4-((1,1,1,3,3,3-hexafluoropropan-2-yl)oxy)-3-oxo-1-((S)-2-oxopyrrolidin-3-yl)butan-2-yl)carbamate (9)

126

(S)-3-((S)-2-Amino-4-((1,1,1,3,3,3-hexafluoropropan-2-yl)oxy)-3-oxobutyl)pyrrolidin-2-one hydrochloride (10)

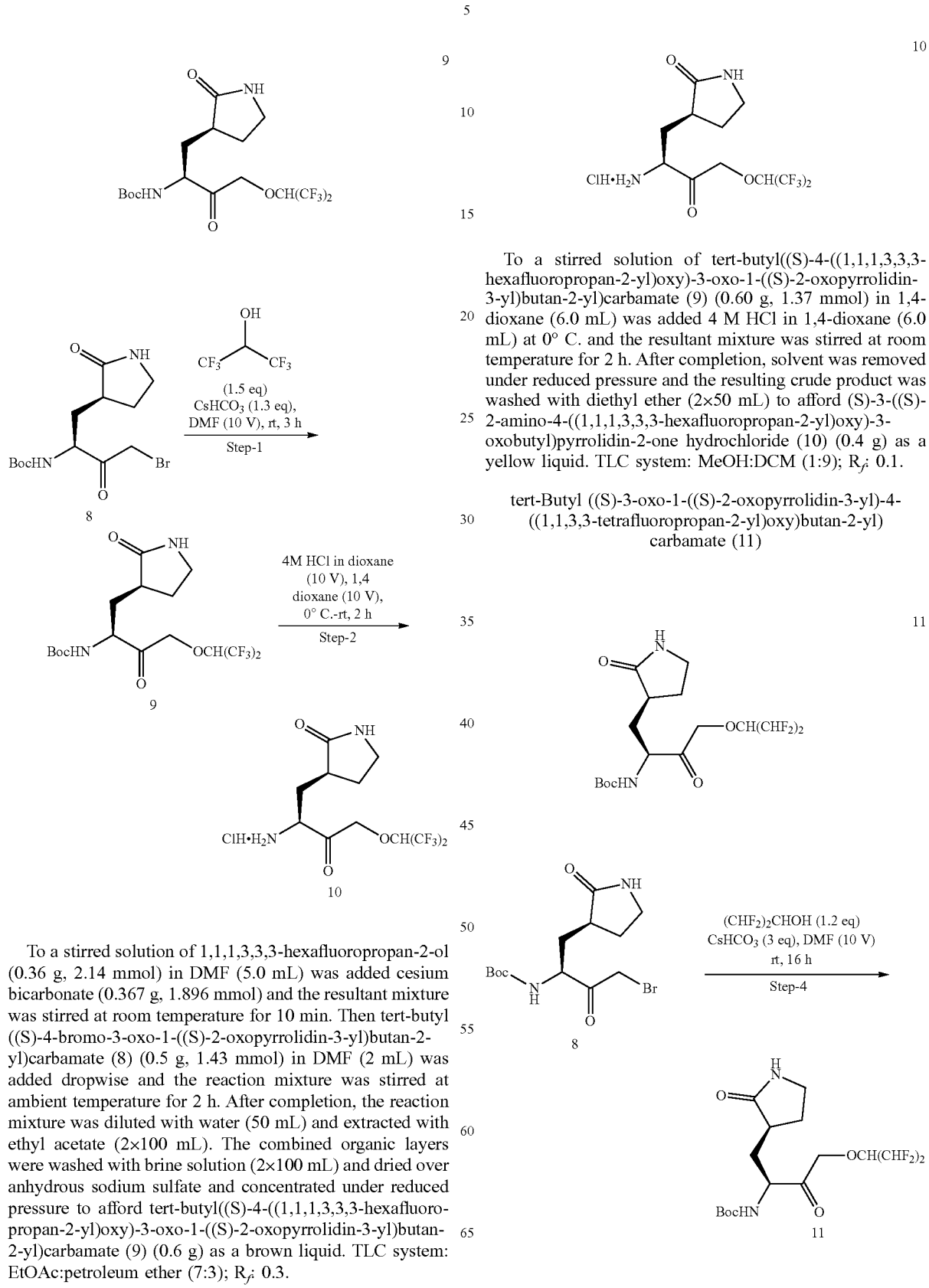

To a stirred solution of tert-butyl((S)-4-((1,1,1,3,3,3-hexafluoropropan-2-yl)oxy)-3-oxo-1-((S)-2-oxopyrrolidin-3-yl)butan-2-yl)carbamate (9) (0.60 g, 1.37 mmol) in 1,4-dioxane (6.0 mL) was added 4 M HCl in 1,4-dioxane (6.0 mL) at 0° C. and the resultant mixture was stirred at room temperature for 2 h. After completion, solvent was removed under reduced pressure and the resulting crude product was washed with diethyl ether (2×50 mL) to afford (S)-3-((S)-2-amino-4-((1,1,1,3,3,3-hexafluoropropan-2-yl)oxy)-3-oxobutyl)pyrrolidin-2-one hydrochloride (10) (0.4 g) as a yellow liquid. TLC system: MeOH:DCM (1:9); $R_f$: 0.1.

tert-Butyl ((S)-3-oxo-1-((S)-2-oxopyrrolidin-3-yl)-4-((1,1,3,3-tetrafluoropropan-2-yl)oxy)butan-2-yl)carbamate (11)

To a stirred solution of 1,1,1,3,3,3-hexafluoropropan-2-ol (0.36 g, 2.14 mmol) in DMF (5.0 mL) was added cesium bicarbonate (0.367 g, 1.896 mmol) and the resultant mixture was stirred at room temperature for 10 min. Then tert-butyl ((S)-4-bromo-3-oxo-1-((S)-2-oxopyrrolidin-3-yl)butan-2-yl)carbamate (8) (0.5 g, 1.43 mmol) in DMF (2 mL) was added dropwise and the reaction mixture was stirred at ambient temperature for 2 h. After completion, the reaction mixture was diluted with water (50 mL) and extracted with ethyl acetate (2×100 mL). The combined organic layers were washed with brine solution (2×100 mL) and dried over anhydrous sodium sulfate and concentrated under reduced pressure to afford tert-butyl((S)-4-((1,1,1,3,3,3-hexafluoropropan-2-yl)oxy)-3-oxo-1-((S)-2-oxopyrrolidin-3-yl)butan-2-yl)carbamate (9) (0.6 g) as a brown liquid. TLC system: EtOAc:petroleum ether (7:3); $R_f$: 0.3.

To a stirred solution tert-butyl ((S)-4-bromo-3-oxo-1-((S)-2-oxopyrrolidin-3-yl)butan-2-yl)carbamate (1 g, 2.86 mmol) in DMF (10 mL), 1,1,3,3-tetrafluoropropan-2-ol (0.491 g, 3.71 mmol) and cesium bicarbonate (1.38 g, 7.15 mmol) were added at 0° C. and the reaction mixture was stirred at ambient temperature for 16 h. After completion, the reaction mixture was quenched with 10% aqueous sodium bicarbonate then extract with EtOAc (3×100 mL). The combined organic layers were dried over anhydrous sodium sulfate, filtered, and concentrated under reduced pressure. The crude residue was then purified by flash column chromatography over Davisil® silica gel using 70-80% EtOAc in petroleum ether as eluent to give tert-butyl ((S)-3-oxo-1-((S)-2-oxopyrrolidin-3-yl)-4-((1,1,3,3-tetrafluoropropan-2-yl)oxy)butan-2-yl)carbamate (11) (0.53 g) as a colorless gum. TLC system: EtOAc:petroleum ether (7:3); R$_f$: 0.5. $^1$H NMR (401 MHz, DMSO-d$_6$) δ ppm 7.64 (s, 1H), 7.43 (d, J=7.8 Hz, 1H), 6.29 (t, J=53.4 Hz, 2H), 4.62 (q, J=17.3 Hz, 2H), 4.20-4.07 (m, 2H), 3.14 (t, J=7.9 Hz, 2H), 2.24-2.13 (m, 2H), 1.87-1.80 (m, 1H), 1.72-1.64 (m, 2H), 1.39 (s, 9H).

2-((2-Fluorophenyl)amino)-2-oxoacetic acid (12)

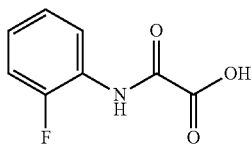

12

Step 1. Ethyl 2-((2-fluorophenyl)amino)-2-oxoacetate

To a stirred solution of 2-fluoroaniline (3.0 g, 26.98 mmol) in DCM (30 mL) at 0° C. was added ethyl 2-chloro-2-oxoacetate (3.7 g, 28.33 mmol). Then TEA (4.02 mL, 28.33 mmol) was added dropwise over 5 min and the mixture was stirred at room temperature for 2 h. After completion, volatiles were removed through vacuum at 25° C. The obtained crude product was dissolved in diethyl ether (100 mL) and filtered through a pad of diatomaceous earth washed with diethyl ether (5×50 mL). The collected filtrate was dried over Na$_2$SO$_4$ and concentrated under reduced pressure to afford ethyl 2-((2-fluorophenyl)amino)-2-oxoacetate (4.0 g) as a colorless gummy liquid. TLC system: EtOAc:petroleum ether (3:7); R 0.6.

Step 2. Synthesis of 2-((2-fluorophenyl)amino)-2-oxoacetic acid (12)

To a solution of 2-oxo-2-(phenylamino)acetate (4.0 g, 20.29 mmol) in THF (30.0 mL) at 0° C., was added LiOH·H$_2$O (1.0 g, 24.35 mmol) in water (10 mL). The resultant mixture was stirred at room temperature for 1 h. After completion, the reaction mixture was acidified to pH ~4 using 5% aq. HCl (40 mL) and the aqueous layer was extracted with ethyl acetate (2×70 mL). The combined organic layers were dried over anhydrous sodium sulfate, filtered and concentrated to yield 2-((2-fluorophenyl)amino)-2-oxoacetic acid (12) (3.2 g) as a colorless gummy liquid. TLC system: EtOAc:petroleum ether (7:3); R$_f$: 0.1.

Methyl (2-((2-fluorophenyl)amino)-2-oxoacetyl)-L-leucinate (13)

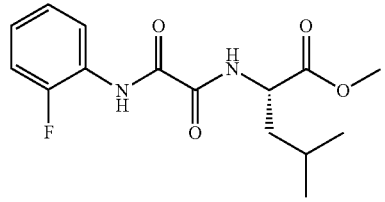

13

To a solution of 2-((2-fluorophenyl)amino)-2-oxoacetic acid (12) (5.0 g, 27.2 mmol) in anhydrous DMF (40 mL) was added methyl L-leucinate hydrochloride (4.0 g, 27.2 mmol), HATU (13.47 g, 35.3 mmol) and DIPEA (14.2 mL, 81.6 mmol) at 0° C. The resultant mixture was stirred at room temperature for 2 h. After completion, the reaction mixture was diluted with ethyl acetate (100 mL) and washed sequentially with saturated aqueous NaHCO$_3$ (70 mL), water (70 mL), and brine (40 mL). The organic layer was dried over anhydrous sodium sulfate, filtered, and concentrated under reduce pressure. The crude product was then purified by column chromatography over silica gel (230-400 mesh) (using 20-30% EtOAc in petroleum ether as eluent) to afford methyl (2-((2-fluorophenyl)amino)-2-oxoacetyl)-L-leucinate 6 (4.0 g) as an off-white solid. TLC system: EtOAc: petroleum ether (3:7); R$_f$: 0.5.

(2-((2-Fluorophenyl)amino)-2-oxoacetyl)-L-leucine (14)

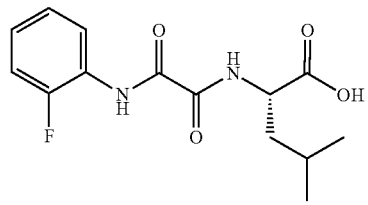

14

To a solution of methyl (2-((2-fluorophenyl)amino)-2-oxoacetyl)-L-leucinate (13) (4.0 g, 12.9 mmol) in THF (30.0 mL) at 0° C., was added LiOH·H$_2$O (0.65 g, 15.48 mmol) in water (7.0 mL). The resultant mixture was stirred at room temperature for 1 h. After completion, the reaction mixture was acidified to pH ~4 using 5% aq. HCl (20 mL) and the aqueous layer was extracted with ethyl acetate (2×70 mL). The combined organic layers were dried over anhydrous sodium sulfate, filtered and concentrated to yield (2-((2-fluorophenyl)amino)-2-oxoacetyl)-L-leucine (14) (3.2 g) as a colorless gummy liquid. TLC system: EtOAc: petroleum ether (7:3); R$_f$: 0.1. LCMS m/z=295.24 (M−H)$^−$; $^1$H NMR (400 MHz, DMSO-d$_6$) δ ppm 12.81 (s, 1H), 10.30 (s, 1H), 9.09 (d, J=8.3 Hz, 1H), 7.69-7.65 (m, 1H), 7.34-7.25 (m, 3H), 4.34-4.29 (m, 1H), 1.83 (t, J=10.5 Hz, 1H), 1.59-1.56 (m, 2H), 0.91-0.87 (m, 6H).

2-((4,4-Difluorocyclohexyl)amino)-2-oxoacetic acid (15)

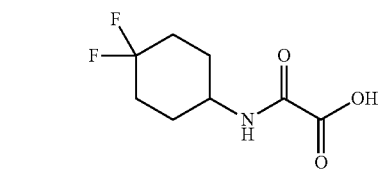

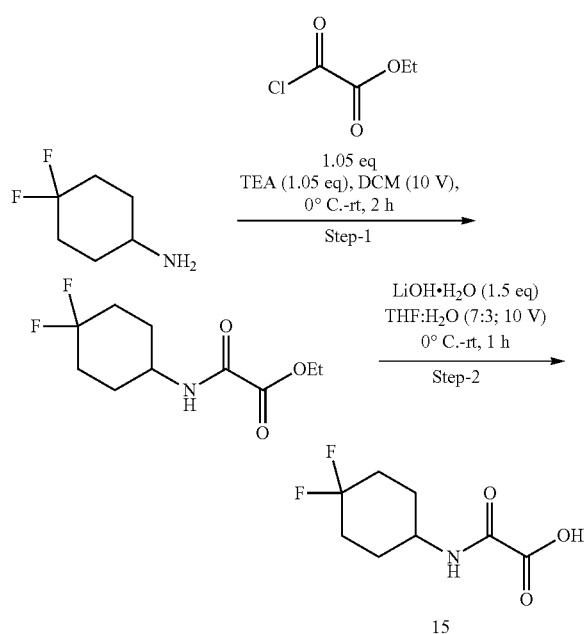

Step 1. Ethyl 2-((4,4-difluorocyclohexyl)amino)-2-oxoacetate

To stirred solution of 4,4-difluorocyclohexan-1-amine (1.0 g, 5.85 mmol) in dichloromethane (10 mL) was added triethylamine (1.6 mL, 11.69 mmol) followed by ethyl 2-chloro-2-oxoacetate (0.7 mL, 5.85 mmol) at 0° C. and the resultant mixture was stirred at room temperature for 2 h. After completion, the reaction mixture was concentrated under reduce pressure (bath temperature <25° C.) to give crude residue. Diethyl ether was added to the residue, the obtained solid was filtered off the filtrate was dried over anhydrous sodium sulfate and concentrate under reduce pressure to give ethyl 2-((4,4-difluorocyclohexyl)amino)-2-oxoacetate (1.6 g) as a brown liquid. TLC system: EtOAc in petroleum ether (3:7); $R_f$: 0.3.

Step 2. Synthesis of 2-((4,4-difluorocyclohexyl)amino)-2-oxoacetic acid

To a solution of ethyl 2-((4,4-difluorocyclohexyl)amino)-2-oxoacetate 3 (1.7 g, 7.23 mmol) in THF (10 mL) and water (5 mL) was added aqueous solution of LiOH·H$_2$O (0.36 g, 8.68 mmol) dropwise over 5 min at 0° C. and the reaction mixture was stirred at ambient temperature for 1 h. After completion, the reaction mixtures were washed with ethyl acetate (2×50 mL) aqueous layer was acidified with 1N HCl and extracted with 10% MeOH in DCM (4×50 mL) combined organic layers were dried over anhydrous sodium sulfate and concentrated under reduced pressure to afford 2-((4,4-difluorocyclohexyl)amino)-2-oxoacetic acid (15) (0.8 g) as a brown solid. TLC system: MeOH in DCM (1:9); $R_f$: 0.2.

(S)-2-Amino-4-methyl-N—((S)-3-oxo-1-((S)-2-oxopyrrolidin-3-yl)-4-(2,3,5,6-tetrafluorophenoxy)butan-2-yl)pentanamide (16)

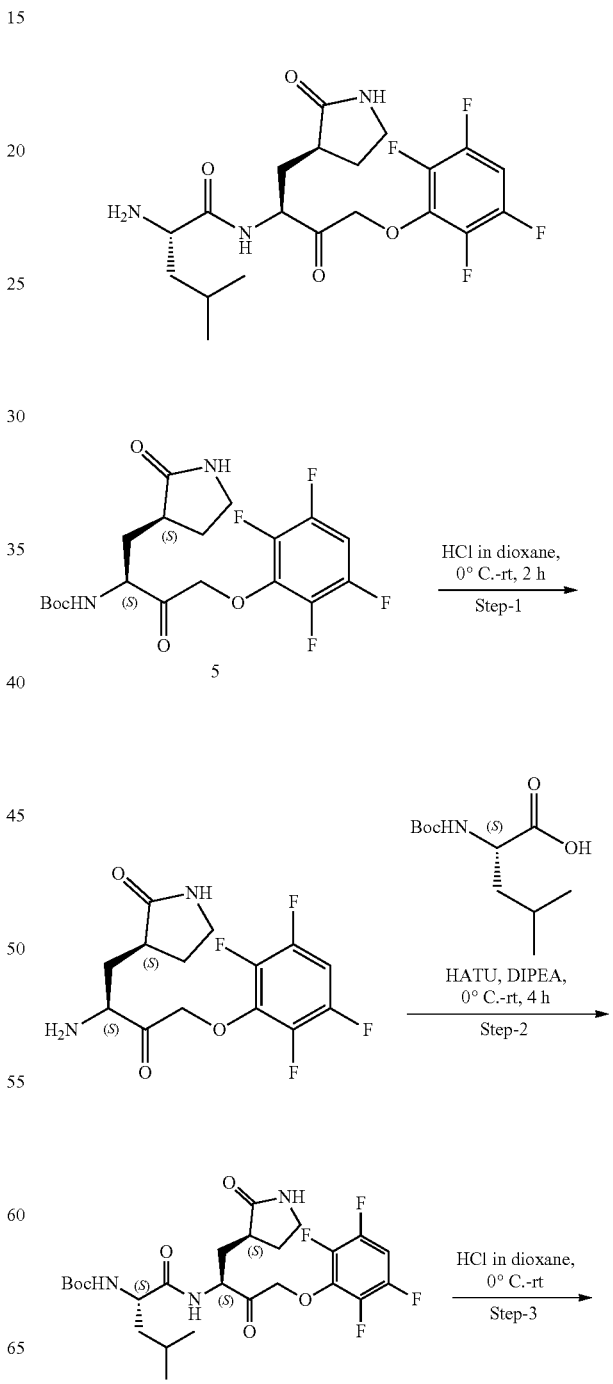

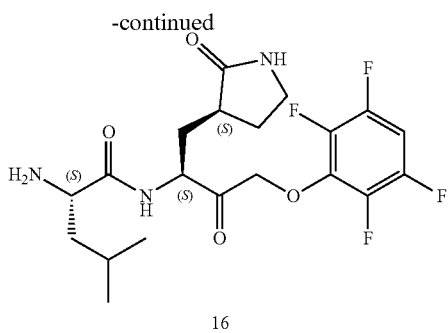

16

Step 1. (S)-3-((S)-2-Amino-3-oxo-4-(2,3,5,6-tetrafluorophenoxy)butyl)pyrrolidin-2-one To a stirred solution of tert-butyl ((S)-3-oxo-1-((S)-2-oxopyrrolidin-3-yl)-4-(2,3,5,6-tetrafluorophenoxy)butan-2-yl)carbamate (5) (3.9 g, 8.66 mmol) in 1,4-dioxane (20 mL) was added 4 M HCl in 1,4-dioxane (8.66 mL, 34.64 mmol) at 0° C. and the resultant mixture was stirred at room temperature for 2 h. After completion, volatiles were removed by under reduced pressure and the resulting crude product was washed with diethyl ether (2×30 mL) to afford (S)-3-((S)-2-amino-3-oxo-4-(2,3,5,6-tetrafluorophenoxy)butyl)pyrrolidin-2-one hydrochloride (3 g) as a yellow oil. TLC system: MeOH:DCM (1:9); $R_f$: 0.2.

Step 2. tert-butyl((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate To a stirred solution (S)-3-((S)-2-amino-3-oxo-4-(2,3,5,6-tetrafluorophenoxy)butyl)pyrrolidin-2-one hydrochloride (3 g, 8.09 mmol) and (tert-butoxycarbonyl)-L-leucine (1.87 g, 8.09 mmol) in DMF (30 mL) was added HATU (4 g, 10.52 mmol) followed by DIPEA (4.4 mL, 24.28 mmol) at 0° C. and the resultant mixture was stirred at room temperature for 4 h. After completion, cold water (40 mL) was added to the reaction mixture and extracted with EtOAc (3×50 mL). The combined organic layers were dried over anhydrous sodium sulfate, filtered, and concentrated under reduced pressure to give crude product. The crude product was then purified by column chromatography over silica gel (230-400 mesh) using 45-50% ethyl acetate in petroleum ether as a gradient to afford tert-butyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate (3 g) as an off-white solid. TLC system: EtOAc: petroleum ether (7:3); $R_f$: 0.6.

Step 3. (S)-2-Amino-4-methyl-N—((S)-3-oxo-1-((S)-2-oxopyrrolidin-3-yl)-4-(2,3,5,6-tetrafluorophenoxy)butan-2-yl)pentanamide hydrochloride (16)

To a stirred solution of tert-butyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate (0.2 g, 0.37 mmol) in 1,4-dioxane (20 mL) was added 4 M HCl in 1,4-dioxane (0.3 mL, 1.46 mmol) at 0° C. and the resultant mixture was stirred at room temperature for 2 h. After completion, solvent was removed under reduced pressure and the resulting crude residue was washed with diethyl ether (2×30 mL) to afford (S)-2-amino-4-methyl-N—((S)-3-oxo-1-((S)-2-oxopyrrolidin-3-yl)-4-(2,3,5,6-tetrafluorophenoxy)butan-2-yl)pentanamide hydrochloride (0.16 g) as brown gummy solid. TLC system: EtOAc (100%); $R_f$: 0.1. LCMS [M+1]: 448.41.

(S)-3-((S)-2-Amino-3-oxo-4-(trifluoromethoxy)butyl)piperidin-2-one hydrochloride (17)

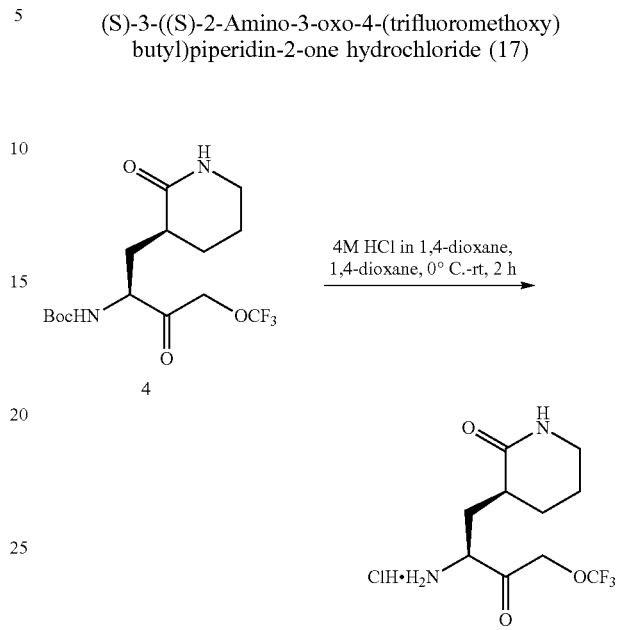

4

To a solution of tert-butyl ((S)-3-oxo-1-((S)-2-oxopiperidin-3-yl)-4-(trifluoromethoxy)butan-2-yl)carbamate (4) (0.15 g, 0.41 mmol) in 1,4-dioxane (1.5 mL) was added 4M HCl in 1,4-dioxane (3 mL) at 0° C. The reaction mixture was stirred at room temperature for 2 h. After completion of reaction by TLC, the reaction mixture was concentrated under reduced pressure to give 0.12 g of (S)-3-((S)-2-amino-3-oxo-4-(trifluoromethoxy)butyl)piperidin-2-one hydrochloride as a pale yellow solid. [TLC system: MeOH:DCM (1:9); $R_f$ value: 0.1].

Similarly, (S)-3-((S)-2-amino-3-oxo-4-(trifluoromethoxy)butyl)pyrrolidin-2-one hydrochloride (18) was prepared from tert-butyl ((S)-3-oxo-1-((S)-2-oxopyrrolidin-3-yl)-4-(trifluoromethoxy)butan-2-yl)carbamate (3).

Methyl (2S)-2-((tert-butoxycarbonyl)amino)-3-(3,3-difluorocyclopentyl)propanoate (19)

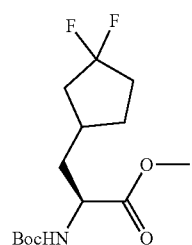

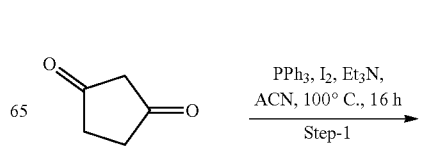

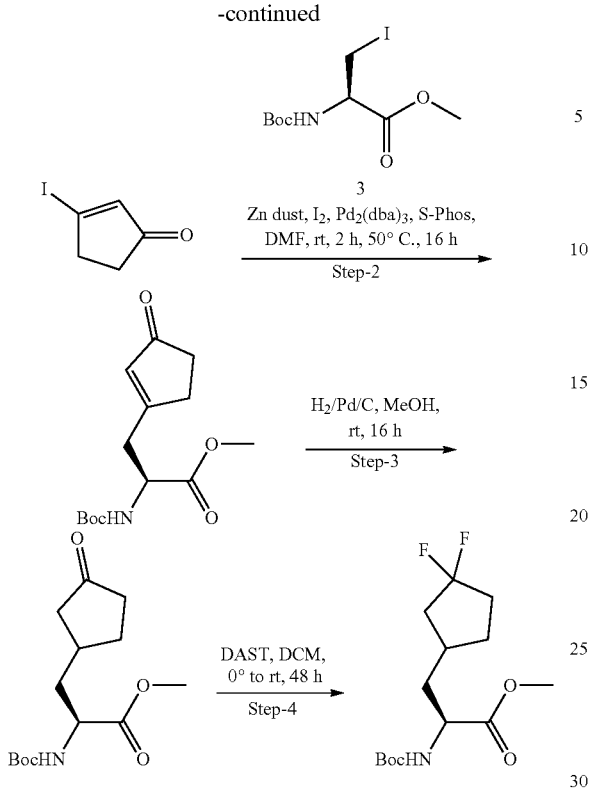

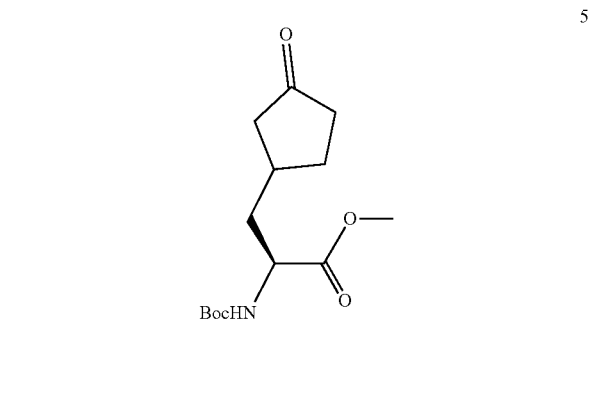 [SMILES: COC(=O)[C@H](CC1CCC(=O)C1)NC(=O)OC(C)(C)C]

Step 1. 3-Iodocyclopent-2-en-1-one

A mixture of iodine (6.21 g, 24.46 mmol) and triphenylphosphine (6.95 g, 26.50 mmol) in ACN (40 mL) was stirred at room temperature for 2 h. Cyclopentane-1,3-dione (2.0 g, 20.39 mmol) and Et₃N (3.41 mL, 24.46 mmol) were added to the reaction mixture, stirred at 100° C. for 16 h. After completion of reaction by TLC, the reaction mixture was concentrated under reduced pressure to give a residue. The residue was purified by column chromatography (using silica gel, 5-10% EtOAc in petroleum ether as an eluent) to afford 2.5 g of 3-iodocyclopent-2-en-1-one as a pale yellow solid. [TLC system: EtOAc:petroleum ether (1:1); $R_f$ value: 0.3]. LCMS [M+1]: m/z 209.0

Step 2. Methyl (S)-2-((tert-butoxycarbonyl)amino)-3-(3-oxocyclopent-1-en-1-yl)propanoate A solution of 3-iodocyclopent-2-en-1-one (2.5 g, 12.02 mmol) in DMF (8 mL), was added to a mixture of zinc dust (2.36 g, 36.06 mmol) and iodine (0.79 g, 3.12 mmol) in DMF (5 mL) under a nitrogen atmosphere. The reaction mixture was stirred at room temperature for 2 h. Then a solution of methyl (R)-2-((tert-butoxycarbonyl)amino)-3-iodopropanoate (3.96 g, 12.02 mmol) in DMF (12 mL) was added and the reaction mixture was degassed with nitrogen for 20 min. Then Pd₂dba₃ (0.27 g, 0.3 mmol) and SPhos (0.25 g, 0.6 mmol) were added and the resultant reaction mixture was stirred at 50° C. for 16 h. After completion of reaction by TLC, the reaction mixture was quenched with water (50 mL), extracted with EtOAc (3*50 mL). The separated and combined organic layers were dried over anhydrous Na₂SO₄, filtered and concentrated under reduced pressure to give a residue. The residue was purified by column chromatography (using silica gel, 20-25% ethyl acetate in petroleum ether as an eluent) to afford 1.7 g of methyl (S)-2-((tert-butoxycarbonyl)amino)-3-(3-oxocyclopent-1-en-1-yl)propanoate as pale yellow oil. [TLC system: EtOAc: petroleum ether (6:4); $R_f$ value: 0.4]. LCMS m/z 228.14 [M-$^t$Bu]

Step 3. Methyl (2S)-2-((tert-butoxycarbonyl)amino)-3-(3-oxocyclopentyl)propanoate To a solution of methyl (S)-2-((tert-butoxycarbonyl)amino)-3-(3-oxocyclopent-1-en-1-yl)propanoate (1.7 g, 6.0 mmol) in MeOH (10 mL), was added 10% Pd/C (0.21 g) under a hydrogen atmosphere and the resultant reaction mixture was stirred at room temperature for 16 h. After completion of reaction by TLC, the reaction mixture was filtered through a bed of diatomaceous earth that was washed with MeOH (100 mL). The filtrate was concentrated under reduced pressure to afford 1.5 g of methyl (2S)-2-((tert-butoxycarbonyl)amino)-3-(3-oxocyclopentyl)propanoate as colorless oil. [TLC system: EtOAc:petroleum ether (6:4); $R_f$ value: 0.7]. LCMS m/z=186.11 [M−Boc+1].

Step 4. Methyl (2S)-2-((tert-butoxycarbonyl)amino)-3-(3,3-difluorocyclopentyl)propanoate (19)

To a solution of methyl (2S)-2-((tert-butoxycarbonyl)amino)-3-(3-oxocyclopentyl)propanoate (1.5 g, 5.26 mmol) in DCM (15 mL), was added DAST (4.17 mL, 31.54 mmol) at 0° C. The reaction mixture was stirred at room temperature for 48 h. After completion of reaction by TLC, the reaction mixture was quenched with saturated NaHCO₃ solution (30 mL), extracted with DCM (3*50 mL). The separated and combined organic layers were dried over anhydrous Na₂SO₄, filtered and concentrated under reduced pressure to give a residue. The residue was purified by column chromatography (using silica gel, 25-30% ethyl acetate in petroleum ether as an eluent) to afford 0.523 g of methyl (2S)-2-((tert-butoxycarbonyl)amino)-3-(3,3-difluorocyclopentyl)propanoate (19) as pale yellow liquid. [TLC system: EtOAc:petroleum ether (3:7); $R_f$ value: 0.6]. Analytical Data: LCMS m/z=252.19 [M−tBu]; $^1$H NMR (400 MHz, DMSO-d₆) δ ppm 7.29 (d, J=8.0 Hz, 1H), 3.97-3.92 (m, 1H), 3.62 (s, 3H), 2.21-1.85 (m, 5H), 1.69 (t, J=7.2 Hz, 3H), 1.45-1.42 (m, 10H).

5-(2-Fluoropropan-2-yl)isoxazole-3-carboxylic acid (20)

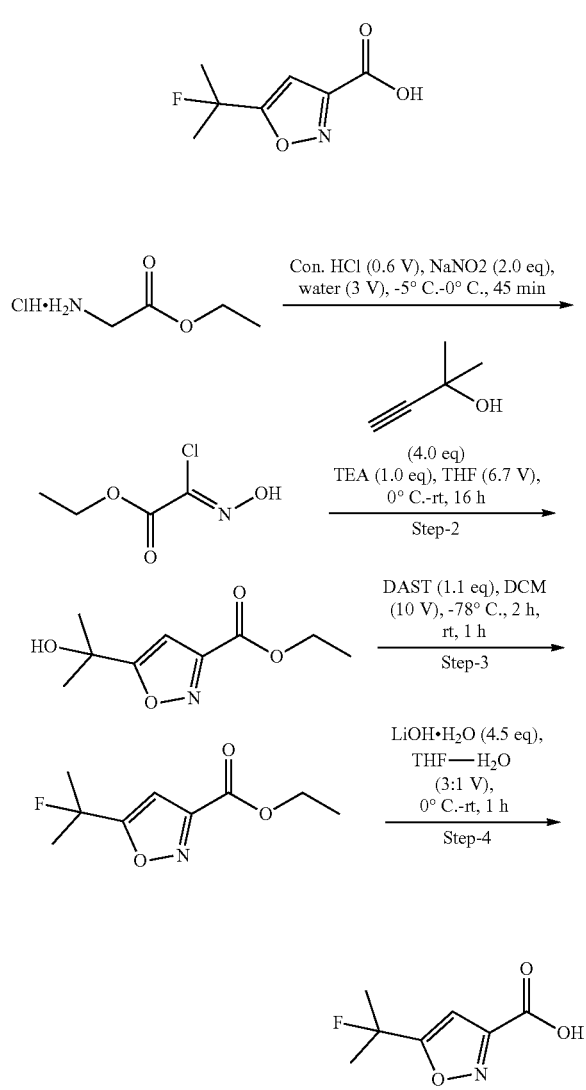

Step 1. Ethyl (Z)-2-chloro-2-(hydroxyimino)acetate

To a stirred solution of ethyl glycinate hydrochloride (5.0 g, 35.82 mmol) in water (7.5 mL), concentrated hydrochloric acid (3.0 mL) was added at 0° C. The resulting mixture was cooled to −5° C. and then sodium nitrite (4.94 g, 71.64 mmol) in water (7.5 mL) was added dropwise at −5° C. and the reaction mixture was stirred at 0° C. for 45 min. After completion of the reaction, the reaction mixture was diluted with brine solution (50 mL) and extracted with ethyl acetate (3×50 mL). The combined organic layers were dried over anhydrous sodium sulfate and concentrated under reduced pressure to give ethyl (Z)-2-chloro-2-(hydroxyimino)acetate (4.5 g, crude) as a yellow liquid that was used for next step without further purification. TLC system: EtOAc:hexane (1:9); $R_f$: 0.5

Step 2. Ethyl 5-(2-hydroxypropan-2-yl)isoxazole-3-carboxylate

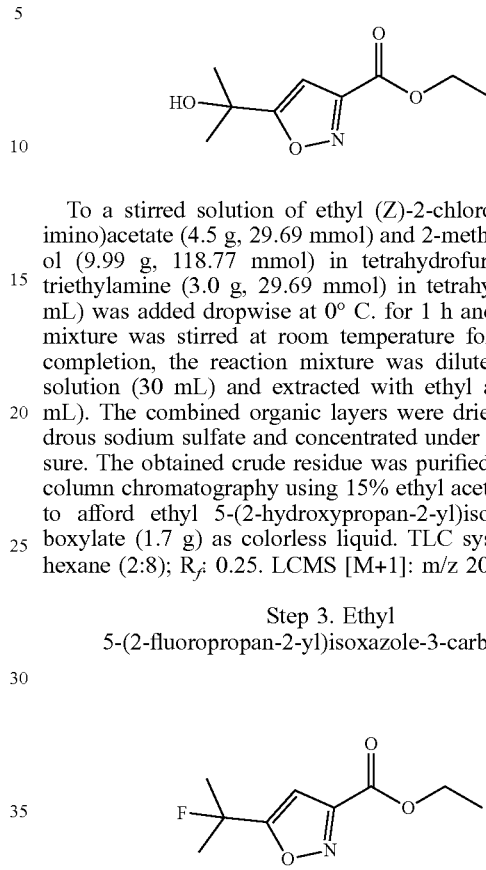

To a stirred solution of ethyl (Z)-2-chloro-2-(hydroxyimino)acetate (4.5 g, 29.69 mmol) and 2-methylbut-3-yn-2-ol (9.99 g, 118.77 mmol) in tetrahydrofuran (20 mL), triethylamine (3.0 g, 29.69 mmol) in tetrahydrofuran (10 mL) was added dropwise at 0° C. for 1 h and the reaction mixture was stirred at room temperature for 16 h. After completion, the reaction mixture was diluted with brine solution (30 mL) and extracted with ethyl acetate (3×50 mL). The combined organic layers were dried over anhydrous sodium sulfate and concentrated under reduced pressure. The obtained crude residue was purified by silica gel column chromatography using 15% ethyl acetate in hexane to afford ethyl 5-(2-hydroxypropan-2-yl)isoxazole-3-carboxylate (1.7 g) as colorless liquid. TLC system: EtOAc:hexane (2:8); $R_f$: 0.25. LCMS [M+1]: m/z 200.30

Step 3. Ethyl 5-(2-fluoropropan-2-yl)isoxazole-3-carboxylate

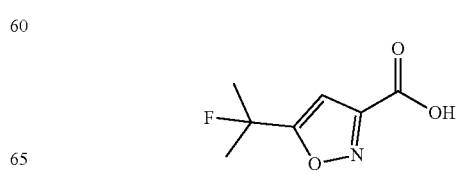

To a stirred solution of ethyl 5-(2-hydroxypropan-2-yl)isoxazole-3-carboxylate (1.5 g, 7.52 mmol) in dichloromethane (10 mL), diethylaminosulfur trifluoride (1.33 g, 8.28 mmol) in dichloromethane (5 mL) was added at −78° C. The reaction mixture was stirred at −78° C. for 2 h and room temperature for 1 h. After completion of the reaction, the reaction mixture was quenched with saturated sodium bicarbonate solution (20 mL) and extracted with dichloromethane (3×40 mL). The combined organic layers were dried over anhydrous sodium sulfate and concentrated under reduced pressure. The obtained crude residue was purified by silica gel column chromatography using 6% ethyl acetate in hexane to afford ethyl 5-(2-fluoropropan-2-yl)isoxazole-3-carboxylate (1.0 g) as colorless liquid. TLC system: EtOAc:hexane (2:8); $R_f$: 0.6. LCMS [M+1]: m/z 202.19

Step 4. 5-(2-fluoropropan-2-yl)isoxazole-3-carboxylic acid (20)

To a stirred solution ethyl 5-(2-fluoropropan-2-yl)isoxazole-3-carboxylate (1.0 g, 4.97 mmol) in tetrahydrofuran (15 mL), lithium hydroxide monohydrate (0.94 g, 22.37 mmol) in water (5 mL) was added at 0° C. and the reaction mixture was stirred at room temperature for 2 h. After completion of the reaction, reaction mixture was concentrated, and the residue was diluted with water (20 mL) and acidified with 2 N hydrochloric acid (pH-3) at 0° C. The resulting mixture was extracted with ethyl acetate (3×30 mL). The combined organic layers were dried over anhydrous sodium sulfate and concentrated under reduced pressure to afford 5-(2-fluoropropan-2-yl)isoxazole-3-carboxylic acid (0.84 g) as pale yellow liquid. TLC system: EtOAc:hexane (2:8); $R_f$: 0.05. LCMS [M+1]: m/z 174.14

(5-(2-Fluoropropan-2-yl)isoxazole-3-carbonyl)-L-leucine (21)

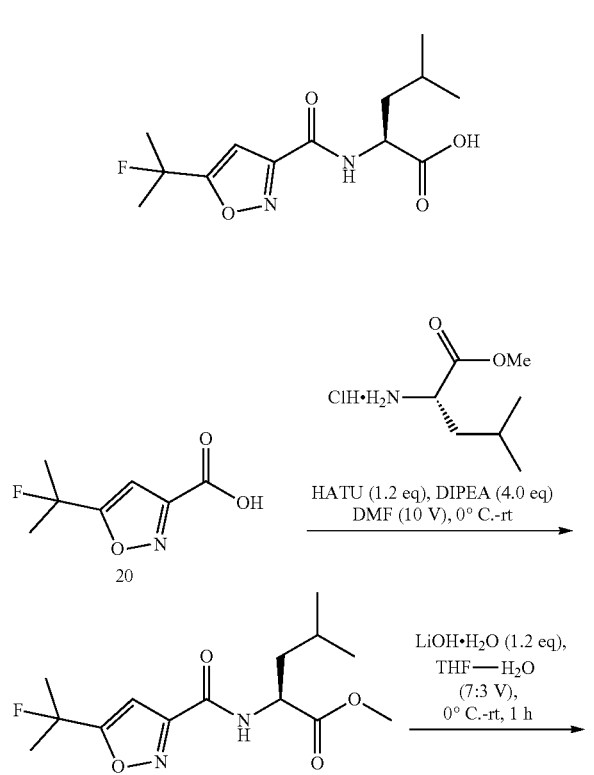

Step 1. Methyl (5-(2-fluoropropan-2-yl)isoxazole-3-carbonyl)-L-leucinate

To a stirred solution of 5-(2-fluoropropan-2-yl)isoxazole-3-carboxylic acid (0.2 g, 1.16 mmol), methyl L-leucinate hydrochloride (0.21 g, 1.16 mmol) and (1-[bis(dimethylamino)methylene]-1H-1,2,3-triazolo[4,5-b]pyridinium 3-oxide hexafluorophosphate (0.53 g, 1.39 mmol) in DMF (5 mL), N,N-diisopropylethylamine (0.6 g, 4.64 mmol) was added at 0° C. and the reaction mixture was stirred at room temperature for 2 h. After completion of the reaction, the reaction mixture was diluted with water (30 mL) and extracted with ethyl acetate (3×30 mL). The combined organic layers were dried over anhydrous sodium sulfate and concentrated under reduced pressure. The obtained crude residue was purified by Davisil® grade silica gel column chromatography using 10% ethyl acetate in hexane to afford methyl (5-(2-fluoropropan-2-yl)isoxazole-3-carbonyl)-L-leucinate (0.27 g) as an off-white solid. TLC system: EtOAc:hexane (2:8); $R_f$: 0.5. LCMS [M+1]: m/z 301.23

Step 2. (5-(2-fluoropropan-2-yl)isoxazole-3-carbonyl)-L-leucine (21)

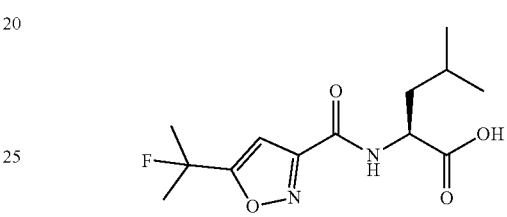

To a stirred solution methyl (5-(2-fluoropropan-2-yl)isoxazole-3-carbonyl)-L-leucinate (0.15 g, 0.5 mmol) in tetrahydrofuran (3 mL), lithium hydroxide monohydrate (0.025 g, 0.6 mmol) in water (1 mL) was added at 0° C. and the reaction mixture was stirred at room temperature for 2 h. After completion, the reaction mixture was concentrated, the residue was diluted with water (10 mL) and acidified with 2 N hydrochloric acid (pH-3) at 0° C. The resulting mixture was extracted with ethyl acetate (3×30 mL). The combined organic layers were dried over anhydrous sodium sulfate and concentrated under reduced pressure to afford (5-(2-fluoropropan-2-yl)isoxazole-3-carbonyl)-L-leucine (0.13 g) as an off-white solid. TLC system: EtOAc:hexane (2:8); $R_f$: 0.05. LCMS [M+1]: m/z 287.31

Synthesis of Compounds of Formula (I)

Example 1. Synthesis of $N^1$-(2-fluorophenyl)-$N^2$—((S)-4-methyl-1-oxo-1-(((S)-3-oxo-1-((S)-2-oxopiperidin-3-yl)-4-(trifluoromethoxy)butan-2-yl)amino)pentan-2-yl)oxalamide (219)

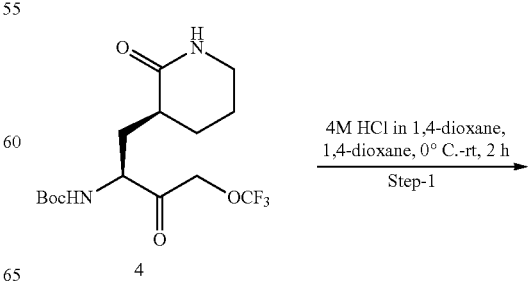

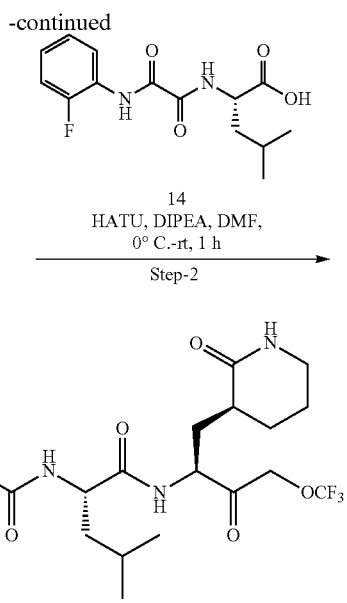

the reaction mixture was quenched with ice water (10 mL). The precipitated solid was filtered off, dried under vacuum to get the crude mass. The crude compound was purified by column chromatography (using Davisil® silica gel, 85-100% EtOAc in petroleum ether as an eluent) to afford 0.0491 g of $N^1$-(2-fluorophenyl)-$N^2$—((S)-4-methyl-1-oxo-1-(((S)-3-oxo-1-((S)-2-oxopiperidin-3-yl)-4-(trifluoromethoxy)butan-2-yl)amino)pentan-2-yl)oxalamide as a pale grey solid. [TLC system: MeOH:DCM (1:9); $R_f$ value: 0.5]. Analytical Data: LCMS m/z=547.49 (M+1); $^1$H NMR (400 MHz, DMSO-$d_6$) δ ppm 10.2 (s, 1H), 9.02 (d, J=8.0 Hz, 1H), 8.56 (d, J=7.6 Hz, 1H), 7.75 (t, J=7.6 Hz, 1H), 7.48 (s, 1H), 7.34-7.22 (m, 3H), 5.00 (q, J=16.8 Hz, 2H), 4.50-4.45 (m, 1H), 4.39-4.34 (m, 1H), 3.11 (s, 2H), 2.16-2.12 (m, 2H), 1.82-1.52 (m, 7H), 1.39-1.33 (m, 1H), 0.91 (d, J=6.0 Hz, 3H), 0.88 (d, J=6.0 Hz, 3H).

Example 2. Synthesis of (S)-3-((S)-2-(2-((2-fluorophenyl)amino)-2-oxoacetamido)-4-methylpentanamido)-2-oxo-4-((S)-2-oxopyrrolidin-3-yl)butyl diphenylphosphinate (125)

Step 1. Synthesis of (S)-3-((S)-2-amino-3-oxo-4-(trifluoromethoxy)butyl)piperidin-2-one hydrochloride To a solution of tert-butyl ((S)-3-oxo-1-((S)-2-oxopiperidin-3-yl)-4-(trifluoromethoxy)butan-2-yl)carbamate (4) (0.15 g, 0.41 mmol) in 1,4-dioxane (1.5 mL) was added 4 M HCl in 1,4-dioxane (3 mL) at 0° C. The reaction mixture was stirred at room temperature for 2 h. After completion of reaction by TLC, the reaction mixture was concentrated under reduced pressure to give 0.12 g of (S)-3-((S)-2-amino-3-oxo-4-(trifluoromethoxy)butyl)piperidin-2-one hydrochloride as a pale yellow solid. [TLC system: MeOH:DCM (1:9); $R_f$ value: 0.1].

Step 2. Synthesis of $N^1$-(2-fluorophenyl)-$N^2$—((S)-4-methyl-1-oxo-1-(((S)-3-oxo-1-((S)-2-oxopiperidin-3-yl)-4-(trifluoromethoxy)butan-2-yl)amino)pentan-2-yl)oxalamide

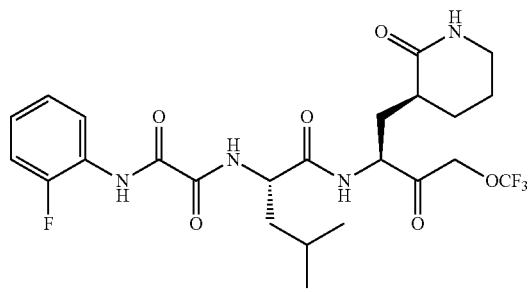 [SMILES: CC(C)C[C@H](NC(=O)C(=O)Nc1ccccc1F)C(=O)N[C@@H](C[C@@H]1CCCNC1=O)C(=O)COC(F)(F)F]

To a solution of (S)-3-((S)-2-amino-3-oxo-4-(trifluoromethoxy)butyl)piperidin-2-one hydrochloride (0.12 g, 0.39 mmol) in DMF (2 mL) was added DIPEA (0.2 mL, 1.18 mmol) and the reaction mixture was cooled to 0° C. 2-((2-Fluorophenyl)amino)-2-oxoacetyl)-L-leucine (14) (0.12 g, 0.39 mmol) and HATU (0.19 g, 0.51 mmol) were added, and the resultant reaction mixture was stirred at room temperature for 1 h. After completion of reaction checked by TLC,

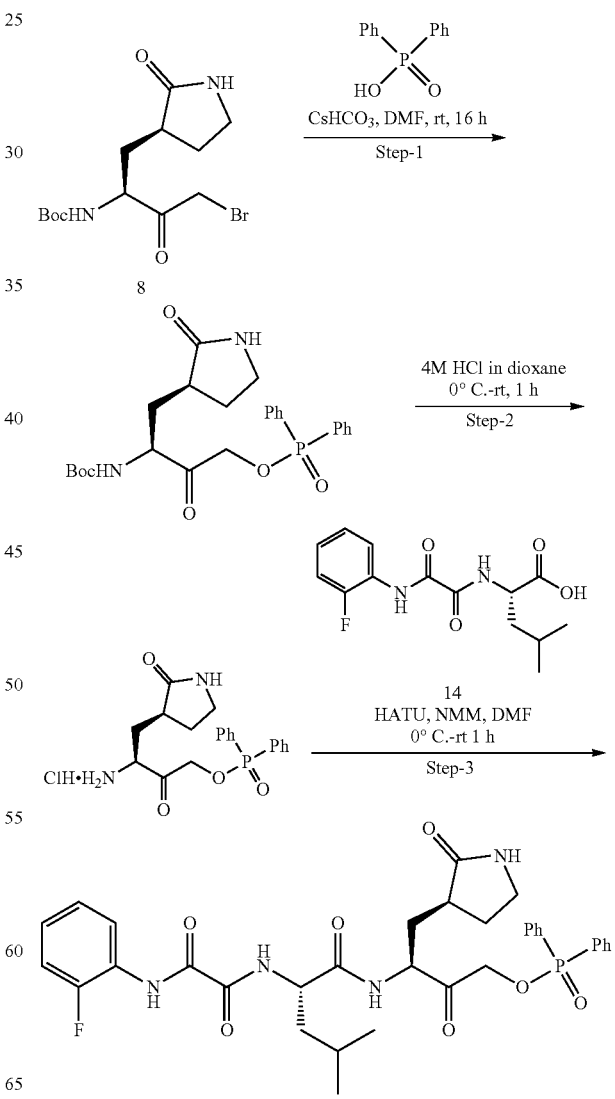

Step 1. Synthesis of tert-butyl ((S)-4-((diphenylphosphoryl)oxy)-3-oxo-1-((S)-2-oxopyrrolidin-3-yl)butan-2-yl)carbamate To the mixture of tert-butyl ((S)-4-bromo-3-oxo-1-((S)-2-oxopyrrolidin-3-yl)butan-2-yl)carbamate (8) (0.3 g, 0.862 mmol) in DMF (5.0 mL) were added diphenylphosphinic acid (0.112 g, 0.517 mmol) and cesium bicarbonate (0.367 g, 1.896 mmol) and the reaction mixture was stirred at room temperature for 3 h. After completion, the reaction mixture was diluted with water (30 mL) and extracted with ethyl acetate (3×30 mL). The combined organic layers were dried over anhydrous sodium sulfate and concentrated under reduced pressure. The crude residue was then purified by silica gel (230-400 mesh) column chromatography using 70-90% ethyl acetate in petroleum ether as a gradient to afford tert-butyl ((S)-4-((diphenylphosphoryl)oxy)-3-oxo-1-((S)-2-oxopyrrolidin-3-yl)butan-2-yl)carbamate 3 (0.21 g) as a brown solid. TLC system: EtOAc:petroleum ether (10:0); R$_f$: 0.3.

Step 2. Synthesis of (S)-3-amino-2-oxo-4-((S)-2-oxopyrrolidin-3-yl)butyl diphenylphosphinate hydrochloride To a stirred solution of ((S)-4-((diphenylphosphoryl)oxy)-3-oxo-1-((S)-2-oxopyrrolidin-3-yl)butan-2-yl)carbamate (0.18 g, 0.370 mmol) in 1,4-dioxane (1.0 mL) was added 4 M HCl in 1,4-dioxane (0.4 mL, 1.48 mmol) at 0° C. and the resultant mixture was stirred at room temperature for 2 h. After completion, solvent was removed under reduced pressure and the resulting crude product was washed with diethyl ether (2×10 mL) to afford ((S)-3-amino-2-oxo-4-((S)-2-oxopyrrolidin-3-yl)butyl diphenylphosphinate hydrochloride (180 mg) as a yellow Solid. TLC system: MeOH: DCM (1:9); Rf: 0.1.

Step 3. Synthesis of (S)-3-((S)-2-(2-((2-fluorophenyl)amino)-2-oxoacetamido)-4-methylpentanamido)-2-oxo-4-((S)-2-oxopyrrolidin-3-yl)butyl diphenylphosphinate To a stirred solution ((2-((2-fluorophenyl)amino)-2-oxoacetyl)-L-leucine (0.13 g, 0.439 mmol) (14) and (S)-3-amino-2-oxo-4-((S)-2-oxopyrrolidin-3-yl)butyl diphenylphosphinate hydrochloride (0.180 g, 0.506 mmol) in DMF (3.0 mL) was added HATU (0.20 g, 0.526 mmol) followed by DIPEA (0.24 mL, 1.317 mmol) at 0° C. and the resultant mixture was stirred at room temperature for 4 h. After reaction completion, cold water (10 mL) was added and to the mixture was extracted with EtOAc (2×15 mL). The combined organic layers were dried over anhydrous sodium sulfate, filtered and concentrated under reduced pressure. The crude product was then purified by column chromatography over silica gel (230-400 mesh) using 2-3% MeOH in DCM as a gradient to afford (S)-3-((S)-2-(2-((2-fluorophenyl)amino)-2-oxoacetamido)-4-methylpentanamido)-2-oxo-4-((S)-2-oxopyrrolidin-3-yl)butyl diphenylphosphinate (15 mg) as an off-white solid. TLC system: MeOH:DCM (1:9); Rf: 0.5. Analytical Data: LCMS m/z 665.68 (M+1); $^1$H NMR (400 MHz, DMSO-d$_6$) δ ppm 10.25 (s, 1H), 8.91 (d, J=8.4 Hz, 1H), 8.56 (d, J=7.6 Hz, 1H), 7.80-7.52 (m, 12H), 7.34-7.25 (m, 4H), 4.84-4.70 (m, 2H), 4.46-4.32 (m, 2H), 3.09 (t, J=7.8 Hz, 2H), 2.24 (t, J=4.6 Hz, 1H), 2.04 (q, J=5.4 Hz, 1H), 1.93-1.87 (m, 1H), 1.70-1.47 (m, 5H), 0.88-0.84 (m, 6H).

Example 3. Synthesis of (S)-3-((S)-2-(2-((2-fluorophenyl)amino)-2-oxoacetamido)-4-methylpentanamido)-2-oxo-4-((S)-2-oxopyrrolidin-3-yl)butyl methyl(phenyl)phosphinate (651)

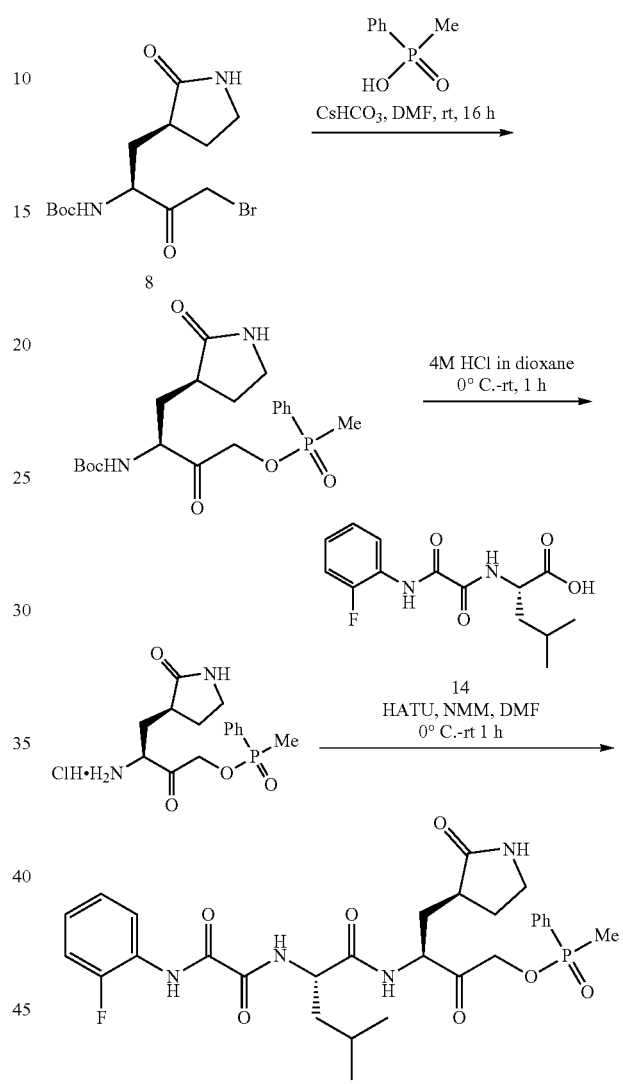

Step 1. Synthesis of tert-butyl ((2S)-4-((methyl(phenyl)phosphoryl)oxy)-3-oxo-1-((S)-2-oxopyrrolidin-3-yl)butan-2-yl)carbamate To the mixture of tert-butyl ((S)-4-bromo-3-oxo-1-((S)-2-oxopyrrolidin-3-yl)butan-2-yl)carbamate (8) (0.5 g, 1.436 mmol) in DMF (5.0 mL) were added methyl(phenyl)phosphinic acid (0.224 g, 1.436 mmol) and cesium bicarbonate and the reaction mixture was stirred at room temperature for 24 h. After completion, the reaction mixture was diluted with water (30 mL) and extracted with ethyl acetate (3×30 mL). The combined organic layers were dried over anhydrous sodium sulfate and concentrated under reduced pressure. The crude residue was then purified by silica gel (230-400 mesh) column chromatography using 70-90% ethyl acetate in petroleum ether as a gradient to afford tert-butyl ((2S)-4-((methyl(phenyl)phosphoryl)oxy)-3-oxo- 1-((S)-2-oxopyrrolidin-3-yl)butan-2-yl)carbamate (0.25 g) as a brown solid. TLC system: EtOAc:petroleum ether (10:0); R$_f$: 0.3.

Step 2. Synthesis of (S)-3-amino-2-oxo-4-((S)-2-oxopyrrolidin-3-yl)butyl methyl(phenyl)phosphinate hydrochloride To a stirred solution of tert-butyl ((2S)-4-((methyl(phenyl)phosphoryl)oxy)-3-oxo-1-((S)-2-oxopyrrolidin-3-yl)butan-2-yl)carbamate (0.25 g, 0.588 mmol) in 1,4-dioxane (2.0 mL) was added 4 M HCl in 1,4-dioxane (0.6 mL, 2.35 mmol) at 0° C. and the resultant mixture was stirred at room temperature for 2 h. After completion, solvent was removed under reduced pressure and the resulting crude product was washed with diethyl ether (2×10 mL) to afford (S)-3-amino-2-oxo-4-((S)-2-oxopyrrolidin-3-yl)butyl methyl(phenyl)phosphinate hydrochloride (0.18 g) as a yellow Solid. TLC system: MeOH:DCM (1:9); Rf: 0.1.

Step 3. Synthesis of (S)-3-((S)-2-(2-((2-fluorophenyl)amino)-2-oxoacetamido)-4-methylpentanamido)-2-oxo-4-((S)-2-oxopyrrolidin-3-yl)butyl methyl(phenyl)phosphinate To a stirred solution ((2-((2-fluorophenyl)amino)-2-oxoacetyl)-L-leucine (0.15 g, 0.506 mmol) (14) and (S)-3-amino-2-oxo-4-((S)-2-oxopyrrolidin-3-yl)butyl methyl(phenyl)phosphinate hydrochloride (0.183 g, 0.506 mmol) in DMF (3.0 mL) was added HATU (0.25 g, 0.658 mmol) followed by DIPEA (0.3 mL, 2.027 mmol) at 0° C. and the resultant mixture was stirred at room temperature for 4 h. After completion of the reaction, cold water (10 mL) was added, and the mixture was extracted with EtOAc (2×15 mL). The combined organic layers were dried over anhydrous sodium sulfate, filtered and concentrated under reduced pressure. The crude product was then purified by column chromatography over silica gel (230-400 mesh) using 2-3% MeOH in DCM as a gradient to afford (S)-3-((S)-2-(2-((2-fluorophenyl)amino)-2-oxoacetamido)-4-methylpentanamido)-2-oxo-4-((S)-2-oxopyrrolidin-3-yl)butyl methyl(phenyl)phosphinate (40 mg) as an off-white solid. TLC system: MeOH:DCM (1:9); Rf: 0.5. Analytical Data: LCMS m/z 603.55 (M+1); $^1$H NMR (400 MHz, DMSO-d$_6$) δ ppm 10.26 (d, J=9.1 Hz, 1H), 8.92 (d, J=8.2 Hz, 1H), 8.54 (t, J=8.5 Hz, 1H), 7.95-7.52 (m, 7H), 7.34-7.21 (m, 3H), 4.83-4.33 (m, 4H), 3.11 (t, J=10.1 Hz, 2H), 2.24 (d, J=9.5 Hz, 1H), 2.11-2.01 (m, 1H), 1.89 (t, J=11.0 Hz, 1H), 1.78-1.52 (m, 8H), 0.90-0.86 (m, 6H).

Example 4. Synthesis of N$^1$-(cyclopentylmethyl)-N$^2$—((S)-4-methyl-1-oxo-1-((S)-3-oxo-1-((S)-2-oxopyrrolidin-3-yl)-4-(2,3,5,6-tetrafluorophenoxy)butan-2-yl)amino)pentan-2-yl)oxalamide (81)

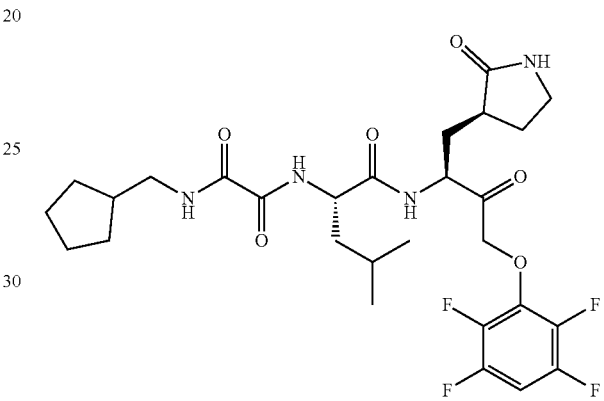

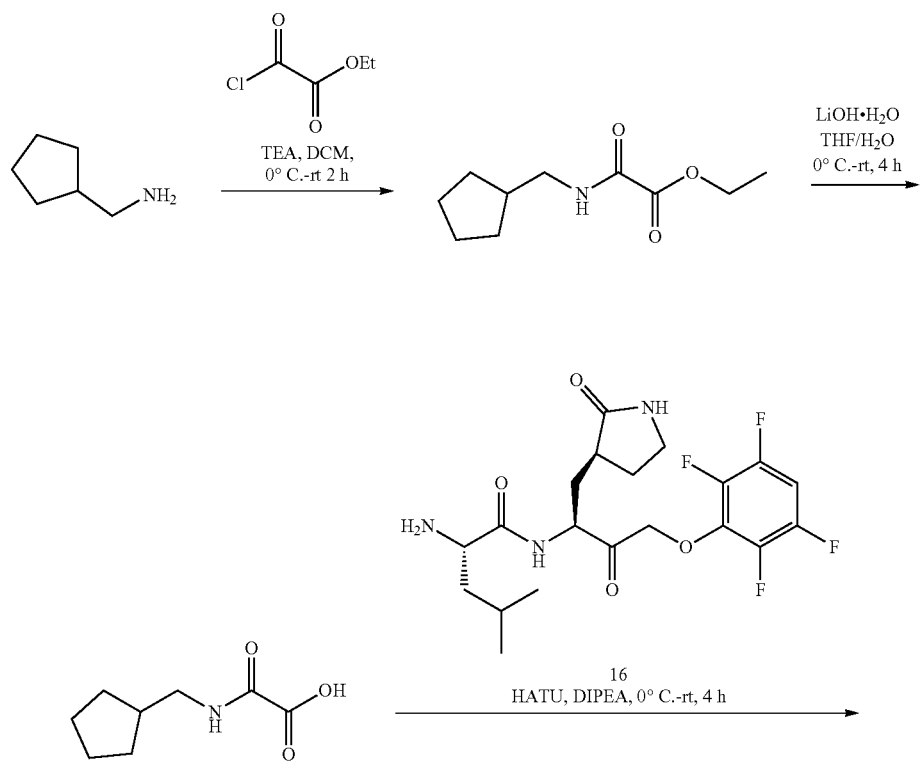

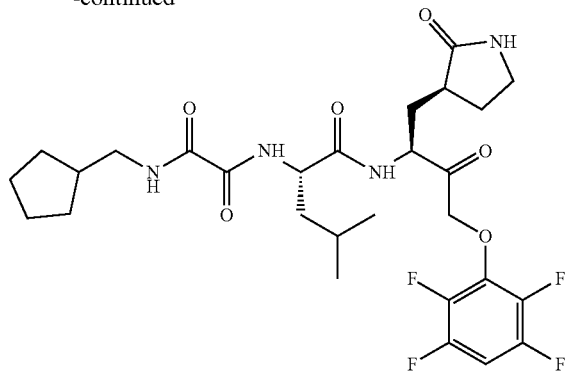

Step 1. Synthesis of ethyl 2-((cyclopentylmethyl)amino)-2-oxoacetate

To a stirred solution of cyclopentanamine (1 g, 10.08 mmol) in DCM (10 mL) were added ethyl 2-chloro-2-oxoacetate (1.4 g, 10.58 mmol) and triethylamine (1.5 mL, 10.58 mmol) at 0° C. The resultant mixture was stirred at room temperature for 2 h. After completion, volatiles were removed under reduced pressure and extracted with diethyl ether (3×50 mL). The combined organic layers were dried over anhydrous sodium sulfate, filtered, and concentrated under reduced pressure. The crude residue was then purified by column chromatography over silica gel (230-400 mesh) using 20% ethyl acetate in petroleum ether as an eluent to afford ethyl 2-((cyclopentylmethyl)amino)-2-oxoacetate (1.8 g) as an off-white solid. TLC system: EtOAc:hexane (3:7); $R_f$: 0.6.

Step 2. Synthesis of 2-((cyclopentylmethyl)amino)-2-oxoacetic acid

To a stirred solution of ethyl 2-((cyclopentylmethyl)amino)-2-oxoacetate (1.8 g, 9.05 mmol) in THF—$H_2O$ (12:4 mL) was added lithium hydroxide monohydrate (0.456 mg, 10.85 mmol), and the resultant mixture was stirred at 0° C. for 2 h. The reaction mixture was acidified by adding 1 N aq. HCl and the pH was adjusted to ~4. The reaction mixture was diluted with ethyl acetate (3×50 mL). The combined organic layers were dried over anhydrous sodium sulfate, filtered and concentrated under reduced pressure to give crude residue. The crude product was then purified by column chromatography over silica gel (230-400 mesh) using 20% ethyl acetate in petroleum ether as an eluent to afford 2-((cyclopentylmethyl)amino)-2-oxoacetic acid (0.4 g) as an off-white solid. TLC system: MeOH:DCM (1:9); $R_f$: 0.3.

Step 3. Synthesis of $N^1$-(cyclopentylmethyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide To a solution of (S)-2-amino-4-methyl-N—((S)-3-oxo-1-((S)-2-oxopyrrolidin-3-yl)-4-(2,3,5,6-tetrafluorophenoxy)butan-2-yl)pentanamide (0.16 g, 0.331 mmol) and 2-((cyclopentylmethyl)amino)-2-oxoacetic acid (0.06 g, 0.331 mmol) in DMF (3 mL) at 0° C. was added HATU (0.16 g, 0.42 mmol) and DIPEA (0.18 mL, 0.99 mmol) and the mixture was stirred at room temperature for 4 h. After completion of the reaction, cold water (40 mL) was added and the mixture was extracted with EtOAc (3×50 mL). The combined organic layers were dried over anhydrous sodium sulfate, filtered and concentrated under reduced pressure. The crude product was then purified by column chromatography over silica gel (230-400 mesh) using 70-80% ethyl acetate in petroleum ether as a gradient to afford 0.1 g of $N^1$-(cyclopentylmethyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide as an off-white solid. TLC system: EtOAc (100%); $R_f$: 0.6. Analytical Data: LCMS 548.48 (M+1); $^1$H NMR (400 MHz, DMSO-$d_6$) δ ppm 8.42 (d, J=8.0 Hz, 1H), 7.62-7.55 (m, 2H), 7.02 (d, J=7.2 Hz, 1H), 5.18 (d, J=12.1 Hz, 2H), 4.43 (s, 1H), 3.90 (d, J=5.8 Hz, 1H), 3.16 (s, 2H), 2.26 (d, J=8.1 Hz, 1H), 2.16-1.96 (m, 2H), 1.61 (t, J=10.4 Hz, 3H), 1.35 (s, 11H), 0.86 (q, J=6.5 Hz, 6H).

Example 5. Synthesis of $N^1$-(4,4-difluorocyclohexyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide (151)

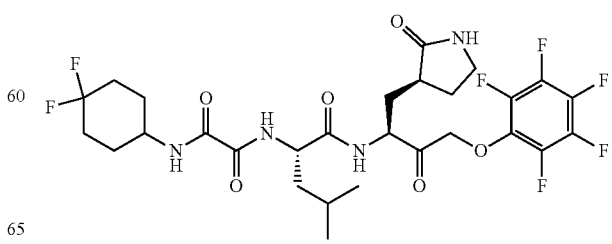

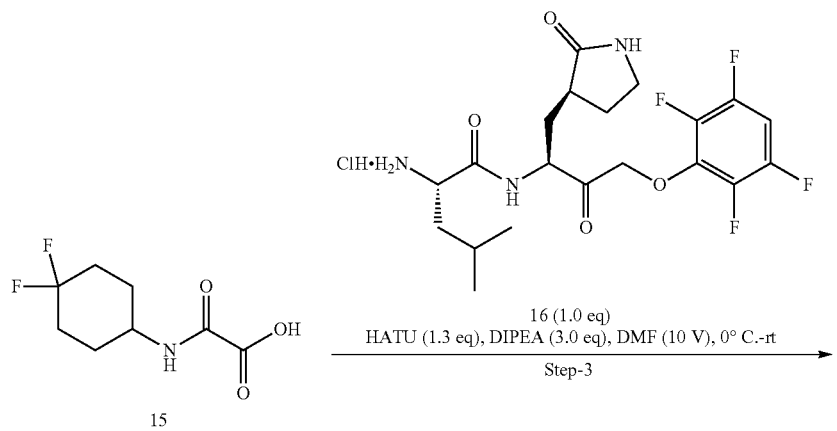

To a stirred solution 2-((4,4-difluorocyclohexyl)amino)-2-oxoacetic acid (0.086 g, 0.414 mmol) and (S)-2-amino-4-methyl-N—((S)-3-oxo-1-((S)-2-oxopyrrolidin-3-yl)-4-(2,3,5,6-tetrafluorophenoxy)butan-2-yl)pentanamide hydrochloride (16) (0.2 g, 0.414 mmol) in DMF (5 mL) was added HATU (0.19 g, 0.497 mmol) followed by NMM (0.2 mL, 1.66 mmol) at 0° C. and the resultant mixture was stirred at room temperature for 1 h. After completion, the reaction mixture was diluted with water (40 mL) and extracted with EtOAc (3×100 mL). The combined organic layers were washed with brine dried over anhydrous sodium sulfate, filtered and concentrated under reduced pressure to give. The residue was then purified by column chromatography using 6% MeOH in DCM to afford $N^1$-(4,4-difluorocyclohexyl)-$N^2$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide (0.05 g) as an off-white solid. TLC system: MeOH in DCM (1:9); $R_f$: 0.6. Analytical Data: LCMS m/z=637.60 (M+1); $^1$H NMR (400 MHz, DMSO-$d_6$) δ ppm 8.78 (d, J=8.4 Hz, 1H), 8.58 (q, J=8.7 Hz, 2H), 7.65-7.54 (m, 2H), 5.20 (q, J=15.2 Hz, 2H), 4.45-433 (m, 2H), 3.80 (d, J=8.0 Hz, 1H), 3.13-3.09 (m, 2H), 2.26 (t, J=6.1 Hz, 1H), 2.08-1.49 (m, 15H), 0.87 (q, J=5.6 Hz, 6H).

Example 6. Synthesis of $N^1$—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-$N^2$—((S)-1,2,3,4-tetrahydronaphthalen-1-yl)oxalamide (145)

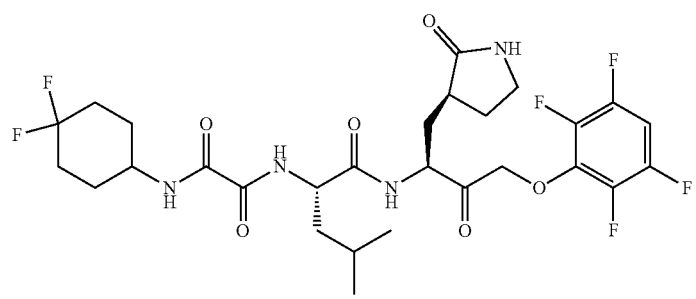

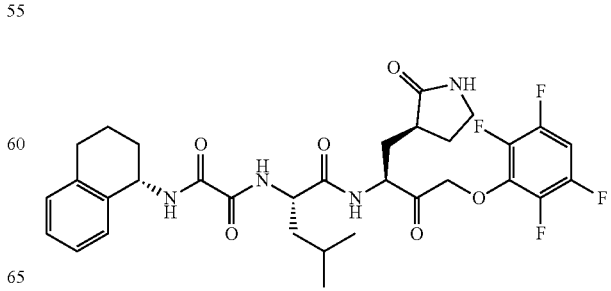

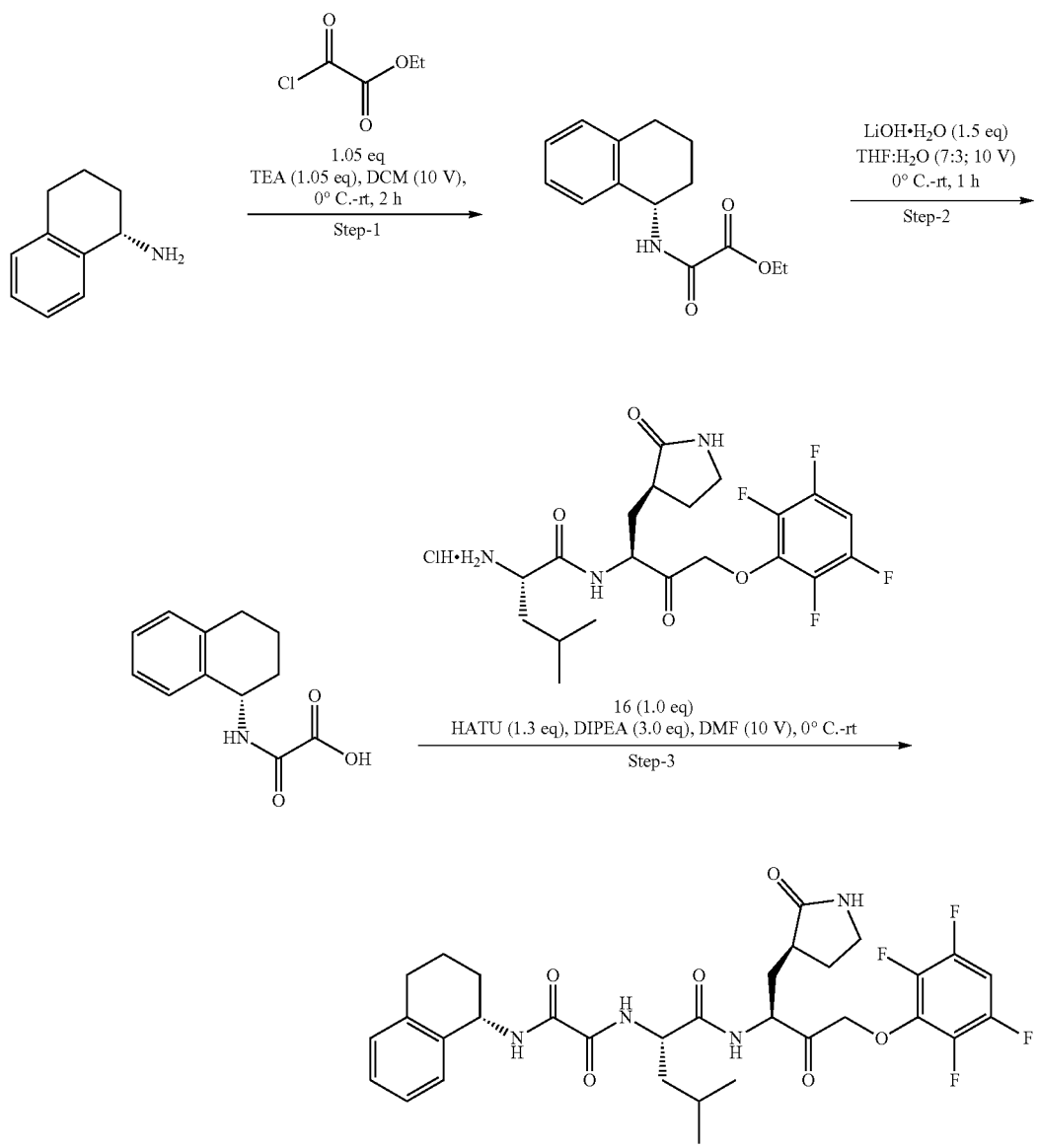

Step 1. Synthesis of ethyl (S)-2-oxo-2-((1,2,3,4-tetrahydronaphthalen-1-yl)amino)acetate To a stirred solution of(S)-1,2,3,4-tetrahydronaphthalen-1-amine (2.0 g, 13.58 mmol) in dichloromethane (20 mL) was added triethylamine (1.4 g, 14.26 mmol) followed by ethyl 2-chloro-2-oxoacetate (1.9 g, 14.26 mmol) at 0° C. and the mixture was stirred at room temperature for 2 h. After completion, the reaction mixture was concentrated under reduced pressure (bath temperature <25° C.). The crude residue was then purified by flash column chromatography over silica gel (Davisil® silica) using 15% EtOAc in petroleum ether as an eluent to afford ethyl (S)-2-oxo-2-((1,2,3,4-tetrahydronaphthalen-1-yl)amino)acetate (2.2 g) as a colorless liquid. TLC system: EtOAc in petroleum ether (4:6); $R_f$: 0.3.

Step 2. Synthesis of (S)-2-oxo-2-((1,2,3,4-tetrahydronaphthalen-1-yl)amino)acetic acid To a solution of ethyl (S)-2-oxo-2-((1,2,3,4-tetrahydronaphthalen-1-yl)amino)acetate (2.2 g, 8.8 mmol) in THF (22 mL) and water (5 mL) was added aqueous solution of LiOH·H$_2$O (0.485 g, 11.56 mmol) dropwise at 0° C. and the mixture was stirred at room temperature for 1 h. After completion, the reaction mixture was washed with ethyl acetate (2×50 mL). The aqueous layer was acidified with acetic acid and extracted with ethyl acetate (2×50 mL). The combined organic layers were dried over anhydrous sodium sulfate and concentrated under reduced pressure to give(S)-2-oxo-2-((1,2,3,4-tetrahydronaphthalen-1-yl)amino)acetic acid (1.5 g) as a colorless solid. TLC system: MeOH and DCM (0.5:9.5); $R_f$: 0.2

Step 3. Synthesis of N¹—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N²—((S)-1,2,3,4-tetrahydronaphthalen-1-yl)oxalamide To a stirred solution (S)-2-oxo-2-((1,2,3,4-tetrahydronaphthalen-1-yl)amino)acetic acid (0.091 g, 0.413 mmol) and (S)-2-amino-4-methyl-N—((S)-3-oxo-1-((S)-2-oxopyrrolidin-3-yl)-4-(2,3,5,6-tetrafluorophenoxy)butan-2-yl)pentanamide hydrochloride (0.2 g, 0.413 mmol) in DMF (5 mL) was added HATU (0.204 g, 0.536 mmol) followed by DIPEA (0.2 mL, 1.239 mmol) at 0° C. and the reaction mixture was stirred at room temperature for 2 h. After completion, water (25 mL) was added to the reaction mixture followed by extraction with ethyl acetate (3×25 mL). The combined organic layers were washed with brine (1×25 mL) dried over anhydrous sodium sulfate, and concentrated under reduced pressure. The crude residue was then purified by flash column chromatography over silica gel (230-400 mesh) using 60-65% EtOAc in petroleum ether as a gradient to afford N¹—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N²—((S)-1,2,3,4-tetrahydronaphthalen-1-yl)oxalamide (0.125 g) as an off-white solid. TLC system: EtOAc (100) R$_f$: 0.3. Analytical Data: ¹H NMR (400 MHz, DMSO-d$_6$) δ ppm 8.91 (d, J=9.2 Hz, 1H), 8.66 (q, J=11.1 Hz, 1H), 7.64-7.52 (m, 2H), 7.16-7.06 (m, 4H), 5.22 (q, J=15.0 Hz, 2H), 5.01 (d, J=4.2 Hz, 1H), 4.46-4.35 (m, 2H), 3.31-3.07 (m, 2H), 2.72-2.66 (m, 2H), 2.18-2.05 (m, 2H), 1.98-1.90 (m, 4H), 1.88-1.52 (m, 6H), 0.89 (q, J=5.8 Hz, 6H).

Example 7. Synthesis of (S)-2-(2-(3-chlorophenyl)acetamido)-4-methyl-N—((S)-3-oxo-1-((S)-2-oxopyrrolidin-3-yl)-4-(2,3,5,6-tetrafluorophenoxy)butan-2-yl)pentanamide (144)

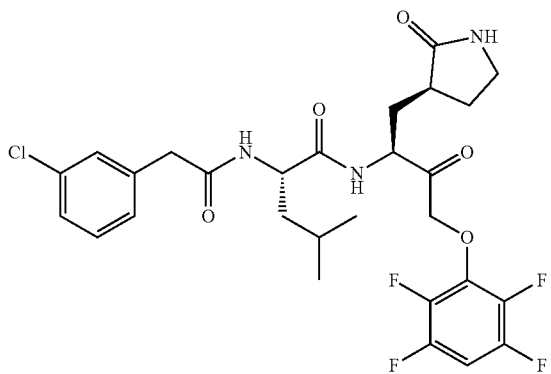 [SMILES: CC(C)C[C@H](NC(=O)Cc1cccc(Cl)c1)C(=O)N[C@@H](C[C@@H]1CCNC1=O)C(=O)COc1c(F)c(F)cc(F)c1F]

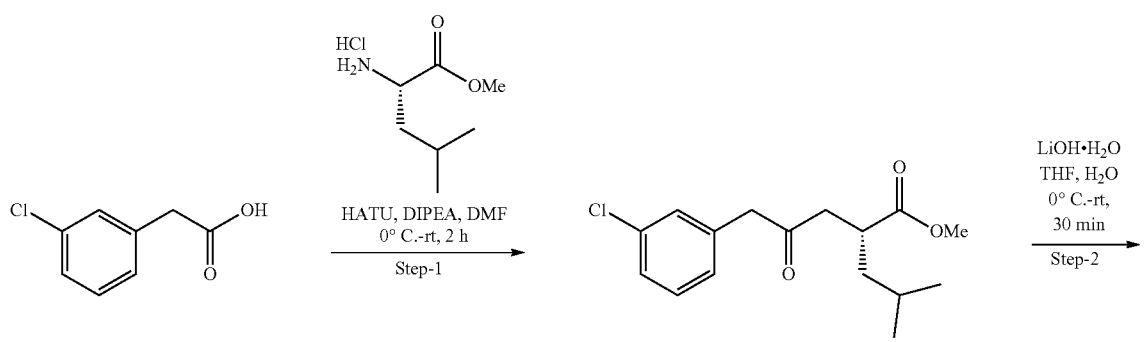

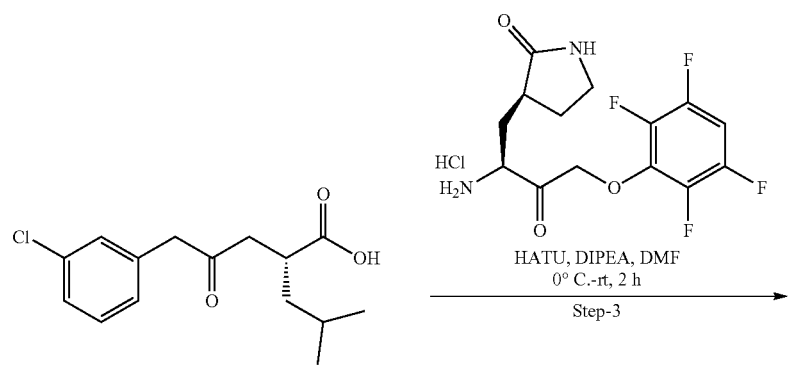

-continued

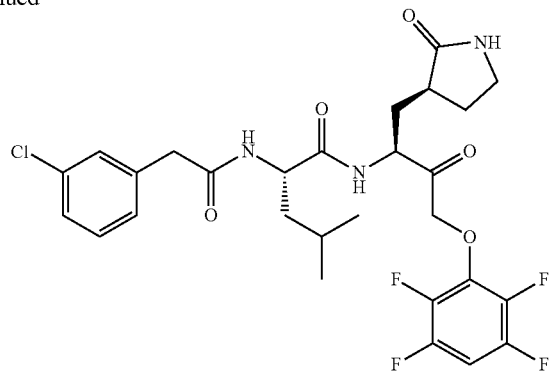

Step 1. Synthesis of methyl (2-(3-chlorophenyl)acetyl)-L-leucinate

To a solution of 2-(3-chlorophenyl)acetic acid (3.0 g, 17.59 mmol) in DMF (30 mL) was added HATU (10.03 g, 26.34 mmol) and DIPEA (12.2 mL, 70.34 mmol) at 0° C. Then methyl L-leucinate hydrochloride (3.19 g, 17.59 mmol) was added, and the mixture was stirred at room temperature for 2 h. After completion of the reaction, the reaction mixture was quenched with cold water and extracted with EtOAc (100 mL×2). The combined organic layers were washed with cold water (100 mL) and brine (100 mL), dried over $Na_2SO_4$, filtered and concentrated under reduced pressure. The crude compound was purified by column chromatography over silica gel (Davisil®) (using 30% EtOAc in petroleum ether as eluent) to afford 4.3 g of methyl (2-(3-chlorophenyl)acetyl)-L-leucinate as an off white solid. [TLC system: EtOAc:petroleum ether (1:1); $R_f$ value: 0.4].

Step 2. Synthesis of (2-(3-chlorophenyl)acetyl)-L-leucine

To a solution of methyl (2-(3-chlorophenyl)acetyl)-L-leucinate (4.3 g, 14.44 mmol) in THF:water (9:1, 43 mL), was added LiOH·$H_2O$ (1.2 g, 28.88 mmol) at 0° C. The reaction mixture was stirred at room temperature for 30 min. After completion of reaction by TLC, the reaction mixture was cooled to 0° C., acidified with aqueous citric acid solution to pH 4 and extracted with EtOAc (100 mL×2). The combined organic layers were washed with cold water (100 mL) and brine (100 mL), dried over $Na_2SO_4$, filtered and concentrated under reduced pressure to afford 3.1 g of (2-(3-chlorophenyl)acetyl)-L-leucine as an off white solid. [TLC system: MeOH:DCM (1:9); $R_f$ value: 0.2].

Synthesis of (S)-2-(2-(3-chlorophenyl)acetamido)-4-methyl-N—((S)-3-oxo-1-((S)-2-oxopyrrolidin-3-yl)-4-(2,3,5,6-tetrafluorophenoxy)butan-2-yl)pentanamide To a solution of (2-(3-chlorophenyl)acetyl)-L-leucine (0.3 g, 1.06 mmol) in DMF (3 mL) was added HATU (0.60 g, 1.59 mmol) and DIPEA (0.56 mL, 3.17 mmol) at 0° C. Then (S)-3-((S)-2-amino-3-oxo-4-(2,3,5,6-tetrafluorophenoxy)butyl)pyrrolidin-2-one hydrochloride (0.43 g, 1.16 mmol) was added and stirred at room temperature for 2 h. After completion of the reaction, the reaction mixture was quenched with cold water and extracted with EtOAc (100 mL×2). The combined organic layers were washed with cold water (100 mL) and brine (100 mL), dried over $Na_2SO_4$, filtered and concentrated under reduced pressure. The crude residue was purified by column chromatography over silica gel (Davisil®) (using EtOAc as eluent) to afford 0.120 g of the title compound as an off white solid. [TLC system: MeOH:DCM (1:9); $R_f$ value: 0.4]. Analytical Data: LCMS m/z=600.51 (M+1); $^1$H NMR (400 MHz, DMSO-$d_6$) δ ppm 8.59 (d, J=7.8 Hz, 1H), 8.36 (d, J=7.5 Hz, 1H), 7.62-7.54 (m, 2H), 7.32-7.25 (m, 3H), 7.19 (d, J=7.0 Hz, 1H), 5.17 (d, J=7.1 Hz, 2H), 4.43-4.22 (m, 2H), 3.48 (s, 2H), 3.15-3.10 (m, 1H), 3.04-2.95 (m, 1H), 2.29-2.19 (m, 1H), 2.10-1.89 (m, 2H), 1.67-1.51 (m, 3H), 1.51-1.41 (m, 2H), 0.89 (d, J=6.4 Hz, 3H), 0.81 (d, J=6.8 Hz, 3H).

Example 8. Synthesis of (S)-2-(2-(5-acetyl-2-methoxyphenyl)acetamido)-4-methyl-N—((S)-3-oxo-1-((S)-2-oxopyrrolidin-3-yl)-4-(2,3,5,6-tetrafluorophenoxy)butan-2-yl)pentanamide (154)

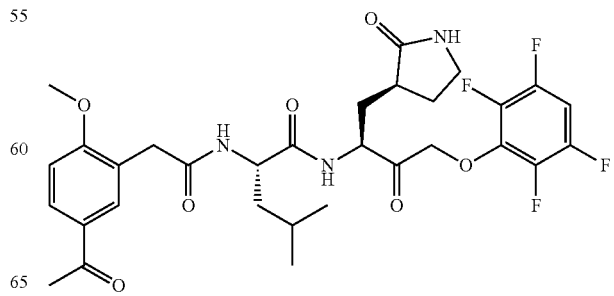

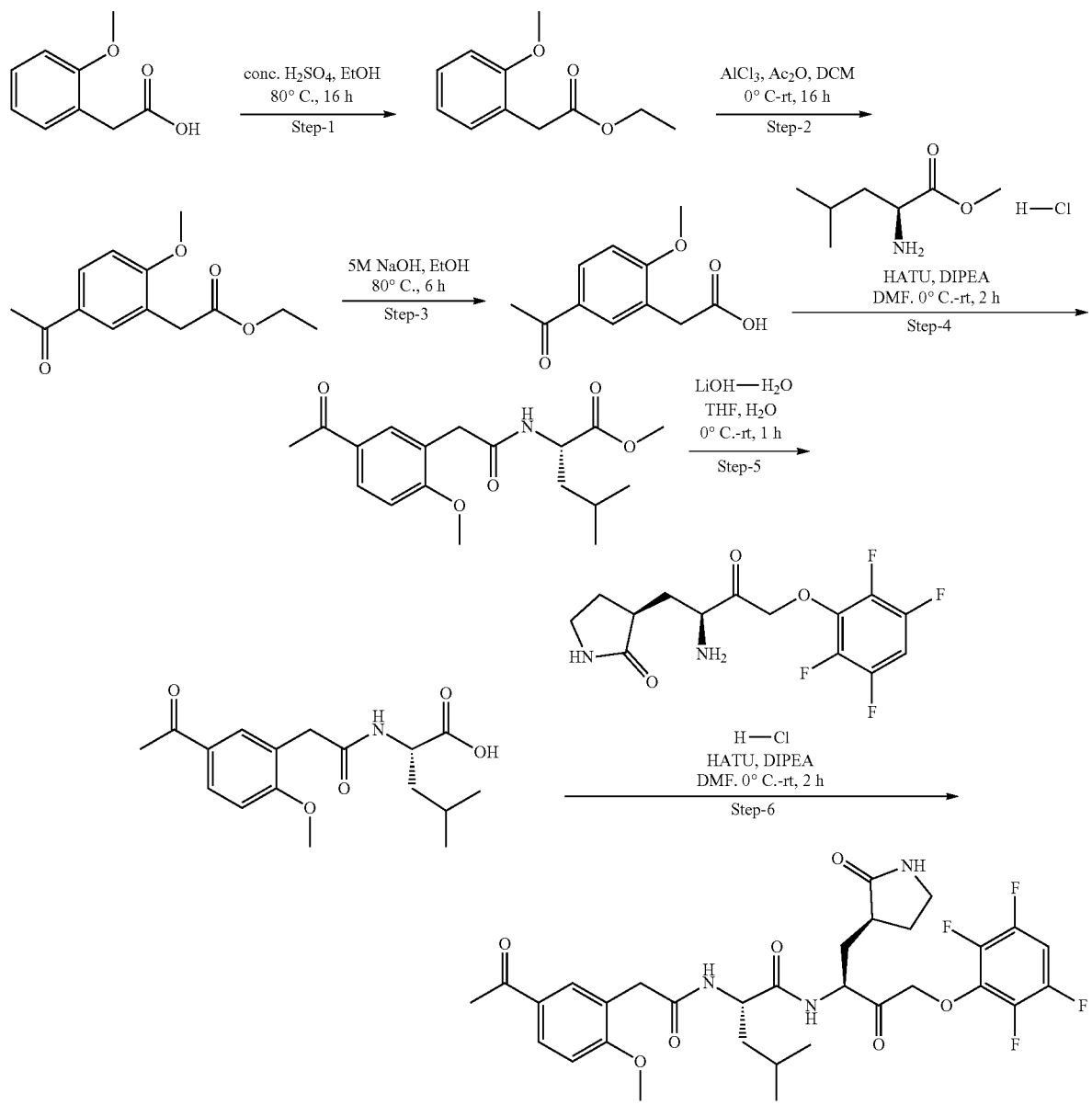

Step 1. Synthesis of ethyl 2-(2-methoxyphenyl)acetate

To a solution of 2-(2-methoxyphenyl)acetic acid (2 g, 12.03 mmol) in EtOH (20 mL), was added conc. H₂SO₄ (3 mL) slowly at 0° C. The reaction mixture was heated to 80° C. and stirred for 16 h. After completion of reaction by TLC, the reaction mixture was concentrated under reduced pressure to give a residue. The residue was diluted with EtOAc (50 mL) and washed with water (2×100 mL). The organic layer was concentrated under reduced pressure to afford 2.0 g of ethyl 2-(2-methoxyphenyl)acetate as colorless oil. [TLC system: EtOAc:petroleum ether (2:8); Rf value: 0.6].

Step 2. Synthesis of ethyl 2-(5-acetyl-2-methoxyphenyl)acetate

To a solution of AlCl₃ (2.06 g, 15.45 mmol) and Ac₂O (0.73 mL, 7.72 mmol) in DCM (20 mL), was added ethyl 2-(2-methoxyphenyl)acetate (1.0 g, 5.15 mmol) at 0° C., stirred at room temperature for 16 h. After completion of reaction by TLC, the reaction mixture was quenched with ice water (40 mL) and extracted with DCM (30 mL). The organic layer was washed with water (50 mL) and saturated brine solution (50 mL), dried over anhydrous Na₂SO₄, filtered and concentrated under reduced pressure to give 1.0 g of ethyl 2-(5-acetyl-2-methoxyphenyl)acetate as an off-white solid. [TLC system: EtOAc:petroleum ether (2:8); Rf value: 0.3].

Step 3. Synthesis of 2-(5-acetyl-2-methoxyphenyl)acetic acid

To a solution of ethyl 2-(5-acetyl-2-methoxyphenyl)acetate (1.0 g, 4.23 mmol) in EtOH (20 mL), was added 5 M NaOH solution (10 mL), stirred at 80° C. for 6 h. After completion of reaction by TLC, the reaction mixture was concentrated under reduced pressure to give a residue. The residue was dissolved in water (40 mL) and washed with EtOAc (30 mL). The aqueous layer was cooled to 0° C., acidified with 2 N HCl to pH 1. The mixture was extracted with EtOAc (2×40 mL), and the combined organic fractions were washed with water (30 mL). The organic layer was dried over anhydrous $Na_2SO_4$, and concentrated under reduced pressure to give 0.8 g of 2-(5-acetyl-2-methoxyphenyl)acetic acid as a white solid. [TLC system: EtOAc: petroleum ether (1:1); Rf value: 0.3].

Step 4. Synthesis of methyl (2-(5-acetyl-2-methoxyphenyl)acetyl)-L-leucinate

To a solution of 2-(5-acetyl-2-methoxyphenyl)acetic acid (0.8 g, 3.84 mmol) in DMF (8 mL), was added DIPEA (2 mL, 11.53 mmol) cooled to 0° C. Then methyl L-leucinate hydrochloride (0.77 g, 4.23 mmol) and HATU (2.2 g, 5.76 mmol) were added. The mixture was stirred at room temperature for 2 h. After completion of reaction by TLC, the reaction mixture was quenched with ice water (30 mL). The precipitated solid was filtered and dried under reduced pressure to afford 1.0 g of methyl (2-(5-acetyl-2-methoxyphenyl)acetyl)-L-leucinate as a white solid. [TLC system: MeOH:DCM (1:9); Rf value: 0.5].

Step 5. Synthesis of (2-(5-acetyl-2-methoxyphenyl)acetyl)-L-leucine

To a solution of methyl (2-(5-acetyl-2-methoxyphenyl) acetyl)-L-leucinate (1.0 g, 2.98 mmol) in THF:water (2:1, 15 mL), was added $LiOH \cdot H_2O$ (0.19 g, 4.47 mmol) at 0° C. The mixture was stirred at room temperature for 1 h. After completion of reaction by TLC, the reaction mixture was cooled to 0° C. and acidified with 1 N HCl to pH 1. A gummy compound precipitated, and the aqueous layer was decanted. The gummy compound was dried under reduced pressure to afford 0.8 g of methyl (2-(5-acetyl-2-methoxyphenyl)acetyl)-L-leucinate as a pale yellow gum. [TLC system: MeOH:DCM (1:9); Rf value: 0.5].

Step 6. Synthesis of (S)-2-(2-(5-acetyl-2-methoxyphenyl)acetamido)-4-methyl-N—((S)-3-oxo-1-((S)-2-oxopyrrolidin-3-yl)-4-(2,3,5,6-tetrafluorophenoxy)butan-2-yl)pentanamide To a solution of (2-(5-acetyl-2-methoxyphenyl)acetyl)-L-leucine (0.3 g, 0.93 mmol) in DMF (3 mL), was added DIPEA (0.5 mL, 2.8 mmol) at 0° C. (S)-3-((S)-2-Amino-3-oxo-4-(2,3,5,6-tetrafluorophenoxy)butyl)pyrrolidin-2-one hydrochloride (0.38 g, 1.03 mmol) and HATU (0.53 g, 1.4 mmol) were added. The reaction mixture was stirred at room temperature for 2 h. After completion of reaction by TLC, the reaction mixture was quenched with ice water (10 mL) and filtered to a give gummy residue. It was purified by column chromatography (using Davisil® silica gel, 95-100% EtOAc in petroleum ether as an eluent) to afford 0.077 g of (S)-2-(2-(5-acetyl-2-methoxyphenyl)acetamido)-4-methyl-N—((S)-3-oxo-1-((S)-2-oxopyrrolidin-3-yl)-4-(2,3,5,6-tetrafluorophenoxy)butan-2-yl)pentanamide as an off-white solid. [TLC system: MeOH:DCM (1:9); Rf value: 0.5]. Analytical Data: LCMS m/z=636.26 (M−1) $^1$H NMR (400 MHz, DMSO-$d_6$) δ ppm 8.55 (d, J=8.0 Hz, 1H), 8.16 (d, J=7.6 Hz, 1H), 7.87 (dd, J=8.4, 2.0 Hz, 1H), 7.80-7.79 (m, 1H), 7.62-7.52 (m, 2H), 7.05 (d, J=8.8 Hz, 1H), 5.18 (q, J=12.0 Hz, 2H), 4.44-4.39 (m, 1H), 4.29-4.27 (m, 1H), 3.82 (s, 3H), 3.50 (q, J=15.2 Hz, 2H), 3.11-3.09 (m, 1H), 3.01- 2.99 (m, 1H), 2.49 (s, 3H), 2.27-2.21 (m, 1H), 2.1-1.90 (m, 2H), 1.65-1.44 (m, 5H), 0.90 (d, J=6.4 Hz, 3H), 0.86 (d, J=6.4 Hz, 3H).

Example 9. Synthesis of 4-fluoro-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide (652)

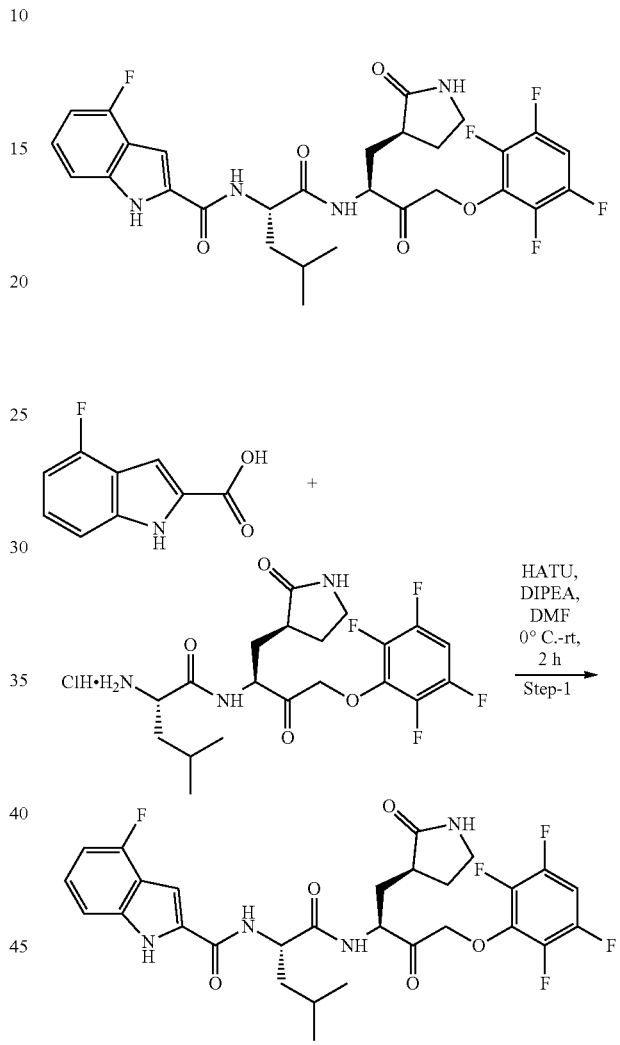

To a solution of 4-fluoro-1H-indole-2-carboxylic acid (0.444 g, 2.48 mmol) in dry DMF (12 mL) at 0° C. was added (S)-2-amino-4-methyl-N—((S)-3-oxo-1-((S)-2-oxopyrrolidin-3-yl)-4-(2,3,5,6-tetrafluorophenoxy)butan-2-yl)pentanamide hydrochloride (1.2 g, 2.48 mmol), HATU (1.131 g, 2.98 mmol) and DIPEA (1.77 mL, 9.92 mmol). The resultant mixture was stirred at room temperature for 2 h. It was diluted with ethyl acetate (50 mL) and washed with saturated aqueous $NaHCO_3$ (30 mL), followed by water (30 mL), and brine (20 mL). The organic layer was dried over anhydrous sodium sulfate, filtered, and concentrated. The obtained residue was then purified by column chromatography over silica gel (230-400 mesh) using 50-55% EtOAc in petroleum ether as an eluent) to afford 4-fluoro-N—((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide (0.6 g) as an off-white solid.

TLC system: ethyl acetate:petroleum ether (70:30); $R_f$ 0.4. Analytical Data: LCMS m/z=609.25 (M+1); $^1$H NMR (400 MHz, DMSO-$d_6$) δ ppm 11.90 (d, J=8.9 Hz, 1H), 8.64-8.59 (m, 2H), 7.64 (s, 1H) 7.59-7.50 (m, 1H), 7.38 (d, J=1.2 Hz, 1H), 7.26 (d, J=8.2 Hz, 1H), 7.19-7.16 (m, 1H), 6.82 (dd, J=10.8, 3.6 Hz, 1H), 5.3-5.18 (m, 2H), 4.52-4.46 (m, 2H), 3.14-3.07 (m, 2H), 2.35-1.95 (m, 3H), 1.78-1.52 (m, 5H), 0.94 (d, J=6.8 Hz, 3H), 0.90 (d, J=6.8 Hz, 3H).

Example 10. Synthesis of (N—((S)-1-(((S)-4-((1,1,1,3,3,3-hexafluoropropan-2-yl)oxy)-3-oxo-1-((S)-2-oxopyrrolidin-3-yl)butan-2-yl)amino)-4-methyl-1-oxopentan-2-yl)-4-methoxy-1H-indole-2-carboxamide (157)

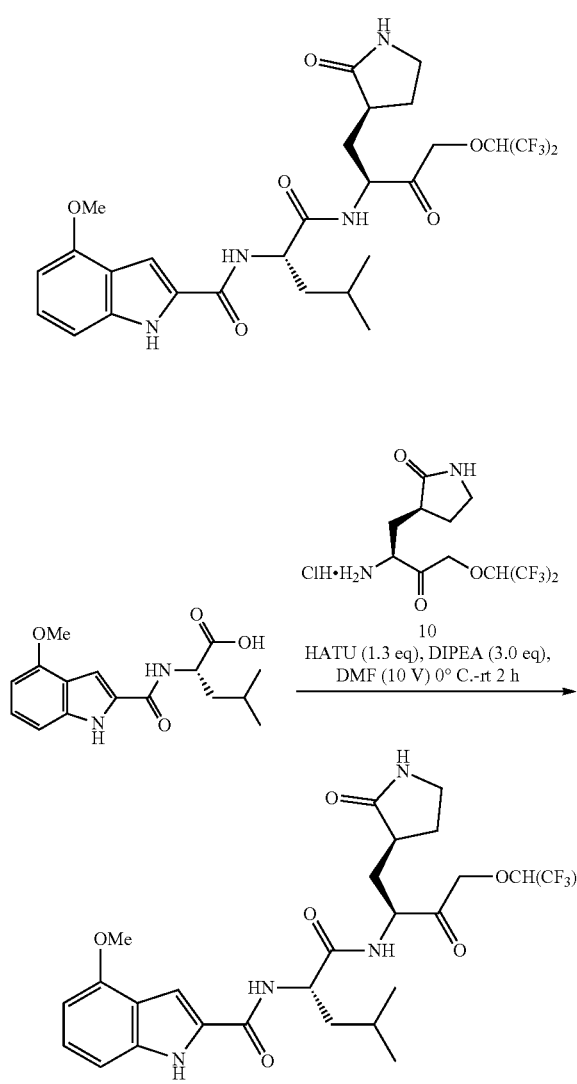

To a stirred solution (S)-3-((S)-2-amino-4-((1,1,1,3,3,3-hexafluoropropan-2-yl)oxy)-3-oxobutyl)pyrrolidin-2-one hydrochloride (0.4 g, 1.07 mmol) and (4-methoxy-1H-indole-2-carbonyl)-L-leucine (0.32 g, 1.07 mmol) in DMF (4.0 mL) was added HATU (0.52 g, 1.39 mmol) followed by DIPEA (0.5 mL, 3.21 mmol) at 0° C. and the resultant mixture was stirred at room temperature for 2 h. After completion, the reaction mixture was diluted with water (50 mL) and extracted with ethyl acetate (2×100 mL). The combined organic layers were washed with brine (2×100 mL), dried over anhydrous sodium sulfate, filtered, and concentrated under reduced pressure. The crude residue was then purified by column chromatography over silica gel (230-400 mesh) using 70-80% EtOAc in petroleum ether as a gradient to afford (N—((S)-1-(((S)-4-((1,1,1,3,3,3-hexafluoropropan-2-yl)oxy)-3-oxo-1-((S)-2-oxopyrrolidin-3-yl)butan-2-yl)amino)-4-methyl-1-oxopentan-2-yl)-4-methoxy-1H-indole-2-carboxamide (102 mg) as an off-white solid. TLC system: MeOH:DCM (1:9); $R_f$ 0.5. Analytical Data: LCMS m/z 623.28 (M+1); $^1$H NMR (400 MHz, DMSO-$d_6$) δ ppm 11.50 (s, 1H), 8.54 (q, J=8.4 Hz, 1H), 8.42 (t, J=6.5 Hz, 1H), 7.64 (d, J=4.3 Hz, 1H), 7.36 (d, J=2.2 Hz, 1H), 7.11-6.99 (m, 2H), 6.51 (d, J=7.7 Hz, 1H), 5.42 (s, 1H), 4.82-4.65 (m, 2H), 4.49-4.44 (m, 2H), 3.88 (s, 3H), 3.13-3.06 (m, 2H), 2.19-2.07 (m, 2H), 1.95-1.73 (m, 1H), 1.68-1.53 (m, 5H), 0.92-0.88 (m, 6H).

Example 11. Synthesis of N—((S)-1-(((S)-4-hydroxy-3-oxo-1-((S)-2-oxopyrrolidin-3-yl)butan-2-yl)amino)-4-methyl-1-oxopentan-2-yl)-4-methoxy-1H-indole-2-carboxamide (PF-00835231)

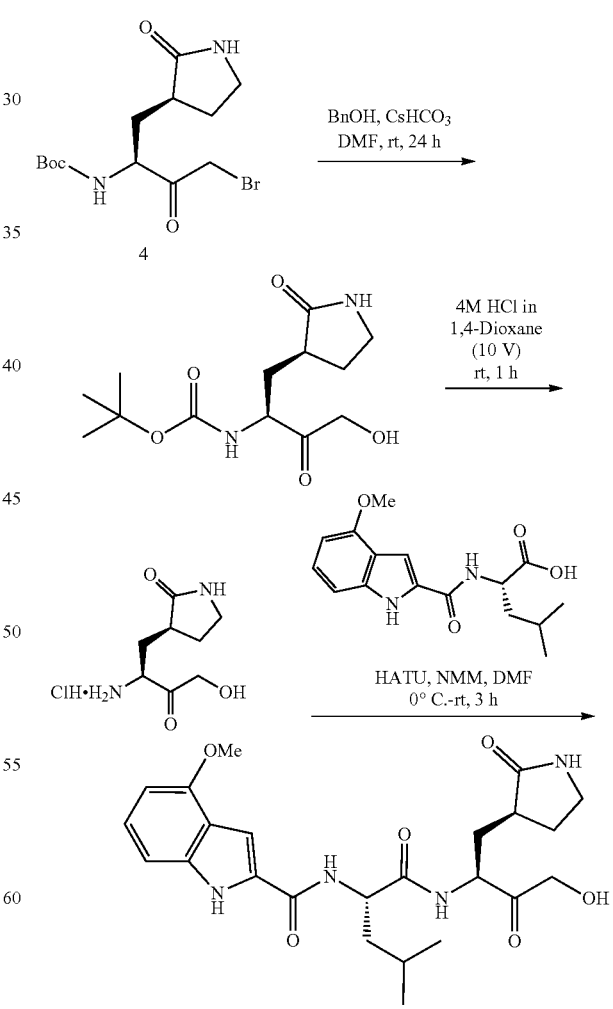

Step 1. Synthesis of tert-butyl ((S)-4-hydroxy-3-oxo-1-((S)-2-oxopyrrolidin-3-yl)butan-2-yl)carbamate To the stirred solution tert-butyl ((S)-4-bromo-3-oxo-1-((S)-2-oxopyrrolidin-3-yl)butan-2-yl)carbamate (8) (4.8 g, 13.8 mmol) and benzyl alcohol (2.97 g, 27.5 mmol) in dimethylformamide (50 mL), cesium bicarbonate (6.47 g, 41.4 mmol) was added and the reaction mixture was stirred at room temperature for 24 h. After completion, the reaction mixture was diluted with water (100 mL) and extracted with ethyl acetate (3×300 mL). The combined organic layers were dried over anhydrous sodium sulfate and concentrated under reduced pressure. The crude residue was then purified by silica gel (230-400 mesh) column chromatography using 5-7% MeOH in DCM as a gradient to afford tert-butyl ((S)-4-hydroxy-3-oxo-1-((S)-2-oxopyrrolidin-3-yl)butan-2-yl)carbamate (2.3 g) as an off-white solid. TLC system: EtOAc:petroleum ether (7:3); $R_f$ 0.5.

The above transformation was carried out using tert-butyl ((S)-4-bromo-3-oxo-1-((S)-2-oxopyrrolidin-3-yl)butan-2-yl)carbamate 8 (200 mg) and cesium bicarbonate (3 eq.) in DMF (2 mL) in the absence of benzyl alcohol under similar reaction condition provided the same product (100 mg) after purification.

Step 2. Synthesis of (S)-3-((S)-2-amino-4-hydroxy-3-oxobutyl)pyrrolidin-2-one hydrochloride To a stirred solution of tert-butyl ((S)-4-hydroxy-3-oxo-1-((S)-2-oxopyrrolidin-3-yl)butan-2-yl)carbamate (0.3 g, 1.048 mmol) in 1,4-dioxane (1.5 mL) was added 4 M HCl in 1,4-dioxane (0.42 mL, 4.19 mmol) at 0° C. and the resultant mixture was stirred at room temperature for 2 h. After completion, volatiles were removed under reduced pressure and the resulting crude product was washed with diethyl ether (2×5 mL) to afford ((S)-3-((S)-2-amino-4-hydroxy-3-oxobutyl)pyrrolidin-2-one hydrochloride (230 mg) as a yellow solid. TLC system: MeOH:DCM (1:9); $R_f$ 0.1.

Step 3. Synthesis of N—((S)-1-(((S)-4-hydroxy-3-oxo-1-((S)-2-oxopyrrolidin-3-yl)butan-2-yl)amino)-4-methyl-1-oxopentan-2-yl)-4-methoxy-1H-indole-2-carboxamide (PF-00835231)

To a solution of (4-methoxy-1H-indole-2-carbonyl)-L-leucine (0.315 g, 1.03 mmol) in dry DMF (4 mL) at 0° C., was added ((S)-3-((S)-2-amino-4-hydroxy-3-oxobutyl)pyrrolidin-2-one hydrochloride (0.23 g, 1.03 mmol), and HATU (0.508 g, 1.339 mmol) followed by NMM (0.45 mL, 4.12 mmol) and the resultant mixture was stirred at room temperature for 2 h. After completion, the reaction mixture was diluted with ethyl acetate (30 mL), and washed with saturated aqueous $NaHCO_3$ (1×20 mL), water (1×20 mL) and brine solution (1×15 mL). The organic layer was dried over anhydrous sodium sulfate, filtered, and concentrated under reduced pressure. The crude residue was then purified by column chromatography over silica gel (230-400 mesh) using 3-4% MeOH in DCM as a gradient to afford N—((S)-1-(((S)-4-hydroxy-3-oxo-1-((S)-2-oxopyrrolidin-3-yl)butan-2-yl)amino)-4-methyl-1-oxopentan-2-yl)-4-methoxy-1H-indole-2-carboxamide PF-00835231 (0.14 g) as an off-white solid along with by-product (250 mg). TLC system: MeOH:DCM (1:9); $R_f$ 0.5. Analytical Data: LCMS m/z=471.48 (M−1) $^1$H NMR (400 MHz, DMSO-$d_6$) δ ppm 11.57 (s, 1H), 8.45 (d, J=8.0 Hz, 2H), 8.40 (d, J=7.6 Hz, 2H), 7.62 (s, 1H), 7.36 (d, J=1.5 Hz, 1H), 7.09 (t, J=7.9 Hz, 1H), 7.00 (d, J=8.2 Hz, 1H), 6.51 (d, J=7.6 Hz, 1H), 5.05 (t, J=5.9 Hz, 1H), 4.49-4.44 (m, 2H), 4.25 (dq, J=8.3, 4.6 Hz, 1H), 3.88 (s, 3H), 3.13-3.06 (m, 2H), 2.28 (d, J=8.5 Hz, 1H), 2.10 (t, J=8.5 Hz, 1H), 1.73-1.53 (m, 5H), 0.94 (d, J=6.0 Hz, 3H), 0.94 (d, J=6.0 Hz, 3H)

Example 12. Synthesis of N—((S)-1-(((S)-4-(difluoromethoxy)-3-oxo-1-((S)-2-oxopyrrolidin-3-yl)butan-2-yl)amino)-4-methyl-1-oxopentan-2-yl)-4-methoxy-1H-indole-2-carboxamide (198)

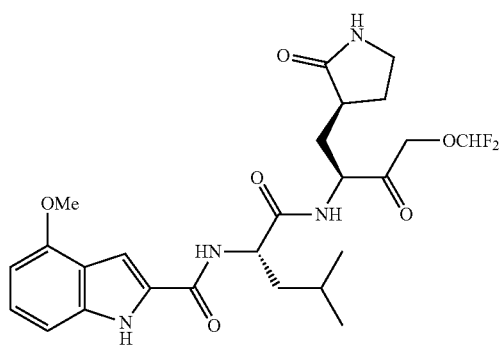 [SMILES: COc1cccc2[nH]c(C(=O)N[C@@H](CC(C)C)C(=O)N[C@@H](C[C@@H]3CCNC3=O)C(=O)COC(F)F)cc12]

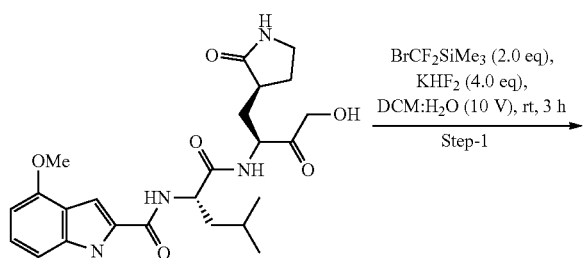

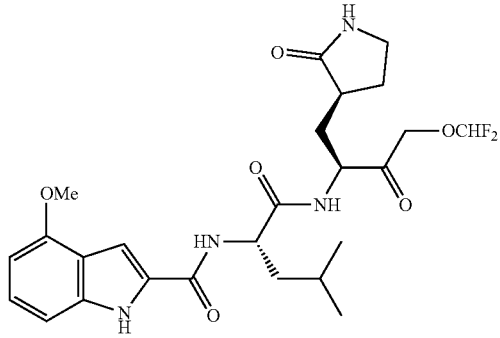

Into a 20-mL plastic tube containing N—((S)-1-(((S)-4-hydroxy-3-oxo-1-((S)-2-oxopyrrolidin-3-yl)butan-2-yl)amino)-4-methyl-1-oxopentan-2-yl)-4-methoxy-1H-indole-2-carboxamide PF-00835231 (0.35 mg, 0.741 mmol) and potassium hydrogen difluoride (0.231 g, 2.964 mmol) was added water (1.0 mL) and DCM (3 mL). After stirring for 5 min, (bromodifluoromethyl)trimethylsilane (0.301 g, 1.48 mmol) was added. The reaction mixture was vigorously stirred at room temperature for 2 h, and then diluted with water (10 mL) and extracted with EtOAc (3×20 mL). The combined organic layers were dried over anhydrous $Na_2SO_4$ and concentrated under reduced pressure. The residue was then purified by flash column chromatography over silica gel (230-400 mesh) using 60-80% EtOAc in petroleum ether as a gradient to afford N—((S)-1-(((S)-4-(difluoromethoxy)-3-oxo-1-((S)-2-oxopyrrolidin-3-yl)butan-2-yl)amino)-4-methyl-1-oxopentan-2-yl)-4-methoxy-1H-indole-2-carboxamide (17 mg) as an off-white solid. TLC system: EtOAc: petroleum ether (7:3); $R_f$ 0.5. Analytical Data: LCMS m/z 523.46 (M+1); $^1$H NMR (400 MHz, DMSO-$d_6$) δ ppm $^1$H NMR (400 MHz, DMSO-$d_6$) δ ppm 11.56 (s, 1H), 8.41 (d, J=6.3 Hz, 2H), 7.32-6.99 (m, 1H), 6.51 (d, J=6.2 Hz, 1H), 5.07 (s, 1H), 4.48 (s, 2H), 4.22 (q, J=15.4 Hz, 2H), 3.88 (s, 3H), 3.32 (s, 2H), 2.16 (s, 1H), 2.00 (d, J=10.7 Hz, 2H), 1.63 (d, J=65.7 Hz, 5H), 0.93 (t, J=9.6 Hz, 6H).

Example 13. Synthesis of 4-methoxy-N—((S)-1-(((S)-4-methoxy-3-oxo-1-((S)-2-oxopyrrolidin-3-yl)butan-2-yl)amino)-4-methyl-1-oxopentan-2-yl)-1H-indole-2-carboxamide

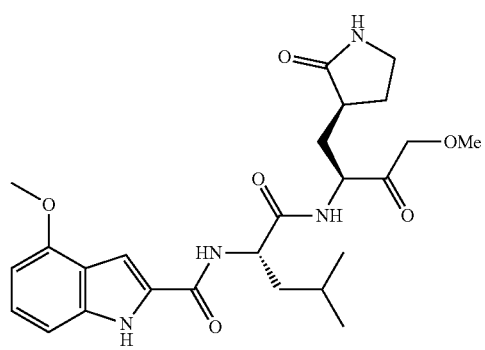 [SMILES: COCC(=O)[C@H](C[C@@H]1CCNC1=O)NC(=O)[C@H](CC(C)C)NC(=O)c1cc2c(OC)cccc2[nH]1]

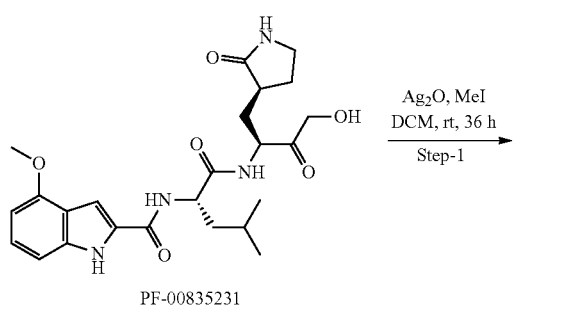

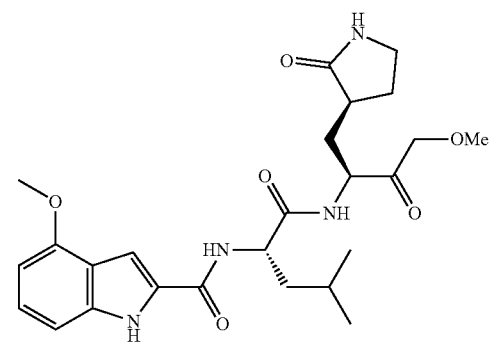

To a stirred solution of N—((S)-1-(((S)-4-hydroxy-3-oxo-1-((S)-2-oxopyrrolidin-3-yl)butan-2-yl)amino)-4-methyl-1-oxopentan-2-yl)-4-methoxy-1H-indole-2-carboxamide PF-00835231 (0.2 g, 0.423 mmol) in DCM (5.0 mL) were added silver oxide (0.196 g, 0.847 mmol) and methyl iodide (0.596 g, 4.23 mmol), and the mixture was stirred at room temperature for 36 h. After completion, the reaction mixture was filtered through a pad of diatomaceous earth that was then washed with ethyl acetate (30 mL). The collected filtrate was dried over $Na_2SO_4$ and concentrated under reduced pressure. The resultant residue was then purified by column chromatography over silica gel (230-400 mesh) using 4-5% MeOH in DCM as a gradient followed by second cycle of purification using SFC (two sequential chromatographies; column: CHIRALPAK®-AS-3 (30×250 mm), 5 μm; % CO2: 80%; % co-solvent 20% MeOH; flow rate: 100 g/min; back pressure: 100 bar; temperature: 30° C.; UV detection: 215 nm. column: CHIRALCEL® OJ-H (30× 250 mm), 5 μm; % CO2: 70%; % co-solvent 30% MeOH; flow rate: 100 g/min; back pressure: 100 bar; temperature: 30° C.; UV detection: 215 nm) furnished 0.016 g of 4-methoxy-N—((S)-1-(((S)-4-methoxy-3-oxo-1-((S)-2-oxopyrrolidin-3-yl)butan-2-yl)amino)-4-methyl-1-oxopentan-2-yl)-1H-indole-2-carboxamide as an off-white solid. TLC system: MeOH:DCM (1:9); $R_f$ 0.4. Analytical Data: LCMS m/z=485.23 (M−1) $^1$H NMR (400 MHz, DMSO-$d_6$) δ ppm 11.58 (s, 1H), 8.50-8.41 (m, 2H), 7.62 (s, 1H), 7.35 (s, 1H), 7.11-6.99 (m, 1H), 6.50 (d, J=7.7 Hz, 1H), 4.38-4.23 (m, 2H), 4.18-4.09 (m, 2H), 3.88 (s, 3H), 3.24 (s, 3H), 3.13-3.07 (m, 2H), 2.30 (q, J=7.3 Hz, 1H), 2.32-2.11 (m, 5H), 1.73-1.62 (m, 1H), 0.93-0.88 (m, 6H).

Example 14. Synthesis of $N^1$-(2-fluorophenyl)-$N^2$—((S)-1-(((S)-4-methoxy-3-oxo-1-((S)-2-oxopyrrolidin-3-yl)butan-2-yl)amino)-4-methyl-1-oxopentan-2-yl)oxalamide

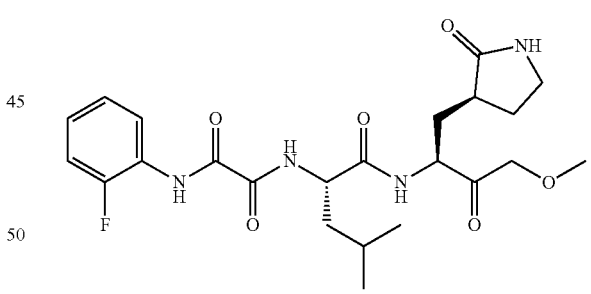

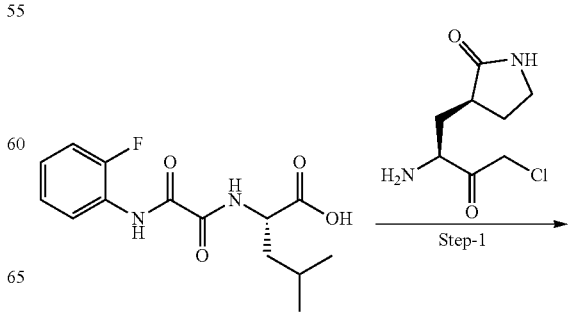

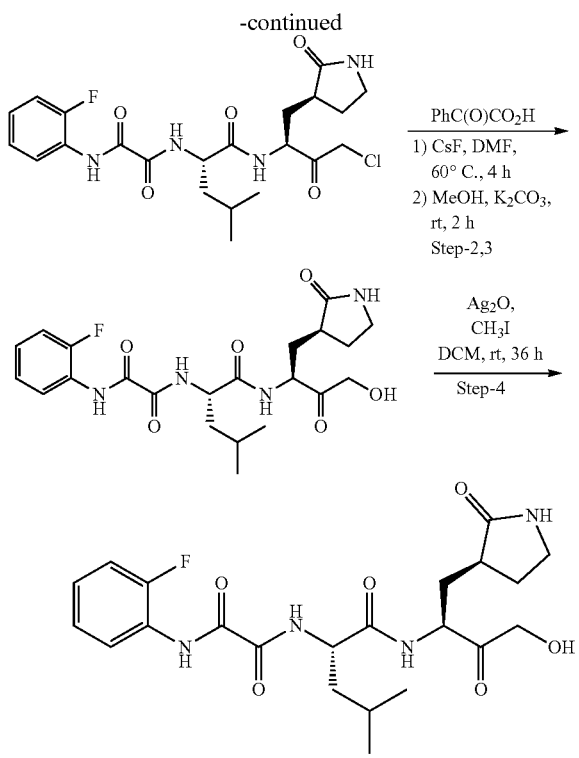

Step 1. Synthesis of N¹—((S)-1-(((S)-4-chloro-3-oxo-1-((S)-2-oxopyrrolidin-3-yl)butan-2-yl)amino)-4-methyl-1-oxopentan-2-yl)-N²-(2-fluorophenyl) oxalamide To a solution of (2-((2-fluorophenyl)amino)-2-oxoacetyl)-L-leucine (1.0 g, 3.378 mmol) in dry DMF (10.0 mL) at 0° C. was added (S)-3-((S)-2-amino-4-chloro-3-oxobutyl) pyrrolidin-2-one hydrochloride (0.810 g, 3.378 mmol), and HATU (1.54 g, 4.05 mmol) followed by DIPEA (2.34 mL, 13.51 mmol). The resultant mixture was stirred at room temperature for 2 h. After completion, the reaction mixture was diluted with ethyl acetate (50 mL), washed with saturated aqueous $NaHCO_3$ (1×30 mL), water (1×30 mL) and brine solution (1×20 mL). The organic layer was dried over anhydrous sodium sulfate, filtered, and concentrated under reduced pressure. The crude residue was then purified by column chromatography over silica gel (230-400 mesh) using 60-70% EtOAc in petroleum ether as a gradient to afford N¹—((S)-1-(((S)-4-chloro-3-oxo-1-((S)-2-oxopyrrolidin-3-yl)butan-2-yl)amino)-4-methyl-1-oxopentan-2-yl)-N²-(2-fluorophenyl)oxalamide (1.03 g) as an off-white solid. TLC system: EtOAc:petroleum ether (70:30); Rf: 0.4.

Step 2,3. Synthesis of N¹-(2-fluorophenyl)-N²—((S)-1-(((S)-4-hydroxy-3-oxo-1-((S)-2-oxopyrrolidin-3-yl)butan-2-yl)amino)-4-methyl-1-oxopentan-2-yl)oxalamide To a solution of N¹—((S)-1-(((S)-4-chloro-3-oxo-1-((S)-2-oxopyrrolidin-3-yl)butan-2-yl)amino)-4-methyl-1-oxopentan-2-yl)-N²-(2-fluorophenyl)oxalamide (1.0 g, 2.07 mmol) in anhydrous DMF (10 mL) was added benzoylformic acid (0.372 g, 2.48 mmol) followed by CsF (0.723 g, 4.76 mmol), and the resultant mixture was stirred at 65° C. for 4 h. After completion, the mixture was diluted with ethyl acetate (50 mL), washed with saturated aqueous $NaHCO_3$ (1×40 mL) solution, water (1×40 mL) and brine solution (1×30 mL). The organic layer was dried over anhydrous sodium sulfate, filtered, and concentrated under reduced pressure. The crude residue was re-dissolved in MeOH (10.0 mL), $K_2CO_3$ (0.03 g, 0.218 mmol) was added, and the mixture was stirred at room temperature for 1 h. After completion, the volatiles were removed under reduced pressure, and the resultant residue was then purified by column chromatography over silica gel (230-400 mesh) using 4-5% MeOH in DCM as a gradient followed by second cycle of purification using SFC furnished 0.410 g of N¹-(2-fluorophenyl)-N²—((S)-1-(((S)-4-hydroxy-3-oxo-1-((S)-2-oxopyrrolidin-3-yl)butan-2-yl)amino)-4-methyl-1-oxopentan-2-yl)oxalamide as an off-white solid. TLC system: MeOH:DCM (1:9); Rf: 0.4.

Step 4. Synthesis of N¹-(2-fluorophenyl)-N²—((S)-1-(((S)-4-methoxy-3-oxo-1-((S)-2-oxopyrrolidin-3-yl)butan-2-yl)amino)-4-methyl-1-oxopentan-2-yl) oxalamide To a stirred solution of N¹-(2-fluorophenyl)-N²—((S)-1-(((S)-4-hydroxy-3-oxo-1-((S)-2-oxopyrrolidin-3-yl)butan-2-yl)amino)-4-methyl-1-oxopentan-2-yl)oxalamide (0.2 g, 0.431 mmol) in DCM (5.0 mL) was added silver oxide (0.2 g, 0.862 mmol) followed by methyl iodide (0.608 g, 4.31 mmol) and the mixture was stirred at room temperature for 36 h. After completion, the reaction mixture was filtered through a pad of diatomaceous earth that was then washed with ethyl acetate (30 mL). The filtrate was dried over anhydrous $Na_2SO_4$, concentrated under reduced pressure to give crude residue. The residue was then purified by column chromatography over silica gel (230-400 mesh) using 4-5% MeOH in DCM as a gradient followed by second cycle of purification using SFC (column: YMC-Pack-Diol (20×250 mm), 5 μml; % $CO_2$: 80%; % co-solvent 20% (IPA:CAN); flow rate: 60 g/min; back pressure: 100 bar; temperature: 30° C.; UV detection: 215 nm) furnished N¹-(2-fluorophenyl)-N²—((S)-1-(((S)-4-methoxy-3-oxo-1-((S)-2-oxopyrrolidin-3-yl)butan-2-yl)amino)-4-methyl-1-oxopentan-2-yl)oxalamide (0.016 g) as an off-white solid. TLC system: MeOH:DCM (1:9); R$_f$ 0.4. Analytical Data: LCMS m/z=477.21 (M−1) ¹H NMR (400 MHz, DMSO-d$_6$) δ ppm 10.27 (s, 1H), 8.90 (d, J=8.2 Hz, 1H), 8.50 (d, J=7.8 Hz, 1H), 7.72-7.65 (m, 1H), 7.33-7.20 (m, 1H), 4.39-4.37 (m, 1H), 4.25 (d, J=17.8 Hz, 1H), 4.12 (d, J=17.8 Hz, 1H), 3.27 (s, 1H), 3.16-3.11 (m, 1H), 2.32-2.27 (m, 1H), 2.12-2.10 (m, 1H), 1.92-1.91 (m, 1H), 1.74-1.54 (m, 1H), 0.89 (t, J=4.3 Hz, 1H).

Example 15. Synthesis of 3-(3-chlorophenyl)propyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate (128)

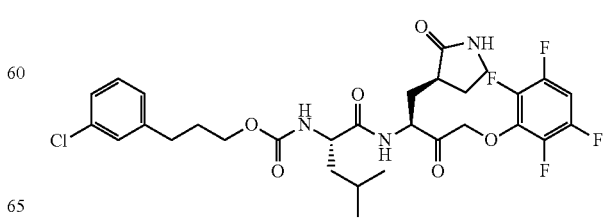

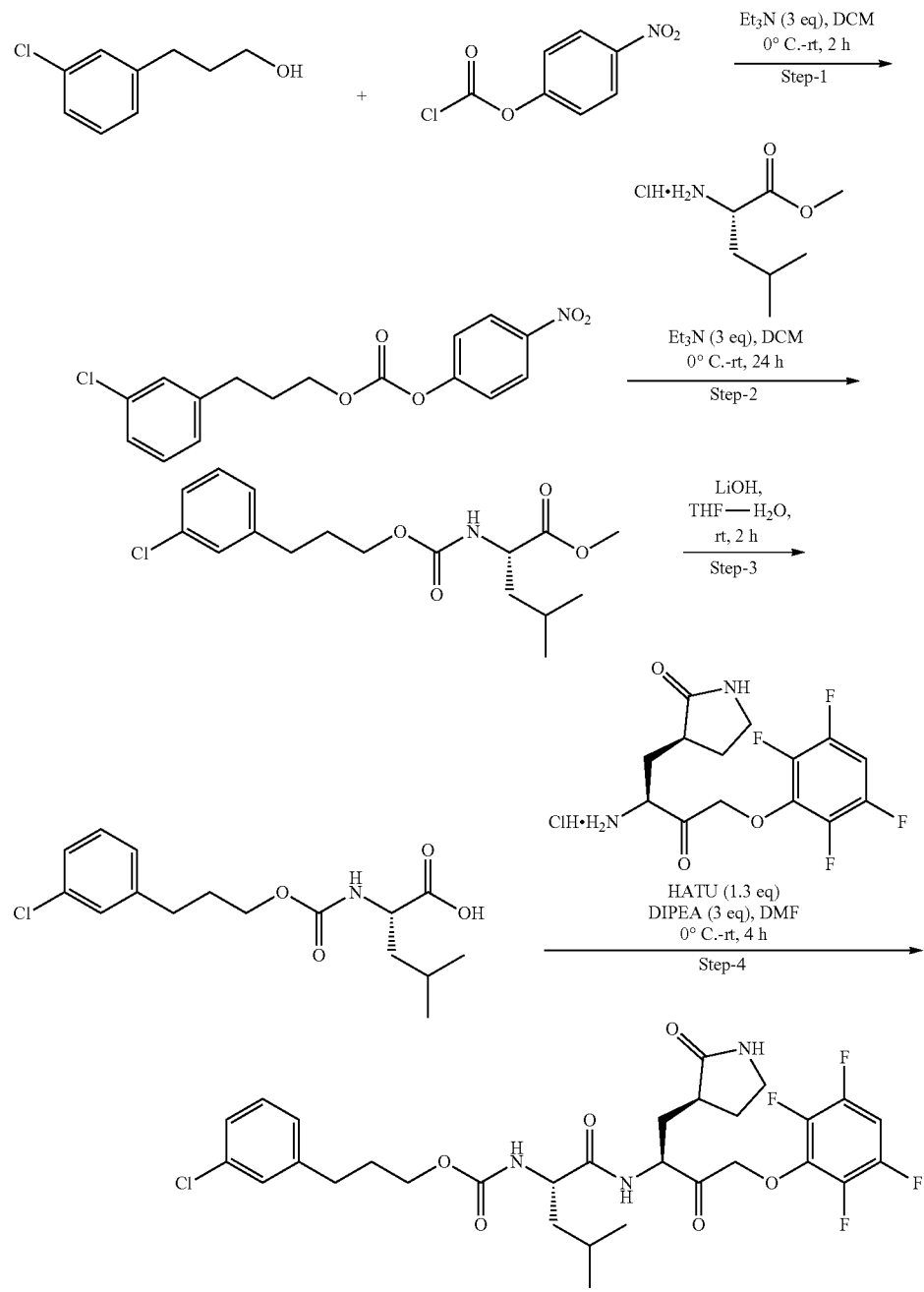

Step 1. Synthesis of 3-(3-chlorophenyl)propyl (4-nitrophenyl) carbonate

To stirred solution of 3-(3-chlorophenyl)propan-1-ol (0.50 g, 2.93 mmol) in dichloromethane (10 mL), trimethylamine (0.41 mL, 2.93 mmol) and 4-nitrophenyl carbonochloridate (0.59 g, 2.93 mmol) were added at 0° C. The mixture was stirred at room temperature for 2 h. After completion, the reaction mixture was concentrated below 25° C. and diethyl ether was added. The obtained solid was filtered through Buchner funnel, and the filtrate was dried over anhydrous sodium sulfate and concentrate to give 3-(3-chlorophenyl)propyl (4-nitrophenyl) carbonate (0.9 g) crude as yellow liquid. TLC system: EtOAc in petroleum ether (2:8); $R_f$ 0.4.

Step 2. Synthesis of methyl ((3-(3-chlorophenyl)propoxy)carbonyl)-L-leucinate To a solution of methyl L-leucinate hydrochloride (0.30 g, 1.65 mmol) and 3-(3-chlorophenyl) propyl (4-nitrophenyl) carbonate (0.55 g, 1.65 mmol), in DCM (10 mL). Then TEA (0.9 mL, 6.6 mmol), was added dropwise at 0° C., and the reaction mixture was stirred at ambient temperature for 24 h. After completion, the reaction mixture was quenched with water and extracted with DCM (150 mL). The combined organic layers were dried over anhydrous sodium sulfate and concentrated. The obtained crude residue was purified by column chromatography using 10-15% EtOAc in petroleum ether to afford methyl ((3-(3-chlorophenyl)propoxy)carbonyl)-L-leucinate, (0.25 g). TLC system: EtOAc in petroleum ether (2:8); R$_f$: 0.3.

Step 3. Synthesis of ((3-(3-chlorophenyl)propoxy)carbonyl)-L-leucine

To a solution of methyl ((3-(3-chlorophenyl)propoxy) carbonyl)-L-leucinate (0.25 g, 0.73 mmol) in THF (3 mL) and water (3 mL) was added dropwise an aqueous solution of LiOH·H$_2$O (0.04 g, 0.95 mmol) at 0° C., and the reaction mixture was stirred at ambient temperature for 2 h. After completion, the reaction mixtures were concentrated and the aqueous layer was acidified with 10% citric acid solution. The mixture was extracted with ethyl acetate (3×30 mL), and the combined organic layers were dried over anhydrous sodium sulfate and concentrated to afford ((3-(3-chlorophenyl)propoxy)carbonyl)-L-leucine, (0.22 g). TLC system: MeOH in DCM (1:9); R$_f$ 0.3.

Step 4. Synthesis of 3-(3-chlorophenyl)propyl ((S)-4-methyl-1-oxo-1-(((S)-3-oxo-1-((S)-2-oxopyrrolidin-3-yl)-4-(2,3,5,6-tetrafluorophenoxy)butan-2-yl) amino)pentan-2-yl)carbamate

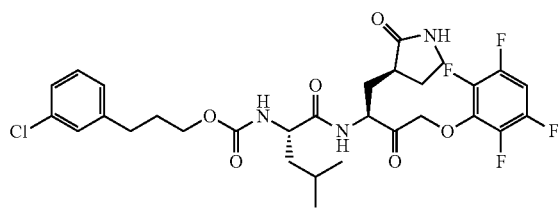 [SMILES: CC(C)C[C@H](NC(=O)OCCCc1cccc(Cl)c1)C(=O)N[C@@H](C[C@@H]1CCNC1=O)C(=O)COc1c(F)c(F)cc(F)c1F]

To a stirred solution ((3-(3-chlorophenyl)propoxy)carbonyl)-L-leucine (0.22 g, 0.67 mmol) and (S)-3-((S)-2-amino-3-oxo-4-(2,3,5,6-tetrafluorophenoxy)butyl)pyrrolidin-2-one hydrochloride (0.25 g, 0.67 mmol) in DMF (5 mL), HATU (0.33 g, 0.87 mmol) and DIPEA (0.35 mL, 2.02 mmol) were added at 0° C. and the reaction mixture was stirred at room temperature for 4 h. After completion, the reaction mixture was diluted with ice-cold water (50 mL) and extracted with EtOAc (3×100 mL). The combined organic layers were wash with brine solution, dried over anhydrous sodium sulfate, filtered, and concentrated under reduced pressure. The residue was purified by column chromatography using 50-70% ethyl acetate in petroleum ether to afford 3-(3-chlorophenyl)propyl ((S)-4-methyl-1-oxo-1-(((S)-3-oxo-1-((S)-2-oxopyrrolidin-3-yl)-4-(2,3,5,6-tetrafluorophenoxy) butan-2-yl)amino)pentan-2-yl)carbamate (0.09 g) as an off-white solid. TLC system: MeOH in DCM (1:9); R$_f$ 0.4. Analytical Data: LCMS m/z=644.66 (M+1); $^1$H NMR (400 MHz, DMSO-d$_6$) δ ppm 8.51 (d, J=8.0 Hz, 1H), 7.64 (s, 1H), 7.62-7.53 (m, 1H), 7.37 (d, J=7.6 Hz, 1H), 7.32-7.25 (m, 3H), 7.17 (d, J=7.6 Hz, 1H), 5.2-5.17 (m, 2H), 4.42 (m, 1H), 4.03-3.89 (m, 3H), 3.25-3.03 (m, 2H), 2.65-2.62 (m, 2H), 2.24 (m, 1H), 2.08-1.86 (m, 2H), 1.84-1.80 (m, 2H), 1.66-1.59 (m, 3H), 1.49-1.46 (m, 2H), 0.90-0.85 (m, 6H).

Example 16. Synthesis of N$^1$—((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl) propan-2-yl)-N$^2$-(o-tolyl)oxalamide (155)

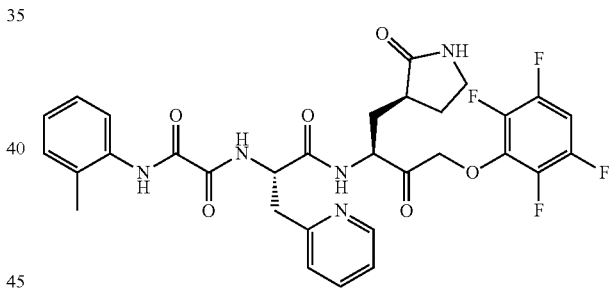

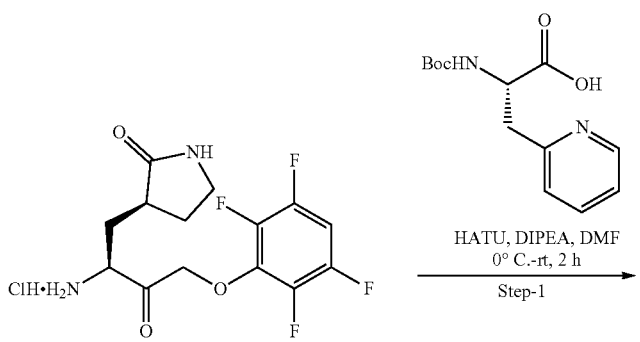

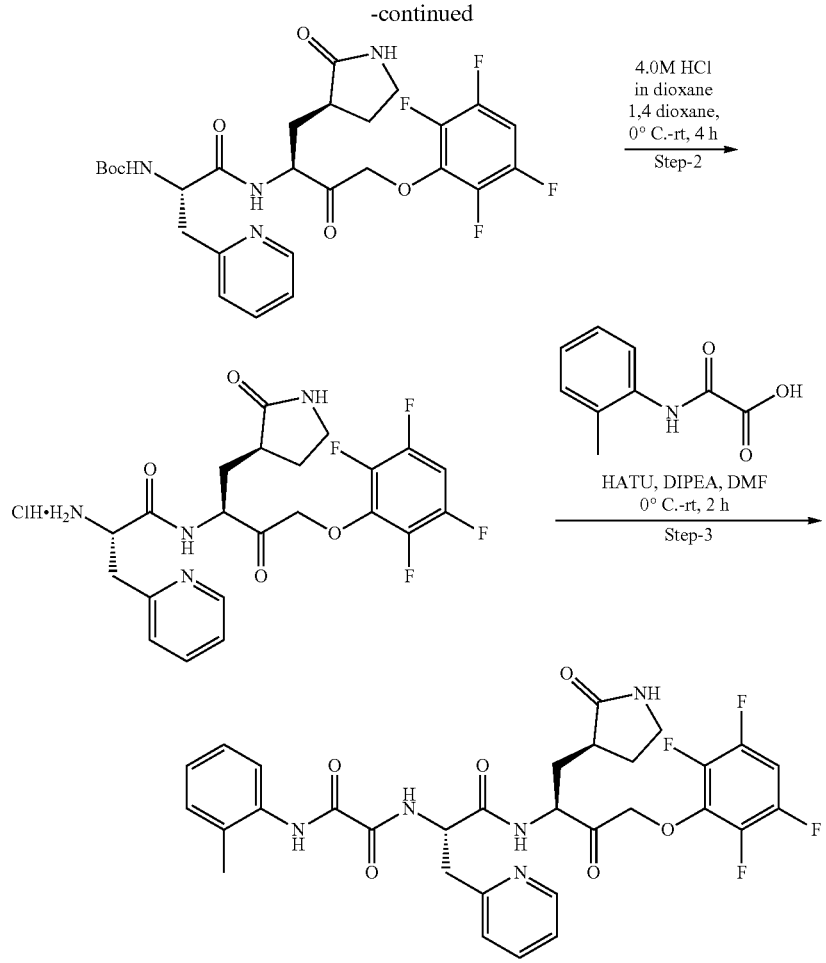

Step 1. Synthesis of tert-butyl ((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl)propan-2-yl)carbamate To a stirred solution (S)-3-((S)-2-amino-3-oxo-4-(2,3,5,6-tetrafluorophenoxy)butyl)pyrrolidin-2-one hydrochloride (1.0 g, 2.70 mmol) and (S)-2-((tert-butoxycarbonyl)amino)-3-(pyridin-2-yl)propanoic acid (0.79 g, 2.70 mmol) in N,N-dimethylformamide (10 mL) was added 1-[bis(dimethylamino)methylene]-1H-1,2,3-triazolo[4,5-b]pyridinium 3-oxide hexafluorophosphate (1.3 g, 3.51 mmol) and N-ethyl-N-isopropylpropan-2-amine (1.9 mL, 10.80 mmol) at 0° C. and the reaction mixture was stirred at room temperature for 2 h. After completion, the reaction mixture was quenched by adding water (100 mL) and extracted with ethyl acetate (2×100 mL). The combined organic layers were washed with brine solution (1×100 mL), dried over anhydrous sodium sulfate and concentrated in vacuo. The residue was then purified by flash column chromatography using Davisil® grade silica gel using 100% ethyl acetate as an eluent to afford 0.25 g of tert-butyl ((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl)propan-2-yl)carbamate as a colorless oil. TLC system: 100% EtOAc; $R_f$ 0.3.

Step 2. Synthesis of (S)-2-amino-N—((S)-3-oxo-1-((S)-2-oxopyrrolidin-3-yl)-4-(2,3,5,6-tetrafluorophenoxy)butan-2-yl)-3-(pyridin-2-yl)propanamide hydrochloride To a stirred solution of tert-butyl ((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl)propan-2-yl)carbamate (0.25 g, 0.34 mmol) in 1,4 dioxane (4.0 mL) was added 4.0 M HCl in dioxane (4.0 mL) at 0° C., and the reaction mixture was stirred at room temperature for 4 h. After completion, the solvent was removed under reduced pressure. The residue was then washed with diethyl ether (2×20 mL) to afford (S)-2-amino-N—((S)-3-oxo-1-((S)-2-oxopyrrolidin-3-yl)-4-(2,3,5,6-tetrafluorophenoxy)butan-2-yl)-3-(pyridin-2-yl)propanamide hydrochloride 4 (0.2 g) as a brown solid. TLC system: MeOH:DCM (10:1); Rf: 0.1.

Step 3. Synthesis of $N^1$—((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl)propan-2-yl)-$N^2$-(o-tolyl)oxalamide To a stirred solution of (S)-2-amino-N—((S)-3-oxo-1-((S)-2-oxopyrrolidin-3-yl)-4-(2,3,5,6-tetrafluorophenoxy)butan-2-yl)-3-(pyridin-2-yl)propanamide hydrochloride (0.2 g, 0.38 mmol) and 2-oxo-2-(o-tolylamino)acetic acid (0.07 g, 0.38 mmol) in N,N-dimethylformamide (2.0 mL) was added 1-[bis(dimethylamino)methylene]-1H-1,2,3-triazolo[4,5-b]pyridinium 3-oxide hexafluorophosphate (0.19 g, 0.50 mmol) and N-ethyl-N-isopropylpropan-2-amine (0.3 mL, 1.54 mmol) at 0° C. and the reaction mixture was stirred at room temperature for 2 h. After completion, the reaction mixture was quenched by adding water (2×50 mL) and extracted with ethyl acetate (2×50 mL). The combined organic layers were washed with brine solution (1×50 mL), dried over anhydrous sodium sulfate and concentrated in vacuo. The residue was then purified by flash column chromatography using Davisil® grade silica gel using 100% ethyl acetate as an eluent to afford $N^1$—((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl)propan-2-yl)-$N^2$-(o-tolyl)oxalamide (0.0274 g) as a colorless oil. TLC system: EtOAc; R: 0.3. Analytical Data: LCMS m/z=642.31 (M−1); $^1$H NMR (400 MHz, DMSO-$d_6$) δ ppm 10.04 (s, 1H), 9.28 (d, J=8.0 Hz, 1H), 8.58 (d, J=8.4 Hz, 1H), 8.46 (d, J=4.0 Hz, 1H), 7.72-7.68 (m, 1H), 7.61-7.47 (m, 3H), 7.30-7.16 (m, 5H), 5.24-5.07 (q, J=18.0 Hz, 2H), 4.78 (q, J=1.6 Hz, 1H), 4.43-4.41 (m, 1H), 3.32-3.26 (m, 2H), 3.16-3.04 (m, 2H), 2.18 (s, 1H), 2.01-1.91 (m, 3H), 1.59-1.56 (m, 2H), 1.24 (s, 2H).

Example 17. $N^1$—((S)-1-(((S)-1-(1H-imidazol-5-yl)-3-oxo-4-(2,3,5,6-tetrafluorophenoxy)butan-2-yl)amino)-4-methyl-1-oxopentan-2-yl)-$N^2$-(2-fluorophenyl)oxalamide trifluoroacetate (135, Peak-1)

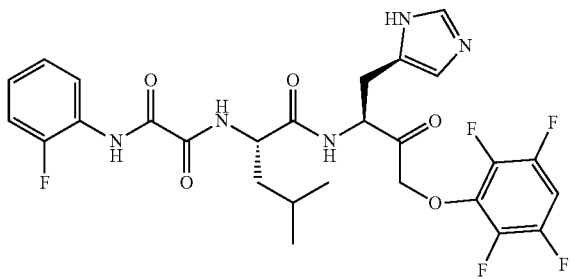

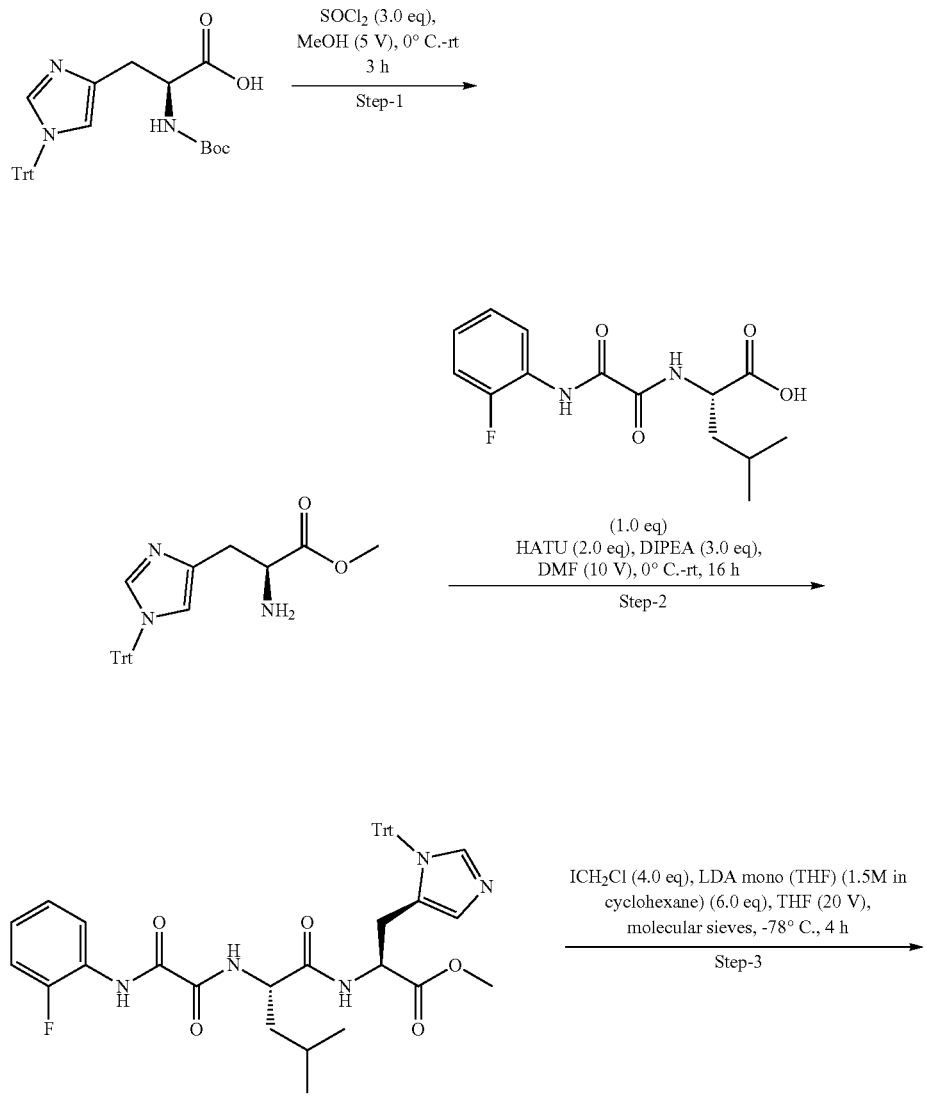

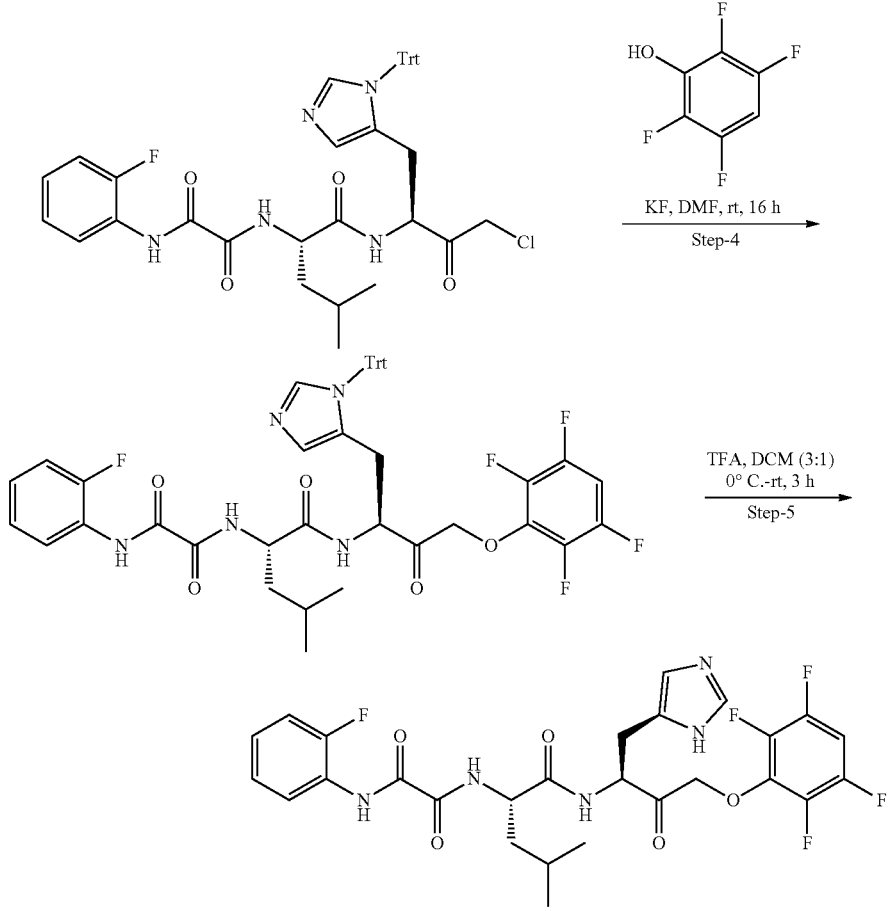

Step 1. Synthesis of methyl N-trityl-L-histidinate

To a stirred solution of N'-(tert-butoxycarbonyl)-M-trityl-L-histidine (2.0 g, 4.02 mmol) in methanol (10 mL), thionyl chloride (0.87 mL, 12.06 mmol) was slowly added at 0° C. and the reaction mixture was stirred at room temperature for 3 h. After completion of reaction, the reaction mixture was concentrated and the residue was dissolved in water (50 mL). The aqueous mixture was basified with saturated sodium bicarbonate solution. The resulting mixture was extracted with ethyl acetate and the combined organic layers were dried over anhydrous sodium sulfate and concentrated to give methyl N'-trityl-L-histidinate (1.25 g, 75.8%) as an off-white solid. [TLC system: MeOH:DCM (1:9); $R_f$ value: 0.4].

Step 2. Methyl $N^\alpha$-((2-((2-fluorophenyl)amino)-2-oxoacetyl)-L-leucyl)-$N^\pi$-trityl-L-histidinate To the mixture of methyl N'-trityl-L-histidinate (0.75 g, 1.82 mmol), (2-((2-fluorophenyl)amino)-2-oxoacetyl)-L-leucine (0.54 g, 1.82 mmol) and (1-[bis(dimethylamino) methylene]-1H-1,2,3-triazolo[4,5-b]pyridinium 3-oxide hexafluorophosphate (1.38 g, 3.64 mmol) in N,N-dimethylformamide (10 mL), N,N-diisopropylethylamine (0.7 g, 5.46 mmol) was added at 0° C. and the reaction mixture was stirred at room temperature for 16 h. After completion of the reaction, the reaction mixture was diluted with water (50 mL) and extracted with ethyl acetate (2×30 mL). The combined organic layers were dried over anhydrous sodium sulfate and concentrated. The obtained crude residue was purified by silica gel column chromatography eluted with 40% ethyl acetate in hexane to afford methyl $N^\alpha$-((2-((2-fluorophenyl)amino)-2-oxoacetyl)-L-leucyl)-$N^\pi$-trityl-L-histidinate (0.95 g, 75.6%) as an off-white solid. [TLC system: EtOAc:hexane (4:6); $R_f$ value: 0.4].

Step 3. $N^1$—((S)-1-(((S)-4-chloro-3-oxo-1-(1-trityl-1H-imidazol-5-yl)butan-2-yl)amino)-4-methyl-1-oxopentan-2-yl)-$N^2$-(2-fluorophenyl)oxalamide To the stirred suspension of molecular sieves, 4 Å (1 g) in tetrahydrofuran (5.7 mL), methyl $N^\alpha$-((2-((2-fluorophenyl)amino)-2-oxoacetyl)-L-leucyl)-$N^\pi$-trityl-L-histidinate (0.95 g, 1.38 mmol) and chloroiodomethane (0.97 g, 5.54 mmol) were added, then lithium diisopropylamide mono(tetrahydrofuran) solution 1.5 M in cyclohexane (5.52 mL, 8.28 mmol) was added at −78° C. and the reaction mixture was stirred at −78° C. for 4 h. After completion of the reaction, the reaction mixture was quenched with acetic acid (3.1 mL) in tetrahydrofuran (19 mL) and stirred for 20 min-78° C. The reaction mixture was warmed up to 0-5° C. and then brine solution (2 g NaCl in 20 mL water) was added. The resulting mixture was filtered, the organic layer was separated, and the aqueous fraction was extracted with ethyl acetate (2×150 mL). The combined organic layers were dried over anhydrous sodium sulfate and concentrated to give $N^1$—((S)-1-(((S)-4-chloro-3-oxo-1-(1-trityl-1H-imidazol-5-yl)butan-2- yl)amino)-4-methyl-1-oxopentan-2-yl)-N²-(2-fluorophenyl)oxalamide (1.0 g, crude) as a brown solid and used as such for the next step. [TLC system: EtOAc:hexane (4:6); R$_f$ value: 0.5].

Step 4. N¹-(2-fluorophenyl)-N²—((S)-4-methyl-1-oxo-1-(((S)-3-oxo-4-(2,3,5,6-tetrafluorophenoxy)-1-(1-trityl-1H-imidazol-5-yl)butan-2-yl)amino)pentan-2-yl)oxalamide Peak-1 and Peak-2

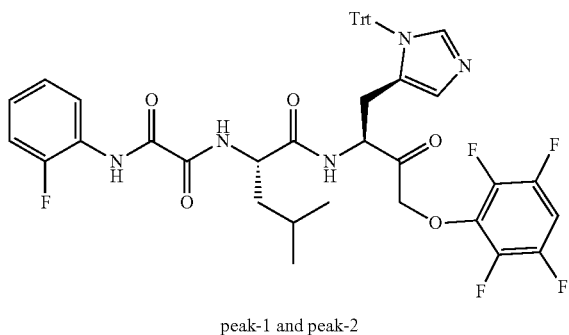

peak-1 and peak-2

To the mixture of N¹—((S)-1-(((S)-4-chloro-3-oxo-1-(1-trityl-1H-imidazol-5-yl)butan-2-yl)amino)-4-methyl-1-oxopentan-2-yl)-N²-(2-fluorophenyl)oxalamide (1.0 g, 1.41 mmol) and 2,3,5,6-tetrafluorophenol (0.28 g, 1.69 mmol) in dimethylformamide (5 mL), potassium fluoride (0.26 g, 4.51 mmol) was added and the reaction mixture was stirred at room temperature for 16 h. After completion of the reaction, the reaction mixture was diluted with water (50 mL) and extracted with ethyl acetate (3×100 mL). The combined organic layers were dried over anhydrous sodium sulfate and concentrated under reduced pressure. The obtained crude residue was purified by Davisil® grade silica gel column chromatography using 30% ethyl acetate in hexane and further purified by preparative SFC using column/dimensions: CHIRALPAK®-IA (4.6×250) mm, 3 m, % CO$_2$:75%, % Co-solvent: 25% (IPA-ACN) (1:1), Flow rate: 3.0 g/min, back pressure: 100 bar, temperature: 30° C., UV: 215 nm. Two fractions containing N¹-(2-fluorophenyl)-N²—((S)-4-methyl-1-oxo-1-(((S)-3-oxo-4-(2,3,5,6-tetrafluorophenoxy)-1-(1-trityl-1H-imidazol-5-yl)butan-2-yl)amino)pentan-2-yl)oxalamide were concentrated separately and designated as peak-1 (0.015 g, pale brown solid) and peak-2 (0.02 g, pale brown solid). [TLC system: EtOAc:hexane (4:6); R$_f$ value: 0.6].

Step 5. N¹—((S)-1-(((S)-1-(1H-imidazol-5-yl)-3-oxo-4-(2,3,5,6-tetrafluorophenoxy)butan-2-yl)amino)-4-methyl-1-oxopentan-2-yl)-N2-(2-fluorophenyl)oxalamide trifluoro acetate (Peak-1)

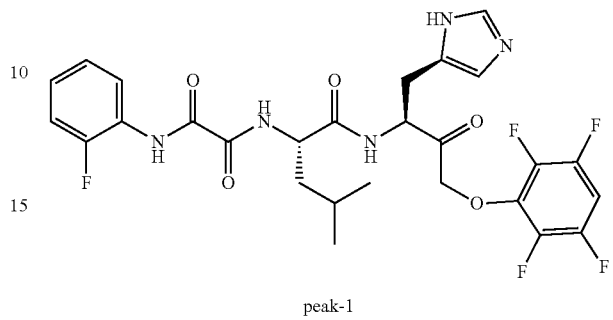

peak-1

To the stirred solution of N¹-(2-fluorophenyl)-N2-((S)-4-methyl-1-oxo-1-(((S)-3-oxo-4-(2,3,5,6-tetrafluorophenoxy)-1-(1-trityl-1H-imidazol-5-yl)butan-2-yl)amino)pentan-2-yl)oxalamide (peak-1) (0.015 g, 0.018 mmol) in dichloromethane (1 mL), trifluoroacetic acid (0.5 mL) in dichloromethane (0.5 mL) was added at 0° C. and the reaction mixture was stirred at room temperature for 3 h. After completion of the reaction, the reaction mixture was concentrated at low temperature. The residue was washed with diethyl ether (2×10 mL) and n-pentane (2×10 mL) and dried to afford N¹—((S)-1-(((S)-1-(1H-imidazol-5-yl)-3-oxo-4-(2,3,5,6-tetrafluorophenoxy)butan-2-yl)amino)-4-methyl-1-oxopentan-2-yl)-N2-(2-fluorophenyl)oxalamide trifluoroacetate (peak-1) (0.11 g) as an off-white solid. [TLC system: EtOAc:hexane (3:7); R$_f$: 0.1]. Analytical Data: LCMS: m/z 594.46 [M−1]; ¹H NMR (400 MHz, DMSO-d$_6$) δ ppm 14.1 (bs, 2H), 10.17 (s, 1H), 8.99 (d, J=8.0 Hz, 1H), 8.94 (s, 1H), 8.65 (d, J=8.4 Hz, 1H), 7.75 (t, J=7.6 Hz, 1H), 7.61-7.55 (m, 1H), 7.35-7.26 (m, 4H), 5.24 (q, J=18.0 Hz, 2H), 4.77-4.72 (m, 1H), 4.29-4.25 (m, 1H), 3.22-3.17 (m, 1H), 2.96-2.92 (m, 1H), 1.67-1.62 (m, 1H), 1.42-1.39 (m, 2H), 0.91-0.85 (m, 6H).

Step 6. N¹—((S)-1-(((S)-1-(1H-imidazol-5-yl)-3-oxo-4-(2,3,5,6-tetrafluorophenoxy)butan-2-yl)amino)-4-methyl-1-oxopentan-2-yl)-N2-(2-fluorophenyl)oxalamide trifluro acetate (Peak-2)

To the stirred solution of N¹-(2-fluorophenyl)-N²—((S)-4-methyl-1-oxo-1-(((S)-3-oxo-4-(2,3,5,6-tetrafluorophenoxy)-1-(1-trityl-1H-imidazol-5-yl)butan-2-yl)amino)pentan-2-yl)oxalamide (peak-2) (0.016 g, 0.019 mmol) in dichloromethane (1 mL), trifluoroacetic acid (0.5 mL) in dichloromethane (0.5 mL) was added at 0° C. and the reaction mixture was stirred at room temperature for 3 h. After completion of the reaction, the reaction mixture was concentrated at low temperature. The residue was washed with diethyl ether (2×10 mL) and n-pentane (2×10 mL) and dried to afford N¹—((S)-1-(((S)-1-(1H-imidazol-5-yl)-3-oxo-4-(2,3,5,6-tetrafluorophenoxy)butan-2-yl)amino)-4-methyl-1-oxopentan-2-yl)-N²-(2-fluorophenyl)oxalamide trifluoroacetate (peak-2) (0.14 g) as light brown solid. [TLC system: EtOAc:hexane (3:7); R$_f$ value: 0.1]. Analytical Data: LCMS: m/z 594.42 [M−1]; ¹H NMR (400 MHz, DMSO-d$_6$) δ ppm 14.1 (bs, 2H), 10.16 (s, 1H), 9.02 (d, J=8.4 Hz, 1H), 8.94 (s, 1H), 8.60 (d, J=8.0 Hz, 1H), 7.78-7.74 (m, 1H), 7.61-7.55 (m, 1H), 7.36-7.27 (m, 4H), 5.19 (q, J=17.65 Hz, 2H), 4.72-4.69 (m, 1H), 4.31-4.28 (m, 1H), 3.25-3.20 (m, 1H), 2.92-2.89 (m, 1H), 1.75-1.66 (m, 1H), 1.52-1.41 (m, 2H), 0.89-0.84 (m, 6H).

Example 18. Synthesis of $N^1$-(2-fluorophenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide (85)

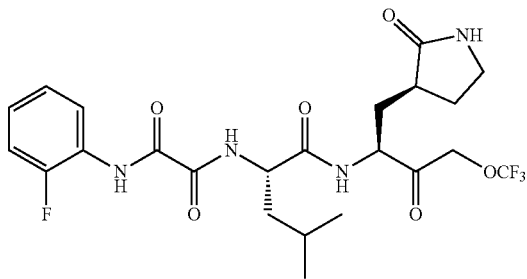 [SMILES: CC(C)C[C@H](NC(=O)C(=O)Nc1ccccc1F)C(=O)N[C@@H](C[C@@H]1CCNC1=O)C(=O)COC(F)(F)F]

To a stirred solution (2-((2-fluorophenyl)amino)-2-oxoacetyl)-D-leucine (0.224 g, 0.757 mmol) and (S)-3-((S)-2-amino-3-oxo-4-(trifluoromethoxy)butyl)pyrrolidin-2-one hydrochloride (0.22 g, 0.757 mmol) in DMF (4 mL) was added HATU (0.374 g, 0.983 mmol) followed by DIPEA (0.53 mL, 3.028 mmol) at 0° C. and the mixture was stirred at room temperature for 2 h. After completion, water (25 mL) was added to the reaction mixture and extracted with ethyl acetate (3×25 mL). The combined organic layers were washed with brine (1×25 mL) dried over anhydrous sodium sulfate, concentrated under reduced pressure. The crude residue was then purified by flash column chromatography over silica gel (230-400 mesh) to afford $N^1$-(2-fluorophenyl)-$N^2$—((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide (0.15 g) as an off-white solid. TLC system: EtOAc (100%); $R_f$: 0.2. Analytical Data: LCMS m/z=533.47 (M+1); $^1$H NMR (400 MHz, DMSO-$d_6$) δ ppm 10.21 (s, 1H), 9.01 (d, J=8.2 Hz, 1H), 8.58 (d, J=7.6 Hz, 1H), 7.76-7.67 (m, 1H), 7.67 (s, 1H), 7.34-7.21 (m, 3H), 4.98 (q, J=15.9 Hz, 2H), 4.42-4.36 (m, 2H), 3.17-3.12 (m, 2H), 2.49-2.26 (m, 2H), 2.10-2.06 (m, 1H), 1.97-1.90 (m, 1H), 1.96-1.54 (m, 5H), 0.90 (q, J=5.6 Hz, 6H).

Example 19. Synthesis of $N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(o-tolyl)oxalamide (206)

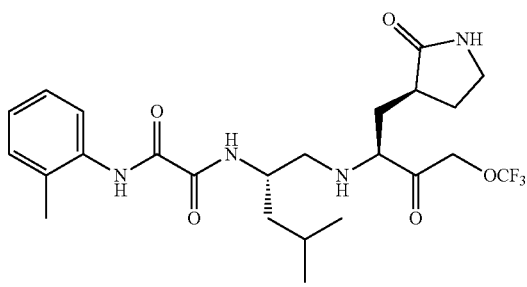 [SMILES: Cc1ccccc1NC(=O)C(=O)N[C@H](CN[C@@H](C[C@@H]1CCNC1=O)C(=O)COC(F)(F)F)CC(C)C]

To a stirred solution of (S)-3-((S)-2-amino-3-oxo-4-(trifluoromethoxy)butyl)pyrrolidin-2-one hydrochloride (0.175 g, 0.60 mmol) and (2-oxo-2-(o-tolylamino)acetyl)-L-leucine (0.176 g, 0.60 mmol) in N,N-dimethylformamide (1.75 mL) was added 1-[bis(dimethylamino)methylene]-1H-1,2,3-triazolo[4,5-b]pyridinium 3-oxide hexafluorophosphate (0.3 g, 0.78 mmol) and N-ethyl-N-isopropylpropan-2-amine (0.41 mL, 2.41 mmol) at 0° C. and the reaction mixture was stirred at room temperature for 30 min. After completion, water (2×50 mL) was added to the reaction mixture followed by extraction with ethyl acetate (2×50 mL). The combined organic layers were washed with brine (50 mL), dried over anhydrous sodium sulfate and concentrated under reduced pressure. The residue was then purified by column chromatography over Davisil® silica gel using 90-100% ethyl acetate in petroleum ether as a gradient to afford of $N^1$—((S)-4-methyl-1-oxo-1-(((S)-3-oxo-1-((S)-2-oxopyrrolidin-3-yl)-4-(trifluoromethoxy)butan-2-yl)amino)pentan-2-yl)-$N^2$-(o-tolyl)oxalamide (0.0585 g V2291609) as an off-white solid. TLC system: EtOAc; $R_f$: 0.3. Analytical Data: LCMS m/z 529.51 (M+1); $^1$H NMR (400 MHz, DMSO-$d_6$) δ ppm 8.93-8.86 (m, 2H), 8.61 (d, J=7.6 Hz, 1H), 7.70 (d, J=15.2 Hz, 1H), 7.53-7.46 (m, 1H), 7.27-7.13 (m, 3H), 5.01-4.93 (m, 2H), 4.43-4.37 (m, 2H), 3.17-3.11 (m, 2H), 2.28-2.20 (m, 5H), 2.12-2.09 (m, 1H), 1.76-1.55 (m, 5H), 0.96-0.88 (m, 6H).

Example 20. Synthesis of 4-methoxy-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-indole-2-carboxamide (158)

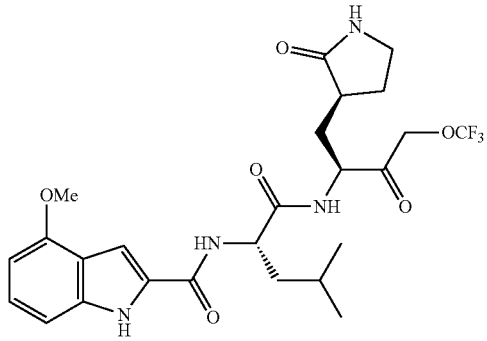 [SMILES: COc1cccc2[nH]c(C(=O)N[C@@H](CC(C)C)C(=O)N[C@@H](C[C@@H]3CCNC3=O)C(=O)COC(F)(F)F)cc12]

To a stirred solution (4-methoxy-1H-indole-2-carbonyl)-L-leucine (0.21 g, 0.69 mmol) and (S)-3-((S)-2-amino-3-oxo-4-(trifluoromethoxy)butyl)pyrrolidin-2-one hydrochloride (0.2 g, 0.69 mmol) in DMF (5 mL) was added HATU (0.34 g, 0.89 mmol) followed by DIPEA (0.5 mL, 2.75 mmol) at 0° C. and the reaction mixture was stirred at room temperature for 2 h. After completion, ice-cold water (50 mL) was added to the reaction mixture which was then extracted with EtOAc (2×100 mL). The combined organic layers were washed with brine (1×100 mL), dried over anhydrous sodium sulfate, filtered and concentrated under reduced pressure. The residue was then purified by column chromatography using 100% ethyl acetate as an eluent to afford 4-methoxy-N—((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-indole-2-carboxamide (70 mg) as an off-white solid. TLC system: EtOAc (100%); $R_f$: 0.3. Analytical Data: LCMS m/z 545.52 (M+1); $^1$H NMR (400 MHz, DMSO-$d_6$) δ ppm 8.83 (s, 1H), 8.71 (d, J=8.4 Hz, 1H), 8.63 (d, J=7.6 Hz, 1H), 7.66 (s, 1H), 7.29 (dd, J=14.4, 7.6 Hz, 1H), 7.12-7.08 (m, 2H), 7.02 (d, J=8.4 Hz, 1H), 4.93 (d, J=4.4 Hz, 2H), 4.54-4.50 (m, 2H), 3.16-3.02 (m, 4H), 2.25-2.22 (m, 1H), 2.08-2.07 (m, 1H), 1.99-1.92 (m, 1H), 1.68-1.61 (m, 2H), 1.25 (s, 3H), 0.67 (dd, J=19.6, 10.8 Hz, 1H), 0.55 (d, J=8.0 Hz, 2H).

Example 21. Synthesis of (1R,2S,5S)-3-((S)-3,3-dimethyl-2-(2,2,2-trifluoroacetamido)butanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide (264)

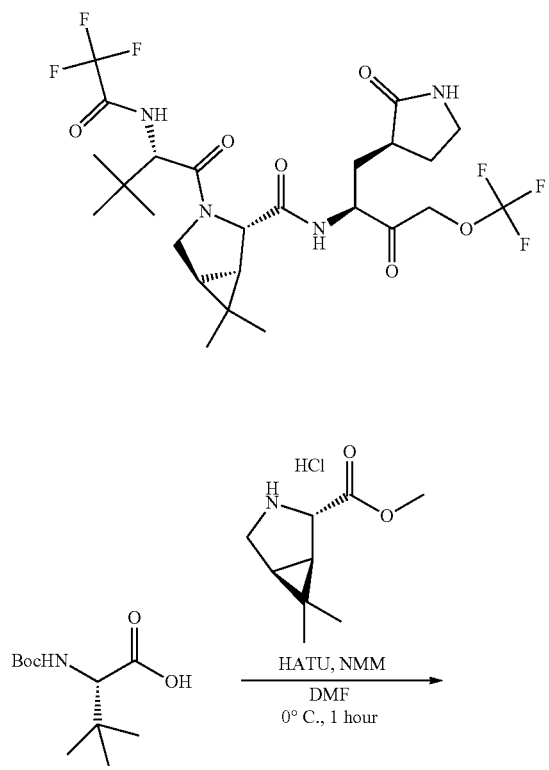

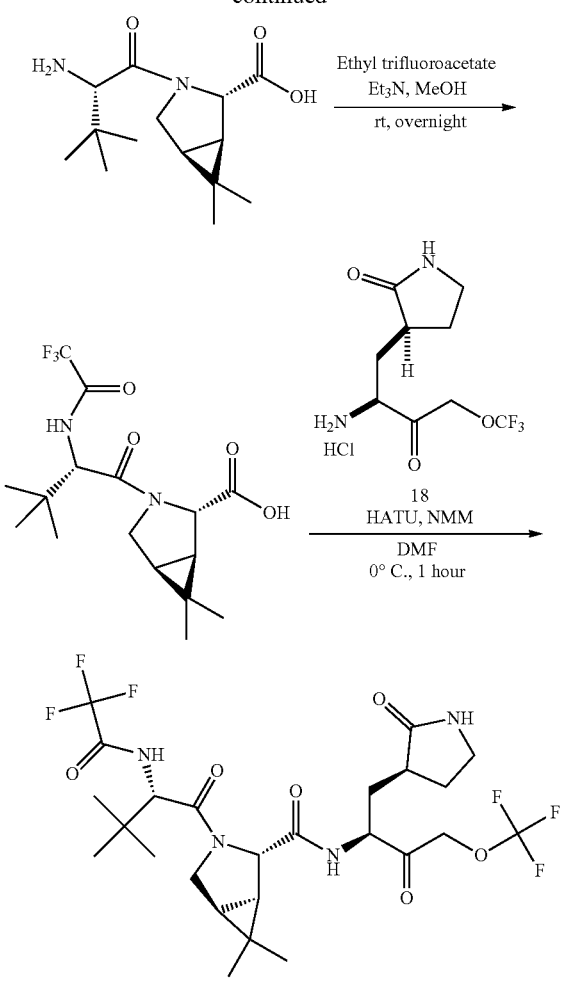

Step 1. Synthesis of methyl (1R,2S,5S)-3-((S)-2-((tert-butoxycarbonyl)amino)-3,3-dimethylbutanoyl)-6,6-dimethyl-3-azabicyclo[3.1.0]hexane-2-carboxylate A solution of (S)-2-((tert-butoxycarbonyl)amino)-3,3-dimethylbutanoic acid (2.16 mmol, 500 mg) in DMF (5 mL) was stirred at 0° C. for 5 min. HATU (1.2 equiv, 2.59 mmol, 986 mg) and NMM (3 equiv, 6.49 mmol, 713 μL) were added dropwise, and after stirring for another 5 min, methyl (1R,2S,5S)-6,6-dimethyl-3-azabicyclo[3.1.0]hexane-2-carboxylate (2.59 mmol, 534 mg) was added. The reaction was continued at 0° C. for 1 hour, and was quenched with H₂O (50 mL) and NaCl (saturated aqueous solution, 20 mL), and then extracted with EtOAc (20 mL). The aqueous layer was separated and extracted with EtOAc (3×20 mL). The combined organic phases were dried over Na₂SO₄, and concentrated in vacuo. Purification by flash column chromatography (SiO₂, graduate elution in CH₃OH; CH₂Cl₂ 0→1.5%) yielded methyl (1R,2S,5S)-3-((S)-2-((tert-butoxycarbonyl)amino)-3,3-dimethylbutanoyl)-6,6-dimethyl-3-azabicyclo[3.1.0]hexane-2-carboxylate as a white solid (750 mg, 91% yield).

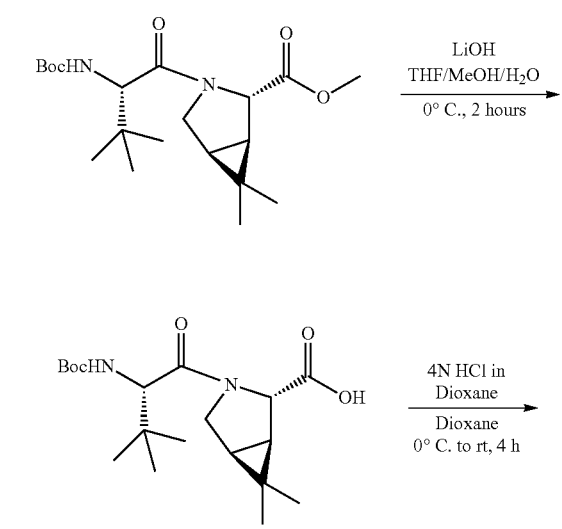

Step 2. Synthesis of (1R,2S,5S)-3-((S)-2-((tert-butoxycarbonyl)amino)-3,3-dimethylbutanoyl)-6,6-dimethyl-3-azabicyclo[3.1.0]hexane-2-carboxylic acid A solution of methyl (1R,2S,5S)-3-((S)-2-((tert-butoxycarbonyl)amino)-3,3-dimethylbutanoyl)-6,6-dimethyl-3-azabicyclo[3.1.0]hexane-2-carboxylate (369 µmol, 141 mg) in THF (1 mL) was stirred at 0° C. for 10 min, and a solution of LiOH (2 equiv; 737.25 µmol, 18 mg) in H₂O (500 mL) was added dropwise. The reaction mixture was then stirred at 0° C. for 2 hours, followed by treatment with HCl (1 M. in H₂O, 3 mL) and EtOAc (10 mL). The aqueous layer was separated and extracted with EtOAc (3×10 mL). The combined organic phases were dried over Na₂SO₄ and concentrated in vacuo thus yielding (1R,2S,5S)-3-((S)-2-((tert-butoxycarbonyl)amino)-3,3-dimethylbutanoyl)-6,6-dimethyl-3-azabicyclo[3.1.0]hexane-2-carboxylic acid as a white solid (120 mg, 88% yield).

Step 3. Synthesis of (1R,2S,5S)-3-((S)-2-amino-3,3-dimethylbutanoyl)-6,6-dimethyl-3-azabicyclo[3.1.0]hexane-2-carboxylic acid hydrochloride A solution of (1R,2S,5S)-3-((S)-2-((tert-butoxycarbonyl)amino)-3,3-dimethylbutanoyl)-6,6-dimethyl-3-azabicyclo[3.1.0]hexane-2-carboxylic acid (325.67 µmol, 120 mg) in dioxane (1 mL) was stirred at 0° C. for 10 min, and a solution of HCl (22 equiv; 7.16 mmol, 1.79 mL) in dioxane (4 M) was added dropwise. The reaction mixture was gradually warmed to room temperature and stirred for another 4 hours. After the reaction was complete, the mixture was concentrated in vacuo to give (1R,2S,5S)-3-((S)-2-amino-3,3-dimethylbutanoyl)-6,6-dimethyl-3-azabicyclo[3.1.0]hexane-2-carboxylic acid hydrochloride. It was used for the next step without further purification.

Step 4. Synthesis of (1R,2S,5S)-3-((S)-3,3-dimethyl-2-(2,2,2-trifluoroacetamido)butanoyl)-6,6-dimethyl-3-azabicyclo[3.1.0]hexane-2-carboxylic acid Triethylamine (4 equiv, 1.49 mmol, 207.19 µL.) was added to a solution of (1R,2S,5S)-3-((S)-2-amino-3,3-dimethylbutanoyl)-6,6-dimethyl-3-azabicyclo[3.1.0]hexane-2-carboxylic acid hydrochloride (372.64 µmol, 100 mg) in MeOH (1 mL). Then ethyl trifluoroacetate (1.3 equiv, 484.43 µmol, 69 mg.) was added and the reaction mixture was stirred at room temperature for 12 h. The solvent was removed by rotary evaporation and the residue was dissolved in H₂O (5 mL) and extracted with EtOAc (3×10 mL). The combined organic phases were washed with brine, dried over Na₂SO₄, and concentrated in vacuo to give (1R,2S,5S)-3-((S)-3,3-dimethyl-2-(2,2,2-trifluoroacetamido)butanoyl)-6,6-dimethyl-3-azabicyclo[3.1.0]hexane-2-carboxylic acid which was used for next step without further purification.

Step 5. Synthesis of (1R,2S,5S)-3-((S)-3,3-dimethyl-2-(2,2,2-trifluoroacetamido)butanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide A solution of (1R,2S,5S)-3-((S)-3,3-dimethyl-2-(2,2,2-trifluoroacetamido)butanoyl)-6,6-dimethyl-3-azabicyclo[3.1.0]hexane-2-carboxylic acid (1 equiv, 205.84 µmol, 75 mg) in DMF (1 mL) was stirred at 0° C. for 5 min. HATU (1.2 equiv, 247.00 µmol, 94 mg) and NMM (1.2 equiv, 617.51 µmol, 68 µL) were added dropwise, and after stirring for another 5 min, (S)-3-((S)-2-amino-3-oxo-4-(trifluoromethoxy)butyl)pyrrolidin-2-one hydrochloride (1.2 equiv, 247.00 µmol, 72 mg) was added. The reaction was continued at 0° C. for 1 hour, and then was quenched with H₂O (5 mL), NaCl (saturated aqueous, 10 mL), and EtOAc (10 mL). The aqueous layer was separated and extracted with EtOAc (3×10 mL). The combined organic phases were dried over Na₂SO₄ and concentrated in vacuo. Purification by flash column chromatography (SiO₂, graduate elution in CH₃OH; CH₂Cl₂ 0→3%) yielded (1R,2S,5S)-3-((S)-3,3-dimethyl-2-(2,2,2-trifluoroacetamido)butanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide as a white solid. This product was obtained as a mixture of stereoisomers. Analytical data: LCMS m/z=601.41 (M+1); ¹H NMR (400 MHz, Chloroform-d) δ ppm 8.31 (d, J=6.3 Hz, 1H), 6.98 (s, 1H), 5.89 (d, J=26.0 Hz, 1H), 4.83-4.66 (m, 2H), 4.59 (d, J=9.4 Hz, 1H), 4.33 (d, J=11.4 Hz, 1H), 4.04 (dd, J=10.2, 5.5 Hz, 1H), 3.83 (t, J=8.5 Hz, 1H), 3.38 (dd, J=9.2, 6.6 Hz, 2H), 2.56 (q, J=7.9 Hz, 1H), 2.51-2.40 (m, 1H), 2.05-1.88 (m, 2H), 1.78 (s, 1H), 1.64-1.46 (m, 2H), 1.28 (s, 1H), 1.07 (d, J=10.8 Hz, 9H), 1.01-0.87 (m, 6H).

Example 22. N-((1R,2R)-2-ethyl-1-(((S)-3-oxo-1-((S)-2-oxopyrrolidin-3-yl)-4-(trifluoromethoxy)butan-2-yl)carbamoyl)cyclopropyl)-5-fluoro-1H-indole-2-carboxamide (261)

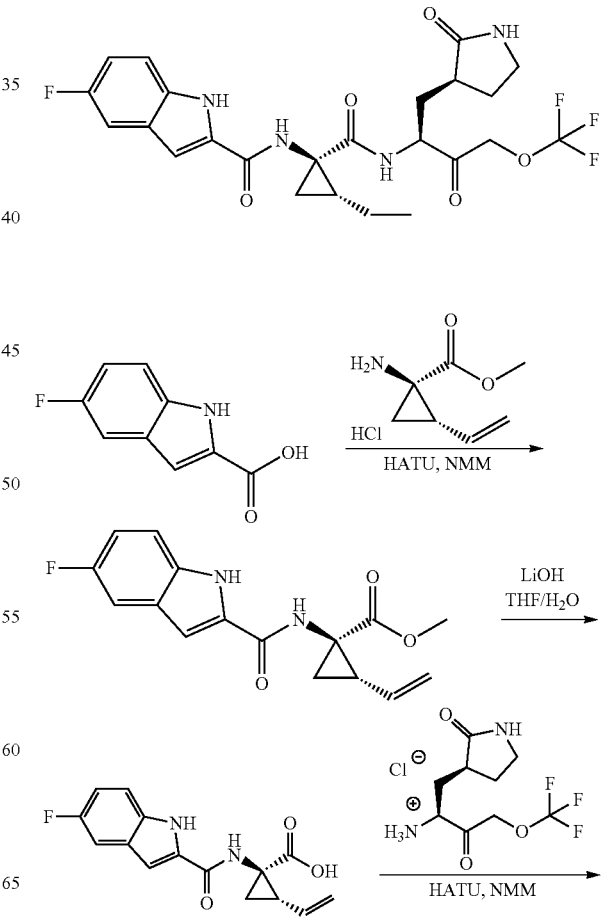

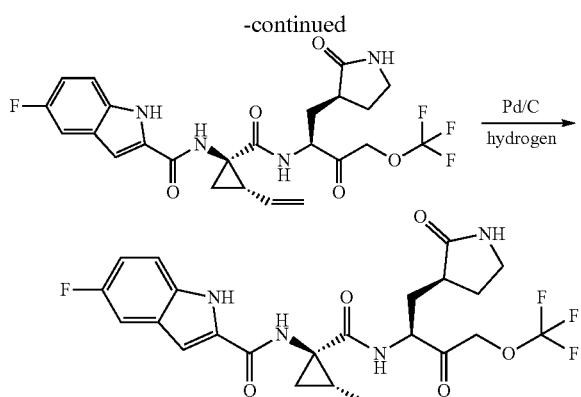

Step 1. methyl (1R,2S)-1-(5-fluoro-1H-indole-2-carboxamido)-2-vinylcyclopropane-1-carboxylate To a stirring solution of 5-fluoroindole-2-carboxylic acid (0.32 g, 1.8 mmol, 1.4 eq) and HATU (0.86 g, 2.3 mmol, 1.8 eq) in 5 mL of DMF at 0° C. was added 4-methylmorpholine (0.40 mL, 3.6 mmol, 2.8 eq) neat. The solution was stirred at 0° C. After 10 minutes methyl (1R,2S)-1-amino-2-vinylcyclopropane-1-carboxylate hydrochloride (0.2 g, 1.3 mmol, 1.0 eq) was added to the solution and the reaction mixture was stirred for 1 hour. The reaction mixture was quenched with 20 mL of water and extracted twice with 20 mL of ethyl acetate. The organic layer was washed once with 20 mL of water and an additional time with 20 mL of brine. The organic layers were dried with sodium sulfate and filtered. The filtrate was concentrated under vacuum on a rotary evaporator. The crude material was purified by normal phase column chromatography (SiO₂, graduate elution in EtOAc:hexane, 0→40%) on a Teledyne ISCO CombiFlash Rf to give methyl (1R,2S)-1-(5-fluoro-1H-indole-2-carboxamido)-2-vinylcyclopropane-1-carboxylate as a white solid (0.27 g, 69%).

Step 2. (1R,2S)-1-(5-fluoro-1H-indole-2-carboxamido)-2-vinylcyclopropane-1-carboxylic acid To a stirred solution of methyl (1R,2S)-1-(5-fluoro-1H-indole-2-carboxamido)-2-vinylcyclopropane-1-carboxylate (0.27 g, 0.85 mmol, 1.0 eq) in 3 mL of THF at room temperature was added lithium hydroxide (0.064 g, 2.7 mmol, 3.2 eq) in 3 mL of water. After 1 hour, the reaction was quenched with 15 mL of 1.2 M HCl solution and the aqueous layer was extracted five times with 15 mL ethyl acetate. The combined organic fractions were dried with sodium sulfate, filtered, and concentrated to yield (1R,2S)-1-(5-fluoro-1H-indole-2-carboxamido)-2-vinylcyclopropane-1-carboxylic acid as a white solid. It was used directly in the next step.

Step 3. 5-fluoro-N-((1R,2S)-1-(((S)-3-oxo-1-((S)-2-oxopyrrolidin-3-yl)-4-(trifluoromethoxy)butan-2-yl)carbamoyl)-2-vinylcyclopropyl)-1H-indole-2-carboxamide A solution of (1R,2S)-1-(5-fluoro-1H-indole-2-carboxamido)-2-vinylcyclopropane-1-carboxylic acid (90 mg, 0.31 mmol, 1.3 eq) and HATU (0.13 g, 0.34 mmol, 1.5 eq) in 2 mL of DMF at 0° C. was stirred for 10 minutes before (S)-3-((S)-2-amino-3-oxo-4-(trifluoromethoxy)butyl)pyrrolidin-2-one hydrochloride (90 mg, 0.23 mmol, 1.0 eq) was added followed by the addition of 4-methyl morpholine (0.070 mL, 0.63 mmol, 2.0 eq). After 1 hour, the reaction mixture was quenched with 20 mL of water and extracted twice with 20 mL of ethyl acetate. The combined organic layers were washed once with water and 20 mL of brine, dried with sodium sulfate and filtered. Concentration yielded a crude yellow oil. The crude material was purified by normal phase column chromatography (SiO₂, graduate elution in MeOH:DCM, 0→5%) on a Teledyne ISCO CombiFlash Rf. Concentration of the fractions and further purification of the resulting material via reverse-phase column chromatography (C18, graduate elution in CH₃CN:H₂O, 0→50%), subsequent concentration of the fractions, and lyophilization of the resulting material yielded 5-fluoro-N-((1R,2S)-1-(((S)-3-oxo-1-((S)-2-oxopyrrolidin-3-yl)-4-(trifluoromethoxy)butan-2-yl)carbamoyl)-2-vinylcyclopropyl)-1H-indole-2-carboxamide as a slightly yellow solid (23 mg, 19%).

Step 4. N-((1R,2R)-2-ethyl-1-(((S)-3-oxo-1-((S)-2-oxopyrrolidin-3-yl)-4-(trifluoromethoxy)butan-2-yl)carbamoyl)cyclopropyl)-5-fluoro-1H-indole-2-carboxamide A mixture of 5-fluoro-N-((1R,2S)-1-(((S)-3-oxo-1-((S)-2-oxopyrrolidin-3-yl)-4-(trifluoromethoxy)butan-2-yl)carbamoyl)-2-vinylcyclopropyl)-1H-indole-2-carboxamide (13 mg, 0.025 mmol) and 10% Pd/C (small scoop) in 2 mL of ethyl acetate was stirred under an atmosphere of hydrogen. After 1 hour, the reduction was complete and the mixture was filtered through a syringe filter (pore size of 0.45 μm, Fisher F2504-3). The solvent was concentrated, and the material was dissolved in 2 mL of acetonitrile before being filtered again. The material was lyophilized to yield N-((1R,2R)-2-ethyl-1-(((S)-3-oxo-1-((S)-2-oxopyrrolidin-3-yl)-4-(trifluoromethoxy)butan-2-yl)carbamoyl)cyclopropyl)-5-fluoro-1H-indole-2-carboxamide as a white fluffy solid (7.2 mg, 55%) as a mixture of diastereomers.

LCMS m/z=527.2706 (M+1); ¹H NMR (500 MHz, DMSO-d₆) δ ppm 11.67 (s, 1H), 8.83 (s, 1H), 8.56-8.52 (m, 1H), 7.65-7.55 (m, 1H), 7.48-7.37 (m, 2H), 7.29-7.18 (m, 1H), 7.05 (td, J=9.2, 2.6, 1H), 5.13-4.80 (m, 2H), 4.46 (ddd, J=11.7, 8.1, 4.0 Hz, 1H), 3.19-3.03 (m, 2H), 2.26-2.07 (m, 2H), 2.06-1.73 (m, 2H), 1.72-1.53 (m, 3H), 1.46 (s, 1H), 1.33-1.27 (m, 1H), 1.08-0.92 (m, 3H), 0.92-0.84 (m, 1H). Due to the presence of epimers, small peaks neighbored the major peaks. Ratio of epimers: 1:2.7:5.3:25.3

Example 23. (1S,3aR,6aS)-2-(2-(tert-butylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide (260)

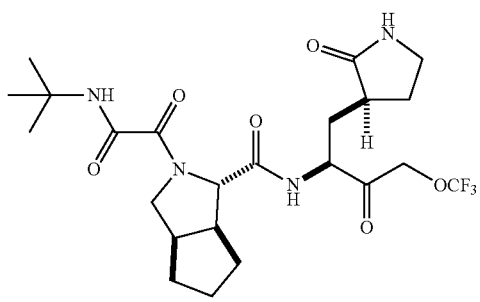

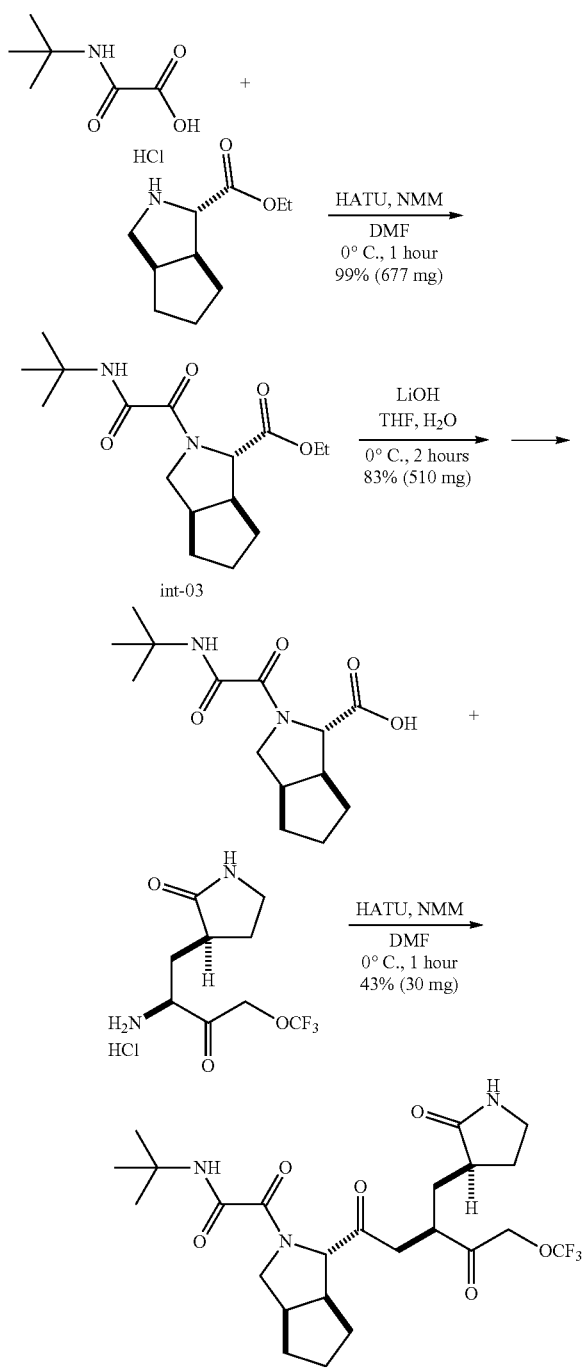

Step 1. ethyl (1S,3aR,6aS)-2-(2-(tert-butylamino)-2-oxoacetyl)octahydrocyclopenta[c]pyrrole-1-carboxylate (Int-03)

To a mixture of aminoester, ethyl (1S,3aR,6aS)-octahydrocyclopenta[c]pyrrole-1-carboxylatem, (int-02; 1 equiv, 2.18 mmol, 479 mg), oxamic acid (int-01; 1.1 equiv, 2.40 mmol, 348 mg), and HATU (1.25 equiv, 2.73 mmol, 1.027 g) was added pre-cooled 0° C. DMF (10.8 mL). This mixture was stirred at 0° C. for 10 min, after which NMM (2.56 equiv, 5.58 mmol, 610 µL) was added dropwise over a 1 min period. The reaction was continued at 0° C. for 1 hour, after which it was quenched with deionized $H_2O$ (50 mL), NaCl (saturated aqueous., 20 mL), and EtOAc (20 mL). The aqueous layer was separated and extracted with EtOAc (3×20 mL). The combined organic phases were dried over $Na_2SO_4$ and concentrated in vacuo. Purification by flash column chromatography ($SiO_2$, graduate elution in 0→1.5% $CH_3OH:CH_2Cl_2$) yielded ethyl (1S,3aR,6aS)-2-(2-(tert-butylamino)-2-oxoacetyl)octahydrocyclopenta[c]pyrrole-1-carboxylate (int-03) as a white solid (677 mg, 99% yield).

Step 2. Synthesis of (1S,3aR,6aS)-2-(2-(tert-butylamino)-2-oxoacetyl)octahydrocyclopenta[c]pyrrole-1-carboxylic acid A solution of ethyl (1S,3aR,6aS)-2-(2-(tert-butylamino)-2-oxoacetyl)octahydrocyclopenta[c]pyrrole-1-carboxylate (1 equiv, 2.18 mmol, 677 mg) in THF (4.4 mL) was stirred at 0° C. for 10 min, and a solution of LiOH (2 equiv, 4.36 mmol, 105 mg) in $H_2O$ (4.4 mL) was added dropwise over a 1 min period. The reaction mixture was then stirred at 0° C. for 2 hours, followed by treatment with HCl (1 M soln. in $H_2O$, 10 mL) and EtOAc (10 mL). The aqueous layer was separated and extracted with EtOAc (3×10 mL). The combined organic phases were dried over $Na_2SO_4$ and concentrated in to yield (1S,3aR,6aS)-2-(2-(tert-butylamino)-2-oxoacetyl)octahydrocyclopenta[c]pyrrole-1-carboxylic acid as a white solid (int-04; 510 mg, 83% yield).

Step 3. Synthesis of (1S,3aR,6aS)-2-(2-(tert-butylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide To a mixture of (S)-3-((S)-2-amino-3-oxo-4-(trifluoromethoxy)butyl)pyrrolidin-2-one hydrochloride (1 equiv, 0.13 mmol, 39 mg), (1S,3aR,6aS)-2-(2-(tert-butylamino)-2-oxoacetyl)octahydrocyclopenta[c]pyrrole-1-carboxylic acid (1.2 equiv, 0.16 mmol, 45 mg), and HATU (1.3 equiv, 0.17 mmol, 64 mg) was added pre-cooled (to 0° C.) DMF (0.9 mL). This mixture was stirred at 0° C. for 10 min, after which NMM (2.7 equiv, 0.35 mmol, 38 µL) was added dropwise over a 1 min period. The reaction was continued at 0° C. for 1 hour, after which it was quenched with $H_2O$ (10 mL), NaCl (saturated aqueous, 5 mL), and EtOAc (5 mL). The aqueous layer was separated and extracted with EtOAc (3×5 mL). The combined organic phases were dried over $Na_2SO_4$ and concentrated in vacuo. Purification by flash column chromatography ($SiO_2$, graduate elution in 0→3% $CH_3OH$; $CH_2Cl_2$) yielded (1S,3aR,6aS)-2-(2-(tert-butylamino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide as a white solid (30 mg, 43% yield) as a mixture of stereoisomers (as judged by $^1H$ NMR, approximate ratio is 1.5:1). Analytical data: LCMS m/z=519.0526 (M+1); $^1H$ NMR (499 MHz, DMSO-$d_6$) δ ppm 8.67 (d, J=7.5 Hz, 0.4H), 8.57 (d, J=7.7 Hz, 0.6H), 7.91 (s, 0.6H), 7.83 (s, 0.4H), 7.66 (s, 0.4H), 7.63 (s, 0.6H), 5.13-4.90 (m, 2H), 4.70 (d, J=2.3 Hz, 0.4H), 4.35 (tt, J=7.6, 3.5 Hz, 1H), 4.12 (d, J=4.1 Hz, 0.6H), 3.93 (dd, J=11.8, 7.8 Hz, 0.6H), 3.68-3.57 (m, 1.4H), 3.48-3.35 (m, 1H), 3.24-2.98 (m, 2H), 2.76-2.63 (m, 1H), 2.35-2.20 (m, 1H), 2.13 (dt, J=13.0, 7.6 Hz, 1H), 2.05-1.35 (m, 9H), 1.30 (s, 3.6H), 1.26 (s, 5.4H).

Example 24. (1S,3aR,6aS)-2-(2-((2-fluorophenyl)amino)-2-oxoacetyl)-N—((S)-3-oxo-1-((S)-2-oxopyrrolidin-3-yl)-4-(trifluoromethoxy)butan-2-yl)octahydrocyclopenta[c]pyrrole-1-carboxamide (256)

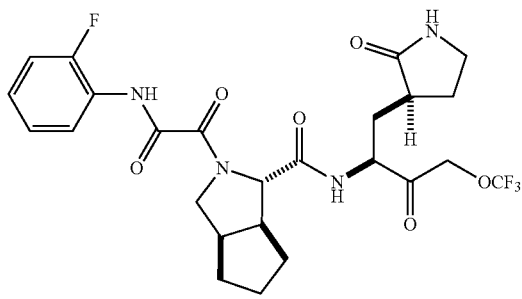

The compound was prepared similarly according to the scheme shown on Example 23 from 2-((2-fluorophenyl)amino)-2-oxoacetic acid as a white solid (20 mg, 20% yield). The title compound was obtained as a mixture of stereoisomers (as judged by $^1$H NMR, approximate ratio is 1.5:1). Analytical data: LCMS m/z=557.3903 (M+1); $^1$H NMR (499 MHz, DMSO-d$_6$) δ ppm 10.21 (app. d, J=14.2 Hz, 1H), 8.71 (d, J=7.6 Hz, 0.4H), 8.60 (d, J=7.6 Hz, 0.6H), 7.81-7.58 (m, 2H), 7.33-7.13 (m, 3H), 5.07-4.88 (m, 2H), 4.81 (d, J=2.8 Hz, 0.6H), 4.38 (dddd, J=27.4, 11.6, 7.8, 3.8 Hz, 1H), 4.23 (d, J=4.2 Hz, 0.4H), 4.04 (dd, J=11.9, 7.9 Hz, 0.4H), 3.79 (dd, J=12.0, 4.2 Hz, 0.4H), 3.72 (dd, J=12.8, 8.4 Hz, 0.6H), 3.49 (dd, J=12.8, 4.7 Hz, 0.6H), 3.15 (dd, J=15.7, 7.7 Hz, 1H), 3.04 (t, J=9.0 Hz, 1H), 2.88-2.79 (m, 1H), 2.77-2.56 (m, 2H), 2.35-2.07 (m, 2H), 2.05-1.31 (m, 8H).

Example 25. N$^1$-(2-fluorophenyl)-N$^2$—((S)-4-methyl-1-oxo-1-(((S)-3-oxo-1-((S)-2-oxopyrrolidin-3-yl)-4-((2-(trifluoromethyl)pyrimidin-4-yl)oxy)butan-2-yl)amino)pentan-2-yl)oxalamide (788)

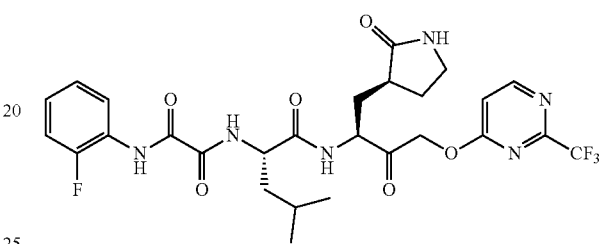

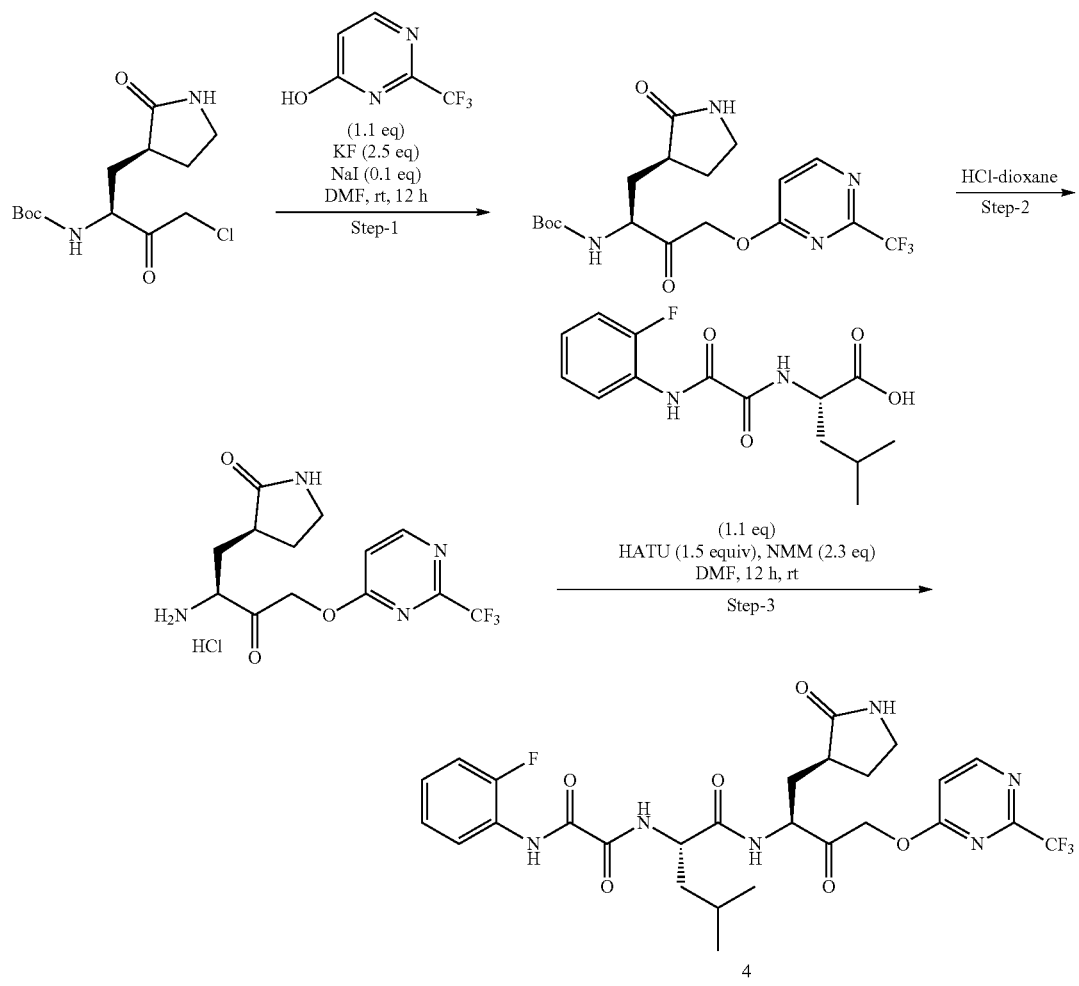

Step 1. tert-butyl ((S)-3-oxo-1-((S)-2-oxopyrrolidin-3-yl)-4-((2-(trifluoromethyl)pyrimidin-4-yl)oxy)butan-2-yl)carbamate To a solution of tert-butyl ((S)-4-chloro-3-oxo-1-((S)-2-oxopyrrolidin-3-yl)butan-2-yl)carbamate (400 mg, 1.3157 mmol) in dry DMF (4 ml) were added KF (192 mg, 3.2895 mmol) and NaI (19.72 mg, 0.1315 mmol) at ambient temperature and the mixture was stirred for 15 min at ambient temperature. 2-(Trifluoromethyl)pyrimidin-4-ol (0.237 mg, 1.4473 mmol) was added with continued stirring at ambient temperature for 12 h. The reaction was monitored by TLC and after completion of the reaction, the reaction mixture was quenched with ice-cold water (10 ml) and then extracted with ethyl acetate (3×10 ml). The combined organic layers were washed with brine (10 ml), dried over $Na_2SO_4$ and concentrated under vacuum to obtained crude product which was purified by column chromatography (0.5% MeOH in DCM) to give tert-butyl ((S)-3-oxo-1-((S)-2-oxopyrrolidin-3-yl)-4-((2-(trifluoromethyl)pyrimidin-4-yl)oxy)butan-2-yl)carbamate (450 mg, 79.23%). LCMS m/z=333.2 [(M+1)-100].

Step 2. (S)-3-((S)-2-amino-3-oxo-4-((2-(trifluoromethyl)pyrimidin-4-yl)oxy)butyl)pyrrolidin-2-one hydrochloride To a solution of tert-butyl ((S)-3-oxo-1-((S)-2-oxopyrrolidin-3-yl)-4-((2-(trifluoromethyl)pyrimidin-4-yl)oxy)butan-2-yl)carbamate (450 mg, 1.0412 mmol) in 1,4-dioxane (5 ml) was added 4 M-HCl in dioxane (4 ml) at 5-10° C., and the mixture was stirred for 2 h at ambient temperature. The progress of reaction was monitored by TLC and after completion of reaction, the reaction mixture was concentrated under reduced pressure to obtained crude material which purified by trituration with diethyl ether to get (S)-3-((S)-2-amino-3-oxo-4-((2-(trifluoromethyl)pyrimidin-4-yl)oxy)butyl)pyrrolidin-2-one hydrochloride (300 mg, 78.33%). LCMS m/z=333.2 (M+1).

Step 3. $N^1$-(2-fluorophenyl)-$N^2$—((S)-4-methyl-1-oxo-1-(((S)-3-oxo-1-((S)-2-oxopyrrolidin-3-yl)-4-((2-(trifluoromethyl)pyrimidin-4-yl)oxy)butan-2-yl)amino)pentan-2-yl)oxalamide To a solution of (2-((2-fluorophenyl)amino)-2-oxoacetyl)-L-leucine (0.297 mg, 1.004 mmol) in DMF (6 ml) was added HATU (578 mg, 1.5060 mmol) at 0-10° C., and the mixture was stirred for 1 h at ambient temperature. (S)-3-((S)-2-Amino-3-oxo-4-((2-(trifluoromethyl)pyrimidin-4-yl)oxy)butyl)pyrrolidin-2-one hydrochloride (300 mg, 0.9036 mmol) and NMM (99 mg, 2.3077 mmol) were added, and the mixture was stirred for 12 h at ambient temperature. The reaction mixture was quenched in ice-cold water (10 ml), and solids was filtered and dried under vacuum to get crude material which was purified by preparative HPLC (Phenomenex® C8 column, 35%-100% acetonitrile/0.1% TFA in water) to get pure $N^1$-(2-fluorophenyl)-$N^2$—((S)-4-methyl-1-oxo-1-(((S)-3-oxo-1-((S)-2-oxopyrrolidin-3-yl)-4-((2-(trifluoromethyl)pyrimidin-4-yl)oxy)butan-2-yl)amino)pentan-2-yl)oxalamide (56 mg, 9.15%). LCMS m/z=611.8 (M+1); $^1$H NMR (400 MHz, DMSO-$d_6$) δ ppm 10.28 (s, 1H), 8.96 (d, J=7.6 Hz, 1H), 8.80 (s, 1H), 8.72 (s, 1H), 7.70 (s, 2H), 7.38-7.23 (m, 3H), 5.35-5.30 (m, 2H), 4.53-4.41 (m, 2H), 3.18-3.16 (m, 2H), 2.15-2.02 (m, 2H) 1.76-1.58 (m, 5H), 0.89 (s, 6H).

Example 26. $N^1$—((S)-1-(((S)-7-amino-2-oxo-1-(2,3,5,6-tetrafluorophenoxy)heptan-3-yl)amino)-4-methyl-1-oxopentan-2-yl)-$N^2$-(2-fluorophenyl)oxalamide hydrochloride (142)

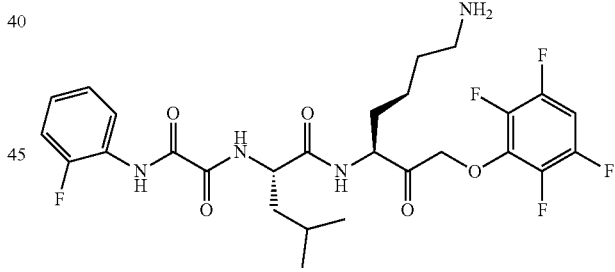

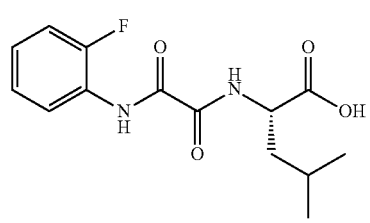 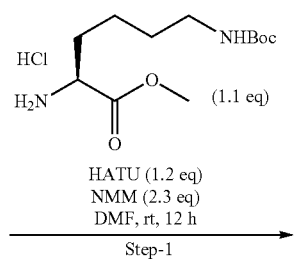

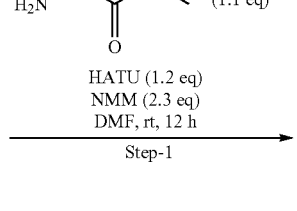

Step-1

-continued

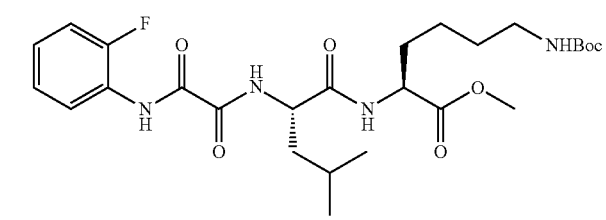
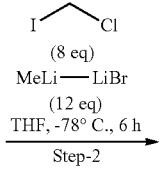

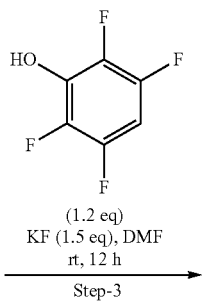

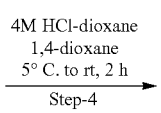
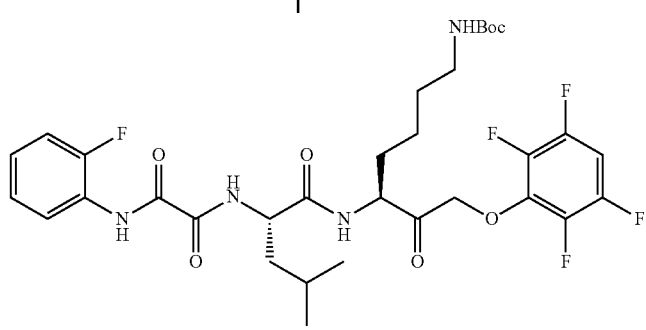

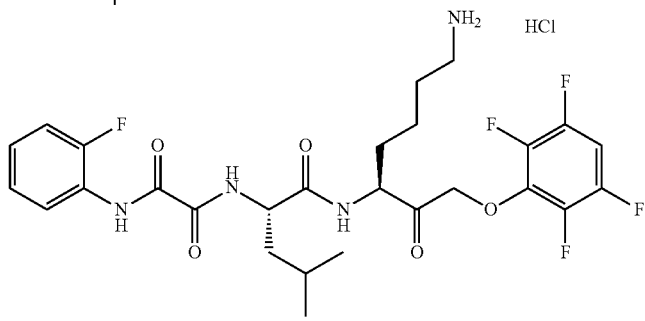

Step 1. methyl N⁶-(tert-butoxycarbonyl)-N²-((2-((2-fluorophenyl)amino)-2-oxoacetyl)-L-leucyl)-L-lysinate To a solution of (2-((2-fluorophenyl)amino)-2-oxoacetyl)-L-leucine (0.250 mg, 0.8445 mmol) in DMF (3 ml) was added HATU (385 mg, 1.013 mmol) at 0-10° C., and the mixture was stirred for 1 h at ambient temperature. Methyl N⁶-(tert-butoxycarbonyl)-L-lysinate hydrochloride (274 mg, 0.9290 mmol) and NMM (200 mg, 1.9688 mmol) were added at ambient temperature, and the resultant mixture was stirred for 12 h at ambient temperature. The reaction mixture was quenched with ice-cold water (10 ml), and the solid was filtered and dried under vacuum to get methyl N⁶-(tert-butoxycarbonyl)-N²-((2-((2-fluorophenyl)amino)-2-oxoacetyl)-L-leucyl)-L-lysinate (450 mg). LCMS m/z=539.7 (M+1).

Step 2. tert-butyl ((S)-7-chloro-5-((S)-2-(2-((2-fluorophenyl)amino)-2-oxoacetamido)-4-methylpentanamido)-6-oxoheptyl)carbamate To a solution of methyl N⁶-(tert-butoxycarbonyl)-N²-((2-((2-fluorophenyl)amino)-2-oxoacetyl)-L-leucyl)-L-lysinate (250 mg, 0.464 mmol) in THF was added chloroiodomethane (654 mg, 3.7174 mmol) at −78° C. 1.5 M MeLi—LiBr (607 mg, 5.5762 mmol) in diethyl ether was added dropwise at −78° C. and stirred at −78° C. for 5 h. The reaction was quenched with saturated aqueous NH₄Cl solution and the mixture was extracted with ethyl acetate (3×20 ml). The combined organic layers were dried over Na₂SO₄ and concentrated under vacuum to obtained crude tert-butyl ((S)-7-chloro-5-((S)-2-(2-((2-fluorophenyl)amino)-2-oxoacetamido)-4-methylpentanamido)-6-oxoheptyl)carbamate (250 mg). This material was used for next reaction without further purification. LCMS m/z=555.3 (M−1).

Step 3. tert-butyl ((S)-5-((S)-2-(2-((2-fluorophenyl)amino)-2-oxoacetamido)-4-methylpentanamido)-6-oxo-7-(2,3,5,6-tetrafluorophenoxy)heptyl)carbamate To a solution of tert-butyl ((S)-7-chloro-5-((S)-2-(2-((2-fluorophenyl)amino)-2-oxoacetamido)-4-methylpentanamido)-6-oxoheptyl)carbamate (250 mg, 0.4496 mmol) in dry DMF (4 ml) was added KF (39 mg, 0.6744 mmol) at 0° C., and the mixture was stirred for 15 min. 2,3,5,6-Tetrafluorophenol (90 mg, 0.5395 mmol) in DMF was added at 0° C., and the mixture was stirred at ambient temperature for 12 h. The reaction was quenched with ice-cold water (10 ml), and the mixture was extracted with ethyl acetate (3×10 ml). The combined the organic layers were washed with brine (10 ml), dried over $Na_2SO_4$ and concentrated under vacuum to obtained crude material which was purified by column chromatography on silica gel (40% ethyl acetate in hexane) to give tert-butyl ((S)-5-((S)-2-(2-((2-fluorophenyl)amino)-2-oxoacetamido)-4-methylpentanamido)-6-oxo-7-(2,3,5,6-tetrafluorophenoxy)heptyl)carbamate (25 mg). LCMS m/z=687.9 (M+1).

Step 4. $N^1$—((S)-1-(((S)-7-amino-2-oxo-1-(2,3,5,6-tetrafluorophenoxy)heptan-3-yl)amino)-4-methyl-1-oxopentan-2-yl)-$N^2$-(2-fluorophenyl)oxalamide To a solution of tert-butyl ((S)-5-((S)-2-(2-((2-fluorophenyl)amino)-2-oxoacetamido)-4-methylpentanamido)-6-oxo-7-(2,3,5,6-tetrafluorophenoxy)heptyl)carbamate (25 mg, 1.0412 mmol) in 1,4-dioxane (1 ml) was added 4 M HCl in dioxane (0.5 ml) at 5-10° C., and the mixture was stirred for 2 h at ambient temperature. The progress of reaction was monitored by TLC and after completion of reaction, the reaction mixture was concentrated under reduced pressure to obtained crude material which purified by trituration with diethyl ether to get $N^1$—((S)-1-(((S)-7-amino-2-oxo-1-(2,3,5,6-tetrafluorophenoxy)heptan-3-yl)amino)-4-methyl-1-oxopentan-2-yl)-$N^2$-(2-fluorophenyl)oxalamide (9 mg). LCMS m/z=587.7 (M+1).

Example 27: (S)-5-((R)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide (362)

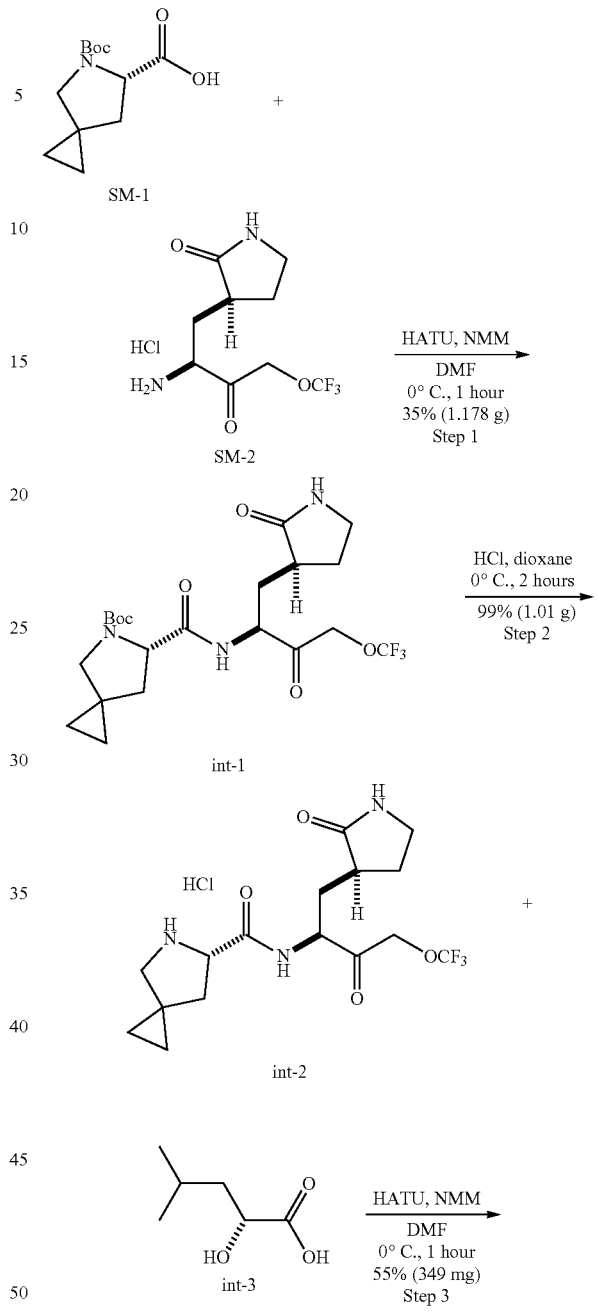

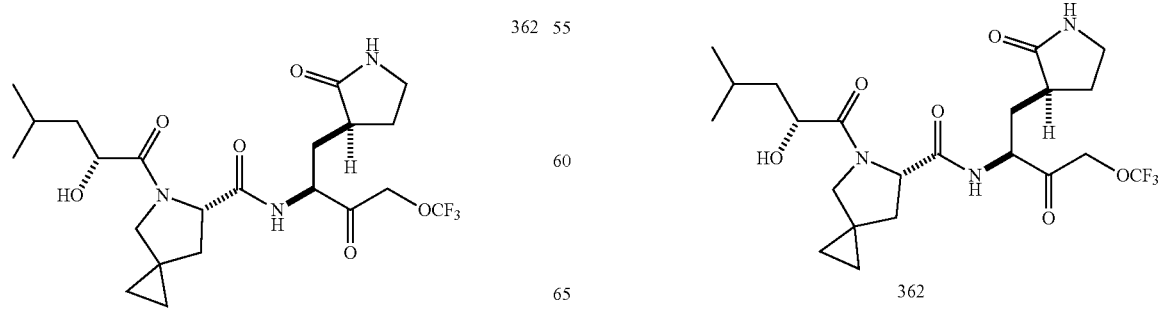

362

Step 1: tert-butyl (S)-6-(((S)-3-oxo-1-((S)-2-oxopyrrolidin-3-yl)-4-(trifluoromethoxy)butan-2-yl)carbamoyl)-5-azaspiro[2.4]heptane-5-carboxylate (Int-1)

To a mixture of Boc-amino acid SM-1 (2.2 g, 9.1 mmol, 1.3 eq), amine hydrochloride SM-2 (2 g, 7 mmol, 1 eq), and HATU (3.46 g, 9.1 mmol, 1.3 eq) was added pre-cooled to 0° C. DMF (47 mL). This mixture was stirred at 0° C. for 10 min, after which NMM (1.92 mL, 17.5 mmol, 2.5 eq) was added dropwise over a 1 min period. The reaction was continued at 0° C. for 1 hour, after which it was quenched with cold deionized H$_2$O (50 mL). This mixture was directly used for purification via reverse-phase flash column chromatography (C18, graduate elution in CH$_3$CN:H$_2$O, 0→20%), which was then followed by an additional purification via normal phase flash column chromatography (SiO$_2$, gradient elution in 0-3% CH$_3$OH:CH$_2$Cl$_2$), thus yielding the desired carbamate as a white solid (int-1; 1.178 g, 35% yield).

Step 2: (S)—N—((S)-3-oxo-1-((S)-2-oxopyrrolidin-3-yl)-4-(trifluoromethoxy)butan-2-yl)-5-azaspiro[2.4]heptane-6-carboxamide hydrochloride (Int-2)

A solution of carbamate int-1 (1.178 g, 2.5 mmol, 1 eq) in dioxane (12.3 mL) was stirred at 0° C. for 10 min, after which a solution of HCl (4 M in dioxane, 20 eq, 12.3 mL) was added dropwise over a 2 min period. The reaction mixture was then stirred at 0° C. for 2 hours, followed by concentration and drying, thus yielding the desired adduct amine hydrochloride as a white solid (int-2; 1.01 g, 99% yield).

Step 3: (S)-5-((R)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide (362)

To a mixture of amine hydrochloride int-2 (563 mg, 1.36 mmol, 1 eq), lactic acid derivative (int-3; 234 mg, 1.77 mmol, 1.3 eq), and HATU (672 mg, 1.77 mmol, 1.3 eq) was added DMF (9 mL, pre-cooled to 0° C.). This mixture was stirred at 0° C. for 10 min, after which NMM (374 µL, 3.4 mmol, 2.5 eq) was added dropwise over a 1 min period. The reaction was continued at 0° C. for 1 hour, after which it was quenched with cold deionized H$_2$O (20 mL). This mixture was directly used for purification via reverse-phase flash column chromatography (C18, gradient elution in CH$_3$CN:H$_2$O, 0→20%), which was then followed by an additional purification via normal phase flash column chromatography (SiO$_2$, gradient elution in 0-3% CH$_3$OH:CH$_2$Cl$_2$) to obtain 362 (349 mg; 55% yield).

LCMS m/z=492.4428 (M+1); $^1$H NMR (400 MHz, DMSO-d$_6$) δ ppm 8.67 (br d, J=7.0 Hz, 0.2H), 8.43 (br d, J=7.7 Hz, 0.7H), 7.73 (br s, 0.2H), 7.67 (br s, 0.7H), 5.10 (d, J=7.3 Hz, 0.2H), 5.02 (d, J=17.4 Hz, 1.2H, some overlap), 4.88 (d, J=17.3 Hz, 1H), 4.60 (d, J=7.3 Hz, 0.7H), 4.35 (m, 1.8H), 4.11 (m, 0.8H), 3.91 (m, 0.2H), 3.58-3.46 (m, 1.8H), 3.22-3.06 (m, 2.2H), 2.30-2.06 (m, 3H), 2.03-1.89 (m, 1H), 1.84-1.54 (m, 4H), 1.51-1.18 (m, 2H), 0.88 (d, J=6.8 Hz, 2.3H), 0.87 (d, J=6.5 Hz, 2.3H), 0.88 (d, J=6.7 Hz, 0.7H), 0.87 (d, J=6.5 Hz, 0.7H), 0.66-0.37 (m, 4H).

Example 28: (S)-5-((S)-3,3-dimethyl-2-(2,2,2-trifluoroacetamido)butanoyl)-N—((S)-3-oxo-1-((S)-2-oxopyrrolidin-3-yl)-4-(trifluoromethoxy)butan-2-yl)-5-azaspiro[2.4]heptane-6-carboxamide (441)

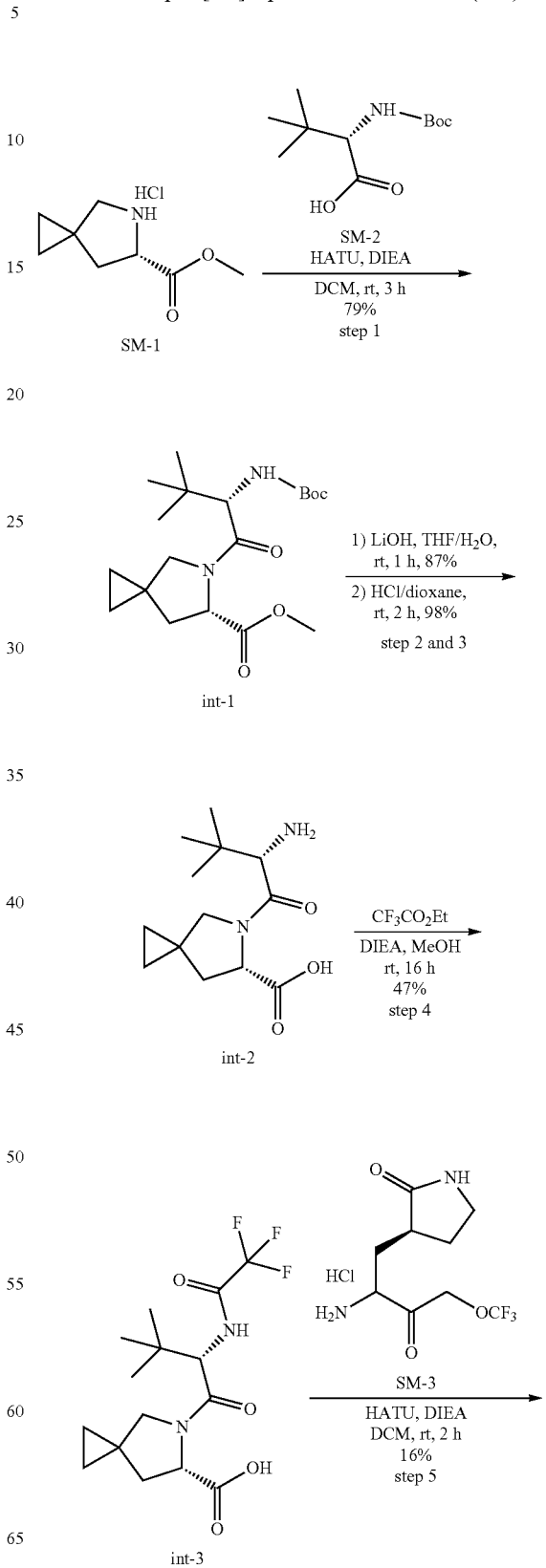

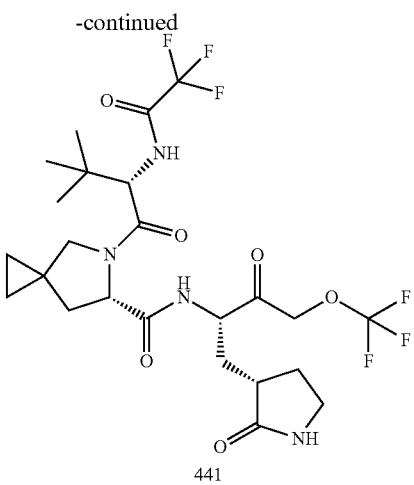

441

Step 1: methyl (6S)-5-[(2S)-2-[(tert-butoxycarbonyl)amino]-3,3-dimethylbutanoyl]-5-azaspiro[2.4]heptane-6-carboxylate (Int-1)

To a stirred solution of SM-1 (3 g, 19.3 mmol, 1 eq), SM-2 (4.5 g, 19.3 mmol, 1 eq), and HATU (8.8 g, 23.2 mmol, 1.2 eq) in DCM (150 mL) was added DIEA (6.3 g, 48.3 mmol, 2.5 eq) dropwise at 0° C. under a $N_2$ atmosphere. The resulted mixture was stirred at room temperature for 3 hours. After the reaction was completed, the reaction was quenched with 100 mL water at 0° C. and then extracted with DCM (2×200 mL). The combined organic layers were washed with 1 N HCl (3×240 mL) and brine (1×310 mL), dried over anhydrous $Na_2SO_4$, filtered, and concentrated under reduced pressure. The residue was purified by silica gel column chromatography, eluted with petroleum ether/THF (1:1) to afford int-1 (5.6 g, 15.2 mmol, 79%) as a white solid.

Steps 2 and 3: (6S)-5-[(2S)-2-amino-3,3-dimethylbutanoyl]-5-azaspiro [2.4]heptane-6-carboxylic acid (Int-2)

To a stirred solution of int-1 (5.6 g, 15.2 mmol, 1 eq) in THF (50 mL) was added a LiOH solution (0.4 g in 26 mL water, 18.2 mmol, 1.2 eq) dropwise at 0° C. The resulted mixture was stirred for 1 h at room temperature. After the reaction was completed, the mixture was diluted with water (20 mL). Then the pH was adjusted to 3 with citric acid at 0° C., and resulting mixture extracted with EtOAc (3×200 mL). The combined organic layers were dried over anhydrous $Na_2SO_4$, filtered, and concentrated in vacuo to yield Boc-int-2 (4.6 g, 86.7%) as a white solid.

To a stirred solution of Boc-int-2 (4.6 g, 13.2 mmol, 1 eq) in DCM (46 mL) was added HCl/dioxane (4 M, 33 mL, 132 mmol, 10 eq) dropwise at 0° C. The resultant mixture was stirred for an additional 2 h at 0° C. After the reaction was completed, the mixture was concentrated under reduced pressure to afford int-2 (3.7 g, 14.5 mmol, 97.8%) as a white solid.

Step 4: (6S)-5-[(2S)-3,3-dimethyl-2-(2,2,2-trifluoroacetamido)butanoyl]-5-azaspiro[2.4]heptane-6-carboxylic acid (Int-3)

To a stirred solution of int-2 (3.7 g, 14.5 mmol, 1.0 eq) and ethyl 2,2,2-trifluoroacetate (6.6 g, 50.9 mmol, 3.5 eq) in MeOH (40 mL, 988.0 mmol, 67.9 eq) was added DIEA (7.5 g, 58.2 mmol, 4 eq) dropwise at room temperature. The resulting mixture was stirred for an additional 16 h at room temperature. After the reaction was completed, the mixture was concentrated under reduced pressure. Then the residue was diluted with EtOAc (100 mL) and washed with 1 N HCl (2×100 mL). The combined organic layers were dried over anhydrous $Na_2SO_4$, filtered, and concentrated in vacuo to yield int-3 (2.4 g, 7.7 mol, 47.1%) as a white solid.

Step 5: (S)-5-((S)-3,3-dimethyl-2-(2,2,2-trifluoroacetamido)butanoyl)-N—((S)-3-oxo-1-((S)-2-oxopyrrolidin-3-yl)-4-(trifluoromethoxy)butan-2-yl)-5-azaspiro[2.4]heptane-6-carboxamide (441)

To a stirred solution of int-3 (2.4 g, 7.7 mmol, 1 eq) and SM-3 (2.7 g, 9.3 mmol, 1.2 eq) and HATU (3.5 g, 9.3 mmol, 1.2 eq) in DCM (80 mL) was added DIEA (2.5 g, 19.3 mmol, 2.5 eq) dropwise at 0° C. under $N_2$ atmosphere. The resulting mixture was stirred for additional 2 h at room temperature. After the reaction was completed, the reaction was quenched with 100 mL water and then extracted with DCM (2×100 mL). The combined organic phase was concentrated under reduced pressure. The residue was purified by silica column and eluted with petroleum ether/THF (45:55) to give the crude product which was further purified with SFC to give 441 (700 mg, 1.27 mmol, 16.5%).

LCMS m/z=587.4788 (M+1); $^1$H NMR (400 MHz, DMSO-$d_6$) δ ppm 9.44-8.89 (m, 1H), 8.70-8.58 (m, 1H), 7.83-7.60 (m, 1H), 4.99 (s, 2H), 4.52-4.36 (m, 3H), 3.71-3.64 (m, 1H), 3.55-3.48 (m, 1H), 3.21-3.13 (m, 1H), 3.08-3.06 (m, 1H), 2.37-2.35 (m, 1H), 2.23-2.11 (m, 1H), 2.06-1.90 (m, 2H), 1.85-1.83 (m, 1H), 1.70-1.56 (m, 2H), 1.00 (s, 9H), 0.71-0.63 (m, 1H), 0.63-0.50 (m, 3H).

Example 29: (1R,2S,5S)-3-((R)-2-methoxybutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide (336)

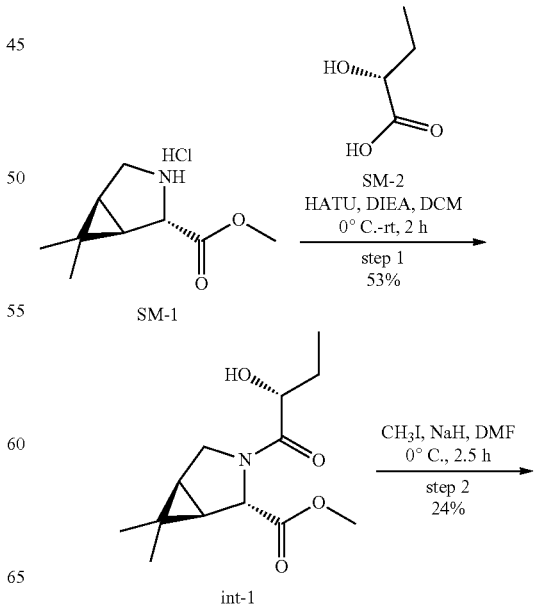

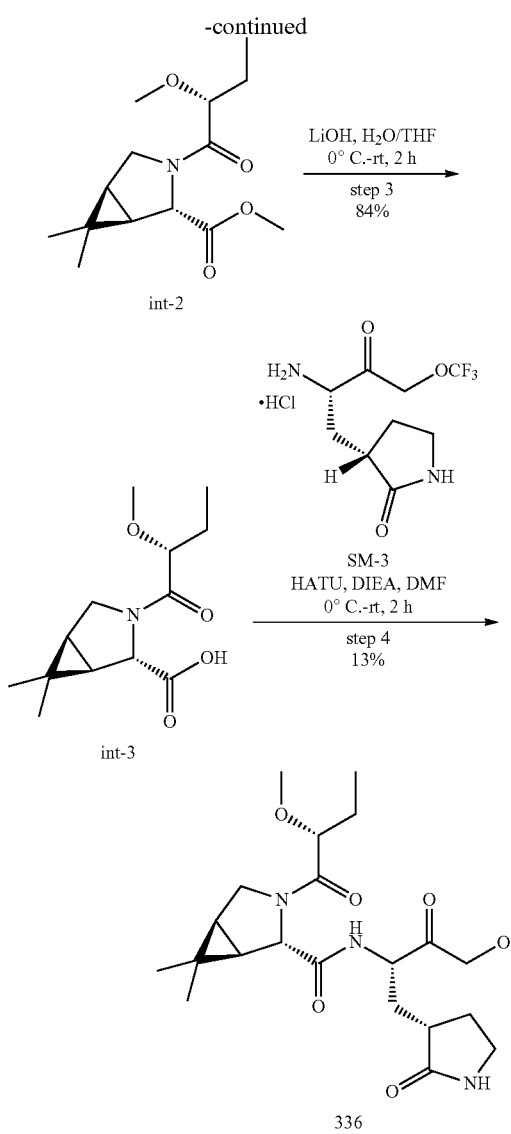

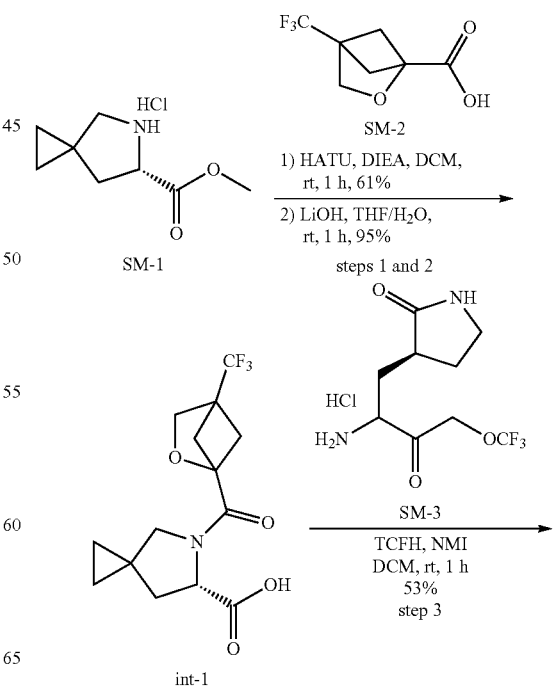

The mixture was stirred at 0° C. before LiOH (16.01 mg, 0.668 mmol, 1.2 eq) was added. The resulting mixture was stirred for an additional 2 h at room temperature. The reaction was monitored by LCMS. After the reaction was completed, 5 mL HCl (1 M) was added, and the mixture was extracted with ethyl acetate (3×20 mL). The combined organic layers were washed with brine (50 mL), dried over anhydrous $Na_2SO_4$, filtered, and concentrated in vacuo to afford int-3 (120 mg, 0.47 mmol, 84%) as a yellow oil.

Step 4: (1R,2S,5S)-3-((R)-2-methoxybutanoyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide (336)

Into a 40 ml bottle were placed a solution of int-3 (115 mg, 0.45 mmol, 1.0 eq), DIEA (174.6 mg, 1.35 mmol, 3 eq) and SM-3 (114.5 mg, 0.45 mmol, 1.0 eq) in DMF (5 mL). To the above mixture was added HATU (205.5 mg, 0.54 mmol, 1.2 eq) in portions at 0° C. The resulting mixture was stirred for additional 2 h at room temperature, diluted with 20 mL $H_2O$, and extracted with ethyl acetate (3×20 mL). The combined organic layers were washed with brine (50 mL), dried over anhydrous $Na_2SO_4$, filtered, and concentrated in vacuo. The residue was purified by preparative HPLC [column: Welflash 120 g Flash Column, Spherical C18, 20-40 μm; mobile phase: Water/0.05% ammonia; MeCN 40% to 60% gradient in 15 min; detector, UV 220 nm] to yield 336 (45 mg, 0.058 mmol, 13%).

LCMS m/z=492.0 (M+1); $^1$H NMR (400 MHz, DMSO-$d_6$) δ ppm 8.77-8.75 (m, 0.4H), 7.65-7.40 (m, 1H), 6.21-5.99 (m, 0.6H), 5.02 (s, 1H), 4.71-4.20 (m, 1H), 3.90-3.53 (m, 4H), 3.32-3.09 (m, 5H), 2.52-2.48 (m, 1H), 2.20-2.02 (m, 1H), 1.97-1.95 (m, 1H), 1.63-1.54 (m, 5H), 1.51-1.31 (m, 2H), 1.28-1.01 (m, 3H), 0.91-0.75 (m, 6H).

Example 30: (6S)—N-[(2S)-3-oxo-1-[(3S)-2-oxopyrrolidin-3-yl]-4-(trifluoromethoxy)butan-2-yl]-5-[4-(trifluoromethyl)-2-oxabicyclo[2.1.1]hexane-1-carbonyl]-5-azaspiro[2.4]heptane-6-carboxamide (317)

Step 2: methyl (1R,2S,5S)-3-((R)-2-methoxybutanoyl)-6,6-dimethyl-3-azabicyclo[3.1.0]hexane-2-carboxylate (Int-2)

Into a 40 ml bottle were placed a solution of int-1 (600 mg, 2.36 mmol, 1.0 eq) in DMF (6 mL). NaH (60%; 112.8 mg, 2.82 mmol, 1.2 eq) was added at 0° C. The mixture was stirred for 0.5 h at the same temperature before $CH_3I$ (400 mg, 2.82 mmol, 1.2 eq) was added. The resulting mixture was stirred for another 2 h at 0° C. The reaction was monitored by LCMS. The reaction was quenched with 50 mL $H_2O$ and extracted with ethyl acetate (3×50 mL). The combined organic layers were washed with brine (50 mL), dried over anhydrous $Na_2SO_4$, filtered, and concentrated in vacuo. The residue was purified by silica gel column chromatography, eluted with EtOAc:petroleum ether=1:5 to afford int-2 (150 mg, 0.56 mmol, 24%) as a yellow oil.

Step 3: (1R,2S,5S)-3-((R)-2-methoxybutanoyl)-6,6-dimethyl-3-azabicyclo[3.1.0]hexane-2-carboxylic acid (Int-3)

Into a 40 ml bottle were placed a solution of int-2 (150 mg, 0.56 mmol, 1.0 eq) in $H_2O$ (0.2 mL) and THF (1 mL).

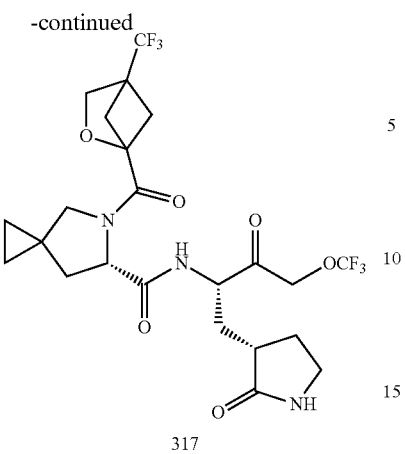

317

Steps 1 and 2: (6S)-5-[4-(trifluoromethyl)-2-oxabicyclo[2.1.1]hexane-1-carbonyl]-5-azaspiro[2.4]heptane-6-carboxylic acid (Int-1)

To a stirred mixture of SM-1 (3.0 g, 15.7 mmol, 1.0 eq), SM-2 (3.1 g, 15.7 mmol, 1.0 eq), and HATU (7.1 g, 18.8 mmol, 1.2 eq) in DCM (150 mL) was added DIEA (5.1 g, 39.1 mmol, 2.5 eq) dropwise at 0° C. The resulting mixture was stirred for an additional 1 h at room temperature, diluted with 100 mL $H_2O$, and extracted with DCM (3×100 mL). The combined organic layers were washed with brine (2×400 mL), dried over anhydrous $Na_2SO_4$, filtered, and concentrated in vacuo. The resultant residue was purified by silica gel column chromatography, eluted with petroleum ether/THF (65:35) to afford the methyl ester of int-1 (3.2 g, 9.6 mmol) as white solid.

The above solid was taken up in THF (32 mL), and to this was added $LiOH \cdot H_2O$ (0.5 g in 8 mL water, 11.5 mmol, 1.2 eq) dropwise at 0° C. The resulting mixture was stirred for an additional 1 h at room temperature and then diluted with water (50 mL). The mixture was washed with ethyl acetate (2×30 mL). The aqueous layer was then acidified to pH=3 with 1 N HCl (aq.) and subsequently extracted with ethyl acetate (2×100 mL). The combined organic layers were dried over anhydrous $Na_2SO_4$, filtered, and concentrated in vacuo to afford int-1 (2.9 g, 9.1 mmol, 95%) as a white solid.

Step 3: (6S)—N-[(2S)-3-oxo-1-[(3S)-2-oxopyrrolidin-3-yl]-4-(trifluoromethoxy)butan-2-yl]-5-[4-(trifluoromethyl)-2-oxabicyclo[2.1.1]hexane-1-carbonyl]-5-azaspiro[2.4]heptane-6-carboxamide (317)

To a stirred mixture of int-1 (2.9 g, 9.1 mmol, 1.0 eq), SM-3 (3.4 g, 11.8 mmol, 1.3 eq), and TCFH (3.1 g, 10.9 mmol, 1.2 eq) in DCM (100 mL) was added NMI (1.9 g, 22.8 mmol, 2.5 eq) dropwise at 0° C. under $N_2$ atmosphere. The resulting mixture was stirred for 1 h at room temperature, quenched by the addition of water (100 mL), and extracted with DCM (3×300 mL). The combined organic layers were washed with 1 N HCl (aq.) (4×300 mL) and brine (2×300 mL), dried over anhydrous $Na_2SO_4$, filtered, and concentrated in vacuo. The residue was purified by silica gel column chromatography, eluted with petroleum ether/THF (45:55) to afford 3 g of 85% (SFC) pure product. It was further purified by SFC with the following conditions: Column: Chiral ART Cellulose-SC, 3×25 cm, 5 m; Mobile Phase A: $CO_2$, Mobile Phase B: IPA:ACN=1:1; Flow rate: 80 mL/min; Gradient: isocratic 30% B; Column Temperature (° C.): 35; Back Pressure (bar): 100; Wave Length: 220 nm; Retention Time (min): 3.47; Sample Solvent: IPA; Injection Volume: 3 mL; Number Of Runs: 25; to give Compound 317 (2.7 g, 4.9 mmol, 53%).

LCMS m/z=556.4128 (M+1); $^1H$ NMR (400 MHz, DMSO-$d_6$) δ ppm 8.55-8.53 (m, 1H), 7.69-7.66 (m, 1H), 5.04-4.86 (m, 2H), 4.42-4.39 (m, 2H), 3.94 (s, 2H), 3.84-3.48 (m, 2H), 3.19-3.10 (m, 2H), 2.50-1.97 (m, 8H), 1.97-1.61 (m, 3H), 0.60-0.54 (m, 4H).

Example 31: (S)-5-(2,2-dimethoxyacetyl)-N—((S)-3-oxo-1-((S)-2-oxopyrrolidin-3-yl)-4-(trifluoromethoxy)butan-2-yl)-5-azaspiro[2.4]heptane-6-carboxamide (340)

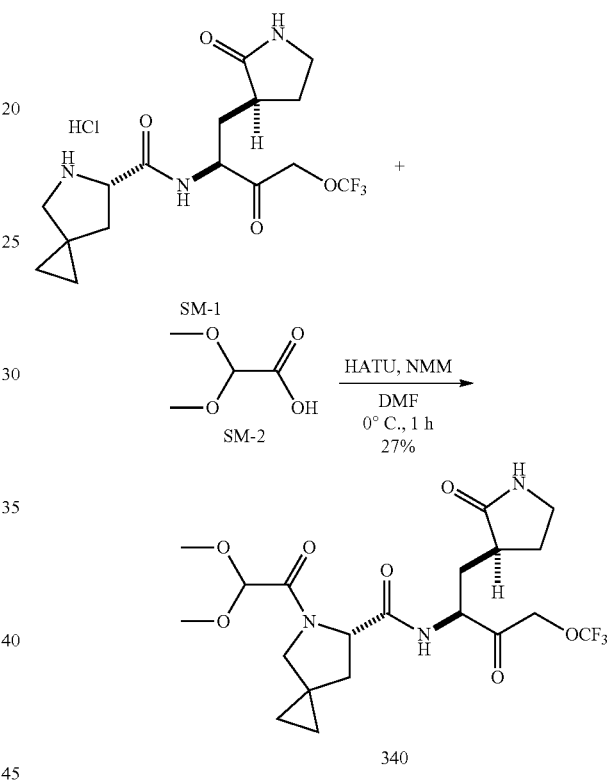

To a mixture of amine hydrochloride SM-1 (204 mg, 0.451 mmol, 1.0 eq), carboxylic acid SM-2 (65.9 mg, 0.549 mmol, 1.2 eq), and HATU (192 mg, 0.506 mmol, 1.1 eq) was added DMF (3 mL). This mixture was stirred at 0° C. for 10 min, after which NMM (114 μL, 0.104 mmol, 2.3 eq) was added dropwise. The reaction was continued at 0° C. for 1 hour, after which it was quenched with cold deionized $H_2O$ (15 mL). The mixture was then extracted with EtOAc (3×5 mL). Then the combined organic layers were washed with brine (5 mL), dried over $Na_2SO_4$, and concentrated. The residue was purified through normal-phase flash column chromatography (silica, gradient elution in 0→5% $CH_3OH$:$CH_2Cl_2$), and then by reverse-phase flash column chromatography (C18, gradient elution in $CH_3CN$:$H_2O$, 0→80%) to yield Compound 340 (58.3 mg, 0.122 mmol, 27%).

LCMS m/z=480.4214 (M+1); $^1H$ NMR (400 MHz, DMSO-$d_6$) δ ppm 8.64 (d, J=7.3 Hz, 0.2H), 8.62 (d, J=7.3 Hz, 0.2H), 8.58 (d, J=7.6 Hz, 0.6H), 7.71 (s, 0.2H), 7.67 (s, 0.7H), 5.10-4.88 (m, 2H), 4.85 (s, 0.8H), 4.73 (s, 0.2H), 4.71 (s, 0.1H), 4.51-4.44 (m, 0.2H), 4.39 (dd, J=8.5, 5.3 Hz, 0.8H), 4.37-4.28 (m, 0.7H), 3.58-3.45 (m, 2H), 3.28 (s, 5.3H), 3.26 (s, 0.8H), 3.24 (s, 0.2H), 3.22-3.05 (m, 2H), 2.45-2.35 (m, 0.1H), 2.34-2.19 (m, 0.8H), 2.19-2.05 (m, 1.7H), 2.05-1.92 (m, 0.8H), 1.78 (dd, J=12.6, 6.1 Hz, 0.2H), 1.72 (dd, J=12.6, 5.4 Hz, 1H), 1.67-1.51 (m, 1.8H), 0.57 (s, 2H), 0.53 (s, 2H).

Example 32: Synthesis of (S)-5-((methylcarbamoyl)-D-leucyl)-N—((S)-3-oxo-1-((S)-2-oxopyrrolidin-3-yl)-4-(trifluoromethoxy)butan-2-yl)-5-azaspiro[2.4]heptane-6-carboxamide (435)

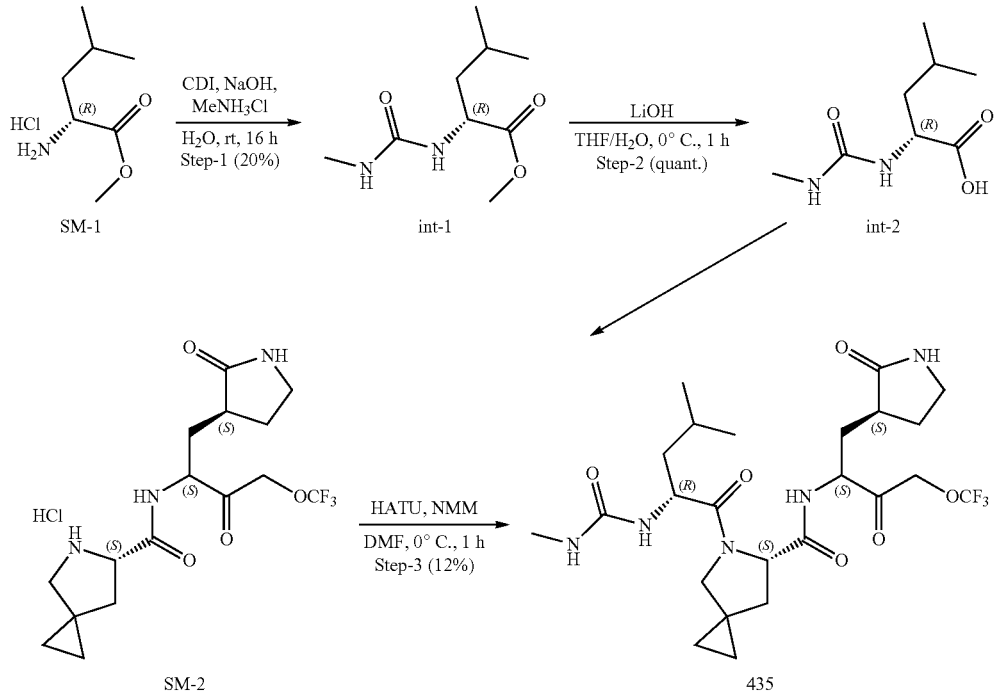

Step 1. methyl (methylcarbamoyl)-D-leucinate (Int-1)

To a stirring solution of D-leucine methyl ester hydrochloride SM-1 (1.0 g, 5.5 mmol, 1.0 eq) and sodium hydroxide (0.22 g, 5.5 mmol, 1 eq) in 10 mL of water at room temperature, was added solid carbonyldiimidazole (1.1 g, 6.6 mmol, 1.2 eq). To aid solubility, 3 mL of THF was added to the mixture. After 1 hour, a solution of methylamine hydrochloride (0.44 g, 6.6 mmol, 1.2 eq) in 5 mL of water was added, followed by solid sodium hydroxide (0.25 g, 1.2 eq). After 16 hours, 20 mL of ethyl acetate was added, and the mixture was transferred to a separatory funnel. The aqueous layer was extracted with further EtOAc (2×20 mL). The combined organic layers were washed with 30 mL of brine, dried over sodium sulfate, filtered, and concentrated in vacuo. The crude material was purified by silica column chromatography (20-50% ethyl acetate/hexanes) on a Teledyne ISCO CombiFlash Rf to yield colorless crystals of methyl (methylcarbamoyl)-D-leucinate int-1 (0.22 g, 1.1 mmol, 20%).

Step 2. (methylcarbamoyl)-D-leucine (Int-2)

To a stirred solution of int-1 (0.11 g, 0.56 mmol, 1.0 eq) in 3 mL of THF at 0° C., was added a solution of lithium hydroxide (0.032 g, 1.3 mmol, 2.4 eq) in 3 mL of water. After 1 h of stirring at 0° C., the reaction mixture was acidified with 10 mL of 1 M HCl solution and solid sodium chloride was added to saturate the solution. The solution was extracted with ethyl acetate (5×15 mL). The combined organic layers were dried over sodium sulfate, filtered, and concentrated in vacuo to yield crude (methylcarbamoyl)-D-leucine int-2 as a colorless solid (0.11 g, quant.). The crude material was used in the next step without further purification.

Step 3. (S)-5-((methylcarbamoyl)-D-leucyl)-N—((S)-3-oxo-1-((S)-2-oxopyrrolidin-3-yl)-4-(trifluoromethoxy)butan-2-yl)-5-azaspiro[2.4]heptane-6-carboxamide (435)

To a mixture of int-2 (0.076 g, 0.40 mmol, 2.0 eq) and HATU (0.146 g, 0.38 mmol, 2.0 eq) was added 2.5 mL of DMF. The resulting solution was cooled to 0° C. After 15 minutes of stirring, solid SM-2 (0.078 g, 0.19 mmol, 1.0 eq) was added, followed by NMM (0.090 mL, 0.81 mmol, 4.3 eq). The solution quickly developed a yellow color. After 1 hour, 20 mL of water was added, and the mixture was extracted with ethyl acetate (3×20 mL). The combined organic layers were washed with 20 mL of water and 20 mL of brine, dried over sodium sulfate, filtered, and concentrated in vacuo. The resulting crude material was purified by normal-phase silica column chromatography (2.5-10% MeOH/DCM) followed by reverse phase chromatography (40% MeCN/H₂O) to yield Compound 435 (0.012 g, 0.023 mmol, 12%).

LCMS m/z=548.5220 (M+1); $^1$H NMR (400 MHz, DMSO-d$_6$) δ ppm 8.56-8.13 (m, 1H), 7.79-7.55 (m, 1H), 6.49-6.01 (m, 1H), 5.96-5.66 (m, 1H), 5.10-4.66 (m, 2H), 4.51-4.41 (m, 1H), 4.40-4.04 (m, 2H), 3.89-3.44 (m, 3H), 3.20-3.06 (m, 2H), 2.29-2.20 (m, 1H), 2.16-2.03 (m, 2H), 2.02-1.89 (m, 1H), 1.82-1.55 (m, 4H), 1.49-1.25 (m, 3H), 0.92-0.81 (m, 6H), 0.77-0.42 (m, 4H).

Example 33-1: Synthesis method 1 of 2 of (R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl tert-butylcarbamate (328)

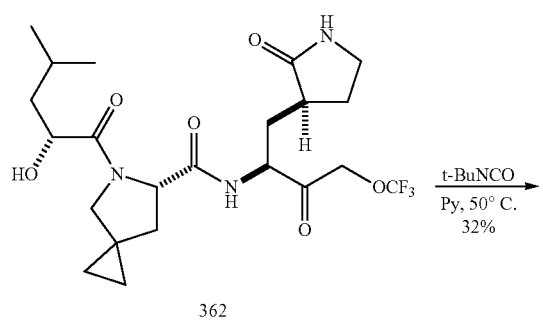

Example 33-2. Synthesis method 2 of 2 of (R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl tert-butylcarbamate (328)

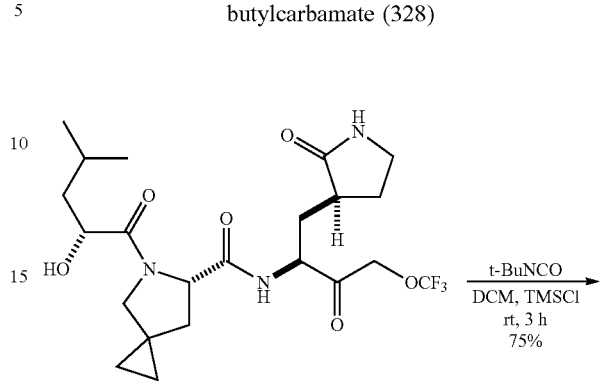

To a mixture of Compound 362 (135 mg, 0.275 mmol, 1 eq) in pyridine (1.38 mL) was added tert-butyl isocyanate (314 µL 2.75 mmol, 10 eq) dropwise at 22° C. This mixture was heated to 50° C. and stirred at this temperature for 27 hours. The reaction mixture was then cooled to 22° C. and treated with an aq. solution of citric acid (0.1 M, 10 mL). Crude product was extracted from aq. solution with dichloromethane (5×5 mL), dried with sodium sulfate, and concentrated in vacuo. Purification via normal phase flash column chromatography (SiO$_2$, gradient elution in 0→3% CH$_3$OH:CH$_2$Cl$_2$) yielded desired adduct carbamate (Compound 328; 52 mg, 0.088 mmol, 32%).

LCMS m/z=591.4183 (M+1); $^1$H NMR (400 MHz, DMSO-d$_6$) δ ppm 8.76 (d, J=6.6 Hz, 0.4H), 7.87 (d, J=8.2 Hz, 0.6H), 7.73 (s, 0.2H), 7.64 (s, 0.8H), 7.20 (s, 0.8H), 7.12 (s, 0.2H), 5.15-5.01 (m, 1H), 5.00-4.89 (m, 1H), 4.82 (d, J=17.4 Hz, 2H), 4.50-4.34 (m, 2H), 3.20-3.03 (m, 4H), 2.25 (dd, J=12.7, 8.4 Hz, 2H), 2.16-1.85 (m, 3H), 1.81-1.49 (m, 5H), 1.47-1.32 (m, 2H), 0.90 (t, J=6.2 Hz, 7H), 0.82 (dd, J=26.5, 6.5 Hz, 5H), 0.68-0.37 (m, 4H).

To a stirred solution of Compound 362 (1 g, 2.03 mmol, 1 eq) and 2-isocyanato-2-methylpropane (2.02 g, 20.35 mmol, 10 eq) in DCM (15 mL) were added chlorotrimethylsilane (4.42 mg, 40.69 mmol, 0.02 eq) at room temperature. The mixture stirred for 3 hours at room temperature, diluted with water (50 mL), and extracted with DCM (2×100 mL). The combined organic layers were concentrated under reduced pressure. The residue was purified by reversed-phase flash column chromatography (Column: YMC-Actus Triart C18, 250*50 mm, 10 m; Mobile Phase A: 0.1% NH$_3$ in H$_2$O, Mobile Phase B: ACN; Flow rate: 70 mL/min; Gradient: 25% B—75% B—17 min) to yield Compound 328 (900 mg, 1.52 mmol, 75%).

LCMS m/z=591.4183 (M+1); $^1$H NMR (400 MHz, DMSO-d$_6$) δ ppm 8.76 (d, J=6.6 Hz, 0.4H), 7.87 (d, J=8.2 Hz, 0.6H), 7.73 (s, 0.2H), 7.64 (s, 0.8H), 7.20 (s, 0.8H), 7.12 (s, 0.2H), 5.15-5.01 (m, 1H), 5.00-4.89 (m, 1H), 4.82 (d, J=17.4 Hz, 2H), 4.50-4.34 (m, 2H), 3.20-3.03 (m, 4H), 2.25 (dd, J=12.7, 8.4 Hz, 2H), 2.16-1.85 (m, 3H), 1.81-1.49 (m, 5H), 1.47-1.32 (m, 2H), 0.90 (t, J=6.2 Hz, 7H), 0.82 (dd, J=26.5, 6.5 Hz, 5H), 0.68-0.37 (m, 4H).

Example 34. Synthesis of (S)-5-((R)-2-(difluoromethoxy)-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide (333)

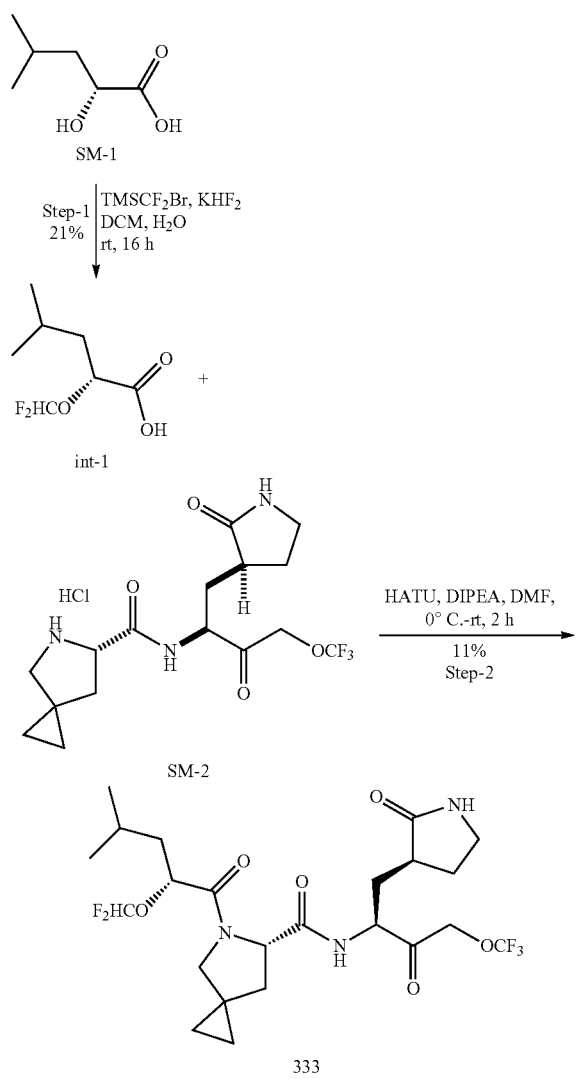

Step-1: Synthesis of (R)-2-(difluoromethoxy)-4-methylpentanoic acid (Int-1)

To a stirred solution of SM-1 (1 g, 7.57 mmol, 1 eq), and (bromodifluoromethyl)trimethylsilane (9.2 g, 45.4 mmol, 6.0 eq) in DCM:H₂O (10 mL, 1:1) was added potassium hydrogen fluoride (3.55 g, 45.4 mmol, 6.0 eq) at 0° C. dropwise. The resultant mixture was stirred at room temperature for 16 h. After completion, the reaction mixture was diluted with water (5 mL) and extracted with ethyl acetate (2×20 mL). The combined organic layers were washed with cold water (15 ml). The organic layer was dried over anhydrous sodium sulfate and concentrated under reduced pressure to give crude product. The crude product was then purified by column chromatography over silica gel using 60-70% ethyl acetate in hexane as a gradient to afford int-1 (290 mg, 1.59 mmol, 21%) as pale yellow liquid.

Step-2: (S)-5-((R)-2-(difluoromethoxy)-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide (333)

To a stirred solution of int-1 (150 mg, 0.82 mmol, 1 eq), and SM-2 (408 mg, 0.99 mmol, 1.2 eq) in DMF (5 mL) was added HATU (407 mg, 1.07 mmol, 1.3 eq), followed by DIPEA (0.58 mL, 3.3 mmol, 4.0 eq) at 0° C. dropwise. The resultant mixture was stirred at room temperature for 3 h, diluted with water (5 mL), and extracted with ethyl acetate (2×20 mL). The combined organic layers were washed with cold water (15 ml), dried over anhydrous sodium sulfate, and concentrated under reduced pressure. The crude product was then purified by column chromatography over silica gel using 60-70% ethyl acetate in hexane as a gradient to afford Compound 333 (50 mg, 0.092 mmol, 11%).

LCMS m/z=542.69 (M+1); ¹H NMR (400 MHz, DMSO-d₆) δ ppm 8.77-8.54 (m, 1H), 7.76-7.68 (m, 1H), 6.75-6.37 (m, 1H), 5.17-4.93 (m, 2H), 4.62-4.58 (m, 1H), 4.39-4.35 (m, 2H), 3.51-3.50 (m, 2H), 3.16-3.10 (m, 2H), 2.49-2.09 (m, 3H), 2.01-1.97 (m, 1H), 1.80-1.59 (m, 5H), 1.51-1.48 (m, 1H), 0.92-0.87 (m, 6H), 0.62-0.52 (m, 4H).

Example 35: methyl ((S)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl)carbamate (433)

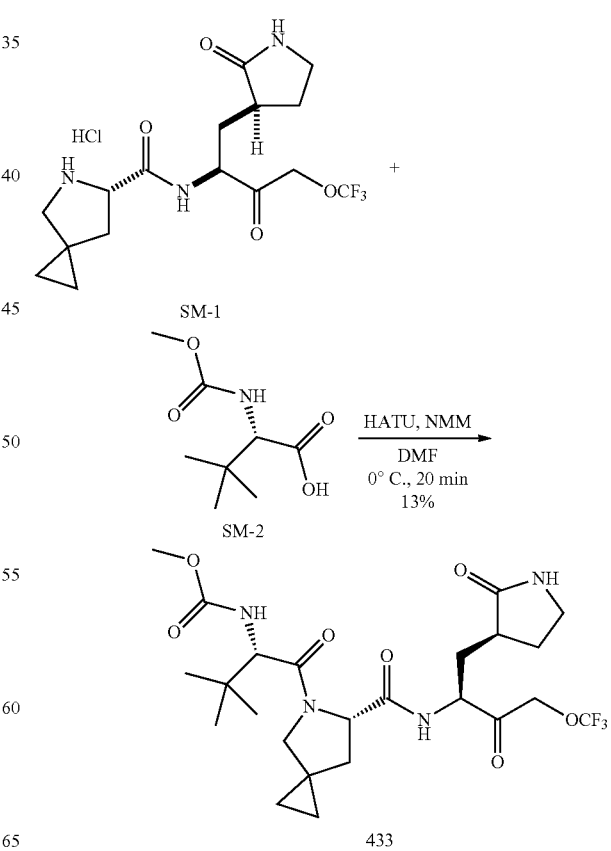

To a solution of methoxycarbonyl-L-tert-leucine (100 mg, 528.51 μmol, 1.1 eq) in DMF was added HATU (219.23 mg, 576.56 μmol, 1.2 eq) and NMM (158 mL, 1.44 mmol, 3 eq). The mixture was stirred at 0° C. for 5 min, and amine hydrochloride (SM-1; 198 mg, 480.46 μmol, 1 eq) was added. The reaction was continued at 0° C. for another 20 min, after which it was quenched with H₂O (5 mL), NaCl (sat. aq. soln., 10 mL), and EtOAc (10 mL). The aqueous layer was separated and extracted with EtOAc (3×10 mL). The combined organic phases were dried over Na₂SO₄ and concentrated in vacuo. Purification by flash column chromatography (SiO₂, graduate elution in 0→10% CH₃OH; CH₂Cl₂) yielded the desired amide. This product was obtained as a mixture of stereoisomers.

LCMS m/z=549.2 (M+1); ¹H NMR (400 MHz, DMSO-d₆) δ ppm 8.58 (d, J=7.9 Hz, 1H), 7.61 (s, 1H), 7.21 (d, J=8.8 Hz, 1H), 4.98 (s, 2H), 4.39 (q, J=8.8 Hz, 2H), 4.07 (d, J=8.8 Hz, 1H), 3.67-3.48 (m, 5H), 3.18-2.99 (m, 2H), 2.40-2.10 (m, 2H), 2.01-1.75 (m, 3H), 1.68-1.53 (m, 2H), 0.94 (s, 9H), 0.67-0.42 (m, 4H).

Example 36: (S)-5-(4,4-difluoro-1-hydroxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide (421)

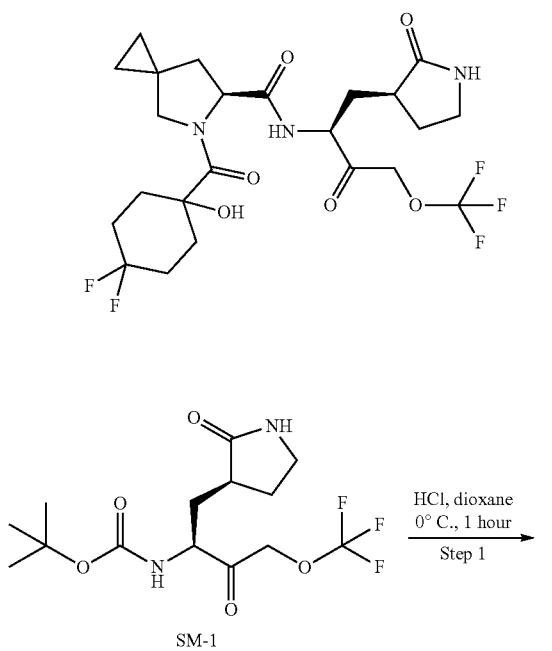

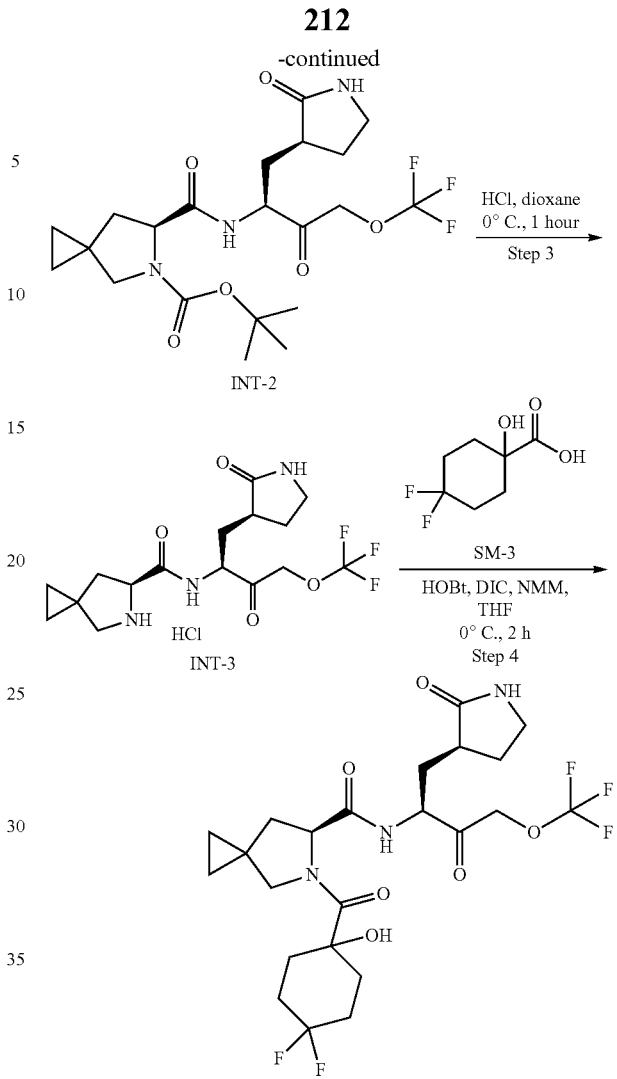

Step 1: (S)-3-((S)-2-amino-3-oxo-4-(trifluoromethoxy)butyl)pyrrolidin-2-one hydrochloride (INT-1)

To a stirred solution of tert-butyl ((S)-3-oxo-1-((S)-2-oxopyrrolidin-3-yl)-4-(trifluoromethoxy)butan-2-yl)carbamate (SM-1; 20 g, 56.5 mmol, 1 eq) in DCM (300 mL) was added HCl (4 M in dioxane, 34.30 mL, 20 eq) dropwise at 0° C. under a nitrogen atmosphere. The resulting mixture was stirred for an additional 1 h at room temperature. The resulting mixture was concentrated under reduced pressure. The residue was purified by trituration with Et₂O (150 mL) to afford (S)-3-((S)-2-amino-3-oxo-4-(trifluoromethoxy)butyl)pyrrolidin-2-one hydrochloride as an off-white solid (INT-1; 16 g, 97% yield). LCMS m/z=255 (M+1).

Step 2: tert-butyl (S)-6-(((S)-3-oxo-1-((S)-2-oxopyrrolidin-3-yl)-4-(trifluoromethoxy)butan-2-yl)carbamoyl)-5-azaspiro[2.4]heptane-5-carboxylate (INT-2)

To a stirred mixture of (S)-5-(tert-butoxycarbonyl)-5-azaspiro[2.4]heptane-6-carboxylic acid (SM-2; 13.28 g, 55.0 mmol, 1 eq) and (S)-3-((S)-2-amino-3-oxo-4-(trifluoromethoxy)butyl)pyrrolidin-2-one hydrochloride (INT-1; 16 g, 55.0 mmol, 1 eq) in DCM (550 mL) were added HATU (25.12 g, 66.0 mmol, 1.2 eq) and DIEA (21.34 g, 165.1 mmol, 3 eq) at 0° C. under a nitrogen atmosphere. The resulting mixture was stirred for an additional 2 h at room temperature. The reaction was quenched with water (100 mL) at room temperature. The resulting mixture was extracted with DCM (2×300 mL). The combined organic layers were washed with brine (300 mL) and dried over anhydrous $Na_2SO_4$. After filtration, the filtrate was concentrated under reduced pressure. The residue was purified by silica gel column chromatography, eluted with petroleum ether/THF (6:4) to afford tert-butyl (S)-6-(((S)-3-oxo-1-((S)-2-oxopyrrolidin-3-yl)-4-(trifluoromethoxy)butan-2-yl)carbamoyl)-5-azaspiro[2.4]heptane-5-carboxylate as a white solid (INT-2; 13 g, 49%). LCMS m/z=478 (M+1); $^1$H NMR (400 MHz, DMSO-$d_6$) δ ppm 8.62-8.53 (m, 1H), 7.69-7.64 (m, 1H), 5.07-4.84 (m, 2H), 4.42-4.20 (m, 2H), 3.37-3.09 (m, 4H), 2.31-1.97 (m, 4H), 1.67-1.59 (m, 3H), 1.40-1.36 (m, 9H), 0.57-0.44 (m, 4H).

Step 3: (S)—N—((S)-3-oxo-1-((S)-2-oxopyrrolidin-3-yl)-4-(trifluoromethoxy)butan-2-yl)-5-azaspiro[2.4]heptane-6-carboxamide hydrochloride (INT-3)

To a stirred solution of tert-butyl (S)-6-(((S)-3-oxo-1-((S)-2-oxopyrrolidin-3-yl)-4-(trifluoromethoxy)butan-2-yl)carbamoyl)-5-azaspiro[2.4]heptane-5-carboxylate (INT-2; 13 g, 27.2 mmol, 1 eq) in DCM (200 mL) were added HCl (4 M in dioxane, 16.54 mL, 544.5 mmol, 20 eq) dropwise at 0° C. under a nitrogen atmosphere. The resulting mixture was stirred for an additional 1 h at room temperature. The resulting mixture was concentrated under reduced pressure. The residue was purified by trituration with $Et_2O$ (100 mL) to afford (S)—N—((S)-3-oxo-1-((S)-2-oxopyrrolidin-3-yl)-4-(trifluoromethoxy)butan-2-yl)-5-azaspiro[2.4]heptane-6-carboxamide hydrochloride as a white solid (INT-3; 11 g, 97%). LCMS m/z=378 (M+1).

Step 4: (S)-5-(4,4-difluoro-1-hydroxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide (421)

To a stirred mixture of 4,4-difluoro-1-hydroxycyclohexane-1-carboxylic acid (SM-3; 0.52 g, 2.9 mmol, 1 eq) and (S)—N—((S)-3-oxo-1-((S)-2-oxopyrrolidin-3-yl)-4-(trifluoromethoxy)butan-2-yl)-5-azaspiro[2.4]heptane-6-carboxamide hydrochloride (INT-3; 1.2 g, 2.9 mmol, 1 eq) in THF (40 mL) were added DIC (0.44 g, 3.5 mmol, 1.2 eq), NMM (1.17 g, 11.6 mmol, 4 eq) and HOBt (0.47 g, 3.5 mmol, 1.2 eq) at 0° C. under a nitrogen atmosphere. The resulting mixture was stirred for 2 h at room temperature. The reaction was quenched with water (10 mL) at room temperature. The resulting mixture was extracted with DCM (2×20 mL). The combined organic layers were washed with brine (40 mL) and dried over anhydrous $Na_2SO_4$. After filtration, the filtrate was concentrated under reduced pressure. The residue was purified by silica gel column chromatography, eluted with petroleum ether/THF (1:1). After concentration, the residue was purified by SFC with the following conditions: Column: CHIRALPAK® IF, 3×25 cm, 5 m; Mobile Phase A: $CO_2$, Mobile Phase B: IPA:ACN=1:1; Flow rate: 80 mL/min; Gradient: isocratic 25% B; Column Temperature (° C.): 35; Back Pressure (bar): 100; Wave Length: 220 nm; retention time 1 (min): 3.4; retention time 2 (min): 4.3 (epimer); Sample Solvent: IPA:ACN=1:1; Injection Volume: 4 mL; Number Of Runs: 9; to afford (S)-5-(4,4-difluoro-1-hydroxycyclohexane-1-carbonyl)-N—((S)-3-oxo-1-((S)-2-oxopyrrolidin-3-yl)-4-(trifluoromethoxy)butan-2-yl)-5-azaspiro[2.4]heptane-6-carboxamide as a yellow solid (421; 800 mg, 51.14%). LCMS m/z=540 (M+1); $^1$H NMR (400 MHz, DMSO-$d_6$) δ ppm 8.59-8.35 (m, 1H), 7.68 (s, 1H), 5.47 (s, 1H), 5.25-4.83 (m, 2H), 4.50-4.36 (m, 1H), 4.37-4.22 (m, 1H), 3.90-3.66 (m, 2H), 3.23-3.01 (m, 2H), 2.38-2.22 (m, 1H), 2.22-2.09 (m, 1H), 2.09-1.84 (m, 8H), 1.84-1.55 (m, 5H), 0.76-0.38 (m, 4H).

Example 37: (S)—N—((S)-3-oxo-1-((S)-2-oxopyrrolidin-3-yl)-4-(trifluoromethoxy)butan-2-yl)-5-((2R,4R)-5,5,5-trifluoro-2-hydroxy-4-methylpentanoyl)-5-azaspiro[2.4]heptane-6-carboxamide (426)

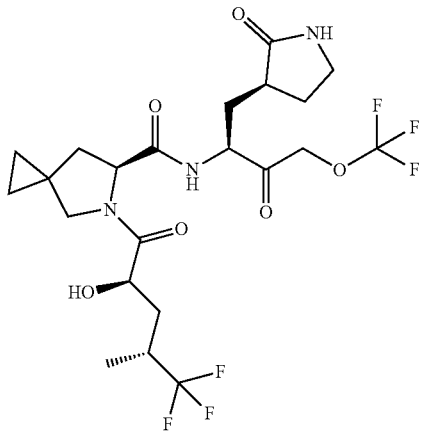 [SMILES: C[C@H](C[C@@H](O)C(=O)N1CC2(CC2)C[C@H]1C(=O)N[C@@H](C[C@@H]1CCNC1=O)C(=O)COC(F)(F)F)C(F)(F)F]

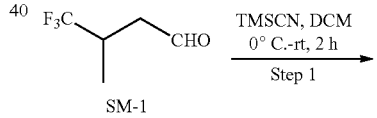

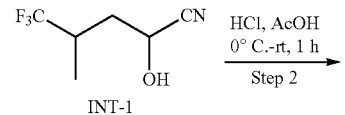

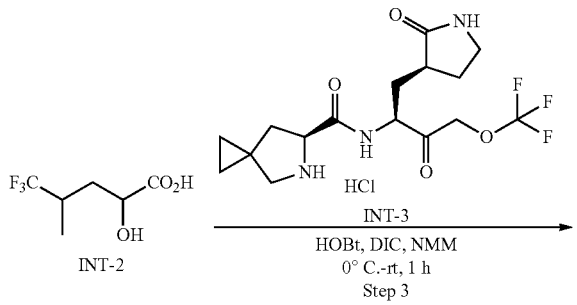

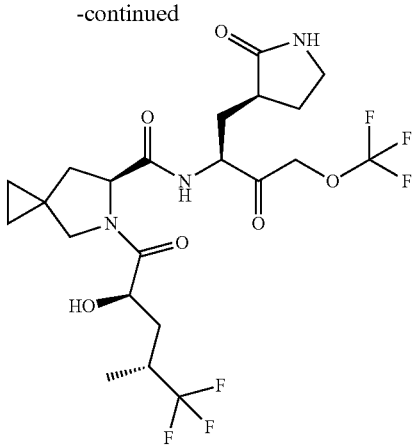

Step 1: 5,5,5-trifluoro-2-hydroxy-4-methylpentanenitrile (INT-1)

To a mixture of SM-1 (5 g, 35.688 mmol, 1 equiv) in anhydrous DCM (50 mL) was added TEA (3611.33 mg, 35.688 mmol, 1 equiv) and TMSCN (7080.97 mg, 71.376 mmol, 2 equiv) at 0° C. The reaction mixture was stirred at room temperature for a period of 2 hours. After completion of the reaction, the reaction mixture was quenched by addition of water (10 mL). The aqueous layer was extracted with ethyl acetate (50 mL×3). The combined organic phases were washed with brine, dried over anhydrous sodium sulfate and concentrated under reduced pressure. The resulting mixture was concentrated under reduced pressure. This gave 5,5,5-trifluoro-2-hydroxy-4-methylpentanenitrile as a white oil (INT-1; 4 g, 67.06%).

Step 2: 5,5,5-trifluoro-2-hydroxy-4-methylpentanoic acid (Int-2)

INT-1 (3.55 g, 21.241 mmol, 1 equiv) was combined with concentrated HCl (30 mL) and AcOH (10 mL). The reaction mixture was stirred at room temperature for a period of 1 h. The reaction mixture was concentrated under reduced pressure. This supplied 5,5,5-trifluoro-2-hydroxy-4-methylpentanoic acid as a white oil (INT-2; 3.6 g, 91.06%).

Step 3: (S)—N—((S)-3-oxo-1-((S)-2-oxopyrrolidin-3-yl)-4-(trifluoromethoxy)butan-2-yl)-5-((2R,4R)-5,5,5-trifluoro-2-hydroxy-4-methylpentanoyl)-5-azaspiro[2.4]heptane-6-carboxamide (426)

To a mixture of INT-2 (3.6 g, 19.341 mmol, 1 equiv), INT-3 (8.03 g, 21.275 mmol, 1.1 equiv) and HOBt (3.14 g, 23.209 mmol, 1.2 equiv) in anhydrous DCM (38 mL) was added DIC (2.93 g, 23.209 mmol, 1.2 equiv) and NMM (4.89 g, 48.353 mmol, 2.5 equiv). The reaction mixture was stirred at room temperature for a period of 1 h. After completion of reaction, the reaction mixture was quenched by addition of water (20 mL). The aqueous layer was extracted with ethyl acetate (30 mL×3). The combined organic phases were washed with brine, dried over anhydrous sodium sulfate, and concentrated under reduced pressure. The residue was further purified by silica gel column chromatography using 40% to 55% petroleum ether:THF gradient to afford (S)—N—((S)-3-oxo-1-((S)-2-oxopyrrolidin-3-yl)-4-(trifluoromethoxy)butan-2-yl)-5-((2R,4R)-5,5,5-trifluoro-2-hydroxy-4-methylpentanoyl)-5-azaspiro[2.4]heptane-6-carboxamide as a white solid (900 mg, 8.53%). The 900 mg of crude material was purified by flash preparative HPLC using the following conditions: Column, C18 reversed phase column; mobile phase, water (0.05% $NH_3H_2O$) and $CH_3CN$ (5% $CH_3CN$ up to 30% in 15 min); Flow rate: 60 mL/min; Detector, 220 nm. Analytical SFC showed four peaks. The four peaks were purified by SFC: CHIRALPAK® IH, 3×25 cm, 5 m; Mobile Phase A: $CO_2$, Mobile Phase B: IPA:ACN=1:1; Flow rate: 80 mL/min; Gradient: isocratic 35% B; Column Temperature (° C.): 35; Back Pressure (bar): 100; Wave Length: 220 nm; Sample Solvent: IPA:ACN=1:1; Injection Volume: 5 mL; Number Of Runs: 5. This resulted in (S)—N—((S)-3-oxo-1-((S)-2-oxopyrrolidin-3-yl)-4-(trifluoromethoxy)butan-2-yl)-5-((2R,4R)-5,5,5-trifluoro-2-hydroxy-4-methylpentanoyl)-5-azaspiro[2.4]heptane-6-carboxamide as a white solid (peak 1 100 mg, 3.79%; peak 2 120 mg, 4.55%; peak 3 170 mg, 6.54%; peak 4 250 mg, 9.48%).

Peak 4: LCMS m/z=546 (M+1); $^1$H NMR (400 MHz, DMSO-$d_6$) δ ppm 8.89-8.33 (m, 1H), 7.79-7.59 (m, 1H), 5.62-5.08 (m, 1H), 5.09-4.83 (m, 2H), 4.53-4.08 (m, 3H), 4.04-3.45 (m, 2H), 3.24-3.03 (m, 2H), 2.49-2.08 (m, 3H), 2.05-1.88 (m, 2H), 1.84-1.40 (m, 5H), 1.32-0.99 (m, 3H), 0.69-0.37 (m, 4H).

Example 38: (1R,2S,5S)-3-((S)-2-hydroxy-2-phenylacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide (416)

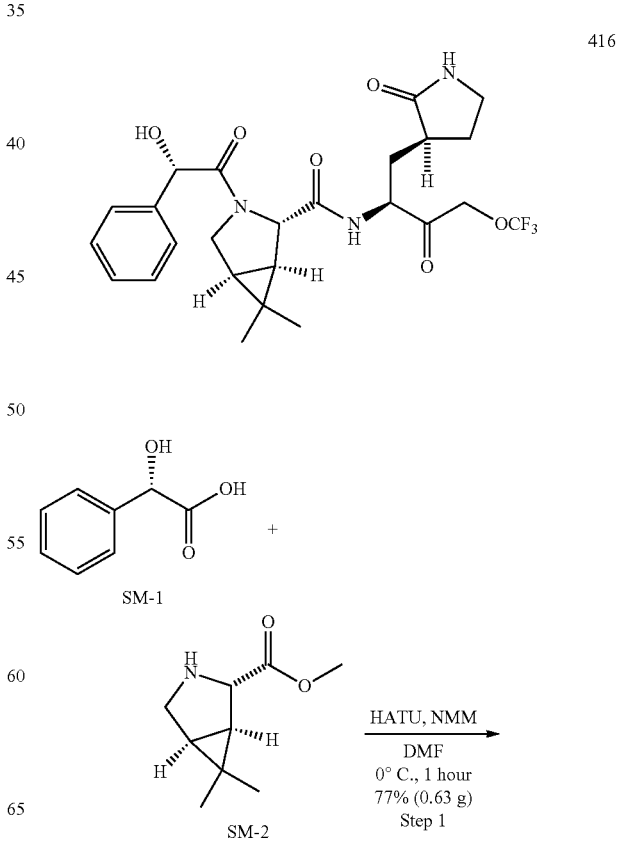

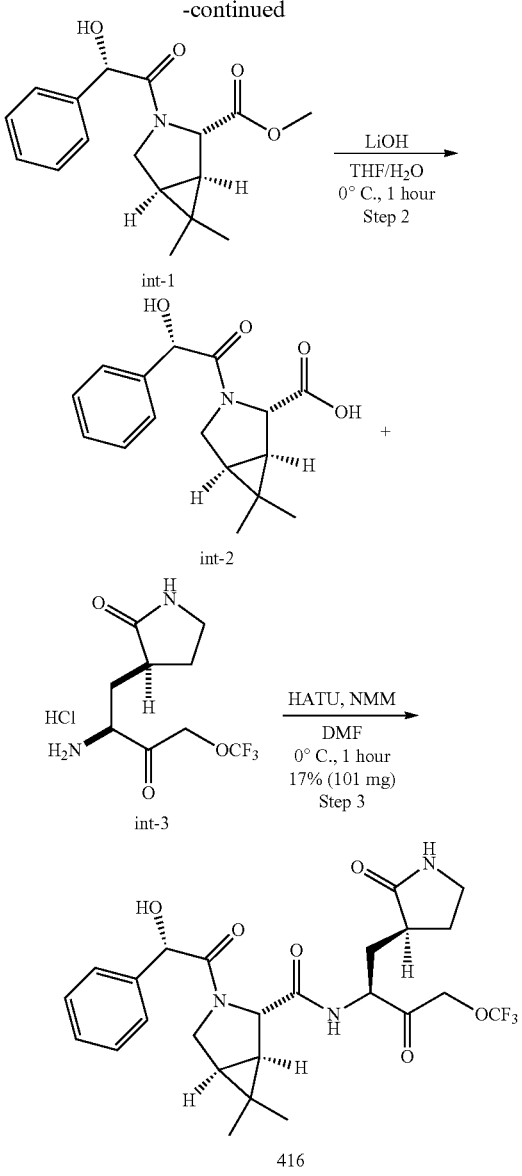

Step 1: methyl (1R,2S,5S)-3-((S)-2-hydroxy-2-phenylacetyl)-6,6-dimethyl-3-azabicyclo[3.1.0]hexane-2-carboxylate (Int-1)

To a mixture of mandelic acid (SM-1, 0.41 g, 2.6 mmol, 1.0 eq) and HATU (0.99 g, 2.6 mmol, 1.0 eq) was added DMF (8 mL), and the mixture was cooled to 0° C. This mixture was stirred at 0° C. for 10 min, after which amine hydrochloride SM-2 (0.58 g, 2.8 mmol, 1.05 eq) was added as a solid, followed by NMM (1.1 mL, 9.9 mmol, 3.8 eq) which was added slowly. The reaction mixture was stirred at 0° C. for 1 hour, after which it was quenched with deionized water (30 mL). The mixture was extracted with ethyl acetate (30 mL) twice, and the combined organic fractions were washed with water (30 mL) and brine (30 mL). The organic fraction was dried with sodium sulfate, filtered, and concentrated. The crude material was purified by normal phase column chromatography (SiO$_2$, graduate elution in EtOAc: hexane, 0→50%). Concentration of the fractions yielded the desired ester as a white solid (int-1; 0.63 g, 77% yield).

Step 2: (1R,2S,5S)-3-((S)-2-hydroxy-2-phenylacetyl)-6,6-dimethyl-3-azabicyclo[3.1.0]hexane-2-carboxylic acid (Int-2)

To a solution of ester int-1 (0.63 g, 2.1 mmol, 1.0 eq) in THF (8 mL) at 0° C. was added a solution of LiOH (0.14 g, 5.6 mmol, 2.7 eq) in deionized water (8 mL). The reaction mixture was then stirred at 0° C. for 1 hour. After this time, 15 mL of 1.0 M HCl solution was added and the mixture extracted five times with 20 mL of EtOAc. The combined organic fractions were dried over sodium sulfate, filtered, and concentrated to yield the titled compound, int-2, as a white solid.

Step 3: (1R,2S,5S)-3-((S)-2-hydroxy-2-phenylacetyl)-6,6-dimethyl-N—((S)-3-oxo-1-((S)-2-oxopyrrolidin-3-yl)-4-(trifluoromethoxy)butan-2-yl)-3-azabicyclo[3.1.0]hexane-2-carboxamide To a mixture of int-2 (320 mg, 1.1 mmol, 1.0 eq), and HATU (480 mg, 1.3 mmol, 1.1 eq) was added DMF (5 mL), and the mixture was cooled to 0° C. This mixture was stirred at 0° C. for 10 min, after which amine hydrochloride int-3 (370 mg, 1.3 mmol, 1.1 eq) was added as a solid, followed by NMM (370 μL, 3.3 mmol, 2.9 eq) which was added slowly. The reaction mixture was stirred at 0° C. for 1 hour, after which it was quenched with deionized water (20 mL). The mixture was extracted with ethyl acetate (20 mL) twice, and the combined organic fractions were washed with water (20 mL) and brine (20 mL). The organic fraction was dried with sodium sulfate, filtered, and concentrated. The crude material was purified by normal phase column chromatography (SiO$_2$, graduate elution in MeOH:DCM, 0→5%). Concentration of the fractions and further purification of the resulting material via reverse-phase column chromatography (C18, graduate elution in CH$_3$CN:H$_2$O, 0→40%), subsequent concentration of the fractions, and lyophilization of the resulting material yielded the titled compound (416) as a fluffy powder (101 mg, 17% yield). LCMS m/z=526.4417 (M+1); $^1$H NMR (400 MHz, DMSO-d$_6$) δ ppm 9.08-8.67 (m, 1H), 7.82-7.60 (m, 1H), 7.49-7.12 (m, 5H), 5.64-5.40 (m, 1H), 5.31-4.61 (m, 3H), 4.58-4.30 (m, 1H), 4.29-4.00 (m, 1H), 3.60 (d, J=10.7 Hz, 1H), 3.21-3.02 (m, 2H), 2.42-2.34 (m, 1H), 2.24-1.87 (m, 2H), 1.80-1.53 (m, 2H), 1.47-1.20 (m, 3H), 1.06-0.19 (m, 6H).

Example 39: (S)-5-(4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide (429)

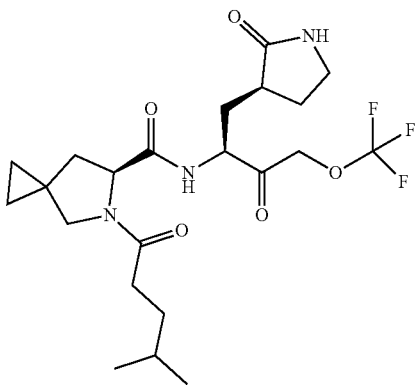

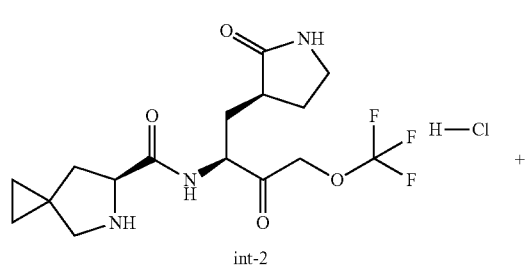

int-2

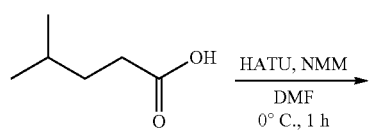

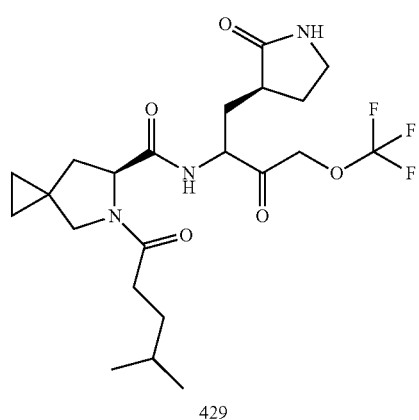

429

To a mixture of (S)—N—((S)-3-oxo-1-((S)-2-oxopyrrolidin-3-yl)-4-(trifluoromethoxy)butan-2-yl)-5-azaspiro[2.4]heptane-6-carboxamide hydrochloride (int-2) (200 mg, 0.485 mmol, 1 eq), 4-methylpentanoic acid (73 mg, 0.631 mmol, 1.3 eq), and HATU (240 mg, 0.631 mmol, 1.3 eq) was added DMF (3.2 mL, pre-cooled to 0° C.). This mixture was stirred at 0° C. for 10 min, after which NMM (133 µL, 1.21 mmol, 2.5 eq) was added dropwise over 1 min period. The reaction was continued at 0° C. for 1 hour, after which it was quenched with cold deionized water (10 mL). This mixture was directly used for purification via reverse-phase flash column chromatography (C18, gradient elution in CH$_3$CN: H$_2$O, 0→20%), which was then followed by an additional purification via normal phase flash column chromatography (SiO$_2$, gradient elution in: 0→3% CH$_3$OH:CH$_2$Cl$_2$) to obtain the titled compound, 429 (135 mg; 58% yield). LCMS m/z=476.6936 (M+1); $^1$H NMR (400 MHz, DMSO-d$_6$) δ ppm 8.72 (d, J=7.4 Hz, 0.3H), 8.38 (d, J=8.0 Hz, 0.7H), 7.72 (s, 0.3H), 7.66 (s, 0.7H), 5.01 (dd, J=16.7, 2.2 Hz, 1.3H), 4.82 (d, J=17.4 Hz, 0.7H), 4.44 (dd, J=7.9, 4.0 Hz, 0.4H), 4.36 (ddt, J=13.1, 9.0, 4.1 Hz, 1.6H), 3.54-3.37 (m, 2.3H), 3.20-3.05 (m, 2.7H), 2.30-2.16 (m, 3H), 2.15-2.04 (m, 1H), 2.03-1.89 (m, 1H), 1.61 (m, 4H), 1.38 (qd, J=7.5, 2.8 Hz, 2H), 0.85 (d, J=6.8 Hz, 6H), 0.65-0.37 (m, 4H).

Example 40: (S)-5-acetyl-N—((S)-3-oxo-1-((S)-2-oxopyrrolidin-3-yl)-4-(trifluoromethoxy)butan-2-yl)-5-azaspiro[2.4]heptane-6-carboxamide (664)

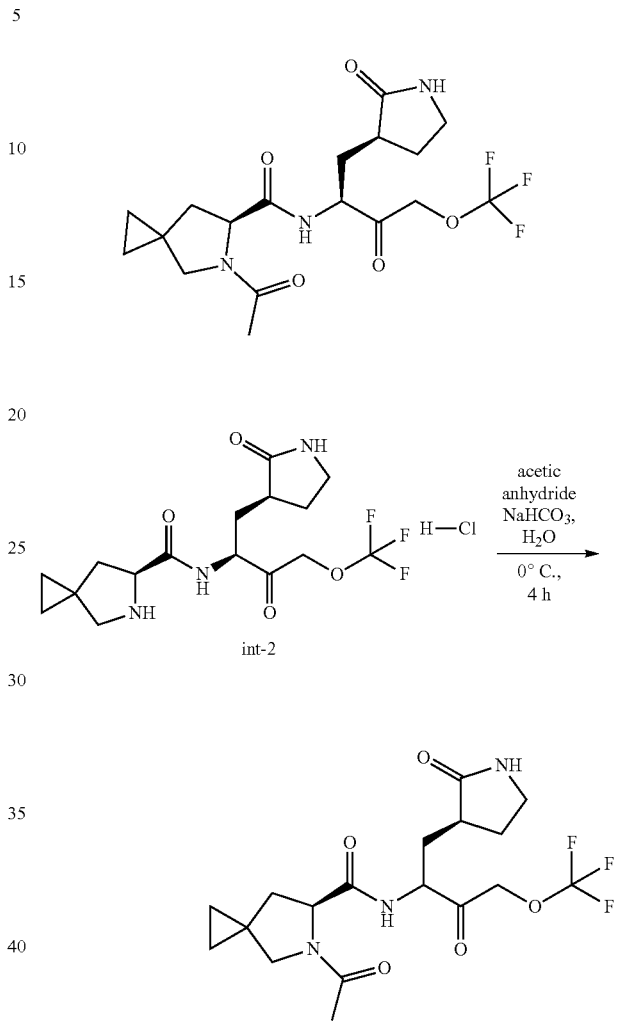

To a cooled mixture of (S)—N—((S)-3-oxo-1-((S)-2-oxopyrrolidin-3-yl)-4-(trifluoromethoxy)butan-2-yl)-5-azaspiro[2.4]heptane-6-carboxamide hydrochloride (int-2) (500 mg, 1.21 mmol, 1 eq) and acetic anhydride (148 mg, 1.45 mmol, 1.2 eq) in distilled water (2.4 mL) was added NaHCO$_3$ (305 mg, 3.63 mmol, 3 eq). This mixture was stirred at 0° C. for 4 hours under N$_2$. TLC (9:1 DCM/MeOH) showed complete consumption of starting material (R$_f$=0.07, UV-active) and formation of product of R$_f$=0.52. Upon completion, the heterogeneous mixture was transferred to a separatory funnel and extracted with EtOAc (4×5 mL). Organic extracts were combined and dried over Na$_2$SO$_4$. The drying agent was removed by vacuum filtration, the filtrate was concentrated, and the residue was purified via normal phase flash column chromatography (SiO$_2$, gradient elution in 0→5% MeOH:DCM) to obtain the titled compound as a white solid (286 mg, 56% yield). LC/MS m/z=420.2459 (M+1); $^1$H NMR (400 MHz, DMSO-d$_6$) δ ppm 8.78-8.45 (m, 1H), 7.70 (d, J=12.5 Hz, 1H), 5.09-4.77 (m, 2H), 4.56-4.29 (m, 2H), 3.56-3.36 (m, 2H), 3.20-3.07 (m, 2H), 2.30-2.05 (m, 3H), 2.02-1.86 (m, 4H), 1.74-1.53 (m, 3H), 0.65-0.41 (m, 4H).

221

Example 41: (2S,4R)-1-((R)-2-hydroxy-4-methyl-pentanoyl)-N—((S)-3-oxo-1-((S)-2-oxopyrrolidin-3-yl)-4-(trifluoromethoxy)butan-2-yl)-4-(trifluoromethyl)pyrrolidine-2-carboxamide (685)

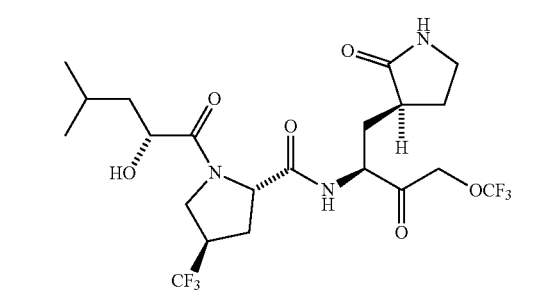

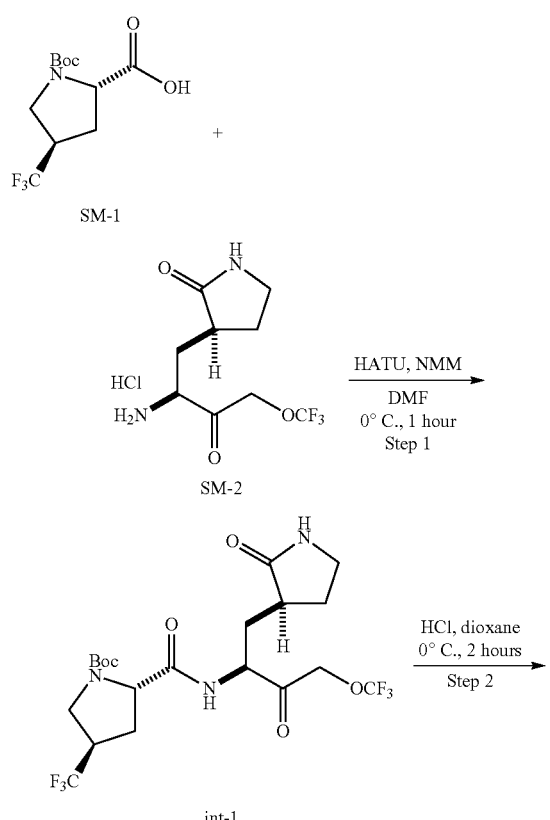

222

-continued

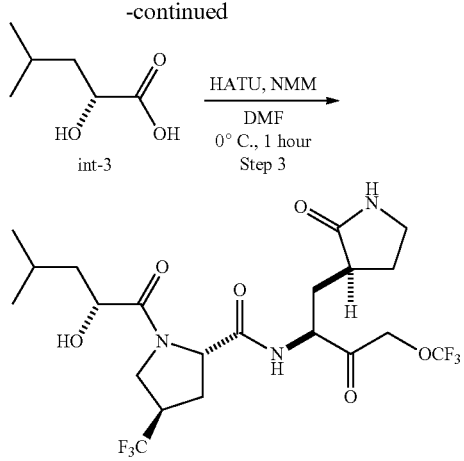

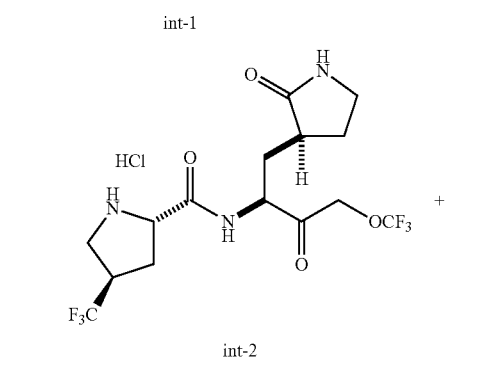

Step 1: tert-butyl (2S,4R)-2-(((S)-3-oxo-1-((S)-2-oxopyrrolidin-3-yl)-4-(trifluoromethoxy)butan-2-yl)carbamoyl)-4-(trifluoromethyl)pyrrolidine-1-carboxylate (Int-1)

To a mixture of (2S,4R)-1-(tert-butoxycarbonyl)-4-(trifluoromethyl)pyrrolidine-2-carboxylic acid SM-1, 0.51 g, 1.8 mmol, 1.0 eq) and HATU (0.68 g, 1.8 mmol, 1.0 eq) was added DMF (8 mL), and the mixture was cooled to 0° C. This mixture was stirred at 0° C. for 10 min, after which (S)-3-((S)-2-amino-3-oxo-4-(trifluoromethoxy)butyl)pyrrolidin-2-one hydrochloride (SM-2, 0.57 g, 1.9 mmol, 1.05 eq) was added as a solid, followed by NMM (0.60 mL, 5.4 mmol, 3.0 eq) which was added slowly. The reaction mixture was stirred at 0° C. for 1 hour, after which it was quenched with deionized water (30 mL). The mixture was extracted with ethyl acetate (30 mL) twice, and the combined organic fractions were washed with water (30 mL) and brine (30 mL). The organic fraction was dried with sodium sulfate, filtered, and concentrated. The crude material was purified by normal phase column chromatography (SiO$_2$, graduate elution in 0→5% MeOH:DCM). Concentration of the fractions and further purification of the resulting material via reverse-phase column chromatography (C18, graduate elution in CH$_3$CN:H$_2$O, 0→80%) and subsequent concentration of fractions yielded the desired carbamate as a white solid (int-1; 0.56 g, 60% yield).

Step 2: (2S,4R)—N—((S)-3-oxo-1-((S)-2-oxopyrrolidin-3-yl)-4-(trifluoromethoxy)butan-2-yl)-4-(trifluoromethyl)pyrrolidine-2-carboxamide hydrochloride (Int-2)

A solution of carbamate int-1 (0.56 g, 1.1 mmol, 1.0 eq) in dioxane (5 mL) was stirred at 0° C. for 5 min, after which a solution of HCl (4 M in dioxane, 37 eq, 10 mL) was added. The reaction mixture was then stirred at 0° C. for 2 hours. After this time, the mixture was concentrated. Repeated addition of methanol and concentration (five times) yielded the amine hydrochloride as an orange solid (int-2).

Step 3: (2S,4R)-1-((R)-2-hydroxy-4-methylpentanoyl)-N—((S)-3-oxo-1-((S)-2-oxopyrrolidin-3-yl)-4-(trifluoromethoxy)butan-2-yl)-4-(trifluoromethyl)pyrrolidine-2-carboxamide To a mixture of (R)-2-hydroxy-4-methylpentanoic acid (int-3; 70 mg, 0.53 mmol, 1.2 eq), and HATU (200 mg, 0.53 mmol, 1.2 eq) was added DMF (5 mL), and the mixture was cooled to 0° C. This mixture was stirred at 0° C. for 10 min, after which amine hydrochloride int-2 (210 mg, 0.46 mmol, 1 eq) was added as a solid, followed by NMM (220 μL, 1.7 mmol, 4.5 eq) which was added slowly. The reaction mixture was stirred at 0° C. for 1 hour, after which it was quenched with deionized water (20 mL). The product was extracted with ethyl acetate (20 mL) twice, and the combined organic fractions were washed with water (20 mL) and brine (20 mL). The organic fraction was dried with sodium sulfate, filtered, and concentrated. The crude material was purified by normal phase column chromatography ($SiO_2$, graduate elution in 0→5% MeOH:DCM). Concentration of the fractions and further purification of the resulting material via reverse-phase column chromatography (C18, graduate elution in $CH_3CN:H_2O$, 0→40%), subsequent evaporation of the fractions, and lyophilization of the resulting material yielded the title compound ($$$) as a fluffy powder (68 mg, 29% yield). LCMS m/z=534.3318 (M+1); $^1H$ NMR (400 MHz, DMSO-$d_6$) δ ppm 8.83-8.56 (m, 1H), 7.80-7.56 (m, 1H), 5.34-4.87 (m, 3H), 4.42 (dd, J=8.8, 4.3 Hz, 1H), 4.38-4.10 (m, 1H), 4.02-3.86 (m, 1H), 3.81-3.56 (m, 1H), 3.19-3.05 (m, 2H), 2.33-2.18 (m, 2H), 2.16-1.83 (m, 3H), 1.83-1.53 (m, 3H), 1.43 (tt, J=9.5, 4.9 Hz, 1H), 1.34-1.17 (m, 2H), 0.96-0.76 (m, 6H).

Biological Examples

Abbreviations: ALI for air-liquid interface; BSL3 for Biosafety Level 3; DAPI for antifade-46-diamidino-2-phenylindole; DMEM for Dulbecco's Modified Eagle Medium; DMSO for dimethyl sulfoxide; DNA for deoxyribonucleic acid; DPBS for Dulbecco's phosphate buffered saline; FBS for fetal bovine serum; LDH for lactate dehydrogenase; MEM for minimum essential medium; MOI for multiplicity of infection; PBS for phosphate buffered saline; PET for polyethylene terephthalate; PFU for plaque-forming unit; RNA for ribonucleic acid; RT for room temperature (ambient temperature); and RT-qPCR for reverse transcription quantitative real-time polymerase chain reaction.

Virus generation. Vero E6 cells (ATCC CRL-1586) were plated in a T225 flask with complete DMEM (Corning 15-013-CV) containing 10% FBS, 1× PenStrep (Corning 20-002-CL), 2 mM L-Glutamine (Corning 25-005-CL) overnight at 37° C. 5% $CO_2$. The media in the flask was removed and 2 mL of SARS-CoV-2 strain USA-WA1/2020 (BEI Resources NR-52281) in complete DMEM was added to the flask at an MOI of 0.5 and was allowed to incubate for 30 minutes at 34° C. 5% $CO_2$. After incubation, 30 mL of complete DMEM was added to the flask. The flask was then placed in a 34° C. incubator at 5% $CO_2$ for 5 days. On day 5 post infection the supernatant was harvested and centrifuged at 1,000×g for 5 minutes. The supernatant was filtered through a 0.22 μM filter and stored at −80° C.

HeLa-ACE2 stable cell line. HeLa-ACE2 cells were generated through transduction of human ACE2 lentivirus. The lentivirus was created by co-transfection of HEK293T cells with pBOB-hACE2 construct and lentiviral packaging plasmids pMDL, pREV, and pVSV-G (Addgene) using Lipofectamine 2000 (Thermo Fisher Scientific, 11668019). Supernatant was collected 48 h after transfection then used to transduce pre-seeded HeLa cells. 12 h after transduction stable cell lines were collected, scaled up and stored. Cells were maintained in DMEM (Gibco, 11965-092) with 10% FBS (Gibco, 10438026) and 1× sodium pyruvate (Gibco, 11360070) at 37° C. 5% $CO_2$.

SARS-CoV-2/HeLa-ACE2 high-content screening assay. Compounds were acoustically transferred into 384-well μclear-bottom plates (Greiner, Part. No. 781090-2B). HeLa-ACE2 cells were seeded in 13 μL DMEM with 2% FBS at a density of 1.0×10$^3$ cells per well. Plated cells were transported to the BSL3 facility where 13 μL of SARS-CoV-2 diluted in assay media was added to achieve ~30-50% infected cells. Plates were incubated for 24 h at 34° C. 5% $CO_2$, and then fixed with final concentration of 4% formaldehyde for 1 h at 34° C. 5% $CO_2$. Plates were washed with 1×PBS 0.05% Tween 20 in between fixation and subsequent primary and secondary antibody staining. Human polyclonal plasma diluted 1:500 in Perm/Wash buffer (BD Biosciences 554723) was added to the plate and incubated at RT for 2 h. Six μg/mL of goat anti-human H+L conjugated Alexa 488 (Thermo Fisher Scientific A11013) together with 8 μM of antifade-46-diamidino-2-phenylindole (DAPI; Thermo Fisher Scientific D1306) in SuperBlock T20 (PBS) buffer (Thermo Fisher Scientific 37515) was added to the plate and incubated at RT for 1.5-2 hr h in the dark. Plates were imaged using the ImageXpress Micro Confocal High-Content Imaging System (Molecular Devices) with a 10× objective, with 4 fields imaged per well. Images were analyzed using the Multi-Wavelength Cell Scoring Application Module (MetaXpress), with DAPI staining identifying the host-cell nuclei (the total number of cells in the images) and the SARS-CoV-2 immunofluorescence signal leading to identification of infected cells.

Calu-3 high-content screening assay. The assay is carried out as outlined for the HeLa-ACE2 assay, with the following exceptions. Calu-3 cells (ATCC HTB-55), a kind gift from Dr. Catherine Chen at NCATS/NIH and Dr. Juan Carlos de la Torre at Scripps Research, were seeded at a density of 5,000 cells per 20 μL per well in assay media (MEM with 2% FBS before SARS-CoV-2 diluted in assay media was added to achieve ~30-60% infected cells. Plates were incubated for 48 h at 34° C. 5% $CO_2$, and then fixed with a final concentration of 4% formaldehyde. Fixed cells were stained and imaged as in the HeLa-ACE2 assay.

Uninfected host cell cytotoxicity counter screens. For both the HeLa-ACE2 and Calu3 cells, compounds were acoustically transferred into 1,536-well μclear plates (Greiner Part. No. 789091). HeLa-ACE2 cells were seeded in the assay-ready plates at 400 cells/well in DMEM with 2% FBS and plates were incubated for 24 h at 37° C. 5% $CO_2$. Calu-3 cells were seeded in MEM with 2% FBS at a density of 600 cells per 5 μL per well and plates were incubated for 48 h at 37° C. 5% $CO_2$. To assess cell viability, 2 μL of 50% Cell-Titer Glo (Promega No G7573) diluted in water was added to the cells and luminescence measured on an EnVision Plate Reader (Perkin Elmer).

SARS-CoV-2 primary ALI HBEC model. Normal primary human bronchial epithelial cells (HBECs) (Lonza) were cultured in Millicell-96 cell culture insert plates with 1 μm PET filters (Sigma) at an air liquid interface for at least 4 weeks using PneumaCult™-ALI Medium (Stemcell Technologies). Briefly, the HBECs were first expanded in cell culture flasks before seeding 10,000 cells per well submerged in PneumaCult™-Ex Plus Medium. After 1 week, the cells were switched into PneumaCult™-ALI Medium and medium was removed from the apical surface. The air liquid interface was maintained, and the medium exchanged every 2-3 days for at least 4 weeks to allow for differentiation of the cells. Prior to infection, the apical surface was rinsed once with DPBS and compounds were added to the basolateral chamber. 20,000 PFU SARS-CoV-2 strain USA-WA1/2020 were added to the apical surface in 50 μL PBS and allowed to incubate for 2 h. The inoculum was then removed, and the cells rinsed once with DPBS. The medium was exchanged, and fresh compound added at 24 and 48 h post-infection. Apical washes were collected at 72 h post-infection by adding 100 μL DPBS to the apical surface for 15 minutes. RNA was isolated from the apical washes using the PureLink™ Pro 96 Viral RNA/DNA Purification Kit (Thermo Fisher) and analyzed for viral RNA levels by RT-qPCR using the SuperScript™ III Platinum™ One-Step qRT-PCR Kit (Thermo Fisher) and the 2019-nCoV N1 CDC Primers and Probe set (Integrated DNA Technologies). A standard curve was generated by isolating RNA from serial dilutions of the stock virus and used to determine the PFU equivalents/mL for each sample. The viral load reductions were then determined for each experimental compound treatment compared to the neutral DMSO control and plotted in log scale. Cytotoxicity was assessed by measuring LDH activity in the basolateral media using a Cytotoxicity Detection kit (LDH) (Sigma) following the manufacturer's instructions. Averages were taken for the experimental samples and presented as a percentage of the positive control puromycin. Technical triplicates were run for both antiviral and cytotoxicity readouts.

Example 42. Results from the assays and characterizing data on exemplary compounds are presented in Table 1 and Table 2 below.

TABLE 1

| Compound | Structure | IUPAC | LCMS [M + 1] | EC50, uM (Hela) |
|---|---|---|---|---|
| 1 | 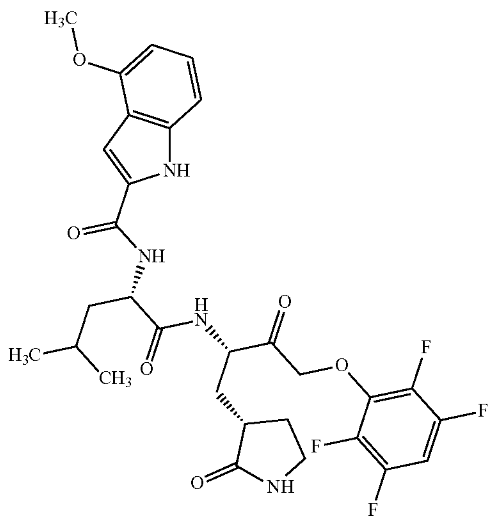 [SMILES: COc1cccc2[nH]c(C(=O)N[C@@H](CC(C)C)C(=O)N[C@@H](C[C@@H]3CCNC3=O)C(=O)COc3c(F)c(F)cc(F)c3F)cc12] | 4-methoxy-N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide | 621.5700 | *** |
| 2 | 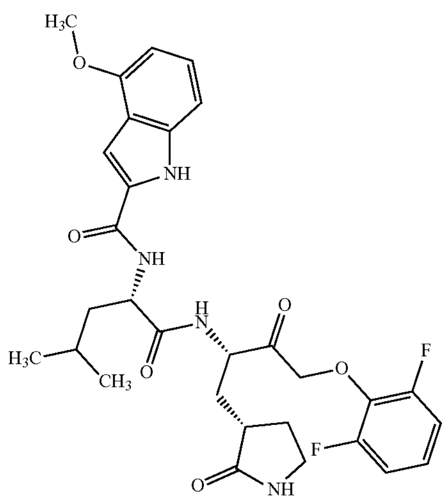 [SMILES: COc1cccc2[nH]c(C(=O)N[C@@H](CC(C)C)C(=O)N[C@@H](C[C@@H]3CCNC3=O)C(=O)COc3c(F)cccc3F)cc12] | N-1-(((S)-4-(2,6-difluorophenoxy)-3-oxo-1-((S)-2-oxopyrrolidin-3-yl)butan-2-yl)amino)-4-methyl-1-oxopentan-2-yl)-4-methoxy-1H-indole-2-carboxamide | 585.2000 | * |

TABLE 1-continued

| Compound | Structure | IUPAC | LCMS [M + 1] | EC50, uM (Hela) |
|---|---|---|---|---|
| 3 | 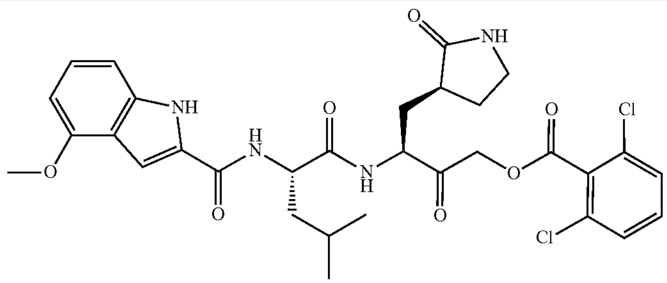 [SMILES: COc1cccc2[nH]c(C(=O)N[C@@H](CC(C)C)C(=O)N[C@@H](C[C@@H]3CCNC3=O)C(=O)COC(=O)c3c(Cl)cccc3Cl)cc12] | (S)-3-((S)-2-(4-methoxy-1H-indole-2-carboxamido)-4-methylpentanamido)-2-oxo-4-((S)-2-oxopyrrolidin-3-yl)butyl 2,6-dichlorobenzoate | 645.2000 | ** |
| 4 | 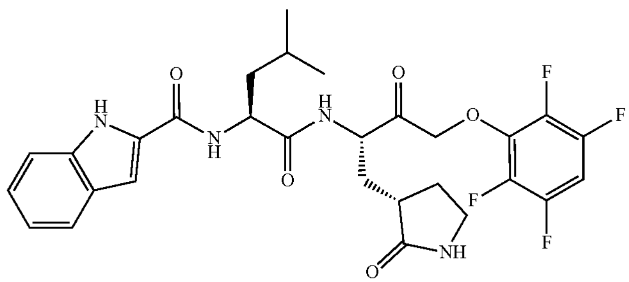 [SMILES: CC(C)C[C@H](NC(=O)c1cc2ccccc2[nH]1)C(=O)N[C@@H](C[C@@H]1CCNC1=O)C(=O)COc1c(F)c(F)cc(F)c1F] | N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide | 591.2200 | **** |
| 5 | 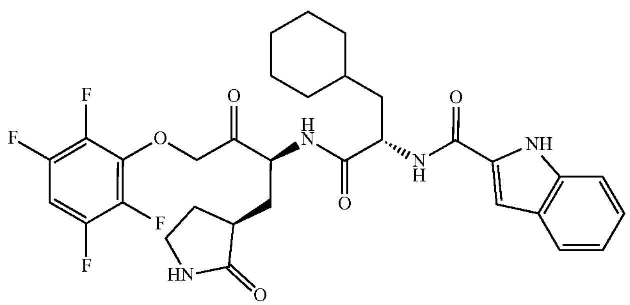 [SMILES: O=C(N[C@@H](CC1CCCCC1)C(=O)N[C@@H](C[C@@H]1CCNC1=O)C(=O)COc1c(F)c(F)cc(F)c1F)c1cc2ccccc2[nH]1] | N-((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-1H-indole-2-carboxamide | 631.2500 | *** |

TABLE 1-continued

| Compound | Structure | IUPAC | LCMS [M + 1] | EC50, uM (Hela) |
|---|---|---|---|---|
| 6 | 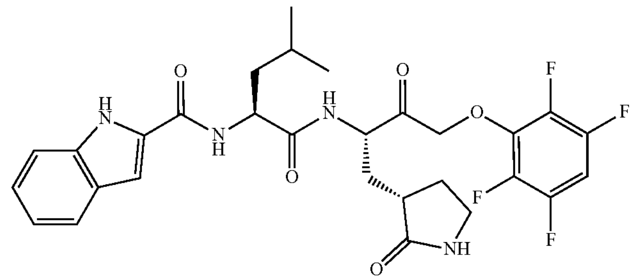 [SMILES: CC(C)C[C@H](NC(=O)c1cc2ccccc2[nH]1)C(=O)N[C@@H](C[C@@H]1CCNC1=O)C(=O)COc1c(F)c(F)cc(F)c1F] | N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide | 591.2000 | **** |
| 7 | 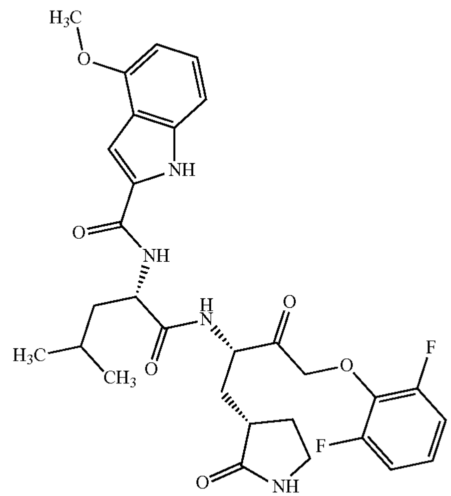 [SMILES: COc1cccc2[nH]c(C(=O)N[C@@H](CC(C)C)C(=O)N[C@@H](C[C@@H]3CCNC3=O)C(=O)COc3c(F)cccc3F)cc12] | N-((S)-1-(((S)-4-(2,6-difluorophenoxy)-3-oxo-1-((S)-2-oxopyrrolidin-3-yl)butan-2-yl)amino)-4-methyl-1-oxopentan-2-yl)-4-methoxy-1H-indole-2-carboxamide | 585.2500 | ** |
| 8 | 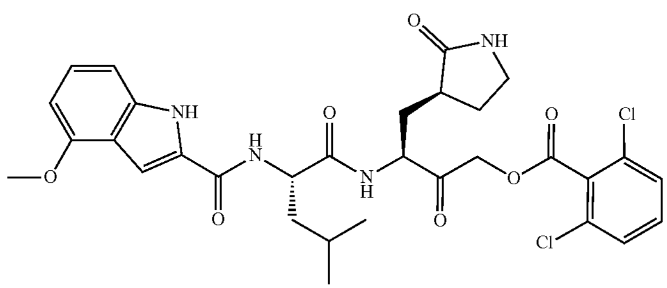 [SMILES: COc1cccc2[nH]c(C(=O)N[C@@H](CC(C)C)C(=O)N[C@@H](C[C@@H]3CCNC3=O)C(=O)COC(=O)c3c(Cl)cccc3Cl)cc12] | (S)-3-((S)-2-(4-methoxy-1H-indole-2-carboxamido)-4-methylpentanamido)-2-oxo-4-((S)-2-oxopyrrolidin-3-yl)butyl 2,6-dichlorobenzoate | 645.4982 | *** |

TABLE 1-continued

| Compound | Structure | IUPAC | LCMS [M + 1] | EC50, uM (Hela) |
|---|---|---|---|---|
| 9 | 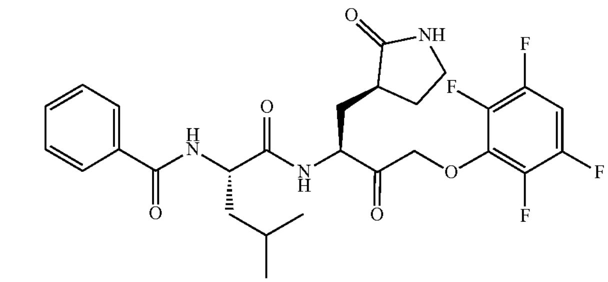 [SMILES: CC(C)C[C@H](NC(=O)c1ccccc1)C(=O)N[C@@H](C[C@@H]1CCNC1=O)C(=O)COc1c(F)c(F)cc(F)c1F] | N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)benzamide | 552.2000 | *** |
| 10 | 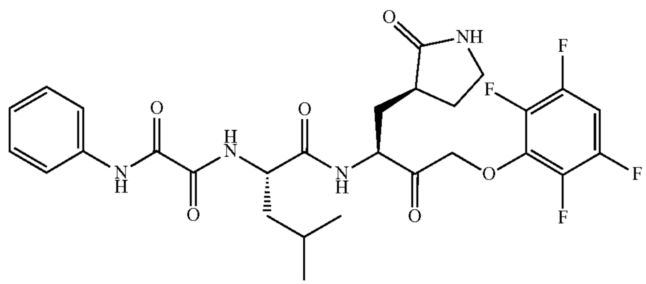 [SMILES: CC(C)C[C@H](NC(=O)C(=O)Nc1ccccc1)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-phenyloxalamide | 595.2100 | **** |
| 11 | 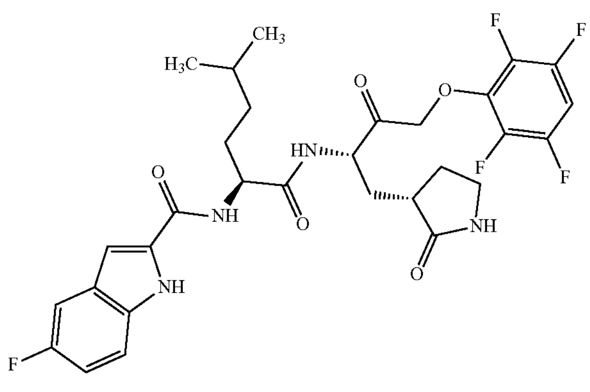 [SMILES: CC(C)CC[C@H](NC(=O)c1cc2cc(F)ccc2[nH]1)C(=O)N[C@@H](C[C@@H]1CCNC1=O)C(=O)COc1c(F)c(F)cc(F)c1F] | 5-fluoro-N-((S)-5-methyl-1-oxo-1-(((S)-3-oxo-1-((S)-2-oxopyrrolidin-3-yl)-4-(2,3,5,6-tetrafluorophenoxy)butan-2-yl)amino)hexan-2-yl)-1H-indole-2-carboxamide | 623.4902 | ** |

TABLE 1-continued

| Compound | Structure | IUPAC | LCMS [M + 1] | EC50, uM (Hela) |
|---|---|---|---|---|
| 12 | 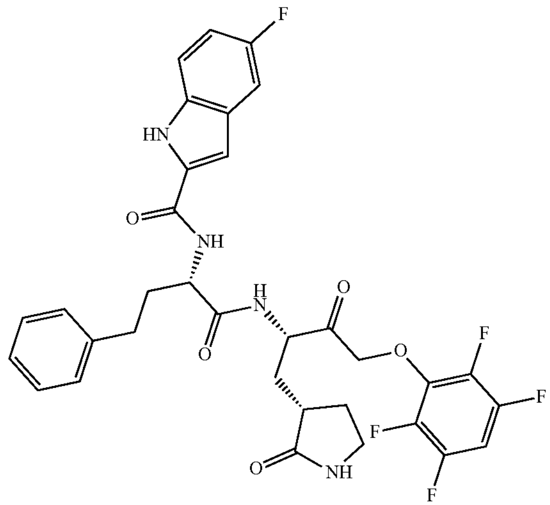 [SMILES: O=C(N[C@@H](CCc1ccccc1)C(=O)N[C@@H](C[C@@H]1CCNC1=O)C(=O)COc1c(F)c(F)cc(F)c1F)c1cc2cc(F)ccc2[nH]1] | 5-fluoro-N-((S)-1-oxo-1-(((S)-3-oxo-1-((S)-2-oxopyrrolidin-3-yl)-4-(2,3,5,6-tetrafluorophenoxy)butan-2-yl)amino)-4-phenylbutan-2-yl)-1H-indole-2-carboxamide | 657.4794 | * |
| 13 | 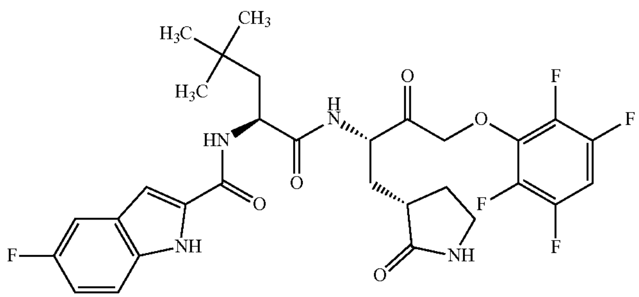 [SMILES: CC(C)(C)C[C@H](NC(=O)c1cc2cc(F)ccc2[nH]1)C(=O)N[C@@H](C[C@@H]1CCNC1=O)C(=O)COc1c(F)c(F)cc(F)c1F] | N-((S)-4,4-dimethyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-5-fluoro-1H-indole-2-carboxamide | 623.4902 | * |

TABLE 1-continued

| Compound | Structure | IUPAC | LCMS [M + 1] | EC50, uM (Hela) |
|---|---|---|---|---|
| 14 | 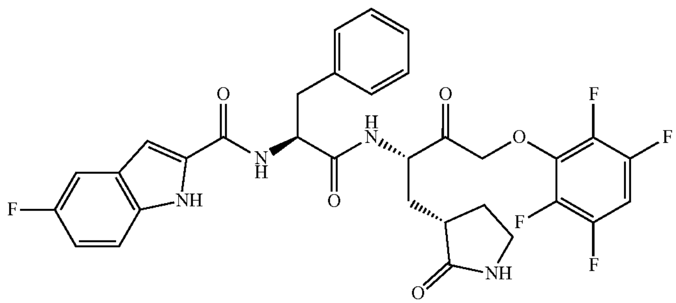 [SMILES: O=C(N[C@@H](Cc1ccccc1)C(=O)N[C@@H](C[C@@H]1CCNC1=O)C(=O)COc1c(F)c(F)cc(F)c1F)c1cc2cc(F)ccc2[nH]1] | 5-fluoro-N-((S)-1-oxo-1-(((S)-3-oxo-1-((S)-2-oxopyrrolidin-3-yl)-4-(2,3,5,6-tetrafluorophenoxy)butan-2-yl)amino)-3-phenylpropan-2-yl)-1H-indole-2-carboxamide | 643.4783 | *** |
| 15 | 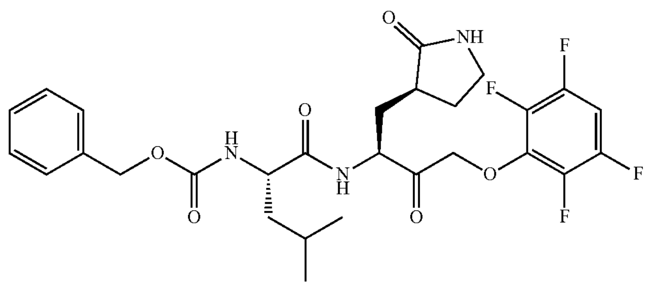 [SMILES: CC(C)C[C@H](NC(=O)OCc1ccccc1)C(=O)N[C@@H](C[C@@H]1CCNC1=O)C(=O)COc1c(F)c(F)cc(F)c1F] | benzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate | 582.4000 | ** |
| 16 | 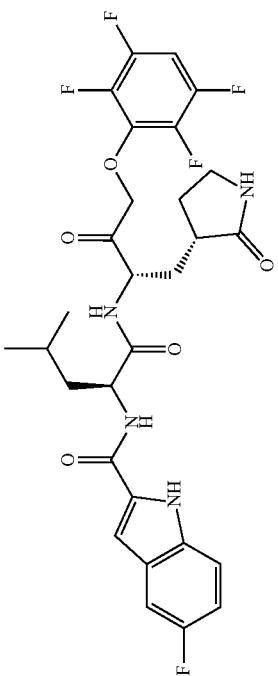 | 5-fluoro-N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide | 609.4000 | *** |

TABLE 1-continued

| Compound | Structure | IUPAC | LCMS [M + 1] | EC50, uM (Hela) |
|---|---|---|---|---|
| 17 | 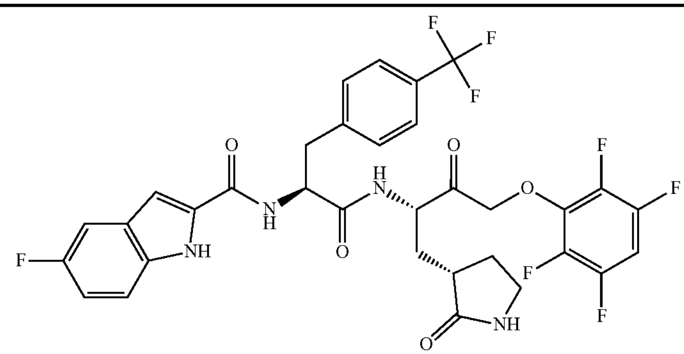 | 5-fluoro-N-((S)-1-oxo-1-(((S)-3-oxo-1-((S)-2-oxopyrrolidin-3-yl)-4-(2,3,5,6-tetrafluorophenoxy)butan-2-yl)amino)-3-(4-(trifluoromethyl)phenyl)propan-2-yl)-1H-indole-2-carboxamide | 711.1800 | ** |
| 18 | 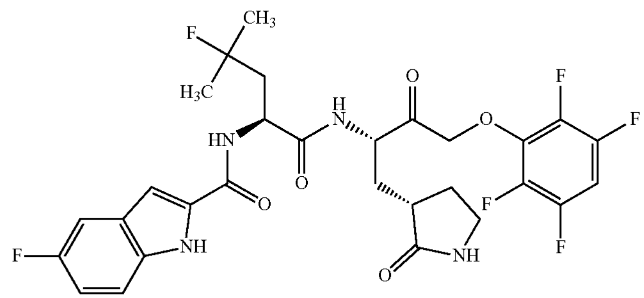 [SMILES: CC(C)(F)C[C@H](NC(=O)c1cc2cc(F)ccc2[nH]1)C(=O)N[C@@H](C[C@@H]1CCNC1=O)C(=O)COc1c(F)c(F)cc(F)c1F] | 5-fluoro-N-((S)-4-fluoro-4-methyl-1-oxo-1-(((S)-3-oxo-1-((S)-2-oxopyrrolidin-3-yl)-4-(2,3,5,6-tetrafluorophenoxy)pentan-2-yl)amino)pentan-2-yl)-1H-indole-2-carboxamide | 627.4000 | * |
| 19 | 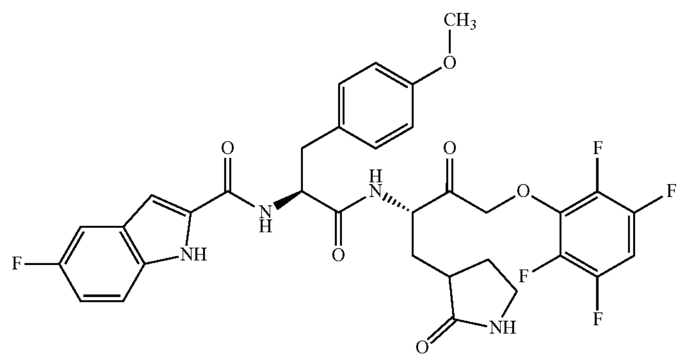 [SMILES: COc1ccc(C[C@H](NC(=O)c2cc3cc(F)ccc3[nH]2)C(=O)N[C@@H](CC2CCNC2=O)C(=O)COc2c(F)c(F)cc(F)c2F)cc1] | 5-fluoro-N-((2S)-3-(4-methoxyphenyl)-1-oxo-1-(((2S)-3-oxo-1-(2-oxopyrrolidin-3-yl)-4-(2,3,5,6-tetrafluorophenoxy)butan-2-yl)amino)propan-2-yl)-1H-indole-2-carboxamide | 673.4700 | ** |

TABLE 1-continued

| Compound | Structure | IUPAC | LCMS [M + 1] | EC50, uM (Hela) |
|---|---|---|---|---|
| 20 | 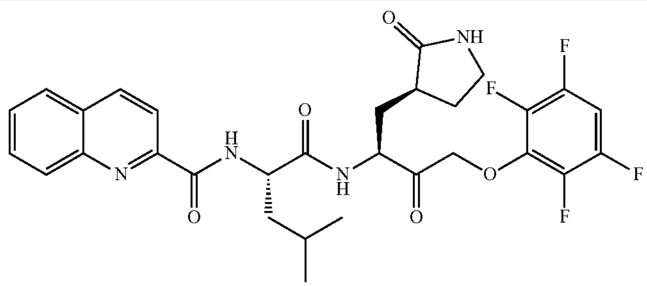 [SMILES: CC(C)C[C@H](NC(=O)c1ccc2ccccc2n1)C(=O)N[C@@H](C[C@@H]1CCNC1=O)C(=O)COc1c(F)c(F)cc(F)c1F] | N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)quinoline-2-carboxamide | 603.4875 | ** |
| 21 | 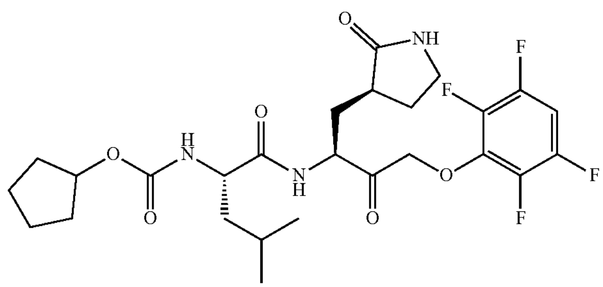 [SMILES: CC(C)C[C@H](NC(=O)OC1CCCC1)C(=O)N[C@@H](C[C@@H]1CCNC1=O)C(=O)COc1c(F)c(F)cc(F)c1F] | cyclopentyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate | 560.2300 | >1 μM |
| 22 | 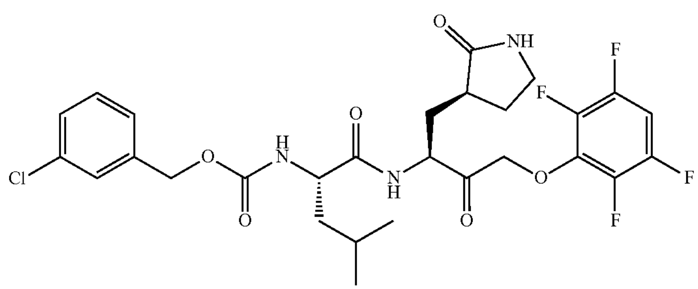 [SMILES: CC(C)C[C@H](NC(=O)OCc1cccc(Cl)c1)C(=O)N[C@@H](C[C@@H]1CCNC1=O)C(=O)COc1c(F)c(F)cc(F)c1F] | 3-chlorobenzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate | 616.1800 | ** |

TABLE 1-continued

| Compound | Structure | IUPAC | LCMS [M + 1] | EC50, uM (Hela) |
|---|---|---|---|---|
| 23 | 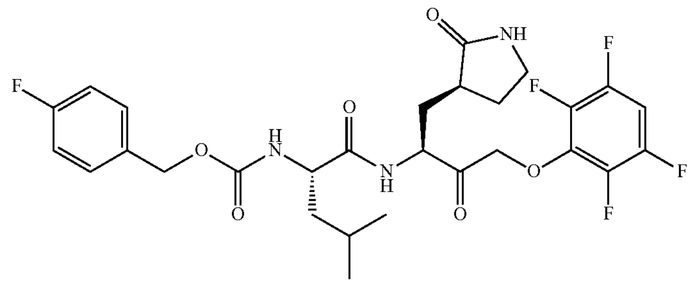 [SMILES: CC(C)C[C@H](NC(=O)OCc1ccc(F)cc1)C(=O)N[C@@H](C[C@@H]1CCNC1=O)C(=O)COc1c(F)c(F)cc(F)c1F] | 4-fluorobenzyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate | 600.2100 | ** |
| 24 | 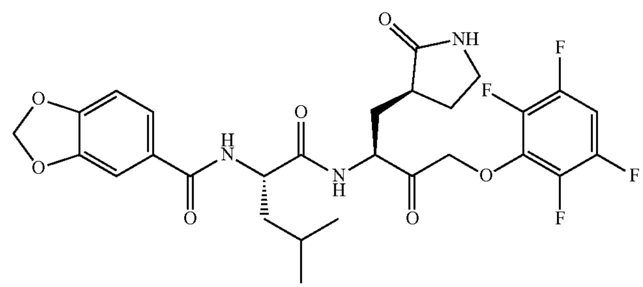 [SMILES: CC(C)C[C@H](NC(=O)c1ccc2c(c1)OCO2)C(=O)N[C@@H](C[C@@H]1CCNC1=O)C(=O)COc1c(F)c(F)cc(F)c1F] | N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)benzo[d][1,3]dioxole-5-carboxamide | 596.1900 | ** |
| 25 | 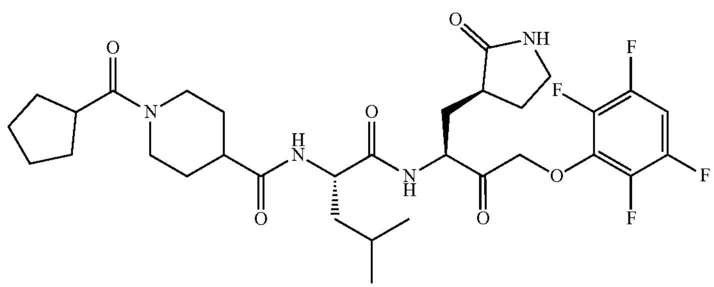 [SMILES: CC(C)C[C@H](NC(=O)C1CCN(C(=O)C2CCCC2)CC1)C(=O)N[C@@H](C[C@@H]1CCNC1=O)C(=O)COc1c(F)c(F)cc(F)c1F] | 1-(cyclopentanecarbonyl)-N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)piperidine-4-carboxamide | 655.5900 | * |

TABLE 1-continued

| Compound | Structure | IUPAC | LCMS [M + 1] | EC50, uM (Hela) |
|---|---|---|---|---|
| 26 | 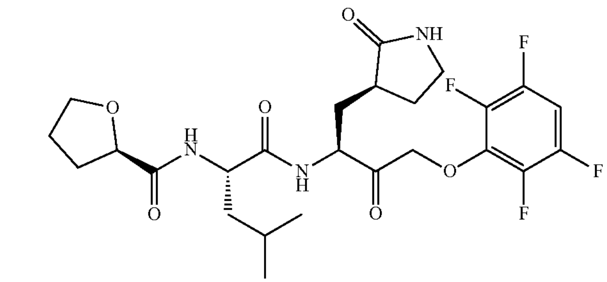 [SMILES: CC(C)C[C@H](NC(=O)[C@H]1CCCO1)C(=O)N[C@@H](C[C@@H]1CCNC1=O)C(=O)COc1c(F)c(F)cc(F)c1F] | (R)-N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)tetrahydrofuran-2-carboxamide | 546.2200 | ** |
| 27 | 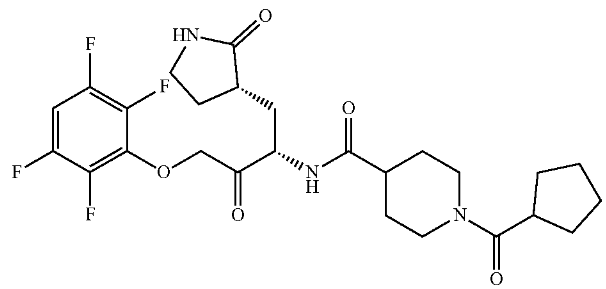 [SMILES: O=C(N[C@@H](C[C@@H]1CCNC1=O)C(=O)COc1c(F)c(F)cc(F)c1F)C1CCN(C(=O)C2CCCC2)CC1] | 1-(cyclopentane-carbonyl)-N-((S)-3-oxo-1-((S)-2-oxopyrrolidin-3-yl)-4-(2,3,5,6-tetrafluorophenoxy)butan-2-yl)piperidine-4-carboxamide | 542.4600 | >1 μM |
| 28 | 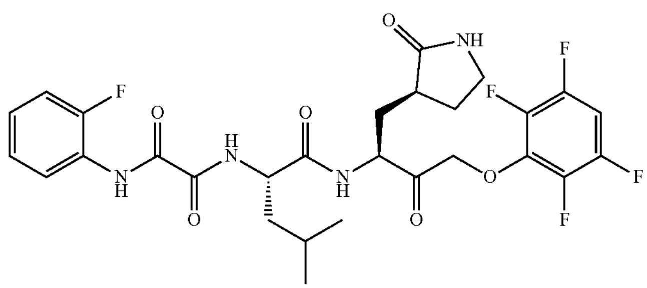 | N1-(2-fluorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 613.4393 | **** |

TABLE 1-continued

| Compound | Structure | IUPAC | LCMS [M + 1] | EC50, uM (Hela) |
|---|---|---|---|---|
| 29 | 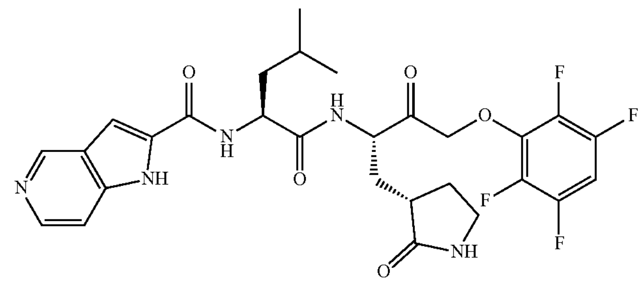 [SMILES: CC(C)C[C@H](NC(=O)c1cc2cnccc2[nH]1)C(=O)N[C@@H](C[C@@H]1CCNC1=O)C(=O)COc1c(F)c(F)cc(F)c1F] | N-((S)-4-methyl-1-oxo-1-(((S)-3-oxo-1-(((S)-2-oxopyrrolidin-3-yl)-4-(2,3,5,6-tetrafluorophenoxy)butan-2-yl)amino)pentan-2-yl)-1H-pyrrolo[3,2-c]pyridine-2-carboxamide | 592.2100 | **** |
| 30 | 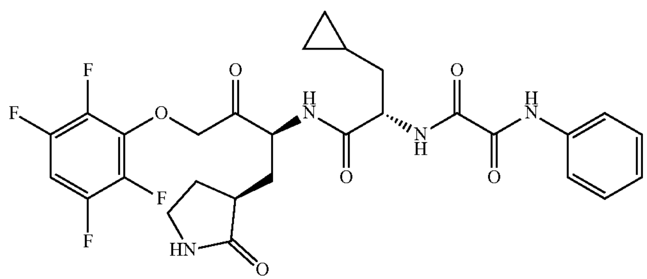 [SMILES: O=C(Nc1ccccc1)C(=O)N[C@@H](CC1CC1)C(=O)N[C@@H](C[C@@H]1CCNC1=O)C(=O)COc1c(F)c(F)cc(F)c1F] | N1-((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N2-phenyloxalamide | 593.1900 | **** |
| 31 | 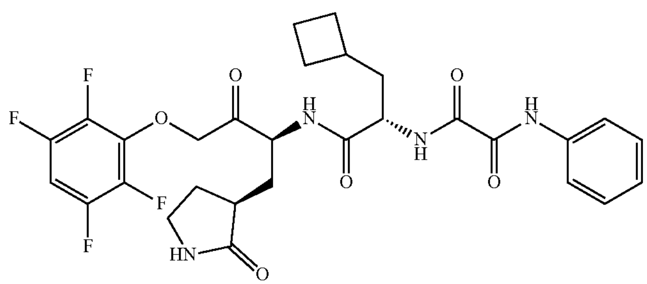 [SMILES: O=C(Nc1ccccc1)C(=O)N[C@@H](CC1CCC1)C(=O)N[C@@H](C[C@@H]1CCNC1=O)C(=O)COc1c(F)c(F)cc(F)c1F] | N1-((S)-3-cyclobutyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N2-phenyloxalamide | 607.2100 | *** |

TABLE 1-continued

| Compound | Structure | IUPAC | LCMS [M + 1] | EC50, uM (Hela) |
|---|---|---|---|---|
| 32 | 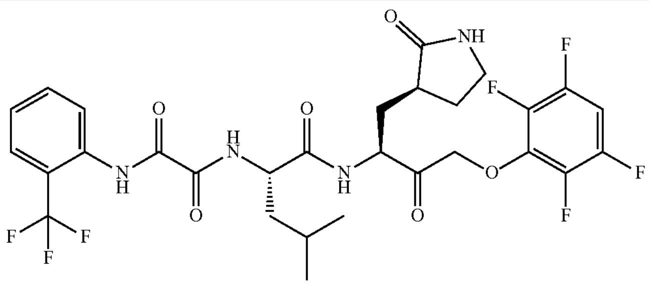 [SMILES: CC(C)C[C@H](NC(=O)C(=O)Nc1ccccc1C(F)(F)F)C(=O)N[C@@H](C[C@@H]1CCNC1=O)C(=O)COc1c(F)c(F)cc(F)c1F] | N1-((S)-4-methyl-1-oxo-1-((S)-3-oxo-1-((S)-2-oxopyrrolidin-3-yl)-4-(2,3,5,6-tetrafluorophenoxy)butan-2-yl)amino)pentan-2-yl)-N2-(2-(trifluoromethyl)phenyl)-oxalamide | 663.2000 | **** |
| 33 | 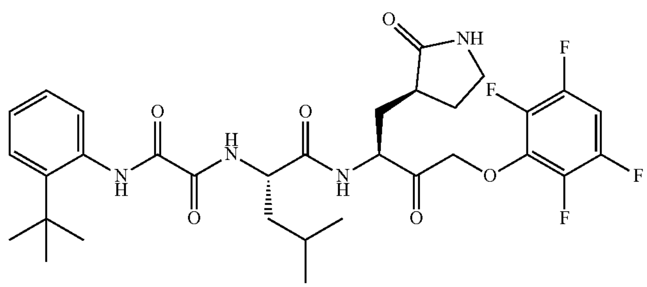 [SMILES: CC(C)C[C@H](NC(=O)C(=O)Nc1ccccc1C(C)(C)C)C(=O)N[C@@H](C[C@@H]1CCNC1=O)C(=O)COc1c(F)c(F)cc(F)c1F] | N1-(2-(tert-butyl)phenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 651.2700 | **** |
| 34 | 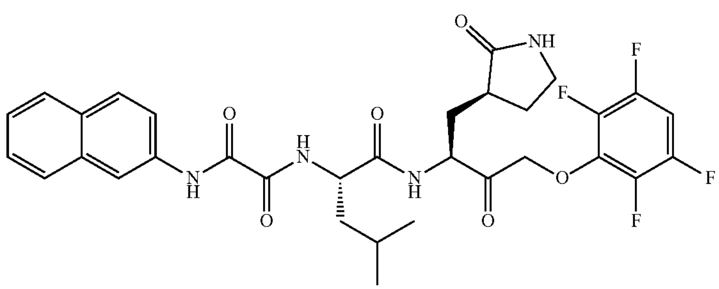 [SMILES: CC(C)C[C@H](NC(=O)C(=O)Nc1ccc2ccccc2c1)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(naphthalen-2-yl)oxalamide | 645.2300 | *** |

TABLE 1-continued

| Compound | Structure | IUPAC | LCMS [M + 1] | EC50, uM (Hela) |
|---|---|---|---|---|
| 35 | 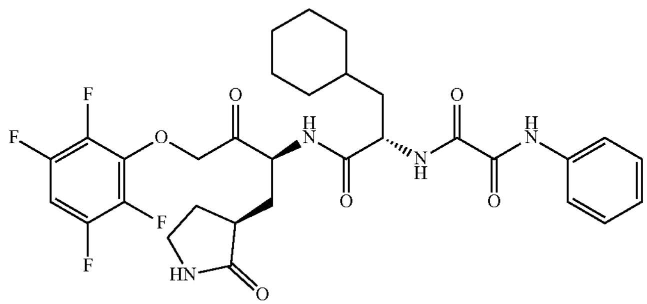 [SMILES: O=C(Nc1ccccc1)C(=O)N[C@@H](CC1CCCCC1)C(=O)N[C@@H](C[C@@H]1CCNC1=O)C(=O)COc1c(F)c(F)cc(F)c1F] | N1-((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N2-phenyloxalamide | 635.2400 | **** |
| 36 | 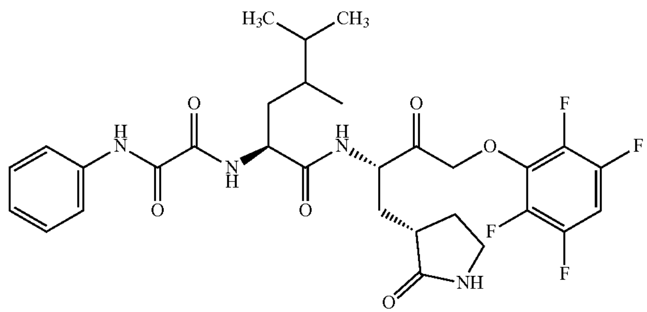 [SMILES: CC(C)C(C)C[C@H](NC(=O)C(=O)Nc1ccccc1)C(=O)N[C@@H](C[C@@H]1CCNC1=O)C(=O)COc1c(F)c(F)cc(F)c1F] | N1-((S)-5-methyl-1-oxo-1-(((S)-3-oxo-1-((S)-2-oxopyrrolidin-3-yl)-4-(2,3,5,6-tetrafluorophenoxy)butan-2-yl)amino)hexan-2-yl)-N2-phenyloxalamide | 609.2300 | **** |
| 37 | 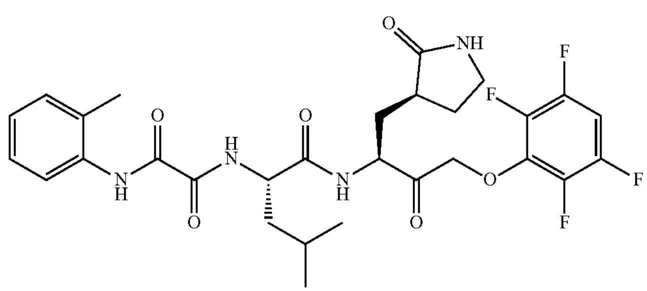 [SMILES: Cc1ccccc1NC(=O)C(=O)N[C@@H](CC(C)C)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(o-tolyl)oxalamide | 609.2300 | **** |

TABLE 1-continued

| Compound | Structure | IUPAC | LCMS [M + 1] | EC50, uM (Hela) |
|---|---|---|---|---|
| 38 | 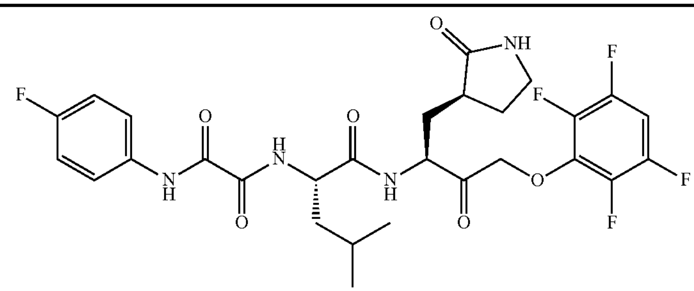 | N1-(4-fluorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 613.4449 | **** |
| 39 | 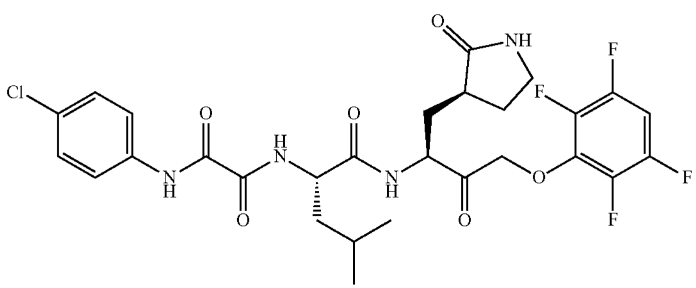 [SMILES: CC(C)C[C@H](NC(=O)C(=O)Nc1ccc(Cl)cc1)C(=O)N[C@@H](C[C@@H]1CCNC1=O)C(=O)COc1c(F)c(F)cc(F)c1F] | N1-(4-chlorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 629.4266 | *** |
| 40 | 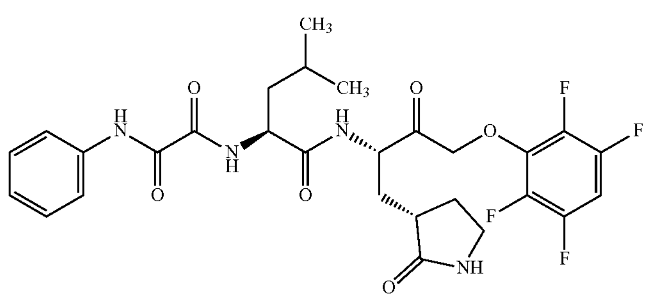 [SMILES: CC(C)C[C@H](NC(=O)C(=O)Nc1ccccc1)C(=O)N[C@@H](C[C@@H]1CCNC1=O)C(=O)COc1c(F)c(F)cc(F)c1F] | (S)-4-methyl-N-((S)-3-oxo-1-((S)-2-oxopyrrolidin-3-yl)-4-(2,3,5,6-tetrafluorophenoxy)butan-2-yl)-2-(2-(phenylamino)acetamido)pentanamide | 580.9900 | **** |

TABLE 1-continued

| Compound | Structure | IUPAC | LCMS [M + 1] | EC50, uM (Hela) |
|---|---|---|---|---|
| 41 | 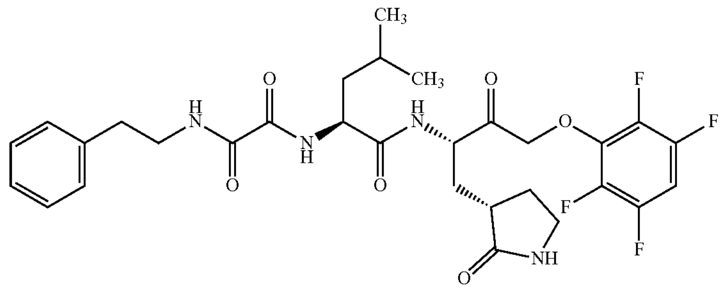 [SMILES: CC(C)C[C@H](NC(=O)C(=O)NCCc1ccccc1)C(=O)N[C@@H](C[C@@H]1CCNC1=O)C(=O)COc1c(F)c(F)cc(F)c1F] | N1-((S)-4-methyl-1-oxo-1-(((S)-3-oxo-1-(((S)-2-oxopyrrolidin-3-yl)-4-(2,3,5,6-tetrafluorophenoxy)butan-2-yl)amino)pentan-2-yl)-N2-phenethyloxalamide | 623.2400 | *** |
| 42 | 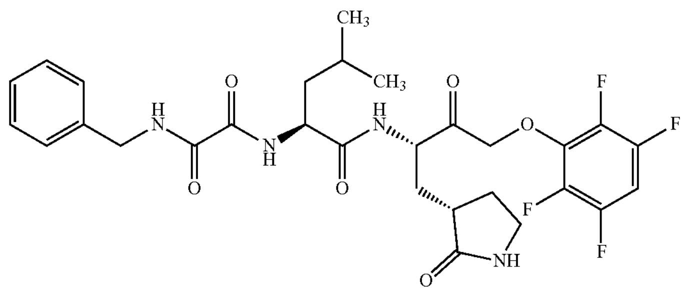 [SMILES: CC(C)C[C@H](NC(=O)C(=O)NCc1ccccc1)C(=O)N[C@@H](C[C@@H]1CCNC1=O)C(=O)COc1c(F)c(F)cc(F)c1F] | N1-benzyl-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 609.2300 | *** |
| 43 | 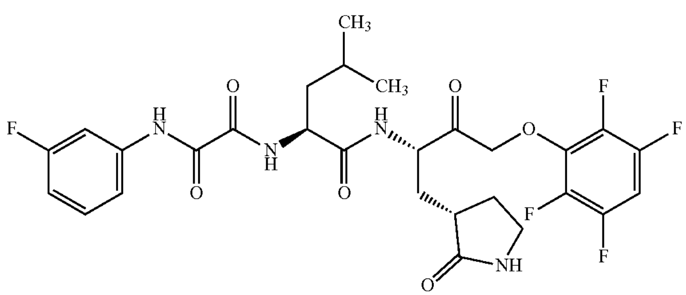 [SMILES: CC(C)C[C@H](NC(=O)C(=O)Nc1cccc(F)c1)C(=O)N[C@@H](C[C@@H]1CCNC1=O)C(=O)COc1c(F)c(F)cc(F)c1F] | N1-(3-fluorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 613.2000 | *** |

TABLE 1-continued

| Compound | Structure | IUPAC | LCMS [M + 1] | EC50, uM (Hela) |
|---|---|---|---|---|
| 44 | 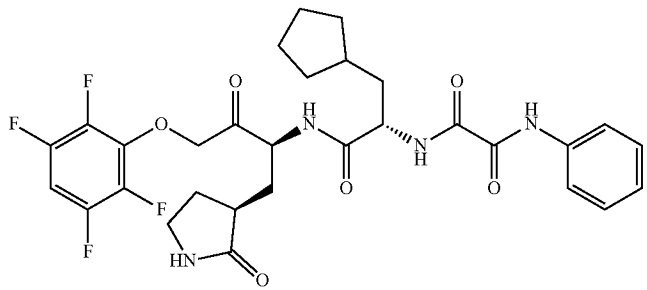 [SMILES: O=C(Nc1ccccc1)C(=O)N[C@@H](CC1CCCC1)C(=O)N[C@@H](C[C@@H]1CCNC1=O)C(=O)COc1c(F)c(F)cc(F)c1F] | N1-((S)-3-cyclopentyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N2-phenyloxalamide | 621.2258 | **** |
| 45 | 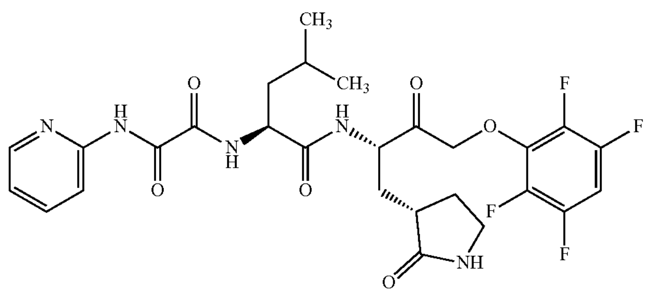 | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(pyridin-2-yl)oxalamide | 596.4100 | *** |
| 46 | 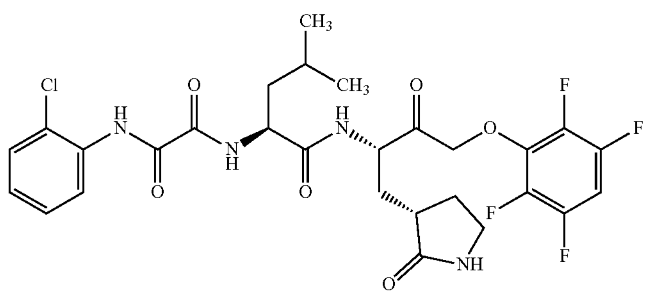 | N1-(2-chlorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 629.1700 | *** |

TABLE 1-continued

| Compound | Structure | IUPAC | LCMS [M + 1] | EC50, uM (Hela) |
|---|---|---|---|---|
| 47 | 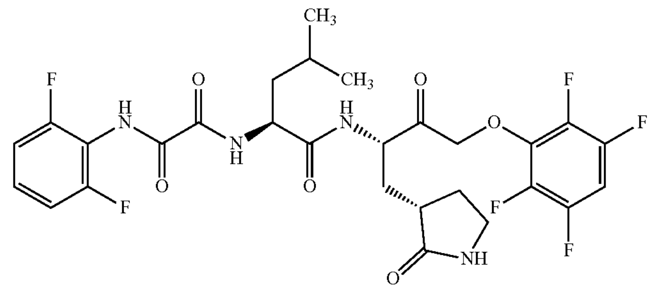 [SMILES: CC(C)C[C@H](NC(=O)C(=O)Nc1c(F)cccc1F)C(=O)N[C@@H](C[C@@H]1CCNC1=O)C(=O)COc1c(F)c(F)cc(F)c1F] | N1-(2,6-difluorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 631.1900 | **** |
| 48 | 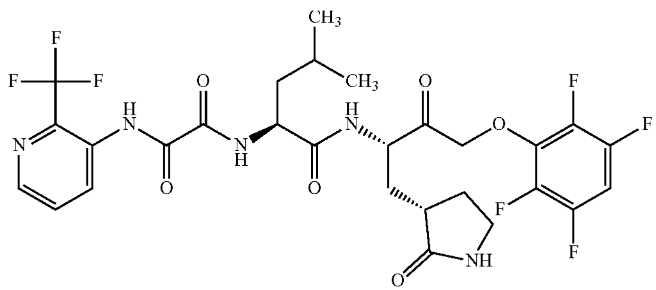 [SMILES: CC(C)C[C@H](NC(=O)C(=O)Nc1cccnc1C(F)(F)F)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(2-(trifluoromethyl)pyridin-3-yl)oxalamide | 664.1900 | **** |
| 49 | 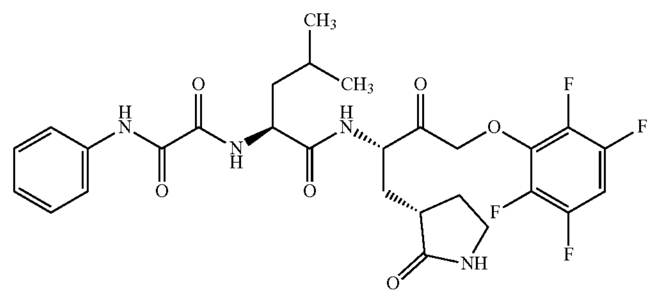 [SMILES: CC(C)C[C@H](NC(=O)C(=O)Nc1ccccc1)C(=O)N[C@@H](C[C@@H]1CCNC1=O)C(=O)COc1c(F)c(F)cc(F)c1F] | N1-((2S)-1-(((2S)-3-hydroxy-1-((S)-2-oxopyrrolidin-3-yl)-4-(2,3,5,6-tetrafluorophenoxy)butan-2-yl)amino)-4-methyl-1-oxopentan-2-yl)-N2-phenyloxalamide | 597.4599 | >1 μM |

TABLE 1-continued

| Compound | Structure | IUPAC | LCMS [M + 1] | EC50, uM (Hela) |
|---|---|---|---|---|
| 50 | 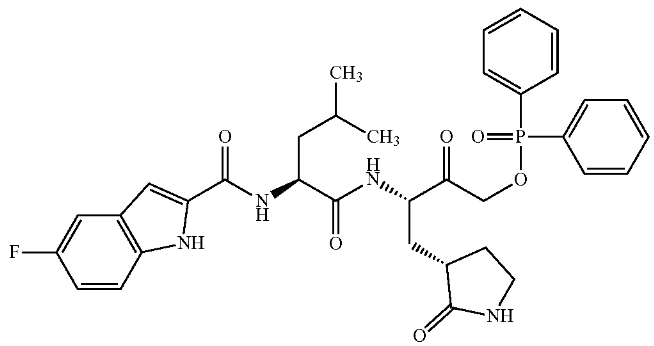 [SMILES: CC(C)C[C@H](NC(=O)c1cc2cc(F)ccc2[nH]1)C(=O)N[C@@H](C[C@@H]1CCNC1=O)C(=O)COP(=O)(c1ccccc1)c1ccccc1] | (S)-3-((S)-2-(5-fluoro-1H-indole-2-carboxamido)-4-methylpentanamido)-2-oxo-4-((S)-2-oxopyrrolidin-3-yl)butyl diphenylphosphinate | 661.5334 | ** |
| 51 | 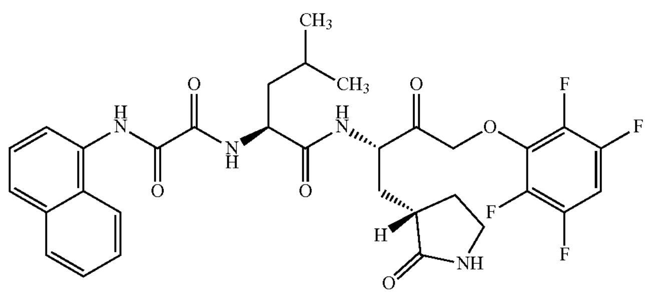 [SMILES: CC(C)C[C@H](NC(=O)C(=O)Nc1cccc2ccccc12)C(=O)N[C@@H](C[C@@H]1CCNC1=O)C(=O)COc1c(F)c(F)cc(F)c1F] | N1-((S)-4-methyl-1-oxo-1-(((S)-2-oxopyrrolidin-3-yl)-4-(2,3,5,6-tetrafluorophenoxy)butan-2-yl)amino)pentan-2-yl)-N2-(naphthalen-1-yl)oxalamide | 645.2300 | **** |
| 52 | 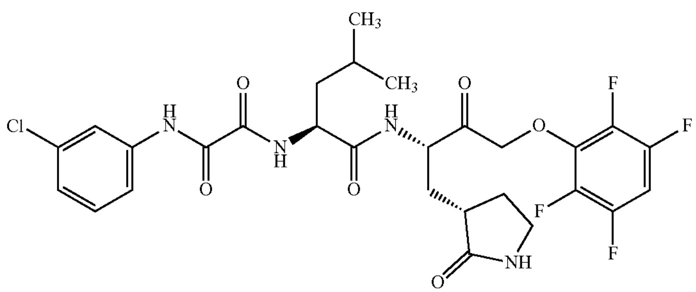 [SMILES: CC(C)C[C@H](NC(=O)C(=O)Nc1cccc(Cl)c1)C(=O)N[C@@H](C[C@@H]1CCNC1=O)C(=O)COc1c(F)c(F)cc(F)c1F] | N1-(3-chlorophenyl)-N2-((S)-4-methyl-1-(((S)-2-oxopyrrolidin-3-yl)-4-(2,3,5,6-tetrafluorophenoxy)butan-2-yl)amino)pentan-2-yl)oxalamide | 629.17 | *** |

TABLE 1-continued

| Compound | Structure | IUPAC | LCMS [M + 1] | EC50, uM (Hela) |
|---|---|---|---|---|
| 53 | 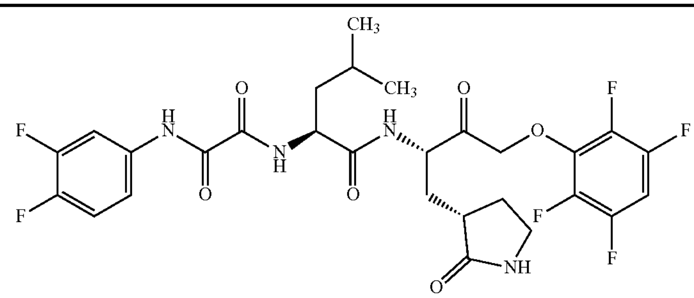 | N1-(3,4-difluorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 631.19 | *** |
| 54 | 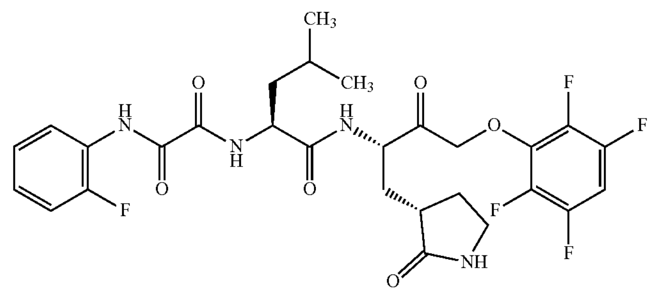 [SMILES: CC(C)C[C@H](NC(=O)C(=O)Nc1ccccc1F)C(=O)N[C@@H](C[C@@H]1CCNC1=O)C(=O)COc1c(F)c(F)cc(F)c1F] | (R)-N4-(2-fluorobenzyl)-2-isobutyl-N1-(((S)-3-oxo-1-((S)-2-oxopyrrolidin-3-yl)-4-(2,3,5,6-tetrafluorophenoxy)butan-2-yl)succinamide | 598.2300 | >1 μM |
| 55 | 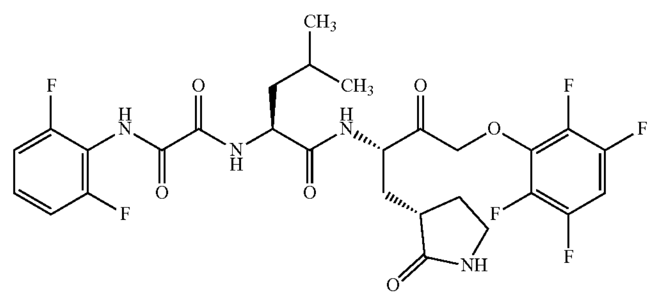 [SMILES: CC(C)C[C@H](NC(=O)C(=O)Nc1c(F)cccc1F)C(=O)N[C@@H](C[C@@H]1CCNC1=O)C(=O)COc1c(F)c(F)cc(F)c1F] | (R)-N4-(2,6-difluorobenzyl)-2-isobutyl-N1-(((S)-3-oxo-1-((S)-2-oxopyrrolidin-3-yl)-4-(2,3,5,6-tetrafluorophenoxy)butan-2-yl)succinamide | 616.4678 | >1 μM |

TABLE 1-continued

| Compound | Structure | IUPAC | LCMS [M + 1] | EC50, uM (Hela) |
|---|---|---|---|---|
| 56 | 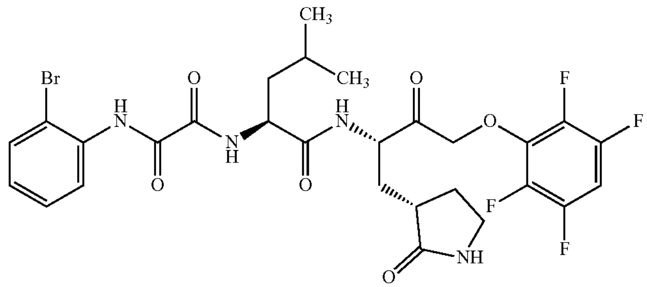 | N1-(2-bromophenyl)-N2-((S)-4-methyl-1-oxo-1-(((S)-2-oxopyrrolidin-3-yl)-4-(2,3,5,6-tetrafluorophenoxy)butan-2-yl)amino)pentan-2-yl)oxalamide | 675.3605 | *** |
| 57 | 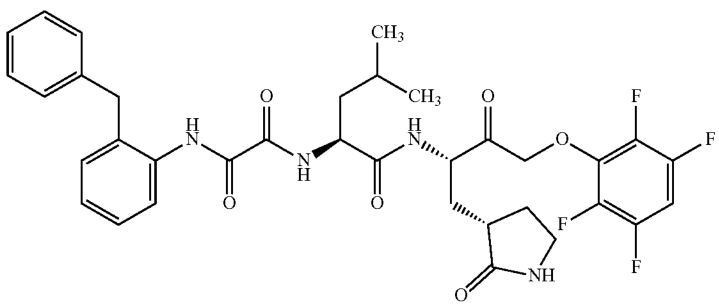 [SMILES: CC(C)C[C@H](NC(=O)C(=O)Nc1ccccc1Cc1ccccc1)C(=O)N[C@@H](C[C@@H]1CCNC1=O)C(=O)COc1c(F)c(F)cc(F)c1F] | N1-(2-benzylphenyl)-N2-((S)-4-methyl-1-oxo-1-(((S)-2-oxopyrrolidin-3-yl)-4-(2,3,5,6-tetrafluorophenoxy)butan-2-yl)amino)pentan-2-yl)oxalamide | 685.2600 | ** |
| 58 | 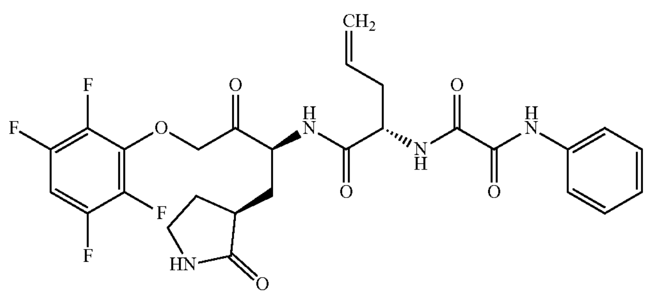 [SMILES: C=CC[C@H](NC(=O)C(=O)Nc1ccccc1)C(=O)N[C@@H](C[C@@H]1CCNC1=O)C(=O)COc1c(F)c(F)cc(F)c1F] | N1-((S)-1-oxo-1-(((S)-3-oxo-1-((S)-2-oxopyrrolidin-3-yl)-4-(2,3,5,6-tetrafluorophenoxy)butan-2-yl)amino)pent-4-en-2-yl)-N2-phenyloxalamide | 579.3276 | ** |

TABLE 1-continued

| Compound | Structure | IUPAC | LCMS [M + 1] | EC50, uM (Hela) |
|---|---|---|---|---|
| 59 | 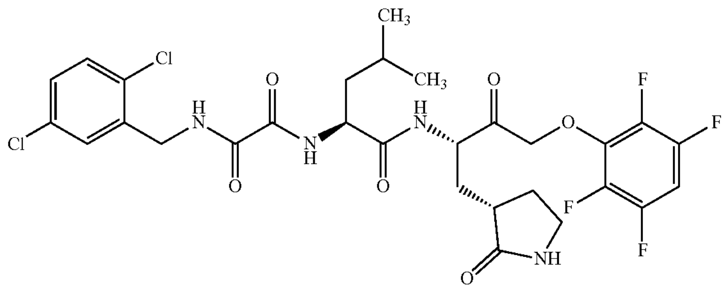 [SMILES: CC(C)C[C@H](NC(=O)C(=O)NCc1cc(Cl)ccc1Cl)C(=O)N[C@@H](C[C@@H]1CCNC1=O)C(=O)COc1c(F)c(F)cc(F)c1F] | N1-(2,5-dichlorobenzyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 677.3512 | ** |
| 60 | 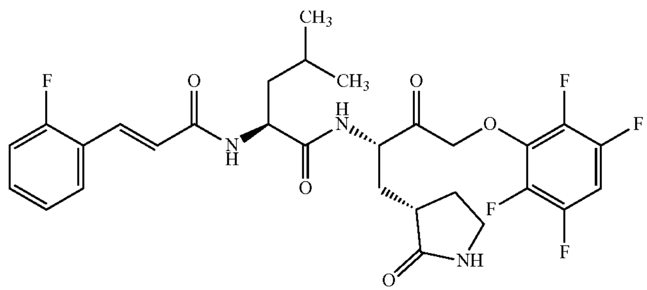 | (S)-2-((E)-3-(2-fluorophenyl)acrylamido)-4-methyl-N-((S)-3-oxo-1-((S)-2-oxopyrrolidin-3-yl)-4-(2,3,5,6-tetrafluorophenoxy)butan-2-yl)pentanamide | 596.2100 | *** |
| 61 | 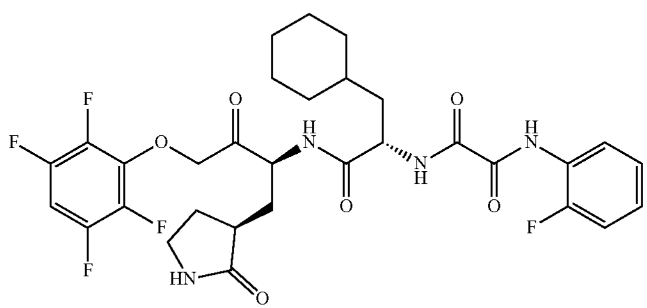 | N1-((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N2-(2-fluorophenyl)oxalamide | 653.4769 | **** |

TABLE 1-continued

| Compound | Structure | IUPAC | LCMS [M + 1] | EC50, uM (Hela) |
|---|---|---|---|---|
| 62 | 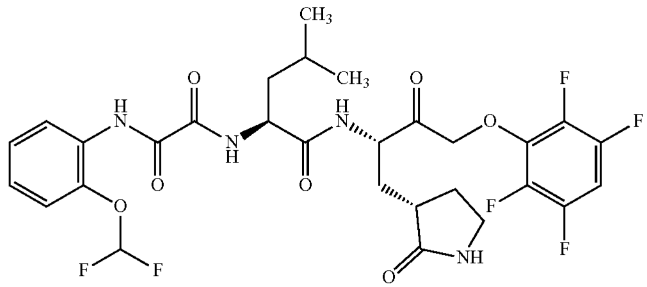 [SMILES: CC(C)C[C@H](NC(=O)C(=O)Nc1ccccc1OC(F)F)C(=O)N[C@@H](C[C@@H]1CCNC1=O)C(=O)COc1c(F)c(F)cc(F)c1F] | N1-(2-(difluoromethoxy)phenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 661.2000 | **** |
| 63 | 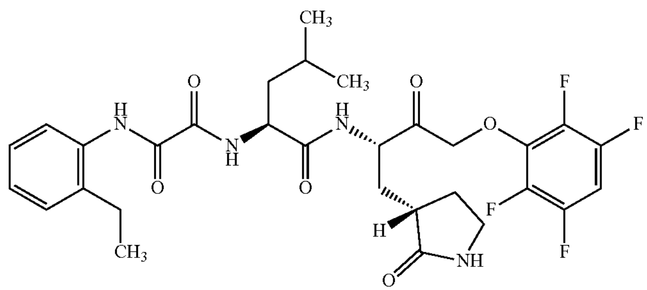 [SMILES: CCc1ccccc1NC(=O)C(=O)N[C@@H](CC(C)C)C(=O)N[C@@H](C[C@@H]1CCNC1=O)C(=O)COc1c(F)c(F)cc(F)c1F] | N1-(2-ethylphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 623.2400 | **** |
| 64 | 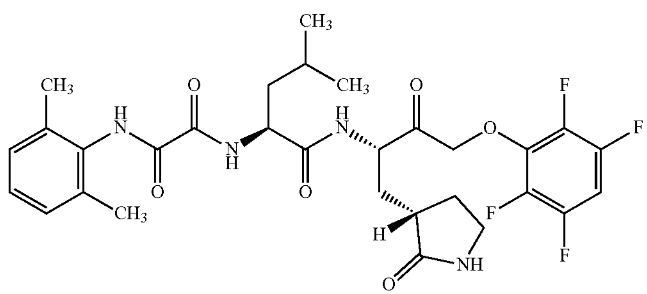 [SMILES: Cc1cccc(C)c1NC(=O)C(=O)N[C@@H](CC(C)C)C(=O)N[C@@H](C[C@@H]1CCNC1=O)C(=O)COc1c(F)c(F)cc(F)c1F] | N1-(2,6-dimethylphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 623.2400 | **** |

TABLE 1-continued

| Compound | Structure | IUPAC | LCMS [M + 1] | EC50, uM (Hela) |
|---|---|---|---|---|
| 65 | 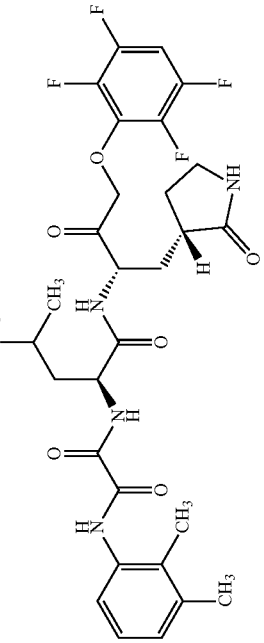 | N1-(2,3-dimethylphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 623.4540 | **** |
| 66 | 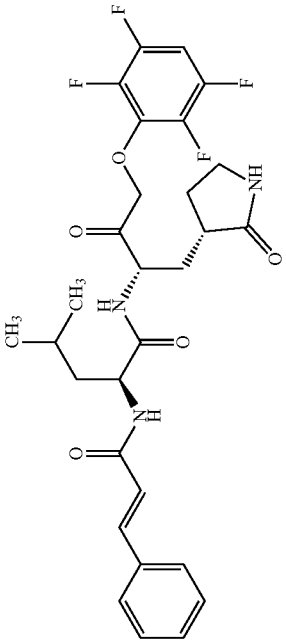 | (S)-2-cinnamamido-4-methyl-N-((S)-3-oxo-1-(((S)-2-oxopyrrolidin-3-yl)-4-(2,3,5,6-tetrafluorophenoxy)butan-2-yl)pentanamide | 578.3855 | *** |
| 67 | 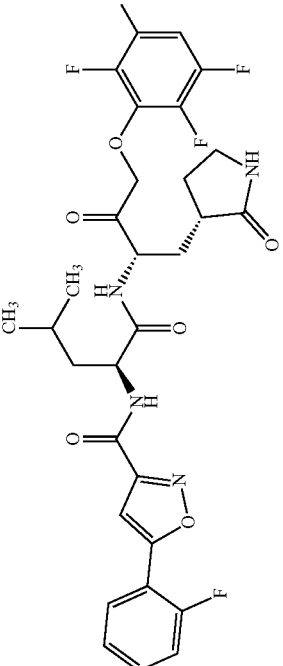 | 5-(2-fluorophenyl)-N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)isoxazole-3-carboxamide | 637.2000 | ** |

TABLE 1-continued

| Compound | Structure | IUPAC | LCMS [M + 1] | EC50, uM (Hela) |
|---|---|---|---|---|
| 68 | 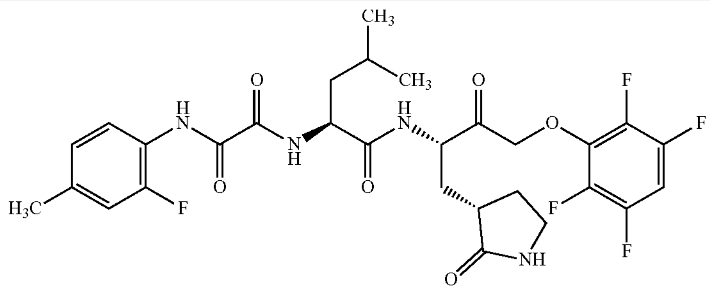 [SMILES: Cc1ccc(NC(=O)C(=O)N[C@@H](CC(C)C)C(=O)N[C@@H](C[C@@H]2CCNC2=O)C(=O)COc2c(F)c(F)cc(F)c2F)c(F)c1] | N1-(2-fluoro-4-methylphenyl)-N2-((S)-4-methyl-1-oxo-1-(((S)-3-oxo-1-((S)-2-oxopyrrolidin-3-yl)-2-(2,3,5,6-tetrafluorophenoxy)butan-2-yl)amino)pentan-2-yl)oxalamide | 627.4300 | **** |
| 69 | 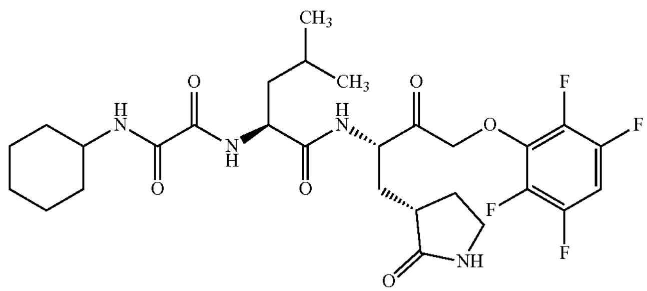 [SMILES: CC(C)C[C@H](NC(=O)C(=O)NC1CCCCC1)C(=O)N[C@@H](C[C@@H]1CCNC1=O)C(=O)COc1c(F)c(F)cc(F)c1F] | N1-cyclohexyl-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 601.2600 | *** |
| 70 | 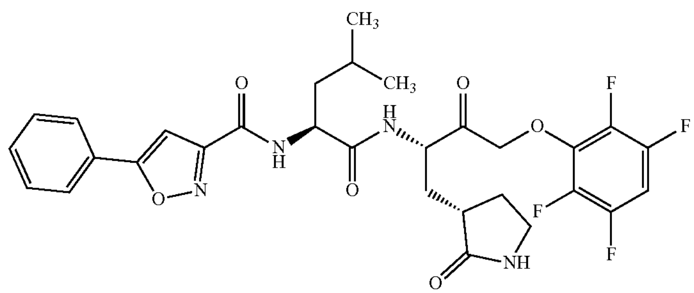 [SMILES: CC(C)C[C@H](NC(=O)c1cc(-c2ccccc2)on1)C(=O)N[C@@H](C[C@@H]1CCNC1=O)C(=O)COc1c(F)c(F)cc(F)c1F] | N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-5-phenylisoxazole-3-carboxamide | 619.21 | ** |

TABLE 1-continued

| Compound | Structure | IUPAC | LCMS [M + 1] | EC50, uM (Hela) |
|---|---|---|---|---|
| 71 | 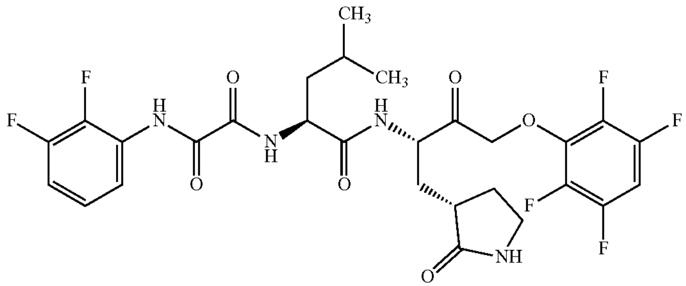 [SMILES: CC(C)C[C@H](NC(=O)C(=O)Nc1cccc(F)c1F)C(=O)N[C@@H](C[C@@H]1CCNC1=O)C(=O)COc1c(F)c(F)cc(F)c1F] | N1-(2,3-difluorophenyl)-N2-((S)-4-methyl-1-oxo-1-(((S)-3-oxo-1-(((S)-2-oxopyrrolidin-3-yl)-4-(2,3,5,6-tetrafluorophenoxy)butan-2-yl)amino)pentan-2-yl)oxalamide | 631.19 | *** |
| 72 | 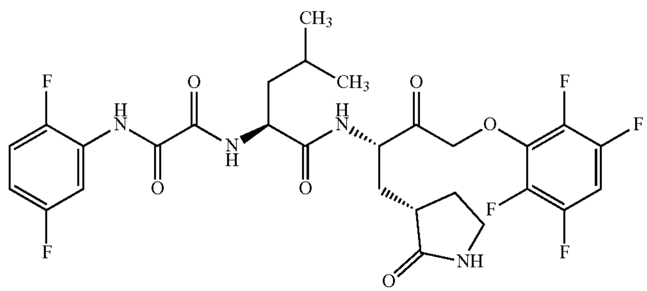 [SMILES: CC(C)C[C@H](NC(=O)C(=O)Nc1cc(F)ccc1F)C(=O)N[C@@H](C[C@@H]1CCNC1=O)C(=O)COc1c(F)c(F)cc(F)c1F] | N1-(2,5-difluorophenyl)-N2-((S)-4-methyl-1-oxo-1-(((S)-3-oxo-1-(((S)-2-oxopyrrolidin-3-yl)-4-(2,3,5,6-tetrafluorophenoxy)butan-2-yl)amino)pentan-2-yl)oxalamide | 631.4174 | *** |
| 73 | 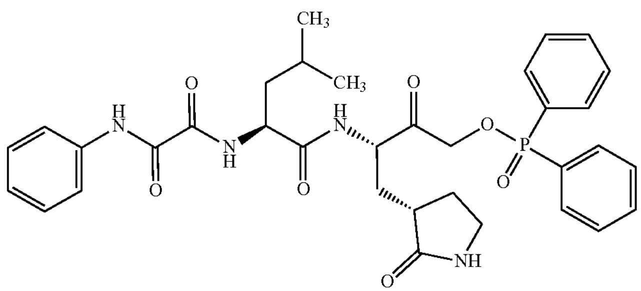 [SMILES: CC(C)C[C@H](NC(=O)C(=O)Nc1ccccc1)C(=O)N[C@@H](C[C@@H]1CCNC1=O)C(=O)COP(=O)(c1ccccc1)c1ccccc1] | (S)-3-((S)-4-methyl-2-(2-oxo-2-(phenylamino)acetamido)-pentanamido)-2-oxo-4-((S)-2-oxopyrrolidin-3-yl)butyl-diphenylphosphinate | 646.9800 | *** |

TABLE 1-continued

| Compound | Structure | IUPAC | LCMS [M + 1] | EC50, uM (Hela) |
|---|---|---|---|---|
| 74 | 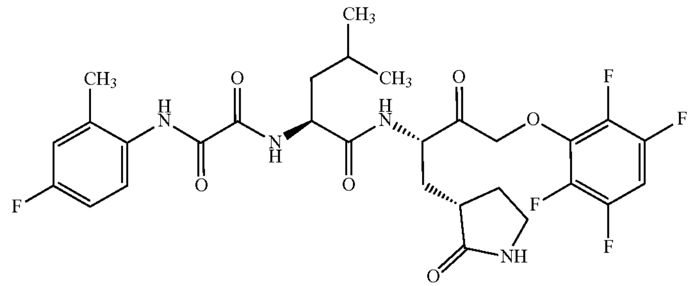 [SMILES: Cc1cc(F)ccc1NC(=O)C(=O)N[C@@H](CC(C)C)C(=O)N[C@@H](C[C@@H]1CCNC1=O)C(=O)COc1c(F)c(F)cc(F)c1F] | N1-(4-fluoro-2-methylphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 627.4357 | ** |
| 75 | 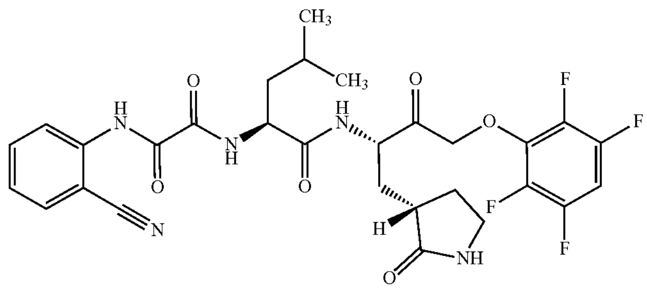 [SMILES: CC(C)C[C@H](NC(=O)C(=O)Nc1ccccc1C#N)C(=O)N[C@@H](C[C@@H]1CCNC1=O)C(=O)COc1c(F)c(F)cc(F)c1F] | N1-(2-cyanophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 620.4496 | *** |
| 76 | 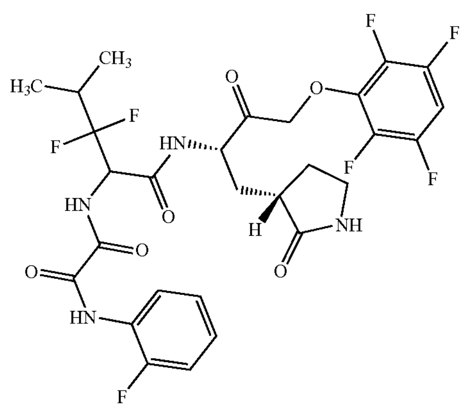 [SMILES: CC(C)C(F)(F)C(NC(=O)C(=O)Nc1ccccc1F)C(=O)N[C@@H](C[C@@H]1CCNC1=O)C(=O)COc1c(F)c(F)cc(F)c1F] | N1-(3,3-difluoro-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(2-fluorophenyl)oxalamide | 649.4075 | *** |

TABLE 1-continued

| Compound | Structure | IUPAC | LCMS [M + 1] | EC50, uM (Hela) |
|---|---|---|---|---|
| 77 | 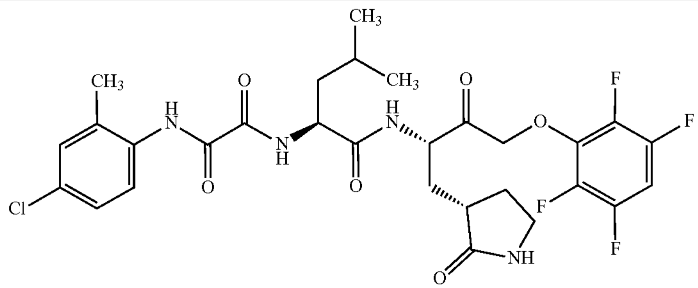 [SMILES: Cc1cc(Cl)ccc1NC(=O)C(=O)N[C@@H](CC(C)C)C(=O)N[C@@H](C[C@@H]1CCNC1=O)C(=O)COc1c(F)c(F)cc(F)c1F] | N1-(4-chloro-2-methylphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 643.4350 | **** |
| 78 | 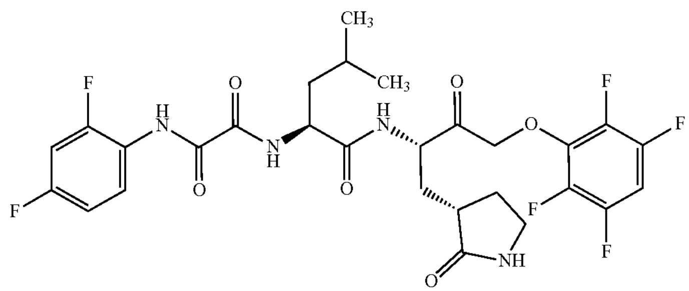 [SMILES: CC(C)C[C@H](NC(=O)C(=O)Nc1ccc(F)cc1F)C(=O)N[C@@H](C[C@@H]1CCNC1=O)C(=O)COc1c(F)c(F)cc(F)c1F] | N1-(2,4-difluorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 631.4441 | **** |
| 79 | 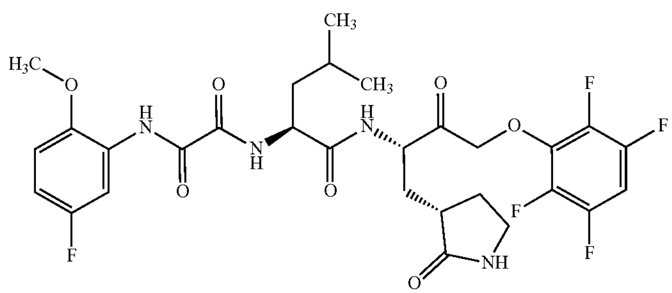 [SMILES: COc1ccc(F)cc1NC(=O)C(=O)N[C@@H](CC(C)C)C(=O)N[C@@H](C[C@@H]1CCNC1=O)C(=O)COc1c(F)c(F)cc(F)c1F] | N1-(5-fluoro-2-methoxyphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 643.4712 | *** |

TABLE 1-continued

| Compound | Structure | IUPAC | LCMS [M + 1] | EC50, uM (Hela) |
|---|---|---|---|---|
| 80 | 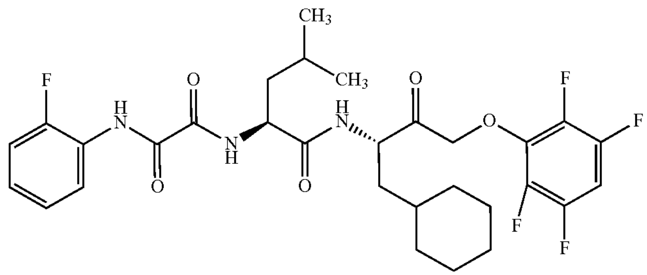 [SMILES: CC(C)C[C@H](NC(=O)C(=O)Nc1ccccc1F)C(=O)N[C@@H](CC1CCCCC1)C(=O)COc1c(F)c(F)cc(F)c1F] | N1-((S)-1-(((S)-1-cyclohexyl-3-oxo-4-(2,3,5,6-tetrafluorophenoxy)butan-2-yl)amino)-4-methyl-1-oxopentan-2-yl)-N2-(2-fluorophenyl)oxalamide | 612.4684 | >1 μM |
| 81 | 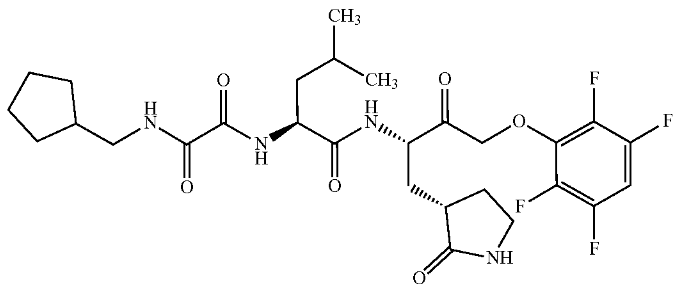 [SMILES: CC(C)C[C@H](NC(=O)C(=O)NCC1CCCC1)C(=O)N[C@@H](C[C@@H]1CCNC1=O)C(=O)COc1c(F)c(F)cc(F)c1F] | N1-(cyclopentylmethyl)-N2-((S)-4-methyl-1-oxo-1-(((S)-2-oxopyrrolidin-3-yl)-4-(2,3,5,6-tetrafluorophenoxy)butan-2-yl)amino)pentan-2-yl)oxalamide | 601.8700 | *** |
| 82 | 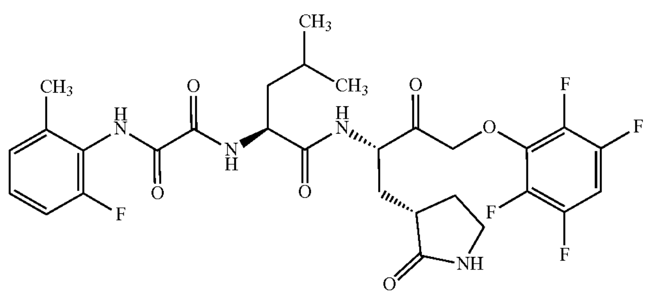 [SMILES: Cc1cccc(F)c1NC(=O)C(=O)N[C@@H](CC(C)C)C(=O)N[C@@H](C[C@@H]1CCNC1=O)C(=O)COc1c(F)c(F)cc(F)c1F] | N1-(2-fluoro-6-methylphenyl)-N2-((S)-4-methyl-1-oxo-1-((((S)-2-oxopyrrolidin-3-yl)-4-(2,3,5,6-tetrafluorophenoxy)butan-2-yl)amino)pentan-2-yl)oxalamide | 627.4017 | **** |

TABLE 1-continued

| Compound | Structure | IUPAC | LCMS [M + 1] | EC50, uM (Hela) |
|---|---|---|---|---|
| 83 | 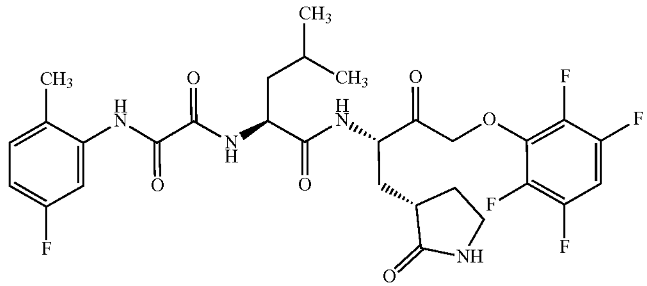 [SMILES: Cc1ccc(F)cc1NC(=O)C(=O)N[C@@H](CC(C)C)C(=O)N[C@@H](C[C@@H]1CCNC1=O)C(=O)COc1c(F)c(F)cc(F)c1F] | N1-(5-fluoro-2-methylphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 627.4101 | **** |
| 84 | 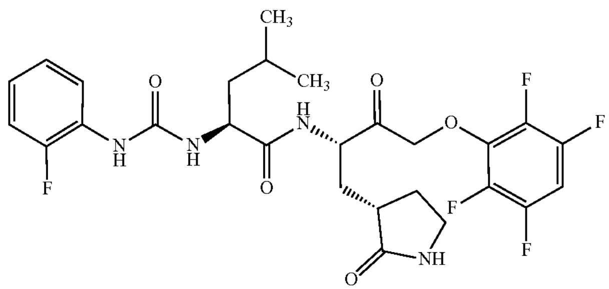 [SMILES: CC(C)C[C@H](NC(=O)Nc1ccccc1F)C(=O)N[C@@H](C[C@@H]1CCNC1=O)C(=O)COc1c(F)c(F)cc(F)c1F] | (S)-2-(3-(2-fluorophenyl)ureido)-4-methyl-N-((S)-3-oxo-1-((S)-2-oxopyrrolidin-3-yl)-4-(2,3,5,6-tetrafluorophenoxy)butan-2-yl)pentanamide | 585.6600 | *** |
| 85 | 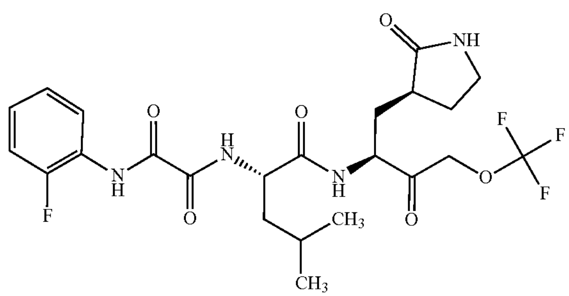 [SMILES: CC(C)C[C@H](NC(=O)C(=O)Nc1ccccc1F)C(=O)N[C@@H](C[C@@H]1CCNC1=O)C(=O)COC(F)(F)F] | N1-(2-fluorophenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 533.0600 | **** |

TABLE 1-continued

| Compound | Structure | IUPAC | LCMS [M + 1] | EC50, uM (Hela) |
|---|---|---|---|---|
| 86 | 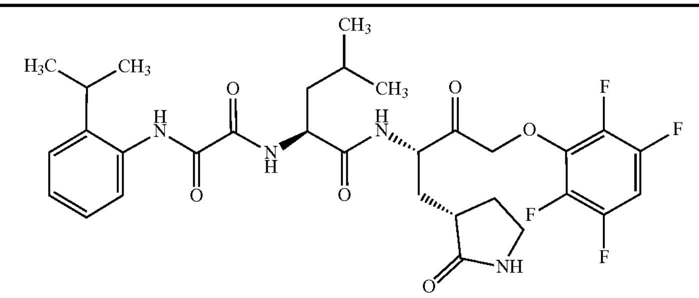 | N1-(2-isopropylphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 637.2600 | **** |
| 87 | 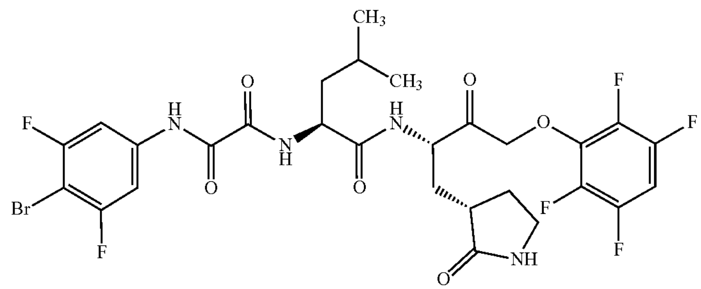 [SMILES: CC(C)C[C@H](NC(=O)C(=O)Nc1cc(F)c(Br)c(F)c1)C(=O)N[C@@H](C[C@@H]1CCNC1=O)C(=O)COc1c(F)c(F)cc(F)c1F] | N1-(4-bromo-3,5-difluorophenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 709.1000 | *** |
| 88 | 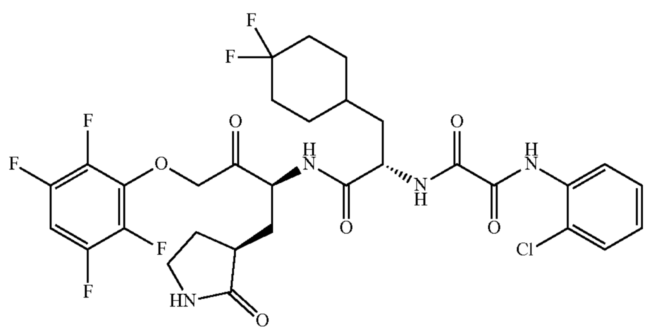 [SMILES: O=C(Nc1ccccc1Cl)C(=O)N[C@@H](CC1CCC(F)(F)CC1)C(=O)N[C@@H](C[C@@H]1CCNC1=O)C(=O)COc1c(F)c(F)cc(F)c1F] | N1-(2-chlorophenyl)-N2-((S)-3-(4,4-difluorocyclohexyl)-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide | 705.1800 | *** |

TABLE 1-continued

| Compound | Structure | IUPAC | LCMS [M + 1] | EC50, uM (Hela) |
|---|---|---|---|---|
| 89 | 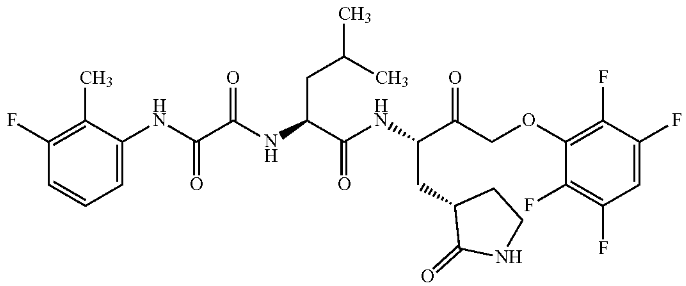 | N1-(3-fluoro-2-methylphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 627.2200 | **** |
| 90 | 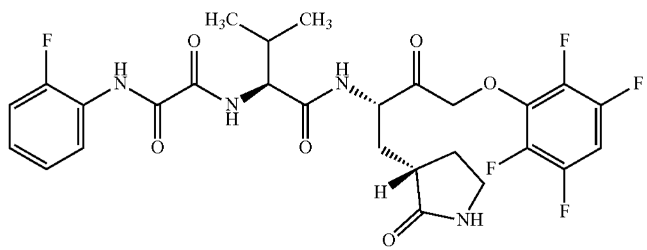 [SMILES: CC(C)[C@H](NC(=O)C(=O)Nc1ccccc1F)C(=O)N[C@@H](C[C@@H]1CCNC1=O)C(=O)COc1c(F)c(F)cc(F)c1F] | N1-(2-fluorophenyl)-N2-((S)-3-methyl-1-oxo-1-(((S)-3-oxo-1-((S)-2-oxopyrrolidin-3-yl)-4-(2,3,5,6-tetrafluorophenoxy)butan-2-yl)amino)butan-2-yl)oxalamide | 599.1800 | *** |
| 91 | 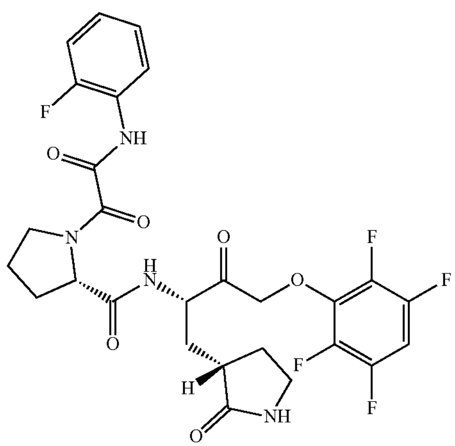 [SMILES: O=C(Nc1ccccc1F)C(=O)N1CCC[C@H]1C(=O)N[C@@H](C[C@@H]1CCNC1=O)C(=O)COc1c(F)c(F)cc(F)c1F] | (S)-1-(2-((2-fluorophenyl)amino)-2-oxoacetyl)-N-((S)-3-oxo-1-((S)-2-oxopyrrolidin-3-yl)-4-(2,3,5,6-tetrafluorophenoxy)butan-2-yl)pyrrolidine-2-carboxamide | 597.1700 | * |

TABLE 1-continued

| Compound | Structure | IUPAC | LCMS [M + 1] | EC50, uM (Hela) |
|---|---|---|---|---|
| 92 | 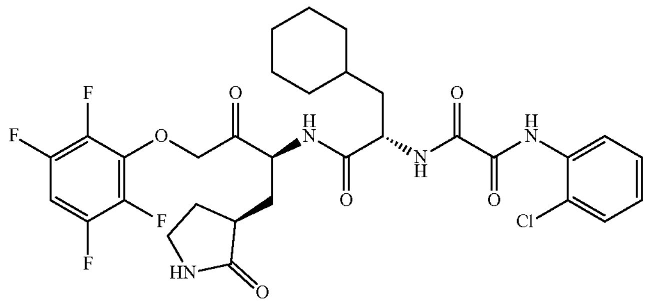 | N1-(2-chlorophenyl)-N2-((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide | 669.3252 | **** |
| 93 | 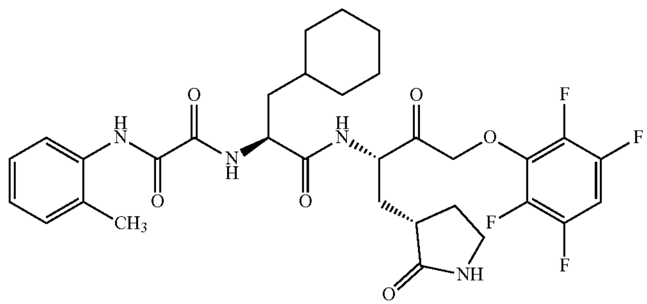 [SMILES: Cc1ccccc1NC(=O)C(=O)N[C@@H](CC1CCCCC1)C(=O)N[C@@H](C[C@@H]1CCNC1=O)C(=O)COc1c(F)c(F)cc(F)c1F] | N1-((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N2-(o-tolyl)oxalamide | 649.3784 | **** |
| 94 | 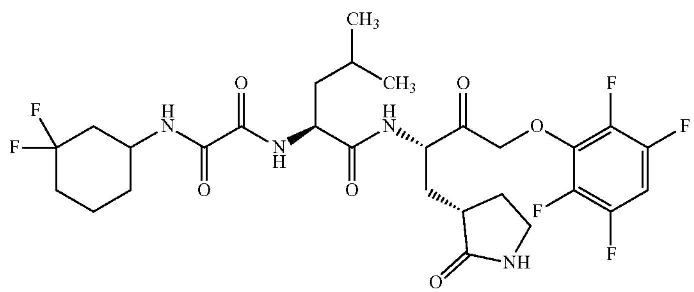 [SMILES: CC(C)C[C@H](NC(=O)C(=O)NC1CCCC(F)(F)C1)C(=O)N[C@@H](C[C@@H]1CCNC1=O)C(=O)COc1c(F)c(F)cc(F)c1F] | N1-(3,3-difluorocyclohexyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 637.3500 | *** |

TABLE 1-continued

| Compound | Structure | IUPAC | LCMS [M + 1] | EC50, uM (Hela) |
|---|---|---|---|---|
| 95 | 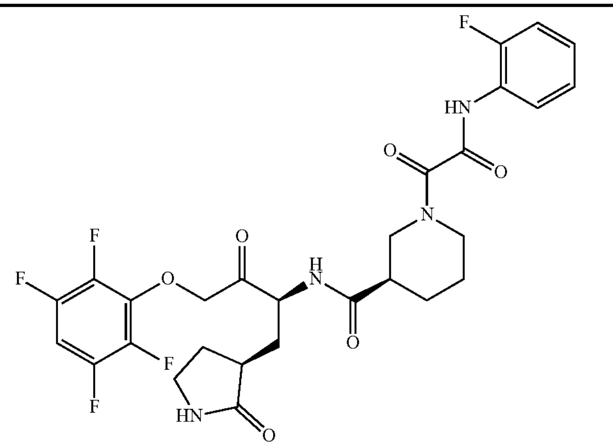 | (R)-1-(2-((2-fluorophenyl)amino)-2-oxoacetyl)-N-((S)-3-oxo-1-((S)-2-oxopyrrolidin-3-yl)-4-(2,3,5,6-tetrafluorophenoxy)butan-2-yl)piperidine-3-carboxamide | 611.6172 | >1 μM |
| 96 | 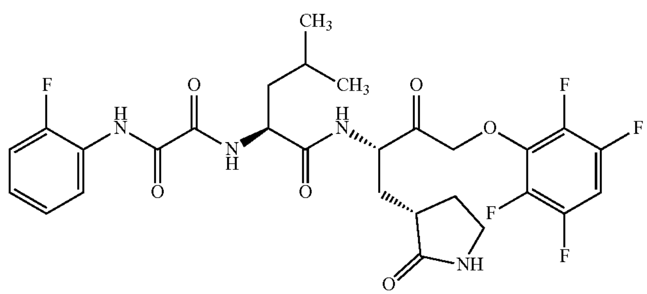 [SMILES: CC(C)C[C@H](NC(=O)C(=O)Nc1ccccc1F)C(=O)N[C@@H](C[C@@H]1CCNC1=O)C(=O)COc1c(F)c(F)cc(F)c1F] | N1-(4-bromo-2-fluorophenyl)-N2-((S)-4-methyl-1-oxo-1-((((S)-3-oxo-1-((S)-2-oxopyrrolidin-3-yl)-4-(2,3,5,6-tetrafluorophenoxy)butan-2-yl)amino)pentan-2-yl)oxalamide | 693.3135 | *** |
| 97 | 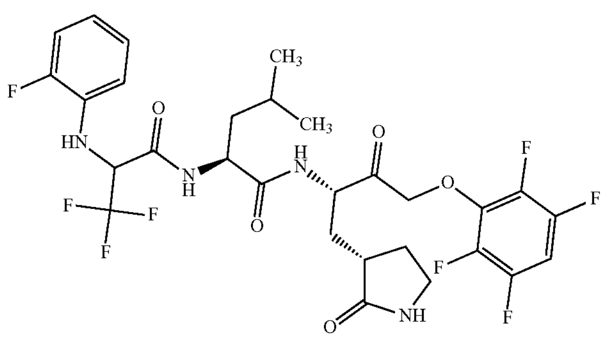 [SMILES: CC(C)C[C@H](NC(=O)C(Nc1ccccc1F)C(F)(F)F)C(=O)N[C@@H](C[C@@H]1CCNC1=O)C(=O)COc1c(F)c(F)cc(F)c1F] | (2S)-4-methyl-N-((S)-3-oxo-1-((S)-2-oxopyrrolidin-3-yl)-4-(2,3,5,6-tetrafluorophenoxy)butan-2-yl)-2-(3,3,3-trifluoro-2-((2-fluorophenyl)amino)propanamido)-pentanamide | 667.2088 | ** |

TABLE 1-continued

| Compound | Structure | IUPAC | LCMS [M + 1] | EC50, uM (Hela) |
|---|---|---|---|---|
| 98 | 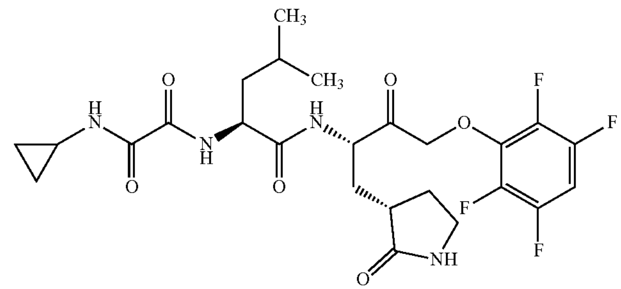 [SMILES: CC(C)C[C@H](NC(=O)C(=O)NC1CC1)C(=O)N[C@@H](C[C@@H]1CCNC1=O)C(=O)COc1c(F)c(F)cc(F)c1F] | N1-cyclopropyl-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 559.2100 | *** |
| 99 | 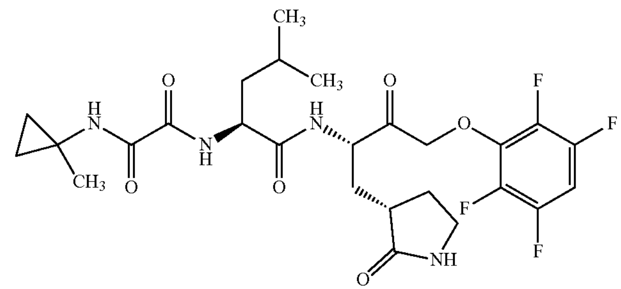 [SMILES: CC(C)C[C@H](NC(=O)C(=O)NC1(C)CC1)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(1-methyl-cyclopropyl)oxalamide | 573.2300 | *** |
| 100 | 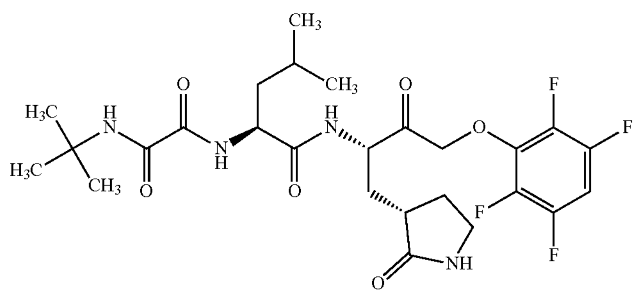 [SMILES: CC(C)C[C@H](NC(=O)C(=O)NC(C)(C)C)C(=O)N[C@@H](C[C@@H]1CCNC1=O)C(=O)COc1c(F)c(F)cc(F)c1F] | N1-(tert-butyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 575.2400 | *** |

TABLE 1-continued

| Compound | Structure | IUPAC | LCMS [M + 1] | EC50, uM (Hela) |
|---|---|---|---|---|
| 101 | 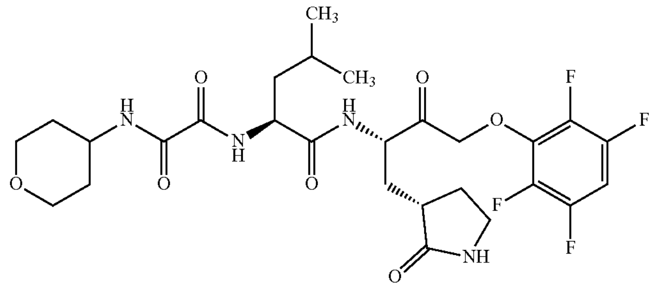 [SMILES: CC(C)C[C@H](NC(=O)C(=O)NC1CCOCC1)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(tetrahydro-2H-pyran-4-yl)oxalamide | 603.2400 | *** |
| 102 | 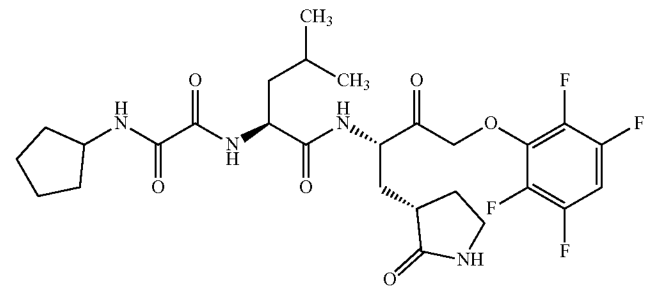 [SMILES: CC(C)C[C@H](NC(=O)C(=O)NC1CCCC1)C(=O)N[C@@H](C[C@@H]1CCNC1=O)C(=O)COc1c(F)c(F)cc(F)c1F] | N1-cyclopentyl-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 587.2400 | *** |
| 103 | 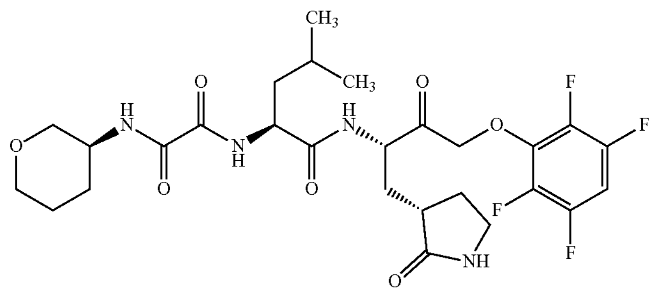 [SMILES: CC(C)C[C@H](NC(=O)C(=O)N[C@H]1CCCOC1)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-((S)-tetrahydro-2H-pyran-3-yl)oxalamide | 603.4348 | *** |

TABLE 1-continued

| Compound | Structure | IUPAC | LCMS [M + 1] | EC50, uM (Hela) |
|---|---|---|---|---|
| 104 | 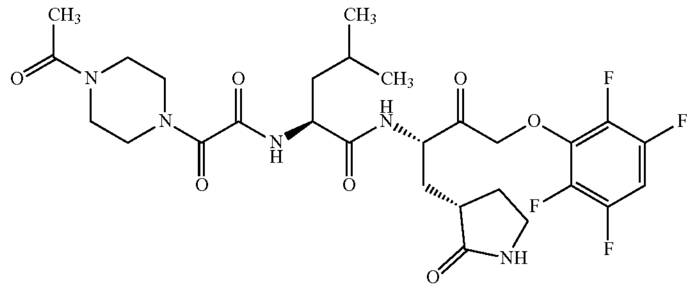 [SMILES: CC(=O)N1CCN(C(=O)C(=O)N[C@@H](CC(C)C)C(=O)N[C@@H](C[C@@H]2CCNC2=O)C(=O)COc2c(F)c(F)cc(F)c2F)CC1] | (S)-2-(2-(4-acetylpiperazin-1-yl)-2-oxoacetamido)-4-methyl-N-((S)-3-oxo-1-(((S)-2-oxopyrrolidin-3-yl)-4-(2,3,5,6-tetrafluorophenoxy)butan-2-yl)pentanamide | 630.1500 | >1 μM |
| 105 | 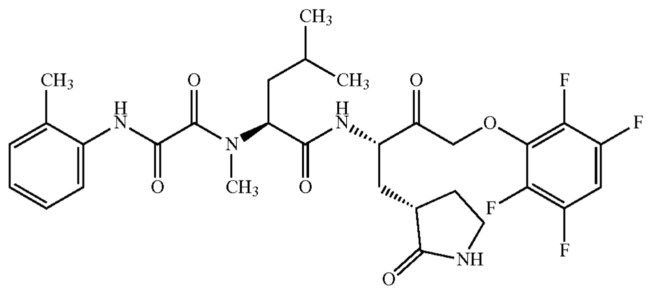 [SMILES: Cc1ccccc1NC(=O)C(=O)N(C)[C@@H](CC(C)C)C(=O)N[C@@H](C[C@@H]1CCNC1=O)C(=O)COc1c(F)c(F)cc(F)c1F] | N1-methyl-N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(o-tolyl)oxalamide | 623.2400 | >1 μM |
| 106 | 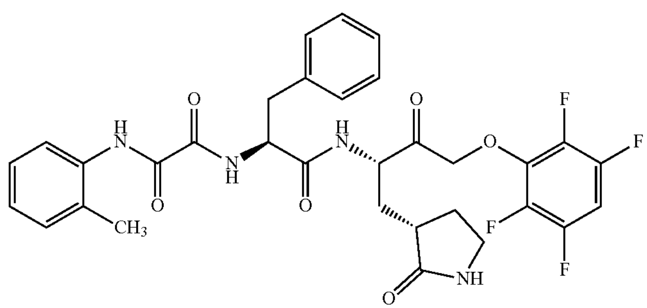 [SMILES: Cc1ccccc1NC(=O)C(=O)N[C@@H](Cc1ccccc1)C(=O)N[C@@H](C[C@@H]1CCNC1=O)C(=O)COc1c(F)c(F)cc(F)c1F] | N1-((S)-1-oxo-1-(((S)-3-oxo-1-((S)-2-oxopyrrolidin-3-yl)-4-(2,3,5,6-tetrafluorophenoxy)butan-2-yl)amino)-3-phenylpropan-2-yl)-N2-(o-tolyl)oxalamide | 643.2100 | **** |

TABLE 1-continued

| Compound | Structure | IUPAC | LCMS [M + 1] | EC50, uM (Hela) |
|---|---|---|---|---|
| 107 | 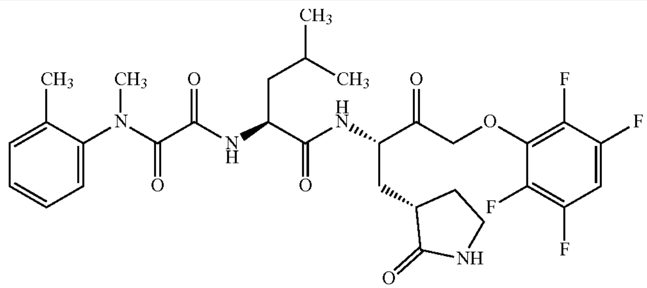 [SMILES: Cc1ccccc1N(C)C(=O)C(=O)N[C@@H](CC(C)C)C(=O)N[C@@H](C[C@@H]1CCNC1=O)C(=O)COc1c(F)c(F)cc(F)c1F] | N1-methyl-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N1-(o-tolyl)oxalamide | 623.2400 | ** |
| 108 | 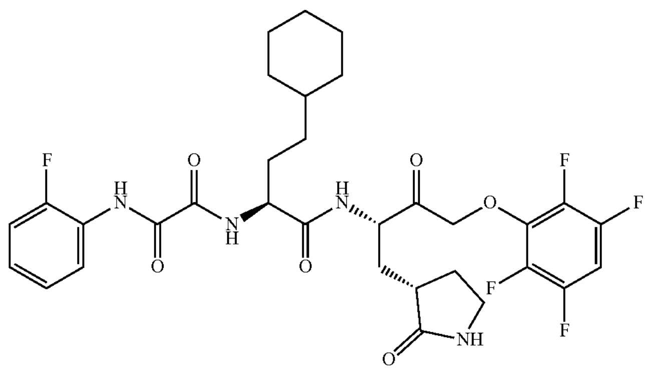 [SMILES: O=C(Nc1ccccc1F)C(=O)N[C@@H](CCC1CCCCC1)C(=O)N[C@@H](C[C@@H]1CCNC1=O)C(=O)COc1c(F)c(F)cc(F)c1F] | N1-((S)-4-cyclohexyl-1-oxo-1-(((S)-3-oxo-1-((S)-2-oxopyrrolidin-3-yl)-4-(2,3,5,6-tetrafluorophenoxy)butan-2-yl)amino)butan-2-yl)-N2-(2-fluorophenyl)oxalamide | 667.2500 | ** |
| 109 | 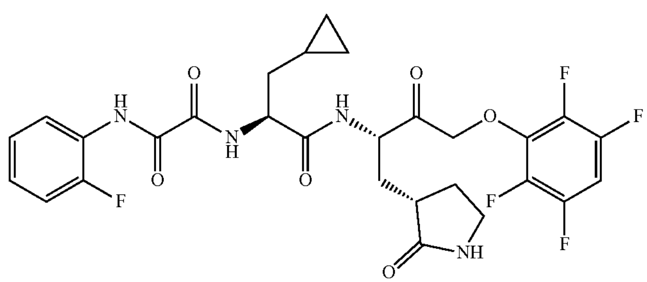 [SMILES: O=C(Nc1ccccc1F)C(=O)N[C@@H](CC1CC1)C(=O)N[C@@H](C[C@@H]1CCNC1=O)C(=O)COc1c(F)c(F)cc(F)c1F] | N1-((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N2-(2-fluorophenyl)oxalamide | 611.1800 | **** |

TABLE 1-continued

| Compound | Structure | IUPAC | LCMS [M + 1] | EC50, uM (Hela) |
|---|---|---|---|---|
| 110 | 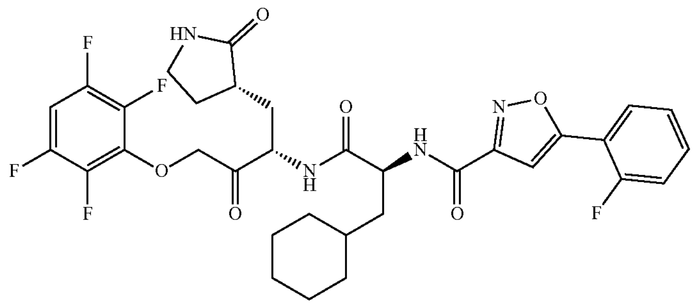 [SMILES: O=C(N[C@@H](CC1CCCCC1)C(=O)N[C@@H](C[C@@H]1CCNC1=O)C(=O)COc1c(F)c(F)cc(F)c1F)c1cc(-c2ccccc2F)on1] | N-((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)-5-(2-fluorophenyl)isoxazole-3-carboxamide | 677.2300 | ** |
| 111 | 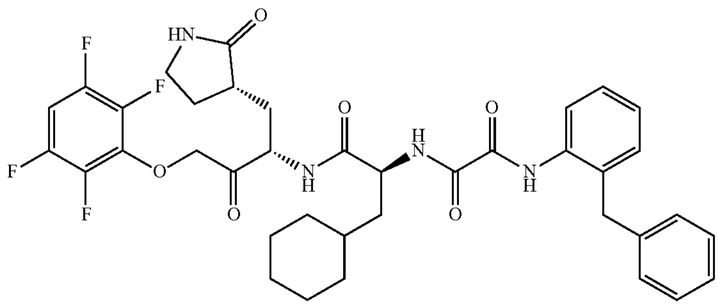 [SMILES: O=C(Nc1ccccc1Cc1ccccc1)C(=O)N[C@@H](CC1CCCCC1)C(=O)N[C@@H](C[C@@H]1CCNC1=O)C(=O)COc1c(F)c(F)cc(F)c1F] | N1-(2-benzylphenyl)-N2-((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide | 725.2900 | *** |
| 112 | 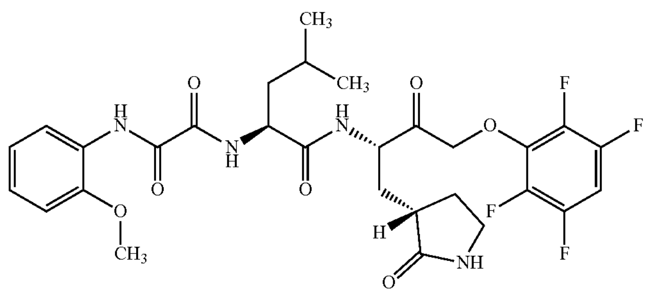 [SMILES: COc1ccccc1NC(=O)C(=O)N[C@@H](CC(C)C)C(=O)N[C@@H](C[C@@H]1CCNC1=O)C(=O)COc1c(F)c(F)cc(F)c1F] | N1-(2-methoxyphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 625.2200 | *** |

TABLE 1-continued

| Compound | Structure | IUPAC | LCMS [M + 1] | EC50, uM (Hela) |
|---|---|---|---|---|
| 113 | 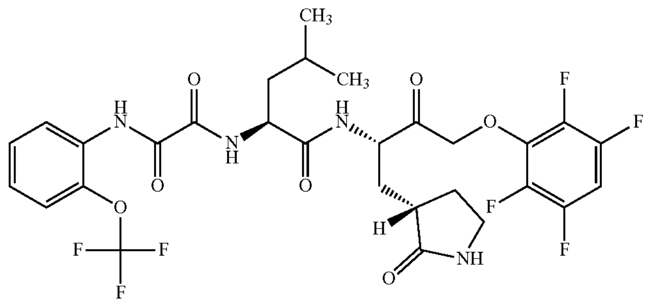 [SMILES: CC(C)C[C@H](NC(=O)C(=O)Nc1ccccc1OC(F)(F)F)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(2-(trifluoromethoxy)phenyl)oxalamide | 679.1900 | **** |
| 114 | 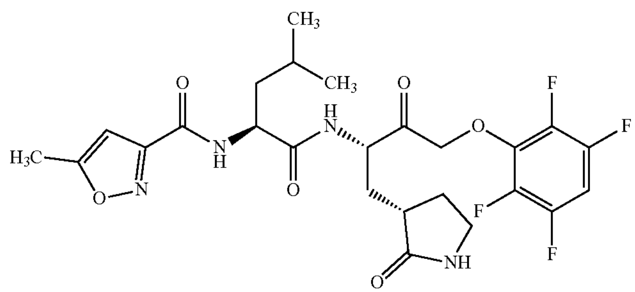 [SMILES: Cc1cc(C(=O)N[C@@H](CC(C)C)C(=O)N[C@@H](C[C@@H]2CCNC2=O)C(=O)COc2c(F)c(F)cc(F)c2F)no1] | 5-methyl-N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)isoxazole-3-carboxamide | 557.1369 | * |
| 115 | 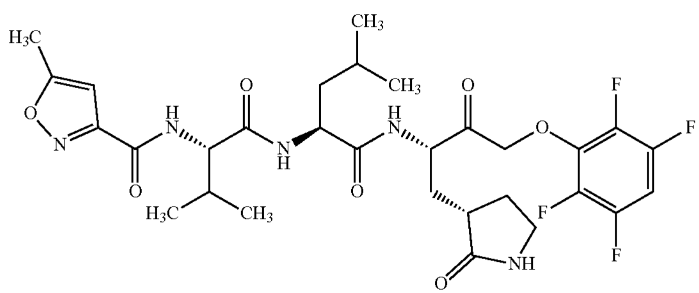 [SMILES: Cc1cc(C(=O)N[C@H](C(=O)N[C@@H](CC(C)C)C(=O)N[C@@H](C[C@@H]2CCNC2=O)C(=O)COc2c(F)c(F)cc(F)c2F)C(C)C)no1] | 5-methyl-N-((S)-3-methyl-1-(((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)amino)-1-oxobutan-2-yl)isoxazole-3-carboxamide | 656.2600 | ** |

TABLE 1-continued

| Compound | Structure | IUPAC | LCMS [M + 1] | EC50, uM (Hela) |
|---|---|---|---|---|
| 116 | 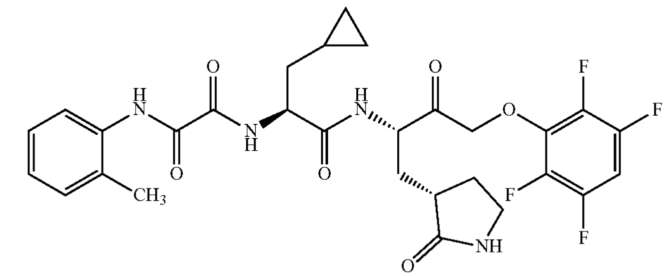 [SMILES: Cc1ccccc1NC(=O)C(=O)N[C@@H](CC1CC1)C(=O)N[C@@H](C[C@@H]1CCNC1=O)C(=O)COc1c(F)c(F)cc(F)c1F] | N1-((S)-3-cyclopropyl-1-oxo-1-(((S)-3-oxo-1-((S)-2-oxopyrrolidin-3-yl)-4-(2,3,5,6-tetrafluorophenoxy)butan-2-yl)amino)propan-2-yl)-N2-(o-tolyl)oxalamide | 607.2100 | **** |
| 117 | 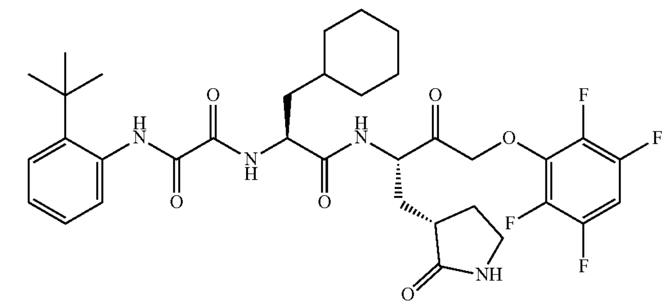 [SMILES: CC(C)(C)c1ccccc1NC(=O)C(=O)N[C@@H](CC1CCCCC1)C(=O)N[C@@H](C[C@@H]1CCNC1=O)C(=O)COc1c(F)c(F)cc(F)c1F] | N1-(2-(tert-butyl)phenyl)-N2-((S)-3-cyclohexyl-1-oxo-1-(((S)-3-oxo-1-((S)-2-oxopyrrolidin-3-yl)-4-(2,3,5,6-tetrafluorophenoxy)butan-2-yl)amino)propan-2-yl)oxalamide | 691.3000 | *** |
| 118 | 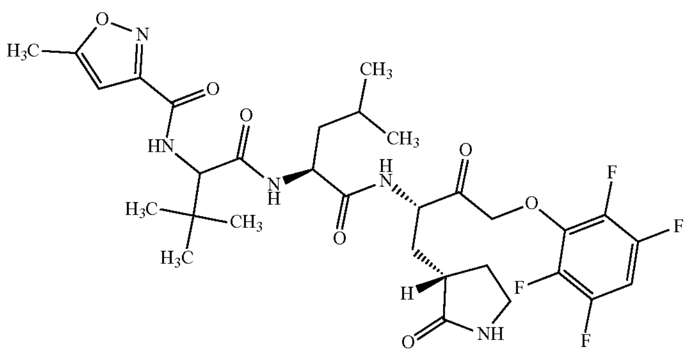 [SMILES: Cc1cc(C(=O)NC(C(=O)N[C@@H](CC(C)C)C(=O)N[C@@H](C[C@@H]2CCNC2=O)C(=O)COc2c(F)c(F)cc(F)c2F)C(C)(C)C)no1] | N-((S)-3,3-dimethyl-1-(((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)amino)-1-oxobutan-2-yl)-5-methylisoxazole-3-carboxamide | 670.2800 | ** |

TABLE 1-continued

| Compound | Structure | IUPAC | LCMS [M + 1] | EC50, uM (Hela) |
|---|---|---|---|---|
| 119 | 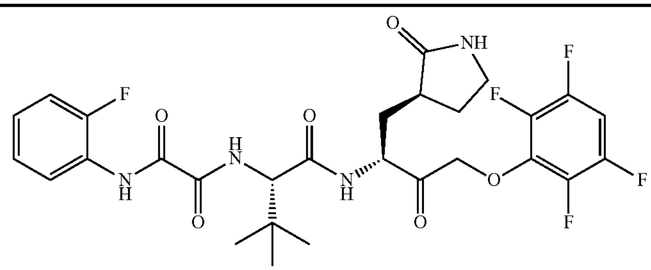 | N1-((S)-3,3-dimethyl-1-oxo-1-(((S)-3-oxo-1-((S)-2-oxopyrrolidin-3-yl)-4-(2,3,5,6-tetrafluorophenoxy)butan-2-yl)amino)butan-2-yl)-N2-(2-fluorophenyl)oxalamide | 613.2000 | ** |
| 120 | 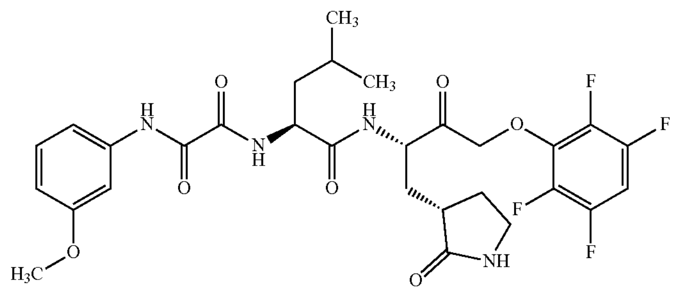 [SMILES: COc1cccc(NC(=O)C(=O)N[C@@H](CC(C)C)C(=O)N[C@@H](C[C@@H]2CCNC2=O)C(=O)COc2c(F)c(F)cc(F)c2F)c1] | N1-(3-methoxyphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 625.2207 | **** |
| 121 | 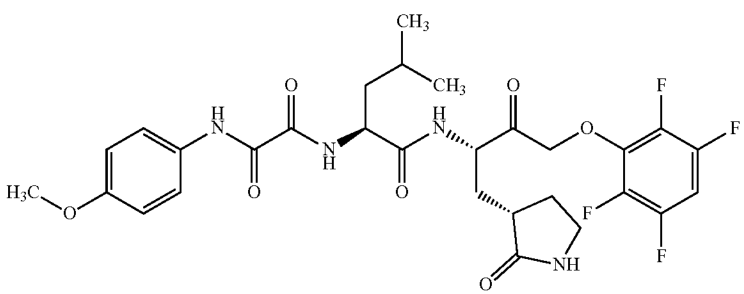 [SMILES: COc1ccc(NC(=O)C(=O)N[C@@H](CC(C)C)C(=O)N[C@@H](C[C@@H]2CCNC2=O)C(=O)COc2c(F)c(F)cc(F)c2F)cc1] | N1-(4-methoxyphenyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 625.2200 | **** |

TABLE 1-continued

| Compound | Structure | IUPAC | LCMS [M + 1] | EC50, uM (Hela) |
|---|---|---|---|---|
| 122 | 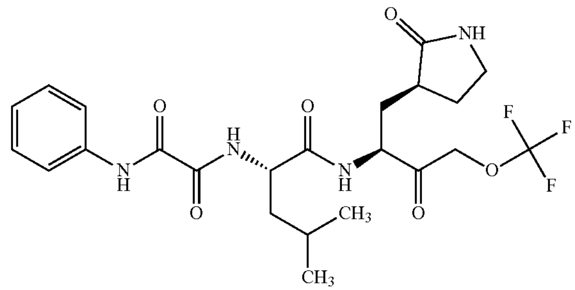 [SMILES: CC(C)C[C@H](NC(=O)C(=O)Nc1ccccc1)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-phenyloxalamide | 515.0340 | **** |
| 123 | 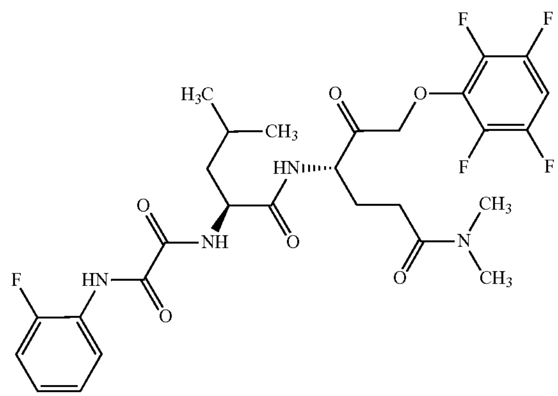 [SMILES: CC(C)C[C@H](NC(=O)C(=O)Nc1ccccc1F)C(=O)N[C@@H](CCC(=O)N(C)C)C(=O)COc1c(F)c(F)cc(F)c1F] | N1-((S)-1-(((S)-6-(dimethylamino)-2,6-dioxo-1-(2,3,5,6-tetrafluorophenoxy)hexan-3-yl)amino)-4-methyl-1-oxopentan-2-yl)-N2-(2-fluorophenyl)oxalamide | 615.2200 | *** |
| 124 | 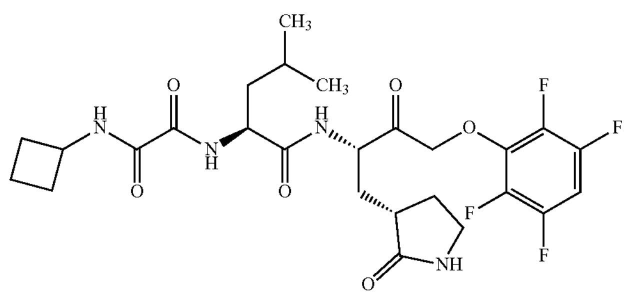 [SMILES: CC(C)C[C@H](NC(=O)C(=O)NC1CCC1)C(=O)N[C@@H](C[C@@H]1CCNC1=O)C(=O)COc1c(F)c(F)cc(F)c1F] | N1-cyclobutyl-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 573.2300 | *** |

TABLE 1-continued

| Compound | Structure | IUPAC | LCMS [M + 1] | EC50, uM (Hela) |
|---|---|---|---|---|
| 125 | 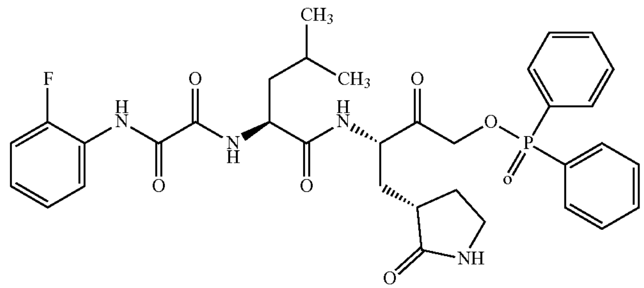 | (S)-3-((S)-2-(2-((2-fluorophenyl)amino)-2-oxoacetamido)-4-methylpentanamido)-2-oxo-4-((S)-2-oxopyrrolidin-3-yl)butyldiphenyl-phosphinate | 665.2500 | **** |
| 126 | 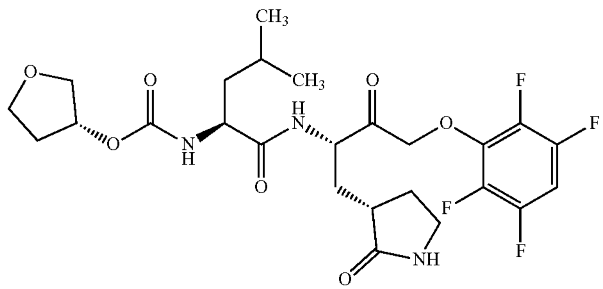 [SMILES: CC(C)C[C@H](NC(=O)O[C@@H]1CCOC1)C(=O)N[C@@H](C[C@@H]1CCNC1=O)C(=O)COc1c(F)c(F)cc(F)c1F] | (R)-tetrahydrofuran-3-yl ((S)-4-methyl-1-oxo-1-(((S)-2-oxo-1-((S)-2-oxopyrrolidin-3-yl)-4-(2,3,5,6-tetrafluorophenoxy)butan-2-yl)amino)pentan-2-yl)carbamate | 562.2100 | >1 μM |
| 127 | 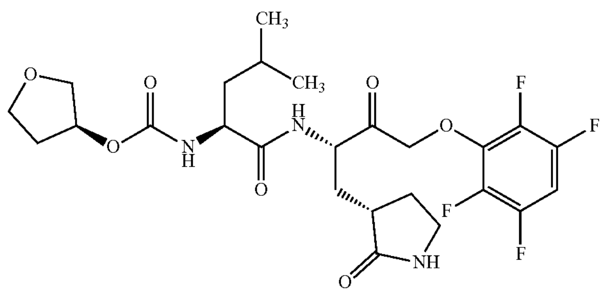 [SMILES: CC(C)C[C@H](NC(=O)O[C@H]1CCOC1)C(=O)N[C@@H](C[C@@H]1CCNC1=O)C(=O)COc1c(F)c(F)cc(F)c1F] | (S)-tetrahydrofuran-3-yl ((S)-4-methyl-1-oxo-1-(((S)-2-oxo-1-((S)-2-oxopyrrolidin-3-yl)-4-(2,3,5,6-tetrafluorophenoxy)butan-2-yl)amino)pentan-2-yl)carbamate | 562.2100 | * |

TABLE 1-continued

| Compound | Structure | IUPAC | LCMS [M + 1] | EC50, uM (Hela) |
|---|---|---|---|---|
| 128 | 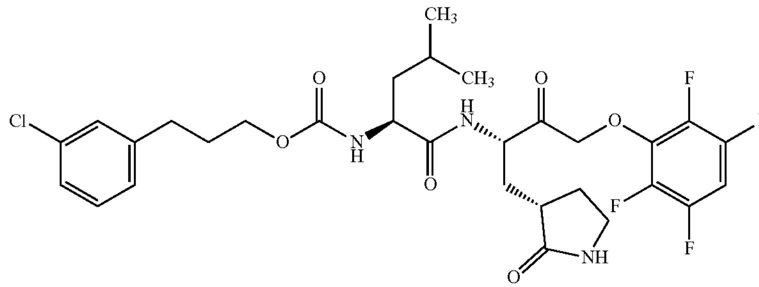 | 3-(3-chlorophenyl)propyl ((S)-4-methyl-1-oxo-1-(((S)-3-oxo-1-((S)-2-oxopyrrolidin-3-yl)-4-(2,3,5,6-Ftetrafluorophenoxy)butan-2-yl)amino)pentan-2-yl)carbamate | 644.2100 | >1 µM |
| 129 | 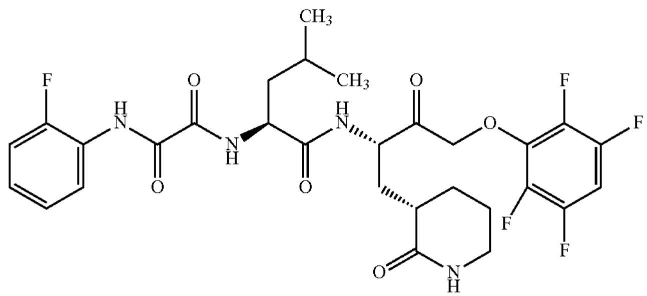 [SMILES: CC(C)C[C@H](NC(=O)C(=O)Nc1ccccc1F)C(=O)N[C@@H](C[C@@H]1CCCNC1=O)C(=O)COc1c(F)c(F)cc(F)c1F] | N1-(2-fluorophenyl)-N2-((S)-4-methyl-1-oxo-1-(((S)-3-oxo-1-((S)-2-oxopiperidin-3-yl)-4-(2,3,5,6-tetrafluorophenoxy)butan-2-yl)amino)pentan-2-yl)oxalamide | 627.2200 | **** |
| 130 | 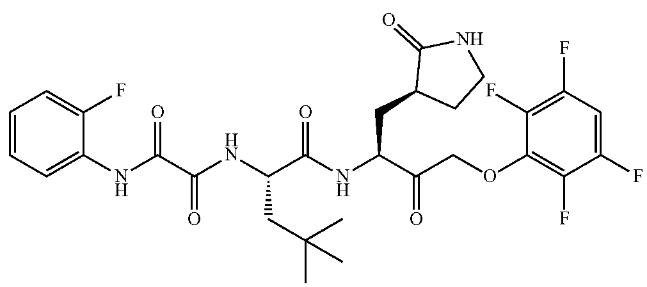 [SMILES: CC(C)(C)C[C@H](NC(=O)C(=O)Nc1ccccc1F)C(=O)N[C@@H](C[C@@H]1CCNC1=O)C(=O)COc1c(F)c(F)cc(F)c1F] | N1-((S)-4,4-dimethyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-(2-fluorophenyl)oxalamide | 627.2200 | **** |

TABLE 1-continued

| Compound | Structure | IUPAC | LCMS [M + 1] | EC50, uM (Hela) |
|---|---|---|---|---|
| 131 | 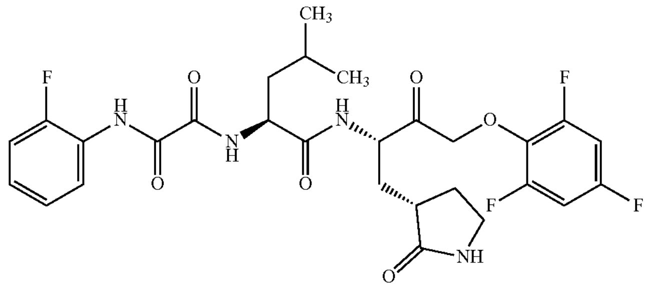 [SMILES: CC(C)C[C@H](NC(=O)C(=O)Nc1ccccc1F)C(=O)N[C@@H](C[C@@H]1CCNC1=O)C(=O)COc1c(F)cc(F)cc1F] | N1-(2-fluorophenyl)-N2-((S)-4-methyl-1-oxo-1-(((S)-2-oxopyrrolidin-3-yl)-4-(2,4,6-trifluorophenoxy)butan-2-yl)amino)pentan-2-yl)oxalamide | 595.4000 | ** |
| 132 | 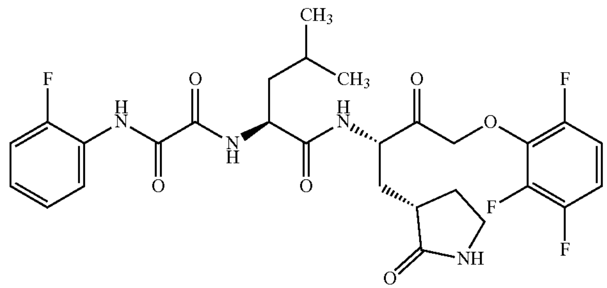 [SMILES: CC(C)C[C@H](NC(=O)C(=O)Nc1ccccc1F)C(=O)N[C@@H](C[C@@H]1CCNC1=O)C(=O)COc1c(F)ccc(F)c1F] | N1-(2-fluorophenyl)-N2-((S)-4-methyl-1-oxo-1-(((S)-2-oxopyrrolidin-3-yl)-4-(2,3,6-trifluorophenoxy)butan-2-yl)amino)pentan-2-yl)oxalamide | 595.1000 | *** |
| 133 | 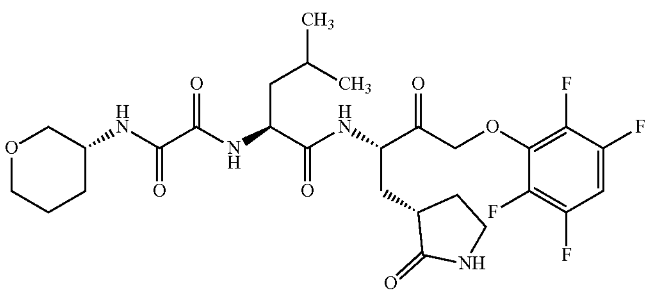 | N1-((S)-4-methyl-1-oxo-1-(((S)-2-oxopyrrolidin-3-yl)-4-(2,3,5,6-tetrafluorophenoxy)butan-2-yl)amino)pentan-2-yl)-N2-((R)-tetrahydro-2H-pyran-3-yl)oxalamide | 603.2400 | *** |

TABLE 1-continued

| Compound | Structure | IUPAC | LCMS [M + 1] | EC50, uM (Hela) |
|---|---|---|---|---|
| 134 | 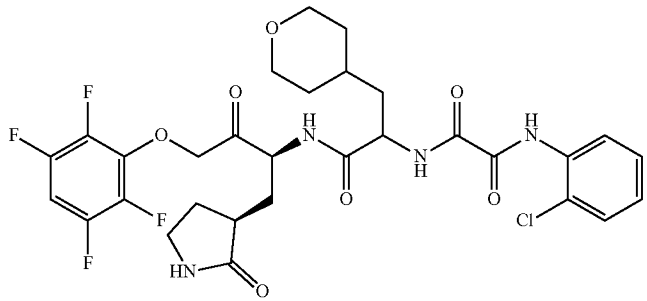 [SMILES: O=C(Nc1ccccc1Cl)C(=O)NC(CC1CCOCC1)C(=O)N[C@@H](C[C@@H]1CCNC1=O)C(=O)COc1c(F)c(F)cc(F)c1F] | N1-(2-chlorophenyl)-N2-(1-oxo-1-(((S)-3-oxo-1-((S)-2-oxopyrrolidin-3-yl)-4-(2,3,5,6-tetrafluorophenoxy)butan-2-yl)amino)-3-((tetrahydro-2H-pyran-4-yl)propan-2-yl)oxalamide | 671.3364 | **** |
| 135 | 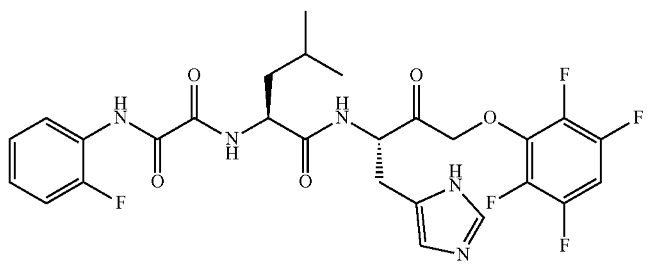 [SMILES: CC(C)C[C@H](NC(=O)C(=O)Nc1ccccc1F)C(=O)N[C@@H](Cc1cnc[nH]1)C(=O)COc1c(F)c(F)cc(F)c1F] | N1-((S)-1-(((S)-1-(1H-imidazol-5-yl)-3-oxo-4-(2,3,5,6-tetrafluorophenoxy)butan-2-yl)amino)-4-methyl-1-oxopentan-2-yl)-N2-(2-fluorophenyl)oxalamide | 596.3414 | * |
| 136 | 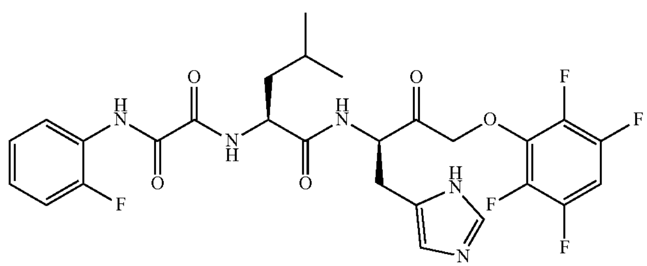 [SMILES: CC(C)C[C@H](NC(=O)C(=O)Nc1ccccc1F)C(=O)N[C@H](Cc1cnc[nH]1)C(=O)COc1c(F)c(F)cc(F)c1F] | N1-((S)-1-(((R)-1-(1H-imidazol-5-yl)-3-oxo-4-(2,3,5,6-tetrafluorophenoxy)butan-2-yl)amino)-4-methyl-1-oxopentan-2-yl)-N2-(2-fluorophenyl)oxalamide | 596.0668 | * |

TABLE 1-continued

| Compound | Structure | IUPAC | LCMS [M + 1] | EC50, uM (Hela) |
|---|---|---|---|---|
| 137 | 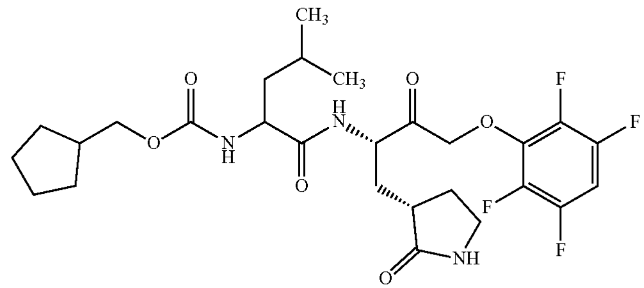 [SMILES: CC(C)CC(NC(=O)OCC1CCCC1)C(=O)N[C@@H](C[C@@H]1CCNC1=O)C(=O)COc1c(F)c(F)cc(F)c1F] | cyclopentylmethyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate | 574.4045 | * |
| 138 | 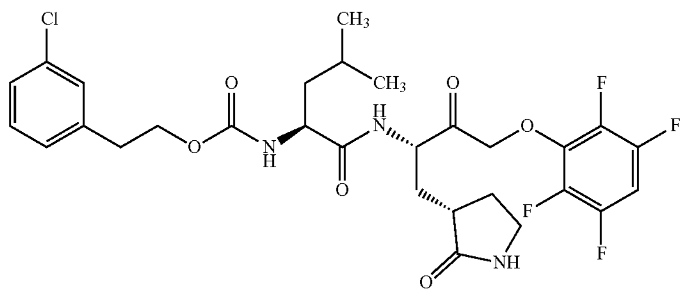 [SMILES: CC(C)C[C@H](NC(=O)OCCc1cccc(Cl)c1)C(=O)N[C@@H](C[C@@H]1CCNC1=O)C(=O)COc1c(F)c(F)cc(F)c1F] | 3-chlorophenethyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate | 630.3400 | >1 μM |
| 139 | 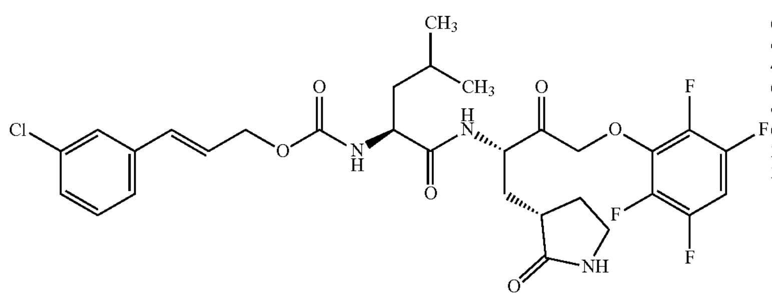 [SMILES: CC(C)C[C@H](NC(=O)OC/C=C/c1cccc(Cl)c1)C(=O)N[C@@H](C[C@@H]1CCNC1=O)C(=O)COc1c(F)c(F)cc(F)c1F] | (E)-3-(3-chlorophenyl)allyl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate | 642.3000 | >1 μM |

TABLE 1-continued

| Compound | Structure | IUPAC | LCMS [M + 1] | EC50, uM (Hela) |
|---|---|---|---|---|
| 140 | 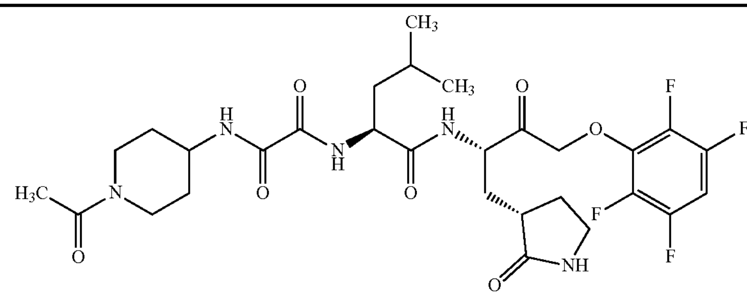 | N1-(1-acetylpiperidin-4-yl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 644.4000 | >1 μM |
| 141 | 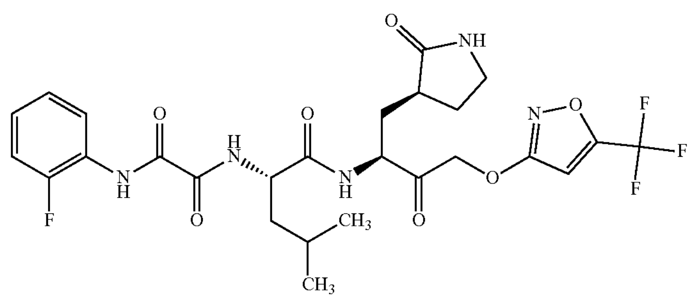 [SMILES: CC(C)C[C@H](NC(=O)C(=O)Nc1ccccc1F)C(=O)N[C@@H](C[C@@H]1CCNC1=O)C(=O)COc1cc(C(F)(F)F)on1] | N1-(2-fluorophenyl)-N2-((S)-4-methyl-1-oxo-1-(((S)-3-oxo-1-((S)-2-oxopyrrolidin-3-yl)-4-((5-(trifluoromethyl)isoxazol-3-yl)oxy)butan-2-yl)amino)pentan-2-yl)oxalamide | 600.3000 | * |
| 142 | 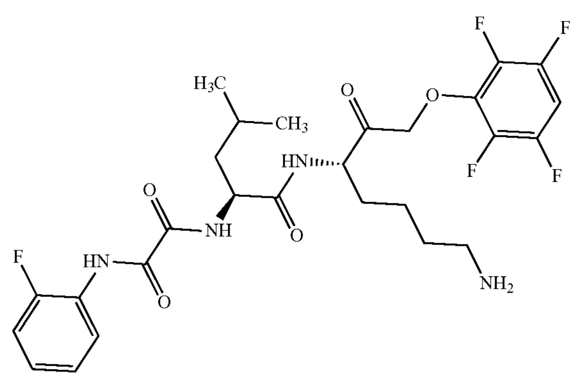 [SMILES: CC(C)C[C@H](NC(=O)C(=O)Nc1ccccc1F)C(=O)N[C@@H](CCCCN)C(=O)COc1c(F)c(F)cc(F)c1F] | N1-((S)-1-(((S)-7-amino-2-oxo-1-(2,3,5,6-tetrafluorophenoxy)heptan-3-yl)amino)-4-methyl-1-oxopentan-2-yl)-N2-(2-fluorophenyl)oxalamide | 587.3775 | **** |

TABLE 1-continued

| Compound | Structure | IUPAC | LCMS [M + 1] | EC50, uM (Hela) |
|---|---|---|---|---|
| 143 | 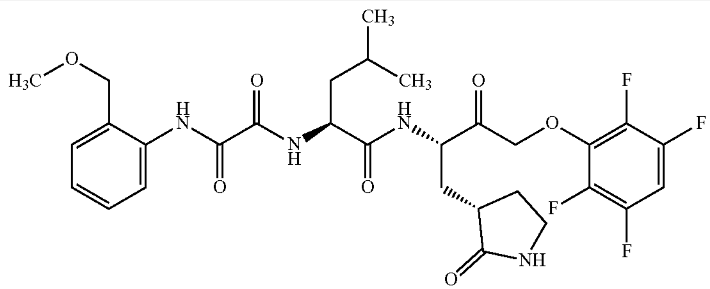 [SMILES: COCc1ccccc1NC(=O)C(=O)N[C@@H](CC(C)C)C(=O)N[C@@H](C[C@@H]1CCNC1=O)C(=O)COc1c(F)c(F)cc(F)c1F] | N1-(2-(methoxymethyl)phenyl)-N2-((S)-4-methyl-1-oxo-1-((S)-3-oxo-1-((S)-2-oxopyrrolidin-3-yl)-4-(2,3,5,6-tetrafluorophenoxy)butan-2-yl)amino)pentan-2-yl)oxalamide | 639.3000 | *** |
| 144 | 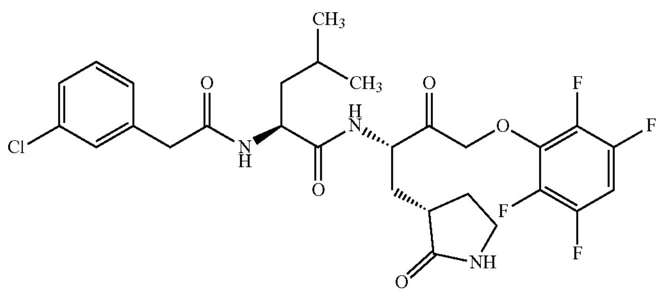 [SMILES: CC(C)C[C@H](NC(=O)Cc1cccc(Cl)c1)C(=O)N[C@@H](C[C@@H]1CCNC1=O)C(=O)COc1c(F)c(F)cc(F)c1F] | (S)-2-(2-(3-chlorophenyl)acetamido)-4-methyl-N-((S)-3-oxo-1-((S)-2-oxopyrrolidin-3-yl)-4-(2,3,5,6-tetrafluorophenoxy)butan-2-yl)pentanamide | 600.3000 | >1 μM |
| 145 | 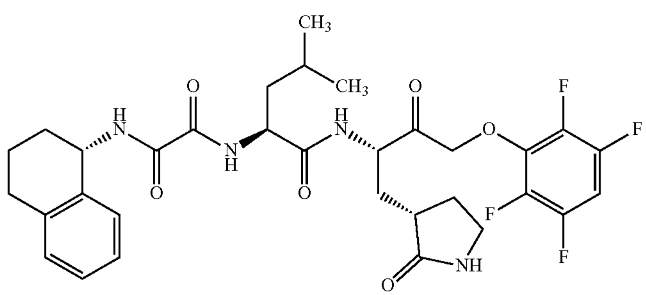 [SMILES: CC(C)C[C@H](NC(=O)C(=O)N[C@H]1CCCc2ccccc21)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-((S)-1,2,3,4-tetrahydronaphthalen-1-yl)oxalamide | 649.3200 | ** |

TABLE 1-continued

| Compound | Structure | IUPAC | LCMS [M + 1] | EC50, uM (Hela) |
|---|---|---|---|---|
| 146 | 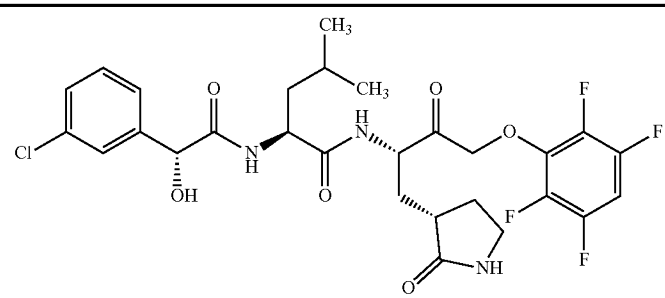 | (S)-2-((R)-2-(3-chlorophenyl)-2-hydroxyacetamido)-4-methyl-N-((S)-3-oxo-1-((S)-2-oxopyrrolidin-3-yl)-4-(2,3,5,6-tetrafluorophenoxy)butan-2-yl)pentanamide | 616.3230 | *** |
| 147 | 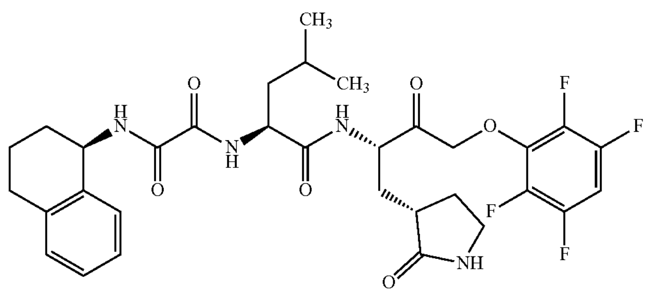 [SMILES: CC(C)C[C@H](NC(=O)C(=O)N[C@@H]1CCCc2ccccc21)C(=O)N[C@@H](C[C@@H]1CCNC1=O)C(=O)COc1c(F)c(F)cc(F)c1F] | N1-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-N2-((R)-1,2,3,4-tetrahydronaphthalen-1-yl)oxalamide | 649.3600 | * |
| 148 | 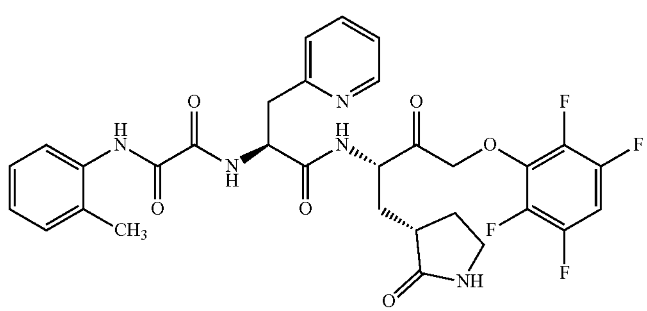 [SMILES: Cc1ccccc1NC(=O)C(=O)N[C@@H](Cc1ccccn1)C(=O)N[C@@H](C[C@@H]1CCNC1=O)C(=O)COc1c(F)c(F)cc(F)c1F] | N1-((S)-1-oxo-1-(((S)-3-oxo-1-((S)-2-oxopyrrolidin-3-yl)-4-(2,3,5,6-tetrafluorophenoxy)butan-2-yl)amino)-3-(pyridin-2-yl)propan-2-yl)-N2-(o-tolyl)oxalamide | 644.3000 | *** |

TABLE 1-continued

| Compound | Structure | IUPAC | LCMS [M + 1] | EC50, uM (Hela) |
|---|---|---|---|---|
| 149 | 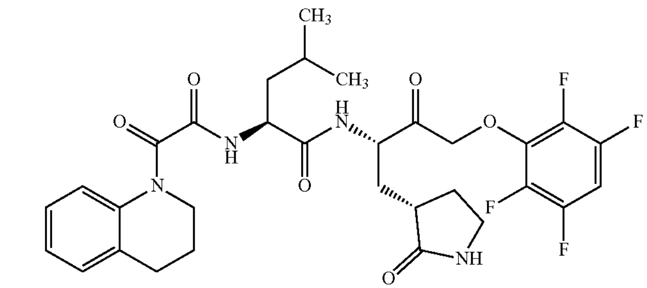 [SMILES: CC(C)C[C@H](NC(=O)C(=O)N1CCCc2ccccc21)C(=O)N[C@@H](C[C@@H]1CCNC1=O)C(=O)COc1c(F)c(F)cc(F)c1F] | (S)-2-(2-(3,4-dihydroquinolin-1(2H)-yl)-2-oxoacetamido)-4-methyl-N-((S)-3-oxo-1-((S)-2-oxopyrrolidin-3-yl)-4-(2,3,5,6-tetrafluorophenoxy)butan-2-yl)pentanamide | 635.3600 | *** |
| 150 | 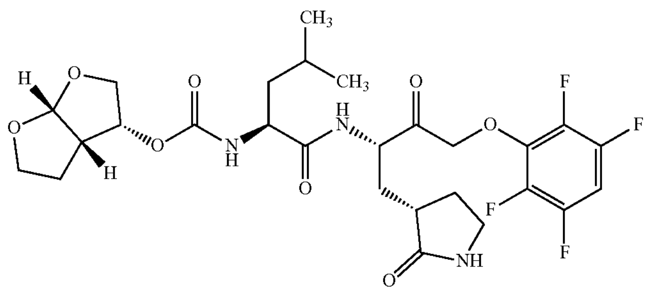 [SMILES: CC(C)C[C@H](NC(=O)O[C@H]1CO[C@H]2OCC[C@H]21)C(=O)N[C@@H](C[C@@H]1CCNC1=O)C(=O)COc1c(F)c(F)cc(F)c1F] | (3R,3aS,6aR)-hexahydrofuro[2,3-b]furan-3-yl ((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)carbamate | 604.3400 | ** |
| 151 | 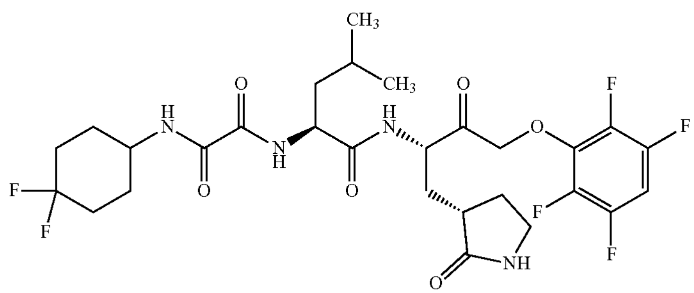 [SMILES: CC(C)C[C@H](NC(=O)C(=O)NC1CCC(F)(F)CC1)C(=O)N[C@@H](C[C@@H]1CCNC1=O)C(=O)COc1c(F)c(F)cc(F)c1F] | N1-(4,4-difluorocyclohexyl)-N2-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)oxalamide | 637.6000 | *** |

TABLE 1-continued

| Compound | Structure | IUPAC | LCMS [M + 1] | EC50, uM (Hela) |
|---|---|---|---|---|
| 152 | 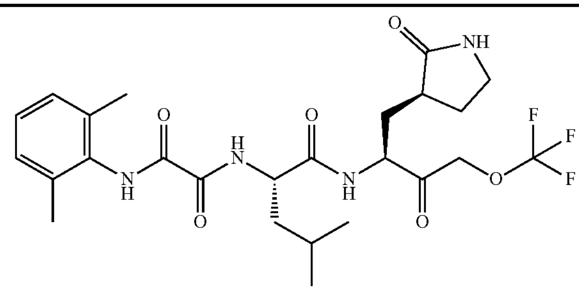 | N1-(2,6-dimethylphenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 543.3442 | **** |
| 153 | 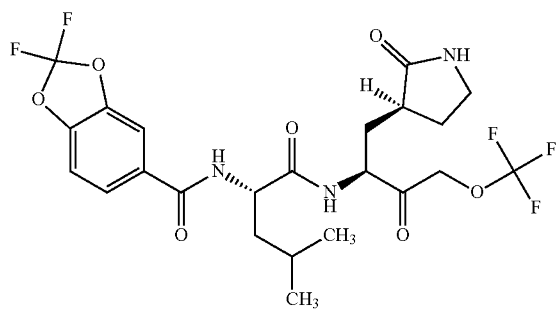 [SMILES: CC(C)C[C@H](NC(=O)c1ccc2c(c1)OC(F)(F)O2)C(=O)N[C@@H](C[C@@H]1CCNC1=O)C(=O)COC(F)(F)F] | 2,2-difluoro-N-((S)-4-methyl-1-oxo-1-(((S)-3-oxo-1-((S)-2-oxopyrrolidin-3-yl)-4-(trifluoromethoxy)butan-2-yl)amino)pentan-2-yl)benzo[d][1,3]dioxole-5-carboxamide | 552.1700 | **** |
| 154 | 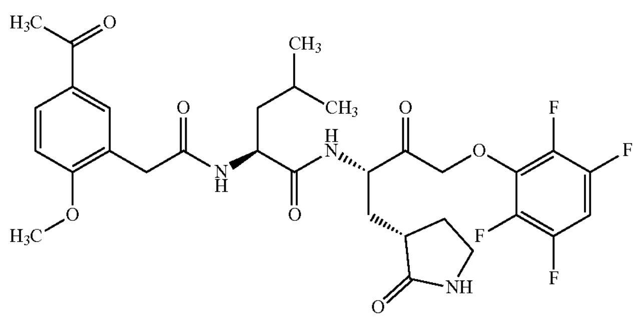 [SMILES: COc1ccc(C(C)=O)cc1CC(=O)N[C@@H](CC(C)C)C(=O)N[C@@H](C[C@@H]1CCNC1=O)C(=O)COc1c(F)c(F)cc(F)c1F] | (S)-2-(2-(5-acetyl-2-methoxyphenyl)-acetamido)-4-methyl-N-((S)-3-oxo-1-((S)-2-oxopyrrolidin-3-yl)-4-(2,3,5,6-tetrafluorophenoxy)butan-2-yl)pentanamide | 638.4000 | **** |

TABLE 1-continued

| Compound | Structure | IUPAC | LCMS [M + 1] | EC50, uM (Hela) |
|---|---|---|---|---|
| 155 | 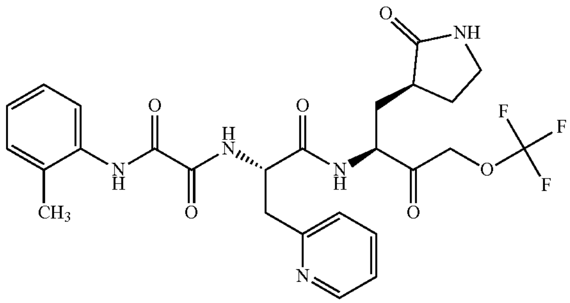 [SMILES: Cc1ccccc1NC(=O)C(=O)N[C@@H](Cc1ccccn1)C(=O)N[C@@H](C[C@@H]1CCNC1=O)C(=O)COC(F)(F)F] | N1-((S)-1-oxo-1-(((S)-3-oxo-1-((S)-2-oxopyrrolidin-3-yl)-4-(trifluoromethoxy)butan-2-yl)amino)-3-(pyridin-2-yl)propan-2-yl)-N2-(o-tolyl)oxalamide | 564.5200 | **** |
| 156 | 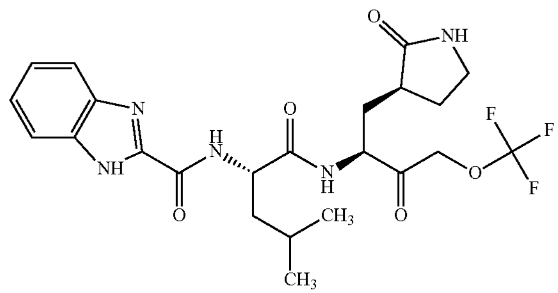 [SMILES: CC(C)C[C@H](NC(=O)c1nc2ccccc2[nH]1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-benzo[d]imidazole-2-carboxamide | 512.2000 | *** |
| 157 | 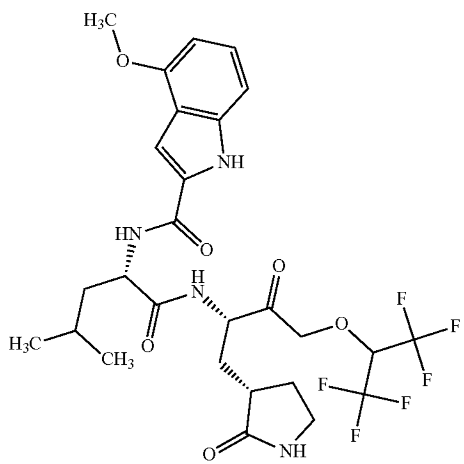 [SMILES: COc1cccc2[nH]c(C(=O)N[C@@H](CC(C)C)C(=O)N[C@@H](C[C@@H]3CCNC3=O)C(=O)COC(C(F)(F)F)C(F)(F)F)cc12] | N-((S)-1-(((S)-4-((1,1,1,3,3,3-hexafluoropropan-2-yl)oxy)-3-oxo-1-((S)-2-oxopyrrolidin-3-yl)butan-2-yl)amino)-4-methyl-1-oxopentan-2-yl)-4-methoxy-1H-indole-2-carboxamide | 623.2800 | >1 μM |

TABLE 1-continued

| Compound | Structure | IUPAC | LCMS [M + 1] | EC50, uM (Hela) |
|---|---|---|---|---|
| 158 | 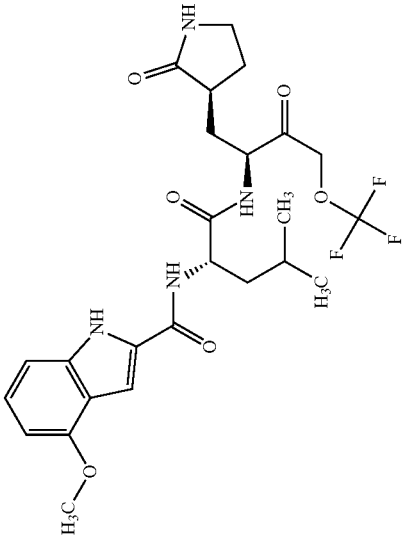 | 4-methoxy-N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-indole-2-carboxamide | 540.9911 | **** |
| 159 | 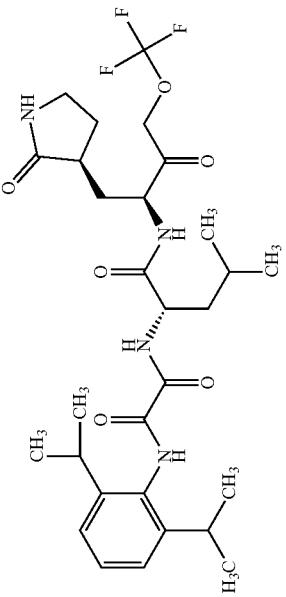 | N1-(2,6-diisopropylphenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 599.3000 | **** |
| 160 | 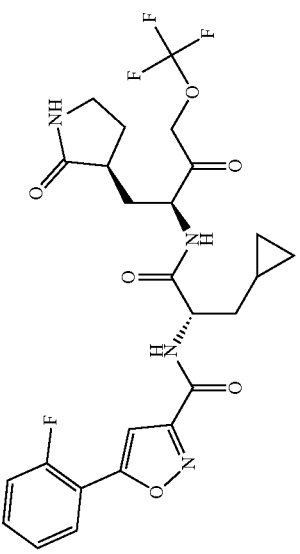 | N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(2-fluorophenyl)isoxazole-3-carboxamide | 555.1800 | **** |

TABLE 1-continued

| Compound | Structure | IUPAC | LCMS [M + 1] | EC50, uM (Hela) |
|---|---|---|---|---|
| 161 | 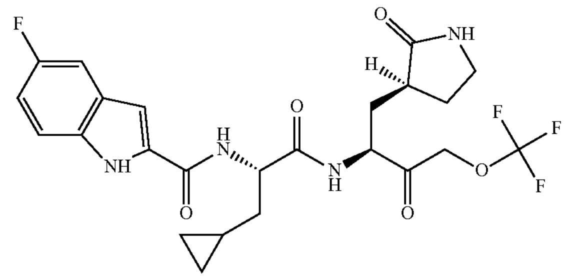 [SMILES: O=C(N[C@@H](CC1CC1)C(=O)N[C@@H](C[C@@H]1CCNC1=O)C(=O)COC(F)(F)F)c1cc2cc(F)ccc2[nH]1] | N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-fluoro-1H-indole-2-carboxamide | 527.1800 | **** |
| 162 | 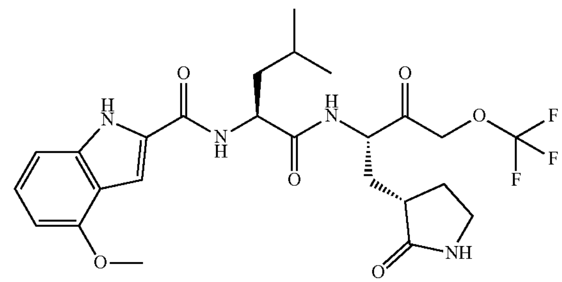 [SMILES: COc1cccc2[nH]c(C(=O)N[C@@H](CC(C)C)C(=O)N[C@@H](C[C@@H]3CCNC3=O)C(=O)COC(F)(F)F)cc12] | 4-methoxy-N-((S)-4-methyl-1-oxo-1-(((S)-3-oxo-1-((S)-2-oxopyrrolidin-3-yl)-4-(2,2,2-trifluoroethoxy)butan-2-yl)amino)pentan-2-yl)-1H-indole-2-carboxamide | 555.2400 | >1 µM |
| 163 | 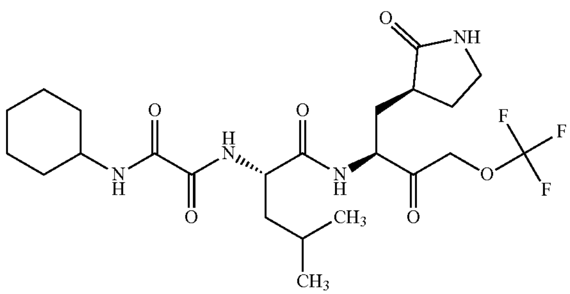 | N1-cyclohexyl-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 521.6500 | **** |

TABLE 1-continued

| Compound | Structure | IUPAC | LCMS [M + 1] | EC50, uM (Hela) |
|---|---|---|---|---|
| 164 | 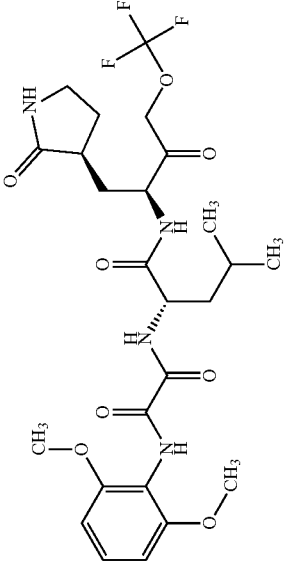 | N1-(2,6-dimethoxyphenyl)-N2-((S)-4-methyl-1-oxo-1-(((S)-3-oxo-1-(((S)-2-oxopyrrolidin-3-yl)-4-(trifluoromethoxy)butan-2-yl)amino)pentan-2-yl)oxalamide | 575.5900 | **** |
| 165 | 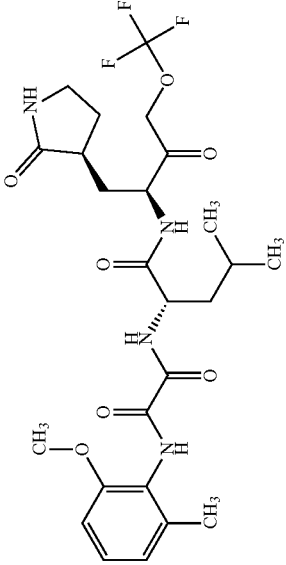 | N1-(2-methoxy-6-methylphenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 559.6348 | **** |
| 166 | 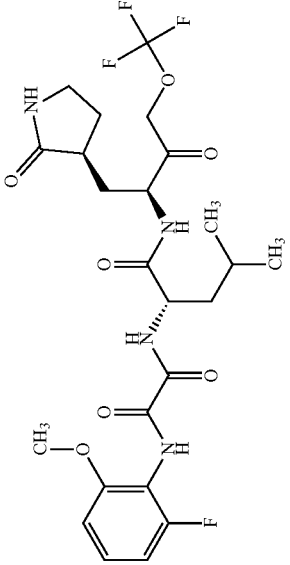 | N1-(2-fluoro-6-methoxyphenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 563.21 | *** |

TABLE 1-continued

| Compound | Structure | IUPAC | LCMS [M + 1] | EC50, uM (Hela) |
|---|---|---|---|---|
| 167 | 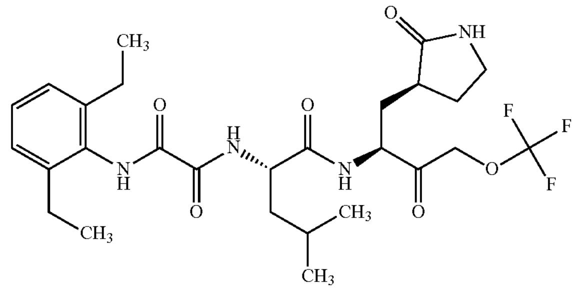 [SMILES: CCc1cccc(CC)c1NC(=O)C(=O)N[C@@H](CC(C)C)C(=O)N[C@@H](C[C@@H]1CCNC1=O)C(=O)COC(F)(F)F] | N1-(2,6-diethylphenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 571.2700 | **** |
| 168 | 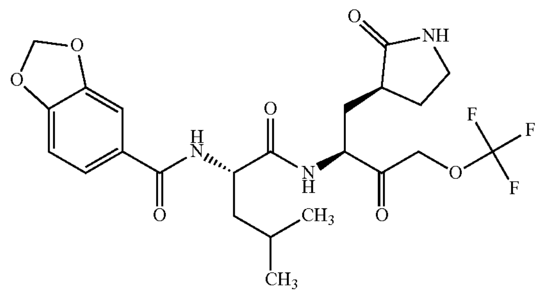 [SMILES: CC(C)C[C@H](NC(=O)c1ccc2c(c1)OCO2)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)benzo[d][1,3]dioxole-5-carboxamide | 516.2600 | *** |
| 169 | 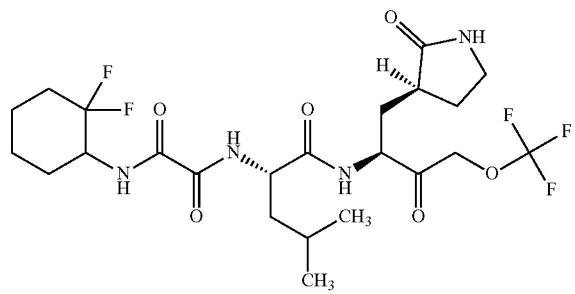 [SMILES: CC(C)C[C@H](NC(=O)C(=O)NC1CCCCC1(F)F)C(=O)N[C@@H](C[C@@H]1CCNC1=O)C(=O)COC(F)(F)F] | N1-(2,2-difluorocyclohexyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 557.2300 | **** |

TABLE 1-continued

| Compound | Structure | IUPAC | LCMS [M + 1] | EC50, uM (Hela) |
|---|---|---|---|---|
| 170 | 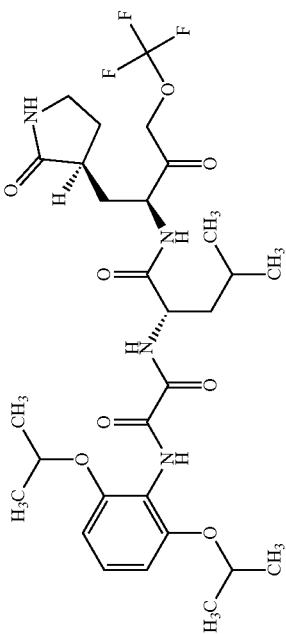 | N1-(2,6-diisopropoxyphenyl)-N2-((S)-4-methyl-1-oxo-1-(((S)-3-oxo-1-(((S)-2-oxopyrrolidin-3-yl)-4-(trifluoromethoxy)butan-2-yl)amino)pentan-2-yl)oxalamide | 631.1641 | **** |
| 171 | 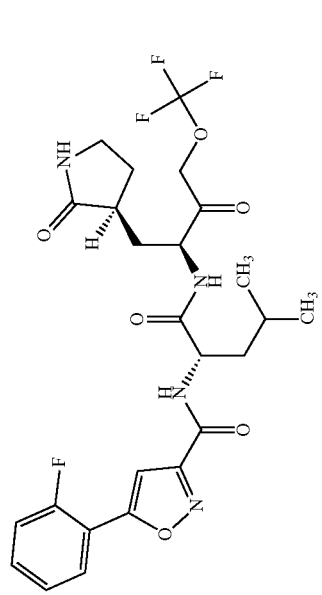 | 5-(2-fluorophenyl)-N-((S)-4-methyl-1-oxo-1-(((S)-3-oxo-1-(((S)-2-oxopyrrolidin-3-yl)-4-(trifluoromethoxy)butan-2-yl)amino)pentan-2-yl)isoxazole-3-carboxamide | 557.1900 | **** |
| 172 | 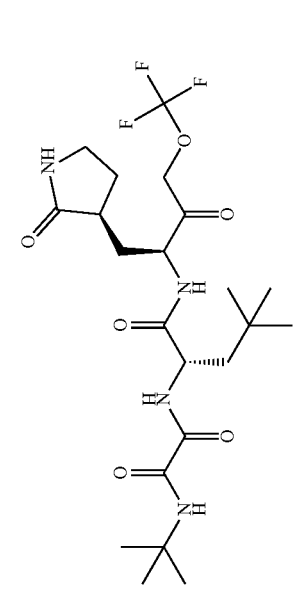 | N1-(tert-butyl)-N2-((S)-4,4-dimethyl-1-oxo-1-(((S)-3-oxo-1-(((S)-2-oxopyrrolidin-3-yl)-4-(trifluoromethoxy)butan-2-yl)amino)pentan-2-yl)oxalamide | 509.2500 | **** |

TABLE 1-continued

| Compound | Structure | IUPAC | LCMS [M + 1] | EC50, uM (Hela) |
|---|---|---|---|---|
| 173 | 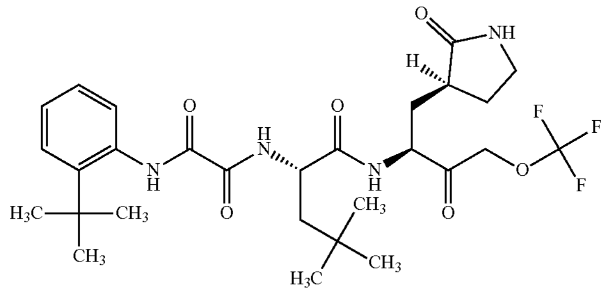 [SMILES: CC(C)(C)C[C@H](NC(=O)C(=O)Nc1ccccc1C(C)(C)C)C(=O)N[C@@H](C[C@@H]1CCNC1=O)C(=O)COC(F)(F)F] | N1-(2-(tert-butyl)phenyl)-N2-((S)-4,4-dimethyl-1-oxo-1-(((S)-2-oxopyrrolidin-3-yl)-4-(trifluoromethoxy)butan-2-yl)amino)pentan-2-yl)oxalamide | 585.2800 | **** |
| 174 | 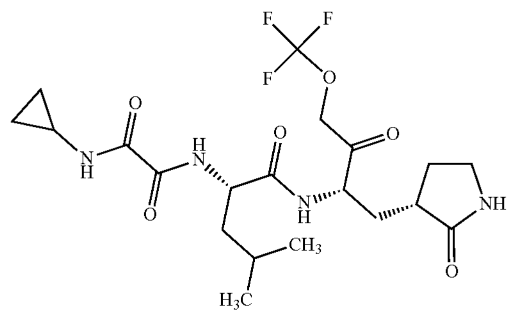 [SMILES: CC(C)C[C@H](NC(=O)C(=O)NC1CC1)C(=O)N[C@@H](C[C@@H]1CCNC1=O)C(=O)COC(F)(F)F] | N1-cyclopropyl-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 479.3000 | **** |
| 175 | 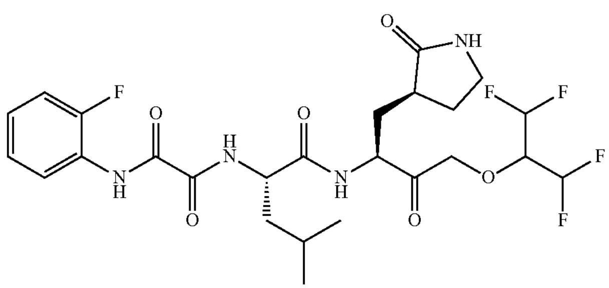 [SMILES: CC(C)C[C@H](NC(=O)C(=O)Nc1ccccc1F)C(=O)N[C@@H](C[C@@H]1CCNC1=O)C(=O)COC(C(F)F)C(F)F] | N1-(2-fluorophenyl)-N2-((S)-4-methyl-1-oxo-1-(((S)-3-oxo-1-((S)-2-oxopyrrolidin-3-yl)-4-((1,1,3,3-tetrafluoropropan-2-yl)oxy)butan-2-yl)amino)pentan-2-yl)oxalamide | 579.3600 | >1 μM |

TABLE 1-continued

| Compound | Structure | IUPAC | LCMS [M + 1] | EC50, uM (Hela) |
|---|---|---|---|---|
| 176 | 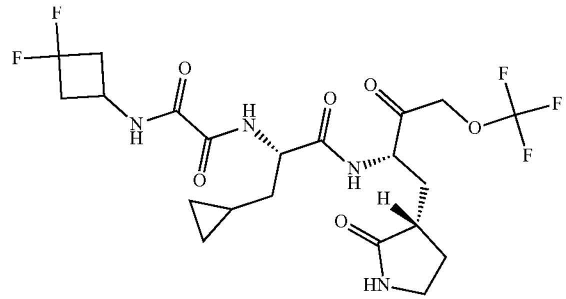 [SMILES: O=C(NC1CC(F)(F)C1)C(=O)N[C@@H](CC1CC1)C(=O)N[C@@H](C[C@@H]1CCNC1=O)C(=O)COC(F)(F)F] | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(3,3-difluorocyclobutyl)-oxalamide | 527.2000 | **** |
| 177 | 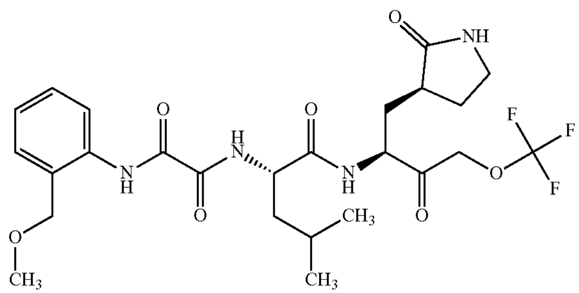 [SMILES: COCc1ccccc1NC(=O)C(=O)N[C@@H](CC(C)C)C(=O)N[C@@H](C[C@@H]1CCNC1=O)C(=O)COC(F)(F)F] | N1-(2-(methoxymethyl)phenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 559.3787 | **** |
| 178 | 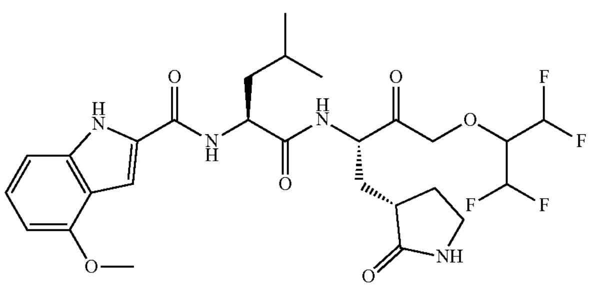 [SMILES: COc1cccc2[nH]c(C(=O)N[C@@H](CC(C)C)C(=O)N[C@@H](C[C@@H]3CCNC3=O)C(=O)COC(C(F)F)C(F)F)cc12] | 4-methoxy-N-((S)-4-methyl-1-oxo-1-(((S)-3-oxo-1-((S)-2-oxopyrrolidin-3-yl)-4-((1,1,3,3-tetrafluoropropan-2-yl)oxy)butan-2-yl)amino)pentan-2-yl)-1H-indole-2-carboxamide | 587.6536 | >1 μM |

TABLE 1-continued

| Compound | Structure | IUPAC | LCMS [M + 1] | EC50, uM (Hela) |
|---|---|---|---|---|
| 179 | 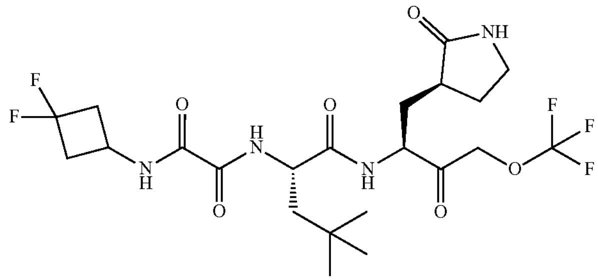 [SMILES: CC(C)(C)C[C@H](NC(=O)C(=O)NC1CC(F)(F)C1)C(=O)N[C@@H](C[C@@H]1CCNC1=O)C(=O)COC(F)(F)F] | N1-(3,3-difluorocyclobutyl)-N2-((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)oxalamide | 543.2200 | **** |
| 180 | 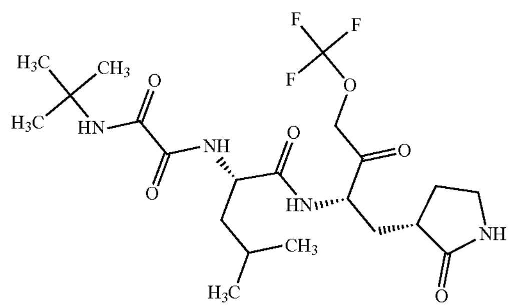 [SMILES: CC(C)C[C@H](NC(=O)C(=O)NC(C)(C)C)C(=O)N[C@@H](C[C@@H]1CCNC1=O)C(=O)COC(F)(F)F] | N1-(tert-butyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 495.2400 | *** |
| 181 | 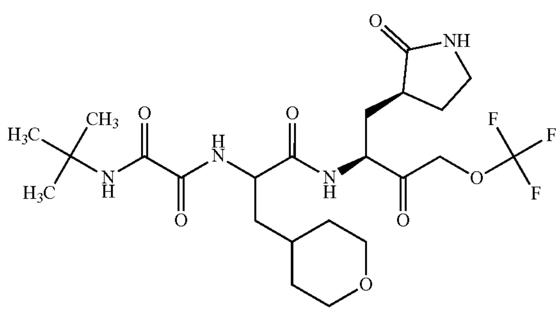 [SMILES: CC(C)(C)NC(=O)C(=O)NC(CC1CCOCC1)C(=O)N[C@@H](C[C@@H]1CCNC1=O)C(=O)COC(F)(F)F] | N1-(tert-butyl)-N2-(1-oxo-1-((S)-2-oxopyrrolidin-3-yl)-4-(trifluoromethoxy)butan-2-yl)amino)-3-(tetrahydro-2H-pyran-4-yl)propan-2-yl)oxalamide | 537.2500 | ** |

TABLE 1-continued

| Compound | Structure | IUPAC | LCMS [M + 1] | EC50, uM (Hela) |
|---|---|---|---|---|
| 182 | 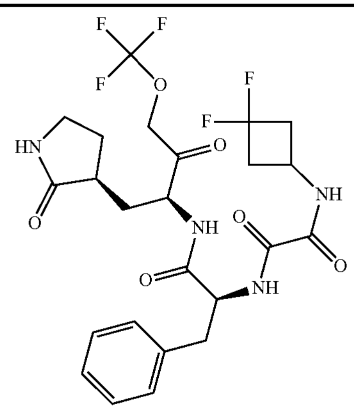 | N1-(3,3-difluorocyclobutyl)-N2-((S)-1-oxo-1-(((S)-3-oxo-1-((S)-2-oxopyrrolidin-3-yl)-4-(trifluoromethoxy)butan-2-yl)amino)-3-phenylpropan-2-yl)oxalamide | 563.0014 | **** |
| 183 | 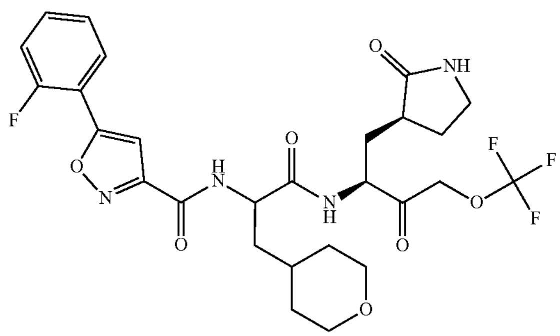 [SMILES: O=C(NC(CC1CCOCC1)C(=O)N[C@@H](C[C@@H]1CCNC1=O)C(=O)COC(F)(F)F)c1cc(-c2ccccc2F)on1] | 5-(2-fluorophenyl)-N-((S)-3-oxo-1-(((S)-2-oxopyrrolidin-3-yl)-4-(trifluoromethoxy)butan-2-yl)amino)-3-(tetrahydro-2H-pyran-4-yl)propan-2-yl)isoxazole-3-carboxamide | 599.3436 | **** |
| 184 | 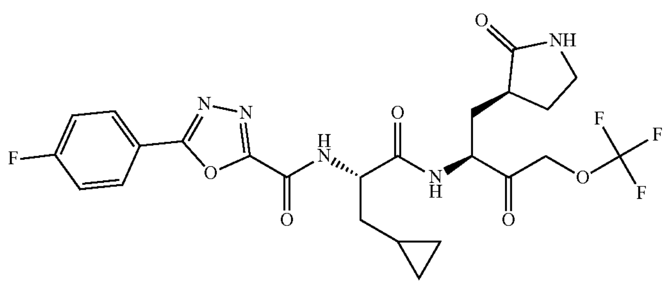 [SMILES: O=C(N[C@@H](CC1CC1)C(=O)N[C@@H](C[C@@H]1CCNC1=O)C(=O)COC(F)(F)F)c1nnc(-c2ccc(F)cc2)o1] | N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(4-fluorophenyl)-1,3,4-oxadiazole-2-carboxamide | 556.3000 | *** |

TABLE 1-continued

| Compound | Structure | IUPAC | LCMS [M + 1] | EC50, uM (Hela) |
|---|---|---|---|---|
| 185 | 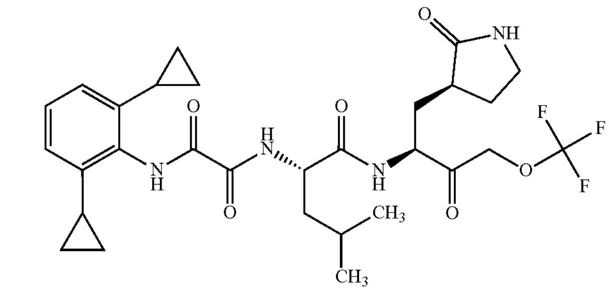 [SMILES: CC(C)C[C@H](NC(=O)C(=O)Nc1c(C2CC2)cccc1C1CC1)C(=O)N[C@@H](C[C@@H]1CCNC1=O)C(=O)COC(F)(F)F] | N1-(2,6-dicyclopropylphenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 595.2700 | **** |
| 186 | 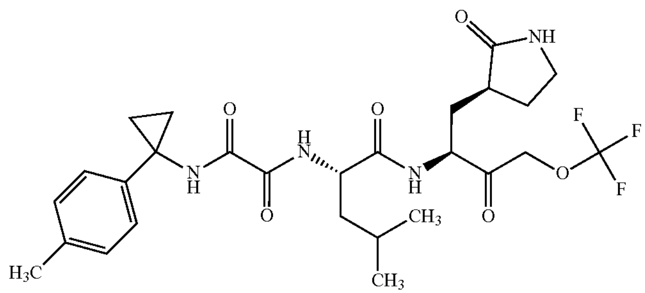 [SMILES: Cc1ccc(C2(NC(=O)C(=O)N[C@@H](CC(C)C)C(=O)N[C@@H](C[C@@H]3CCNC3=O)C(=O)COC(F)(F)F)CC2)cc1] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(1-(p-tyolyl)cyclopropyl)oxalamide | 569.2500 | **** |
| 187 | 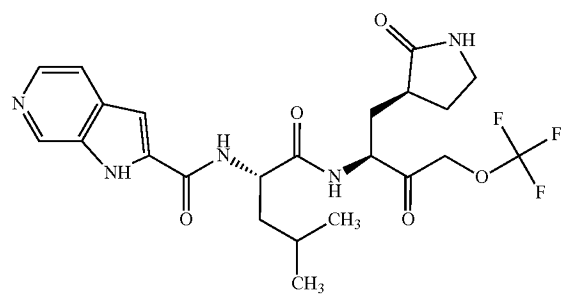 [SMILES: CC(C)C[C@H](NC(=O)c1cc2ccncc2[nH]1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-c]pyridine-2-carboxamide | 512.3462 | *** |

TABLE 1-continued

| Compound | Structure | IUPAC | LCMS [M + 1] | EC50, uM (Hela) |
|---|---|---|---|---|
| 188 | 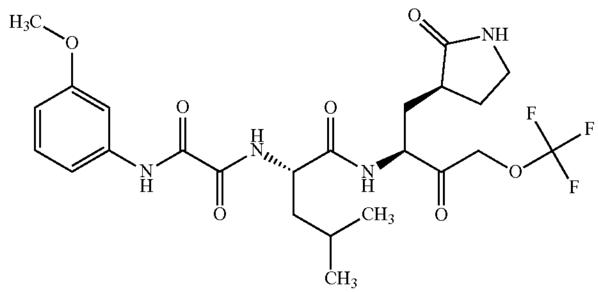 [SMILES: COc1cccc(NC(=O)C(=O)N[C@@H](CC(C)C)C(=O)N[C@@H](C[C@@H]2CCNC2=O)C(=O)COC(F)(F)F)c1] | N1-(3-methoxyphenyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 545.2100 | **** |
| 189 | 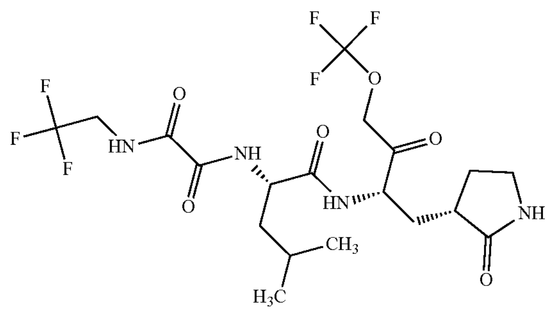 [SMILES: CC(C)C[C@H](NC(=O)C(=O)NCC(F)(F)F)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(2,2,2-trifluoroethyl)oxalamide | 521.1800 | **** |
| 190 | 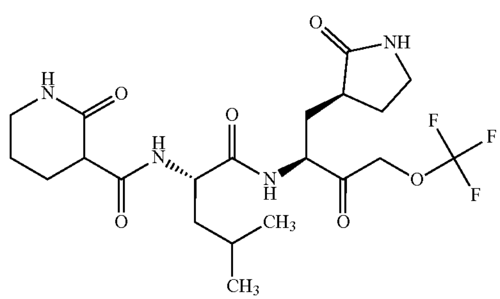 [SMILES: CC(C)C[C@H](NC(=O)C1CCCNC1=O)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-2-oxopiperidine-3-carboxamide | 493.6700 | >1 μM |

TABLE 1-continued

| Compound | Structure | IUPAC | LCMS [M + 1] | EC50, uM (Hela) |
|---|---|---|---|---|
| 191 | 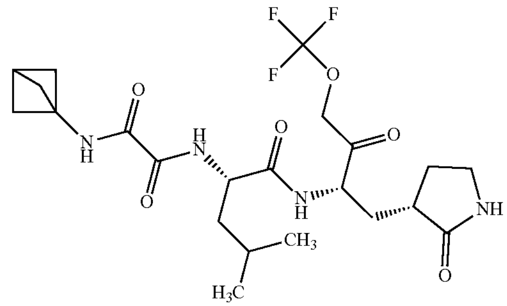 [SMILES: CC(C)C[C@H](NC(=O)C(=O)NC12CC(C1)C2)C(=O)N[C@@H](C[C@@H]1CCNC1=O)C(=O)COC(F)(F)F] | N1-(bicyclo[1.1.1]-pentan-1-yl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 505.2200 | **** |
| 192 | 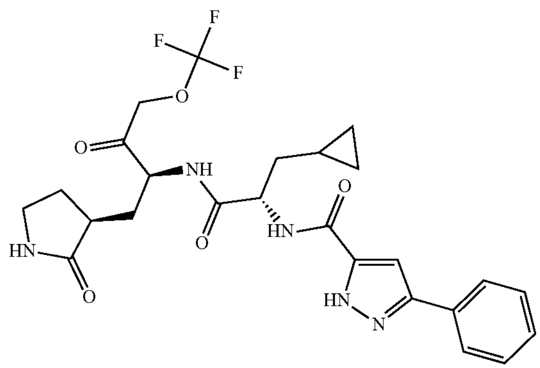 [SMILES: O=C(N[C@@H](CC1CC1)C(=O)N[C@@H](C[C@@H]1CCNC1=O)C(=O)COC(F)(F)F)c1cc(-c2ccccc2)n[nH]1] | N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-3-phenyl-1H-pyrazole-5-carboxamide | 537.2000 | *** |

TABLE 1-continued
| Compound | Structure | IUPAC | LCMS [M + 1] | EC50, uM (Hela) |
|---|---|---|---|---|
| 193 | 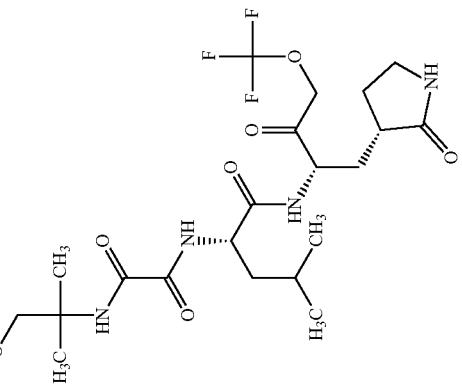 | N1-(1-methoxy-2-methylpropan-2-yl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 525.2500 | **** |
| 194 | 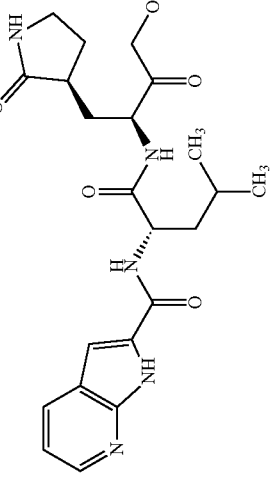 | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-b]pyridine-2-carboxamide | 512.3443 | **** |

TABLE 1-continued

| Compound | Structure | IUPAC | LCMS [M + 1] | EC50, uM (Hela) |
|---|---|---|---|---|
| 195 | 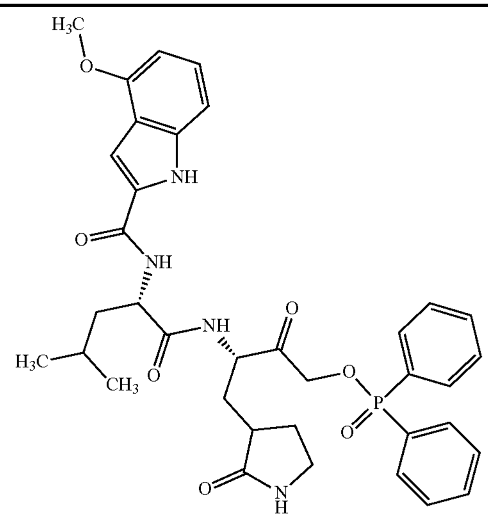 | (3S)-3-((S)-2-(4-methoxy-1H-indole-2-carboxamido)-4-methylpentanamido)-2-oxo-4-(2-oxopyrrolidin-3-yl)butyl diphenylphosphinate | 673.3334 | *** |
| 196 | 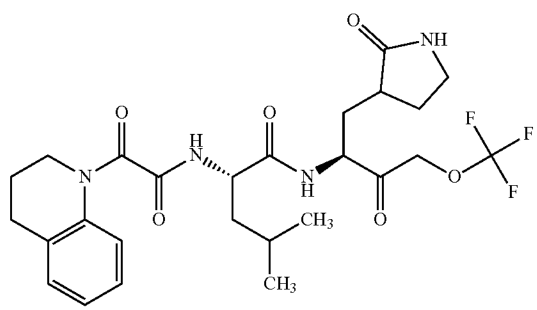 [SMILES: CC(C)C[C@H](NC(=O)C(=O)N1CCCc2ccccc21)C(=O)N[C@@H](CC1CCNC1=O)C(=O)COC(F)(F)F] | (2S)-2-(2-(3,4-dihydroquinolin-1(2H)-yl)-2-oxoacetamido)-4-methyl-N-((2S)-3-oxo-1-(2-oxopyrrolidin-3-yl)-4-(trifluoromethoxy)butan-2-yl)pentanamide | 555.5200 | **** |

TABLE 1-continued

| Compound | Structure | IUPAC | LCMS [M + 1] | EC50, uM (Hela) |
|---|---|---|---|---|
| 197 | 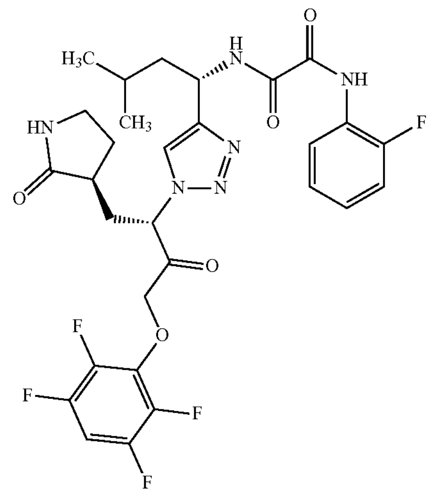 [SMILES: CC(C)C[C@H](NC(=O)C(=O)Nc1ccccc1F)c1cn([C@@H](C[C@@H]2CCNC2=O)C(=O)COc2c(F)c(F)cc(F)c2F)nn1] | N1-(2-fluorophenyl)-N2-((S)-3-methyl-1-(1-((S)-3-oxo-1-((S)-2-oxopyrrolidin-3-yl)-4-(2,3,5,6-tetrafluorophenoxy)butan-2-yl)-1H-1,2,3-triazol-4-yl)butyl)oxalamide | 637.1005 | * |
| 198 | 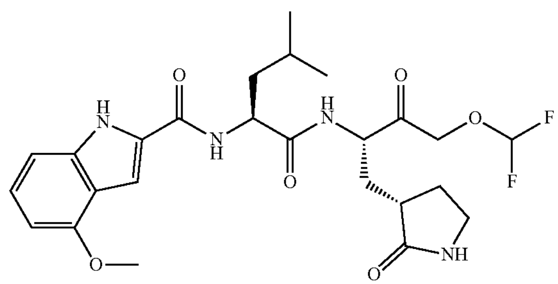 [SMILES: COc1cccc2[nH]c(C(=O)N[C@@H](CC(C)C)C(=O)N[C@@H](C[C@@H]3CCNC3=O)C(=O)COC(F)F)cc12] | N-((S)-1-(((S)-4-(difluoromethoxy)-3-oxo-1-((S)-2-oxopyrrolidin-3-yl)butan-2-yl)amino)-4-methyl-1-oxopentan-2-yl)-4-methoxy-1H-indole-2-carboxamide | 523.2300 | ** |
| 199 | 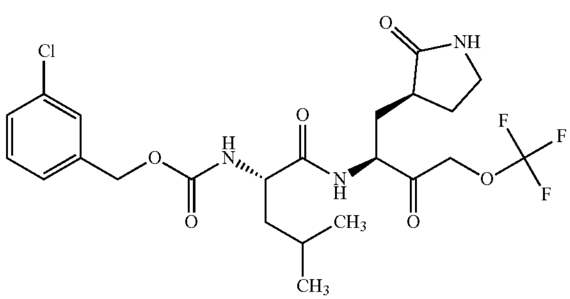 [SMILES: CC(C)C[C@H](NC(=O)OCc1cccc(Cl)c1)C(=O)N[C@@H](C[C@@H]1CCNC1=O)C(=O)COC(F)(F)F] | 3-chlorobenzyl ((S)-4-methyl-1-oxo-1-(((S)-3-oxo-1-((S)-2-oxopyrrolidin-3-yl)-4-(trifluoromethoxy)butan-2-yl)amino)pentan-2-yl)carbamate | 536.6107 | **** |

TABLE 1-continued

| Compound | Structure | IUPAC | LCMS [M + 1] | EC50, uM (Hela) |
|---|---|---|---|---|
| 200 | 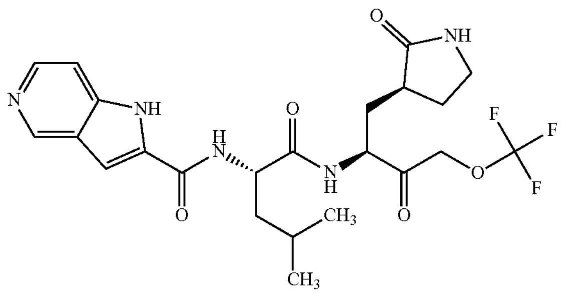 [SMILES: CC(C)C[C@H](NC(=O)c1cc2cnccc2[nH]1)C(=O)N[C@@H](C[C@@H]1CCNC1=O)C(=O)COC(F)(F)F] | N-((S)-4-methyl-1-oxo-1-(((S)-2-oxopyrrolidin-3-yl)-4-(trifluoromethoxy)butan-2-yl)amino)pentan-2-yl)-1H-pyrrolo[3,2-c]pyridine-2-carboxamide | 512.6084 | ** |
| 201 | 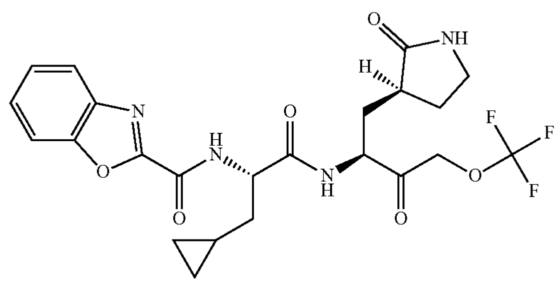 [SMILES: O=C(N[C@@H](CC1CC1)C(=O)N[C@@H](C[C@@H]1CCNC1=O)C(=O)COC(F)(F)F)c1nc2ccccc2o1] | N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)benzo[d]oxazole-2-carboxamide | 511.6000 | **** |
| 202 | 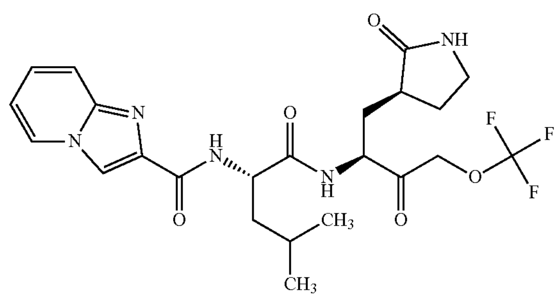 | N-((S)-4-methyl-1-oxo-1-(((S)-2-oxopyrrolidin-3-yl)-4-(trifluoromethoxy)butan-2-yl)amino)pentan-2-yl)imidazo[1,2-a]pyridine-2-carboxamide | 512.2804 | *** |

TABLE 1-continued

| Compound | Structure | IUPAC | LCMS [M + 1] | EC50, uM (Hela) |
|---|---|---|---|---|
| 203 | 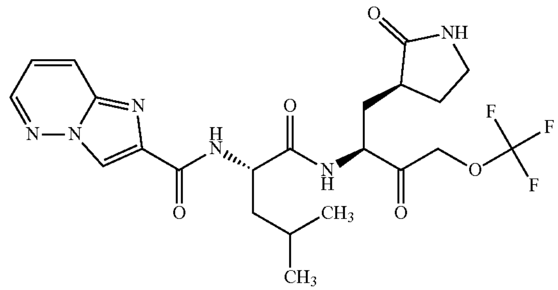 [SMILES: CC(C)C[C@H](NC(=O)c1cn2ncccc2n1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)imidazo[1,2-b]pyridazine-2-carboxamide | 513.2300 | *** |
| 204 | 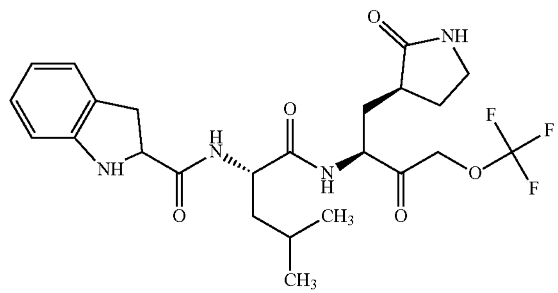 | N-((S)-4-methyl-1-oxo-1-(((S)-3-oxo-1-((S)-2-oxopyrrolidin-3-yl)-4-(trifluoromethoxy)butan-2-yl)amino)pentan-2-yl)indoline-2-carboxamide | 513.3104 | *** |
| 205 | 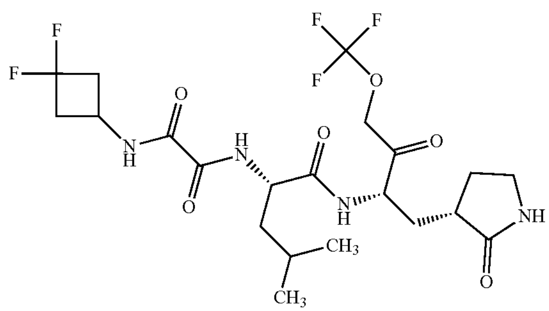 [SMILES: CC(C)C[C@H](NC(=O)C(=O)NC1CC(F)(F)C1)C(=O)N[C@@H](C[C@@H]1CCNC1=O)C(=O)COC(F)(F)F] | N1-(3,3-difluorocyclobutyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 529.2000 | **** |

TABLE 1-continued

| Compound | Structure | IUPAC | LCMS [M + 1] | EC50, uM (Hela) |
|---|---|---|---|---|
| 206 | 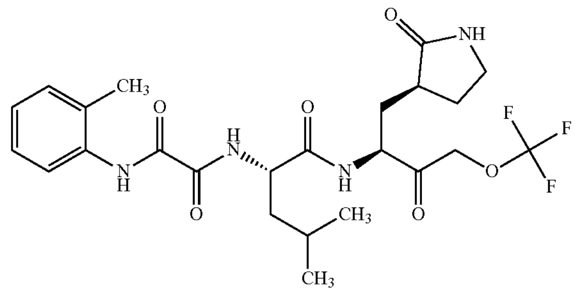 [SMILES: Cc1ccccc1NC(=O)C(=O)N[C@@H](CC(C)C)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(o-tolyl)oxalamide | 529.2200 | **** |
| 207 | 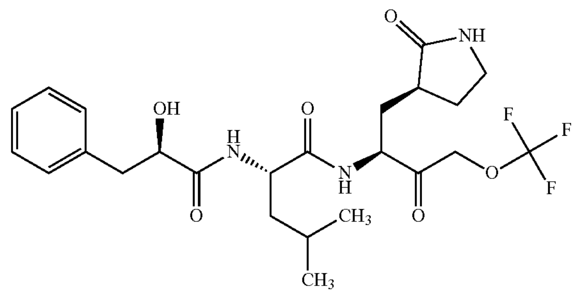 [SMILES: CC(C)C[C@H](NC(=O)[C@H](O)Cc1ccccc1)C(=O)N[C@@H](C[C@@H]1CCNC1=O)C(=O)COC(F)(F)F] | (S)-2-((R)-2-hydroxy-3-phenylpropanamido)-4-methyl-N-((S)-3-oxo-1-((S)-2-oxopyrrolidin-3-yl)-4-(trifluoromethoxy)butan-2-yl)pentanamide | 516.2200 | **** |
| 208 | 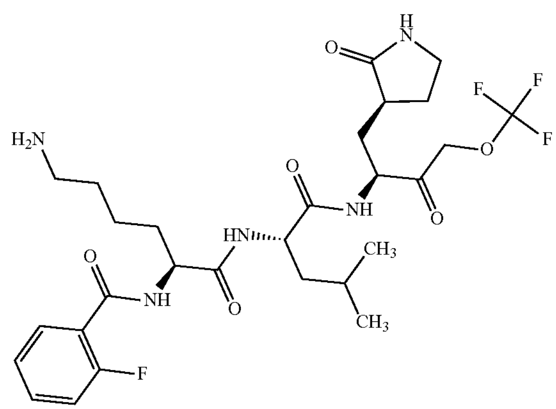 [SMILES: CC(C)C[C@H](NC(=O)[C@H](CCCCN)NC(=O)c1ccccc1F)C(=O)N[C@@H](C[C@@H]1CCNC1=O)C(=O)COC(F)(F)F] | N-((S)-6-amino-1-(((S)-4-methyl-1-oxo-1-(((S)-3-oxo-1-((S)-2-oxopyrrolidin-3-yl)-4-(trifluoromethoxy)butan-2-yl)amino)pentan-2-yl)amino)-1-oxohexan-2-yl)-2-fluorobenzamide | 618.4358 | >1 μM |

TABLE 1-continued

| Compound | Structure | IUPAC | LCMS [M + 1] | EC50, uM (Hela) |
|---|---|---|---|---|
| 209 | 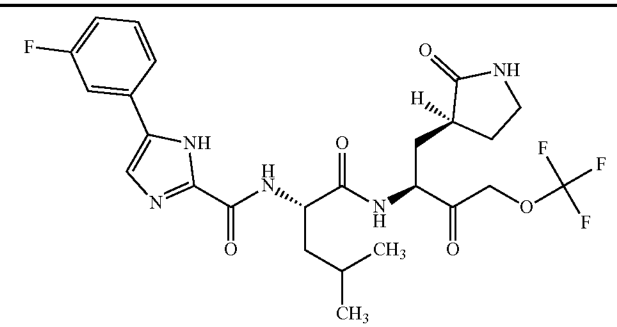 | 5-(3-fluorophenyl)-N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-imidazole-2-carboxamide | 556.2100 | **** |
| 210 | 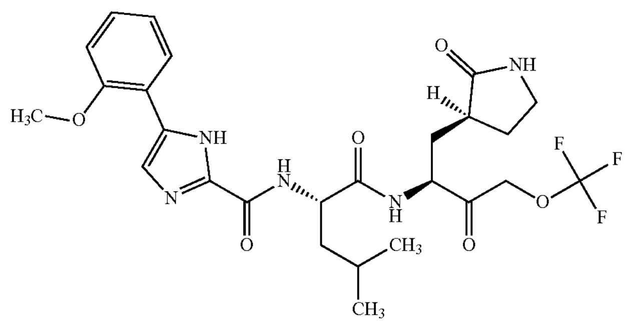 [SMILES: COc1ccccc1-c1cnc(C(=O)N[C@@H](CC(C)C)C(=O)N[C@@H](C[C@@H]2CCNC2=O)C(=O)COC(F)(F)F)[nH]1] | 5-(2-methoxyphenyl)-N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-imidazole-2-carboxamide | 568.6487 | *** |
| 211 | 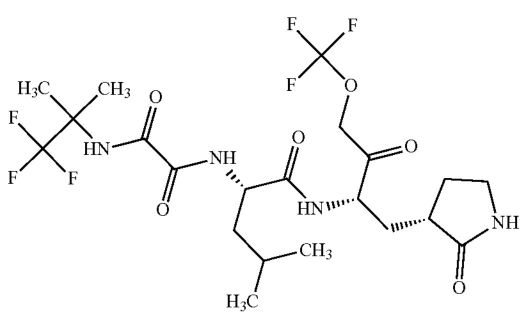 [SMILES: CC(C)C[C@H](NC(=O)C(=O)NC(C)(C)C(F)(F)F)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(1,1,1-trifluoro-2-methylpropan-2-yl)oxalamide | 549.2100 | **** |

TABLE 1-continued

| Compound | Structure | IUPAC | LCMS [M + 1] | EC50, uM (Hela) |
|---|---|---|---|---|
| 212 | 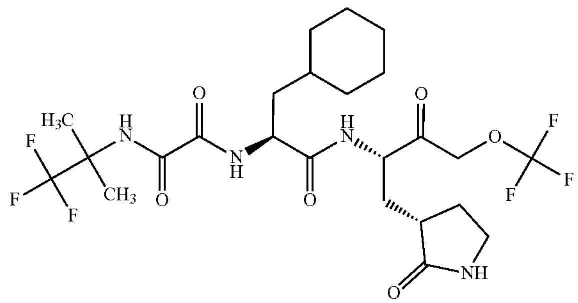 [SMILES: CC(C)(NC(=O)C(=O)N[C@@H](CC1CCCCC1)C(=O)N[C@@H](C[C@@H]1CCNC1=O)C(=O)COC(F)(F)F)C(F)(F)F] | N1-((S)-3-cyclohexyl-1-oxo-1-(((S)-3-oxo-1-((S)-2-oxopyrrolidin-3-yl)-4-(trifluoromethoxy)butan-2-yl)amino)propan-2-yl)-N2-(1,1,1-trifluoro-2-methylpropan-2-yl)oxalamide | 589.2400 | **** |
| 213 | 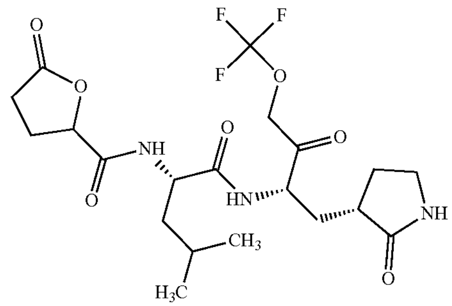 [SMILES: CC(C)C[C@H](NC(=O)C1CCC(=O)O1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-5-oxotetrahydrofuran-2-carboxamide | 480.19 | * |
| 214 | 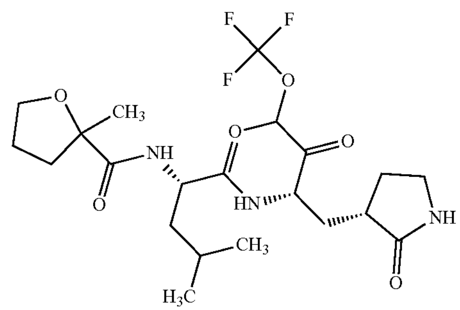 | 2-methyl-N-((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide | 480.2200 | *** |

TABLE 1-continued

| Compound | Structure | IUPAC | LCMS [M + 1] | EC50, uM (Hela) |
|---|---|---|---|---|
| 215 | 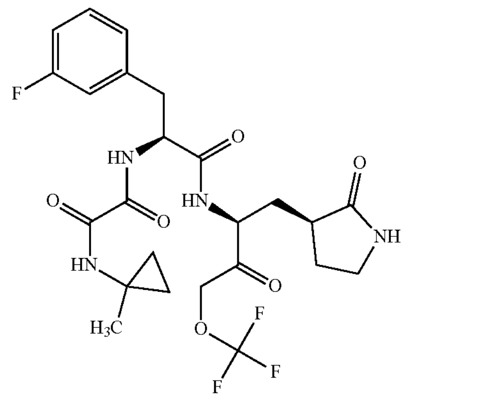 [SMILES: CC1(NC(=O)C(=O)N[C@@H](Cc2cccc(F)c2)C(=O)N[C@@H](C[C@@H]2CCNC2=O)C(=O)COC(F)(F)F)CC1] | N1-((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-N2-(1-methylcyclopropyl)oxalamide | 545.1900 | **** |
| 216 | 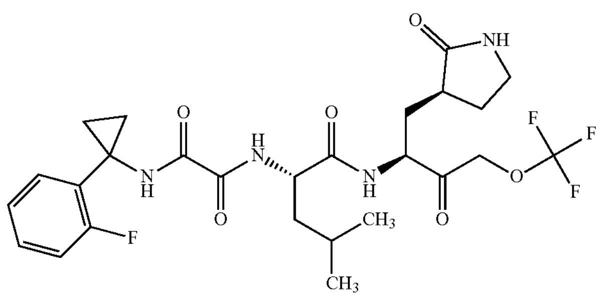 [SMILES: CC(C)C[C@H](NC(=O)C(=O)NC1(c2ccccc2F)CC1)C(=O)N[C@@H](C[C@@H]1CCNC1=O)C(=O)COC(F)(F)F] | N1-(1-(2-fluorophenyl)cyclopropyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 573.2300 | **** |
| 217 | 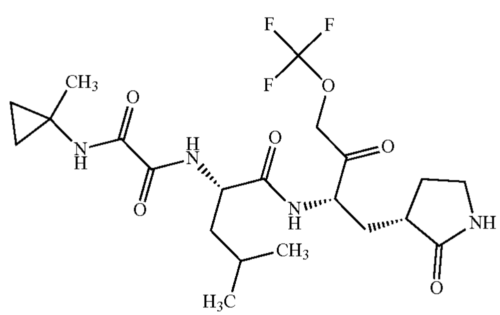 [SMILES: CC(C)C[C@H](NC(=O)C(=O)NC1(C)CC1)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(1-methylcyclopropyl)oxalamide | 493.5200 | **** |

TABLE 1-continued

| Compound | Structure | IUPAC | LCMS [M + 1] | EC50, uM (Hela) |
|---|---|---|---|---|
| 218 | 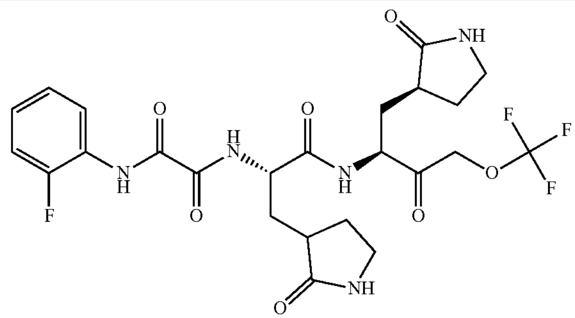 [SMILES: O=C(Nc1ccccc1F)C(=O)N[C@@H](CC1CCNC1=O)C(=O)N[C@@H](C[C@@H]1CCNC1=O)C(=O)COC(F)(F)F] | N1-(2-fluorophenyl)-N2-((2S)-1-oxo-1-(((S)-3-oxo-1-((S)-2-oxopyrrolidin-3-yl)-4-(trifluoromethoxy)butan-2-yl)amino)-3-(2-oxopyrrolidin-3-yl)propan-2-yl)oxalamide | 574.18 | * |
| 219 | 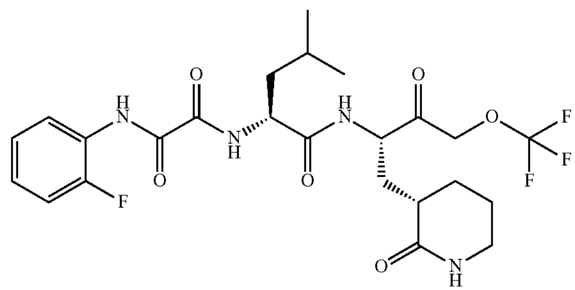 | N1-(2-fluorophenyl)-N2-((S)-4-methyl-1-oxo-1-(((S)-3-oxo-1-((S)-2-oxopiperidin-3-yl)-4-(trifluoromethoxy)butan-2-yl)amino)pentan-2-yl)oxalamide | 547.2100 | **** |
| 220 | 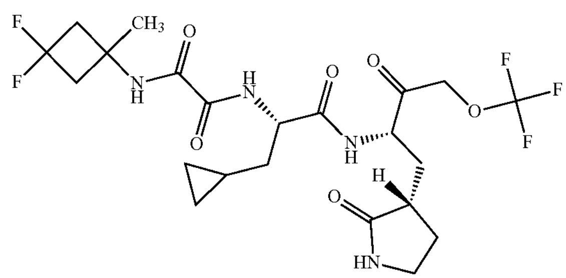 [SMILES: CC1(NC(=O)C(=O)N[C@@H](CC2CC2)C(=O)N[C@@H](C[C@@H]2CCNC2=O)C(=O)COC(F)(F)F)CC(F)(F)C1] | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(3,3-difluoro-1-methylcyclobutyl)-oxalamide | 541.1000 | **** |

TABLE 1-continued

| Compound | Structure | IUPAC | LCMS [M + 1] | EC50, uM (Hela) |
|---|---|---|---|---|
| 221 | 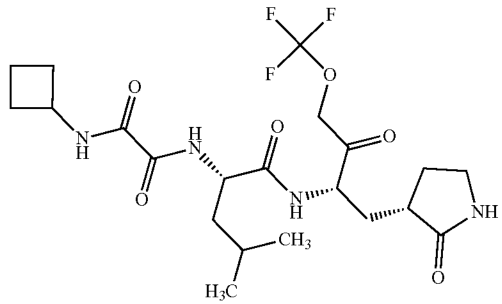 [SMILES: CC(C)C[C@H](NC(=O)C(=O)NC1CCC1)C(=O)N[C@@H](C[C@@H]1CCNC1=O)C(=O)COC(F)(F)F] | N1-cyclobutyl-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 493.0583 | **** |
| 222 | 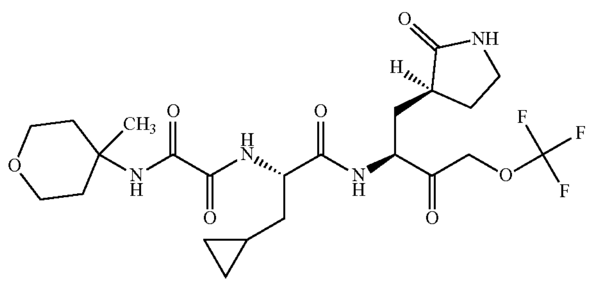 [SMILES: CC1(NC(=O)C(=O)N[C@@H](CC2CC2)C(=O)N[C@@H](C[C@@H]2CCNC2=O)C(=O)COC(F)(F)F)CCOCC1] | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(4-methyltetrahydro-2H-pyran-4-yl)oxalamide | 535.3530 | *** |
| 223 | 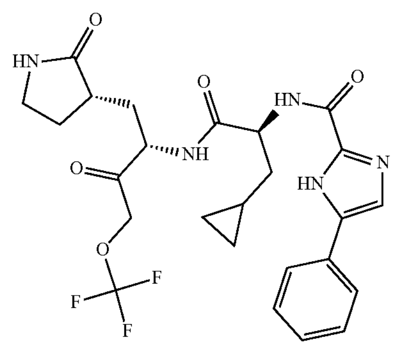 [SMILES: O=C(N[C@@H](CC1CC1)C(=O)N[C@@H](C[C@@H]1CCNC1=O)C(=O)COC(F)(F)F)c1ncc(-c2ccccc2)[nH]1] | N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-phenyl-1H-imidazole-2-carboxamide | 536.2000 | *** |

TABLE 1-continued

| Compound | Structure | IUPAC | LCMS [M + 1] | EC50, uM (Hela) |
|---|---|---|---|---|
| 224 | 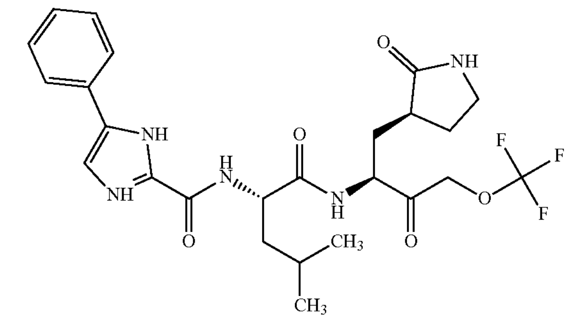 [SMILES: CC(C)C[C@H](NC(=O)c1ncc(-c2ccccc2)[nH]1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-5-phenyl-1H-imidazole-2-carboxamide | 538.3451 | **** |
| 225 | 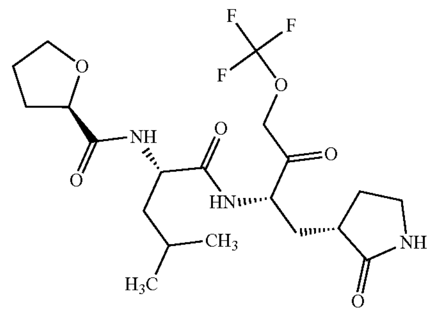 [SMILES: CC(C)C[C@H](NC(=O)[C@H]1CCCO1)C(=O)N[C@@H](C[C@@H]1CCNC1=O)C(=O)COC(F)(F)F] | (R)-N-((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide | 466.2100 | *** |
| 226 | 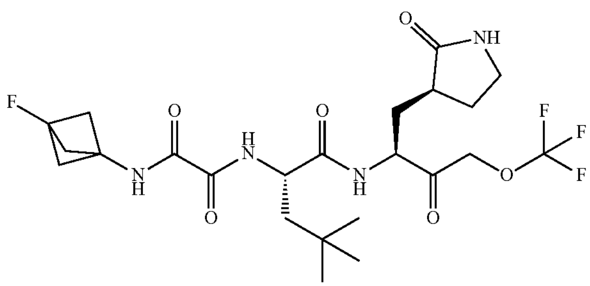 [SMILES: CC(C)(C)C[C@H](NC(=O)C(=O)NC12CC(F)(C1)C2)C(=O)N[C@@H](C[C@@H]1CCNC1=O)C(=O)COC(F)(F)F] | N1-((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-N2-(3-fluorobicyclo[1.1.1]pentan-1-yl)oxalamide | 537.2300 | **** |

TABLE 1-continued

| Compound | Structure | IUPAC | LCMS [M + 1] | EC50, uM (Hela) |
|---|---|---|---|---|
| 227 | 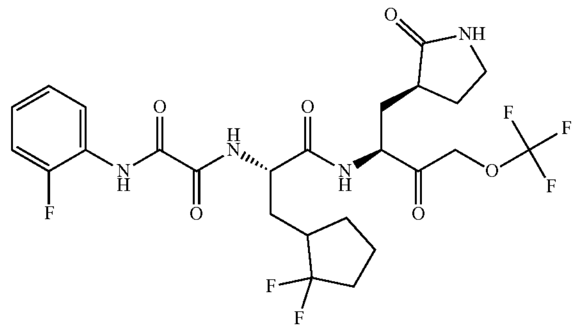 [SMILES: O=C(Nc1ccccc1F)C(=O)N[C@@H](CC1CCCC1(F)F)C(=O)N[C@@H](C[C@@H]1CCNC1=O)C(=O)COC(F)(F)F] | N1-((2S)-3-(2,2-difluorocyclopentyl)-1-oxo-1-(((S)-3-oxo-1-((S)-2-oxopyrrolidin-3-yl)-4-(trifluoromethoxy)butan-2-yl)amino)propan-2-yl)-N2-(2-fluorophenyl)-oxalamide | 595.1900 | **** |
| 228 | 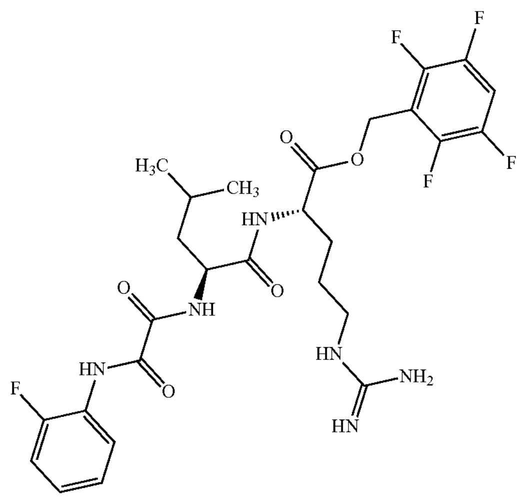 [SMILES: CC(C)C[C@H](NC(=O)C(=O)Nc1ccccc1F)C(=O)N[C@@H](CCCNC(=N)N)C(=O)OCc1c(F)c(F)cc(F)c1F] | N1-(2-fluorophenyl)-N2-((S)-1-(((S)-6-guanidino-2-oxo-1-(2,3,5,6-tetrafluorophenoxy)-hexan-3-yl)amino)-4-methyl-1-oxopentan-2-yl)oxalamide | 615.2300 | ** |

TABLE 1-continued

| Compound | Structure | IUPAC | LCMS [M + 1] | EC50, uM (Hela) |
|---|---|---|---|---|
| 229 | 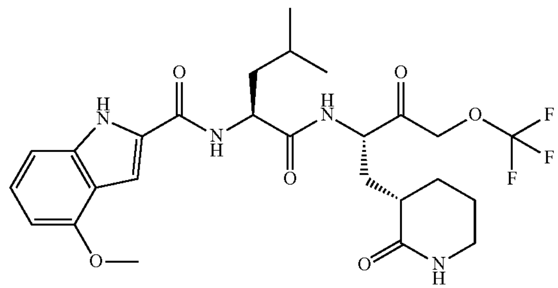 [SMILES: COc1cccc2[nH]c(C(=O)N[C@@H](CC(C)C)C(=O)N[C@@H](C[C@@H]3CCCNC3=O)C(=O)COC(F)(F)F)cc12] | 4-methoxy-N-((S)-4-methyl-1-oxo-1-(((S)-3-oxo-1-((S)-2-oxopiperidin-3-yl)-4-(trifluoromethoxy)butan-2-yl)amino)pentan-2-yl)-1H-indole-2-carboxamide | 555.2400 | **** |
| 230 | 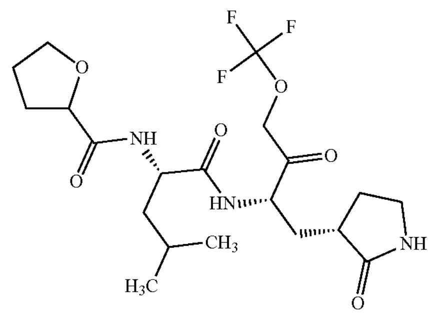 [SMILES: CC(C)C[C@H](NC(=O)C1CCCO1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-3-carboxamide | 466.3025 | * |
| 231 | 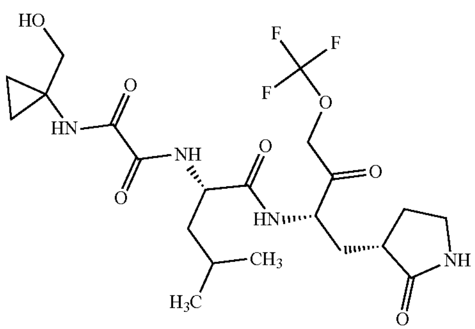 [SMILES: CC(C)C[C@H](NC(=O)C(=O)NC1(CO)CC1)C(=O)N[C@@H](C[C@@H]1CCNC1=O)C(=O)COC(F)(F)F] | N1-(1-(hydroxymethyl)cyclopropyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 509.21 | * |

TABLE 1-continued

| Compound | Structure | IUPAC | LCMS [M + 1] | EC50, uM (Hela) |
|---|---|---|---|---|
| 232 | 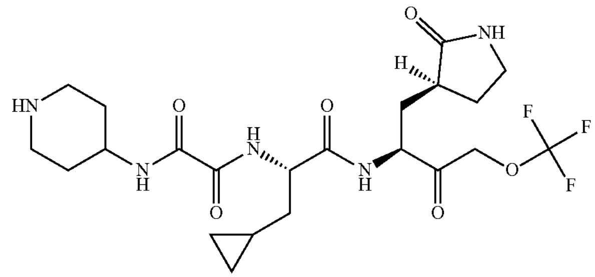 [SMILES: O=C(NC1CCNCC1)C(=O)N[C@@H](CC1CC1)C(=O)N[C@@H](C[C@@H]1CCNC1=O)C(=O)COC(F)(F)F] | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(piperidin-4-yl)oxalamide | 519.9576 | >1 μM |
| 233 | 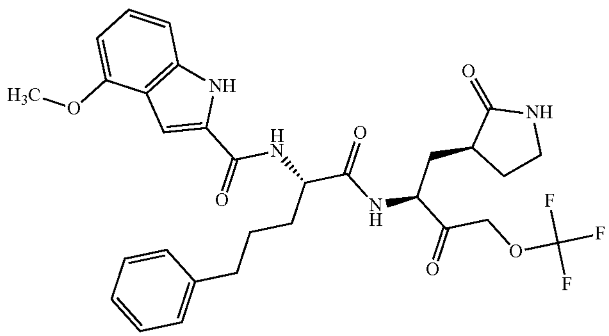 [SMILES: COc1cccc2[nH]c(C(=O)N[C@@H](CCCc3ccccc3)C(=O)N[C@@H](C[C@@H]3CCNC3=O)C(=O)COC(F)(F)F)cc12] | 4-methoxy-N-((S)-1-oxo-1-(((S)-3-oxo-1-((S)-2-oxopyrrolidin-3-yl)-4-(trifluoromethoxy)butan-2-yl)amino)-5-phenylpentan-2-yl)-1H-indole-2-carboxamide | 603.2400 | *** |
| 234 | 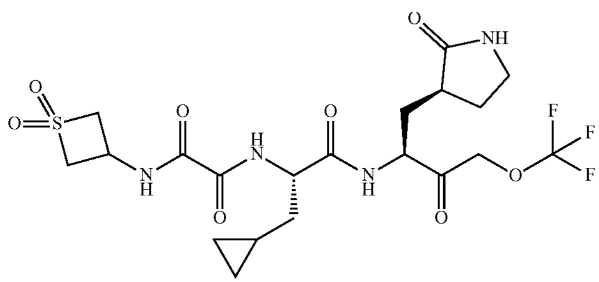 [SMILES: O=C(NC1CS(=O)(=O)C1)C(=O)N[C@@H](CC1CC1)C(=O)N[C@@H](C[C@@H]1CCNC1=O)C(=O)COC(F)(F)F] | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(1,1-dioxidothietan-3-yl)oxalamide | 541.2446 | >1 μM |

TABLE 1-continued

| Compound | Structure | IUPAC | LCMS [M + 1] | EC50, uM (Hela) |
|---|---|---|---|---|
| 235 | 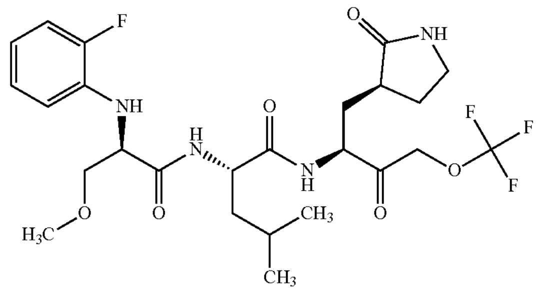 [SMILES: COC[C@@H](Nc1ccccc1F)C(=O)N[C@@H](CC(C)C)C(=O)N[C@@H](C[C@@H]1CCNC1=O)C(=O)COC(F)(F)F] | (S)-2-((R)-2-((2-fluorophenyl)amino)-3-methoxypropanamido)-4-methyl-N-((S)-3-oxo-1-((S)-2-oxopyrrolidin-3-yl)-4-(trifluoromethoxy)butan-2-yl)pentanamide | 563.4900 | **** |
| 236 | 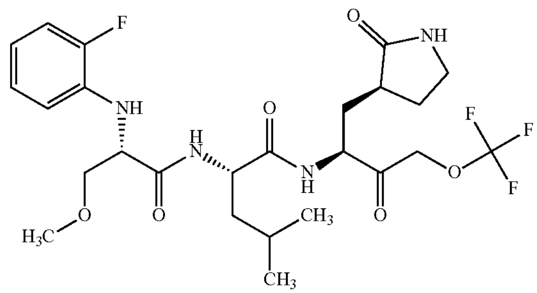 [SMILES: COC[C@H](Nc1ccccc1F)C(=O)N[C@@H](CC(C)C)C(=O)N[C@@H](C[C@@H]1CCNC1=O)C(=O)COC(F)(F)F] | (S)-2-((S)-2-((2-fluorophenyl)amino)-3-methoxypropanamido)-4-methyl-N-((S)-3-oxo-1-((S)-2-oxopyrrolidin-3-yl)-4-(trifluoromethoxy)butan-2-yl)pentanamide | 563.4900 | **** |
| 237 | 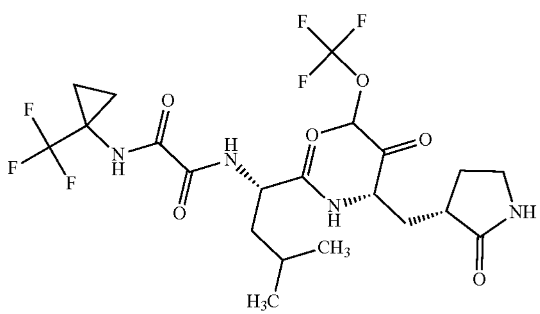 | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(1-(trifluoromethyl)cyclopropyl)oxalamide | 547.1900 | **** |

TABLE 1-continued

| Compound | Structure | IUPAC | LCMS [M + 1] | EC50, uM (Hela) |
|---|---|---|---|---|
| 238 | 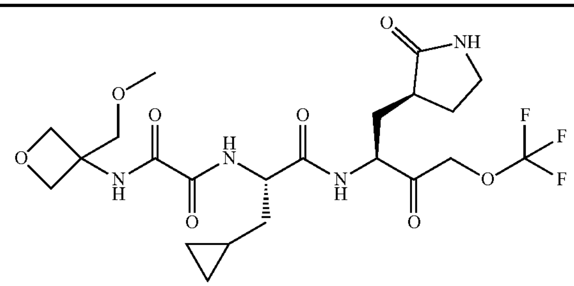 | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(3-(methoxymethyl)oxetan-3-yl)oxalamide | 537.5000 | ** |
| 239 | 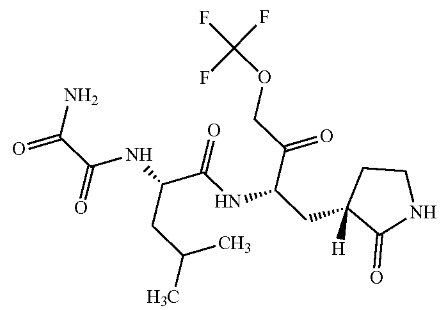 [SMILES: CC(C)C[C@H](NC(=O)C(N)=O)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 439.2556 | >1 μM |
| 240 | 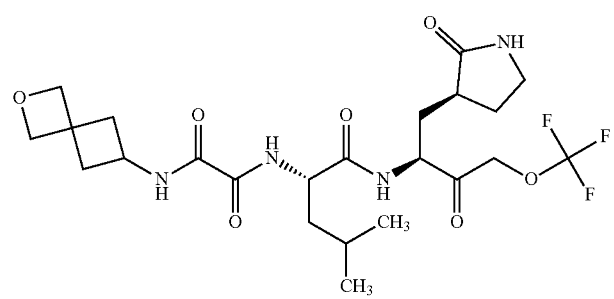 [SMILES: CC(C)C[C@H](NC(=O)C(=O)NC1CC2(COC2)C1)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(2-oxaspiro[3.3]heptan-6-yl)oxalamide | 535.3700 | *** |

TABLE 1-continued

| Compound | Structure | IUPAC | LCMS [M + 1] | EC50, uM (Hela) |
|---|---|---|---|---|
| 241 | 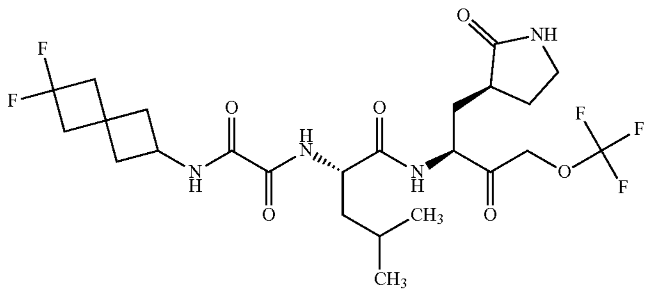 [SMILES: CC(C)C[C@H](NC(=O)C(=O)NC1CC2(C1)CC(F)(F)C2)C(=O)N[C@@H](C[C@@H]1CCNC1=O)C(=O)COC(F)(F)F] | N1-(6,6-difluorospiro[3.3]heptan-2-yl)-N2-((S)-4-methyl-1-oxo-1-(((S)-3-oxo-1-(((S)-2-oxopyrrolidin-3-yl)-4-(trifluoromethoxy)butan-2-yl)amino)pentan-2-yl)oxalamide | 569.2300 | **** |
| 242 | 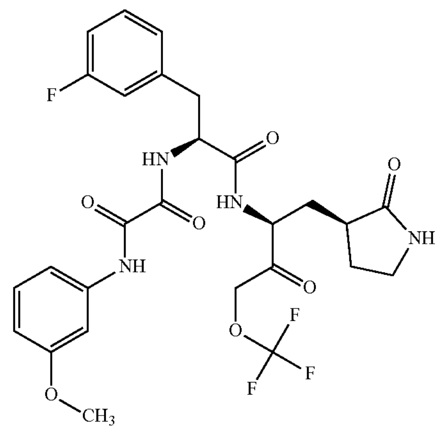 [SMILES: COc1cccc(NC(=O)C(=O)N[C@@H](Cc2cccc(F)c2)C(=O)N[C@@H](C[C@@H]2CCNC2=O)C(=O)COC(F)(F)F)c1] | N1-((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-N2-(3-methoxyphenyl)oxalamide | 597.3549 | **** |
| 243 | 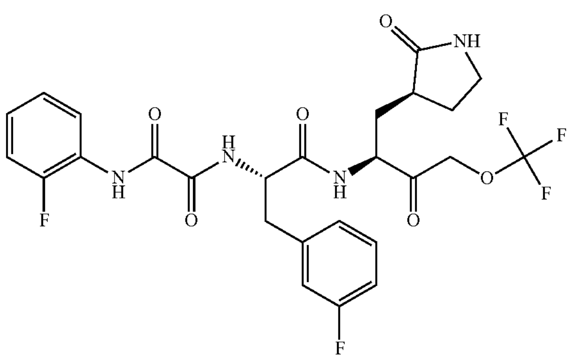 [SMILES: O=C(Nc1ccccc1F)C(=O)N[C@@H](Cc1cccc(F)c1)C(=O)N[C@@H](C[C@@H]1CCNC1=O)C(=O)COC(F)(F)F] | N1-(2-fluorophenyl)-N2-((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)oxalamide | 585.1700 | **** |

TABLE 1-continued

| Compound | Structure | IUPAC | LCMS [M + 1] | EC50, uM (Hela) |
|---|---|---|---|---|
| 244 | 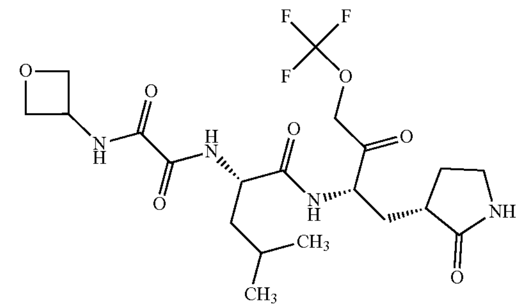 [SMILES: CC(C)C[C@H](NC(=O)C(=O)NC1COC1)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(oxetan-3-yl)oxalamide | 495.2000 | *** |
| 245 | 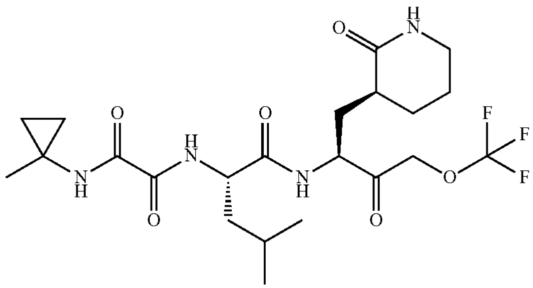 [SMILES: CC(C)C[C@H](NC(=O)C(=O)NC1(C)CC1)C(=O)N[C@@H](C[C@@H]1CCCNC1=O)C(=O)COC(F)(F)F] | N1-((S)-4-methyl-1-oxo-1-(((S)-3-oxo-1-((S)-2-oxopiperidin-3-yl)-4-(trifluoromethoxy)butan-2-yl)amino)pentan-2-yl)-N2-(1-methylcyclopropyl)oxalamide | 507.0331 | **** |
| 246 | 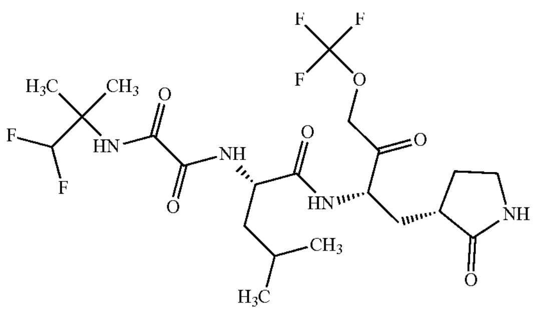 [SMILES: CC(C)C[C@H](NC(=O)C(=O)NC(C)(C)C(F)F)C(=O)N[C@@H](C[C@@H]1CCNC1=O)C(=O)COC(F)(F)F] | N1-(1,1-difluoro-2-methylpropan-2-yl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 531.2200 | **** |

TABLE 1-continued

| Compound | Structure | IUPAC | LCMS [M + 1] | EC50, uM (Hela) |
|---|---|---|---|---|
| 247 | 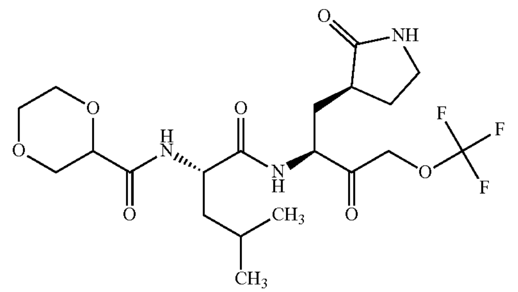 [SMILES: CC(C)C[C@H](NC(=O)C1COCCO1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1,4-dioxane-2-carboxamide | 482.0000 | *** |
| 248 | 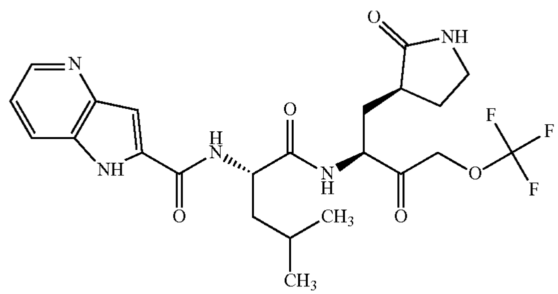 | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[3,2-b]pyridine-2-carboxamide | 512.3000 | ** |
| 249 | 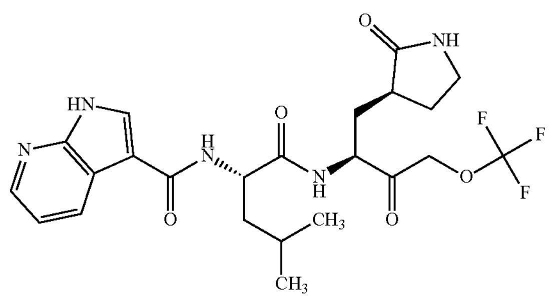 [SMILES: CC(C)C[C@H](NC(=O)c1c[nH]c2ncccc12)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[2,3-b]pyridine-3-carboxamide | 512.3090 | ** |

TABLE 1-continued

| Compound | Structure | IUPAC | LCMS [M + 1] | EC50, uM (Hela) |
|---|---|---|---|---|
| 250 | 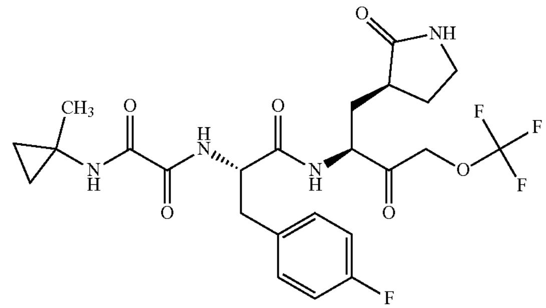 [SMILES: CC1(NC(=O)C(=O)N[C@@H](Cc2ccc(F)cc2)C(=O)N[C@@H](C[C@@H]2CCNC2=O)C(=O)COC(F)(F)F)CC1] | N1-((S)-3-(4-fluorophenyl)-1-oxo-1-(((S)-3-oxo-1-((S)-2-oxopyrrolidin-3-yl)-4-(trifluoromethoxy)butan-2-yl)amino)propan-2-yl)-N2-(1-methylcyclopropyl)oxalamide | 545.3459 | **** |
| 251 | 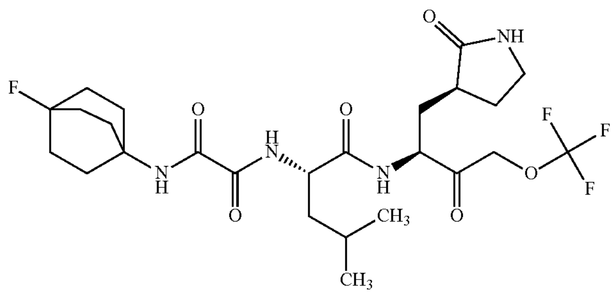 [SMILES: CC(C)C[C@H](NC(=O)C(=O)NC12CCC(F)(CC1)CC2)C(=O)N[C@@H](C[C@@H]1CCNC1=O)C(=O)COC(F)(F)F] | N1-(4-fluorobicyclo[2.2.2]octan-1-yl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 565.2600 | **** |
| 252 | 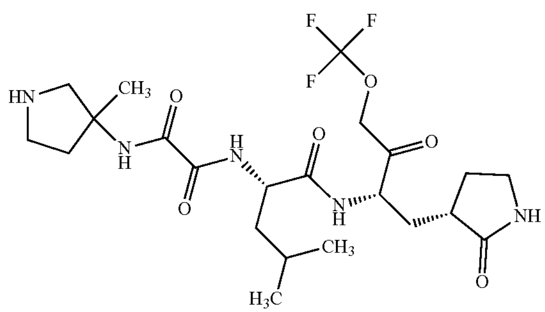 [SMILES: CC(C)C[C@H](NC(=O)C(=O)NC1(C)CCNC1)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(3-methylpyrrolidin-3-yl)oxalamide | 522.6366 | ** |

TABLE 1-continued

| Compound | Structure | IUPAC | LCMS [M + 1] | EC50, uM (Hela) |
|---|---|---|---|---|
| 253 | 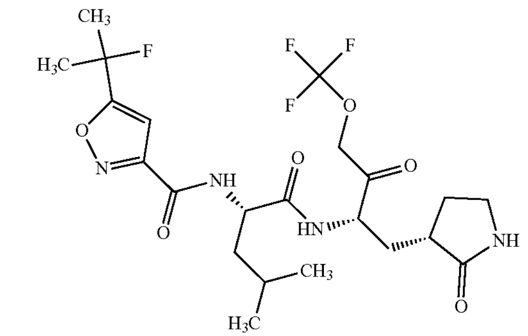 [SMILES: CC(C)C[C@H](NC(=O)c1cc(C(C)(C)F)on1)C(=O)N[C@@H](C[C@@H]1CCNC1=O)C(=O)COC(F)(F)F] | 5-(2-fluoropropan-2-yl)-N-((S)-4-methyl-1-oxo-1-(((S)-3-oxo-1-((S)-2-oxopyrrolidin-3-yl)-4-(trifluoromethoxy)butan-2-yl)amino)pentan-2-yl)isoxazole-3-carboxamide | 523.4600 | **** |
| 254 | 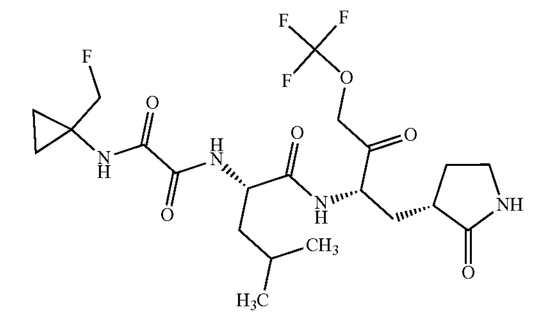 [SMILES: CC(C)C[C@H](NC(=O)C(=O)NC1(CF)CC1)C(=O)N[C@@H](C[C@@H]1CCNC1=O)C(=O)COC(F)(F)F] | N1-(1-(fluoromethyl)cyclopropyl)-N2-((S)-4-methyl-1-oxo-1-(((S)-3-oxo-1-((S)-2-oxopyrrolidin-3-yl)-2-(trifluoromethoxy)butan-2-yl)amino)pentan-2-yl)oxalamide | 511.4900 | **** |
| 255 | 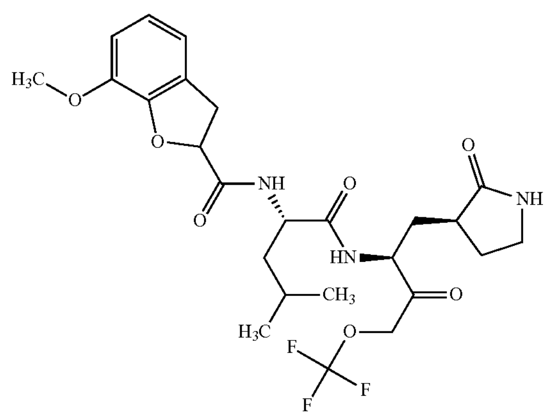 [SMILES: COc1cccc2c1OC(C(=O)N[C@@H](CC(C)C)C(=O)N[C@@H](C[C@@H]1CCNC1=O)C(=O)COC(F)(F)F)C2] | 7-methoxy-N-((S)-4-methyl-1-oxo-1-(((S)-3-oxo-1-((S)-2-oxopyrrolidin-3-yl)-4-(trifluoromethoxy)butan-2-yl)amino)pentan-2-yl)-2,3-dihydrobenzofuran-2-carboxamide | 544.4600 | **** |

TABLE 1-continued

| Compound | Structure | IUPAC | LCMS [M + 1] | EC50, uM (Hela) |
|---|---|---|---|---|
| 256 | 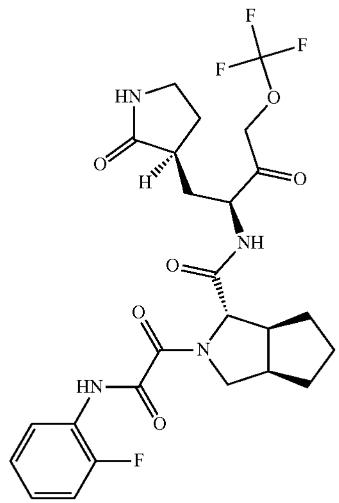 [SMILES: O=C(Nc1ccccc1F)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-((2-fluorophenyl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 557.3903 | **** |
| 257 | 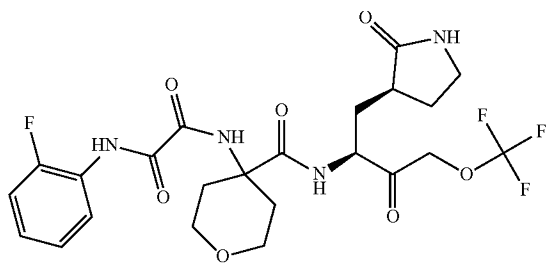 [SMILES: O=C(Nc1ccccc1F)C(=O)NC1(C(=O)N[C@@H](C[C@@H]2CCNC2=O)C(=O)COC(F)(F)F)CCOCC1] | N1-(2-fluorophenyl)-N2-(4-(((S)-3-oxo-1-((S)-2-oxopyrrolidin-3-yl)-4-(trifluoromethoxy)butan-2-yl)carbamoyl)-tetrahydro-2H-pyran-4-yl)oxalamide | 547.3227 | >1 μM |

TABLE 1-continued

| Compound | Structure | IUPAC | LCMS [M + 1] | EC50, uM (Hela) |
|---|---|---|---|---|
| 258 | 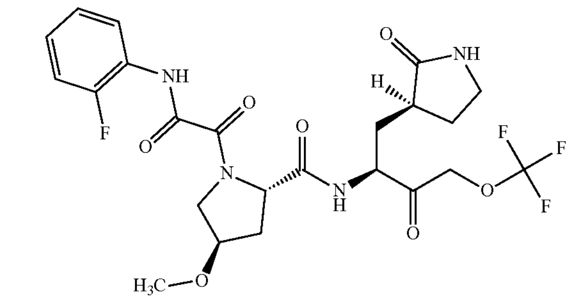 [SMILES: CO[C@@H]1C[C@@H](C(=O)N[C@@H](C[C@@H]2CCNC2=O)C(=O)COC(F)(F)F)N(C(=O)C(=O)Nc2ccccc2F)C1] | (2S,4R)-1-(2-((2-fluorophenyl)amino)-2-oxoacetyl)-4-methoxy-N-((S)-3-oxo-1-(((S)-2-oxopyrrolidin-3-yl)-4-(trifluoromethoxy)butan-2-yl)pyrrolidine-2-carboxamide | 547.3277 | >1 µM |
| 259 | 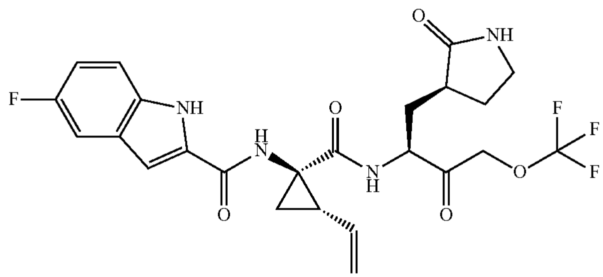 [SMILES: C=C[C@@H]1C[C@]1(NC(=O)c1cc2cc(F)ccc2[nH]1)C(=O)N[C@@H](C[C@@H]1CCNC1=O)C(=O)COC(F)(F)F] | 5-fluoro-N-((1R,2S)-1-(((S)-3-oxo-1-((S)-2-oxopyrrolidin-3-yl)-4-(trifluoromethoxy)butan-2-yl)carbamoyl)-2-vinylcyclopropyl)-1H-indole-2-carboxamide | 525.5328 | >1 µM |
| 260 | 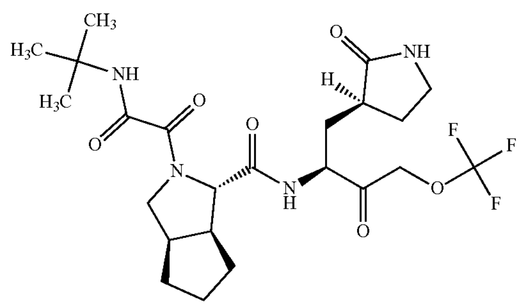 [SMILES: CC(C)(C)NC(=O)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-(tert-butylamino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 519.0526 | **** |

TABLE 1-continued

| Compound | Structure | IUPAC | LCMS [M + 1] | EC50, uM (Hela) |
|---|---|---|---|---|
| 261 | 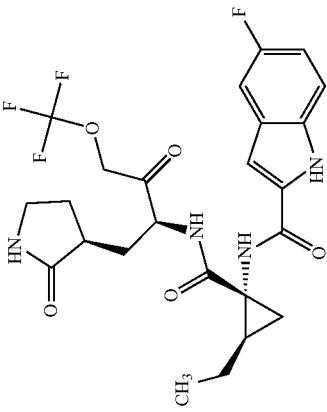 | N-((1R,2R)-2-ethyl-1-(((S)-3-oxo-1-((S)-2-oxopyrrolidin-3-yl)-4-(trifluoromethoxy)butan-2-yl)carbamoyl)cyclopropyl)-5-fluoro-1H-indole-2-carboxamide | 527.2706 | * |
| 262 | 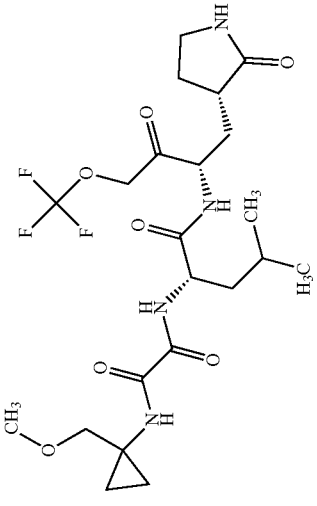 | N1-(1-(methoxymethyl)cyclopropyl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 523.3245 | *** |
| 263 | 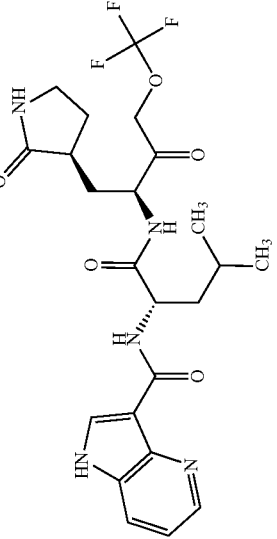 | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1H-pyrrolo[3,2-b]pyridine-3-carboxamide | 512.3188 | ** |

TABLE 1-continued

| Compound | Structure | IUPAC | LCMS [M + 1] | EC50, uM (Hela) |
|---|---|---|---|---|
| 264 | 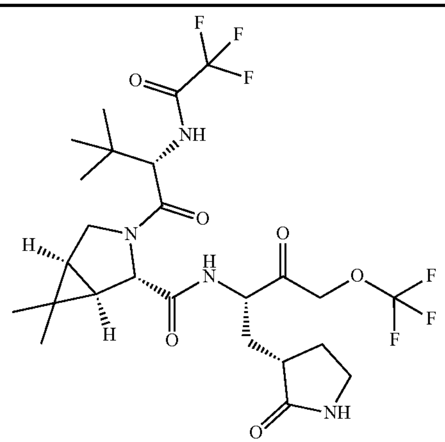 | (1R,2S,5S)-3-((S)-3,3-dimethyl-2-(2,2,2-trifluoroacetamido)butanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 601.4100 | **** |
| 265 | 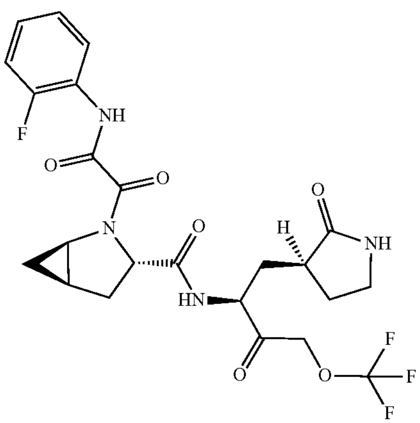 [SMILES: O=C(Nc1ccccc1F)C(=O)N1[C@@H]2C[C@@H]2C[C@H]1C(=O)N[C@@H](C[C@@H]1CCNC1=O)C(=O)COC(F)(F)F] | (1R,S 5R)-2-(2-((2-fluorophenyl)amino)-2-oxoacetyl)-N-((S)-3-oxo-1-((S)-2-oxopyrrolidin-3-yl)-4-(trifluoromethoxy)butan-2-yl)-2-azabicyclo[3.1.0]-hexane-3-carboxamide | 529.0445 | *** |

TABLE 1-continued

| Compound | Structure | IUPAC | LCMS [M + 1] | EC50, uM (Hela) |
|---|---|---|---|---|
| 266 | 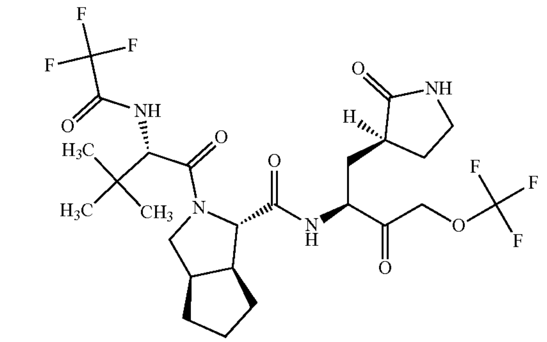 [SMILES: CC(C)(C)[C@H](NC(=O)C(F)(F)F)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-((S)-3,3-dimethyl-2-(2,2,2-trifluoroacetamido)-butanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 601.4092 | **** |
| 267 | 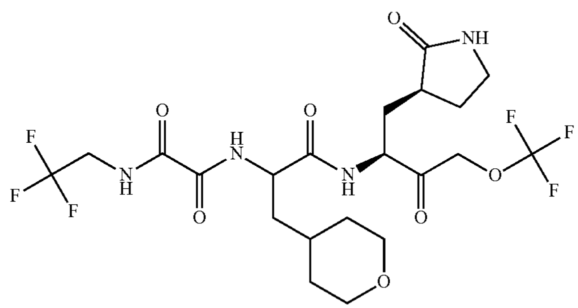 [SMILES: O=C(NCC(F)(F)F)C(=O)NC(CC1CCOCC1)C(=O)N[C@@H](C[C@@H]1CCNC1=O)C(=O)COC(F)(F)F] | N1-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)-N2-(2,2,2-trifluoroethyl)-oxalamide | 563.19 | * |

TABLE 1-continued

| Compound | Structure | IUPAC | LCMS [M + 1] | EC50, uM (Hela) |
|---|---|---|---|---|
| 268 | 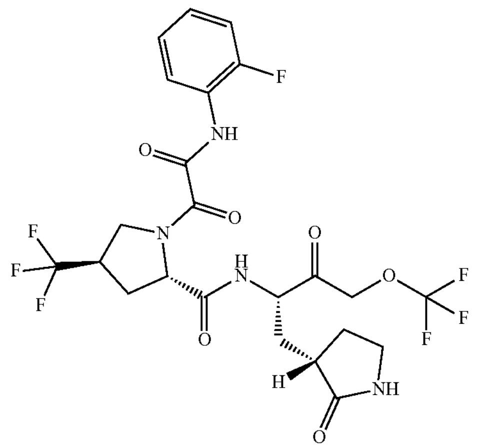 [SMILES: O=C(Nc1ccccc1F)C(=O)N1C[C@H](C(F)(F)F)C[C@H]1C(=O)N[C@@H](C[C@@H]1CCNC1=O)C(=O)COC(F)(F)F] | (2S,4R)-1-(2-((2-fluorophenyl)amino)-2-oxoacetyl)-N-((S)-3-oxo-1-((S)-2-oxopyrrolidin-3-yl)-4-(trifluoromethoxy)butan-2-yl)-4-(trifluoromethyl)-pyrrolidine-2-carboxamide | 585.1506 | |
| 269 | 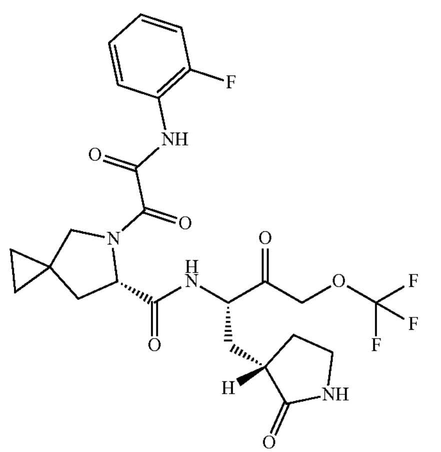 [SMILES: O=C(Nc1ccccc1F)C(=O)N1CC2(CC2)C[C@H]1C(=O)N[C@@H](C[C@@H]1CCNC1=O)C(=O)COC(F)(F)F] | (S)-5-(2-((2-fluorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 543.1788 | **** |

TABLE 1-continued

| Compound | Structure | IUPAC | LCMS [M + 1] | EC50, uM (Hela) |
|---|---|---|---|---|
| 270 | 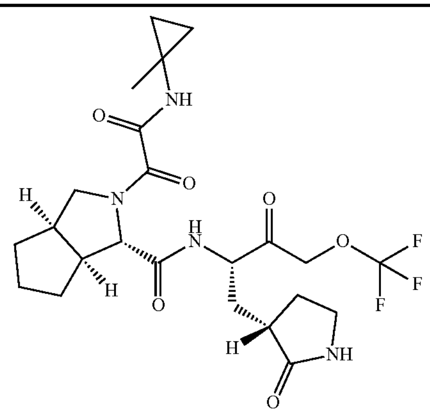 | (1S,3aR,6aS)-2-(2-((1-methylcyclopropyl)-amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 517.2196 | *** |
| 271 | 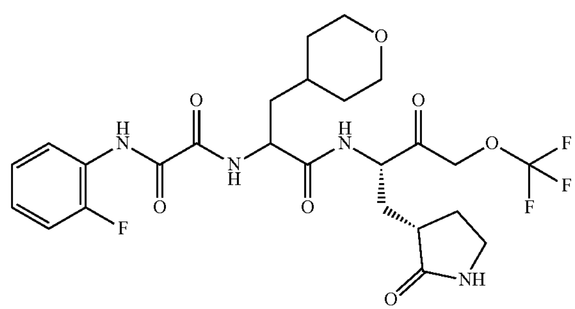 [SMILES: O=C(Nc1ccccc1F)C(=O)NC(CC1CCOCC1)C(=O)N[C@@H](C[C@@H]1CCNC1=O)C(=O)COC(F)(F)F] | N1-(2-fluorophenyl)-N2-(1-oxo-1-((S)-2-oxopyrrolidin-3-yl)-2-((S)-3-oxo-1-((S)-2-oxopyrrolidin-3-yl)-4-(trifluoromethoxy)butan-2-yl)amino)-3-(tetrahydro-2H-pyran-4-yl)propan-2-yl)oxalamide | 575.2051 | **** |

TABLE 1-continued
| Compound | Structure | IUPAC | LCMS [M + 1] | EC50, uM (Hela) |
|---|---|---|---|---|
| 272 | 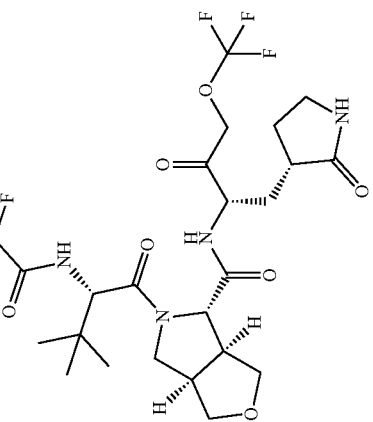 | (3aS,4S,6aR)-5-((S)-3,3-dimethyl-2-(2,2,2-trifluoroacetamido)butanoyl)-N-((S)-3-oxo-1-((S)-2-oxopyrrolidin-3-yl)-4-(trifluoromethoxy)butan-2-yl)hexahydro-1H-furo[3,4-c]pyrrole-4-carboxamide | 603.2175 | |
| 273 | 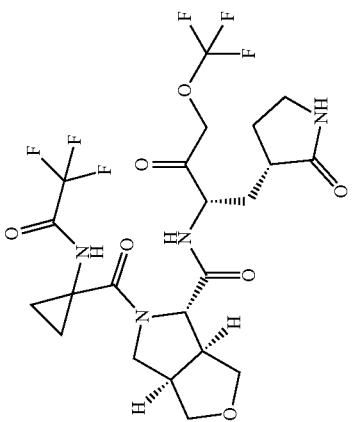 | (1S,3aR,6aS)-N-((S)-3-oxo-1-((S)-2-oxopyrrolidin-3-yl)-4-(trifluoromethoxy)butan-2-yl)-2-(1-(2,2,2-trifluoroacetamido)cyclopropane-1-carbonyl)octahydrocyclopenta[c]pyrrole-1-carboxamide | 571.1913 | |

TABLE 1-continued

| Compound | Structure | IUPAC | LCMS [M + 1] | EC50, uM (Hela) |
|---|---|---|---|---|
| 274 | 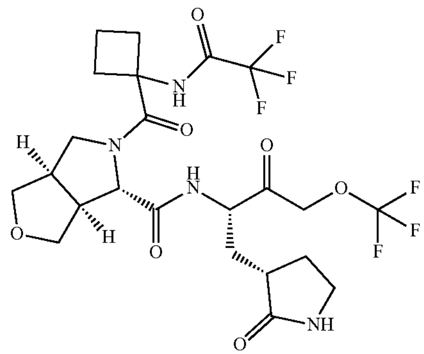 [SMILES: O=C1NCC[C@H]1C[C@H](NC(=O)[C@@H]1[C@H]2COC[C@H]2CN1C(=O)C1(NC(=O)C(F)(F)F)CCC1)C(=O)COC(F)(F)F] | (1S,3aR,6aS)-N-((S)-3-oxo-1-((S)-2-oxopyrrolidin-3-yl)-4-(trifluoromethoxy)butan-2-yl)-2-(1-(2,2,2-trifluoroacetamido)cyclobutane-1-carbonyl)octahydrocyclopenta[c]pyrrole-1-carboxamide | 585.21 | ** |
| 275 | 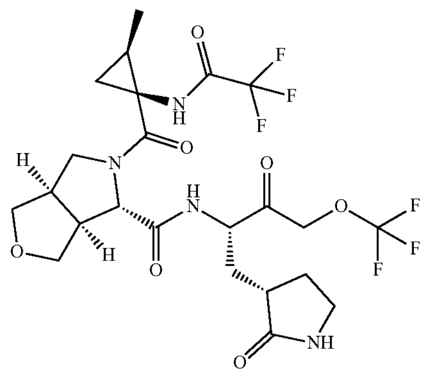 [SMILES: C[C@@H]1C[C@@]1(NC(=O)C(F)(F)F)C(=O)N1C[C@@H]2COC[C@@H]2[C@H]1C(=O)N[C@@H](C[C@@H]1CCNC1=O)C(=O)COC(F)(F)F] | (1S,3aR,6aS)-2-((1S,2R)-2-methyl-1-(2,2,2-trifluoroacetamido)cyclopropane-1-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 585.2070 | |

TABLE 1-continued

| Compound | Structure | IUPAC | LCMS [M + 1] | EC50, uM (Hela) |
|---|---|---|---|---|
| 276 | 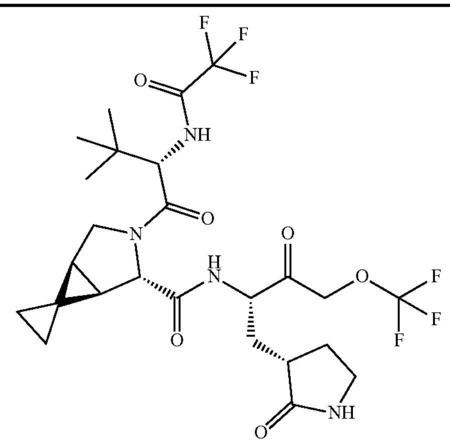 | (1R,2S,5S)-3-((S)-3,3-dimethyl-2-(2,2,2-trifluoroacetamido)butanoyl)-N-((S)-3-oxo-1-((S)-2-oxopyrrolidin-3-yl)-4-(trifluoromethoxy)butan-2-yl)-3-azaspiro[bicyclo[3.1.0]hexane-6,1'-cyclopropane]-2-carboxamide | 599.2226 | |
| 277 | 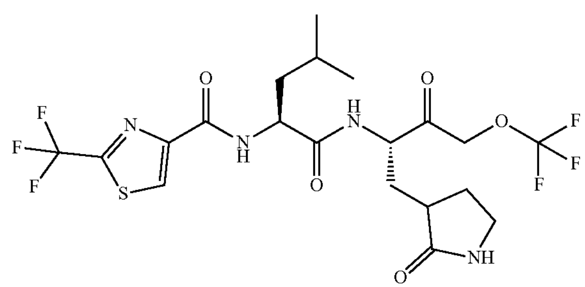 [SMILES: CC(C)C[C@H](NC(=O)c1csc(C(F)(F)F)n1)C(=O)N[C@@H](CC1CCNC1=O)C(=O)COC(F)(F)F] | N-((2S)-4-methyl-1-oxo-1-(((2S)-3-oxo-1-(2-oxopyrrolidin-3-yl)-4-(trifluoromethoxy)butan-2-yl)amino)pentan-2-yl)-2-(trifluoromethyl)-thiazole-4-carboxamide | 547.1372 | **** |

TABLE 1-continued
| Compound | Structure | IUPAC | LCMS [M + 1] | EC50, uM (Hela) |
|---|---|---|---|---|
| 278 | 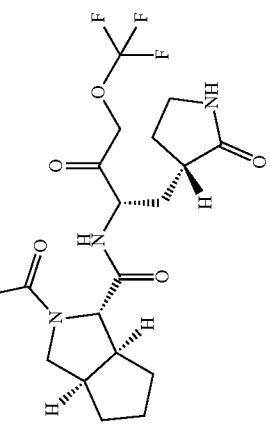 | (1S,3aR,7aS)-N-((S)-3-oxo-1-((S)-2-oxopyrrolidin-3-yl)-4-(trifluoromethoxy)butan-2-yl)-2-(2-(trifluoromethyl)thiazole-4-carbonyl)octahydro-1H-isoindole-1-carboxamide | 585.1528 | |
| 279 | 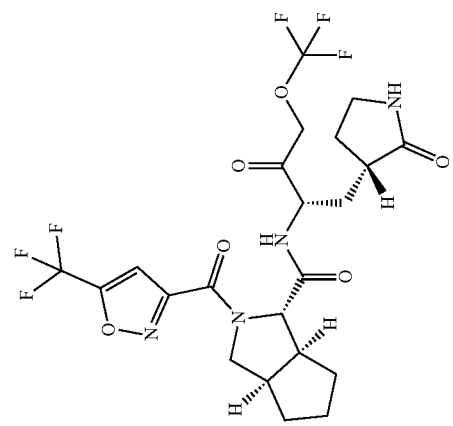 | (1S,3aR,7aS)-N-((S)-3-oxo-1-((S)-2-oxopyrrolidin-3-yl)-4-(trifluoromethoxy)butan-2-yl)-2-(5-(trifluoromethyl)isoxazole-3-carbonyl)octahydro-1H-isoindole-1-carboxamide | 569.1757 | |

TABLE 1-continued
| Compound | Structure | IUPAC | LCMS [M + 1] | EC50, uM (Hela) |
|---|---|---|---|---|
| 280 | 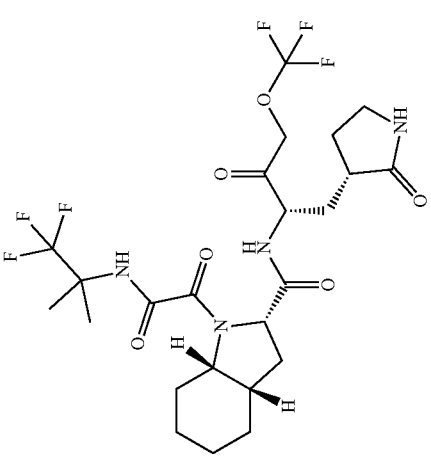 | (2S,3aS,7aS)-N-((S)-3-oxo-1-((S)-2-oxopyrrolidin-3-yl)-4-(trifluoromethoxy)butan-2-yl)-1-(2-oxo-2-((1,1,1-trifluoro-2-methylpropan-2-yl)amino)acetyl)-octahydro-1H-indole-2-carboxamide | 587.2226 | |
| 281 | 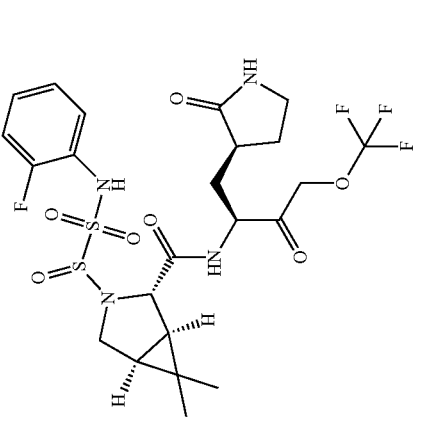 | (1R,2S,5S)-3-((N-(2-fluorophenyl)-sulfamoyl)carbonyl)-6,6-dimethyl-N-((S)-2-oxo-1-((S)-2-oxopyrrolidin-3-yl)-4-(trifluoromethoxy)butan-2-yl)-3-azabicyclo-[3.1.0]hexane-2-carboxamide | 593.1615 | |

TABLE 1-continued
| Compound | Structure | IUPAC | LCMS [M + 1] | EC50, uM (Hela) |
|---|---|---|---|---|
| 282 | 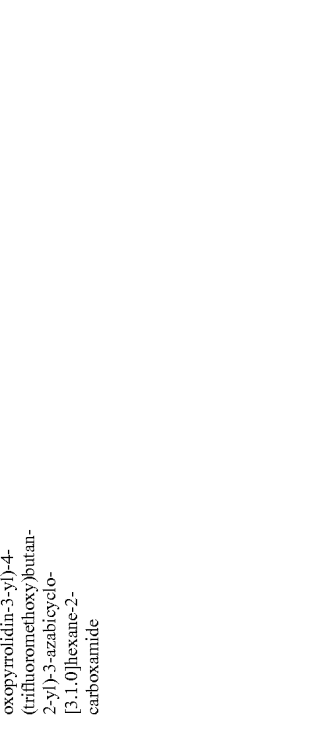 | (1R,2S,5S)-3-(N-(2-fluorophenyl)-sulfamoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 565.1666 | |
| 283 | 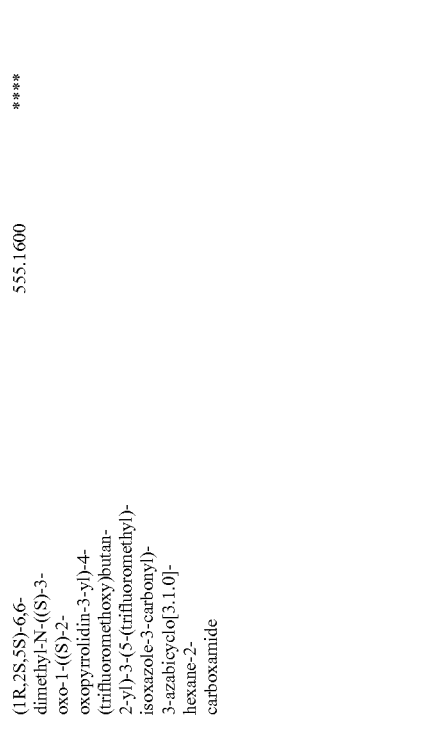 | (1R,2S,5S)-6,6-dimethyl-N-((S)-3-oxo-1-((S)-2-oxopyrrolidin-3-yl)-4-(trifluoromethoxy)butan-2-yl)-3-(5-(trifluoromethyl)-isoxazole-3-carbonyl)-3-azabicyclo[3.1.0]-hexane-2-carboxamide | 555.1600 | **** |

TABLE 1-continued

| Compound | Structure | IUPAC | LCMS [M + 1] | EC50, uM (Hela) |
|---|---|---|---|---|
| 284 | 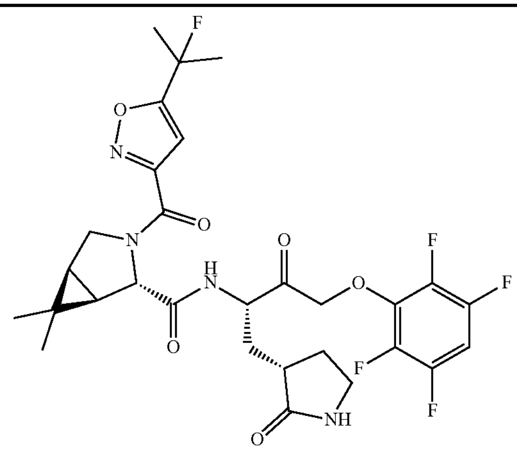 | (1R,2S,5S)-3-(5-(2-fluoropropan-2-yl)isoxazole-3-carbonyl)-6,6-dimethyl-N-((S)-3-oxo-1-((S)-2-oxopyrrolidin-3-yl)-4-(2,3,5,6-tetrafluorophenoxy)butan-2-yl)-3-azabicyclo[3.1.0]hexane-2-carboxamide | 627.2164 | ** |
| 285 | 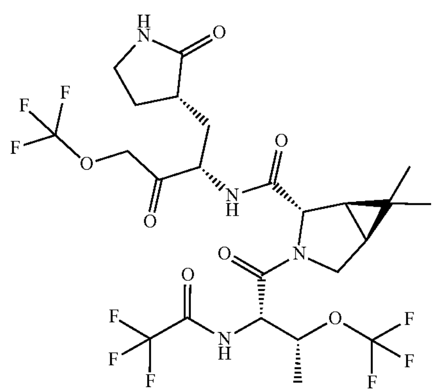 [SMILES: C[C@@H](OC(F)(F)F)[C@H](NC(=O)C(F)(F)F)C(=O)N1C[C@H]2[C@@H]([C@H]1C(=O)N[C@@H](C[C@@H]1CCNC1=O)C(=O)COC(F)(F)F)C2(C)C] | (1S,2R,5S)-6,6-dimethyl-N-((S)-3-oxo-1-((S)-2-oxopyrrolidin-3-yl)-4-(trifluoromethoxy)butan-2-yl)-3-(N-(2,2,2-trifluoroacetyl)-O-(trifluoromethyl)-L-threonyl)bicyclo[3.1.0]hexane-2-carboxamide | 656.1940 | |

TABLE 1-continued

| Compound | Structure | IUPAC | LCMS [M + 1] | EC50, uM (Hela) |
|---|---|---|---|---|
| 286 | 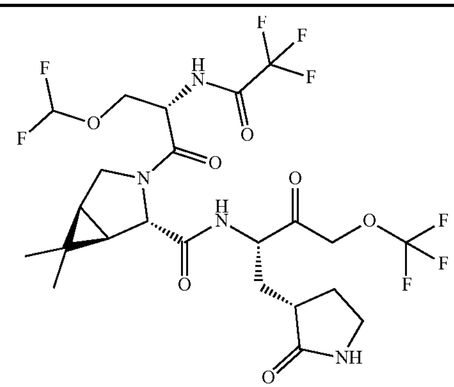 | (1R,2S,5S)-3-(O-(difluoromethyl)-N-(2,2,2-trifluoroacetyl)-L-seryl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 625.1830 | |
| 287 | 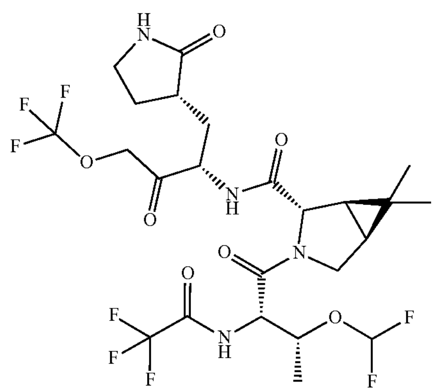 [SMILES: C[C@@H](OC(F)F)[C@H](NC(=O)C(F)(F)F)C(=O)N1C[C@H]2[C@@H]([C@H]1C(=O)N[C@@H](C[C@@H]1CCNC1=O)C(=O)COC(F)(F)F)C2(C)C] | (1S,2R,5S)-3-(O-(difluoromethyl)-N-(2,2,2-trifluoroacetyl)-L-threonyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 638.2034 | |

TABLE 1-continued

| Compound | Structure | IUPAC | LCMS [M + 1] | EC50, uM (Hela) |
|---|---|---|---|---|
| 288 | 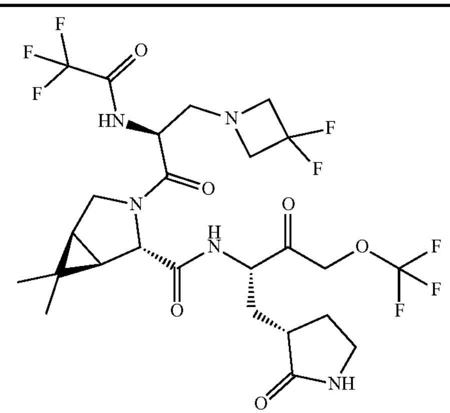 | (1R,2S,5S)-3-((S)-3-(3,3-difluoroazetidin-1-yl)-2-(2,2,2-trifluoroacetamido)propanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 650.2147 | |
| 289 | 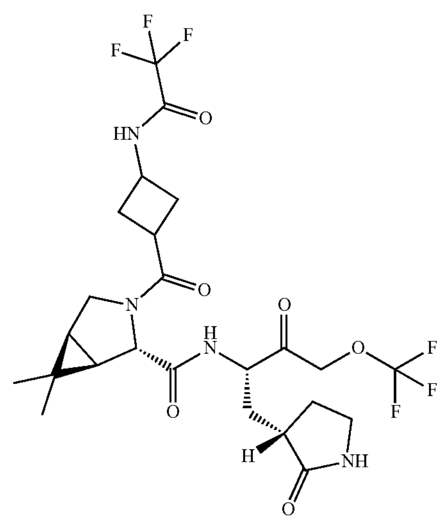 [SMILES: CC1(C)[C@@H]2[C@@H](C(=O)N[C@@H](C[C@@H]3CCNC3=O)C(=O)COC(F)(F)F)N(C(=O)C3CC(NC(=O)C(F)(F)F)C3)C[C@@H]21] | (1R,2S,5S)-6,6-dimethyl-N-((S)-3-oxo-1-((S)-2-oxopyrrolidin-3-yl)-4-(trifluoromethoxy)butan-2-yl)-3-(3-(2,2,2-trifluoroacetamido)cyclobutane-1-carbonyl)-3-azabicyclo[3.1.0]-hexane-2-carboxamide | 585.2070 | |

TABLE 1-continued

| Compound | Structure | IUPAC | LCMS [M + 1] | EC50, uM (Hela) |
|---|---|---|---|---|
| 290 | 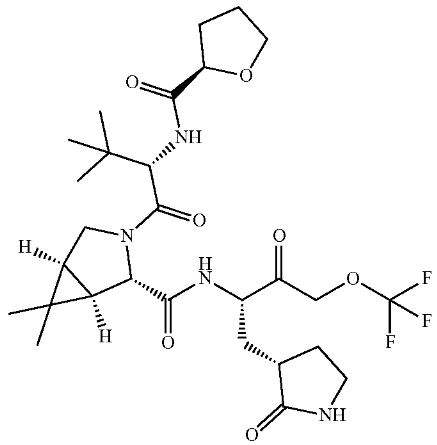 [SMILES: CC(C)(C)[C@H](NC(=O)[C@H]1CCCO1)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((S)-3,3-dimethyl-2-((R)-tetrahydrofuran-2-carboxamido)butanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 603.29 | ** |
| 291 | 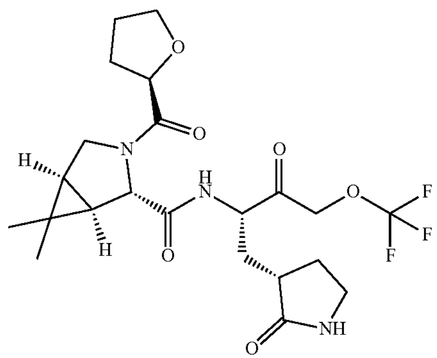 [SMILES: CC1(C)[C@@H]2[C@@H](C(=O)N[C@@H](C[C@@H]3CCNC3=O)C(=O)COC(F)(F)F)N(C(=O)[C@H]3CCCO3)C[C@@H]21] | (1R,2S,5S)-6,6-dimethyl-N-((S)-3-oxo-1-((S)-2-oxopyrrolidin-3-yl)-4-(trifluoromethoxy)butan-2-yl)-3-((R)-tetrahydrofuran-2-carbonyl)-3-azabicyclo[3.1.0]hexane-2-carboxamide | 490.21 | *** |

TABLE 1-continued

| Compound | Structure | IUPAC | LCMS [M + 1] | EC50, uM (Hela) |
|---|---|---|---|---|
| 292 | 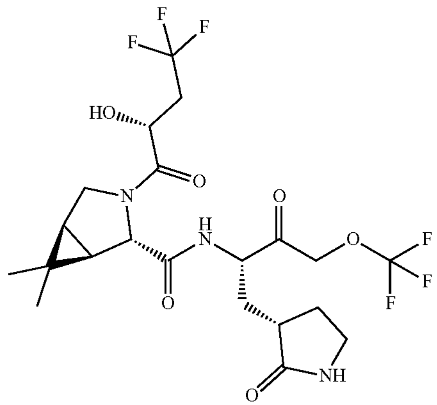 [SMILES: CC1(C)[C@@H]2[C@@H](C(=O)N[C@@H](C[C@@H]3CCNC3=O)C(=O)COC(F)(F)F)N(C(=O)[C@H](O)CC(F)(F)F)C[C@@H]21] | (1R,2S,5S)-6,6-dimethyl-N-((2S)-3-oxo-1-(2-oxopyrrolidin-3-yl)-4-(trifluoromethoxy)butan-2-yl)-3-((R)-4,4,4-trifluoro-2-hydroxybutanoyl)-3-azabicyclo[3.1.0]hexane-2-carboxamide | 532.1804 | |
| 293 | 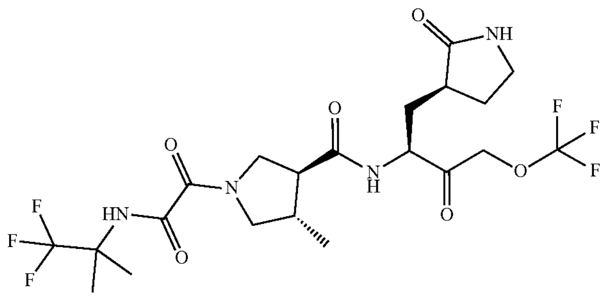 [SMILES: C[C@@H]1CN(C(=O)C(=O)NC(C)(C)C(F)(F)F)C[C@H]1C(=O)N[C@@H](C[C@@H]1CCNC1=O)C(=O)COC(F)(F)F] | (3S,4S)-4-methyl-N-((S)-3-oxo-1-((S)-2-oxopyrrolidin-3-yl)-4-(trifluoromethoxy)butan-2-yl)-1-(2-oxo-2-((1,1,1-trifluoro-2-methylpropan-2-yl)amino)acetyl)-pyrrolidine-3-carboxamide | 547.5 | >1 μM |
| 294 | 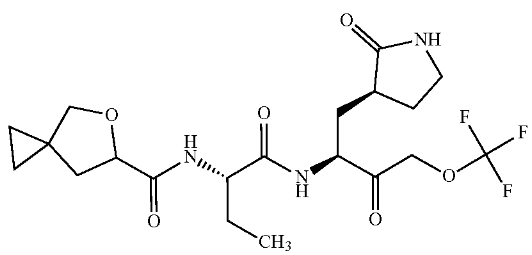 [SMILES: CC[C@H](NC(=O)C1CC2(CC2)CO1)C(=O)N[C@@H](C[C@@H]1CCNC1=O)C(=O)COC(F)(F)F] | N-((S)-1-oxo-1-(((S)-3-oxo-1-((S)-2-oxopyrrolidin-3-yl)-4-(trifluoromethoxy)butan-2-yl)amino)butan-2-yl)-5-oxaspiro[2.4]heptane-6-carboxamide | 492.4428 | **** |

TABLE 1-continued

| Compound | Structure | IUPAC | LCMS [M + 1] | EC50, uM (Hela) |
|---|---|---|---|---|
| 295 | 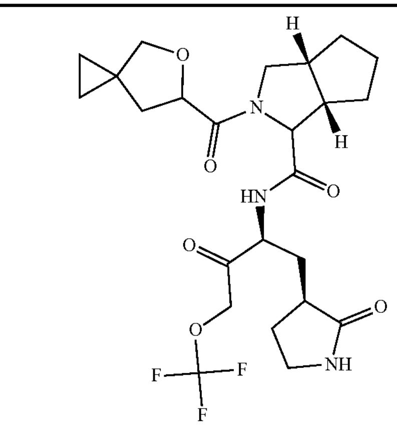 | (1S,3aR,6aS)-N-((S)-3-oxo-1-((S)-2-oxopyrrolidin-3-yl)-4-(trifluoromethoxy)butan-2-yl)-2-(5-oxaspiro[2.4]heptane-6-carbonyl)octahydrocyclopenta[c]pyrrole-1-carboxamide | 516.22 | *** |
| 298 | 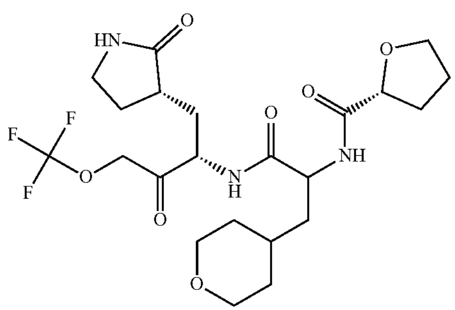 [SMILES: O=C(N[C@@H](C[C@@H]1CCNC1=O)C(=O)COC(F)(F)F)C(CC1CCOCC1)NC(=O)[C@H]1CCCO1] | (2R)-N-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)tetrahydrofuran-2-carboxamide | 508.4 | * |

TABLE 1-continued

| Compound | Structure | IUPAC | LCMS [M + 1] | EC50, uM (Hela) |
|---|---|---|---|---|
| 299 | 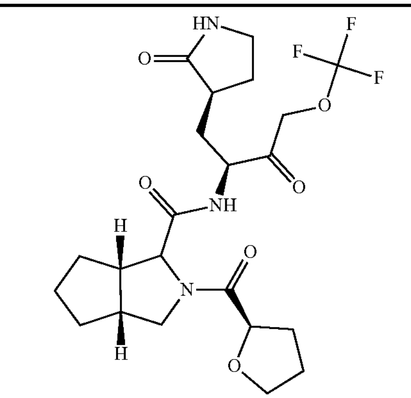 | (1S,3aR,6aS)-N-((S)-3-oxo-1-((S)-2-oxopyrrolidin-3-yl)-4-(trifluoromethoxy)butan-2-yl)-2-((R)-tetrahydrofuran-2-carbonyl)octahydrocyclopenta[c]pyrrole-1-carboxamide | 490.6326 | *** |
| 300 | 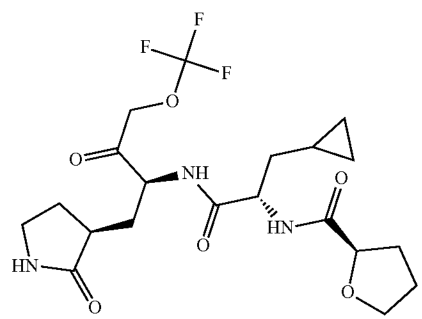 [SMILES: O=C1NCC[C@H]1C[C@H](NC(=O)[C@H](CC1CC1)NC(=O)[C@H]1CCCO1)C(=O)COC(F)(F)F] | (R)-N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)tetrahydrofuran-2-carboxamide | 464.637 | **** |
| 301 | 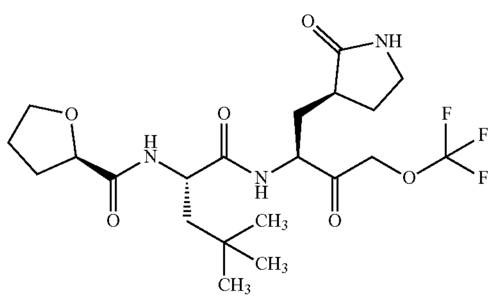 [SMILES: CC(C)(C)C[C@H](NC(=O)[C@H]1CCCO1)C(=O)N[C@@H](C[C@@H]1CCNC1=O)C(=O)COC(F)(F)F] | (R)-N-((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide | 480.4181 | **** |

TABLE 1-continued

| Compound | Structure | IUPAC | LCMS [M + 1] | EC50, uM (Hela) |
|---|---|---|---|---|
| 302 | 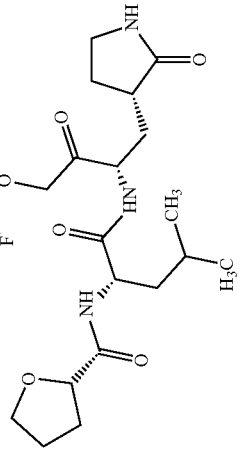 | (S)-N-((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide | 466.4274 | *** |
| 303 | 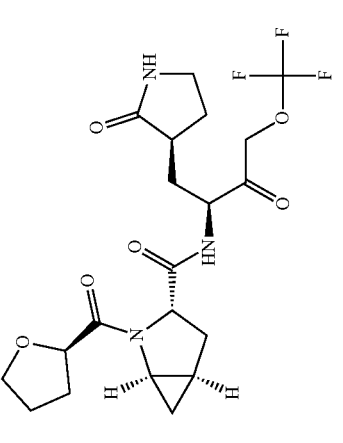 | (1R,3S,5R)-N-((S)-3-oxo-1-((S)-2-oxopyrrolidin-3-yl)-4-(trifluoromethoxy)butan-2-yl)-2-((R)-tetrahydrofuran-2-carbonyl)-2-azabicyclo[3.1.0]-hexane-3-carboxamide | 462.18 | >1 µM |
| 304 | 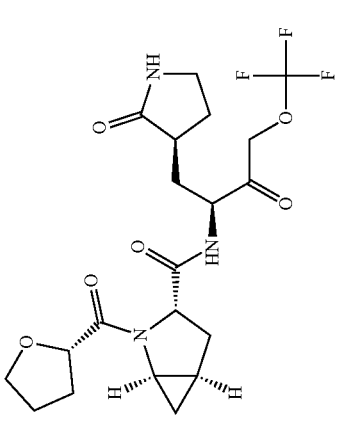 | (1R,3S,5R)-N-(3-oxo-1-((S)-2-oxopyrrolidin-3-yl)-4-(trifluoromethoxy)butan-2-yl)-2-((S)-tetrahydrofuran-2-carbonyl)-2-azabicyclo[3.1.0]-hexane-3-carboxamide | 462.356 | >1 µM |

TABLE 1-continued
| Compound | Structure | IUPAC | LCMS [M + 1] | EC50, uM (Hela) |
|---|---|---|---|---|
| 305 | 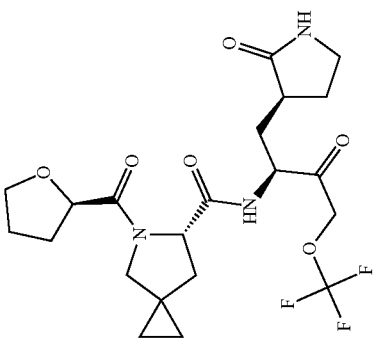 | (S)-N-((S)-3-oxo-1-((S)-2-oxopyrrolidin-3-yl)-4-(trifluoromethoxy)butan-2-yl)-5-((R)-tetrahydrofuran-2-carbonyl)-5-azaspiro[2.4]heptane-6-carboxamide | 476.4069 | ** |
| 306 | 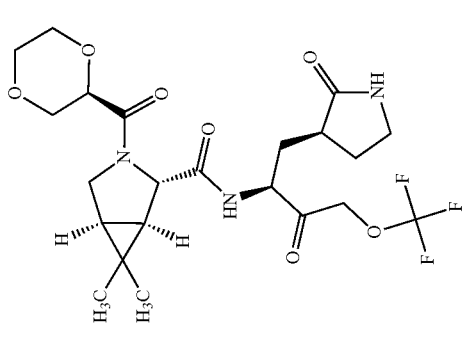 | (1R,2S,5S)-3-((R)-1,4-dioxane-2-carbonyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 506.3 | *** |

TABLE 1-continued

| Compound | Structure | IUPAC | LCMS [M + 1] | EC50, uM (Hela) |
|---|---|---|---|---|
| 307 | 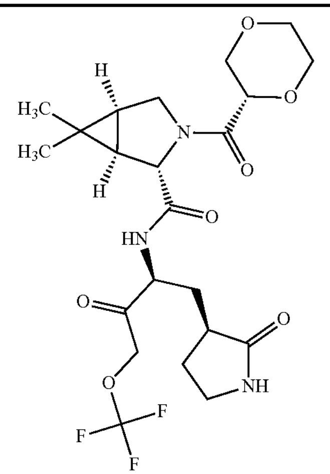 | (1R,2S,5S)-3-((S)-1,4-dioxane-2-carbonyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 506.442 | ** |
| 308 | 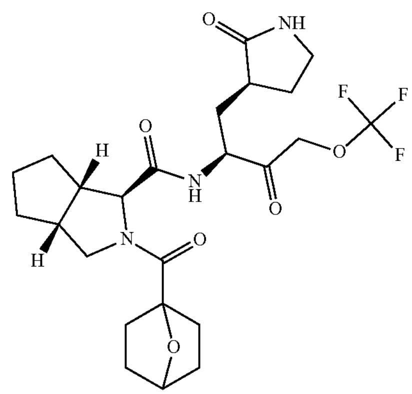 [SMILES: O=C1NCC[C@H]1C[C@H](NC(=O)[C@@H]1[C@H]2CCC[C@H]2CN1C(=O)C12CCC(CC1)O2)C(=O)COC(F)(F)F] | (1S,3aR,6aS)-2-(7-oxabicyclo[2.2.1]heptane-1-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 516.4 | *** |

TABLE 1-continued

| Compound | Structure | IUPAC | LCMS [M + 1] | EC50, uM (Hela) |
|---|---|---|---|---|
| 309 | 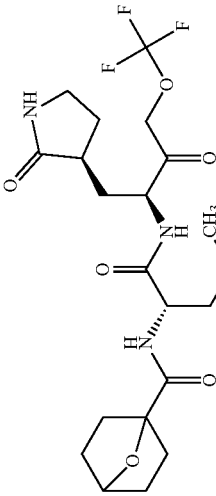 | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-7-oxabicyclo[2.2.1]-heptane-1-carboxamide | 492.41 | **** |
| 310 | 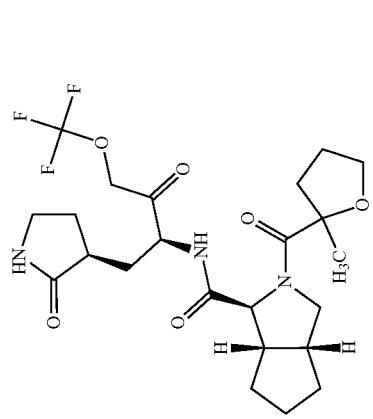 | (1S,3aR,6aS)-2-(2-methyltetrahydrofuran-2-carbonyl)-N-((S)-3-oxo-1-((S)-2-oxopyrrolidin-3-yl)-4-(trifluoromethoxy)butan-2-yl)octahydro-cyclopenta[c]pyrrole-1-carboxamide | 518.4 | >1 μM |
| 311 | 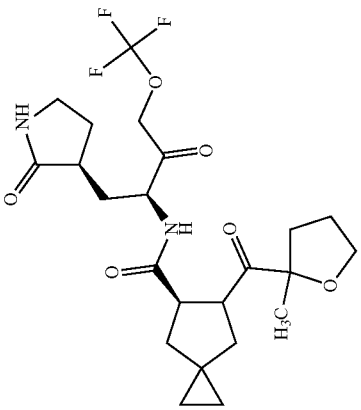 | (6S)-5-(2-methyltetrahydrofuran-2-carbonyl)-N-((S)-3-oxo-1-((S)-2-oxopyrrolidin-3-yl)-4-(trifluoromethoxy)butan-2-yl)-5-azaspiro[2.4]-heptane-6-carboxamide | 476.4 | ** |

TABLE 1-continued

| Compound | Structure | IUPAC | LCMS [M + 1] | EC50, uM (Hela) |
|---|---|---|---|---|
| 312 | 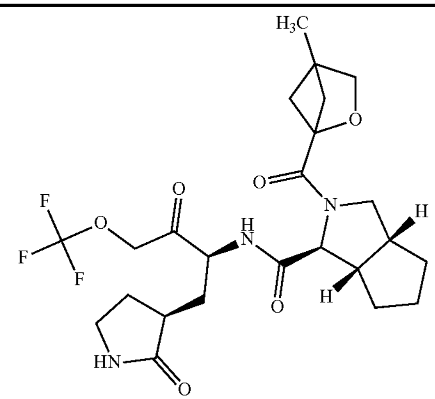 | (1S,3aR,6aS)-2-(4-methyl-2-oxabicyclo[2.1.1]hexane-1-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 516.22 | *** |
| 313 | 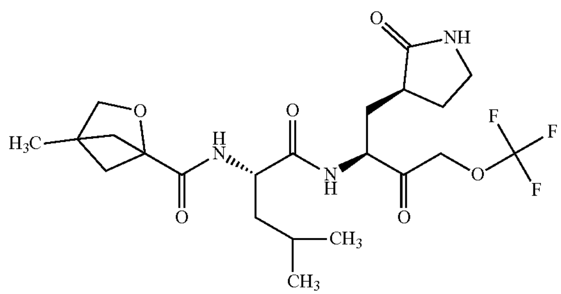 [SMILES: CC(C)C[C@H](NC(=O)C12CC(C)(CO1)C2)C(=O)N[C@@H](C[C@@H]1CCNC1=O)C(=O)COC(F)(F)F] | 4-methyl-N-((S)-4-methyl-1-oxo-1-(((S)-3-oxo-1-((S)-2-oxopyrrolidin-3-yl)-4-(trifluoromethoxy)butan-2-yl)amino)pentan-2-yl)-2-oxabicyclo[2.1.1]hexane-1-carboxamide | 492.22 | *** |
| 314 | 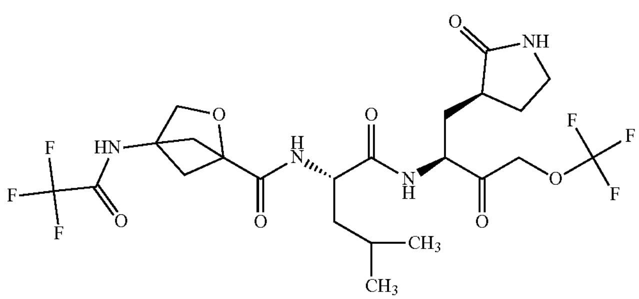 [SMILES: CC(C)C[C@H](NC(=O)C12CC(NC(=O)C(F)(F)F)(CO1)C2)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-4-(2,2,2-trifluoroacetamido)-2-oxabicyclo[2.1.1]hexane-1-carboxamide | 589.4388 | ** |

TABLE 1-continued

| Compound | Structure | IUPAC | LCMS [M + 1] | EC50, uM (Hela) |
|---|---|---|---|---|
| 315 | 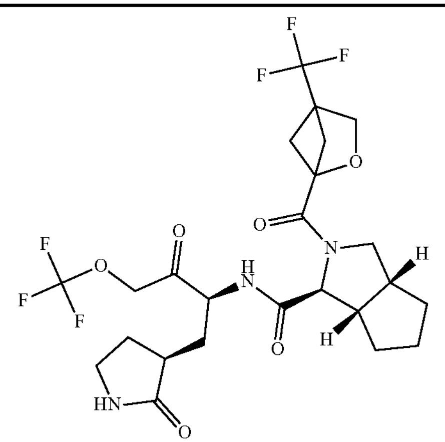 | (1S,3aR,6aS)-N-((S)-3-oxo-1-((S)-2-oxopyrrolidin-3-yl)-4-(trifluoromethoxy)butan-2-yl)-2-(4-(trifluoromethyl)-2-oxabicyclo[2.1.1]hexane-1-carbonyl)octahydrocyclopenta[c]pyrrole-1-carboxamide | 570.4225 | **** |
| 316 | 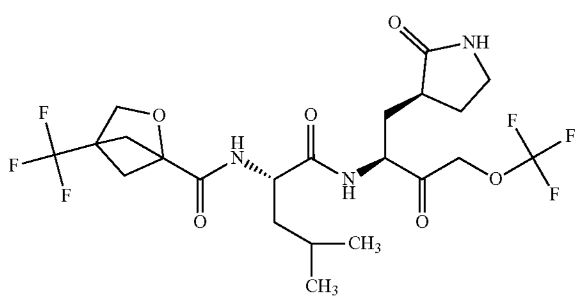 [SMILES: CC(C)C[C@H](NC(=O)C12CC(C(F)(F)F)(CO1)C2)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-4-(trifluoromethyl)-2-oxabicyclo[2.1.1]hexane-1-carboxamide | 546.168 | **** |

TABLE 1-continued

| Compound | Structure | IUPAC | LCMS [M + 1] | EC50, uM (Hela) |
|---|---|---|---|---|
| 317 | 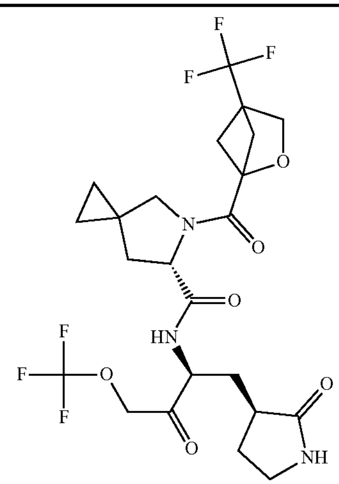 | (S)-N-((S)-3-oxo-1-((S)-2-oxopyrrolidin-3-yl)-4-(trifluoromethoxy)butan-2-yl)-5-(4-(trifluoromethyl)-2-oxabicyclo[2.1.1]hexane-1-carbonyl)-5-azaspiro[2.4]heptane-6-carboxamide | 556.4128 | **** |
| 318 | 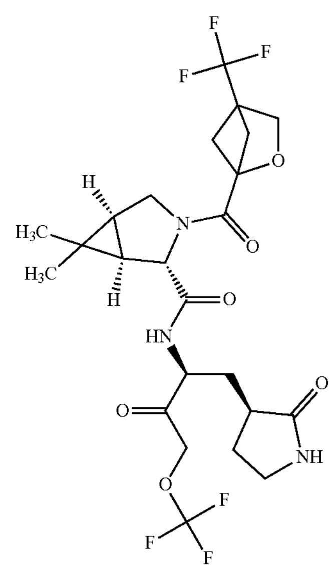 [SMILES: CC1(C)[C@@H]2[C@@H](C(=O)N[C@@H](C[C@@H]3CCNC3=O)C(=O)COC(F)(F)F)N(C(=O)C34CC(C(F)(F)F)(CO3)C4)C[C@@H]21] | (1R,2S,5S)-6,6-dimethyl-N-((S)-3-oxo-1-((S)-2-oxopyrrolidin-3-yl)-4-(trifluoromethoxy)butan-2-yl)-3-(4-(trifluoromethyl)-2-oxabicyclo[2.1.1]hexane-1-carbonyl)-3-azabicyclo[3.1.0]hexane-2-carboxamide | 570.47 | *** |

TABLE 1-continued

| Compound | Structure | IUPAC | LCMS [M + 1] | EC50, uM (Hela) |
|---|---|---|---|---|
| 319 | 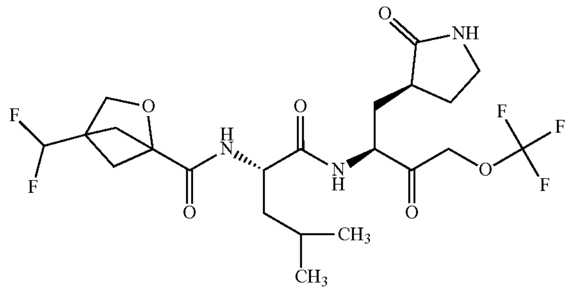 [SMILES: CC(C)C[C@H](NC(=O)C12CC(C(F)F)(CO1)C2)C(=O)N[C@@H](C[C@@H]1CCNC1=O)C(=O)COC(F)(F)F] | 4-(difluoromethyl)-N-((S)-4-methyl-1-oxo-1-(((S)-3-oxo-1-((S)-2-oxopyrrolidin-3-yl)-4-(trifluoromethoxy)butan-2-yl)amino)pentan-2-yl)-2-oxabicyclo[2.1.1]hexane-1-carboxamide | 528.4 | **** |
| 320 | 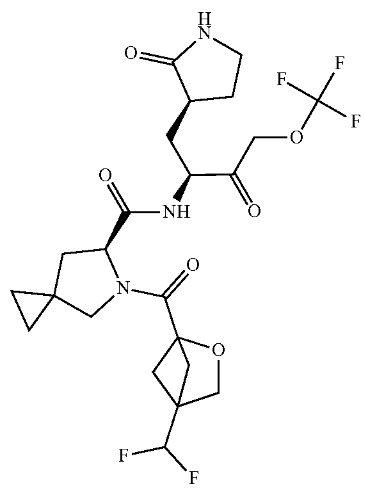 [SMILES: O=C1NCC[C@H]1C[C@H](NC(=O)[C@@H]1CC2(CC2)CN1C(=O)C12CC(C(F)F)(CO1)C2)C(=O)COC(F)(F)F] | (S)-5-(4-(difluoromethyl)-2-oxabicyclo[2.1.1]hexane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 538.43 | ** |

TABLE 1-continued

| Compound | Structure | IUPAC | LCMS [M + 1] | EC50, uM (Hela) |
|---|---|---|---|---|
| 321 | 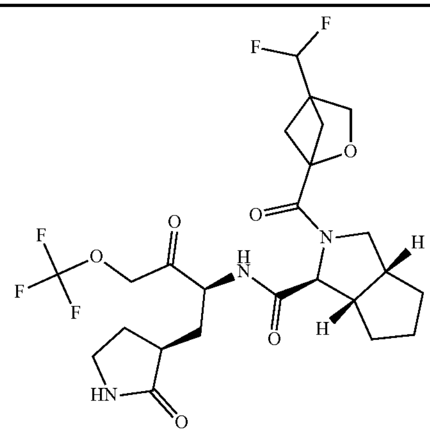 | (1S,3aR,6aS)-2-(4-(difluoromethyl)-2-oxabicyclo[2.1.1]hexane-1-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 552.5 | *** |
| 322 | 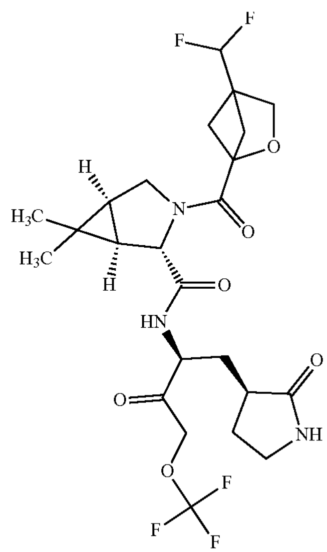 [SMILES: CC1(C)[C@@H]2[C@@H](C(=O)N[C@@H](C[C@@H]3CCNC3=O)C(=O)COC(F)(F)F)N(C(=O)C34CC(C(F)F)(CO3)C4)C[C@@H]21] | (1R,2S,5S)-3-(4-(difluoromethyl)-2-oxabicyclo[2.1.1]hexane-1-carbonyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 552.4473 | *** |

TABLE 1-continued

| Compound | Structure | IUPAC | LCMS [M + 1] | EC50, uM (Hela) |
|---|---|---|---|---|
| 323 | 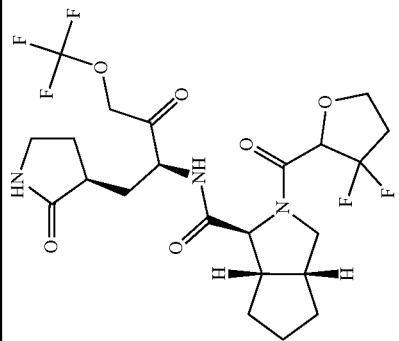 | (1S,3aR,6aS)-2-(3,3-difluorotetrahydrofuran-2-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 526.4017 | *** |
| 324 | 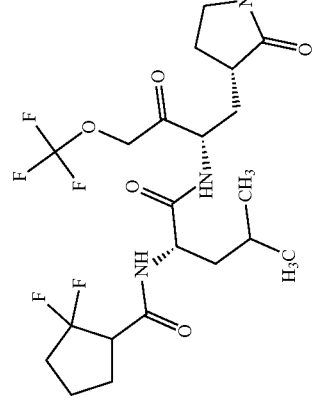 | 3,3-difluoro-N-((S)-4-methyl-1-oxo-1-(((S)-3-oxo-1-((S)-2-oxopyrrolidin-3-yl)-4-(trifluoromethoxy)butan-2-yl)amino)pentan-2-yl)tetrahydrofuran-2-carboxamide | 502.3887 | *** |
| 326 | 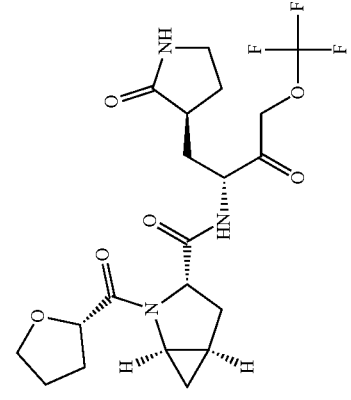 | (1R,3S,5R)-N-(3-oxo-1-((S)-2-oxopyrrolidin-3-yl)-4-(trifluoromethoxy)butan-2-yl)-2-((S)-tetrahydrofuran-2-carbonyl)-2-azabicyclo[3.1.0]hexane-3-carboxamide | 462.356 | >1 μM |

TABLE 1-continued

| Compound | Structure | IUPAC | LCMS [M + 1] | EC50, uM (Hela) |
|---|---|---|---|---|
| 327 | 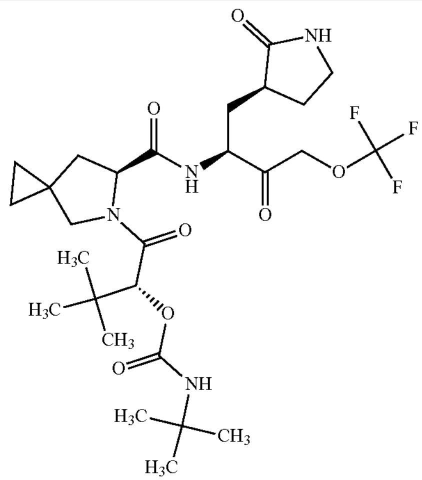 [SMILES: CC(C)(C)NC(=O)O[C@@H](C(=O)N1CC2(CC2)C[C@H]1C(=O)N[C@@H](C[C@@H]1CCNC1=O)C(=O)COC(F)(F)F)C(C)(C)C] | (R)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl tert-butylcarbamate | 591.5485 | * |
| 328 | 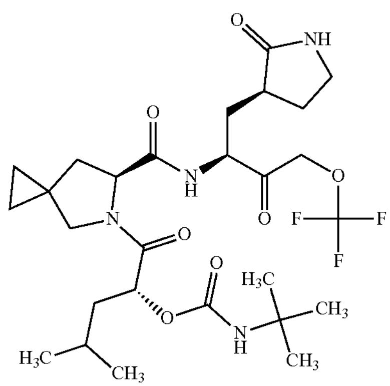 [SMILES: CC(C)C[C@@H](OC(=O)NC(C)(C)C)C(=O)N1CC2(CC2)C[C@H]1C(=O)N[C@@H](C[C@@H]1CCNC1=O)C(=O)COC(F)(F)F] | (R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl tert-butylcarbamate | 591.563 | **** |

TABLE 1-continued

| Compound | Structure | IUPAC | LCMS [M + 1] | EC50, uM (Hela) |
|---|---|---|---|---|
| 329 | 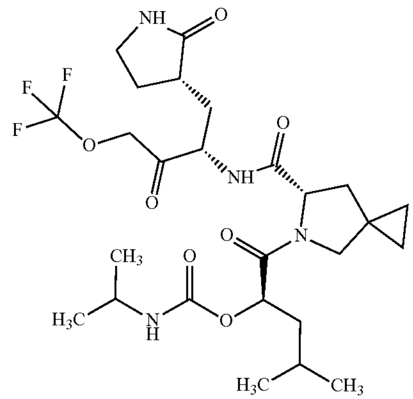 [SMILES: CC(C)C[C@@H](OC(=O)NC(C)C)C(=O)N1CC2(CC2)C[C@H]1C(=O)N[C@@H](C[C@@H]1CCNC1=O)C(=O)COC(F)(F)F] | (R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl isopropylcarbamate | 577.4815 | **** |
| 330 | 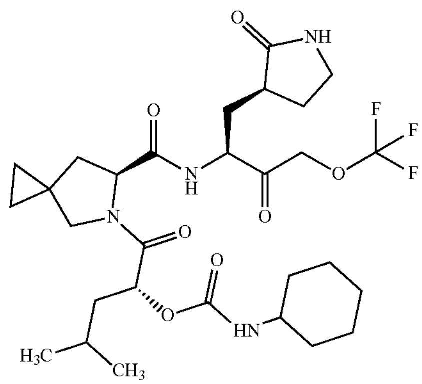 [SMILES: CC(C)C[C@@H](OC(=O)NC1CCCCC1)C(=O)N1CC2(CC2)C[C@H]1C(=O)N[C@@H](C[C@@H]1CCNC1=O)C(=O)COC(F)(F)F] | (R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl cyclohexylcarbamate | 617.5537 | **** |

TABLE 1-continued

| Compound | Structure | IUPAC | LCMS [M + 1] | EC50, uM (Hela) |
|---|---|---|---|---|
| 331 | 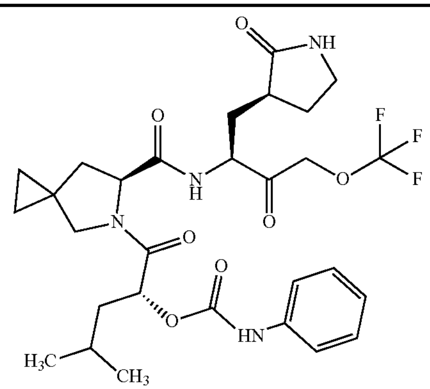 | (R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl phenylcarbamate | 611.5448 | **** |
| 332 | 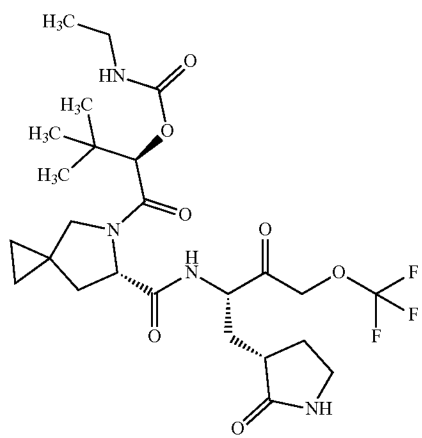 [SMILES: CCNC(=O)O[C@@H](C(=O)N1CC2(CC2)C[C@H]1C(=O)N[C@@H](C[C@@H]1CCNC1=O)C(=O)COC(F)(F)F)C(C)(C)C] | (R)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl ethylcarbamate | 563.5 | * |

TABLE 1-continued

| Compound | Structure | IUPAC | LCMS [M + 1] | EC50, uM (Hela) |
|---|---|---|---|---|
| 333 | 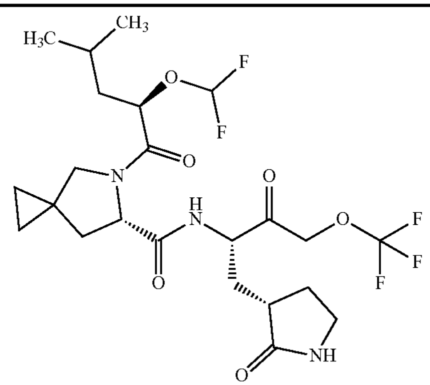 | (S)-5-((R)-2-(difluoromethoxy)-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 542.4607 | **** |
| 334 | 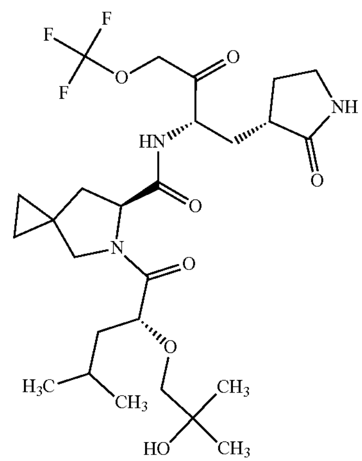 [SMILES: CC(C)C[C@@H](OCC(C)(C)O)C(=O)N1CC2(CC2)C[C@H]1C(=O)N[C@@H](C[C@@H]1CCNC1=O)C(=O)COC(F)(F)F] | (S)-5-((R)-2-(2-hydroxy-2-methylpropoxy)-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 564.5637 | *** |

TABLE 1-continued

| Compound | Structure | IUPAC | LCMS [M + 1] | EC50, uM (Hela) |
|---|---|---|---|---|
| 335 | 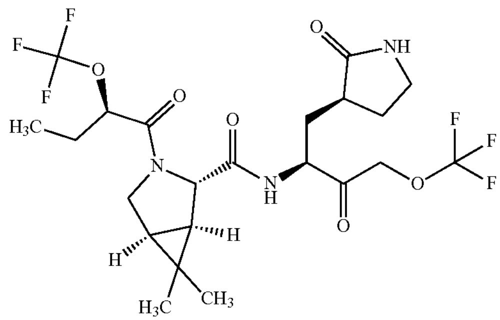 [SMILES: CC[C@@H](OC(F)(F)F)C(=O)N1C[C@H]2[C@@H]([C@H]1C(=O)N[C@@H](C[C@@H]1CCNC1=O)C(=O)COC(F)(F)F)C2(C)C] | (1R,2S,5S)-6,6-dimethyl-N-((S)-3-oxopyrrolidin-3-yl)-4-(trifluoromethoxy)butan-2-yl)-3-((R)-2-(trifluoromethoxy)butanoyl)-3-azabicyclo[3.1.0]-hexane-2-carboxamide | 568.3 | **** |
| 336 | 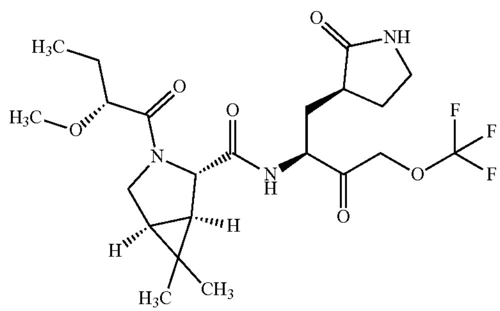 [SMILES: CC[C@@H](OC)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((R)-2-methoxybutanoyl)-6,6-dimethyl-N-((S)-3-oxo-1-((S)-2-oxopyrrolidin-3-yl)-4-(trifluoromethoxy)butan-2-yl)-3-azabicyclo[3.1.0]-hexane-2-carboxamide | 492.3 | *** |
| 337 | 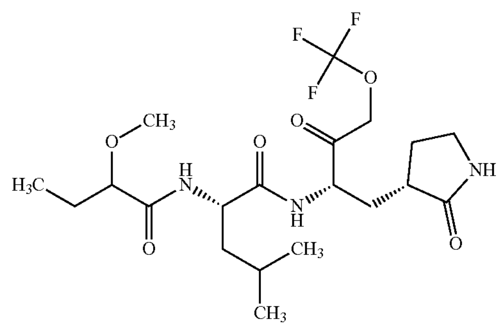 [SMILES: CCC(OC)C(=O)N[C@@H](CC(C)C)C(=O)N[C@@H](C[C@@H]1CCNC1=O)C(=O)COC(F)(F)F] | (S)-2-((R)-2-methoxybutanamido)-4-methyl-N-((S)-3-oxo-1-((S)-2-oxopyrrolidin-3-yl)-4-(trifluoromethoxy)butan-2-yl)pentanamide | 468.3 | *** |

TABLE 1-continued

| Compound | Structure | IUPAC | LCMS [M + 1] | EC50, uM (Hela) |
|---|---|---|---|---|
| 338 | 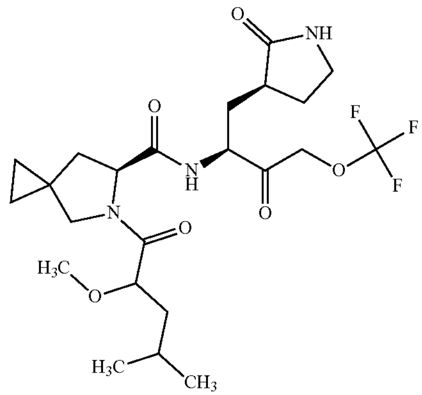 | (6S)-5-(2-methoxy-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 506.4176 | **** |
| 339 | 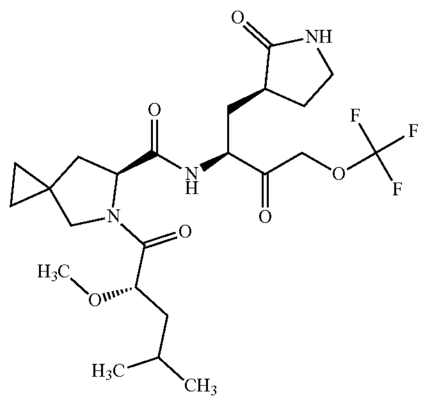 [SMILES: CO[C@@H](CC(C)C)C(=O)N1CC2(CC2)C[C@H]1C(=O)N[C@@H](C[C@@H]1CCNC1=O)C(=O)COC(F)(F)F] | (S)-5-((S)-2-methoxy-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 506.7434 | *** |

TABLE 1-continued

| Compound | Structure | IUPAC | LCMS [M + 1] | EC50, uM (Hela) |
|---|---|---|---|---|
| 340 | 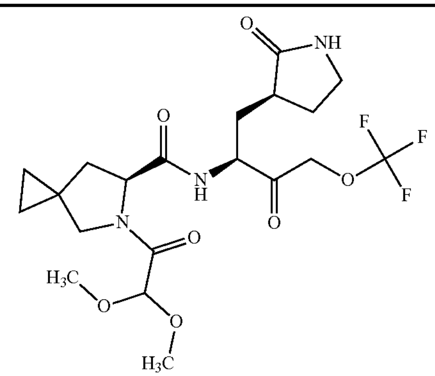 | (S)-5-(2,2-dimethoxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 480.4214 | ** |
| 341 | 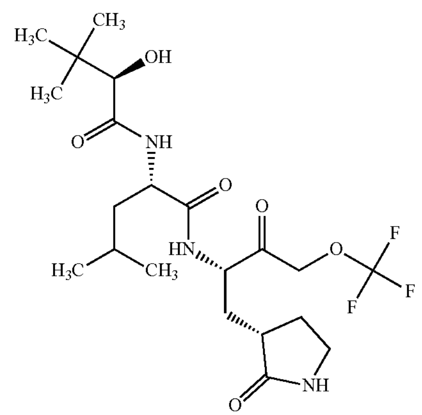 | (S)-2-((R)-2-hydroxy-3,3-dimethylbutanamido)-4-methyl-N-((S)-3-oxo-1-((S)-2-oxopyrrolidin-3-yl)-4-(trifluoromethoxy)butan-2-yl)pentanamide | 482.4141 | *** |

TABLE 1-continued

| Compound | Structure | IUPAC | LCMS [M + 1] | EC50, uM (Hela) |
|---|---|---|---|---|
| 342 | 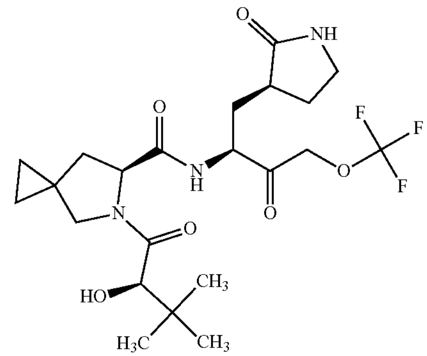 | (S)-5-((R)-2-hydroxy-3,3-dimethylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 492.4156 | *** |
| 343 | 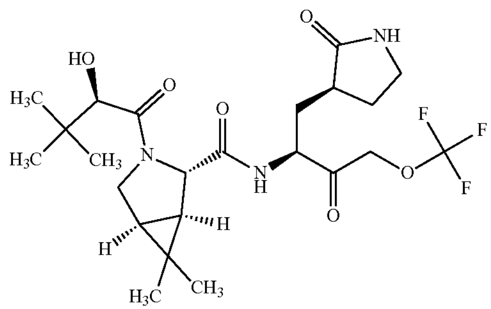 [SMILES: CC(C)(C)[C@@H](O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((R)-2-hydroxy-3,3-dimethylbutanoyl)-6,6-dimethyl-N-((S)-3-oxo-1-((S)-2-oxopyrrolidin-3-yl)butan-2-yl)-4-(trifluoromethoxy)butan-2-yl)-3-azabicyclo[3.1.0]hexane-2-carboxamide | 506.24 | *** |
| 344 | 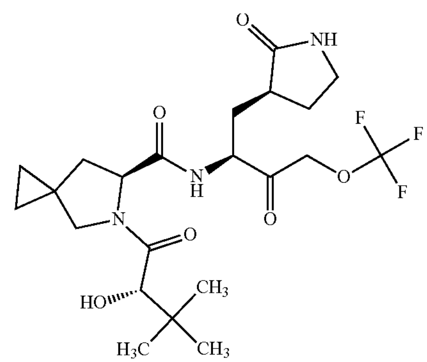 [SMILES: CC(C)(C)[C@H](O)C(=O)N1CC2(CC2)C[C@H]1C(=O)N[C@@H](C[C@@H]1CCNC1=O)C(=O)COC(F)(F)F] | (S)-5-((S)-2-hydroxy-3,3-dimethylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 492.4311 | **** |

TABLE 1-continued

| Compound | Structure | IUPAC | LCMS [M + 1] | EC50, uM (Hela) |
|---|---|---|---|---|
| 345 | 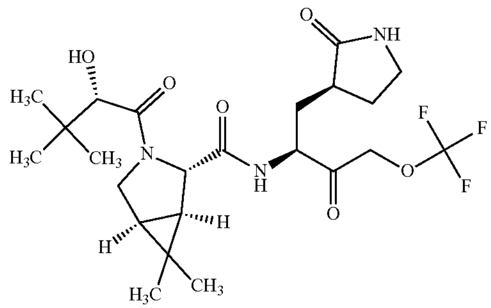 [SMILES: CC(C)(C)[C@H](O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((S)-2-hydroxy-3,3-dimethylbutanoyl)-6,6-dimethyl-N-((S)-2-oxo-1-((S)-2-oxopyrrolidin-3-yl)-4-(trifluoromethoxy)butan-2-yl)-3-azabicyclo[3.1.0]hexane-2-carboxamide | 506.4562 | **** |
| 346 | 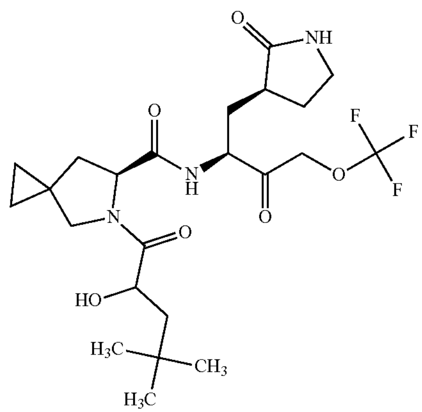 [SMILES: CC(C)(C)CC(O)C(=O)N1CC2(CC2)C[C@H]1C(=O)N[C@@H](C[C@@H]1CCNC1=O)C(=O)COC(F)(F)F] | (6S)-5-(2-hydroxy-4,4-dimethylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 506.4938 | **** |
| 347 | 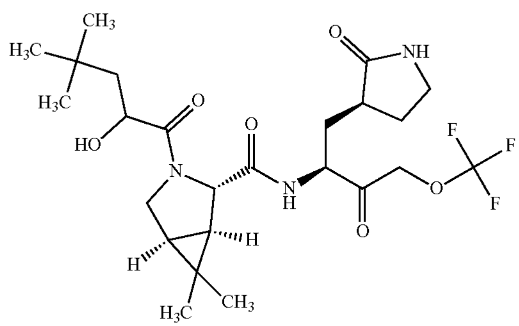 [SMILES: CC(C)(C)CC(O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-(2-hydroxy-4,4-dimethylpentanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 520.4 | **** |

TABLE 1-continued

| Compound | Structure | IUPAC | LCMS [M + 1] | EC50, uM (Hela) |
|---|---|---|---|---|
| 348 | 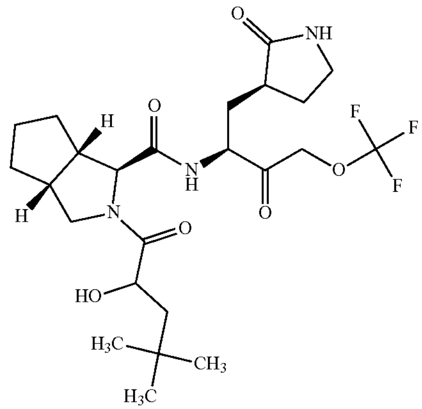 [SMILES: CC(C)(C)CC(O)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-hydroxy-4,4-dimethylpentanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 520.26 | **** |
| 349 | 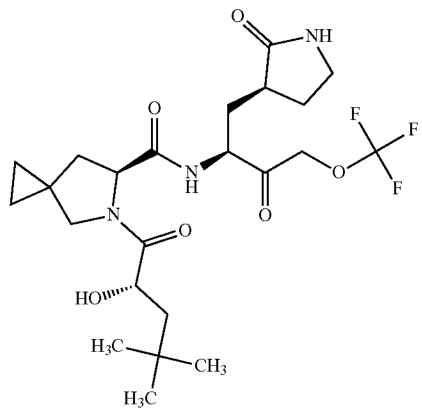 | (S)-5-((S)-2-hydroxy-4,4-dimethylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 506.4779 | **** |

TABLE 1-continued

| Compound | Structure | IUPAC | LCMS [M + 1] | EC50, uM (Hela) |
|---|---|---|---|---|
| 350 | 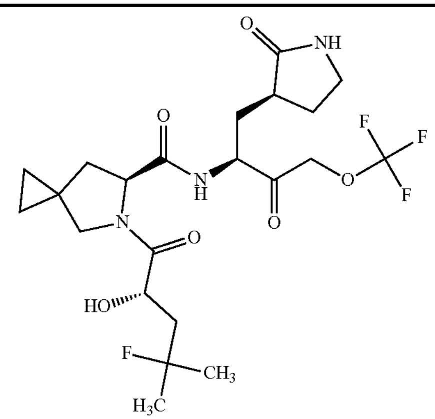 | (S)-5-((S)-4-fluoro-2-hydroxy-4-methylpentanoyl)-N-((S)-3-oxo-1-((S)-2-oxopyrrolidin-3-yl)-4-(trifluoromethoxy)butan-2-yl)-5-azaspiro[2.4]-heptane-6-carboxamide | 510.4428 | *** |
| 351 | 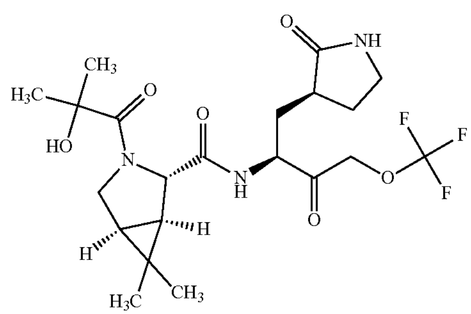 [SMILES: CC(C)(O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-(2-hydroxy-2-methylpropanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 478.0694 | *** |
| 352 | 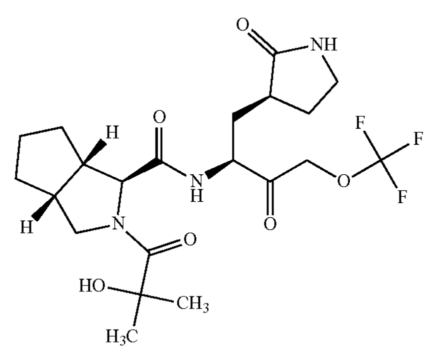 [SMILES: CC(C)(O)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-hydroxy-2-methylpropanoyl)-N-((S)-3-oxo-1-((S)-2-oxopyrrolidin-3-yl)-4-(trifluoromethoxy)butan-2-yl)-4-octahydrocyclopenta[c]pyrrole-1-carboxamide | 478.21 | *** |

TABLE 1-continued

| Compound | Structure | IUPAC | LCMS [M + 1] | EC50, uM (Hela) |
|---|---|---|---|---|
| 353 | 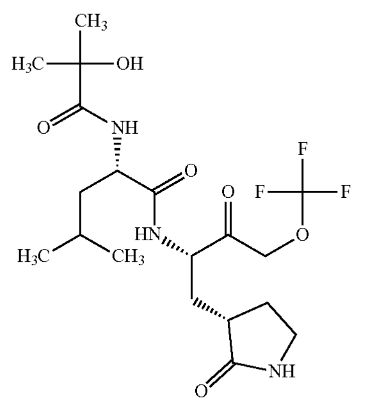 [SMILES: CC(C)C[C@H](NC(=O)C(C)(C)O)C(=O)N[C@@H](C[C@@H]1CCNC1=O)C(=O)COC(F)(F)F] | (S)-2-(2-hydroxy-2-methylpropanamido)-4-methyl-N-((S)-3-oxo-1-((S)-2-oxopyrrolidin-3-yl)-4-(trifluoromethoxy)butan-2-yl)pentanamide | 454.4114 | *** |
| 354 | 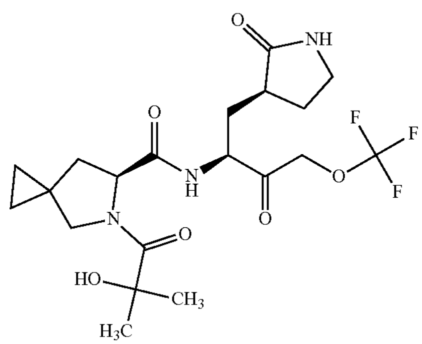 [SMILES: CC(C)(O)C(=O)N1CC2(CC2)C[C@H]1C(=O)N[C@@H](C[C@@H]1CCNC1=O)C(=O)COC(F)(F)F] | (S)-5-(2-hydroxy-2-methylpropanoyl)-N-((S)-3-oxo-1-((S)-2-oxopyrrolidin-3-yl)-4-(trifluoromethoxy)butan-2-yl)-5-azaspiro[2.4]heptane-6-carboxamide | 464.456 | *** |

TABLE 1-continued

| Compound | Structure | IUPAC | LCMS [M + 1] | EC50, uM (Hela) |
|---|---|---|---|---|
| 355 | 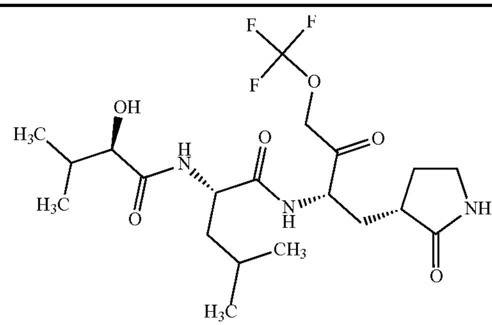 | (S)-2-((R)-2-hydroxy-3-methylbutanamido)-4-methyl-N-((S)-3-oxo-1-((S)-2-oxopyrrolidin-3-yl)-4-(trifluoromethoxy)butan-2-yl)pentanamide | 468.4025 | *** |
| 356 | 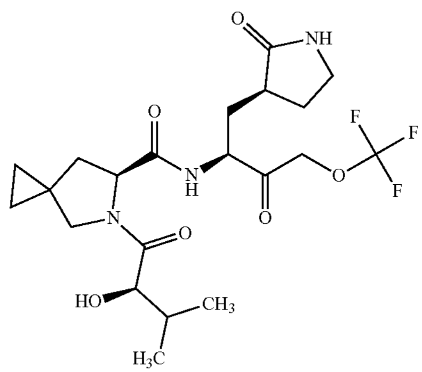 | (S)-5-((R)-2-hydroxy-3-methylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 478.3953 | *** |
| 357 | 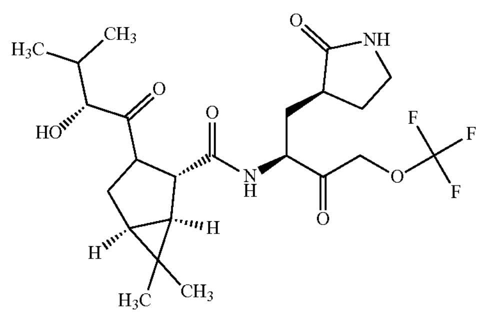 [SMILES: CC(C)[C@@H](O)C(=O)C1C[C@H]2[C@@H]([C@H]1C(=O)N[C@@H](C[C@@H]1CCNC1=O)C(=O)COC(F)(F)F)C2(C)C] | (1R,2S,5S)-3-((R)-2-hydroxy-3-methylbutanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 492.22 | *** |

TABLE 1-continued

| Compound | Structure | IUPAC | LCMS [M + 1] | EC50, uM (Hela) |
|---|---|---|---|---|
| 358 | 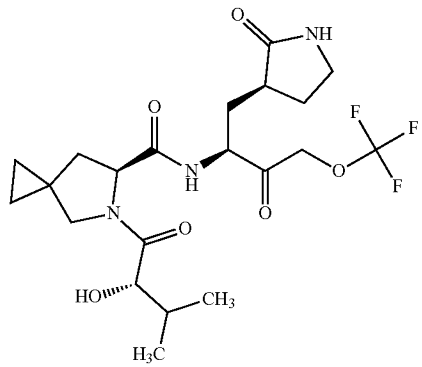 [SMILES: CC(C)[C@H](O)C(=O)N1CC2(CC2)C[C@H]1C(=O)N[C@@H](C[C@@H]1CCNC1=O)C(=O)COC(F)(F)F] | (S)-5-((S)-2-hydroxy-3-methylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 478.21 | *** |
| 359 | 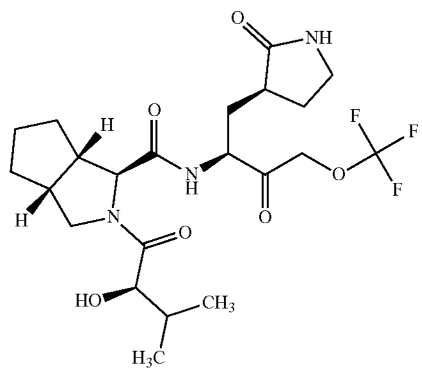 [SMILES: CC(C)[C@@H](O)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-((R)-2-hydroxy-3-methylbutanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 492.4 | *** |

TABLE 1-continued

| Compound | Structure | IUPAC | LCMS [M + 1] | EC50, uM (Hela) |
|---|---|---|---|---|
| 360 | 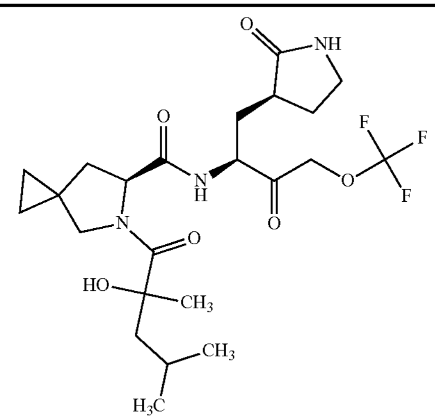 | (6S)-5-(2-hydroxy-2,4-dimethylpentanoyl)-N-((S)-3-oxo-1-((S)-2-oxopyrrolidin-3-yl)-4-(trifluoromethoxy)butan-2-yl)-5-azaspiro[2.4]-heptane-6-carboxamide | 506.49 | **** |
| 361 | 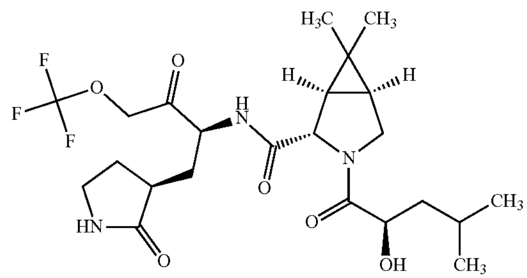 [SMILES: CC(C)C[C@@H](O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((R)-2-hydroxy-4-methylpentanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 506.7796 | **** |

TABLE 1-continued
| Compound | Structure | IUPAC | LCMS [M + 1] | EC50, uM (Hela) |
|---|---|---|---|---|
| 362 | 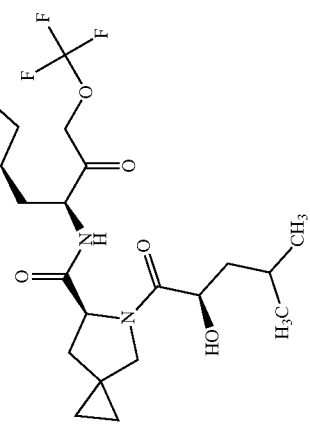 | (S)-5-((R)-2-hydroxy-4-methylpentanoyl)-N-((S)-3-oxo-1-((S)-2-oxopyrrolidin-3-yl)-4-(trifluoromethoxy)butan-2-yl)-5-azaspiro[2.4]-heptane-6-carboxamide | 492.4428 | **** |
| 363 | 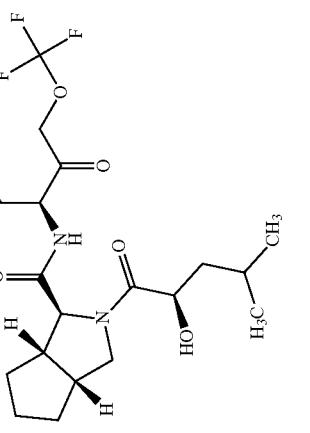 | (1S,3aR,6aS)-2-((R)-2-hydroxy-4-methylpentanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 506.4538 | **** |

TABLE 1-continued

| Compound | Structure | IUPAC | LCMS [M + 1] | EC50, uM (Hela) |
|---|---|---|---|---|
| 364 | 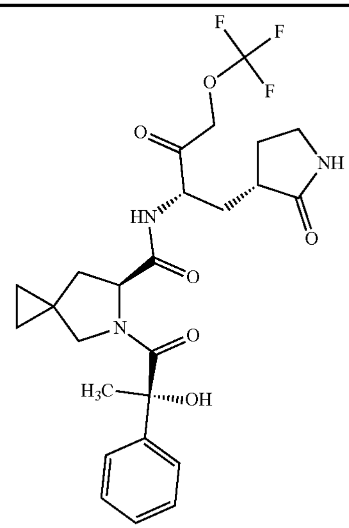 | (S)-5-((S)-2-hydroxy-2-phenylpropanoyl)-N-((S)-3-oxo-1-((S)-2-oxopyrrolidin-3-yl)-4-(trifluoromethoxy)butan-2-yl)-5-azaspiro[2.4]-heptane-6-carboxamide | 526.4101 | **** |
| 365 | 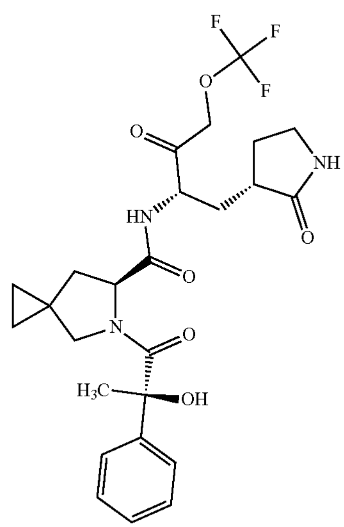 [SMILES: C[C@](O)(C(=O)N1CC2(CC2)C[C@H]1C(=O)N[C@@H](C[C@@H]1CCNC1=O)C(=O)COC(F)(F)F)c1ccccc1] | (S)-5-((R)-2-hydroxy-2-phenylpropanoyl)-N-((S)-3-oxo-1-((S)-2-oxopyrrolidin-3-yl)-4-(trifluoromethoxy)butan-2-yl)-5-azaspiro[2.4]-heptane-6-carboxamide | 526.3871 | **** |

TABLE 1-continued

| Compound | Structure | IUPAC | LCMS [M + 1] | EC50, uM (Hela) |
|---|---|---|---|---|
| 366 | 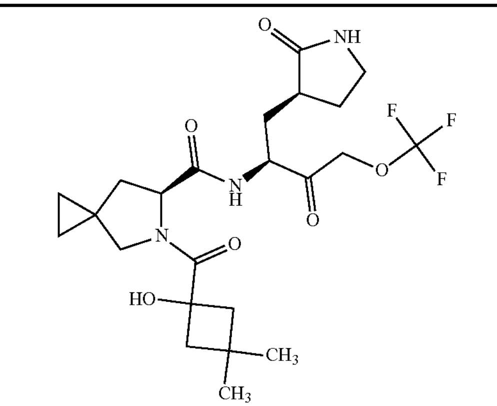 | (S)-5-(l-hydroxy-3,3-dimethylcyclobutane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 504.6798 | **** |
| 367 | 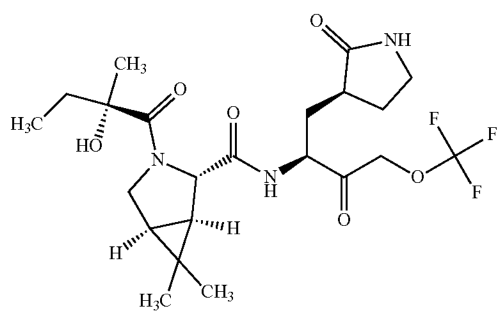 [SMILES: CC[C@](C)(O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((S)-2-hydroxy-2-methylbutanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 492.3 | >1 μM |
| 368 | 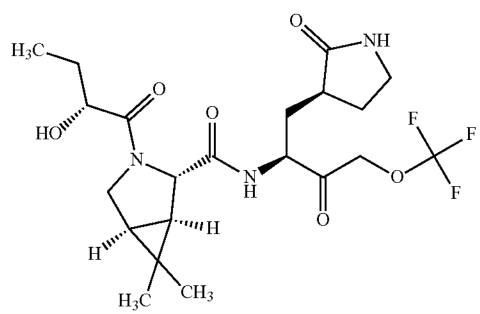 [SMILES: CC[C@@H](O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((R)-2-hydroxybutanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 478.4315 | *** |

TABLE 1-continued

| Compound | Structure | IUPAC | LCMS [M + 1] | EC50, uM (Hela) |
|---|---|---|---|---|
| 369 | 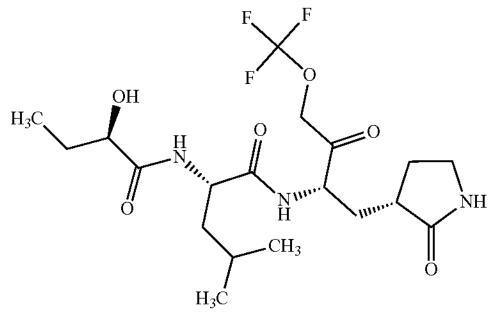 [SMILES: CC[C@@H](O)C(=O)N[C@@H](CC(C)C)C(=O)N[C@@H](C[C@@H]1CCNC1=O)C(=O)COC(F)(F)F] | (S)-2-((R)-2-hydroxybutanamido)-4-methyl-N-((S)-3-oxo-1-((S)-2-oxopyrrolidin-3-yl)-4-(trifluoromethoxy)butan-2-yl)pentanamide | 454.3905 | *** |
| 370 | 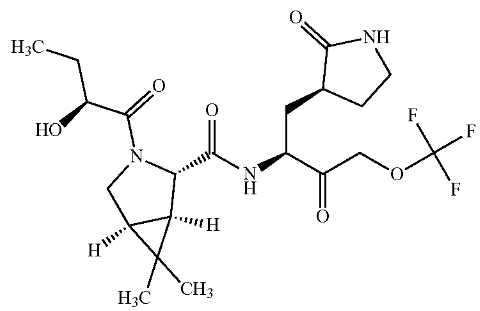 [SMILES: CC[C@H](O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((S)-2-hydroxybutanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 478.4111 | *** |
| 371 | 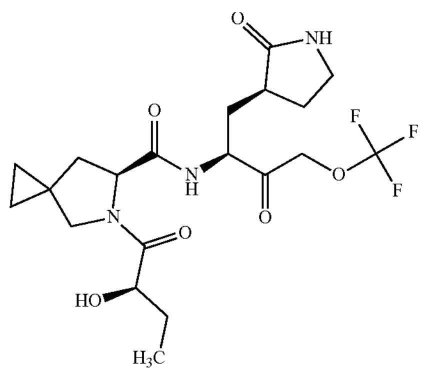 [SMILES: CC[C@@H](O)C(=O)N1CC2(CC2)C[C@H]1C(=O)N[C@@H](C[C@@H]1CCNC1=O)C(=O)COC(F)(F)F] | (S)-5-((R)-2-hydroxybutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 464.407 | *** |

TABLE 1-continued

| Compound | Structure | IUPAC | LCMS [M + 1] | EC50, uM (Hela) |
|---|---|---|---|---|
| 372 | 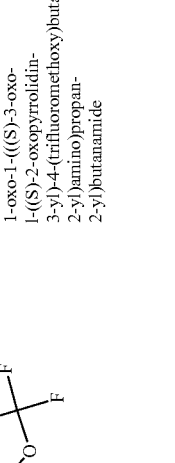 | (2R)-2-hydroxy-N-(3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)butanamide | 466.4 | ** |
| 373 | 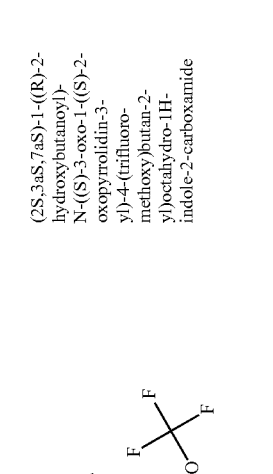 | (2S,3aS,7aS)-1-((R)-2-hydroxybutanoyl)-N-((S)-3-oxo-1-((S)-2-oxopyrrolidin-3-yl)-4-(trifluoromethoxy)butan-2-yl)octahydro-1H-indole-2-carboxamide | 492.4 | ** |
| 374 | 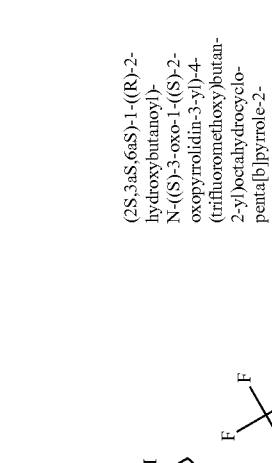 | (2S,3aS,6aS)-1-((R)-2-hydroxybutanoyl)-N-((S)-3-oxo-1-((S)-2-oxopyrrolidin-3-yl)-4-(trifluoromethoxy)butan-2-yl)octahydrocyclopenta[b]pyrrole-2-carboxamide | 478.4 | * |

TABLE 1-continued

| Compound | Structure | IUPAC | LCMS [M + 1] | EC50, uM (Hela) |
|---|---|---|---|---|
| 375 | 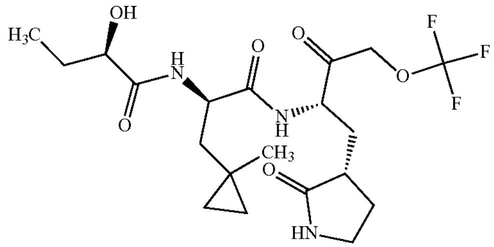 | (R)-2-hydroxy-N-((R)-3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)butanamide | 466.6646 | *** |
| 376 | 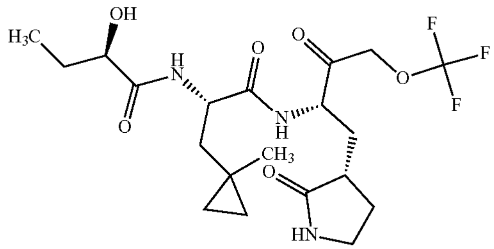 [SMILES: CC[C@@H](O)C(=O)NC(CC1(C)CC1)C(=O)N[C@@H](C[C@@H]1CCNC1=O)C(=O)COC(F)(F)F] | (R)-2-hydroxy-N-((S)-3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)butanamide | 466.1577 | >1 μM |
| 377 | 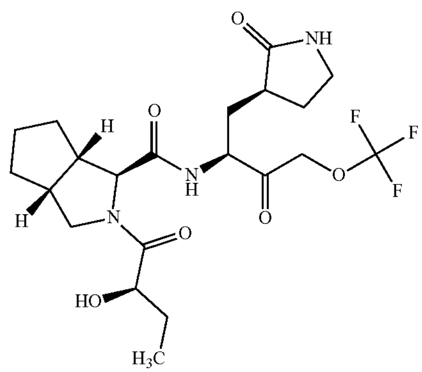 | (1S,3aR,6aS)-2-((R)-2-hydroxybutanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 478.4137 | *** |

TABLE 1-continued

| Compound | Structure | IUPAC | LCMS [M + 1] | EC50, uM (Hela) |
|---|---|---|---|---|
| 378 | 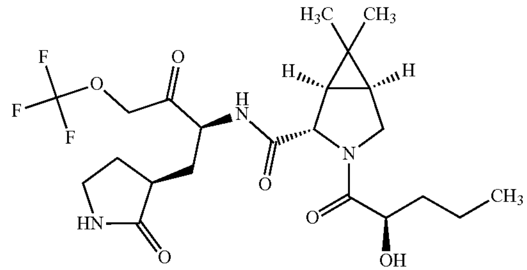 [SMILES: CCC[C@@H](O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((R)-2-hydroxypentanoyl)-6,6-dimethyl-N-((S)-3-oxo-1-((S)-2-oxopyrrolidin-3-yl)-4-(trifluoromethoxy)butan-2-yl)-3-azabicyclo[3.1.0]-hexane-2-carboxamide | 492.4443 | **** |
| 379 | 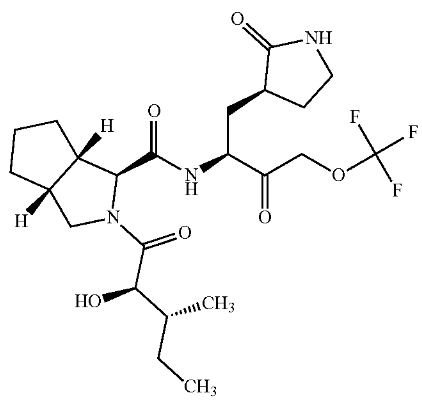 [SMILES: CC[C@@H](C)[C@@H](O)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-((2R,3R)-2-hydroxy-3-methylpentanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 506.462 | **** |
| 380 | 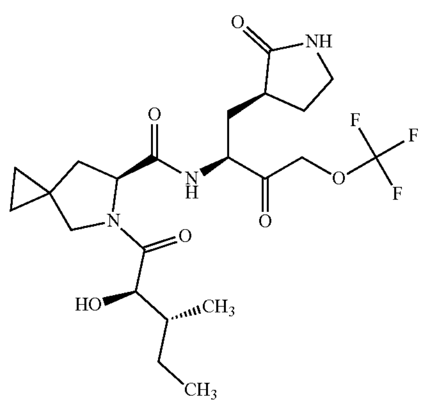 [SMILES: CC[C@@H](C)[C@@H](O)C(=O)N1CC2(CC2)C[C@H]1C(=O)N[C@@H](C[C@@H]1CCNC1=O)C(=O)COC(F)(F)F] | (S)-5-((2R,3R)-2-hydroxy-3-methylpentanoyl)-N-((S)-3-oxo-1-((S)-2-oxopyrrolidin-3-yl)-4-(trifluoromethoxy)butan-2-yl)-5-azaspiro[2.4]-heptane-6-carboxamide | 492.51 | *** |

TABLE 1-continued

| Compound | Structure | IUPAC | LCMS [M + 1] | EC50, uM (Hela) |
|---|---|---|---|---|
| 381 | 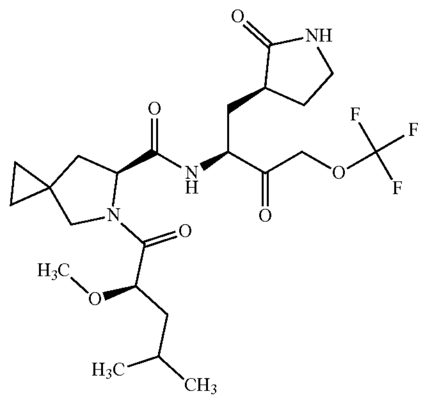 [SMILES: CO[C@H](CC(C)C)C(=O)N1CC2(CC2)C[C@H]1C(=O)N[C@@H](C[C@@H]1CCNC1=O)C(=O)COC(F)(F)F] | (S)-5-((R)-2-methoxy-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 507.4313 | **** |
| 382 | 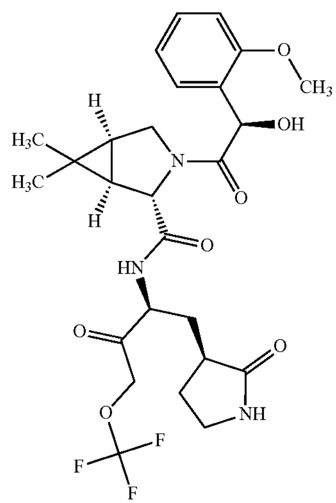 | (1R,2S,5S)-3-((R)-2-hydroxy-2-(2-methoxyphenyl)acetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 556.4641 | **** |

TABLE 1-continued

| Compound | Structure | IUPAC | LCMS [M + 1] | EC50, uM (Hela) |
|---|---|---|---|---|
| 383 | 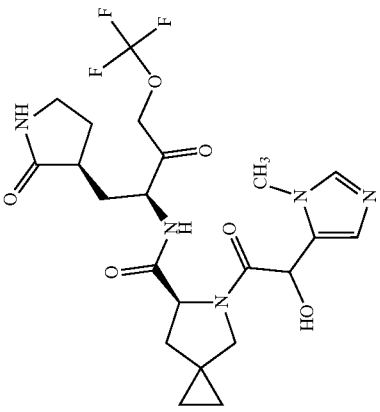 | (6S)-5-(2-hydroxy-2-(1-methyl-1H-imidazol-5-yl)acetyl)-N-((S)-3-oxo-1-((S)-2-oxopyrrolidin-3-yl)-4-(trifluoromethoxy)butan-2-yl)-5-azaspiro[2.4]heptane-6-carboxamide | 516.2 | >1 µM |
| 384 | 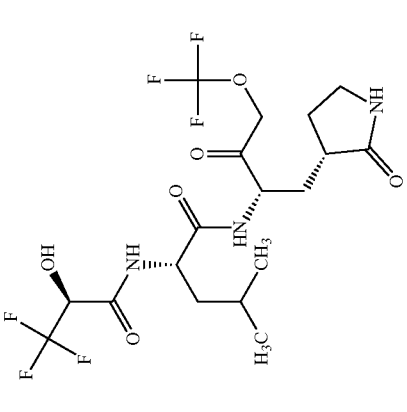 | (S)-4-methyl-N-((S)-3-oxo-1-((S)-2-oxopyrrolidin-3-yl)-4-(trifluoromethoxy)butan-2-yl)-2-((S)-3,3,3-trifluoro-2-hydroxypropanamido)-pentanamide | 494.3617 | *** |
| 385 | 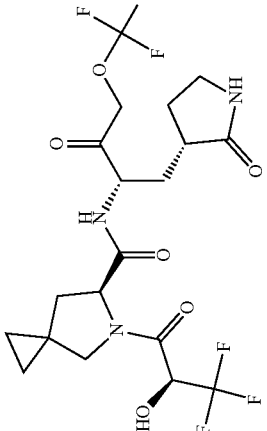 | (S)-N-((S)-3-oxo-1-((S)-2-oxopyrrolidin-3-yl)-4-(trifluoromethoxy)butan-2-yl)-5-((S)-3,3,3-trifluoro-2-hydroxypropanoyl)-5-azaspiro[2.4]heptane-6-carboxamide | 504.3683 | *** |

TABLE 1-continued

| Compound | Structure | IUPAC | LCMS [M + 1] | EC50, uM (Hela) |
|---|---|---|---|---|
| 386 | 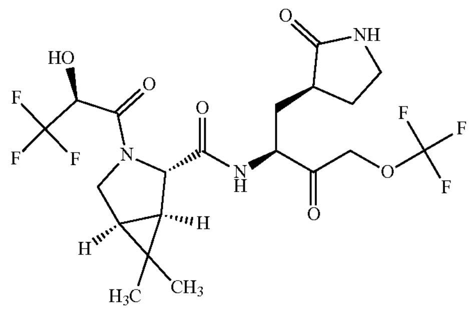 [SMILES: CC1(C)[C@@H]2[C@@H](C(=O)N[C@@H](C[C@@H]3CCNC3=O)C(=O)COC(F)(F)F)N(C(=O)[C@H](O)C(F)(F)F)C[C@@H]21] | (1R,2S,5S)-6,6-dimethyl-N-((S)-3-oxo-1-((S)-2-oxopyrrolidin-3-yl)-4-(trifluoromethoxy)butan-2-yl)-3-((S)-3,3,3-trifluoro-2-hydroxypropanoyl)-3-azabicyclo[3.1.0]-hexane-2-carboxamide | 518.16 | *** |
| 387 | 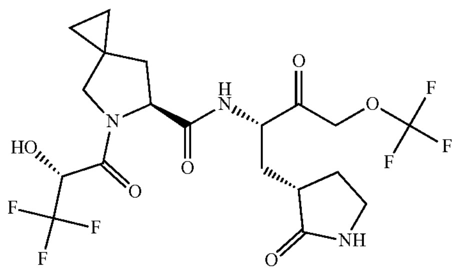 [SMILES: O=C1NCC[C@H]1C[C@H](NC(=O)[C@@H]1CC2(CC2)CN1C(=O)[C@@H](O)C(F)(F)F)C(=O)COC(F)(F)F] | (S)-N-((S)-3-oxo-1-((S)-2-oxopyrrolidin-3-yl)-4-(trifluoromethoxy)butan-2-yl)-5-((R)-3,3,3-trifluoro-2-hydroxypropanoyl)-5-azaspiro[2.4]-heptane-6-carboxamide | 504.15 | *** |
| 388 | 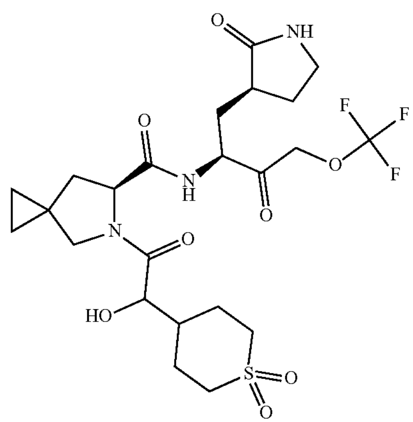 [SMILES: O=C1NCC[C@H]1C[C@H](NC(=O)[C@@H]1CC2(CC2)CN1C(=O)C(O)C1CCS(=O)(=O)CC1)C(=O)COC(F)(F)F] | (6S)-5-(2-(1,1-dioxidotetrahydro-2H-thiopyran-4-yl)-2-hydroxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 568.2 | >1 µM |

TABLE 1-continued

| Compound | Structure | IUPAC | LCMS [M + 1] | EC50, uM (Hela) |
|---|---|---|---|---|
| 389 | 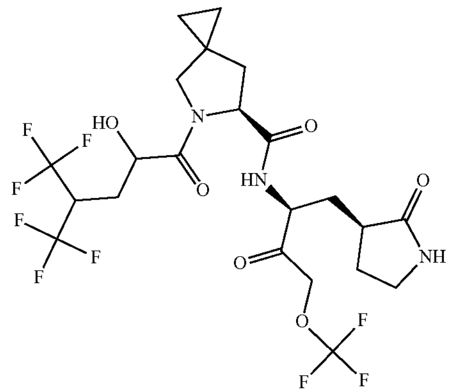 [SMILES: O=C1NCC[C@H]1C[C@H](NC(=O)[C@@H]1CC2(CC2)CN1C(=O)C(O)CC(C(F)(F)F)C(F)(F)F)C(=O)COC(F)(F)F] | (6S)-N-((S)-3-oxo-1-((S)-2-oxopyrrolidin-3-yl)-4-(trifluoromethoxy)butan-2-yl)-5-(5,5,5-trifluoro-2-hydroxy-4-(trifluoromethyl)pentanoyl)-5-azaspiro[2.4]heptane-6-carboxamide | 600.4673 | **** |
| 390 | 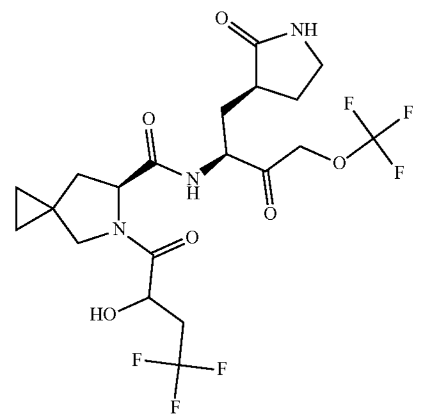 [SMILES: O=C1NCC[C@H]1C[C@H](NC(=O)[C@@H]1CC2(CC2)CN1C(=O)C(O)CC(F)(F)F)C(=O)COC(F)(F)F] | (6S)-N-((S)-3-oxo-1-((S)-2-oxopyrrolidin-3-yl)-4-(trifluoromethoxy)butan-2-yl)-5-(4,4,4-trifluoro-2-hydroxybutanoyl)-5-azaspiro[2.4]heptane-6-carboxamide | 518.4 | *** |

TABLE 1-continued

| Compound | Structure | IUPAC | LCMS [M + 1] | EC50, uM (Hela) |
|---|---|---|---|---|
| 391 | 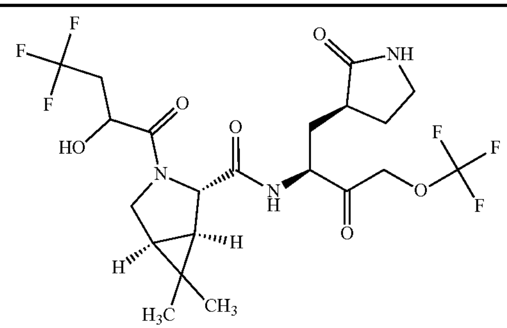 | (1R,2S,5S)-6,6-dimethyl-N-((S)-3-oxopyrrolidin-3-yl)-4-(trifluoromethoxy)butan-2-yl)-3-(4,4,4-trifluoro-2-hydroxybutanoyl)-3-azabicyclo[3.1.0]hexane-2-carboxamide | 532.439 | *** |
| 392 | 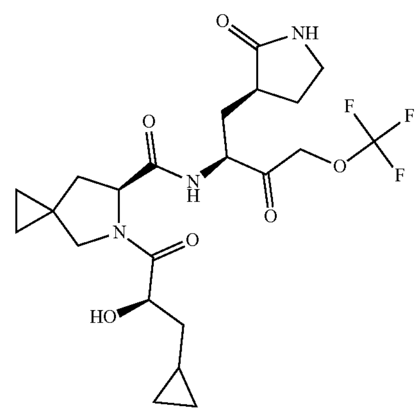 [SMILES: O=C1NCC[C@H]1C[C@H](NC(=O)[C@@H]1CC2(CC2)CN1C(=O)[C@H](O)CC1CC1)C(=O)COC(F)(F)F] | (S)-5-((R)-3-cyclopropyl-2-hydroxypropanoyl)-N-((S)-3-oxo-1-((S)-2-(trifluoromethoxy)butan-2-yl)-4-oxopyrrolidin-3-yl)-5-azaspiro[2.4]heptane-6-carboxamide | 490.4516 | *** |

TABLE 1-continued

| Compound | Structure | IUPAC | LCMS [M + 1] | EC50, uM (Hela) |
|---|---|---|---|---|
| 393 | 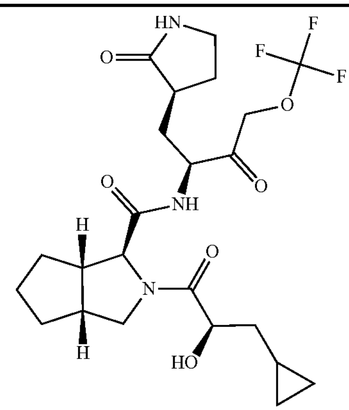 | (1S,3aR,6aS)-2-((R)-3-cyclopropyl-2-hydroxypropanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 504.22 | **** |
| 394 | 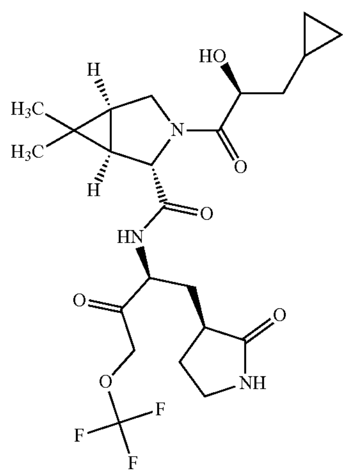 [SMILES: CC1(C)[C@@H]2[C@@H](C(=O)N[C@@H](C[C@@H]3CCNC3=O)C(=O)COC(F)(F)F)N(C(=O)[C@@H](O)CC3CC3)C[C@@H]21] | (1R,2S,5S)-3-((S)-3-cyclopropyl-2-hydroxypropanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 504.4 | **** |

TABLE 1-continued

| Compound | Structure | IUPAC | LCMS [M + 1] | EC50, uM (Hela) |
|---|---|---|---|---|
| 395 | 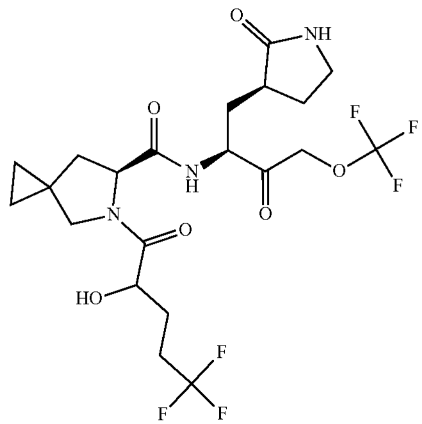 [SMILES: O=C1NCC[C@H]1C[C@H](NC(=O)[C@@H]1CC2(CC2)CN1C(=O)C(O)CCC(F)(F)F)C(=O)COC(F)(F)F] | (6S)-N-((S)-3-oxo-1-((S)-2-oxopyrrolidin-3-yl)-4-(trifluoromethoxy)butan-2-yl)-5-((5,5,5-trifluoro-2-hydroxypentanoyl)-5-azaspiro[2.4]heptane-6-carboxamide | 532.4277 | *** |
| 396 | 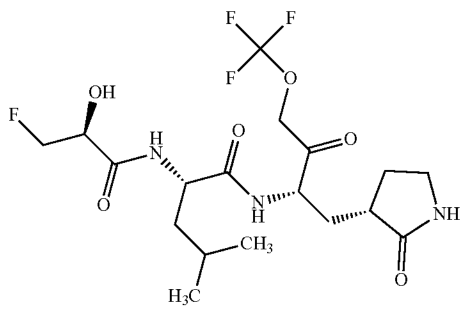 [SMILES: CC(C)C[C@H](NC(=O)[C@H](O)CF)C(=O)N[C@@H](C[C@@H]1CCNC1=O)C(=O)COC(F)(F)F] | (S)-2-((S)-3-fluoro-2-hydroxypropanamido)-4-methyl-N-((S)-3-oxo-1-((S)-2-oxopyrrolidin-3-yl)-4-(trifluoromethoxy)butan-2-yl)pentanamide | 458.3371 | ** |

TABLE 1-continued

| Compound | Structure | IUPAC | LCMS [M + 1] | EC50, uM (Hela) |
|---|---|---|---|---|
| 397 | 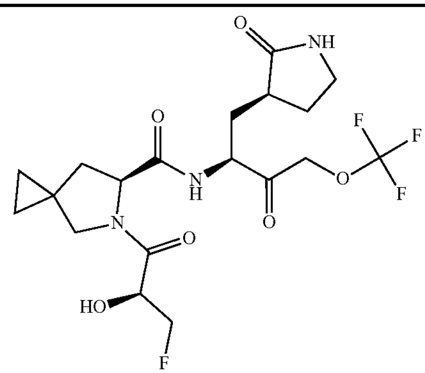 | (S)-5-((S)-3-fluoro-2-hydroxypropanoyl)-N-((S)-3-oxo-1-((S)-2-(trifluoromethoxy)butan-2-yl)-4-oxopyrrolidin-3-yl)-5-azaspiro[2.4]heptane-6-carboxamide | 468.3301 | *** |
| 398 | 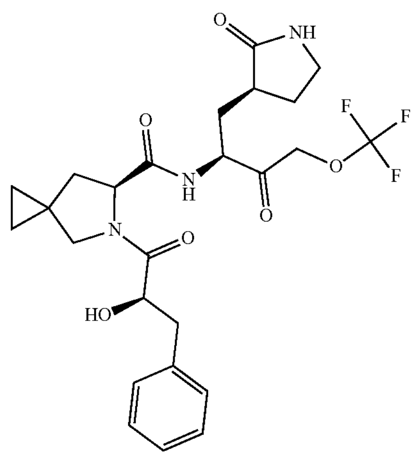 [SMILES: O=C1NCC[C@H]1C[C@H](NC(=O)[C@@H]1CC2(CC2)CN1C(=O)[C@H](O)Cc1ccccc1)C(=O)COC(F)(F)F] | (S)-5-((R)-2-hydroxy-3-phenylpropanoyl)-N-((S)-3-oxo-1-((S)-2-(trifluoromethoxy)butan-2-yl)-4-oxopyrrolidin-3-yl)-5-azaspiro[2.4]heptane-6-carboxamide | 526.3807 | *** |

TABLE 1-continued

| Compound | Structure | IUPAC | LCMS [M + 1] | EC50, uM (Hela) |
|---|---|---|---|---|
| 399 | 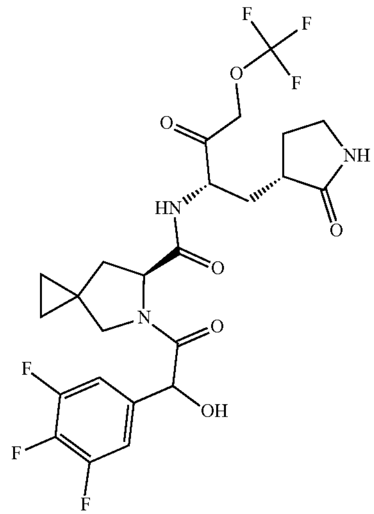 [SMILES: O=C1NCC[C@H]1C[C@H](NC(=O)[C@@H]1CC2(CC2)CN1C(=O)C(O)c1cc(F)c(F)c(F)c1)C(=O)COC(F)(F)F] | (6S)-5-(2-hydroxy-2-(3,4,5-trifluorophenyl)acetyl)-N-((S)-3-oxo-1-((S)-2-oxopyrrolidin-3-yl)-4-(trifluoromethoxy)butan-2-yl)-5-azaspiro[2.4]heptane-6-carboxamide | 566.16 | *** |
| 400 | 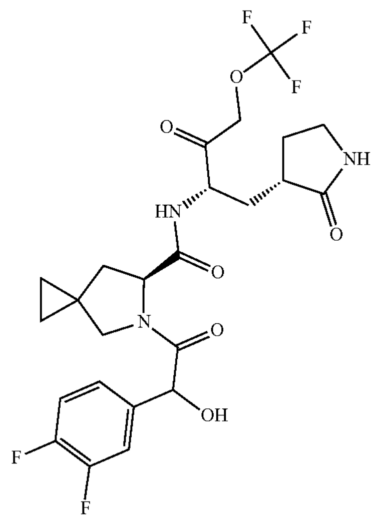 [SMILES: O=C1NCC[C@H]1C[C@H](NC(=O)[C@@H]1CC2(CC2)CN1C(=O)C(O)c1ccc(F)c(F)c1)C(=O)COC(F)(F)F] | (6S)-5-(2-(3,4-difluorophenyl)-2-hydroxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 548.3992 | *** |

TABLE 1-continued

| Compound | Structure | IUPAC | LCMS [M + 1] | EC50, uM (Hela) |
|---|---|---|---|---|
| 401 | 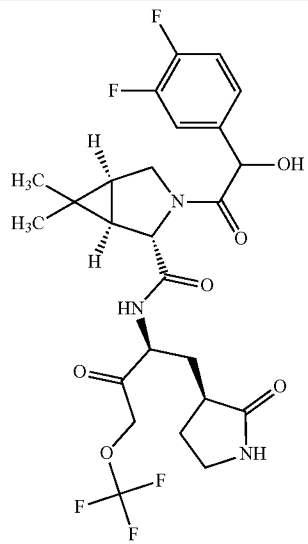 [SMILES: CC1(C)[C@@H]2[C@@H](C(=O)N[C@@H](C[C@@H]3CCNC3=O)C(=O)COC(F)(F)F)N(C(=O)C(O)c3ccc(F)c(F)c3)C[C@@H]21] | (1R,2S,5S)-3-(2-(3,4-difluorophenyl)-2-hydroxyacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 562.4 | **** |
| 402 | 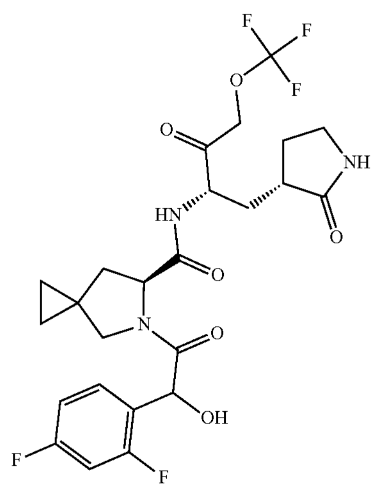 [SMILES: O=C1NCC[C@H]1C[C@H](NC(=O)[C@@H]1CC2(CC2)CN1C(=O)C(O)c1ccc(F)cc1F)C(=O)COC(F)(F)F] | (6S)-5-(2-(2,4-difluorophenyl)-2-hydroxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 548.17 | *** |

TABLE 1-continued

| Compound | Structure | IUPAC | LCMS [M + 1] | EC50, uM (Hela) |
|---|---|---|---|---|
| 403 | 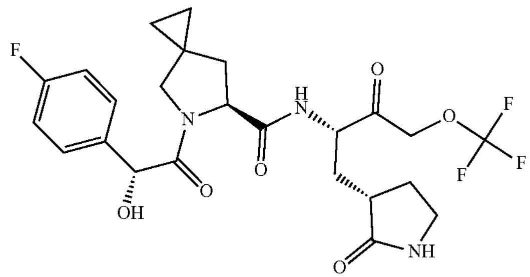 [SMILES: O=C1NCC[C@H]1C[C@H](NC(=O)[C@@H]1CC2(CC2)CN1C(=O)[C@H](O)c1ccc(F)cc1)C(=O)COC(F)(F)F] | (S)-5-((R)-2-(4-fluorophenyl)-2-hydroxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 530.18 | *** |
| 404 | 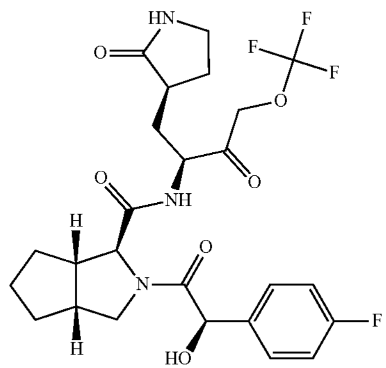 [SMILES: O=C1NCC[C@H]1C[C@H](NC(=O)[C@@H]1[C@H]2CCC[C@H]2CN1C(=O)[C@H](O)c1ccc(F)cc1)C(=O)COC(F)(F)F] | (1S,3aR,6aS)-2-((R)-2-(4-fluorophenyl)-2-hydroxyacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 544.3851 | **** |

TABLE 1-continued

| Compound | Structure | IUPAC | LCMS [M + 1] | EC50, uM (Hela) |
|---|---|---|---|---|
| 405 | 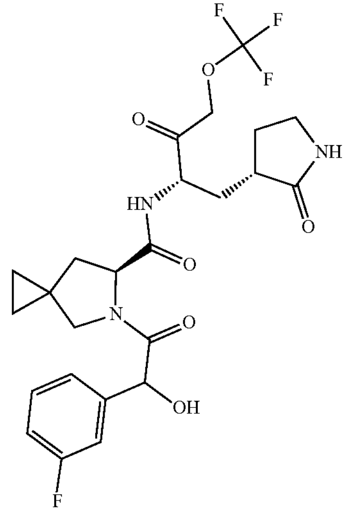 [SMILES: O=C1NCC[C@H]1C[C@H](NC(=O)[C@@H]1CC2(CC2)CN1C(=O)C(O)c1cccc(F)c1)C(=O)COC(F)(F)F] | (6S)-5-(2-(3-fluorophenyl)-2-hydroxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 530.4059 | *** |
| 406 | 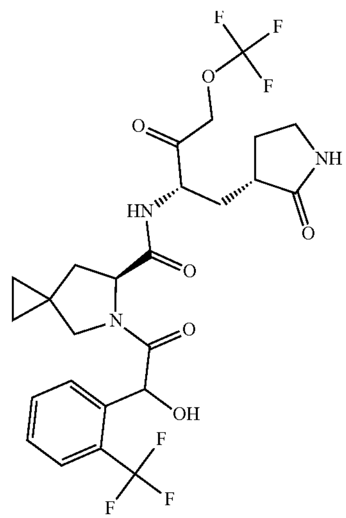 [SMILES: O=C1NCC[C@H]1C[C@H](NC(=O)[C@@H]1CC2(CC2)CN1C(=O)C(O)c1ccccc1C(F)(F)F)C(=O)COC(F)(F)F] | (6S)-5-(2-hydroxy-2-(2-(trifluoromethyl)phenyl)acetyl)-N-((S)-3-oxo-1-((S)-2-oxopyrrolidin-3-yl)-4-(trifluoromethoxy)butan-2-yl)-5-azaspiro[2.4]heptane-6-carboxamide | 580.4 | *** |

TABLE 1-continued

| Compound | Structure | IUPAC | LCMS [M + 1] | EC50, uM (Hela) |
|---|---|---|---|---|
| 407 | 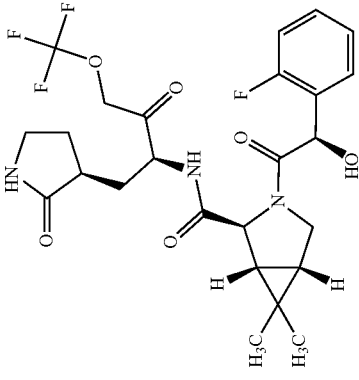 | (1R,2S,5S)-3-((R)-2-(2-fluorophenyl)-2-hydroxy acetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 544.4518 | **** |
| 408 | 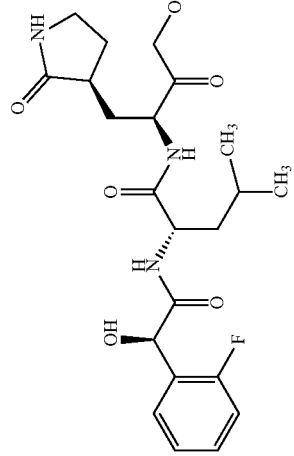 | (S)-2-((R)-2-(2-fluorophenyl)-2-hydroxyacetamido)-4-methyl-N-((S)-3-oxo-1-((S)-2-oxopyrrolidin-3-yl)-4-(trifluoromethoxy)butan-2-yl)pentanamide | 520.2111 | **** |
| 409 | 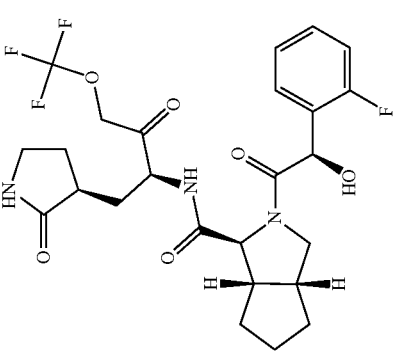 | (1S,3aR,6aS)-2-((R)-2-(2-fluorophenyl)-2-hydroxyacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 544.4448 | *** |

TABLE 1-continued

| Compound | Structure | IUPAC | LCMS [M + 1] | EC50, uM (Hela) |
|---|---|---|---|---|
| 410 | 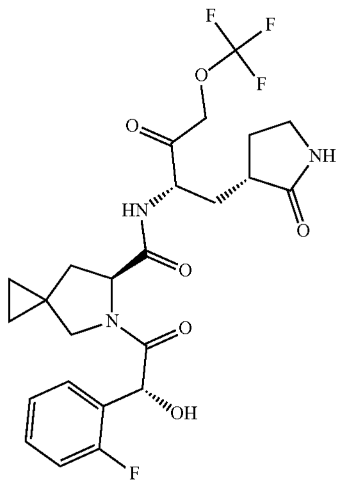 [SMILES: O=C1NCC[C@H]1C[C@H](NC(=O)[C@@H]1CC2(CC2)CN1C(=O)[C@H](O)c1ccccc1F)C(=O)COC(F)(F)F] | (S)-5-((R)-2-(2-fluorophenyl)-2-hydroxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 530.18 | *** |
| 411 | 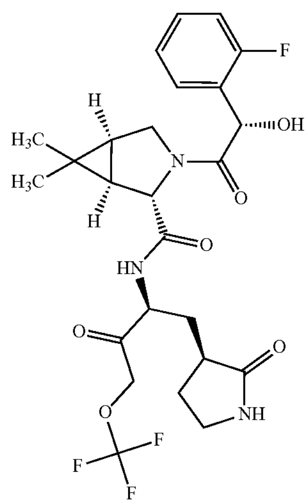 [SMILES: CC1(C)[C@@H]2[C@@H](C(=O)N[C@@H](C[C@@H]3CCNC3=O)C(=O)COC(F)(F)F)N(C(=O)[C@@H](O)c3ccccc3F)C[C@@H]21] | (1R,2S,5S)-3-((S)-2-(2-fluorophenyl)-2-hydroxyacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 544.2 | **** |

TABLE 1-continued

| Compound | Structure | IUPAC | LCMS [M + 1] | EC50, uM (Hela) |
|---|---|---|---|---|
| 412 | 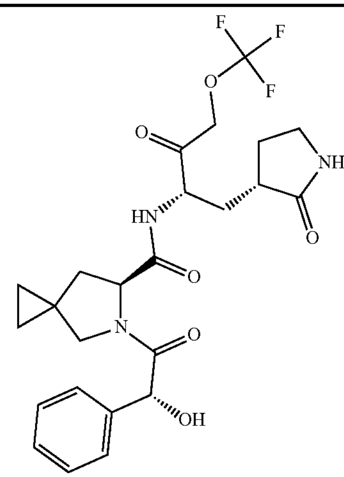 | (S)-5-((R)-2-hydroxy-2-phenylacetyl)-N-((S)-3-oxo-1-((S)-2-oxopyrrolidin-3-yl)-4-(trifluoromethoxy)butan-2-yl)-5-azaspiro[2.4]-heptane-6-carboxamide | 512.4113 | *** |
| 413 | 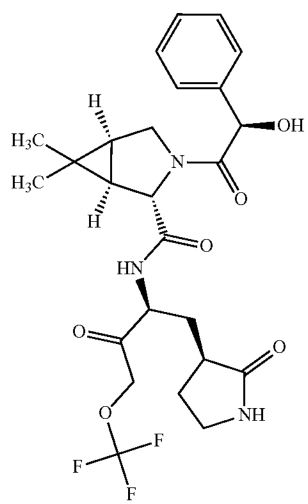 [SMILES: CC1(C)[C@@H]2[C@@H](C(=O)N[C@@H](C[C@@H]3CCNC3=O)C(=O)COC(F)(F)F)N(C(=O)[C@H](O)c3ccccc3)C[C@@H]21] | (1R,2S,5S)-3-((R)-2-hydroxy-2-phenylacetyl)-6,6-dimethyl-N-((S)-3-oxo-1-((S)-2-oxopyrrolidin-3-yl)-4-(trifluoromethoxy)butan-2-yl)-3-azabicyclo[3.1.0]-hexane-2-carboxamide | 526.4252 | **** |

TABLE 1-continued
| Compound | Structure | IUPAC | LCMS [M + 1] | EC50, uM (Hela) |
|---|---|---|---|---|
| 414 | 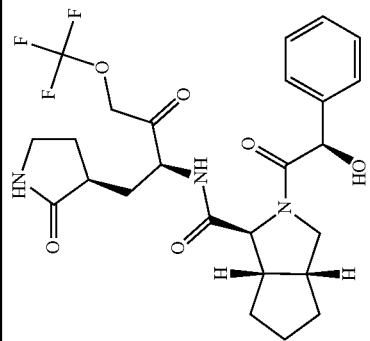 | (1S,3aR,6aS)-2-((R)-2-hydroxy-2-phenylacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 526.4507 | **** |
| 415 | 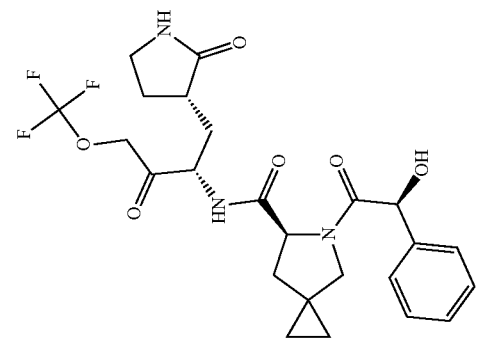 | (S)-5-((S)-2-hydroxy-2-phenylacetyl)-N-((S)-3-oxo-1-((S)-2-oxopyrrolidin-3-yl)-4-(trifluoromethoxy)butan-2-yl)-5-azaspiro[2.4]heptane-6-carboxamide | 512.3909 | *** |

TABLE 1-continued

| Compound | Structure | IUPAC | LCMS [M + 1] | EC50, uM (Hela) |
|---|---|---|---|---|
| 416 | 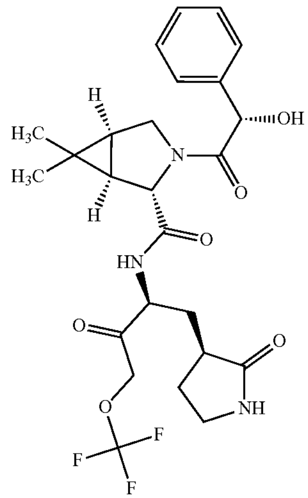 [SMILES: CC1(C)[C@@H]2[C@@H](C(=O)N[C@@H](C[C@@H]3CCNC3=O)C(=O)COC(F)(F)F)N(C(=O)[C@@H](O)c3ccccc3)C[C@@H]21] | (1R,2S,5S)-3-((S)-2-hydroxy-2-phenylacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 526.4417 | **** |
| 417 | 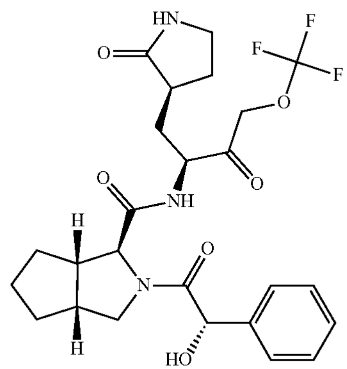 [SMILES: O=C1NCC[C@H]1C[C@H](NC(=O)[C@@H]1[C@H]2CCC[C@H]2CN1C(=O)[C@@H](O)c1ccccc1)C(=O)COC(F)(F)F] | (1S,3aR,6aS)-2-((S)-2-hydroxy-2-phenylacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 526.4408 | **** |

TABLE 1-continued

| Compound | Structure | IUPAC | LCMS [M + 1] | EC50, uM (Hela) |
|---|---|---|---|---|
| 418 | 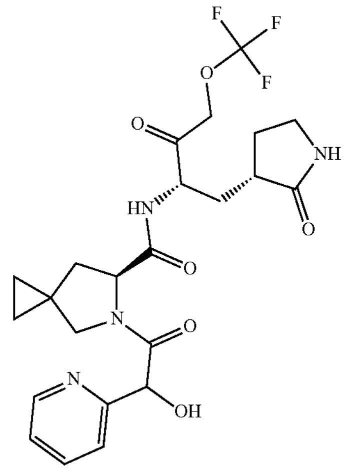 [SMILES: O=C1NCC[C@H]1C[C@H](NC(=O)[C@@H]1CC2(CC2)CN1C(=O)C(O)c1ccccn1)C(=O)COC(F)(F)F] | (6S)-5-(2-hydroxy-2-(pyridin-2-yl)acetyl)-N-((S)-3-oxo-1-((S)-2-oxopyrrolidin-3-yl)-4-(trifluoromethoxy)butan-2-yl)-5-azaspiro[2.4]heptane-6-carboxamide | 513.2 | *** |
| 419 | 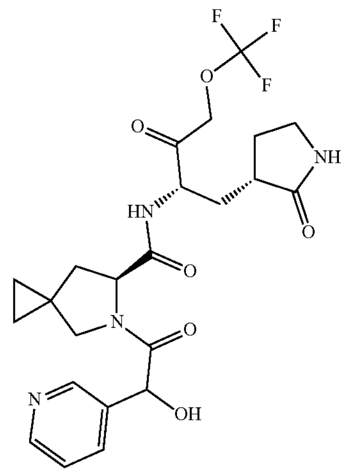 | (6S)-5-(2-hydroxy-2-(pyridin-3-yl)acetyl)-N-((S)-3-oxo-1-((S)-2-oxopyrrolidin-3-yl)-4-(trifluoromethoxy)butan-2-yl)-5-azaspiro[2.4]heptane-6-carboxamide | 513.2 | * |

TABLE 1-continued

| Compound | Structure | IUPAC | LCMS [M + 1] | EC50, uM (Hela) |
|---|---|---|---|---|
| 420 | 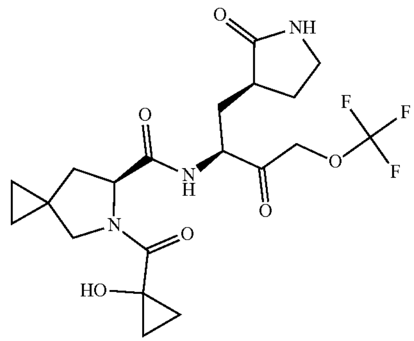 [SMILES: O=C1NCC[C@H]1C[C@H](NC(=O)[C@@H]1CC2(CC2)CN1C(=O)C1(O)CC1)C(=O)COC(F)(F)F] | (S)-5-(1-hydroxycyclopropane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 462.4284 | *** |
| 421 | 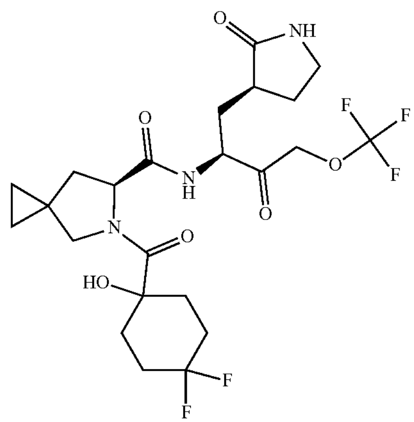 [SMILES: O=C1NCC[C@H]1C[C@H](NC(=O)[C@@H]1CC2(CC2)CN1C(=O)C1(O)CCC(F)(F)CC1)C(=O)COC(F)(F)F] | (S)-5-(4,4-difluoro-1-hydroxy cyclohexane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 540.5 | **** |

TABLE 1-continued

| Compound | Structure | IUPAC | LCMS [M + 1] | EC50, uM (Hela) |
|---|---|---|---|---|
| 422 | 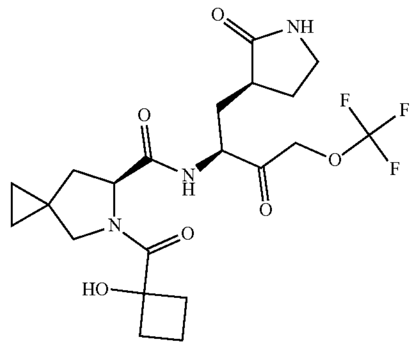 [SMILES: O=C1NCC[C@H]1C[C@H](NC(=O)[C@@H]1CC2(CC2)CN1C(=O)C1(O)CCC1)C(=O)COC(F)(F)F] | (S)-5-(1-hydroxycyclobutane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 476.4402 | *** |
| 423 | 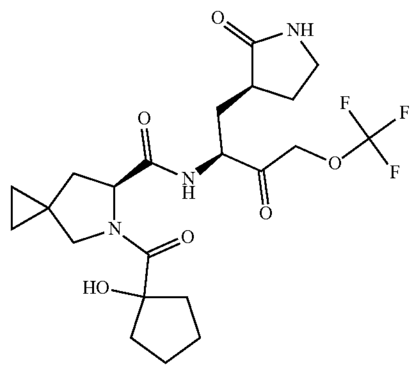 [SMILES: O=C1NCC[C@H]1C[C@H](NC(=O)[C@@H]1CC2(CC2)CN1C(=O)C1(O)CCCC1)C(=O)COC(F)(F)F] | (S)-5-(1-hydroxycyclopentane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 490.4516 | *** |

TABLE 1-continued
| Compound | Structure | IUPAC | LCMS [M + 1] | EC50, uM (Hela) |
|---|---|---|---|---|
| 424 | 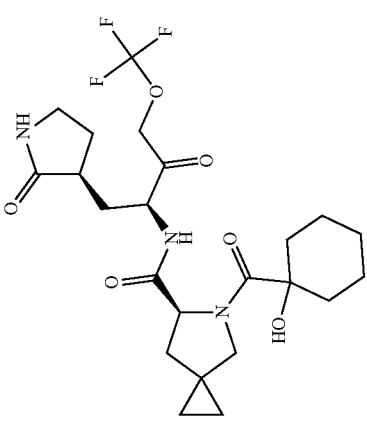 | (S)-5-(1-hydroxycyclohexane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 504.4626 | *** |
| 425 | 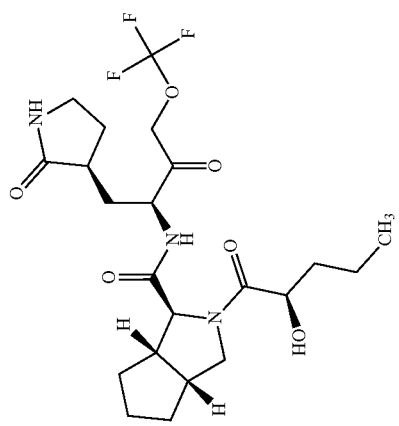 | (1S,3aR,6aS)-2-((R)-2-hydroxypentanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 492.4352 | *** |

TABLE 1-continued

| Compound | Structure | IUPAC | LCMS [M + 1] | EC50, uM (Hela) |
|---|---|---|---|---|
| 426 | 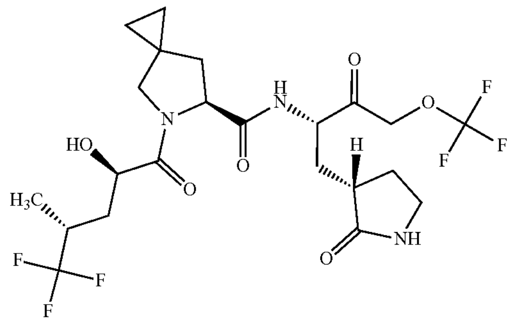 [SMILES: C[C@H](C[C@@H](O)C(=O)N1CC2(CC2)C[C@H]1C(=O)N[C@@H](C[C@@H]1CCNC1=O)C(=O)COC(F)(F)F)C(F)(F)F] | (S)-N-((S)-3-oxo-1-((S)-2-oxopyrrolidin-3-yl)-4-(trifluoromethoxy)butan-2-yl)-5-((2R,4R)-5,5,5-trifluoro-2-hydroxy-4-methylpentanoyl)-5-azaspiro[2.4]heptane-6-carboxamide | 546.4576 | **** |
| 427 | 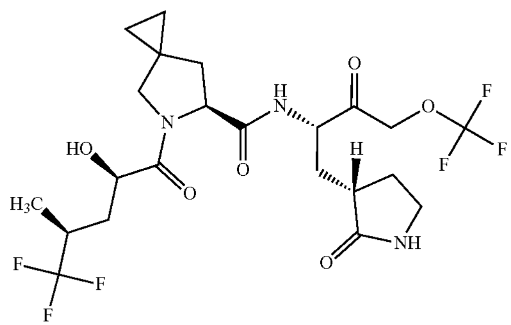 [SMILES: C[C@@H](C[C@@H](O)C(=O)N1CC2(CC2)C[C@H]1C(=O)N[C@@H](C[C@@H]1CCNC1=O)C(=O)COC(F)(F)F)C(F)(F)F] | (S)-N-((S)-3-oxo-1-((S)-2-oxopyrrolidin-3-yl)-4-(trifluoromethoxy)butan-2-yl)-5-((2R,4S)-5,5,5-trifluoro-2-hydroxy-4-methylpentanoyl)-5-azaspiro[2.4]heptane-6-carboxamide | 546.4576 | **** |
| 428 | 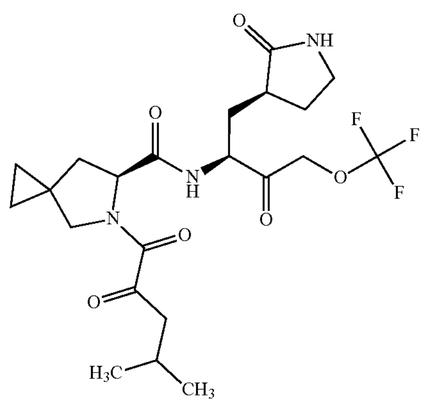 [SMILES: CC(C)CC(=O)C(=O)N1CC2(CC2)C[C@H]1C(=O)N[C@@H](C[C@@H]1CCNC1=O)C(=O)COC(F)(F)F] | (S)-5-(4-methyl-2-oxopentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 490.1619 | **** |

TABLE 1-continued

| Compound | Structure | IUPAC | LCMS [M + 1] | EC50, uM (Hela) |
|---|---|---|---|---|
| 429 | 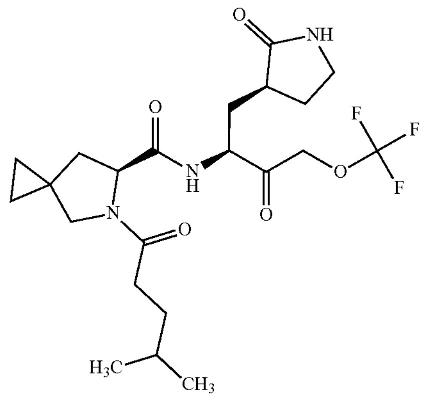 [SMILES: CC(C)CCC(=O)N1CC2(CC2)C[C@H]1C(=O)N[C@@H](C[C@@H]1CCNC1=O)C(=O)COC(F)(F)F] | (S)-5-(4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 476.6936 | **** |
| 430 | 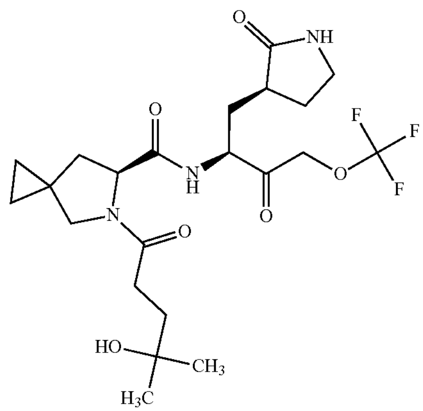 [SMILES: CC(C)(O)CCC(=O)N1CC2(CC2)C[C@H]1C(=O)N[C@@H](C[C@@H]1CCNC1=O)C(=O)COC(F)(F)F] | (S)-5-(4-hydroxy-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 492.3095 | ** |

TABLE 1-continued
| Compound | Structure | IUPAC | LCMS [M + 1] | EC50, uM (Hela) |
|---|---|---|---|---|
| 431 | 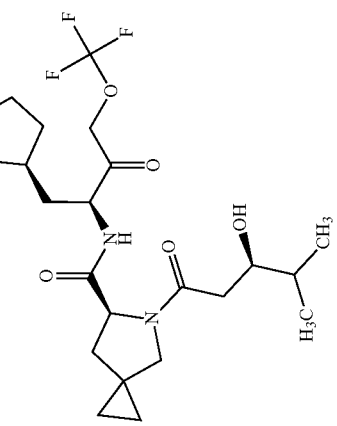 | (S)-5-((R)-3-hydroxy-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 492.4066 | *** |
| 432 | 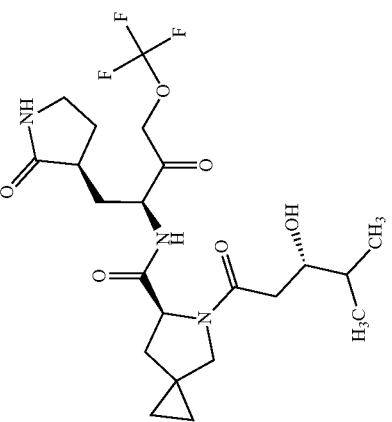 | (S)-5-((S)-3-hydroxy-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 492.4066 | *** |

TABLE 1-continued

| Compound | Structure | IUPAC | LCMS [M + 1] | EC50, uM (Hela) |
|---|---|---|---|---|
| 433 | 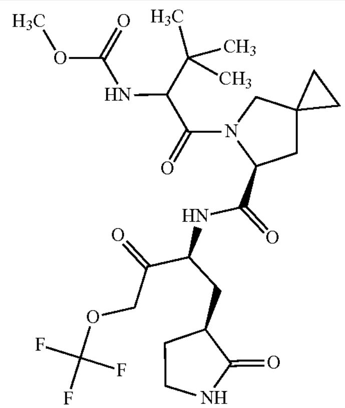 [SMILES: COC(=O)NC(C(=O)N1CC2(CC2)C[C@H]1C(=O)N[C@@H](C[C@@H]1CCNC1=O)C(=O)COC(F)(F)F)C(C)(C)C] | methyl ((S)-3,3-dimethyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)butan-2-yl)carbamate | 549.2 | *** |
| 434 | 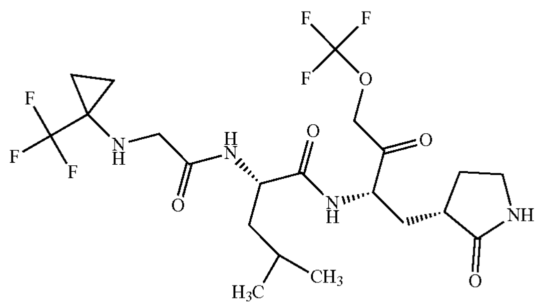 [SMILES: CC(C)C[C@H](NC(=O)CNC1(C(F)(F)F)CC1)C(=O)N[C@@H](C[C@@H]1CCNC1=O)C(=O)COC(F)(F)F] | (S)-4-methyl-N-((S)-3-oxo-1-((S)-2-oxopyrrolidin-3-yl)-4-(trifluoromethoxy)butan-2-yl)-2-(2-((1-(trifluoromethyl)cyclopropyl)amino)acetamido)pentanamide | 533.1716 | **** |

TABLE 1-continued

| Compound | Structure | IUPAC | LCMS [M + 1] | EC50, uM (Hela) |
|---|---|---|---|---|
| 435 | 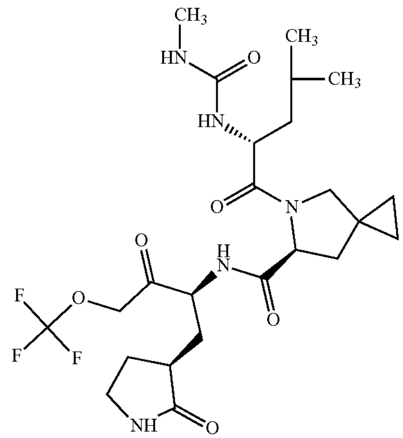 [SMILES: CNC(=O)N[C@H](CC(C)C)C(=O)N1CC2(CC2)C[C@H]1C(=O)N[C@@H](C[C@@H]1CCNC1=O)C(=O)COC(F)(F)F] | (S)-5-(((methylcarbamoyl)-D-leucyl)-N-((S)-3-oxo-1-((S)-2-oxopyrrolidin-3-yl)-4-(trifluoromethoxy)butan-2-yl)-5-azaspiro[2.4]heptane-6-carboxamide | 548.522 | ** |
| 436 | 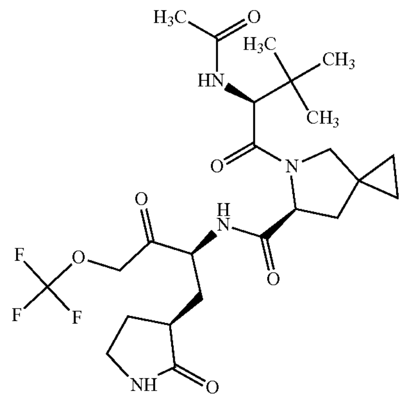 [SMILES: CC(=O)N[C@H](C(=O)N1CC2(CC2)C[C@H]1C(=O)N[C@@H](C[C@@H]1CCNC1=O)C(=O)COC(F)(F)F)C(C)(C)C] | (S)-5-(((S)-2-acetamido-3,3-dimethylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 533.28 | >1 μM |

TABLE 1-continued

| Compound | Structure | IUPAC | LCMS [M + 1] | EC50, uM (Hela) |
|---|---|---|---|---|
| 437 | 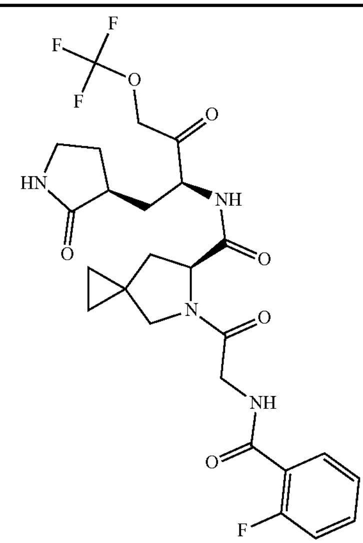 | (S)-5-((2-fluorobenzoyl)glycyl)-N-((S)-3-oxo-1-((S)-2-oxopyrrolidin-3-yl)-4-(trifluoromethoxy)butan-2-yl)-5-azaspiro[2.4]heptane-6-carboxamide | 557.4257 | *** |
| 438 | 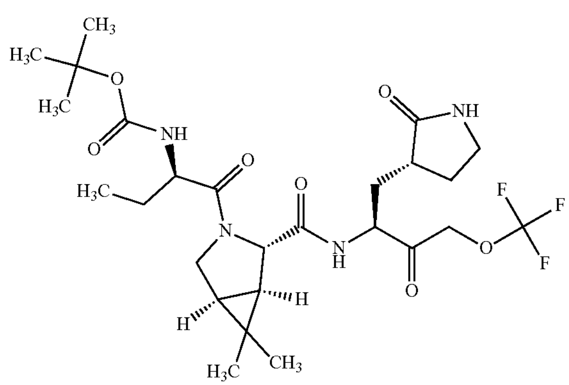 [SMILES: CC[C@@H](NC(=O)OC(C)(C)C)C(=O)N1C[C@H]2[C@@H]([C@H]1C(=O)N[C@@H](C[C@H]1CCNC1=O)C(=O)COC(F)(F)F)C2(C)C] | tert-butyl ((R)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-1-oxobutan-2-yl)carbamate | 577.5 | **** |

TABLE 1-continued

| Compound | Structure | IUPAC | LCMS [M + 1] | EC50, uM (Hela) |
|---|---|---|---|---|
| 439 | 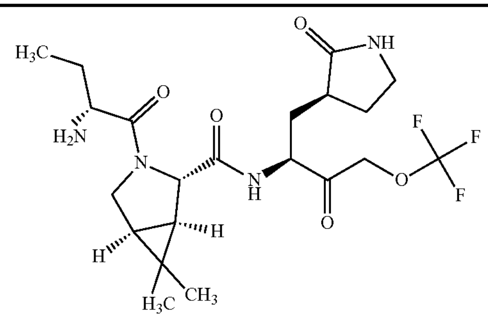 | (1R,2S,5S)-3-((R)-2-aminobutanoyl)-6,6-dimethyl-N-((S)-3-oxo-1-((S)-2-oxopyrrolidin-3-yl)-4-(trifluoromethoxy)butan-2-yl)-3-azabicyclo[3.1.0]-hexane-2-carboxamide | 477.3 | ** |
| 440 | 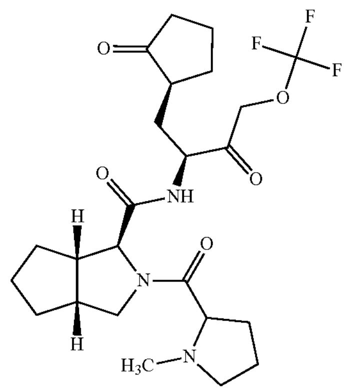 [SMILES: CN1CCCC1C(=O)N1C[C@@H]2CCC[C@@H]2[C@H]1C(=O)N[C@@H](C[C@@H]1CCCC1=O)C(=O)COC(F)(F)F] | (1S,3aR,6aS)-2-(methylprolyl)-N-((S)-3-oxo-1-((S)-2-oxopyrrolidin-3-yl)-4-(trifluoromethoxy)butan-2-yl)octahydrocyclopenta[c]pyrrole-1-carboxamide | 503.2 | * |

TABLE 1-continued

| Compound | Structure | IUPAC | LCMS [M + 1] | EC50, uM (Hela) |
|---|---|---|---|---|
| 441 | 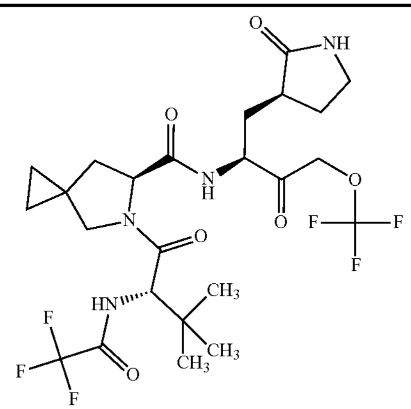 | (S)-5-((S)-3,3-dimethyl-2-(2,2,2-trifluoroacetamido)butanoyl)-N-((S)-3-oxo-1-((S)-2-oxopyrrolidin-3-yl)-4-(trifluoromethoxy)butan-2-yl)-5-azaspiro[2.4]heptane-6-carboxamide | 587.4788 | **** |
| 442 | 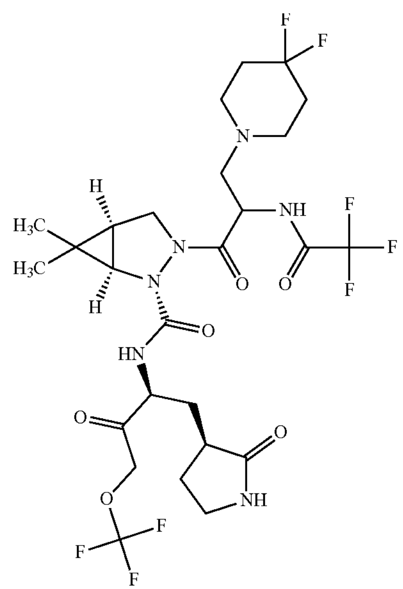 | (1R,2S, 5S)-3-(3-(4,4-difluoropiperidin-1-yl)-2-(2,2,2-trifluoroacetamido)propanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 678.5095 | ** |

TABLE 1-continued

| Compound | Structure | IUPAC | LCMS [M + 1] | EC50, uM (Hela) |
|---|---|---|---|---|
| 445 | 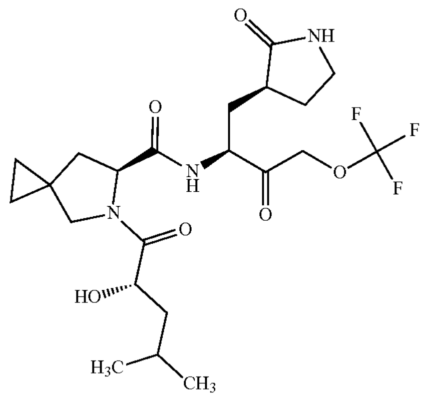 [SMILES: CC(C)C[C@H](O)C(=O)N1CC2(CC2)C[C@H]1C(=O)N[C@@H](C[C@@H]1CCNC1=O)C(=O)COC(F)(F)F] | (S)-5-((S)-2-hydroxy-4-methylpentanoyl)-N-((S)-3-oxo-1-((S)-2-oxopyrrolidin-3-yl)-4-(trifluoromethoxy)butan-2-yl)-5-azaspiro[2.4]-heptane-6-carboxamide | 492.3425 | *** |
| 446 | 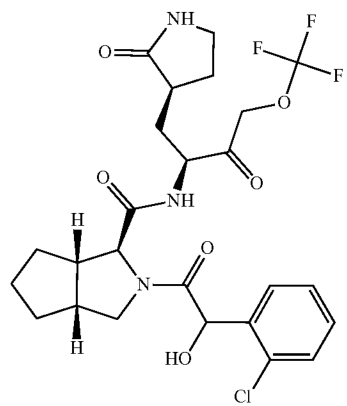 [SMILES: O=C1NCC[C@H]1C[C@H](NC(=O)[C@@H]1[C@H]2CCC[C@H]2CN1C(=O)C(O)c1ccccc1Cl)C(=O)COC(F)(F)F] | (1S,3aR,6aS)-2-(2-(2-chlorophenyl)-2-hydroxyacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 560.364 | |

TABLE 1-continued

| Compound | Structure | IUPAC | LCMS [M + 1] | EC50, uM (Hela) |
|---|---|---|---|---|
| 447 | 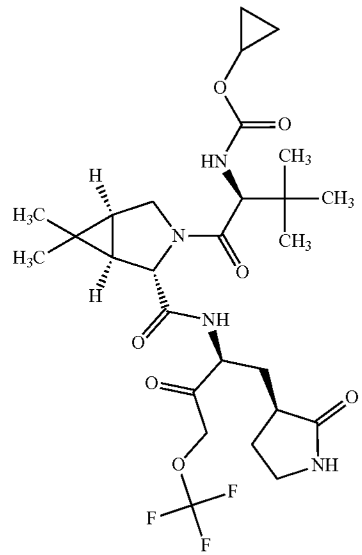 [SMILES: CC(C)(C)[C@H](NC(=O)OC1CC1)C(=O)N1C[C@H]2[C@@H]([C@H]1C(=O)N[C@@H](C[C@@H]1CCNC1=O)C(=O)COC(F)(F)F)C2(C)C] | cyclopropyl ((S)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-3,3-dimethyl-1-oxobutan-2-yl)carbamate | 589.5359 | **** |
| 448 | 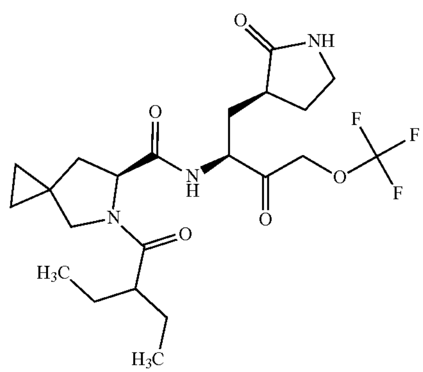 [SMILES: CCC(CC)C(=O)N1CC2(CC2)C[C@H]1C(=O)N[C@@H](C[C@@H]1CCNC1=O)C(=O)COC(F)(F)F] | (S)-5-(2-ethylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 476.4 | *** |

TABLE 1-continued

| Compound | Structure | IUPAC | LCMS [M + 1] | EC50, uM (Hela) |
|---|---|---|---|---|
| 449 | 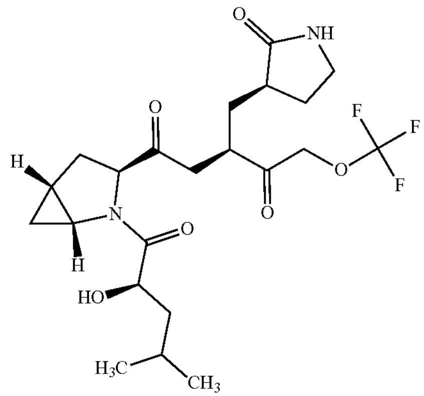 [SMILES: CC(C)C[C@@H](O)C(=O)N1[C@@H]2C[C@@H]2C[C@H]1C(=O)C[C@@H](C[C@@H]1CCNC1=O)C(=O)COC(F)(F)F] | (1R,3S,5R)-2-((R)-2-hydroxy-4-methylpentanoyl)-5-methyl-N-((S)-3-oxo-1-((S)-2-oxopyrrolidin-3-yl)-4-(trifluoromethoxy)butan-2-yl)-2-azabicyclo[3.1.0]-hexane-3-carboxamide | 492.3 | *** |
| 450 | 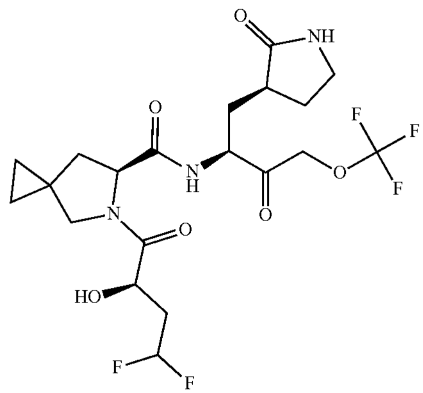 [SMILES: O=C1NCC[C@H]1C[C@H](NC(=O)[C@@H]1CC2(CC2)CN1C(=O)[C@H](O)CC(F)F)C(=O)COC(F)(F)F] | (S)-5-((R)-4,4-difluoro-2-hydroxybutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 501.3491 | *** |

TABLE 1-continued

| Compound | Structure | IUPAC | LCMS [M + 1] | EC50, uM (Hela) |
|---|---|---|---|---|
| 451 | 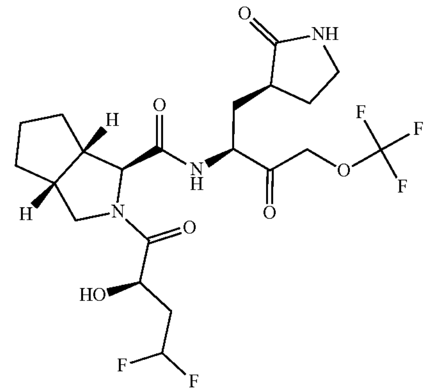 [SMILES: O=C1NCC[C@H]1C[C@H](NC(=O)[C@@H]1[C@H]2CCC[C@H]2CN1C(=O)[C@H](O)CC(F)F)C(=O)COC(F)(F)F] | (1S,3aR,6aS)-2-((R)-4,4-difluoro-2-hydroxybutanoyl)-N-((S)-3-oxo-1-((S)-2-oxopyrrolidin-3-yl)-4-(trifluoromethoxy)butan-2-yl)octahydrocyclopenta[c]pyrrole-1-carboxamide | 514.3824 | |
| 452 | 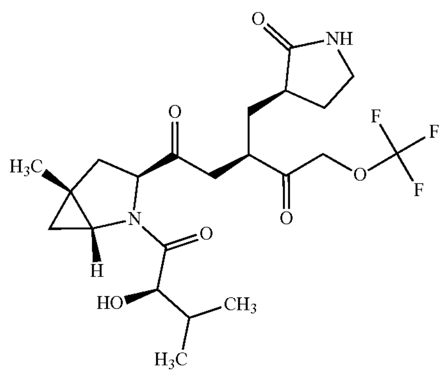 [SMILES: CC(C)[C@@H](O)C(=O)N1[C@H](C(=O)C[C@@H](C[C@@H]2CCNC2=O)C(=O)COC(F)(F)F)C[C@@]2(C)C[C@@H]12] | (1R,3S,5R)-2-((R)-2-hydroxy-3-methylbutanoyl)-5-methyl-N-((S)-3-oxo-1-((S)-2-oxopyrrolidin-3-yl)-4-(trifluoromethoxy)butan-2-yl)-2-azabicyclo[3.1.0]hexane-3-carboxamide | 478.1 | *** |

TABLE 1-continued

| Compound | Structure | IUPAC | LCMS [M + 1] | EC50, uM (Hela) |
|---|---|---|---|---|
| 453 | 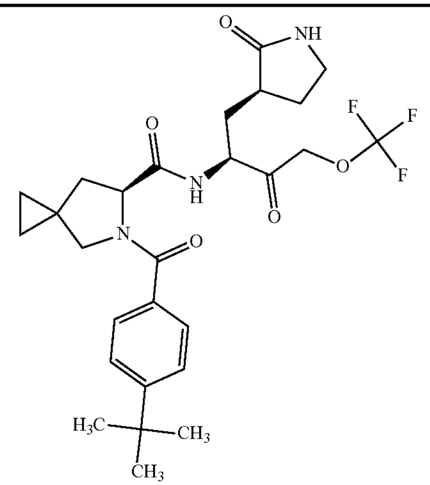 | (S)-5-(4-(tert-butyl)benzoyl)-N-((S)-3-oxo-1-((S)-2-oxopyrrolidin-3-yl)-4-(trifluoromethoxy)butan-2-yl)-5-azaspiro[2.4]heptane-6-carboxamide | 538.4932 | **** |
| 454 | 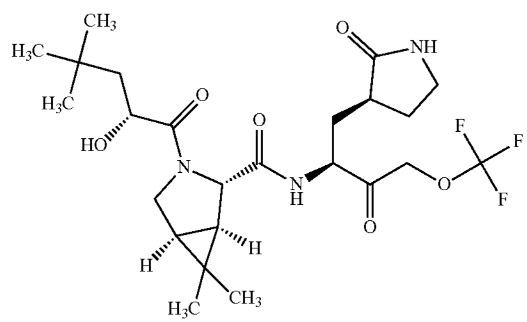 [SMILES: CC(C)(C)C[C@@H](O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-((R)-2-hydroxy-4,4-dimethylpentanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 520.4869 | **** |

TABLE 1-continued
| Compound | Structure | IUPAC | LCMS [M + 1] | EC50, uM (Hela) |
|---|---|---|---|---|
| 455 | 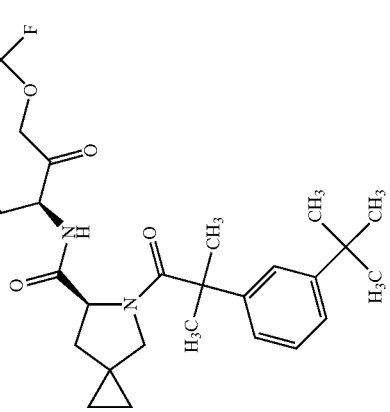 | (S)-5-(2-(3-(tert-butyl)phenyl)-2-methylpropanoyl)-N-((S)-3-oxo-1-((S)-2-oxopyrrolidin-3-yl)-4-(trifluoromethoxy)butan-2-yl)-5-azaspiro[2.4]heptane-6-carboxamide | 580.486 | *** |

TABLE 1-continued

| Compound | Structure | IUPAC | LCMS [M + 1] | EC50, uM (Hela) |
|---|---|---|---|---|
| 456 | 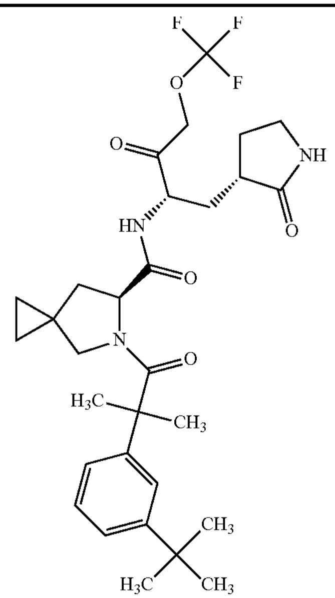 | (S)-5-(2-methyl-2-(3-(trifluoromethyl)phenyl)propanoyl)-N-((S)-3-oxo-1-((S)-2-oxopyrrolidin-3-yl)-4-(trifluoromethoxy)butan-2-yl)-4-(trifluoromethoxy)-5-azaspiro[2.4]heptane-6-carboxamide | 592.3956 | **** |
| 457 | 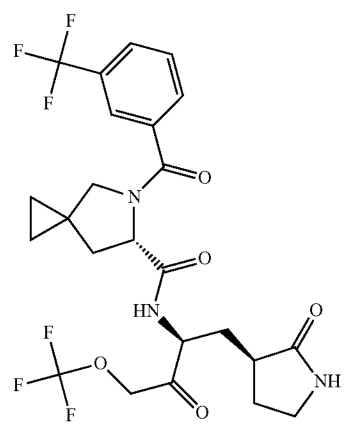 [SMILES: O=C1NCC[C@H]1C[C@H](NC(=O)[C@@H]1CC2(CC2)CN1C(=O)c1cccc(C(F)(F)F)c1)C(=O)COC(F)(F)F] | (S)-N-((S)-3-oxo-1-((S)-2-oxopyrrolidin-3-yl)-2-(trifluoromethoxy)butan-2-yl)-5-(3-(trifluoromethyl)benzoyl)-5-azaspiro[2.4]heptane-6-carboxamide | 550.3673 | **** |

TABLE 1-continued

| Compound | Structure | IUPAC | LCMS [M + 1] | EC50, uM (Hela) |
|---|---|---|---|---|
| 458 | 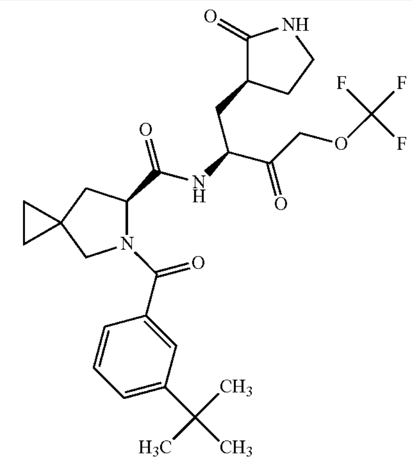 [SMILES: CC(C)(C)c1cccc(C(=O)N2CC3(CC3)C[C@H]2C(=O)N[C@@H](C[C@@H]2CCNC2=O)C(=O)COC(F)(F)F)c1] | (S)-5-(3-(tert-butyl)benzoyl)-N-((S)-3-oxo-1-((S)-2-oxopyrrolidin-3-yl)-4-(trifluoromethoxy)butan-2-yl)-5-azaspiro[2.4]heptane-6-carboxamide | 538.4208 | **** |
| 459 | 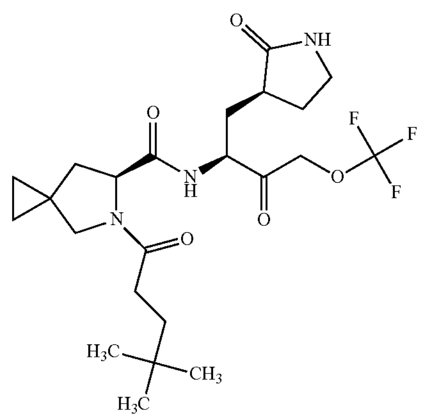 [SMILES: CC(C)(C)CCC(=O)N1CC2(CC2)C[C@H]1C(=O)N[C@@H](C[C@@H]1CCNC1=O)C(=O)COC(F)(F)F] | (S)-5-(4,4-dimethylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 490.4 | **** |

TABLE 1-continued

| Compound | Structure | IUPAC | LCMS [M + 1] | EC50, uM (Hela) |
|---|---|---|---|---|
| 460 | 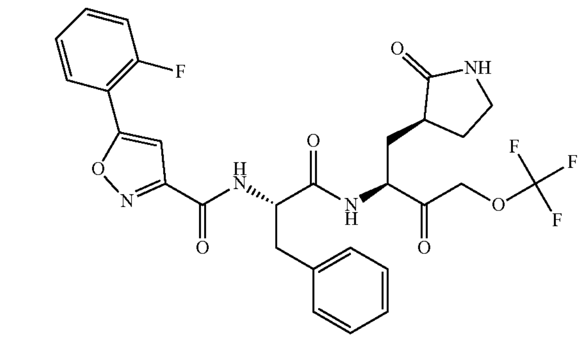 [SMILES: O=C(N[C@@H](Cc1ccccc1)C(=O)N[C@@H](C[C@@H]1CCNC1=O)C(=O)COC(F)(F)F)c1cc(-c2ccccc2F)on1] | 5-(2-fluorophenyl)-N-((S)-1-oxo-1-(((S)-3-oxo-1-((S)-2-oxopyrrolidin-3-yl)-4-(trifluoromethoxy)butan-2-yl)amino)-3-phenylpropan-2-yl)isoxazole-3-carboxamide | 591.5992 | **** |
| 461 | 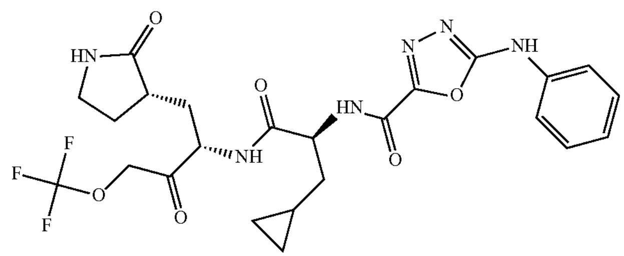 [SMILES: O=C(N[C@@H](CC1CC1)C(=O)N[C@@H](C[C@@H]1CCNC1=O)C(=O)COC(F)(F)F)c1nnc(Nc2ccccc2)o1] | N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(phenylamino)-1,3,4-oxadiazole-2-carboxamide | 554.3 | ** |
| 462 | 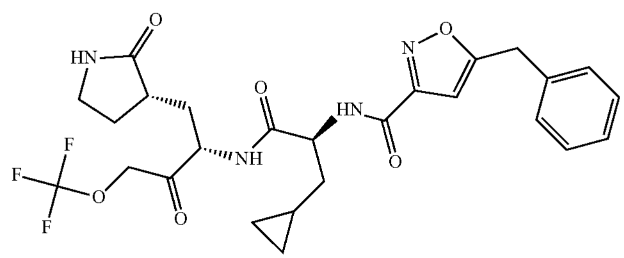 [SMILES: O=C(N[C@@H](CC1CC1)C(=O)N[C@@H](C[C@@H]1CCNC1=O)C(=O)COC(F)(F)F)c1cc(Cc2ccccc2)on1] | 5-benzyl-N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)isoxazole-3-carboxamide | 551.6343 | **** |

TABLE 1-continued

| Compound | Structure | IUPAC | LCMS [M + 1] | EC50, uM (Hela) |
|---|---|---|---|---|
| 463 | 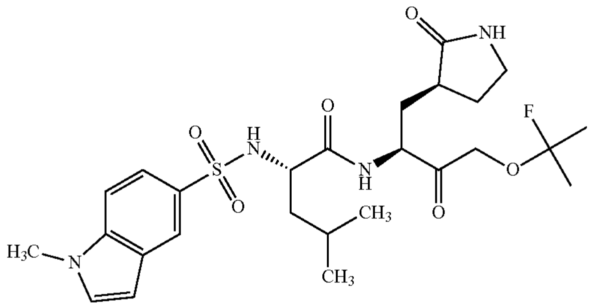 [SMILES: CC(C)C[C@H](NS(=O)(=O)c1ccc2c(ccn2C)c1)C(=O)N[C@@H](C[C@@H]1CCNC1=O)C(=O)COC(C)(C)F] | (S)-4-methyl-2-((1-methyl-1H-indole)-5-sulfonamido)-N-((S)-3-oxo-1-((S)-2-oxopyrrolidin-3-yl)-4-(trifluoromethoxy)butan-2-yl)pentanamide | 561.3411 | ** |
| 464 | 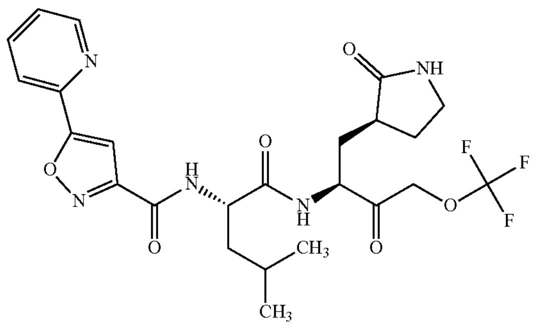 [SMILES: CC(C)C[C@H](NC(=O)c1cc(-c2ccccn2)on1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-5-(pyridin-2-yl)isoxazole-3-carboxamide | 540.2 | **** |
| 465 | 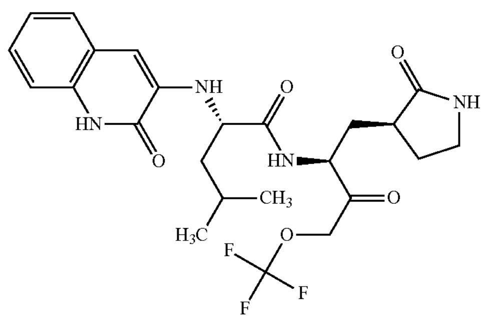 [SMILES: CC(C)C[C@H](Nc1cc2ccccc2[nH]c1=O)C(=O)N[C@@H](C[C@@H]1CCNC1=O)C(=O)COC(F)(F)F] | (S)-4-methyl-2-((2-oxo-1,2-dihydroquinolin-3-yl)amino)-N-((S)-3-oxo-1-((S)-2-oxopyrrolidin-3-yl)-4-(trifluoromethoxy)butan-2-yl)pentanamide | 511.0879 | ** |

TABLE 1-continued

| Compound | Structure | IUPAC | LCMS [M + 1] | EC50, uM (Hela) |
|---|---|---|---|---|
| 466 | 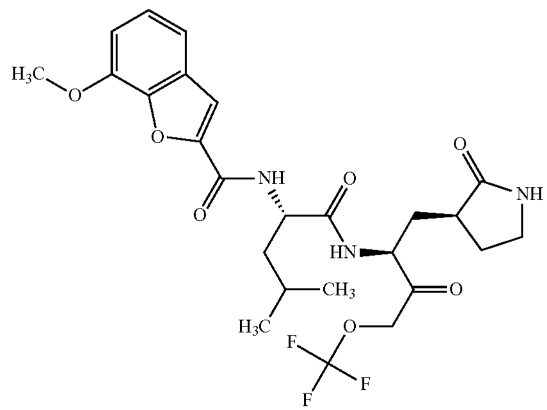 [SMILES: COc1cccc2cc(C(=O)N[C@@H](CC(C)C)C(=O)N[C@@H](C[C@@H]3CCNC3=O)C(=O)COC(F)(F)F)oc12] | 7-methoxy-N-((S)-4-methyl-1-oxo-1-(((S)-3-oxo-1-((S)-2-oxopyrrolidin-3-yl)-4-(trifluoromethoxy)butan-2-yl)amino)pentan-2-yl)benzofuran-2-carboxamide | 542.6926 | **** |
| 467 | 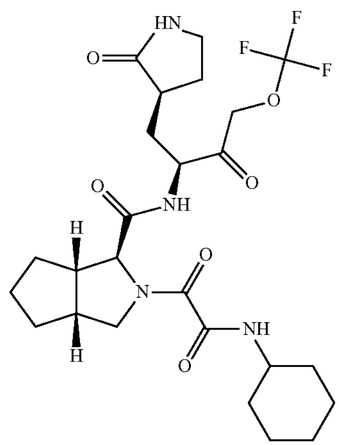 [SMILES: O=C(NC1CCCCC1)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-(cyclohexylamino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 545.25 | * |

TABLE 1-continued

| Compound | Structure | IUPAC | LCMS [M + 1] | EC50, uM (Hela) |
|---|---|---|---|---|
| 468 | 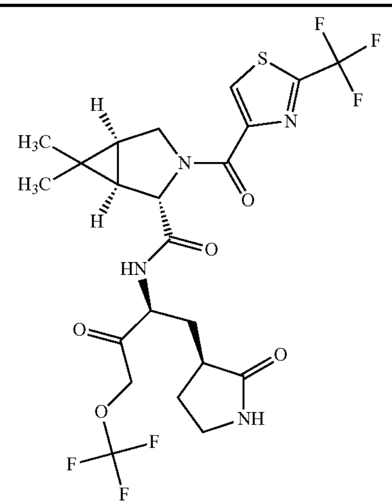 | (1R,2S,5S)-6,6-dimethyl-N-((S)-3-oxo-1-((S)-2-oxopyrrolidin-3-yl)-4-(trifluoromethoxy)butan-2-yl)-3-(2-(trifluoromethyl)-thiazole-4-carbonyl)-3-azabicyclo[3.1.0]-hexane-2-carboxamide | 571.27 | *** |
| 469 | 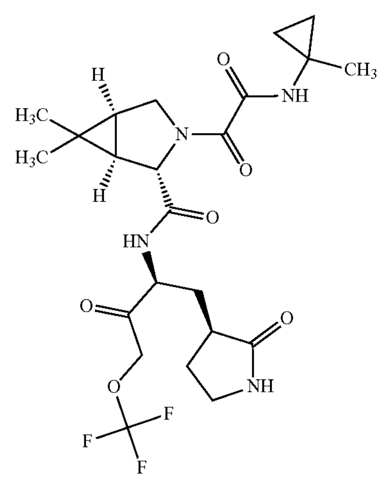 | (1R,2S,5S)-6,6-dimethyl-3-(2-((1-methylcyclopropyl)-amino)-2-oxoacetyl)-N-((S)-3-oxo-1-((S)-2-oxopyrrolidin-3-yl)-4-(trifluoromethoxy)butan-2-yl)-3-azabicyclo[3.1.0]-hexane-2-carboxamide | 517.351 | *** |

TABLE 1-continued

| Compound | Structure | IUPAC | LCMS [M + 1] | EC50, uM (Hela) |
|---|---|---|---|---|
| 470 | 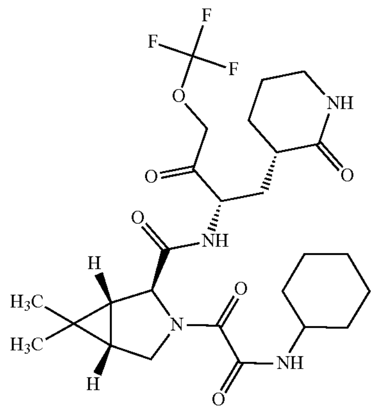 [SMILES: CC1(C)[C@@H]2[C@@H](C(=O)N[C@@H](C[C@@H]3CCCNC3=O)C(=O)COC(F)(F)F)N(C(=O)C(=O)NC3CCCCC3)C[C@@H]21] | (1R,2S,5S)-3-(2-(cyclohexylamino)-2-oxoacetyl)-6,6-dimethyl-N-((S)-3-oxo-1-((S)-2-oxopiperidin-3-yl)-4-(trifluoromethoxy)butan-2-yl)-3-azabicyclo[3.1.0]hexane-2-carboxamide | 559.7433 | **** |
| 471 | 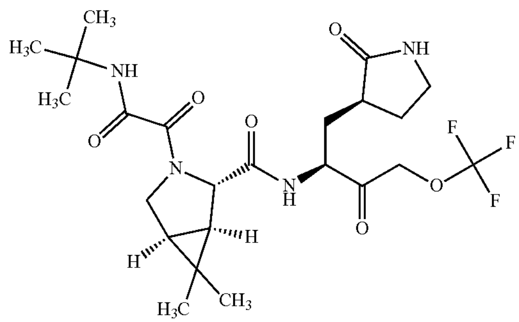 [SMILES: CC(C)(C)NC(=O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-3-(2-(tert-butylamino)-2-oxoacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 519.38 | *** |

TABLE 1-continued

| Compound | Structure | IUPAC | LCMS [M + 1] | EC50, uM (Hela) |
|---|---|---|---|---|
| 472 | 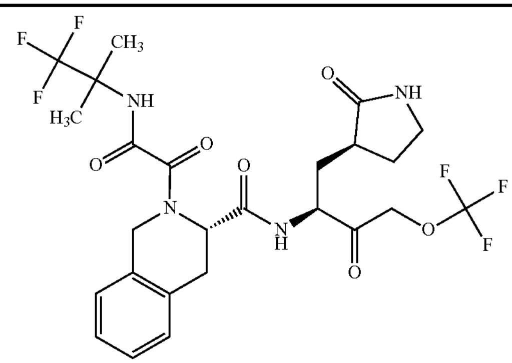 | (S)-N-((S)-3-oxo-1-((S)-2-oxopyrrolidin-3-yl)-4-(trifluoromethoxy)butan-2-yl)-2-(2-oxo-2-((1,1,1-trifluoro-2-methylpropan-2-yl)amino)acetyl)-1,2,3,4-tetrahydroisoquinoline-3-carboxamide | 595.5812 | *** |
| 473 | 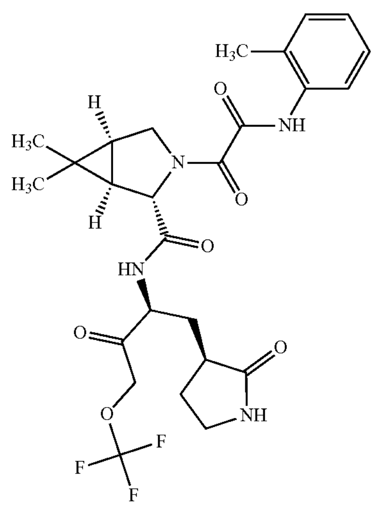 [SMILES: Cc1ccccc1NC(=O)C(=O)N1C[C@H]2[C@@H]([C@H]1C(=O)N[C@@H](C[C@@H]1CCNC1=O)C(=O)COC(F)(F)F)C2(C)C] | (1R,2S,5S)-6,6-dimethyl-N-((S)-3-oxo-1-((S)-2-oxopyrrolidin-3-yl)-4-(trifluoromethoxy)butan-2-yl)-3-(2-oxo-2-(o-tolylamino)acetyl)-3-azabicyclo[3.1.0]hexane-2-carboxamide | 553.36 | **** |

TABLE 1-continued

| Compound | Structure | IUPAC | LCMS [M + 1] | EC50, uM (Hela) |
|---|---|---|---|---|
| 475 | 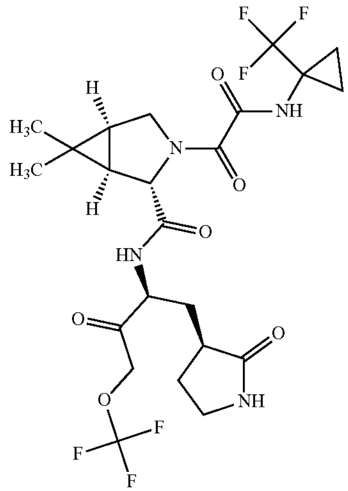 [SMILES: CC1(C)[C@@H]2[C@@H](C(=O)N[C@@H](C[C@@H]3CCNC3=O)C(=O)COC(F)(F)F)N(C(=O)C(=O)NC3(C(F)(F)F)CC3)C[C@@H]21] | (1R,2S,5S)-6,6-dimethyl-N-((S)-3-oxo-1-((S)-2-oxopyrrolidin-3-yl)-4-(trifluoromethoxy)butan-2-yl)-3-(2-oxo-2-((1-(trifluoromethyl)cyclopropyl)amino)acetyl)-3-zabicyclo[3.1.0]hexane-2-carboxamide | 571.19 | *** |
| 476 | 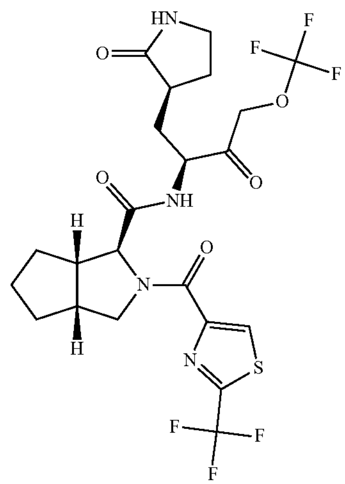 [SMILES: O=C1NCC[C@H]1C[C@H](NC(=O)[C@@H]1[C@H]2CCC[C@H]2CN1C(=O)c1csc(C(F)(F)F)n1)C(=O)COC(F)(F)F] | (1S,3aR,6aS)-N-((S)-3-oxo-1-((S)-2-oxopyrrolidin-3-yl)-4-(trifluoromethoxy)butan-2-yl)-2-(2-(trifluoromethyl)thiazole-4-carbonyl)-octahydrocyclo-penta[c]pyrrole-1-carboxamide | 571.3223 | **** |

TABLE 1-continued
| Compound | Structure | IUPAC | LCMS [M + 1] | EC50, uM (Hela) |
|---|---|---|---|---|
| 477 | 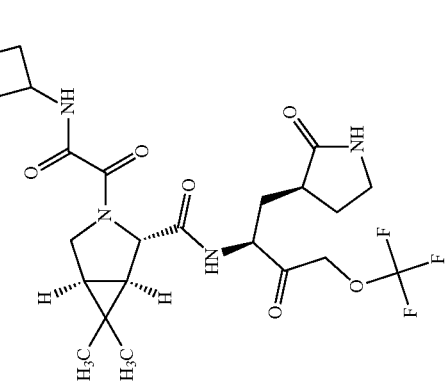 | (1R,2S,5S)-3-(2-((3,3-difluorocyclobutyl)amino)-2-oxoacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 553.0824 | *** |
| 478 | 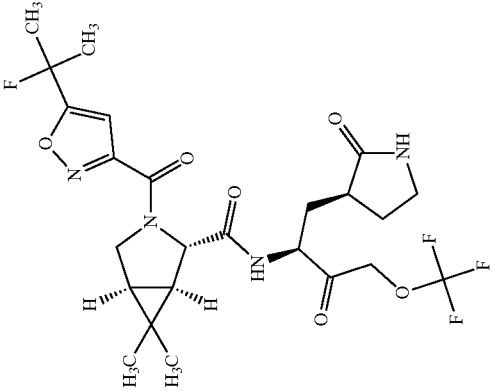 | (1R,2S,5S)-3-(5-(2-fluoropropan-2-yl)isoxazole-3-carbonyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 547.4194 | **** |

TABLE 1-continued

| Compound | Structure | IUPAC | LCMS [M + 1] | EC50, uM (Hela) |
|---|---|---|---|---|
| 482 | 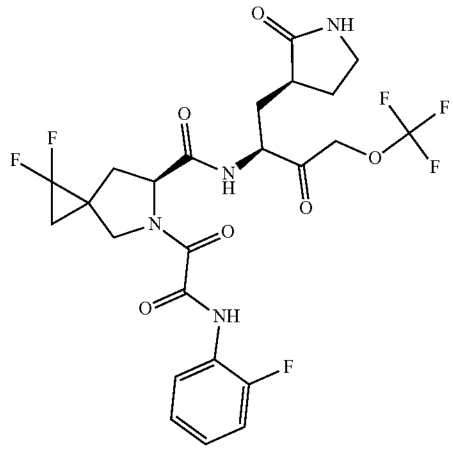 [SMILES: O=C(Nc1ccccc1F)C(=O)N1CC2(C[C@H]1C(=O)N[C@@H](C[C@@H]1CCNC1=O)C(=O)COC(F)(F)F)CC2(F)F] | (6S)-1,1-difluoro-5-(2-((2-fluorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 579.3488 | *** |
| 483 | 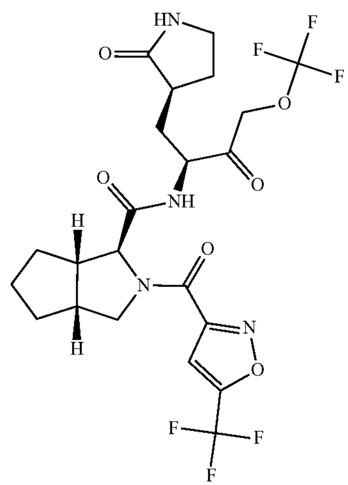 [SMILES: O=C1NCC[C@H]1C[C@H](NC(=O)[C@@H]1[C@H]2CCC[C@H]2CN1C(=O)c1cc(C(F)(F)F)on1)C(=O)COC(F)(F)F] | (1S,3aR,6aS)-N-((S)-3-oxo-1-((S)-2-oxopyrrolidin-3-yl)-4-(trifluoromethoxy)butan-2-yl)-2-(5-(trifluoromethyl)isoxazole-3-carbonyl)octahydrocyclopenta[c]pyrrole-1-carboxamide | 555.363 | *** |

TABLE 1-continued

| Compound | Structure | IUPAC | LCMS [M + 1] | EC50, uM (Hela) |
|---|---|---|---|---|
| 484 | 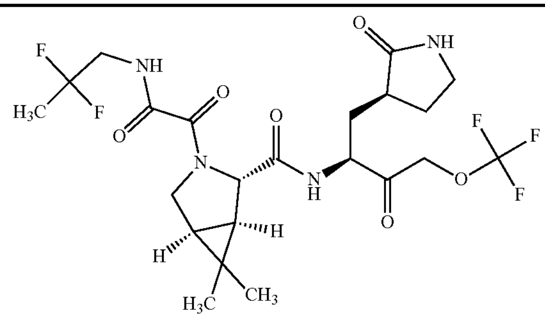 | (1R,2S,5S)-3-(2-((2,2-difluoropropyl)amino)-2-oxoacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 541.0998 | *** |
| 486 | 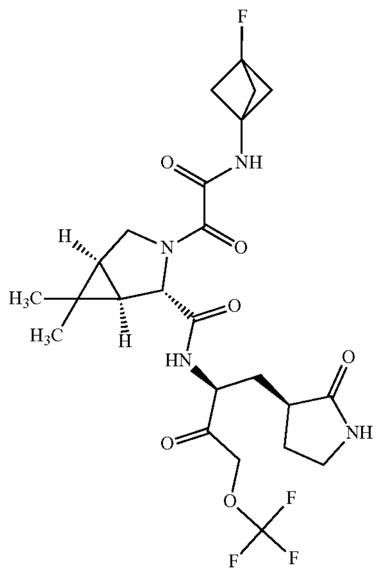 [SMILES: CC1(C)[C@@H]2[C@@H](C(=O)N[C@@H](C[C@@H]3CCNC3=O)C(=O)COC(F)(F)F)N(C(=O)C(=O)NC34CC(F)(C3)C4)C[C@@H]21] | (1R,2S,5S)-3-(2-((3-fluorobicyclo[1.1.1]pentan-1-yl)amino)-2-oxoacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 547.3 | *** |

TABLE 1-continued

| Compound | Structure | IUPAC | LCMS [M + 1] | EC50, uM (Hela) |
|---|---|---|---|---|
| 487 | 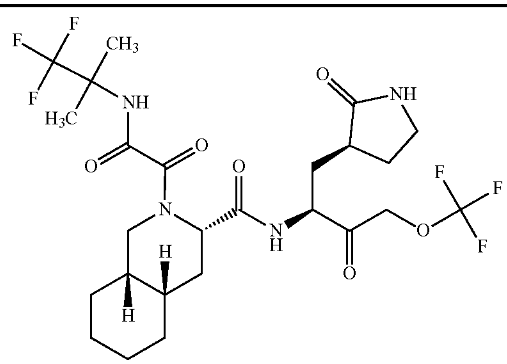 | (3S,4aS,8aS)-N-((S)-3-oxo-1-((S)-2-oxopyrrolidin-3-yl)-4-(trifluoromethoxy)butan-2-yl)-2-(2-oxo-2-(((1,1,1-trifluoro-2-methylpropan-2-yl)amino)acetyl)-decahydroiso-quinoline-3-carboxamide | 602.459 | *** |
| 488 | 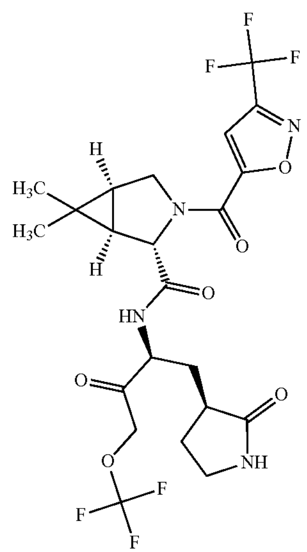 [SMILES: CC1(C)[C@@H]2[C@@H](C(=O)N[C@@H](C[C@@H]3CCNC3=O)C(=O)COC(F)(F)F)N(C(=O)c3cc(C(F)(F)F)no3)C[C@@H]21] | (1R,2S,5S)-6,6-dimethyl-N-((S)-3-oxo-1-((S)-2-oxopyrrolidin-3-yl)-4-(trifluoromethoxy)butan-2-yl)-3-(3-(trifluoromethyl)isoxazole-5-carbonyl)-3-azabicyclo[3.1.0]-hexane-2-carboxamide | 555.3430 | *** |

TABLE 1-continued

| Compound | Structure | IUPAC | LCMS [M + 1] | EC50, uM (Hela) |
|---|---|---|---|---|
| 489 | 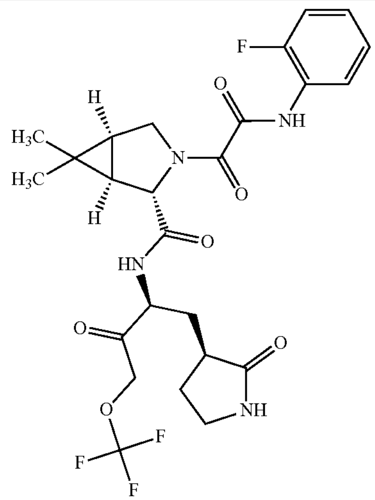 [SMILES: CC1(C)[C@@H]2[C@@H](C(=O)N[C@@H](C[C@@H]3CCNC3=O)C(=O)COC(F)(F)F)N(C(=O)C(=O)Nc3ccccc3F)C[C@@H]21] | (1R,2S,5S)-3-(2-((2-fluorophenyl)amino)-2-oxoacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 557.3965 | **** |
| 490 | 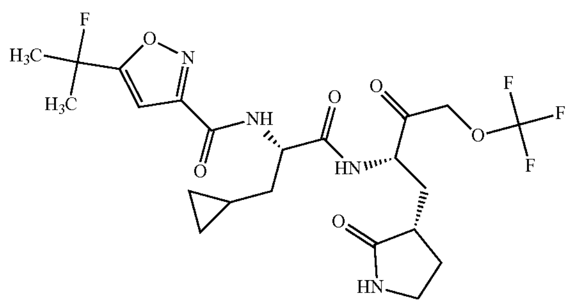 [SMILES: CC(C)(F)c1cc(C(=O)N[C@@H](CC2CC2)C(=O)N[C@@H](C[C@@H]2CCNC2=O)C(=O)COC(F)(F)F)no1] | N-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-5-(2-fluoropropan-2-yl)isoxazole-3-carboxamide | 521.403 | **** |

TABLE 1-continued
| Compound | Structure | IUPAC | LCMS [M + 1] | EC50, uM (Hela) |
|---|---|---|---|---|
| 491 | 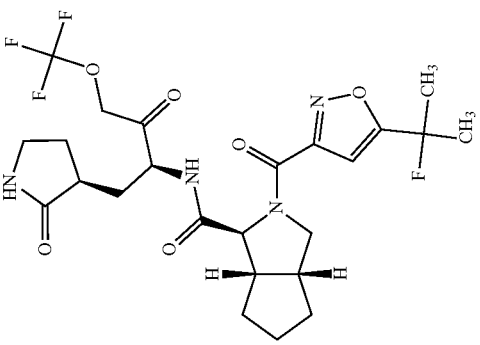 | (1S,3aR,6aS)-2-(5-(2-fluoropropan-2-yl)isoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 547.21 | **** |
| 492 | 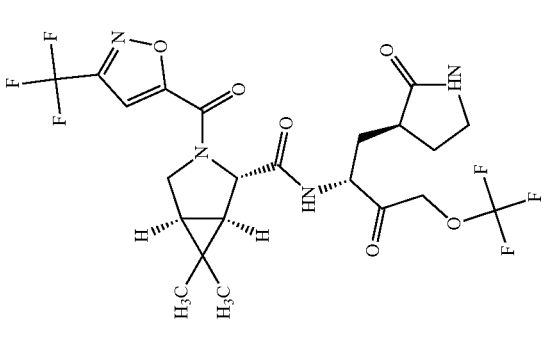 | (1R,2S,5S)-6,6-dimethyl-N-((R)-3-oxo-1-((S)-2-oxopyrrolidin-3-yl)-4-(trifluoromethoxy)butan-2-yl)-3-(3-(trifluoromethyl)isoxazole-5-carbonyl)-3-azabicyclo[3.1.0]hexane-2-carboxamide | 555.16 | *** |

TABLE 1-continued

| Compound | Structure | IUPAC | LCMS [M + 1] | EC50, uM (Hela) |
|---|---|---|---|---|
| 493 | 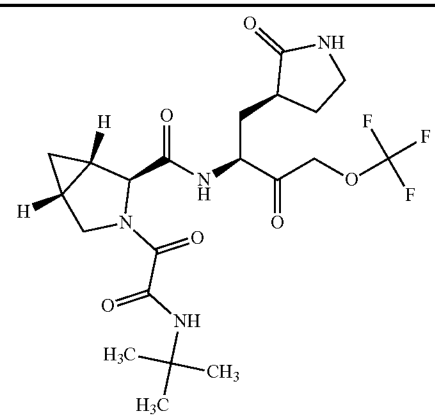 | (1S,2S,5R)-3-(2-(tert-butyl)amino)-2-oxoacetyl)-N-((S)-3-oxo-1-((S)-2-oxopyrrolidin-3-yl)-4-(trifluoromethoxy)butan-2-yl)-3-azabicyclo[3.1.0]hexane-2-carboxamide | 491.4048 | ** |
| 495 | 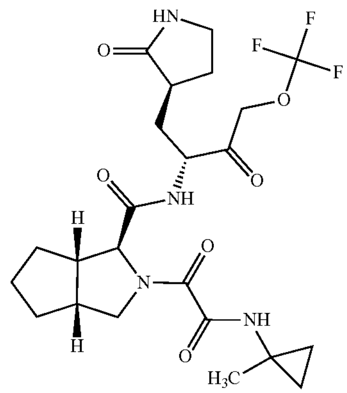 [SMILES: CC1(NC(=O)C(=O)N2C[C@@H]3CCC[C@@H]3[C@H]2C(=O)N[C@H](C[C@@H]2CCNC2=O)C(=O)COC(F)(F)F)CC1] | (1S,3aR,6aS)-2-(2-((1-methylcyclopropyl)amino)-2-oxoacetyl)-N-((R)-3-oxo-1-((S)-2-oxopyrrolidin-3-yl)-4-(trifluoromethoxy)butan-2-yl)octahydrocyclopenta[c]pyrrole-1-carboxamide | 517.4584 | >1 μM |

TABLE 1-continued

| Compound | Structure | IUPAC | LCMS [M + 1] | EC50, uM (Hela) |
|---|---|---|---|---|
| 496 | 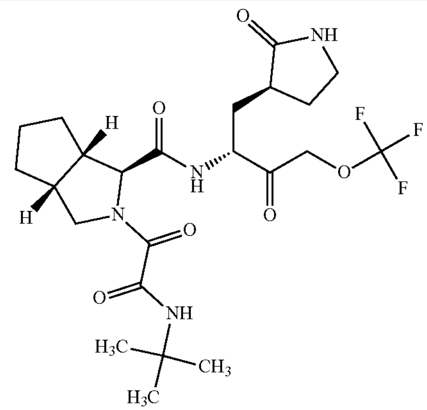 [SMILES: CC(C)(C)NC(=O)C(=O)N1C[C@@H]2CCC[C@@H]2[C@H]1C(=O)N[C@H](C[C@@H]1CCNC1=O)C(=O)COC(F)(F)F] | (1S,3aR,6aS)-2-(2-(tert-butyl)amino)-2-oxoacetyl)-N-((R)-3-oxo-1-((S)-2-oxopyrrolidin-3-yl)-4-(trifluoromethoxy)butan-2-yl)octahydrocyclopenta[c]pyrrole-1-carboxamide | 519.0887 | *** |
| 497 | 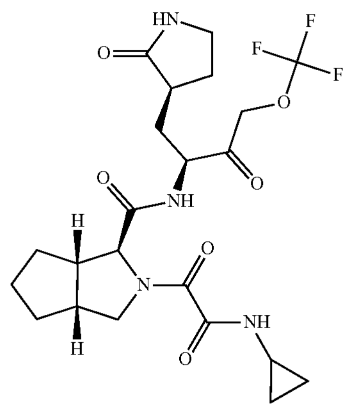 [SMILES: O=C(NC1CC1)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-(cyclopropylamino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 503.0869 | *** |

TABLE 1-continued

| Compound | Structure | IUPAC | LCMS [M + 1] | EC50, uM (Hela) |
|---|---|---|---|---|
| 498 | 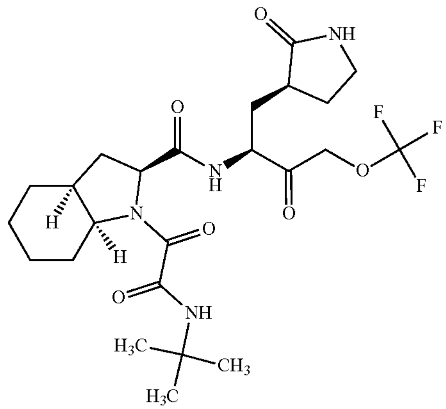 | (2S,3aS,7aS)-1-(2-(tert-butyl)amino)-2-oxoacetyl)-N-((S)-3-oxo-1-((S)-2-oxopyrrolidin-3-yl)-4-(trifluoromethoxy)butan-2-yl)octahydro-1H-indole-2-carboxamide | 533.1353 | *** |
| 499 | 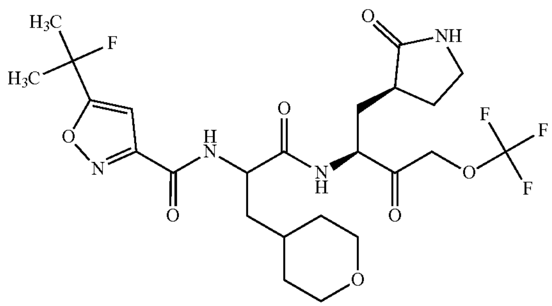 [SMILES: CC(C)(F)c1cc(C(=O)NC(CC2CCOCC2)C(=O)N[C@@H](C[C@@H]2CCNC2=O)C(=O)COC(F)(F)F)no1] | 5-(2-fluoropropan-2-yl)-N-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)isoxazole-3-carboxamide | 565.3962 | *** |

TABLE 1-continued
| Compound | Structure | IUPAC | LCMS [M + 1] | EC50, uM (Hela) |
|---|---|---|---|---|
| 500 | 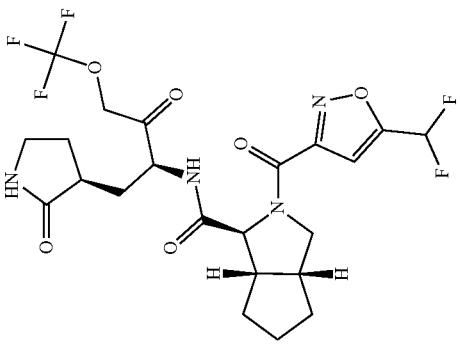 | (1S,3aR,6aS)-2-(5-(difluoromethyl)-isoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 537.3708 | **** |
| 501 | 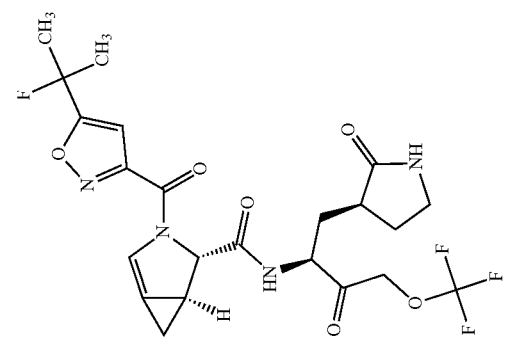 | (1S,2S)-3-(5-(2-fluoropropan-2-yl)isoxazole-3-carbonyl)-N-((S)-3-oxo-1-((S)-2-oxopyrrolidin-3-yl)-4-(trifluoromethoxy)butan-2-yl)-3-azabicyclo[3.1.0]hex-4-ene-2-carboxamide | 517.351 | >1 μM |

TABLE 1-continued

| Compound | Structure | IUPAC | LCMS [M + 1] | EC50, uM (Hela) |
|---|---|---|---|---|
| 502 | 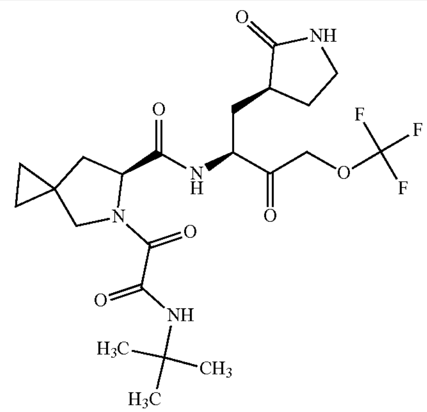 [SMILES: CC(C)(C)NC(=O)C(=O)N1CC2(CC2)C[C@H]1C(=O)N[C@@H](C[C@@H]1CCNC1=O)C(=O)COC(F)(F)F] | (S)-5-(2-(tert-butylamino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 505.4159 | **** |
| 503 | 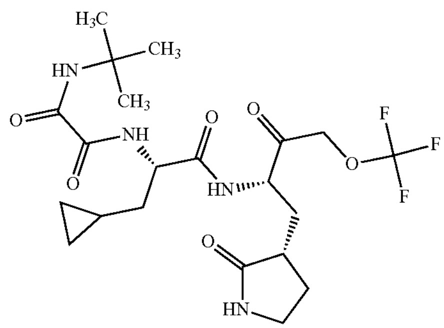 [SMILES: CC(C)(C)NC(=O)C(=O)N[C@@H](CC1CC1)C(=O)N[C@@H](C[C@@H]1CCNC1=O)C(=O)COC(F)(F)F] | N1-(tert-butyl)-N2-((S)-3-cyclopropyl-1-((S)-3-oxo-1-((S)-2-oxopyrrolidin-3-yl)-4-(trifluoromethoxy)butan-2-yl)amino)propan-2-yl)oxalamide | 493.2 | **** |
| 504 | 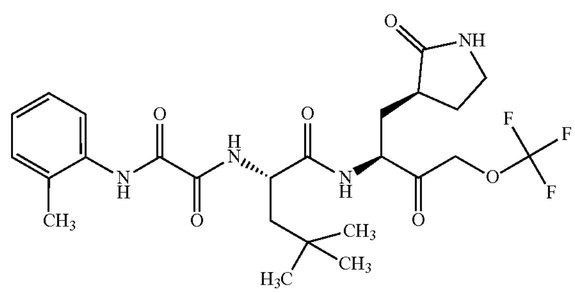 [SMILES: Cc1ccccc1NC(=O)C(=O)N[C@@H](CC(C)(C)C)C(=O)N[C@@H](C[C@@H]1CCNC1=O)C(=O)COC(F)(F)F] | N1-((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-N2-(o-tolyl)oxalamide | 543.4167 | **** |

TABLE 1-continued

| Compound | Structure | IUPAC | LCMS [M + 1] | EC50, uM (Hela) |
|---|---|---|---|---|
| 505 | 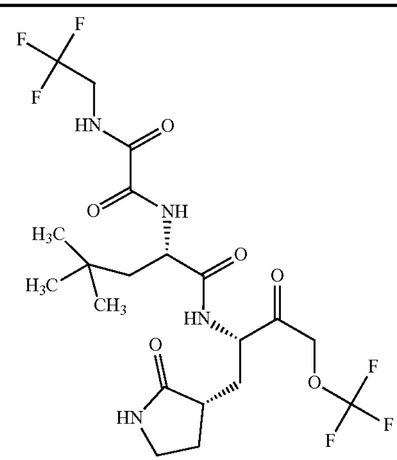 | N1-((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-N2-(2,2,2-trifluoroethyl)-oxalamide | 535.7419 | **** |
| 506 | 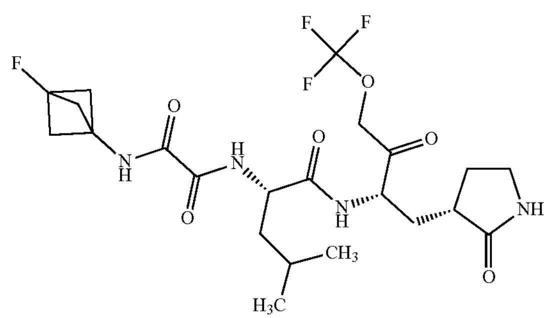 [SMILES: CC(C)C[C@H](NC(=O)C(=O)NC12CC(F)(C1)C2)C(=O)N[C@@H](C[C@@H]1CCNC1=O)C(=O)COC(F)(F)F] | N1-(3-fluorobicyclo[1.1.1]pentan-1-yl)-N2-((S)-4-methyl-1-oxo-1-(((S)-3-oxo-1-((S)-2-oxopyrrolidin-3-yl)-4-(trifluoromethoxy)butan-2-yl)amino)pentan-2-yl)oxalamide | 523.4171 | **** |
| 507 | 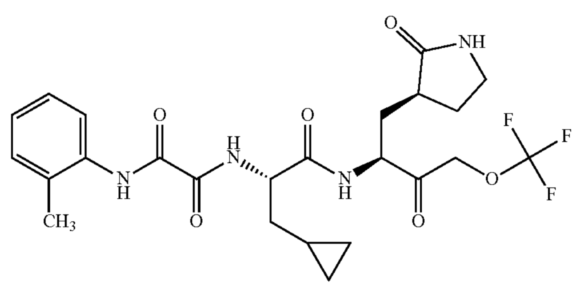 [SMILES: Cc1ccccc1NC(=O)C(=O)N[C@@H](CC1CC1)C(=O)N[C@@H](C[C@@H]1CCNC1=O)C(=O)COC(F)(F)F] | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(o-tolyl)oxalamide | 527.20 | **** |

TABLE 1-continued

| Compound | Structure | IUPAC | LCMS [M + 1] | EC50, uM (Hela) |
|---|---|---|---|---|
| 508 | 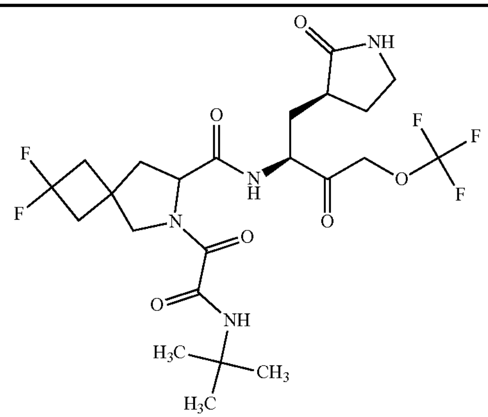 | 6-(2-(tert-butylamino)-2-oxoacetyl)-2,2-difluoro-N-((S)-3-oxo-1-((S)-2-oxopyrrolidin-3-yl)-4-(trifluoromethoxy)butan-2-yl)-6-azaspiro[3.4]octane-7-carboxamide | 555.3 | *** |
| 509 | 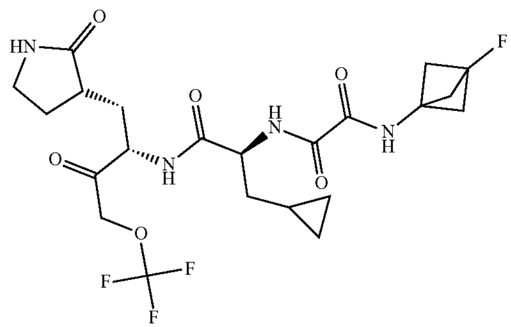 | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(3-fluorobicyclo[1.1.1]-pentan-1-yl)oxalamide | 521.66 | **** |

TABLE 1-continued

| Compound | Structure | IUPAC | LCMS [M + 1] | EC50, uM (Hela) |
|---|---|---|---|---|
| 510 | 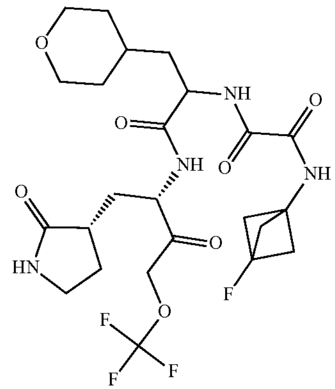 [SMILES: O=C(NC(CC1CCOCC1)C(=O)N[C@@H](C[C@@H]1CCNC1=O)C(=O)COC(F)(F)F)C(=O)NC12CC(F)(C1)C2] | N1-(3-fluorobicyclo-[1.1.1]pentan-1-yl)-N2-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)oxalamide | 565.4 | ** |
| 511 | 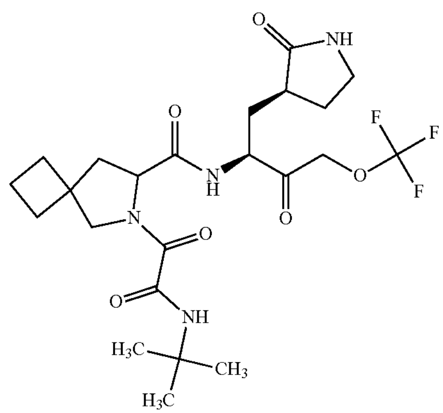 [SMILES: CC(C)(C)NC(=O)C(=O)N1CC2(CCC2)CC1C(=O)N[C@@H](C[C@@H]1CCNC1=O)C(=O)COC(F)(F)F] | 6-(2-(tert-butylamino)-2-oxoacetyl)-N-((S)-3-oxo-1-((S)-2-oxopyrrolidin-3-yl)-4-(trifluoromethoxy)butan-2-yl)-6-azaspiro[3.4]-octane-7-carboxamide | 519.4167 | *** |
| 512 | 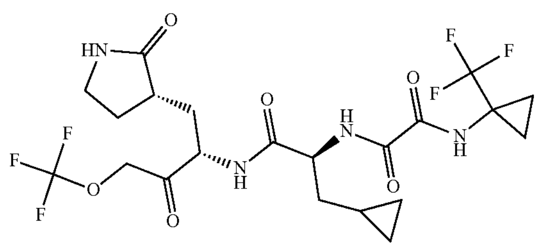 [SMILES: O=C(N[C@@H](CC1CC1)C(=O)N[C@@H](C[C@@H]1CCNC1=O)C(=O)COC(F)(F)F)C(=O)NC1(C(F)(F)F)CC1] | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(1-(trifluoromethyl)-cyclopropyl)-oxalamide | 545.3 | *** |

TABLE 1-continued

| Compound | Structure | IUPAC | LCMS [M + 1] | EC50, uM (Hela) |
|---|---|---|---|---|
| 513 | 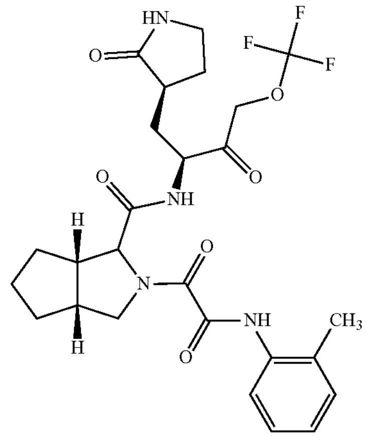 [SMILES: Cc1ccccc1NC(=O)C(=O)N1C[C@@H]2CCC[C@@H]2C1C(=O)N[C@@H](C[C@@H]1CCNC1=O)C(=O)COC(F)(F)F] | (1S,3aR,6aS)-N-((S)-3-oxo-1-((S)-2-oxopyrrolidin-3-yl)-4-(trifluoromethoxy)butan-2-yl)-2-(2-oxo-2-(o-tolylamino)acetyl)-octahydrocyclopenta[c]pyrrole-1-carboxamide | 553.191 | **** |
| 514 | 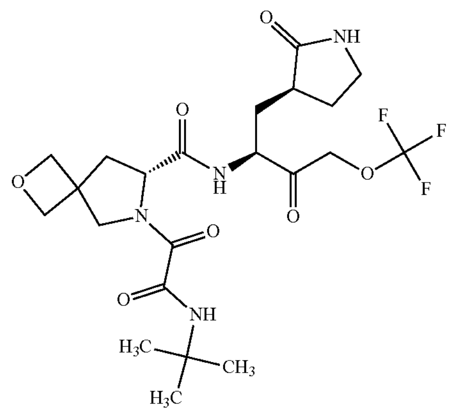 [SMILES: CC(C)(C)NC(=O)C(=O)N1CC2(COC2)C[C@@H]1C(=O)N[C@@H](C[C@@H]1CCNC1=O)C(=O)COC(F)(F)F] | (R)-6-(2-(tert-butylamino)-2-oxoacetyl)-N-((S)-3-oxo-1-((S)-2-oxopyrrolidin-3-yl)-4-(trifluoromethoxy)butan-2-yl)-2-oxa-6-azaspiro[3.4]octane-7-carboxamide | 521.3 | * |

TABLE 1-continued

| Compound | Structure | IUPAC | LCMS [M + 1] | EC50, uM (Hela) |
|---|---|---|---|---|
| 515 | 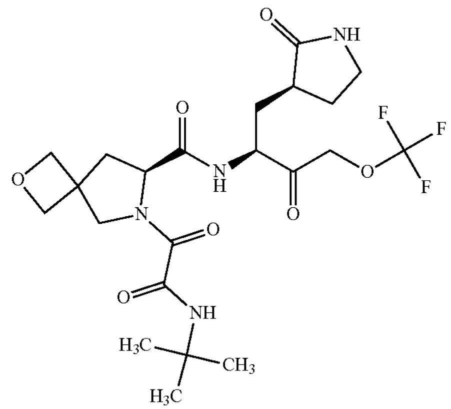 [SMILES: CC(C)(C)NC(=O)C(=O)N1CC2(COC2)C[C@H]1C(=O)N[C@@H](C[C@@H]1CCNC1=O)C(=O)COC(F)(F)F] | (S)-6-(2-(tert-butylamino)-2-oxoacetyl)-N-((S)-3-oxo-1-((S)-2-oxopyrrolidin-3-yl)-4-(trifluoromethoxy)butan-2-yl)-2-oxa-6-azaspiro[3.4]octane-7-carboxamide | 521.4262 | >1 μM |
| 516 | 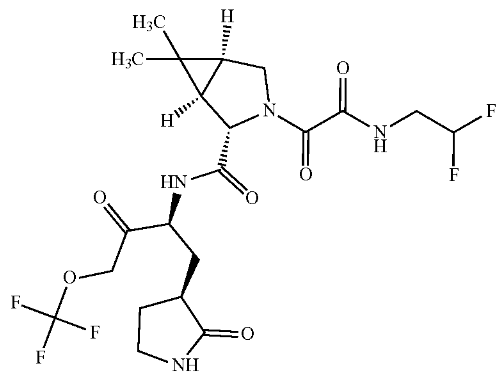 [SMILES: CC1(C)[C@@H]2[C@@H](C(=O)N[C@@H](C[C@@H]3CCNC3=O)C(=O)COC(F)(F)F)N(C(=O)C(=O)NCC(F)F)C[C@@H]21] | (1R,2S,5S)-3-(2-((2,2-difluoroethyl)amino)-2-oxoacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 527.52 | *** |

TABLE 1-continued

| Compound | Structure | IUPAC | LCMS [M + 1] | EC50, uM (Hela) |
|---|---|---|---|---|
| 517 | 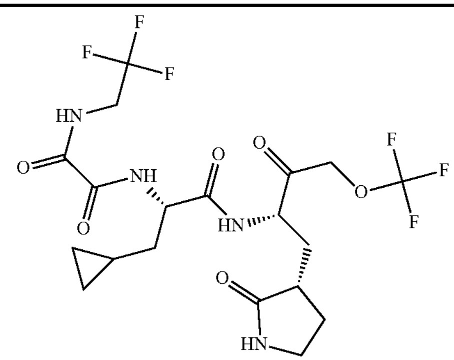 | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(2,2,2-trifluoroethyl)oxalamide | 519.0526 | **** |
| 518 | 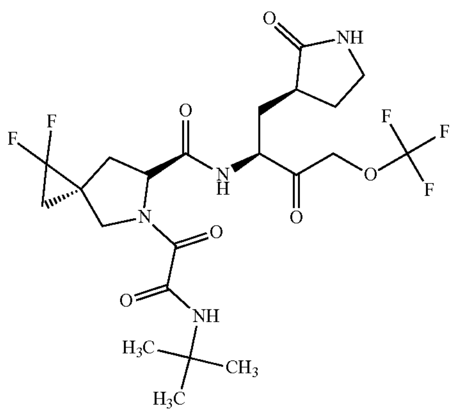 | (3R,6S)-5-(2-(tert-butylamino)-2-oxoacetyl)-1,1-difluoro-N-((S)-3-oxo-1-((S)-2-oxopyrrolidin-3-yl)-4-(trifluoromethoxy)butan-2-yl)-5-azaspiro[2.4]heptane-6-carboxamide | 541.0998 | *** |

TABLE 1-continued

| Compound | Structure | IUPAC | LCMS [M + 1] | EC50, uM (Hela) |
|---|---|---|---|---|
| 519 | 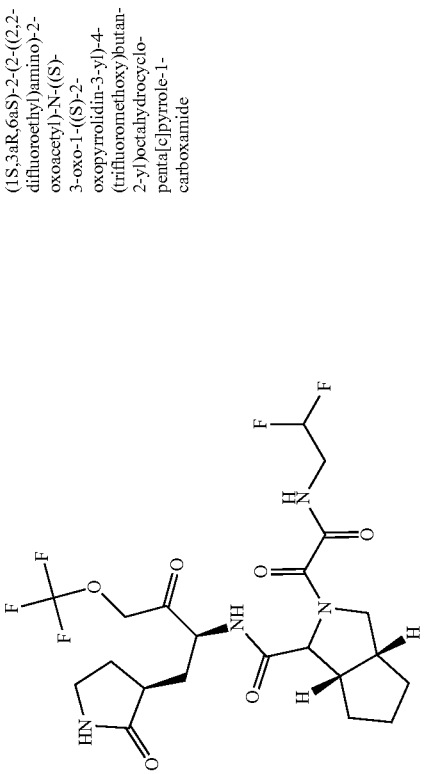 | (1S,3aR,6aS)-2-(2-((2,2-difluoroethyl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 527.1851 | ** |
| 520 | 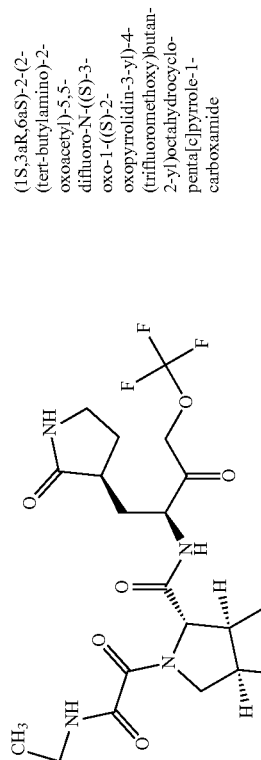 | (1S,3aR,6aS)-2-(2-(tert-butylamino)-2-oxoacetyl)-5,5-difluoro-N-((S)-3-oxo-1-((S)-2-oxopyrrolidin-3-yl)-4-(trifluoromethoxy)butan-2-yl)octahydrocyclopenta[c]pyrrole-1-carboxamide | 555.4406 | *** |
| 521 | 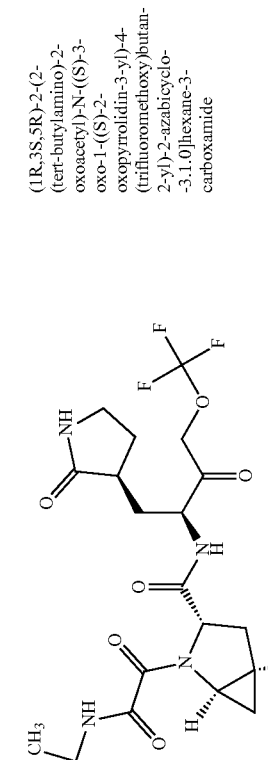 | (1R,3S,5R)-2-(2-(tert-butylamino)-2-oxoacetyl)-N-((S)-3-oxo-1-((S)-2-oxopyrrolidin-3-yl)-4-(trifluoromethoxy)butan-2-yl)-2-azabicyclo-3.1.0]hexane-3-carboxamide | 491.4198 | ** |

TABLE 1-continued

| Compound | Structure | IUPAC | LCMS [M + 1] | EC50, uM (Hela) |
|---|---|---|---|---|
| 522 | 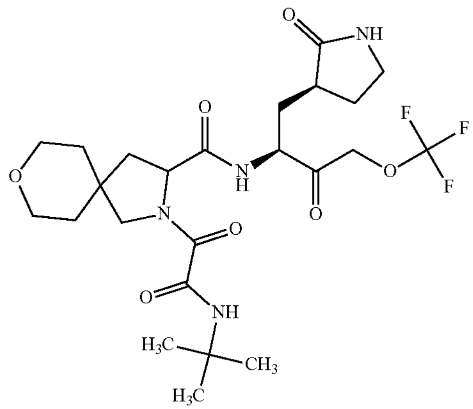 [SMILES: CC(C)(C)NC(=O)C(=O)N1CC2(CCOCC2)CC1C(=O)N[C@@H](C[C@@H]1CCNC1=O)C(=O)COC(F)(F)F] | 2-(2-(tert-butylamino)-2-oxoacetyl)-N-((S)-3-oxo-1-((S)-2-oxopyrrolidin-3-yl)-4-(trifluoromethoxy)butan-2-yl)-8-oxa-2-azaspiro[4.5]decane-3-carboxamide | 549.4558 | * |
| 523 | 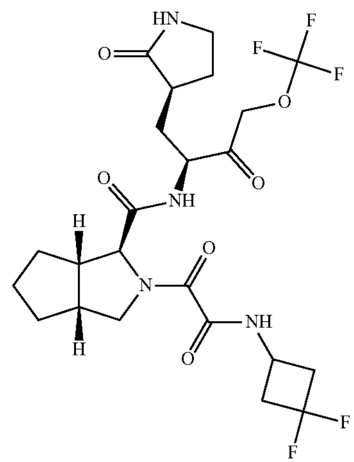 [SMILES: O=C(NC1CC(F)(F)C1)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-((3,3-difluorocyclobutyl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 553.4806 | **** |

TABLE 1-continued

| Compound | Structure | IUPAC | LCMS [M + 1] | EC50, uM (Hela) |
|---|---|---|---|---|
| 524 | 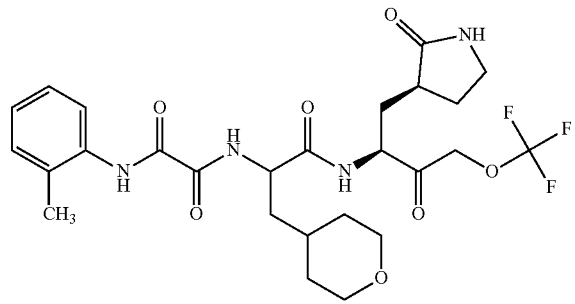 [SMILES: Cc1ccccc1NC(=O)C(=O)NC(CC1CCOCC1)C(=O)N[C@@H](C[C@@H]1CCNC1=O)C(=O)COC(F)(F)F] | N1-(1-oxo-1-(((S)-3-oxo-1-((S)-2-oxopyrrolidin-3-yl)-4-(trifluoromethoxy)butan-2-yl)amino)-3-(tetrahydro-2H-pyran-4-yl)propan-2-yl)-N2-(o-tolyl)oxalamide | 571.4723 | **** |
| 525 | 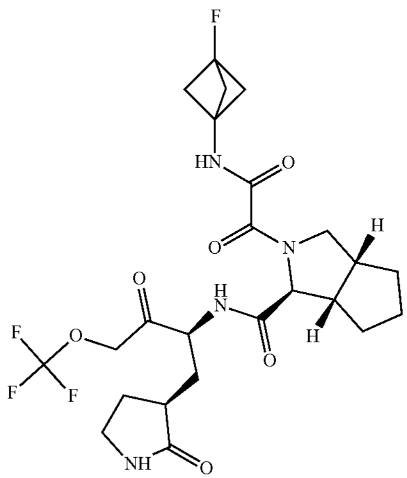 [SMILES: O=C(NC12CC(F)(C1)C2)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-((3-fluorobicyclo[1.1.1]-pentan-1-yl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 547.4573 | **** |

TABLE 1-continued

| Compound | Structure | IUPAC | LCMS [M + 1] | EC50, uM (Hela) |
|---|---|---|---|---|
| 526 | 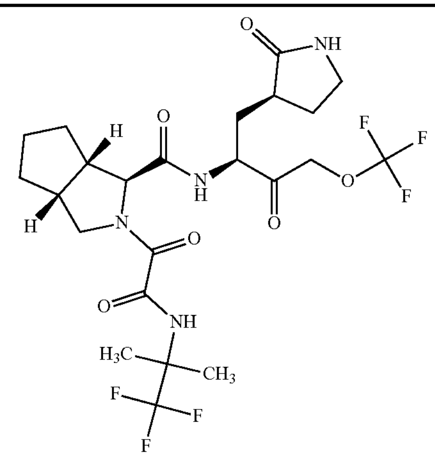 | (1S,3aR,6aS)-N-((S)-3-oxo-1-((S)-2-oxopyrrolidin-3-yl)-4-(trifluoromethoxy)butan-2-yl)-2-(2-oxo-2-(((1,1,1-trifluoro-2-methylpropan-2-yl)amino)acetyl)-octahydrocyclopenta[c]-pyrrole-1-carboxamide | 573.4 | **** |
| 527 | 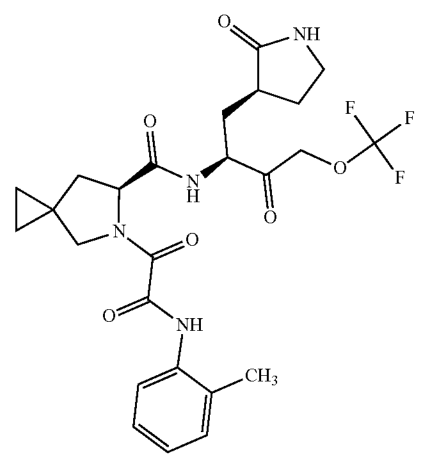 [SMILES: Cc1ccccc1NC(=O)C(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-(2-oxo-2-(o-tolylamino)acetyl)-5-azaspiro[2.4]heptane-6-carboxamide | 539.3 | **** |

TABLE 1-continued

| Compound | Structure | IUPAC | LCMS [M + 1] | EC50, uM (Hela) |
|---|---|---|---|---|
| 528 | 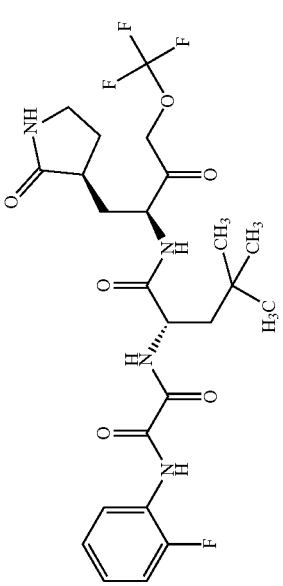 | N1-((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-N2-(2-fluorophenyl)-oxalamide | 547.467 | **** |
| 529 | 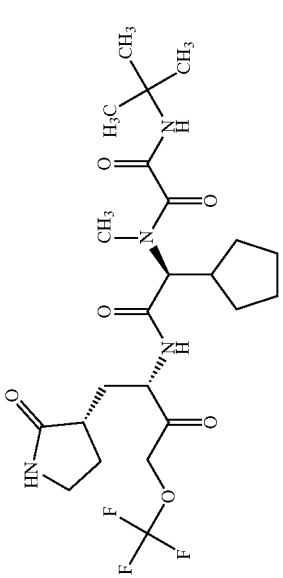 | N1-(tert-butyl)-N2-((S)-1-cyclopentyl-2-oxo-2-(((S)-3-oxo-1-((S)-2-oxopyrrolidin-3-yl)-4-(trifluoromethoxy)butan-2-yl)amino)ethyl)-N2-methyloxalamide | 521.442 | *** |
| 530 | 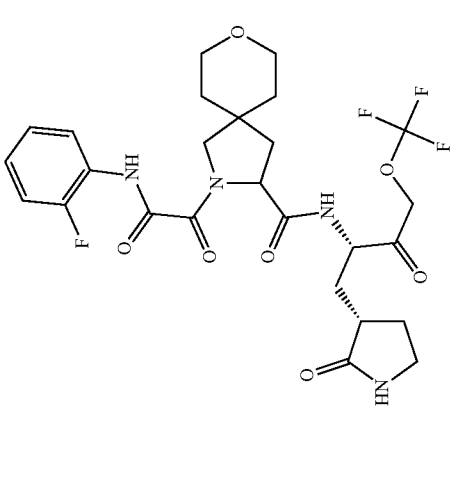 | 2-(2-((2-fluorophenyl)amino)-2-oxoacetyl)-N-((S)-3-oxo-1-((S)-2-oxopyrrolidin-3-yl)-4-(trifluoromethoxy)butan-2-yl)-8-oxa-2-azaspiro[4.5]decane-3-carboxamide | 587.4363 | * |

TABLE 1-continued

| Compound | Structure | IUPAC | LCMS [M + 1] | EC50, uM (Hela) |
|---|---|---|---|---|
| 531 | 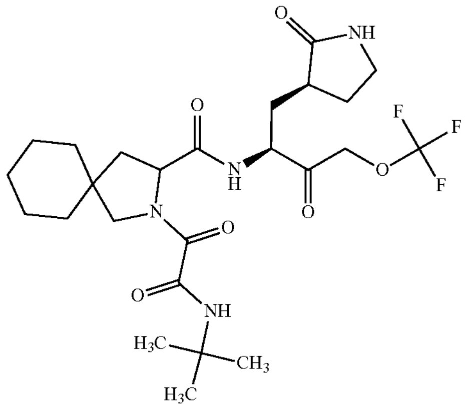 [SMILES: CC(C)(C)NC(=O)C(=O)N1CC2(CCCCC2)CC1C(=O)N[C@@H](C[C@@H]1CCNC1=O)C(=O)COC(F)(F)F] | 2-(2-(tert-butylamino)-2-oxoacetyl)-N-((S)-3-oxo-1-((S)-2-oxopyrrolidin-3-yl)-4-(trifluoromethoxy)butan-2-yl)-2-azaspiro[4.5]decane-3-carboxamide | 547.7971 | **** |
| 532 | 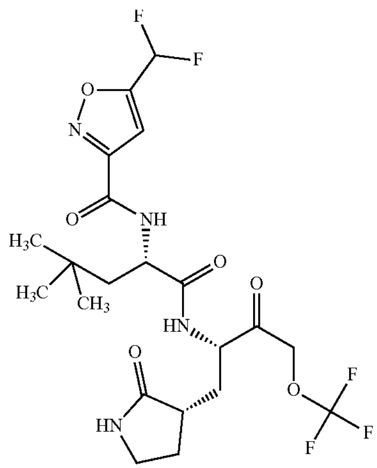 [SMILES: CC(C)(C)C[C@H](NC(=O)c1cc(C(F)F)on1)C(=O)N[C@@H](C[C@@H]1CCNC1=O)C(=O)COC(F)(F)F] | 5-(difluoromethyl)-N-((S)-4,4-dimethyl-1-oxo-1-((S)-3-oxo-1-((S)-2-oxopyrrolidin-3-yl)-4-(trifluoromethoxy)butan-2-yl)amino)pentan-2-yl)isoxazole-3-carboxamide | 527.3995 | **** |

TABLE 1-continued
| Compound | Structure | IUPAC | LCMS [M + 1] | EC50, uM (Hela) |
|---|---|---|---|---|
| 533 | 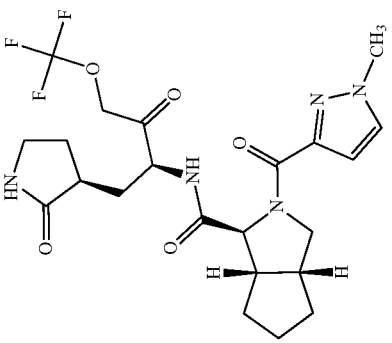 | (1S,3aR,6aS)-2-(1-methyl-1H-pyrazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 500.5 | * |
| 534 | 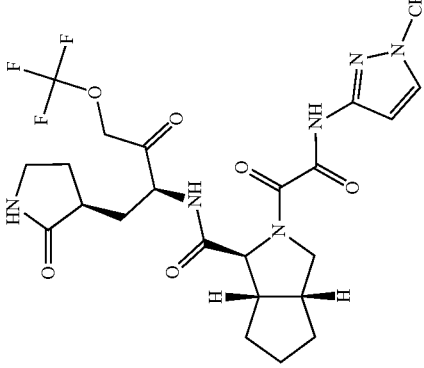 | (1S,3aR,6aS)-2-(2-((1-methyl-1H-pyrazol-3-yl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 543.4 | *** |

TABLE 1-continued

| Compound | Structure | IUPAC | LCMS [M + 1] | EC50, uM (Hela) |
|---|---|---|---|---|
| 535 | 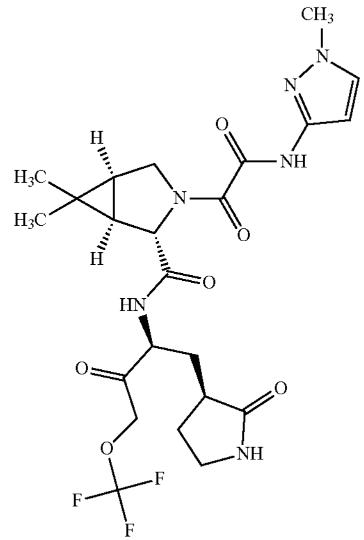 [SMILES: Cn1ccc(NC(=O)C(=O)N2C[C@H]3[C@@H]([C@H]2C(=O)N[C@@H](C[C@@H]2CCNC2=O)C(=O)COC(F)(F)F)C3(C)C)n1] | (1R,2S,5S)-6,6-dimethyl-3-(2-((1-methyl-1H-pyrazol-3-yl)amino)-2-oxoacetyl)-N-((S)-3-oxo-1-((S)-2-oxopyrrolidin-3-yl)-4-(trifluoromethoxy)butan-2-yl)-3-azabicyclo[3.1.0]hexane-2-carboxamide | 543.4 | *** |
| 536 | 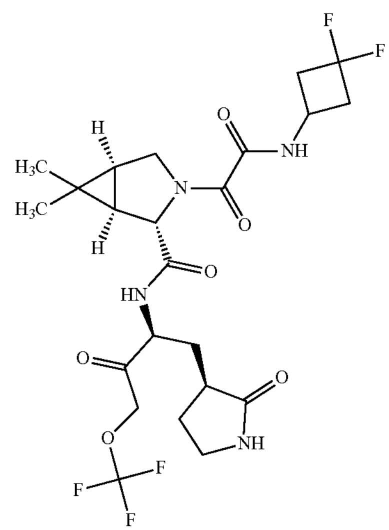 [SMILES: CC1(C)[C@@H]2[C@@H](C(=O)N[C@@H](C[C@@H]3CCNC3=O)C(=O)COC(F)(F)F)N(C(=O)C(=O)NC3CC(F)(F)C3)C[C@@H]21] | (1R,2S,5S)-3-(2-((3,3-difluorocyclobutyl)amino)-2-oxoacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 553.4 | *** |

TABLE 1-continued

| Compound | Structure | IUPAC | LCMS [M + 1] | EC50, uM (Hela) |
|---|---|---|---|---|
| 537 | 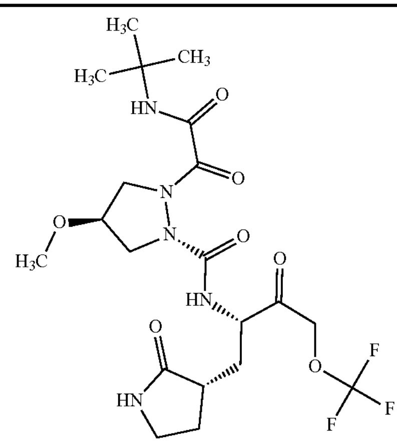 | (2S,4R)-1-(2-(tert-butylamino)-2-oxoacetyl)-4-methoxy-N-((S)-3-oxo-1-((S)-2-oxopyrrolidin-3-yl)-4-(trifluoromethoxy)butan-2-yl)pyrrolidine-2-carboxamide | 509.5 | >1 μM |
| 538 | 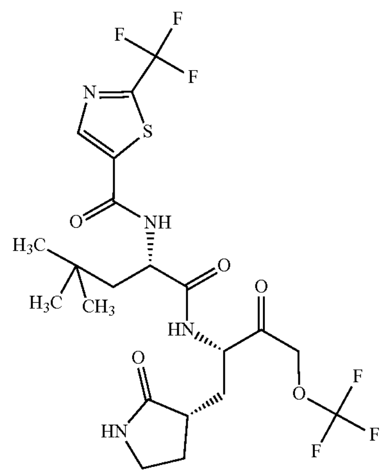 [SMILES: CC(C)(C)C[C@H](NC(=O)c1cnc(C(F)(F)F)s1)C(=O)N[C@@H](C[C@@H]1CCNC1=O)C(=O)COC(F)(F)F] | N-((S)-4,4-dimethyl-1-oxo-1-(((S)-3-oxo-1-((S)-2-oxopyrrolidin-3-yl)-4-(trifluoromethoxy)butan-2-yl)amino)pentan-2-yl)-2-(trifluoromethyl)thiazole-5-carboxamide | 561.4053 | **** |

TABLE 1-continued

| Compound | Structure | IUPAC | LCMS [M + 1] | EC50, uM (Hela) |
|---|---|---|---|---|
| 539 | 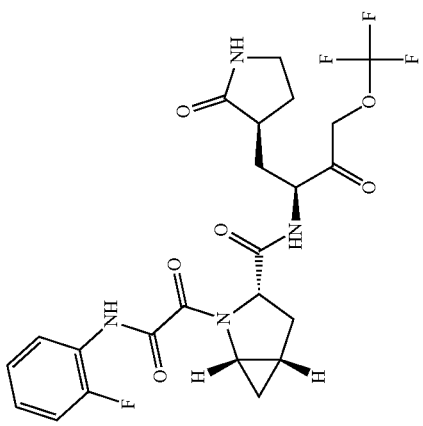 | (1S,3S,5S)-2-(2-((2-fluorophenyl)amino)-2-oxoacetyl)-N-((S)-3-oxo-1-((S)-2-oxopyrrolidin-3-yl)-4-(trifluoromethoxy)butan-2-yl)-2-azabicyclo-[3.1.0]hexane-3-carboxamide | 529.5 | *** |
| 540 | 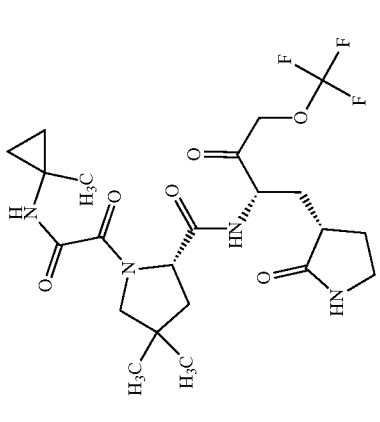 | (S)-4,4-dimethyl-1-(2-((1-methylcyclopropyl)amino)-2-oxoacetyl)-N-((S)-3-oxo-1-((S)-2-oxopyrrolidin-3-yl)-4-(trifluoromethoxy)butan-2-yl)pyrrolidine-2-carboxamide | 505.4 | >1 μM |
| 541 | 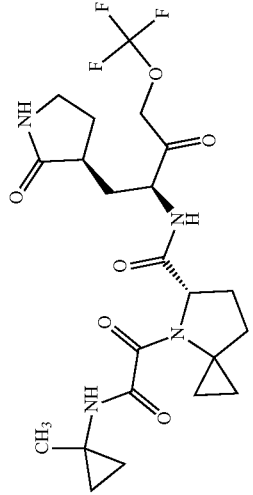 | (S)-4-(2-((1-methylcyclopropyl)amino)-2-oxoacetyl)-N-((S)-3-oxo-1-((S)-2-oxopyrrolidin-3-yl)-4-(trifluoromethoxy)butan-2-yl)-4-azaspiro-[2.4]heptane-5-carboxamide | 503.4 | >1 μM |

TABLE 1-continued

| Compound | Structure | IUPAC | LCMS [M + 1] | EC50, uM (Hela) |
|---|---|---|---|---|
| 542 | 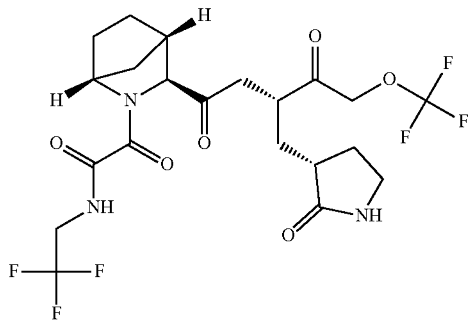 [SMILES: O=C(NCC(F)(F)F)C(=O)N1[C@@H]2CC[C@@H](C2)[C@H]1C(=O)C[C@@H](C[C@@H]1CCNC1=O)C(=O)COC(F)(F)F] | (1R,3S,4S)-N-((S)-3-oxo-1-((S)-2-oxopyrrolidin-3-yl)-4-(trifluoromethoxy)butan-2-yl)-2-(2-oxo-2-((2,2,2-trifluoroethyl)amino)acetyl)-2-azabicyclo[2.2.1]heptane-3-carboxamide | 531.6 | *** |
| 543 | 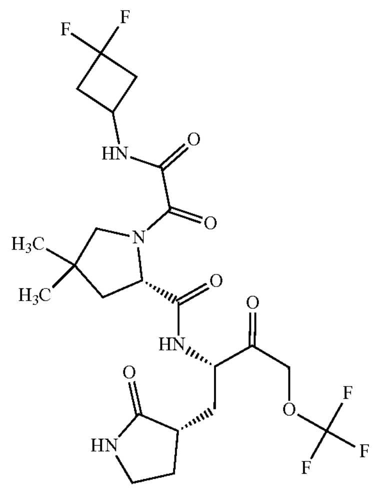 [SMILES: CC1(C)C[C@@H](C(=O)N[C@@H](C[C@@H]2CCNC2=O)C(=O)COC(F)(F)F)N(C(=O)C(=O)NC2CC(F)(F)C2)C1] | (S)-1-(2-((3,3-difluorocyclobutyl)amino)-2-oxoacetyl)-4,4-dimethyl-N-((S)-3-oxo-1-((S)-2-oxopyrrolidin-3-yl)-4-(trifluoromethoxy)butan-2-yl)pyrrolidine-2-carboxamide | 541.4 | * |

TABLE 1-continued
| Compound | Structure | IUPAC | LCMS [M + 1] | EC50, uM (Hela) |
|---|---|---|---|---|
| 544 | 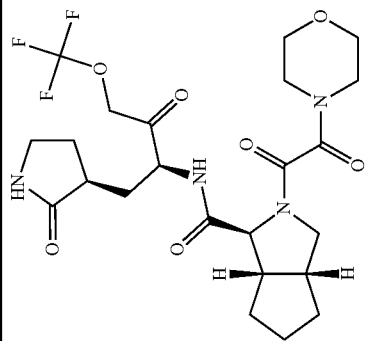 | (1S,3aR,6aS)-2-(2-morpholino-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 533.1716 | * |
| 545 | 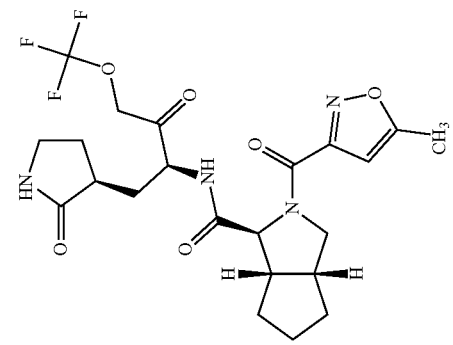 | (1S,3aR,6aS)-2-(5-methylisoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 501.1681 | *** |

TABLE 1-continued

| Compound | Structure | IUPAC | LCMS [M + 1] | EC50, uM (Hela) |
|---|---|---|---|---|
| 546 | 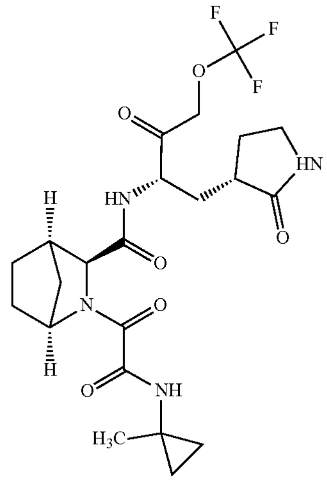 [SMILES: CC1(NC(=O)C(=O)N2[C@H]3CC[C@H](C3)[C@H]2C(=O)N[C@@H](C[C@@H]2CCNC2=O)C(=O)COC(F)(F)F)CC1] | (1S,3S,4R)-2-(2-((1-methylcyclopropyl)amino)-2-oxoacetyl)-N-((S)-3-oxo-1-((S)-2-oxopyrrolidin-3-yl)-4-(trifluoromethoxy)butan-2-yl)-2-azabicyclo[2.2.1]heptane-3-carboxamide | 503.7 | ** |
| 547 | 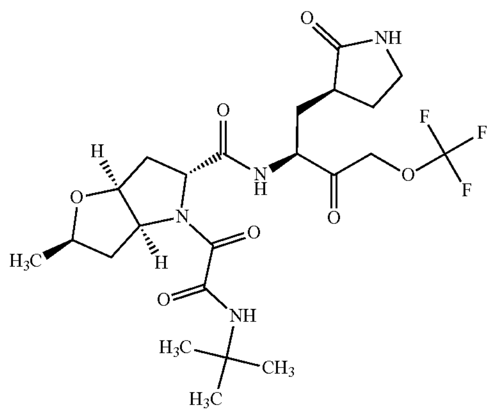 [SMILES: C[C@@H]1C[C@H]2[C@H](C[C@H](C(=O)N[C@@H](C[C@@H]3CCNC3=O)C(=O)COC(F)(F)F)N2C(=O)C(=O)NC(C)(C)C)O1] | (2R,3aS,5R,6aS)-4-(2-(tert-butylamino)-2-oxoacetyl)-2-methyl-N-((S)-3-oxo-1-((S)-2-oxopyrrolidin-3-yl)-4-(trifluoromethoxy)butan-2-yl)hexahydro-2H-furo[3,2-b]pyrrole-5-carboxamide | 535.4 | >1 μM |

TABLE 1-continued
| Compound | Structure | IUPAC | LCMS [M + 1] | EC50, uM (Hela) |
|---|---|---|---|---|
| 548 | 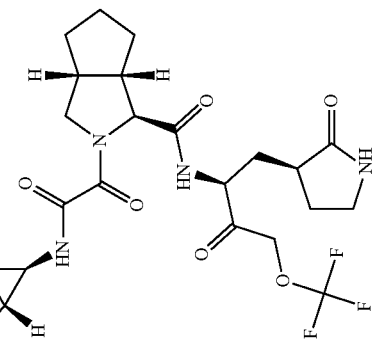 | (1S,3aR,6aS)-2-(2-(((1R,5S,6r)-3-oxabicyclo[3.1.0]-hexan-6-yl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 545.4279 | ** |
| 549 | 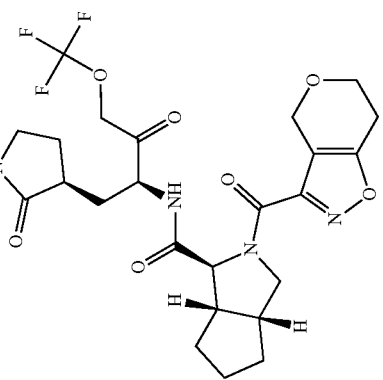 | (1S,3aR,6aS)-2-(6,7-dihydro-4H-pyrano[3,4-d]isoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 543.6339 | *** |

TABLE 1-continued
| Compound | Structure | IUPAC | LCMS [M + 1] | EC50, uM (Hela) |
|---|---|---|---|---|
| 550 | 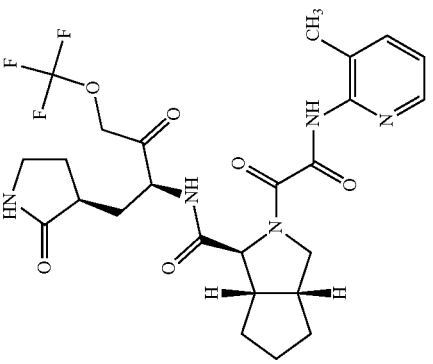 | (1S,3aR,6aS)-2-(2-((3-methylpyridin-2-yl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 554.4156 | >1 μM |
| 551 | 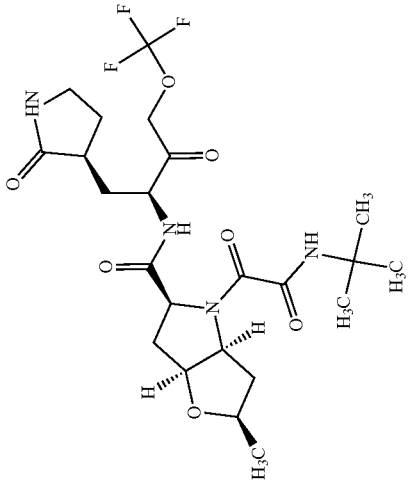 | (2R,3aS,5S,6aS)-4-(2-(tert-butylamino)-2-oxoacetyl)-2-methyl-N-((S)-3-oxo-1-((S)-2-oxopyrrolidin-3-yl)-4-(trifluoromethoxy)butan-2-yl)hexahydro-2H-furo[3,2-b]pyrrole-5-carboxamide | 534.4421 | >1 μM |

TABLE 1-continued

| Compound | Structure | IUPAC | LCMS [M + 1] | EC50, uM (Hela) |
|---|---|---|---|---|
| 552 | 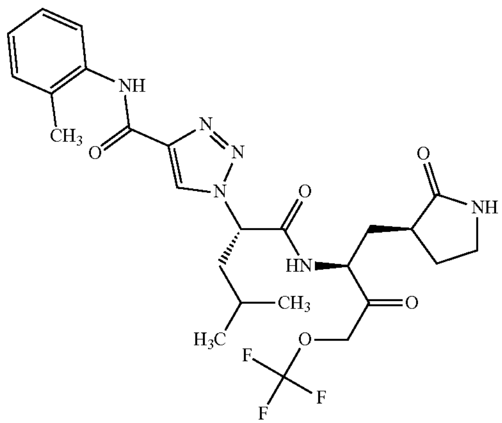 [SMILES: Cc1ccccc1NC(=O)c1cn([C@@H](CC(C)C)C(=O)N[C@@H](C[C@@H]2CCNC2=O)C(=O)COC(F)(F)F)nn1] | 1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N-(o-tolyl)-1H-1,2,3-triazole-4-carboxamide | 553.4917 | **** |
| 553 | 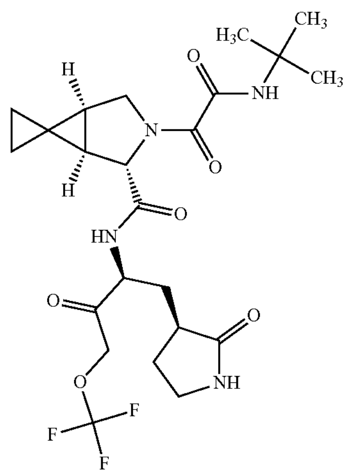 [SMILES: CC(C)(C)NC(=O)C(=O)N1C[C@H]2[C@@H]([C@H]1C(=O)N[C@@H](C[C@@H]1CCNC1=O)C(=O)COC(F)(F)F)C21CC1] | (1R,2S,5S)-3-(2-(tert-butylamino)-2-oxoacetyl)-N-((S)-3-oxo-1-((S)-2-oxopyrrolidin-3-yl)-4-(trifluoromethoxy)butan-2-yl)-3-azaspiro[bicyclo[3.1.0]hexane-6,1'-cyclopropane]-2-carboxamide | 517.22 | *** |

TABLE 1-continued

| Compound | Structure | IUPAC | LCMS [M + 1] | EC50, uM (Hela) |
|---|---|---|---|---|
| 554 | 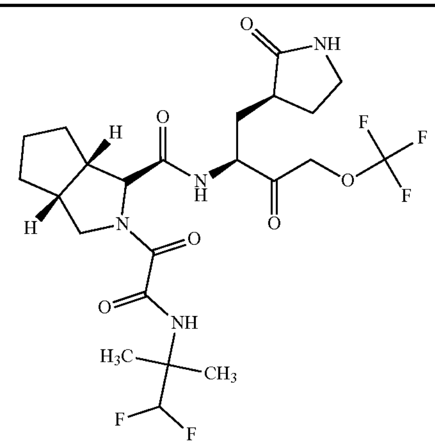 | (1S,3aR,6aS)-2-(2-((1,1-difluoro-2-methylpropan-2-yl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 555.4847 | *** |
| 555 | 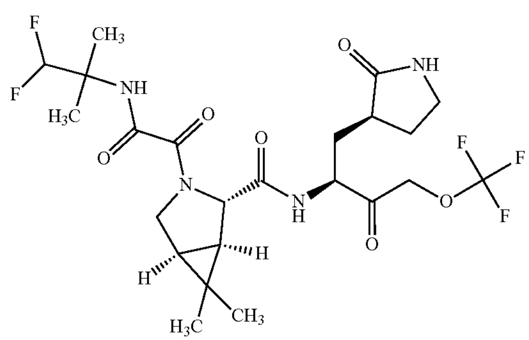 [SMILES: CC(C)(NC(=O)C(=O)N1C[C@H]2[C@@H]([C@H]1C(=O)N[C@@H](C[C@@H]1CCNC1=O)C(=O)COC(F)(F)F)C2(C)C)C(F)F] | (1R,2S,5S)-3-(2-((1,1-difluoro-2-methylpropan-2-yl)amino)-2-oxoacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 555.4819 | **** |

TABLE 1-continued

| Compound | Structure | IUPAC | LCMS [M + 1] | EC50, uM (Hela) |
|---|---|---|---|---|
| 556 | 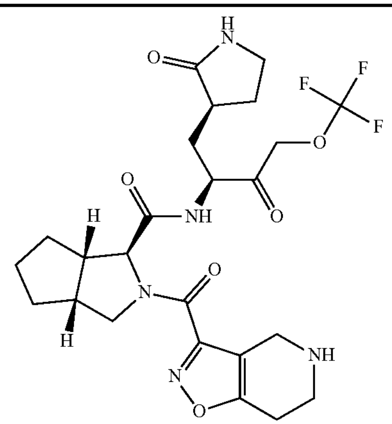 | (1S,3aR,6aS)-N-((S)-3-oxo-1-((S)-2-oxopyrrolidin-3-yl)-4-(trifluoromethoxy)butan-2-yl)-2-(4,5,6,7-tetrahydroisoxazolo[4,5-c]pyridine-3-carbonyl)octahydro-cyclopenta[c]pyrrole-1-carboxamide | 542.4434 | >1 μM |
| 557 | 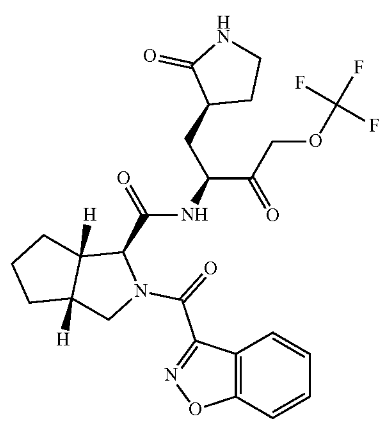 [SMILES: O=C1NCC[C@H]1C[C@H](NC(=O)[C@@H]1[C@H]2CCC[C@H]2CN1C(=O)c1noc2ccccc12)C(=O)COC(F)(F)F] | (1S,3aR,6aS)-2-(benzo[d]isoxazole-3-carbonyl)-N-((S)-3-oxo-1-((S)-2-oxopyrrolidin-3-yl)-4-(trifluoromethoxy)butan-2-yl)octahydro-cyclopenta[c]pyrrole-1-carboxamide | 537.4434 | **** |

TABLE 1-continued

| Compound | Structure | IUPAC | LCMS [M + 1] | EC50, uM (Hela) |
|---|---|---|---|---|
| 558 | 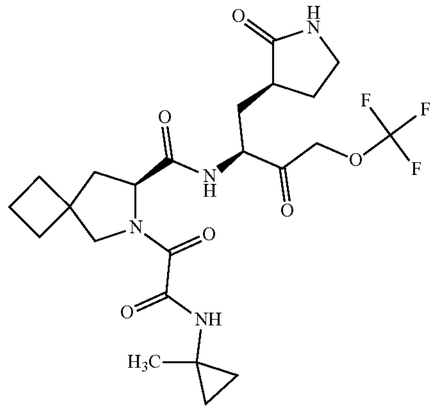 [SMILES: CC1(NC(=O)C(=O)N2CC3(CCC3)C[C@H]2C(=O)N[C@@H](C[C@@H]2CCNC2=O)C(=O)COC(F)(F)F)CC1] | (S)-6-(2-((1-methylcyclopropyl)-amino)-2-oxoacetyl)-N-((S)-3-oxo-1-((S)-2-oxopyrrolidin-3-yl)-4-(trifluoromethoxy)butan-2-yl)-6-azaspiro[3.4]octane-7-carboxamide | 517.4 | >1 μM |
| 559 | 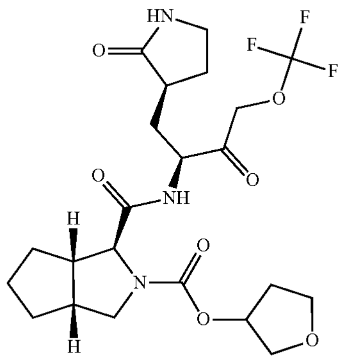 [SMILES: O=C1NCC[C@H]1C[C@H](NC(=O)[C@@H]1[C@H]2CCC[C@H]2CN1C(=O)OC1CCOC1)C(=O)COC(F)(F)F] | tetrahydrofuran-3-yl (1S,3aR,6aS)-1-(((S)-3-oxo-1-((S)-2-oxopyrrolidin-3-yl)-4-(trifluoromethoxy)butan-2-yl)carbamoyl)-hexahydrocyclopenta[c]-pyrrole-2(1H)-carboxylate | 506.421 | *** |

TABLE 1-continued

| Compound | Structure | IUPAC | LCMS [M + 1] | EC50, uM (Hela) |
|---|---|---|---|---|
| 560 | 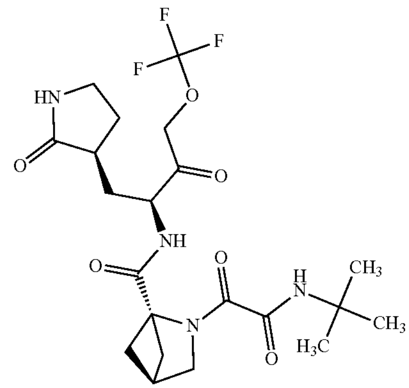 [SMILES: CC(C)(C)NC(=O)C(=O)N1C[C@H]2C[C@]1(C(=O)N[C@@H](C[C@@H]1CCNC1=O)C(=O)COC(F)(F)F)C2] | (1s,4R)-2-(2-(tert-butylamino)-2-oxoacetyl)-N-((S)-3-oxo-1-((S)-2-oxopyrrolidin-3-yl)-4-(trifluoromethoxy)butan-2-yl)-2-azabicyclo[2.1.1]hexane-1-carboxamide | 491.4291 | >1 μM |
| 561 | 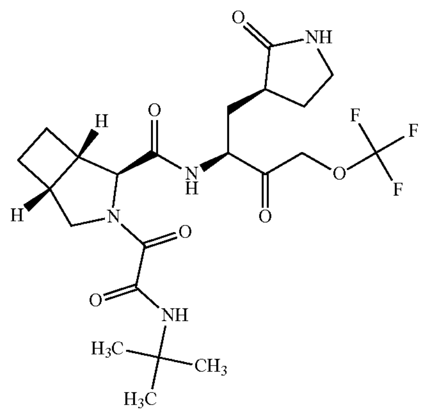 [SMILES: CC(C)(C)NC(=O)C(=O)N1C[C@@H]2CC[C@@H]2[C@H]1C(=O)N[C@@H](C[C@@H]1CCNC1=O)C(=O)COC(F)(F)F] | (1S,2S,5R)-3-(2-(tert-butylamino)-2-oxoacetyl)-N-((S)-3-oxo-1-((S)-2-oxopyrrolidin-3-yl)-4-(trifluoromethoxy)butan-2-yl)-3-azabicyclo[3.2.0]heptane-2-carboxamide | 505.7297 | ** |

TABLE 1-continued

| Compound | Structure | IUPAC | LCMS [M + 1] | EC50, uM (Hela) |
|---|---|---|---|---|
| 562 | 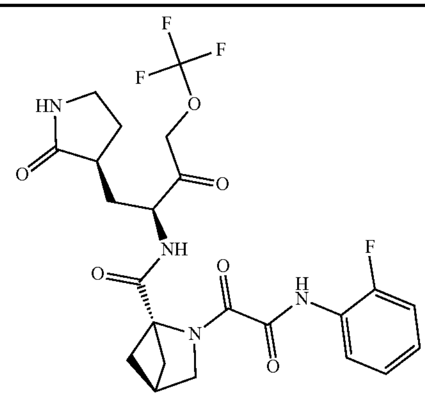 | (1s,4R)-2-(2-((2-fluorophenyl)amino)-2-oxoacetyl)-N-((S)-3-oxo-1-((S)-2-oxopyrrolidin-3-yl)-4-(trifluoromethoxy)butan-2-yl)-2-azabicyclo[2.1.1]hexane-1-carboxamide | 529.4066 | >1 μM |
| 563 | 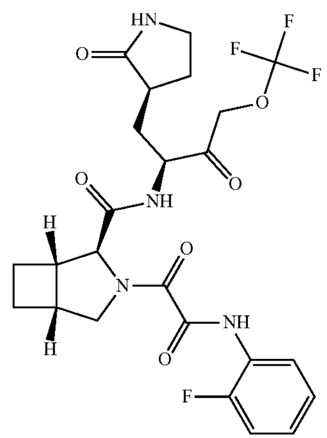 [SMILES: O=C(Nc1ccccc1F)C(=O)N1C[C@@H]2CC[C@@H]2[C@H]1C(=O)N[C@@H](C[C@@H]1CCNC1=O)C(=O)COC(F)(F)F] | (1S,2S, 5R)-3-(2-((2-fluorophenyl)amino)-2-oxoacetyl)-N-((S)-3-oxo-1-((S)-2-oxopyrrolidin-3-yl)-4-(trifluoromethoxy)butan-2-yl)-3-azabicyclo[3.2.0]heptane-2-carboxamide | 543.4167 | *** |

TABLE 1-continued

| Compound | Structure | IUPAC | LCMS [M + 1] | EC50, uM (Hela) |
|---|---|---|---|---|
| 564 | 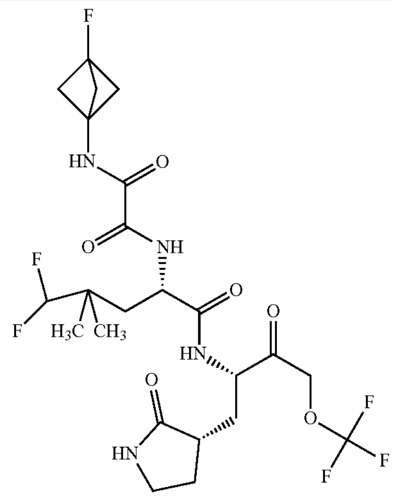 [SMILES: CC(C)(C[C@H](NC(=O)C(=O)NC12CC(F)(C1)C2)C(=O)N[C@@H](C[C@@H]1CCNC1=O)C(=O)COC(F)(F)F)C(F)F] | N1-((S)-5,5-difluoro-4,4-dimethyl-1-oxo-1-(((S)-3-oxo-1-((S)-2-oxopyrrolidin-3-yl)-4-(trifluoromethoxy)butan-2-yl)amino)pentan-2-yl)-N2-(3-fluorobicyclo[1.1.1]-pentan-1-yl)oxalamide | 573.4297 | **** |
| 565 | 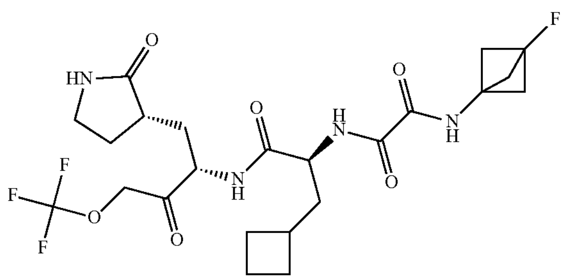 [SMILES: O=C(N[C@@H](CC1CCC1)C(=O)N[C@@H](C[C@@H]1CCNC1=O)C(=O)COC(F)(F)F)C(=O)NC12CC(F)(C1)C2] | N1-((S)-3-cyclobutyl-1-oxo-1-(((S)-3-oxo-1-((S)-2-oxopyrrolidin-3-yl)-4-(trifluoromethoxy)butan-2-yl)amino)propan-2-yl)-N2-(3-fluorobicyclo[1.1.1]-pentan-1-yl)oxalamide | 535.4 | **** |

TABLE 1-continued

| Compound | Structure | IUPAC | LCMS [M + 1] | EC50, uM (Hela) |
|---|---|---|---|---|
| 566 | 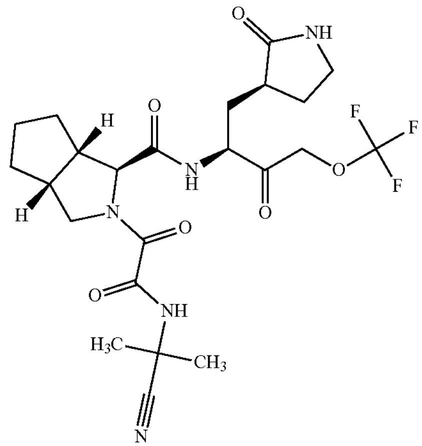 [SMILES: CC(C)(C#N)NC(=O)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-((2-cyanopropan-2-yl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 530.4471 | *** |
| 567 | 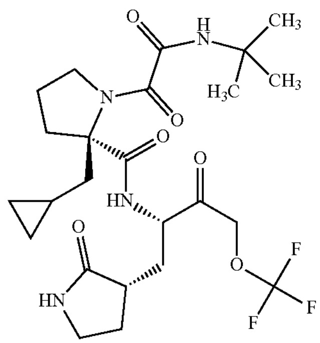 [SMILES: CC(C)(C)NC(=O)C(=O)N1CCC[C@@]1(CC1CC1)C(=O)N[C@@H](C[C@@H]1CCNC1=O)C(=O)COC(F)(F)F] | (R)-1-(2-(tert-butylamino)-2-oxoacetyl)-2-(cyclopropylmethyl)-N-((S)-3-oxo-1-((S)-2-oxopyrrolidin-3-yl)-4-(trifluoromethoxy)butan-2-yl)pyrrolidine-2-carboxamide | 533.4783 | ** |

TABLE 1-continued

| Compound | Structure | IUPAC | LCMS [M + 1] | EC50, uM (Hela) |
|---|---|---|---|---|
| 568 | 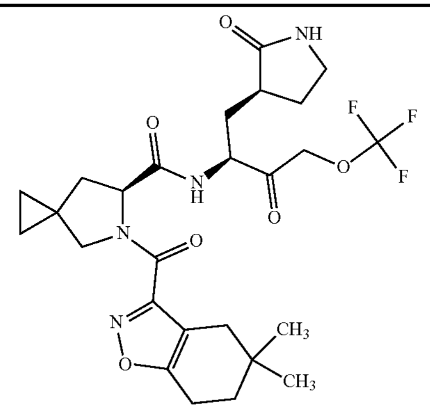 | (S)-5-(5,5-dimethyl-4,5,6,7-tetrahydrobenzo[d]isoxazole-3-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 555.4415 | *** |
| 569 | 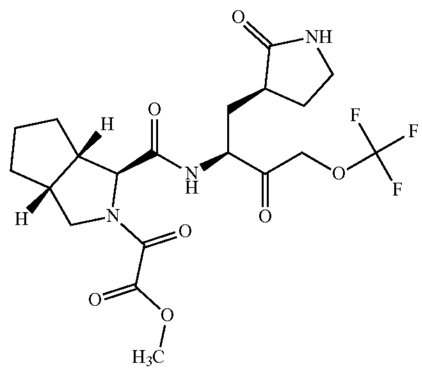 [SMILES: COC(=O)C(=O)N1C[C@@H]2CCC[C@@H]2[C@H]1C(=O)N[C@@H](C[C@@H]1CCNC1=O)C(=O)COC(F)(F)F] | methyl 2-oxo-2-((1S,3aR,6aS)-1-(((S)-3-oxo-1-((S)-2-oxopyrrolidin-3-yl)-4-(trifluoromethoxy)butan-2-yl)carbamoyl)hexahydrocyclopenta[c]pyrrol-2(1H)-yl)acetate | 478.3 | >1 μM |

TABLE 1-continued

| Compound | Structure | IUPAC | LCMS [M + 1] | EC50, uM (Hela) |
|---|---|---|---|---|
| 570 | 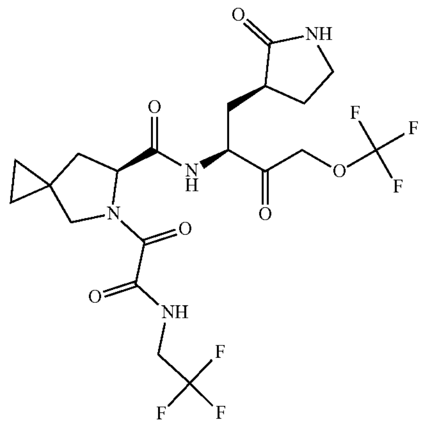 [SMILES: O=C(NCC(F)(F)F)C(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-(2-oxo-2-((2,2,2-trifluoroethyl)amino)acetyl)-5-azaspiro[2.4]heptane-6-carboxamide | 531.3 | *** |
| 571 | 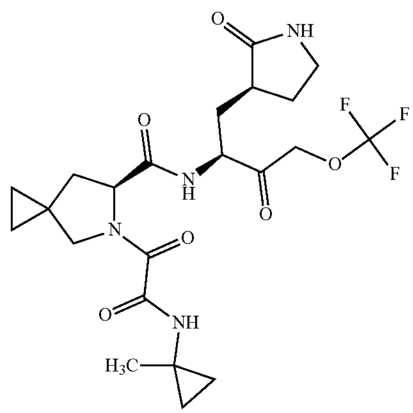 [SMILES: CC1(NC(=O)C(=O)N2CC3(CC3)C[C@H]2C(=O)N[C@@H](C[C@@H]2CCNC2=O)C(=O)COC(F)(F)F)CC1] | (S)-5-(2-((1-methylcyclopropyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 503.6 | *** |

TABLE 1-continued

| Compound | Structure | IUPAC | LCMS [M + 1] | EC50, uM (Hela) |
|---|---|---|---|---|
| 572 | 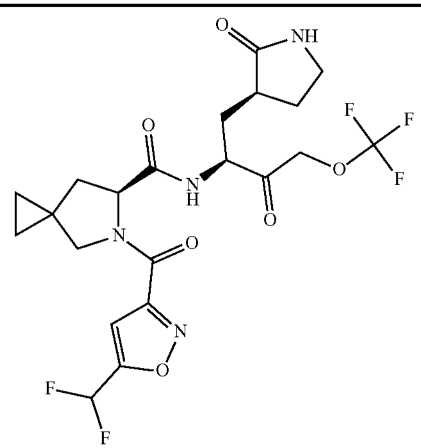 | (S)-5-(5-(difluoromethyl)-isoxazole-3-carbonyl)-N-((S)-3-oxo-1-((S)-2-oxopyrrolidin-3-yl)-4-(trifluoromethoxy)butan-2-yl)-5-azaspiro[2.4]-heptane-6-carboxamide | 523.3 | **** |
| 573 | 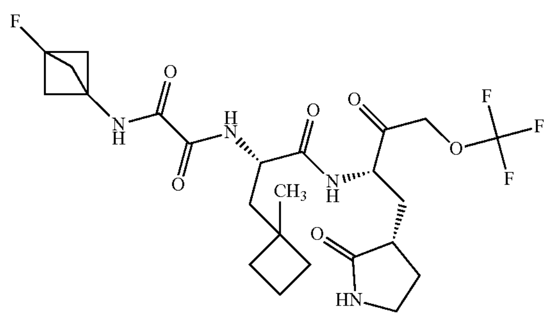 [SMILES: CC1(C[C@H](NC(=O)C(=O)NC23CC(F)(C2)C3)C(=O)N[C@@H](C[C@@H]2CCNC2=O)C(=O)COC(F)(F)F)CCC1] | N1-(3-fluorobicyclo[1.1.1]pentan-1-yl)-N2-((S)-3-(1-methylcyclobutyl)-1-oxo-1-(((S)-3-oxo-1-((S)-2-oxopyrrolidin-3-yl)-4-(trifluoromethoxy)butan-2-yl)amino)propan-2-yl)oxalamide | 549.23 | **** |

TABLE 1-continued

| Compound | Structure | IUPAC | LCMS [M + 1] | EC50, uM (Hela) |
|---|---|---|---|---|
| 574 | 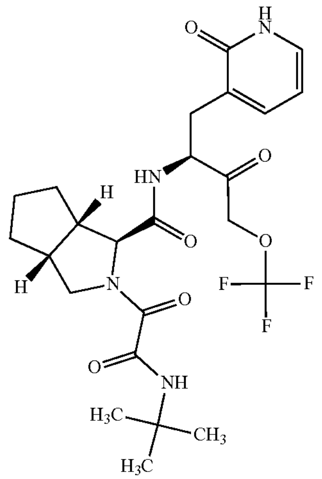 [SMILES: CC(C)(C)NC(=O)C(=O)N1C[C@@H]2CCC[C@@H]2[C@H]1C(=O)N[C@@H](Cc1ccc[nH]c1=O)C(=O)COC(F)(F)F] | (1S,3aR,6aS)-2-(2-(2-(tert-butylamino)-2-oxoacetyl)-N-((S)-3-oxo-1-(2-oxo-1,2-dihydropyridin-3-yl)-4-(trifluoromethoxy)butan-2-yl)octahydrocyclopenta[c]pyrrole-1-carboxamide | 529.4204 | * |
| 575 | 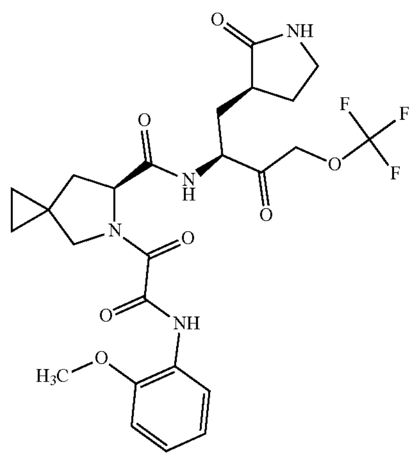 [SMILES: COc1ccccc1NC(=O)C(=O)N1CC2(CC2)C[C@H]1C(=O)N[C@@H](C[C@@H]1CCNC1=O)C(=O)COC(F)(F)F] | (S)-5-(2-((2-methoxyphenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 555.2 | * |

TABLE 1-continued
| Compound | Structure | IUPAC | LCMS [M + 1] | EC50, uM (Hela) |
|---|---|---|---|---|
| 576 | 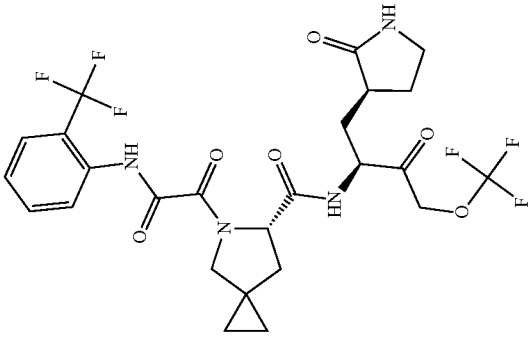 | (S)-N-((S)-3-oxo-1-((S)-2-oxopyrrolidin-3-yl)-4-(trifluoromethoxy)butan-2-yl)-5-(2-oxo-2-((2-(trifluoromethyl)phenyl)amino)acetyl)-5-azaspiro[2.4]-heptane-6-carboxamide | 593.18 | **** |
| 577 | 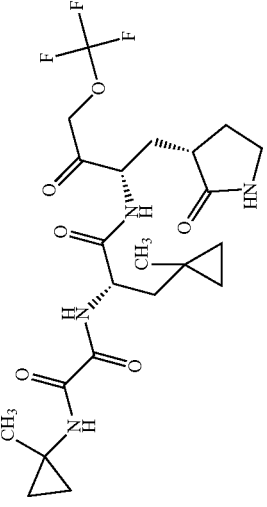 | N1-(1-methylcyclopropyl)-N2-(3-(1-methylcyclopropyl)-1-oxo-1-((S)-3-oxo-1-((S)-2-oxopyrrolidin-3-yl)-4-(trifluoromethoxy)butan-2-yl)amino)propan-2-yl)oxalamide | 505.3 | **** |

TABLE 1-continued

| Compound | Structure | IUPAC | LCMS [M + 1] | EC50, uM (Hela) |
|---|---|---|---|---|
| 578 | 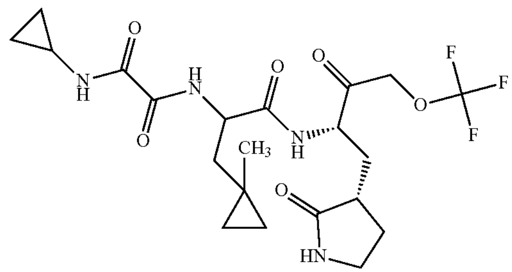 [SMILES: CC1(CC(NC(=O)C(=O)NC2CC2)C(=O)N[C@@H](C[C@@H]2CCNC2=O)C(=O)COC(F)(F)F)CC1] | N1-cyclopropyl-N2-(3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)oxalamide | 491.3 | **** |
| 579 | 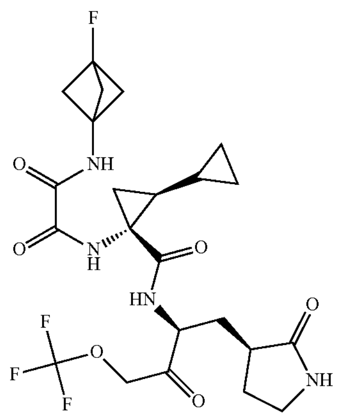 [SMILES: O=C(NC12CC(F)(C1)C2)C(=O)N[C@]1(C(=O)N[C@@H](C[C@@H]2CCNC2=O)C(=O)COC(F)(F)F)C[C@H]1C1CC1] | N1-(3-fluorobicyclo-[1.1.1]pentan-1-yl)-N2-((1S,2R)-2-(((S)-3-oxo-1-((S)-2-oxopyrrolidin-3-yl)-4-(trifluoromethoxy)butan-2-yl)carbamoyl)-[1,1'-bi(cyclopropan)]-2-yl)oxalamide | 533.3894 | >1 μM |
| 580 | 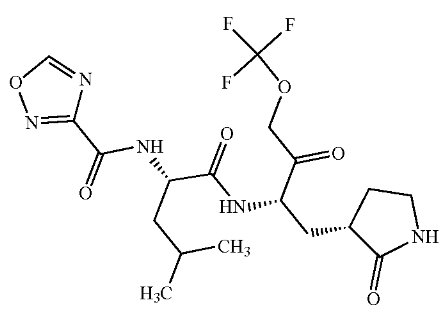 [SMILES: CC(C)C[C@H](NC(=O)c1ncon1)C(=O)N[C@@H](C[C@@H]1CCNC1=O)C(=O)COC(F)(F)F] | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-1,2,4-oxadiazole-3-carboxamide | 464.3551 | ** |

TABLE 1-continued

| Compound | Structure | IUPAC | LCMS [M + 1] | EC50, uM (Hela) |
|---|---|---|---|---|
| 581 | 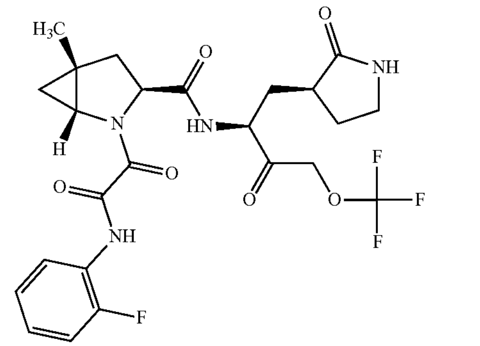 [SMILES: C[C@@]12C[C@@H](C(=O)N[C@@H](C[C@@H]3CCNC3=O)C(=O)COC(F)(F)F)N(C(=O)C(=O)Nc3ccccc3F)[C@@H]1C2] | (1R, 3S, 5R)-2-(2-((2-fluorophenyl)amino)-2-oxoacetyl)-5-methyl-N-((S)-3-oxo-1-((S)-2-oxopyrrolidin-3-yl)-4-(trifluoromethoxy)butan-2-yl)-2-azabicyclo[3.1.0]hexane-3-carboxamide | 543.3 | >1 μM |
| 582 | 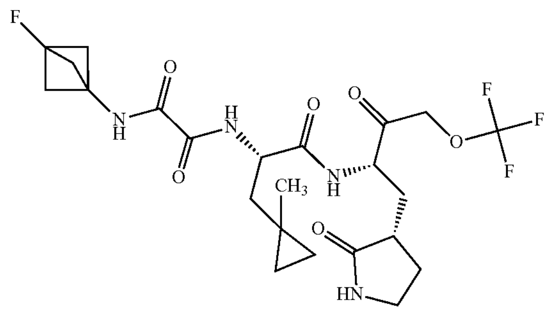 [SMILES: CC1(C[C@H](NC(=O)C(=O)NC23CC(F)(C2)C3)C(=O)N[C@@H](C[C@@H]2CCNC2=O)C(=O)COC(F)(F)F)CC1] | N1-(3-fluorobicyclo[1.1.1]pentan-1-yl)-N2-((S)-3-(1-methylcyclopropyl)-1-oxo-1-(((S)-3-oxo-1-((S)-2-oxopyrrolidin-3-yl)-4-(trifluoromethoxy)butan-2-yl)amino)propan-2-yl)oxalamide | 535.4 | **** |

TABLE 1-continued

| Compound | Structure | IUPAC | LCMS [M + 1] | EC50, uM (Hela) |
|---|---|---|---|---|
| 583 | 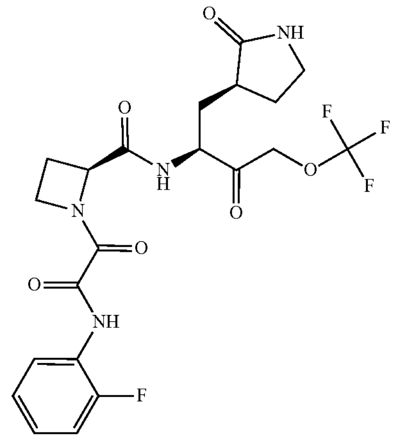 [SMILES: O=C(Nc1ccccc1F)C(=O)N1CC[C@H]1C(=O)N[C@@H](C[C@@H]1CCNC1=O)C(=O)COC(F)(F)F] | (S)-1-(2-((2-fluorophenyl)amino)-2-oxoacetyl)-N-((S)-3-oxo-1-((S)-2-oxopyrrolidin-3-yl)-4-(trifluoromethoxy)butan-2-yl)azetidine-2-carboxamide | 503.3765 | *** |
| 584 | 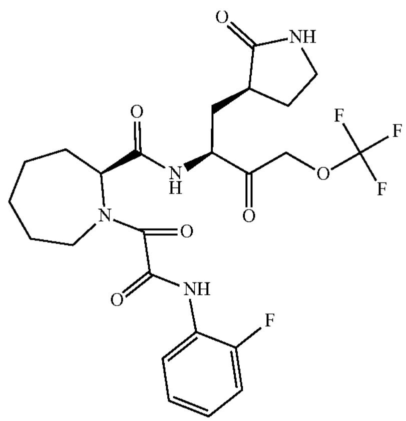 [SMILES: O=C(Nc1ccccc1F)C(=O)N1CCCCC[C@H]1C(=O)N[C@@H](C[C@@H]1CCNC1=O)C(=O)COC(F)(F)F] | (S)-1-(2-((2-fluorophenyl)amino)-2-oxoacetyl)-N-((S)-3-oxo-1-((S)-2-oxopyrrolidin-3-yl)-4-(trifluoromethoxy)butan-2-yl)azepane-2-carboxamide | 545.444 | **** |

TABLE 1-continued

| Compound | Structure | IUPAC | LCMS [M + 1] | EC50, uM (Hela) |
|---|---|---|---|---|
| 585 | 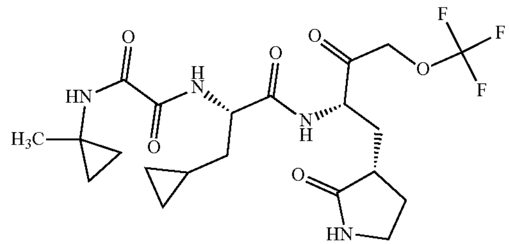 [SMILES: CC1(NC(=O)C(=O)N[C@@H](CC2CC2)C(=O)N[C@@H](C[C@@H]2CCNC2=O)C(=O)COC(F)(F)F)CC1] | N1-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)-N2-(1-methylcyclopropyl)oxalamide | 491.2 | **** |
| 586 | 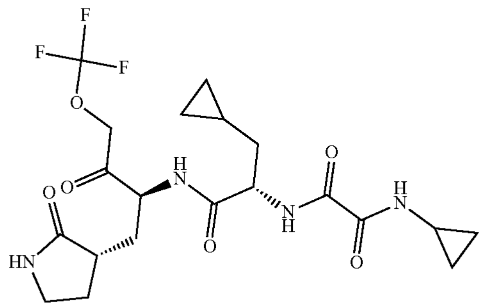 [SMILES: O=C(NC1CC1)C(=O)N[C@@H](CC1CC1)C(=O)N[C@@H](C[C@@H]1CCNC1=O)C(=O)COC(F)(F)F] | N1-cyclopropyl-N2-((S)-3-cyclopropyl-1-oxo-1-(((S)-3-oxo-1-((S)-2-oxopyrrolidin-3-yl)-4-(trifluoromethoxy)butan-2-yl)amino)propan-2-yl)oxalamide | 477.2 | **** |
| 587 | 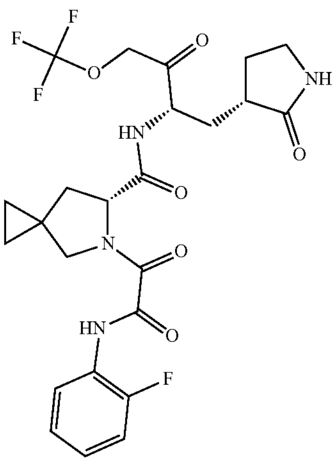 [SMILES: O=C(Nc1ccccc1F)C(=O)N1CC2(CC2)C[C@@H]1C(=O)N[C@@H](C[C@@H]1CCNC1=O)C(=O)COC(F)(F)F] | (R)-5-(2-(2-fluorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]-heptane-6-carboxamide | 543.4 | * |

TABLE 1-continued

| Compound | Structure | IUPAC | LCMS [M + 1] | EC50, uM (Hela) |
|---|---|---|---|---|
| 588 | 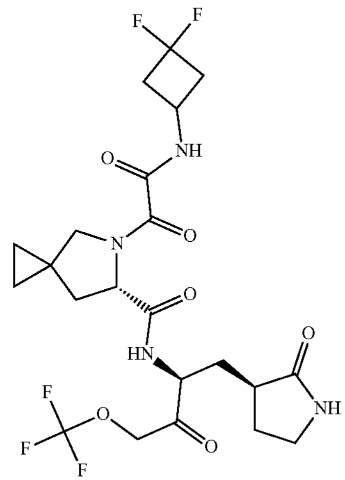 [SMILES: O=C(NC1CC(F)(F)C1)C(=O)N1CC2(CC2)C[C@H]1C(=O)N[C@@H](C[C@@H]1CCNC1=O)C(=O)COC(F)(F)F] | (S)-5-(2-((3,3-difluorocyclobutyl)-amino)-2-oxoacetyl)-N-((S)-3-oxo-1-((S)-2-oxopyrrolidin-3-yl)-4-(trifluoromethoxy)butan-2-yl)-5-azaspiro[2.4]-heptane-6-carboxamide | 539.18 | ** |
| 589 | 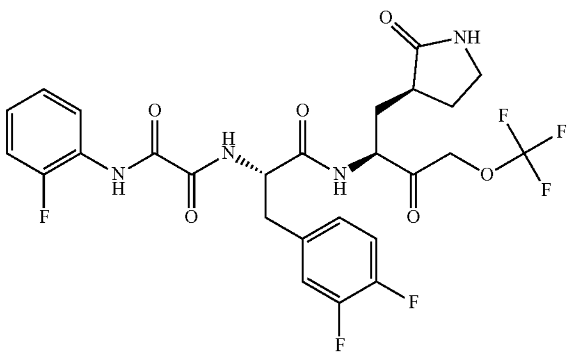 [SMILES: O=C(Nc1ccccc1F)C(=O)N[C@@H](Cc1ccc(F)c(F)c1)C(=O)N[C@@H](C[C@@H]1CCNC1=O)C(=O)COC(F)(F)F] | N1-((S)-3-(3,4-difluorophenyl)-1-oxo-1-((S)-3-oxo-1-((S)-2-oxopyrrolidin-3-yl)-4-(trifluoromethoxy)butan-2-yl)amino)propan-2-yl)-N2-(2-fluorophenyl)oxalamide | 604.5 | *** |

TABLE 1-continued

| Compound | Structure | IUPAC | LCMS [M + 1] | EC50, uM (Hela) |
|---|---|---|---|---|
| 590 | 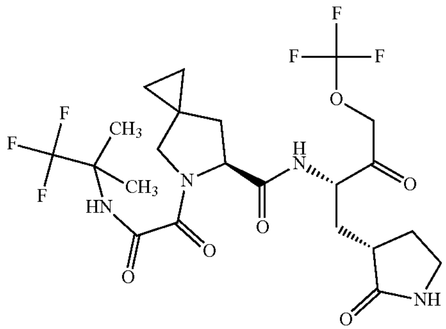 [SMILES: CC(C)(NC(=O)C(=O)N1CC2(CC2)C[C@H]1C(=O)N[C@@H](C[C@@H]1CCNC1=O)C(=O)COC(F)(F)F)C(F)(F)F] | (S)-N-((S)-3-oxo-1-((S)-2-oxopyrrolidin-3-yl)-4-(trifluoromethoxy)butan-2-yl)-5-(2-oxo-2-(((1,1,1-trifluoro-2-methylpropan-2-yl)amino)acetyl)-5-azaspiro[2.4]heptane-6-carboxamide | 559.19 | *** |
| 591 | 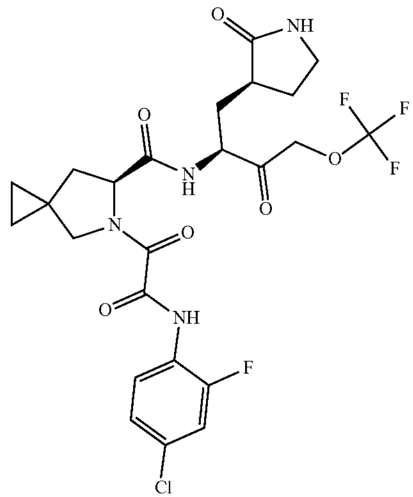 [SMILES: O=C(Nc1ccc(Cl)cc1F)C(=O)N1CC2(CC2)C[C@H]1C(=O)N[C@@H](C[C@@H]1CCNC1=O)C(=O)COC(F)(F)F] | (S)-5-(2-(4-chloro-2-fluorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]-heptane-6-carboxamide | 577.2 | **** |

TABLE 1-continued

| Compound | Structure | IUPAC | LCMS [M + 1] | EC50, uM (Hela) |
|---|---|---|---|---|
| 592 | 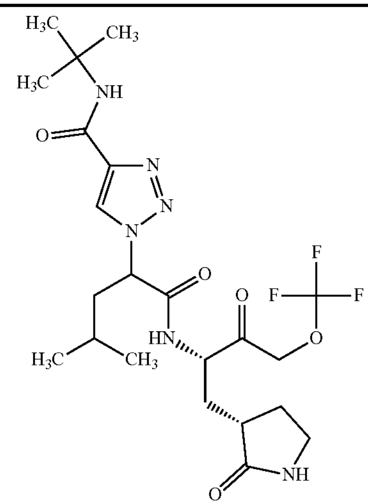 | N-(tert-butyl)-1-(4-methyl-1-oxo-1-(((S)-3-oxo-1-((S)-2-oxopyrrolidin-3-yl)-4-(trifluoromethoxy)butan-2-yl)amino)pentan-2-yl)-1H-1,2,3-triazole-4-carboxamide | 519.3 | *** |
| 593 | 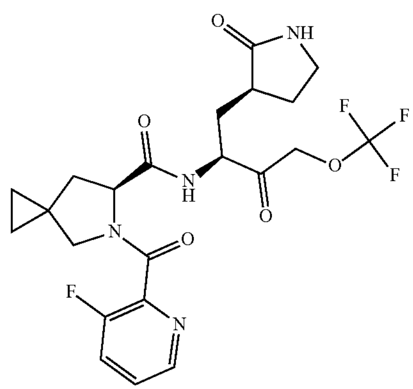 [SMILES: O=C1NCC[C@H]1C[C@H](NC(=O)[C@@H]1CC2(CC2)CN1C(=O)c1ncccc1F)C(=O)COC(F)(F)F] | (S)-5-(3-fluoropicolinoyl)-N-((S)-3-oxo-1-((S)-2-oxopyrrolidin-3-yl)-4-(trifluoromethoxy)butan-2-yl)-5-azaspiro[2.4]-heptane-6-carboxamide | 501.3658 | ** |

TABLE 1-continued

| Compound | Structure | IUPAC | LCMS [M + 1] | EC50, uM (Hela) |
|---|---|---|---|---|
| 594 | 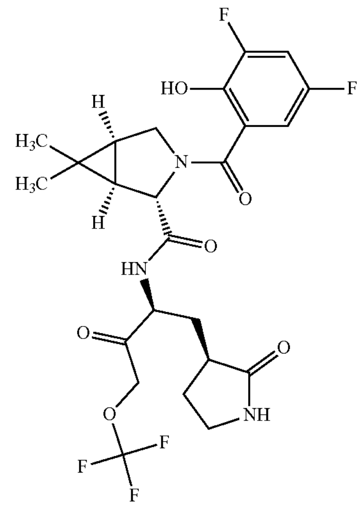 [SMILES: CC1(C)[C@@H]2[C@@H](C(=O)N[C@@H](C[C@@H]3CCNC3=O)C(=O)COC(F)(F)F)N(C(=O)c3cc(F)cc(F)c3O)C[C@@H]21] | (1R,2S,5S)-3-(3,5-difluoro-2-hydroxybenzoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 548.4398 | *** |
| 595 | 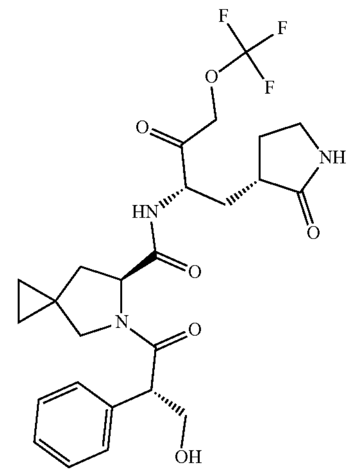 [SMILES: O=C1NCC[C@H]1C[C@H](NC(=O)[C@@H]1CC2(CC2)CN1C(=O)[C@H](CO)c1ccccc1)C(=O)COC(F)(F)F] | (S)-5-((S)-3-hydroxy-2-phenylpropanoyl)-N-((S)-3-oxo-1-((S)-2-oxopyrrolidin-3-yl)-4-(trifluoromethoxy)butan-2-yl)-5-azaspiro[2.4]heptane-6-carboxamide | 526.3837 | *** |

TABLE 1-continued

| Compound | Structure | IUPAC | LCMS [M + 1] | EC50, uM (Hela) |
|---|---|---|---|---|
| 596 | 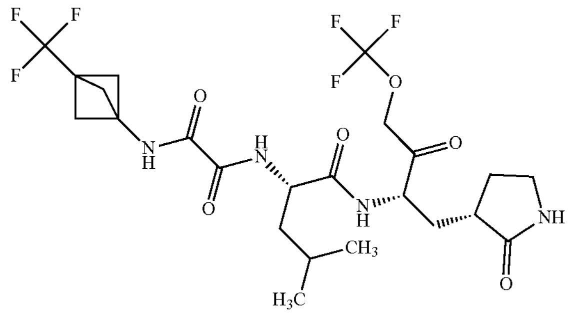 [SMILES: CC(C)C[C@H](NC(=O)C(=O)NC12CC(C(F)(F)F)(C1)C2)C(=O)N[C@@H](C[C@@H]1CCNC1=O)C(=O)COC(F)(F)F] | N1-((S)-4-methyl-1-oxo-1-(((S)-3-oxo-1-((S)-2-oxopyrrolidin-3-yl)-4-(trifluoromethoxy)butan-2-yl)amino)pentan-2-yl)-N2-(3-(trifluoromethyl)bicyclo[1.1.1]pentan-1-yl)oxalamide | 573.2 | **** |
| 597 | 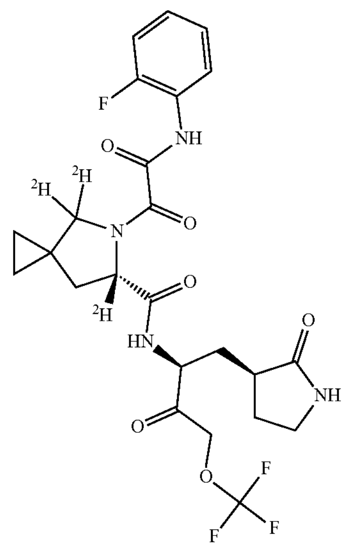 [SMILES: [2H]C1([2H])N(C(=O)C(=O)Nc2ccccc2F)[C@]([2H])(C(=O)N[C@@H](C[C@@H]2CCNC2=O)C(=O)COC(F)(F)F)CC12CC2] | (S)-5-(2-((2-fluorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-4,4,6-d3-6-carboxamide | 546.3 | **** |

TABLE 1-continued

| Compound | Structure | IUPAC | LCMS [M + 1] | EC50, uM (Hela) |
|---|---|---|---|---|
| 598 | 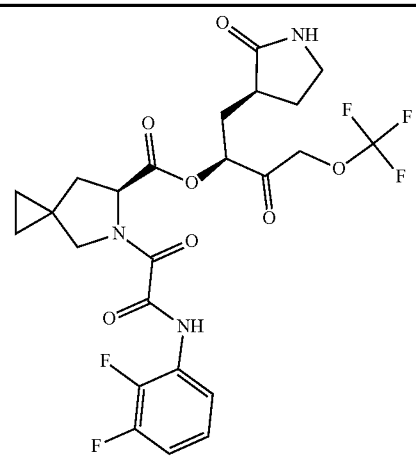 | (S)-5-(2-((2,3-difluorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 561.4104 | **** |
| 599 | 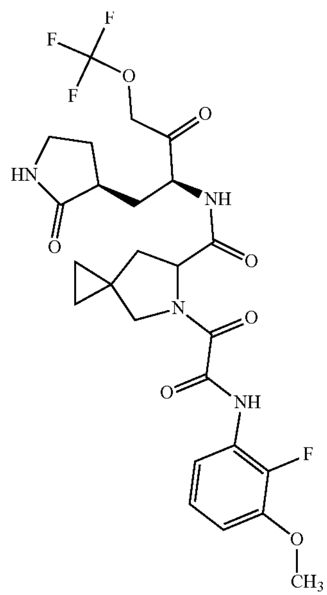 [SMILES: COc1cccc(NC(=O)C(=O)N2CC3(CC3)CC2C(=O)N[C@@H](C[C@@H]2CCNC2=O)C(=O)COC(F)(F)F)c1F] | (S)-5-(2-((2-fluoro-3-methoxyphenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 573.3971 | **** |

TABLE 1-continued

| Compound | Structure | IUPAC | LCMS [M + 1] | EC50, uM (Hela) |
|---|---|---|---|---|
| 600 | 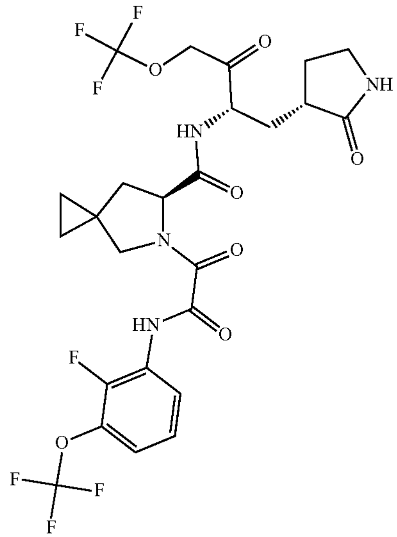 [SMILES: O=C(Nc1cccc(OC(F)(F)F)c1F)C(=O)N1CC2(CC2)C[C@H]1C(=O)N[C@@H](C[C@@H]1CCNC1=O)C(=O)COC(F)(F)F] | (S)-5-(2-((2-fluoro-3-(trifluoromethoxy)-phenyl)amino)-2-oxoacetyl)-N-((S)-3-oxo-1-((S)-2-oxopyrrolidin-3-yl)-4-(trifluoromethoxy)-butan-2-yl)-5-azaspiro[2.4]heptane-6-carboxamide | 627.16 | **** |
| 601 | 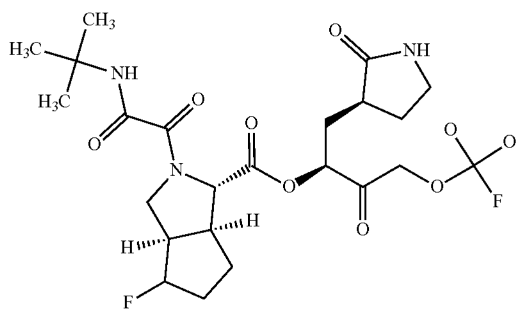 [SMILES: CC(C)(C)NC(=O)C(=O)N1C[C@@H]2C(F)CC[C@@H]2[C@H]1C(=O)O[C@@H](C[C@@H]1CCNC1=O)C(=O)COC(O)(O)F] | (1S,3aR,6aS)-2-(2-(tert-butylamino)-2-oxoacetyl)-4-fluoro-N-((S)-3-oxo-1-((S)-2-oxopyrrolidin-3-yl)-4-(trifluoromethoxy)butan-2-yl)octahydrocyclopenta[c]pyrrole-1-carboxamide | 537.4255 | *** |

TABLE 1-continued

| Compound | Structure | IUPAC | LCMS [M + 1] | EC50, uM (Hela) |
|---|---|---|---|---|
| 602 | 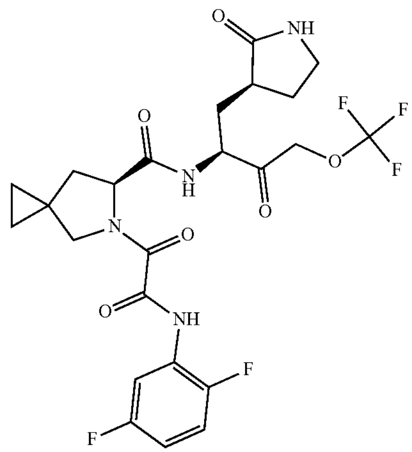 [SMILES: O=C(Nc1cc(F)ccc1F)C(=O)N1CC2(CC2)C[C@H]1C(=O)N[C@@H](C[C@@H]1CCNC1=O)C(=O)COC(F)(F)F] | (S)-5-(2-((2,5-difluorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 561.17 | **** |
| 603 | 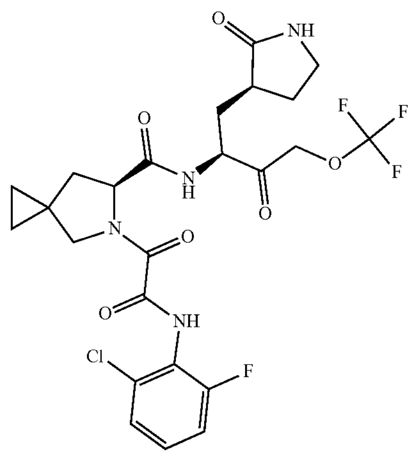 [SMILES: O=C(Nc1c(F)cccc1Cl)C(=O)N1CC2(CC2)C[C@H]1C(=O)N[C@@H](C[C@@H]1CCNC1=O)C(=O)COC(F)(F)F] | (S)-5-(2-(2-chloro-6-fluorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 577.14 | *** |

TABLE 1-continued

| Compound | Structure | IUPAC | LCMS [M + 1] | EC50, uM (Hela) |
|---|---|---|---|---|
| 604 | 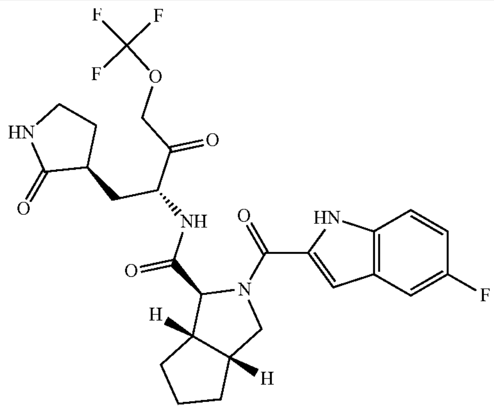 [SMILES: O=C1NCC[C@H]1C[C@@H](NC(=O)[C@@H]1[C@H]2CCC[C@H]2CN1C(=O)c1cc2cc(F)ccc2[nH]1)C(=O)COC(F)(F)F] | (1S,3aR,6aS)-2-(5-fluoro-1H-indole-2-carbonyl)-N-((R)-3-oxo-1-((S)-2-oxopyrrolidin-3-yl)-4-(trifluoromethoxy)butan-2-yl)octahydrocyclopenta[c]pyrrole-1-carboxamide | 553.53 | **** |
| 605 | 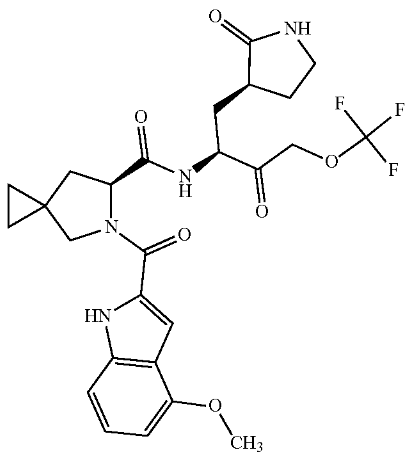 [SMILES: COc1cccc2[nH]c(C(=O)N3CC4(CC4)C[C@H]3C(=O)N[C@@H](C[C@@H]3CCNC3=O)C(=O)COC(F)(F)F)cc12] | (S)-5-(4-methoxy-1H-indole-2-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 551.53 | **** |

TABLE 1-continued

| Compound | Structure | IUPAC | LCMS [M + 1] | EC50, uM (Hela) |
|---|---|---|---|---|
| 606 | 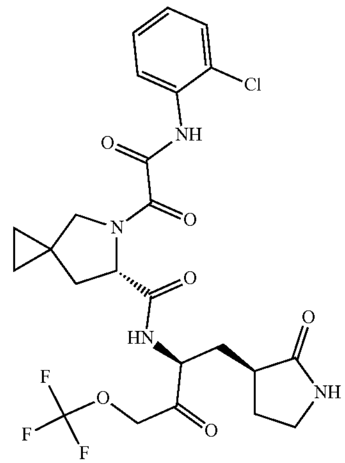 [SMILES: O=C(Nc1ccccc1Cl)C(=O)N1CC2(CC2)C[C@H]1C(=O)N[C@@H](C[C@@H]1CCNC1=O)C(=O)COC(F)(F)F] | (S)-5-(2-((2-chlorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 559.4193 | **** |
| 607 | 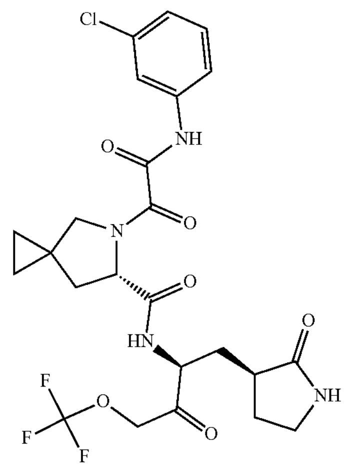 [SMILES: O=C(Nc1cccc(Cl)c1)C(=O)N1CC2(CC2)C[C@H]1C(=O)N[C@@H](C[C@@H]1CCNC1=O)C(=O)COC(F)(F)F] | (S)-5-(2-((3-chlorophenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 559.2 | **** |

TABLE 1-continued

| Compound | Structure | IUPAC | LCMS [M + 1] | EC50, uM (Hela) |
|---|---|---|---|---|
| 608 | 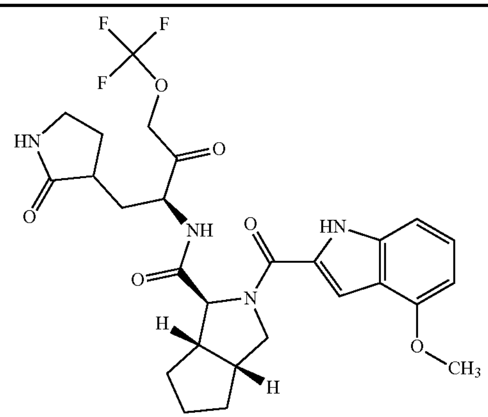 | (1S,3aR,6aS)-2-(4-methoxy-1H-indole-2-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 565.41 | **** |
| 609 | 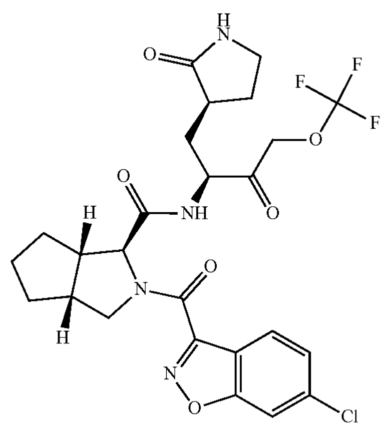 [SMILES: O=C1NCC[C@H]1C[C@H](NC(=O)[C@@H]1[C@H]2CCC[C@H]2CN1C(=O)c1noc2cc(Cl)ccc12)C(=O)COC(F)(F)F] | (1S,3aR,6aS)-2-(6-chlorobenzo[d]isoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 571.38 | **** |

TABLE 1-continued

| Compound | Structure | IUPAC | LCMS [M + 1] | EC50, uM (Hela) |
|---|---|---|---|---|
| 610 | 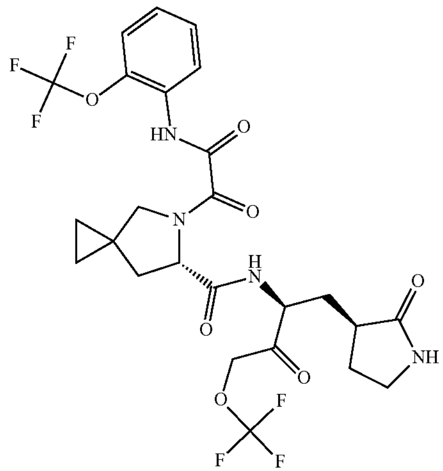 [SMILES: O=C(Nc1ccccc1OC(F)(F)F)C(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-(2-oxo-2-((2-(trifluoromethoxy)phenyl)amino)acetyl)-5-azaspiro[2.4]heptane-6-carboxamide | 609.5 | **** |
| 611 | 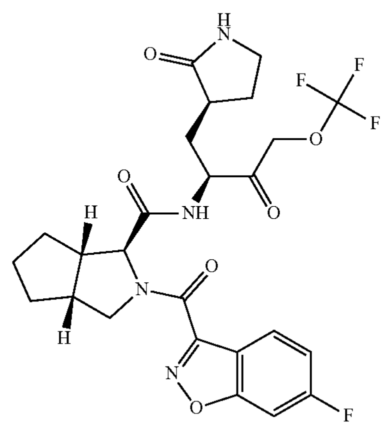 [SMILES: O=C1NCC[C@H]1C[C@H](NC(=O)[C@@H]1[C@H]2CCC[C@H]2CN1C(=O)c1noc2cc(F)ccc12)C(=O)COC(F)(F)F] | (1S,3aR,6aS)-2-(6-fluorobenzo[d]isoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 555.43 | **** |

TABLE 1-continued

| Compound | Structure | IUPAC | LCMS [M + 1] | EC50, uM (Hela) |
|---|---|---|---|---|
| 612 | 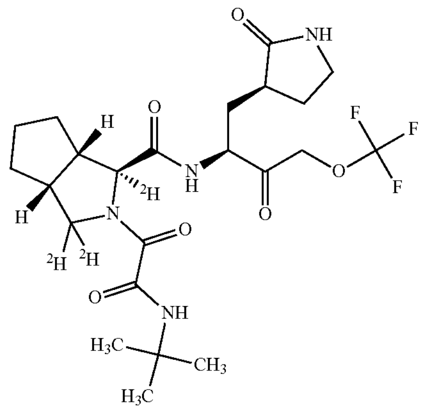 [SMILES: [2H]C1([2H])[C@@H]2CCC[C@@H]2[C@@]([2H])(C(=O)N[C@@H](C[C@@H]2CCNC2=O)C(=O)COC(F)(F)F)N1C(=O)C(=O)NC(C)(C)C] | (1S,3aR,6aS)-2-(2-(tert-butyl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1,3,3-d3-1-carboxamide | 522.3 | **** |
| 613 | 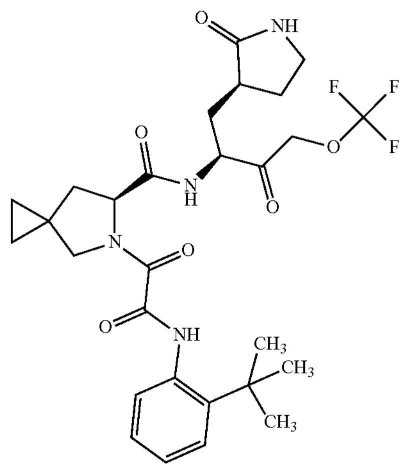 [SMILES: CC(C)(C)c1ccccc1NC(=O)C(=O)N1CC2(CC2)C[C@H]1C(=O)N[C@@H](C[C@@H]1CCNC1=O)C(=O)COC(F)(F)F] | (S)-5-(2-((2-(tert-butyl)phenyl)amino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 581.4 | **** |

TABLE 1-continued

| Compound | Structure | IUPAC | LCMS [M + 1] | EC50, uM (Hela) |
|---|---|---|---|---|
| 614 | 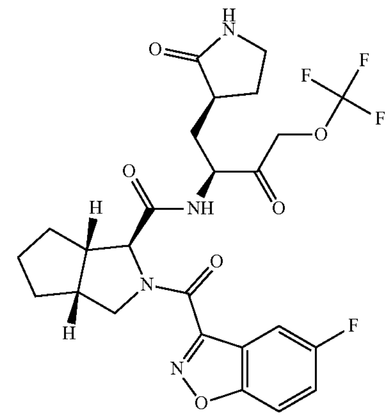 [SMILES: O=C1NCC[C@H]1C[C@H](NC(=O)[C@@H]1[C@H]2CCC[C@H]2CN1C(=O)c1noc2ccc(F)cc12)C(=O)COC(F)(F)F] | (1S,3aR,6aS)-2-(5-fluorobenzo[d]isoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 555.4393 | **** |
| 615 | 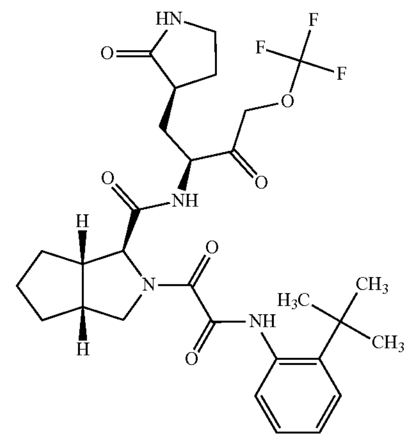 [SMILES: CC(C)(C)c1ccccc1NC(=O)C(=O)N1C[C@@H]2CCC[C@@H]2[C@H]1C(=O)N[C@@H](C[C@@H]1CCNC1=O)C(=O)COC(F)(F)F] | (1S,3aR,6aS)-2-(2-((2-(tert-butyl)phenyl)amino)-2-oxoacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 595.5487 | **** |

TABLE 1-continued

| Compound | Structure | IUPAC | LCMS [M + 1] | EC50, uM (Hela) |
|---|---|---|---|---|
| 616 | 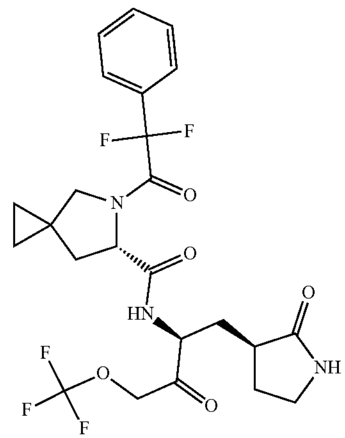 [SMILES: O=C1NCC[C@H]1C[C@H](NC(=O)[C@@H]1CC2(CC2)CN1C(=O)C(F)(F)c1ccccc1)C(=O)COC(F)(F)F] | (S)-5-(2,2-difluoro-2-phenylacetyl)-N-((S)-3-oxo-1-((S)-2-oxopyrrolidin-3-yl)-4-(trifluoromethoxy)butan-2-yl)-5-azaspiro[2.4]heptane-6-carboxamide | 532.3751 | **** |
| 617 | 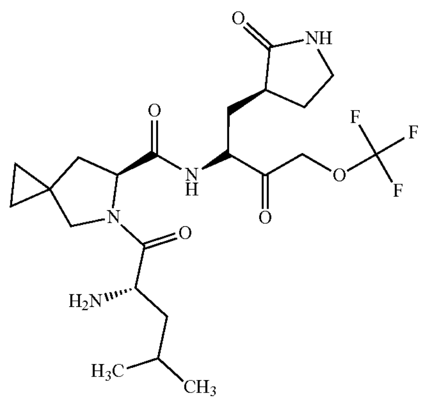 | (S)-5-(L-leucyl)-N-((S)-3-oxo-1-((S)-2-oxopyrrolidin-3-yl)-4-(trifluoromethoxy)butan-2-yl)-5-azaspiro[2.4]heptane-6-carboxamide | 491.4681 | |

TABLE 1-continued

| Compound | Structure | IUPAC | LCMS [M + 1] | EC50, uM (Hela) |
|---|---|---|---|---|
| 618 | 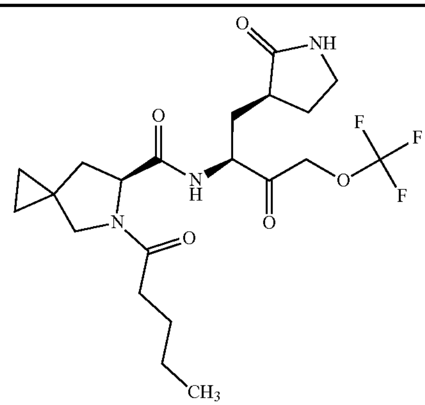 | (S)-N-((S)-3-oxo-1-((S)-2-oxopyrrolidin-3-yl)-4-(trifluorom ethoxy)butan-2-yl)-5-pentanoyl-5-azaspiro[2.4]heptane-6-carboxamide | 462.4 | *** |
| 619 | 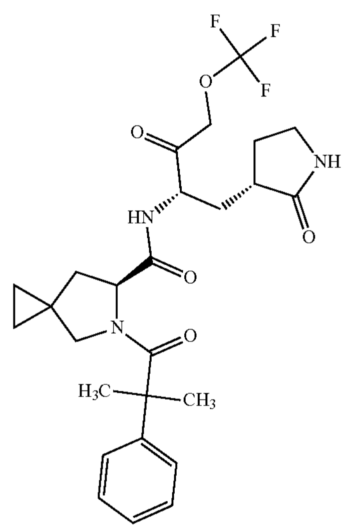 [SMILES: CC(C)(C(=O)N1CC2(CC2)C[C@H]1C(=O)N[C@@H](C[C@@H]1CCNC1=O)C(=O)COC(F)(F)F)c1ccccc1] | (S)-5-(2-methyl-2-phenylpropanoyl)-N-((S)-3-oxo-1-((S)-2-oxopyrrolidin-3-yl)-4-(trifluoromethoxy)butan-2-yl)-5-azaspiro[2.4]heptane-6-carboxamide | 524.4066 | **** |

TABLE 1-continued
| Compound | Structure | IUPAC | LCMS [M + 1] | EC50, uM (Hela) |
|---|---|---|---|---|
| 620 | 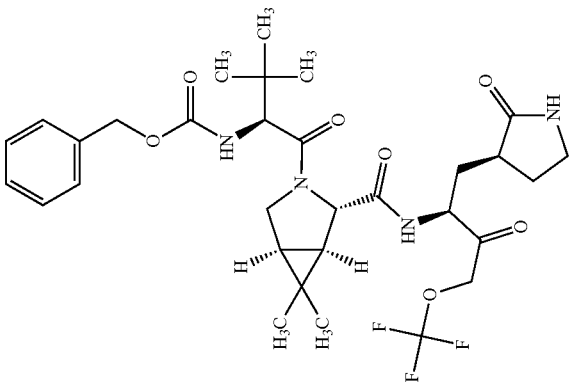 | benzyl ((S)-1-((1R,2S,5S)-6,6-dimethyl-2-(((S)-3-oxo-1-((S)-2-oxopyrrolidin-3-yl)-4-(trifluoromethoxy)butan-2-yl)carbamoyl)-3-azabicyclo[3.1.0]hexan-3-yl)-3,3-dimethyl-1-oxobutan-2-yl)carbamate | 639.6 | **** |
| 621 | 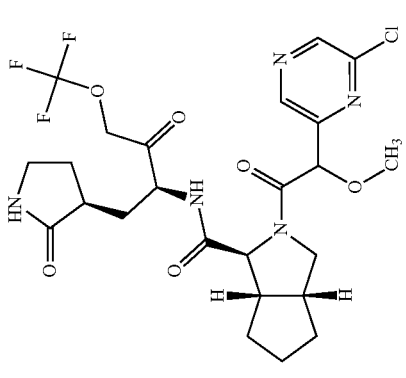 | (1S,3aR,6aS)-2-(2-(6-chloropyrazin-2-yl)-2-methoxyacetyl)-N-((S)-3-oxo-1-((S)-2-oxopyrrolidin-3-yl)-4-(trifluoromethoxy)butan-2-yl)octahydrocyclopenta[c]pyrrole-1-carboxamide | 576.4012 | *** |

TABLE 1-continued

| Compound | Structure | IUPAC | LCMS [M + 1] | EC50, uM (Hela) |
|---|---|---|---|---|
| 622 | 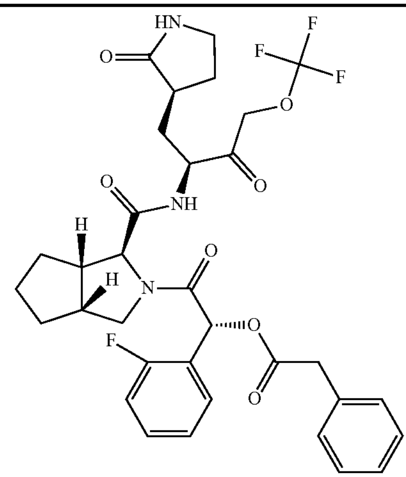 | (R)-1-(2-fluorophenyl)-2-oxo-2-((1S,3aR,6aS)-1-(((S)-3-oxo-1-((S)-2-oxopyrrolidin-3-yl)-4-(trifluoromethoxy)butan-2-yl)carbamoyl)hexahydrocyclopenta[c]pyrrol-2(1H)-yl)ethyl 2-phenylacetate | 662.5097 | *** |
| 623 | 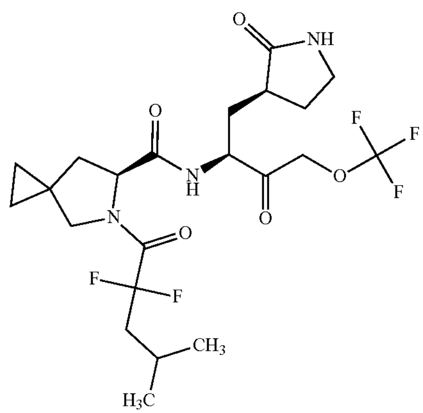 [SMILES: CC(C)CC(F)(F)C(=O)N1CC2(CC2)C[C@H]1C(=O)N[C@@H](C[C@@H]1CCNC1=O)C(=O)COC(F)(F)F] | (S)-5-(2,2-difluoro-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 512.4407 | **** |

TABLE 1-continued

| Compound | Structure | IUPAC | LCMS [M + 1] | EC50, uM (Hela) |
|---|---|---|---|---|
| 624 | 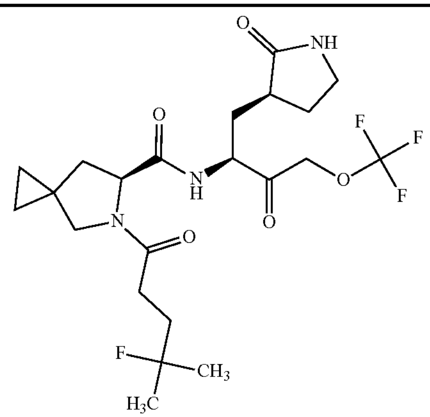 | (S)-5-(4-fluoro-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 494.4271 | *** |
| 625 | 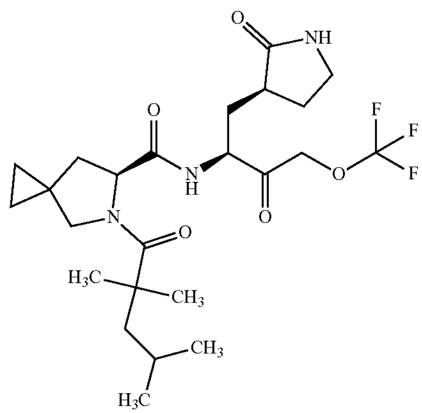 [SMILES: CC(C)CC(C)(C)C(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-(2,2,4-trimethylpentanoyl)-5-azaspiro[2.4]heptane-6-carboxamide | 504.3842 | **** |

TABLE 1-continued

| Compound | Structure | IUPAC | LCMS [M + 1] | EC50, uM (Hela) |
|---|---|---|---|---|
| 626 | 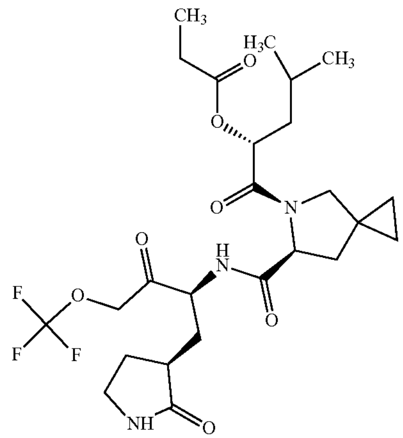 | (R)-4-methyl-1-oxo-1-((S)-6-((((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl propionate | 549.3898 | **** |
| 627 | 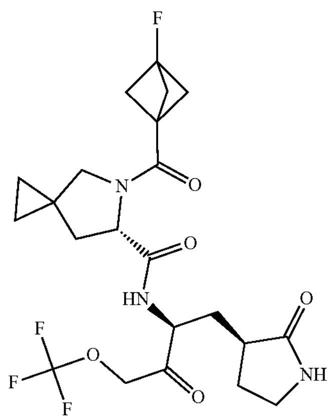 [SMILES: O=C1NCC[C@H]1C[C@H](NC(=O)[C@@H]1CC2(CC2)CN1C(=O)C12CC(F)(C1)C2)C(=O)COC(F)(F)F] | (S)-5-(3-fluorobicyclo[1.1.1]pentane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 490.0533 | *** |

TABLE 1-continued

| Compound | Structure | IUPAC | LCMS [M + 1] | EC50, uM (Hela) |
|---|---|---|---|---|
| 628 | 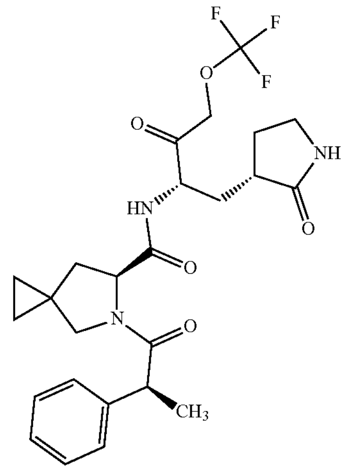 [SMILES: C[C@H](C(=O)N1CC2(CC2)C[C@H]1C(=O)N[C@@H](C[C@@H]1CCNC1=O)C(=O)COC(F)(F)F)c1ccccc1] | (S)-N-((S)-3-oxo-1-((S)-2-oxopyrrolidin-3-yl)-4-(trifluoromethoxy)butan-2-yl)-5-((S)-2-phenylpropanoyl)-5-azaspiro[2.4]heptane-6-carboxamide | 510.3638 | *** |
| 629 | 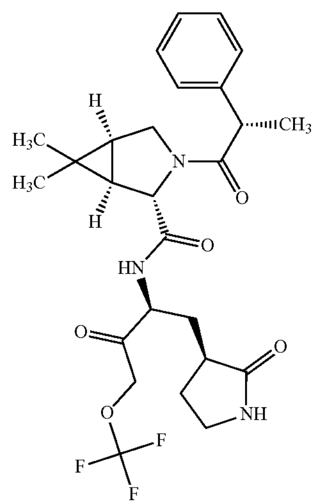 [SMILES: C[C@H](C(=O)N1C[C@H]2[C@@H]([C@H]1C(=O)N[C@@H](C[C@@H]1CCNC1=O)C(=O)COC(F)(F)F)C2(C)C)c1ccccc1] | (1R,2S,5S)-6,6-dimethyl-N-((S)-3-oxo-1-((S)-2-oxopyrrolidin-3-yl)-4-(trifluoromethoxy)butan-2-yl)-3-((S)-2-phenylpropanoyl)-3-azabicyclo[3.1.0]hexane-2-carboxamide | 523.553 | **** |

TABLE 1-continued

| Compound | Structure | IUPAC | LCMS [M + 1] | EC50, uM (Hela) |
|---|---|---|---|---|
| 630 | 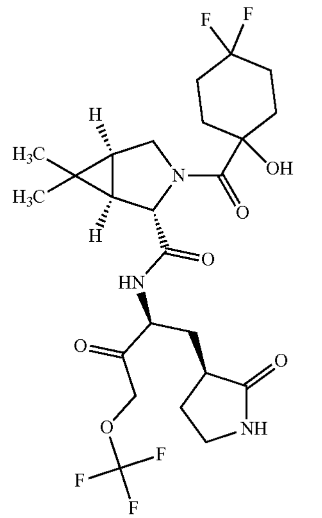 [SMILES: CC1(C)[C@@H]2[C@@H](C(=O)N[C@@H](C[C@@H]3CCNC3=O)C(=O)COC(F)(F)F)N(C(=O)C3(O)CCC(F)(F)CC3)C[C@@H]21] | (1R,2S,5S)-3-(4,4-difluoro-1-hydroxycyclohexane-1-carbonyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 554.4 | *** |
| 631 | 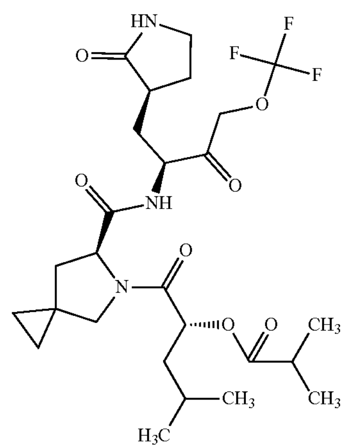 [SMILES: CC(C)C[C@@H](OC(=O)C(C)C)C(=O)N1CC2(CC2)C[C@H]1C(=O)N[C@@H](C[C@@H]1CCNC1=O)C(=O)COC(F)(F)F] | (R)-4-methyl-1-oxo-1-((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl isobutyrate | 562.2 | ** |

TABLE 1-continued

| Compound | Structure | IUPAC | LCMS [M + 1] | EC50, uM (Hela) |
|---|---|---|---|---|
| 632 | 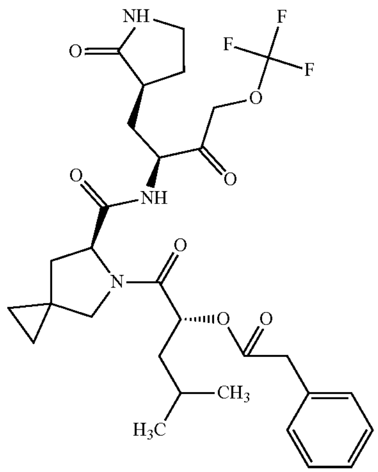 [SMILES: CC(C)C[C@@H](OC(=O)Cc1ccccc1)C(=O)N1CC2(CC2)C[C@H]1C(=O)N[C@@H](C[C@@H]1CCNC1=O)C(=O)COC(F)(F)F] | (R)-4-methyl-1-oxo-1-((S)-6-((((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl 2-phenylacetate | 610.2 | **** |
| 633 | 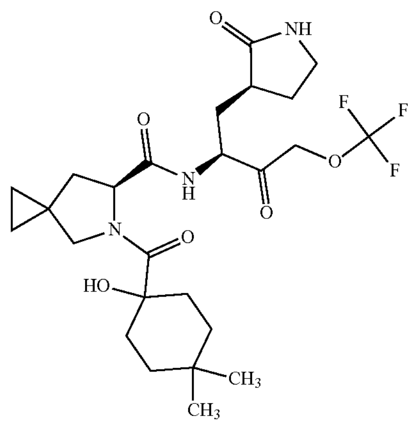 [SMILES: CC1(C)CCC(O)(C(=O)N2CC3(CC3)C[C@H]2C(=O)N[C@@H](C[C@@H]2CCNC2=O)C(=O)COC(F)(F)F)CC1] | (S)-5-(1-hydroxy-4,4-dimethylcyclohexane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 532.4545 | **** |

TABLE 1-continued

| Compound | Structure | IUPAC | LCMS [M + 1] | EC50, uM (Hela) |
|---|---|---|---|---|
| 634 | 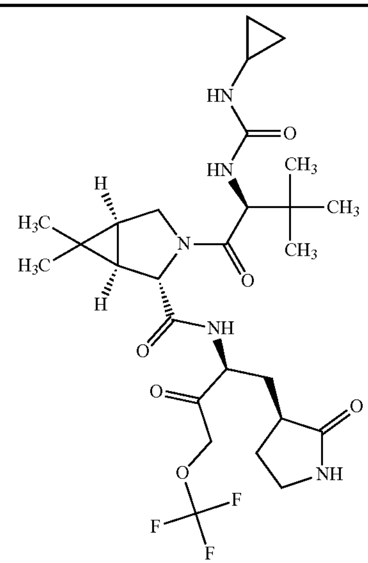 | (1R,2S,5S)-3-((S)-2-(3-cyclopropylureido)-3,3-dimethylbutanoyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 588.5333 | >1 μM |
| 635 | 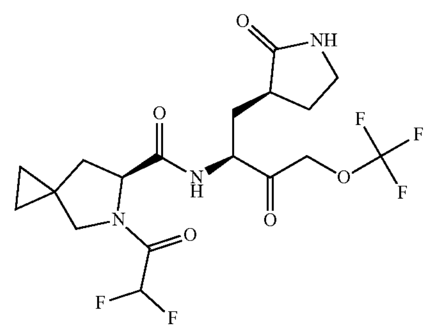 [SMILES: O=C1NCC[C@H]1C[C@H](NC(=O)[C@@H]1CC2(CC2)CN1C(=O)C(F)F)C(=O)COC(F)(F)F] | (S)-5-(2,2-difluoroacetyl)-N-((S)-3-oxo-1-((S)-2-oxopyrrolidin-3-yl)-4-(trifluoromethoxy)butan-2-yl)-5-azaspiro[2.4]heptane-6-carboxamide | 456.4 | *** |

TABLE 1-continued

| Compound | Structure | IUPAC | LCMS [M + 1] | EC50, uM (Hela) |
|---|---|---|---|---|
| 636 | 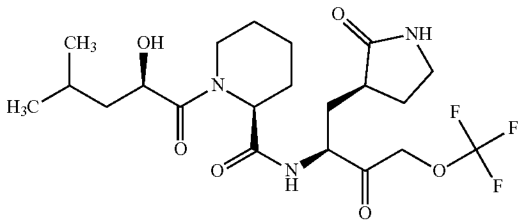 [SMILES: CC(C)C[C@@H](O)C(=O)N1CCCC[C@H]1C(=O)N[C@@H](C[C@@H]1CCNC1=O)C(=O)COC(F)(F)F] | (S)-1-((R)-2-hydroxy-4-methylpentanoyl)-N-((S)-3-oxo-1-((S)-2-oxopyrrolidin-3-yl)-4-(trifluoromethoxy)butan-2-yl)piperidine-2-carboxamide | 480.3504 | *** |
| 637 | 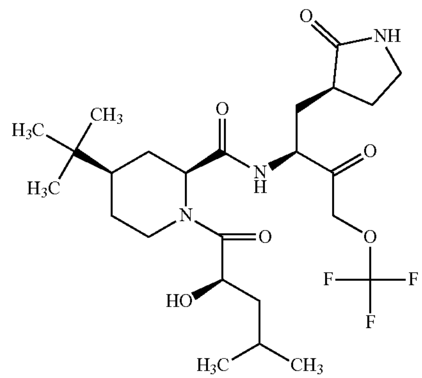 [SMILES: CC(C)C[C@@H](O)C(=O)N1CC[C@@H](C(C)(C)C)C[C@H]1C(=O)N[C@@H](C[C@@H]1CCNC1=O)C(=O)COC(F)(F)F] | (2S,4R)-4-(tert-butyl)-1-((R)-2-hydroxy-4-methylpentanoyl)-N-((S)-3-oxo-1-((S)-2-oxopyrrolidin-3-yl)-4-(trifluoromethoxy)butan-2-yl)piperidine-2-carboxamide | 536.4659 | **** |
| 638 | 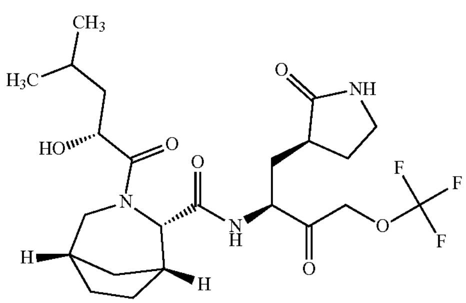 [SMILES: CC(C)C[C@@H](O)C(=O)N1C[C@H]2CC[C@H](C2)[C@H]1C(=O)N[C@@H](C[C@@H]1CCNC1=O)C(=O)COC(F)(F)F] | (1R,2S,5S)-3-((R)-2-hydroxy-4-methylpentanoyl)-N-((S)-3-oxo-1-((S)-2-oxopyrrolidin-3-yl)-4-(trifluoromethoxy)butan-2-yl)-3-azabicyclo[3.2.1]octane-2-carboxamide | 506.3814 | *** |

TABLE 1-continued

| Compound | Structure | IUPAC | LCMS [M + 1] | EC50, uM (Hela) |
|---|---|---|---|---|
| 639 | 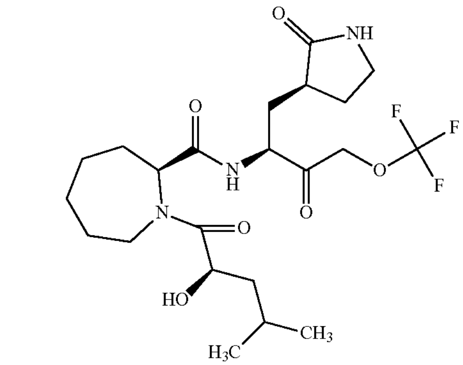 [SMILES: CC(C)C[C@@H](O)C(=O)N1CCCCC[C@H]1C(=O)N[C@@H](C[C@@H]1CCNC1=O)C(=O)COC(F)(F)F] | (S)-1-((R)-2-hydroxy-4-methylpentanoyl)-N-((S)-3-oxo-1-((S)-2-oxopyrrolidin-3-yl)-4-(trifluoromethoxy)butan-2-yl)azepane-2-carboxamide | 494.3617 | **** |
| 640 | 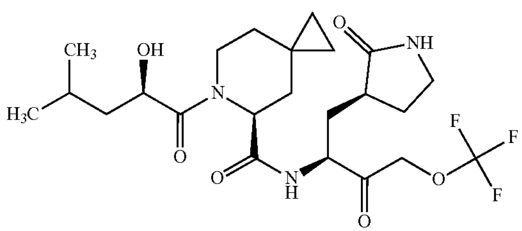 [SMILES: CC(C)C[C@@H](O)C(=O)N1CCC2(CC2)C[C@H]1C(=O)N[C@@H](C[C@@H]1CCNC1=O)C(=O)COC(F)(F)F] | (S)-6-((R)-2-hydroxy-4-methylpentanoyl)-N-((S)-3-oxo-1-((S)-2-oxopyrrolidin-3-yl)-4-(trifluoromethoxy)butan-2-yl)-6-azaspiro[2.5]octane-5-carboxamide | 506.3452 | *** |
| 641 | 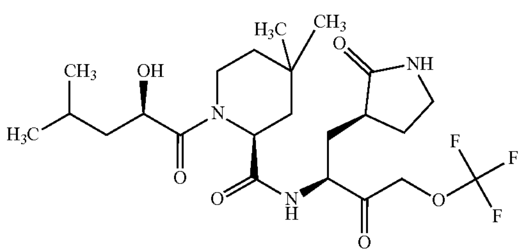 [SMILES: CC(C)C[C@@H](O)C(=O)N1CCC(C)(C)C[C@H]1C(=O)N[C@@H](C[C@@H]1CCNC1=O)C(=O)COC(F)(F)F] | (S)-1-((R)-2-hydroxy-4-methylpentanoyl)-4,4-dimethyl-N-((S)-3-oxo-1-((S)-2-oxopyrrolidin-3-yl)-4-(trifluoromethoxy)butan-2-yl)piperidine-2-carboxamide | 508.4088 | **** |

TABLE 1-continued

| Compound | Structure | IUPAC | LCMS [M + 1] | EC50, uM (Hela) |
|---|---|---|---|---|
| 642 | 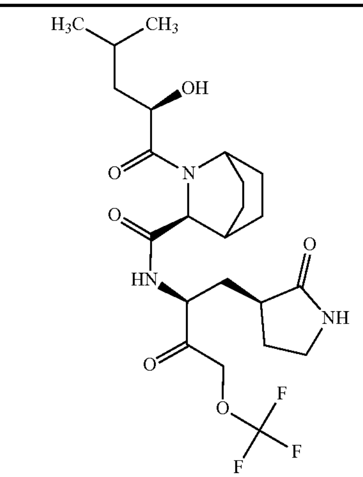 | (S)-2-((R)-2-hydroxy-4-methylpentanoyl)-N-((S)-3-oxo-1-((S)-2-oxopyrrolidin-3-yl)-4-(trifluoromethoxy)butan-2-yl)-2-azabicyclo[2.2.2]octane-3-carboxamide | 506.3814 | **** |
| 643 | 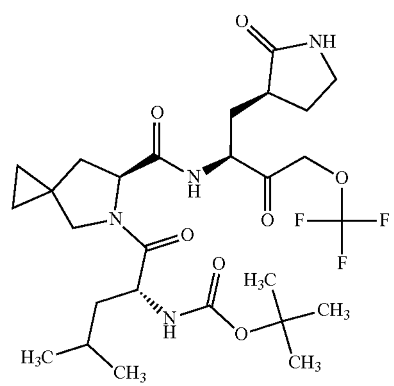 [SMILES: CC(C)C[C@@H](NC(=O)OC(C)(C)C)C(=O)N1CC2(CC2)C[C@H]1C(=O)N[C@@H](C[C@@H]1CCNC1=O)C(=O)COC(F)(F)F] | tert-butyl ((R)-4-methyl-1-oxo-1-((S)-6-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl)carbamate | 591.5269 | **** |

TABLE 1-continued

| Compound | Structure | IUPAC | LCMS [M + 1] | EC50, uM (Hela) |
|---|---|---|---|---|
| 644 | 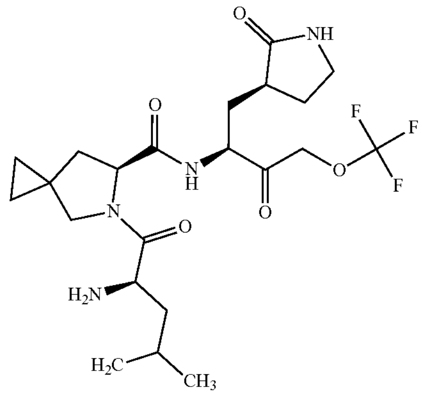 [SMILES: CC(C)C[C@@H](N)C(=O)N1CC2(CC2)C[C@H]1C(=O)N[C@@H](C[C@@H]1CCNC1=O)C(=O)COC(F)(F)F] | (S)-5-(D-leucyl)-N-((S)-3-oxo-1-((S)-2-oxopyrrolidin-3-yl)-4-(trifluoromethoxy)butan-2-yl)-5-azaspiro[2.4]heptane-6-carboxamide | 491.3205 | ** |
| 645 | 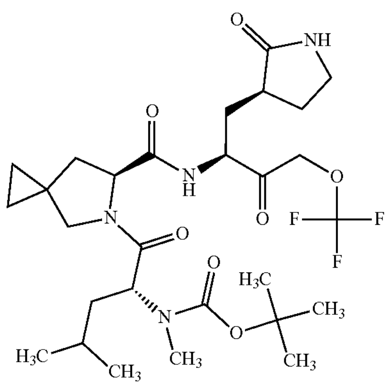 [SMILES: CC(C)C[C@H](C(=O)N1CC2(CC2)C[C@H]1C(=O)N[C@@H](C[C@@H]1CCNC1=O)C(=O)COC(F)(F)F)N(C)C(=O)OC(C)(C)C] | tert-butyl methyl(((R)-4-methyl-1-oxo-1-(((S)-3-oxo-1-((S)-2-oxopyrrolidin-3-yl)-4-(trifluoromethoxy)butan-2-yl)carbamoyl)-5-azaspiro[2.4]heptan-5-yl)pentan-2-yl)carbamate | 605.5358 | *** |

TABLE 1-continued

| Compound | Structure | IUPAC | LCMS [M + 1] | EC50, uM (Hela) |
|---|---|---|---|---|
| 646 | 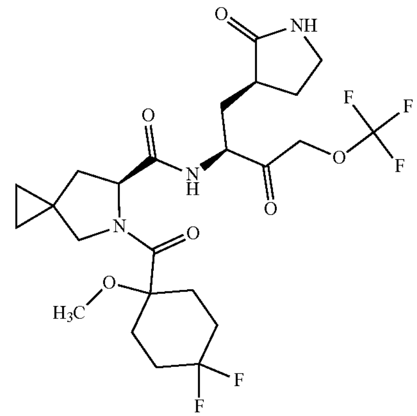 [SMILES: COC1(C(=O)N2CC3(CC3)C[C@H]2C(=O)N[C@@H](C[C@@H]2CCNC2=O)C(=O)COC(F)(F)F)CCC(F)(F)CC1] | (S)-5-(4,4-difluoro-1-methoxy cyclohexane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 554.3856 | **** |
| 647 | 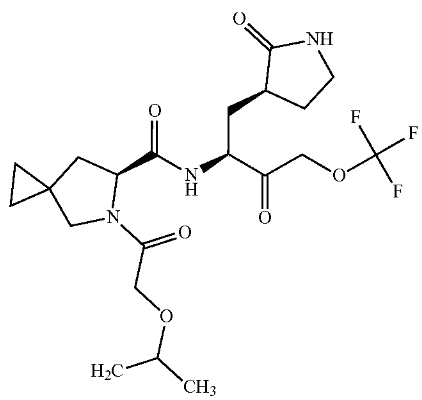 | (888S)-5-(2-isopropoxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 478.6849 | *** |

TABLE 1-continued

| Compound | Structure | IUPAC | LCMS [M + 1] | EC50, uM (Hela) |
|---|---|---|---|---|
| 648 | 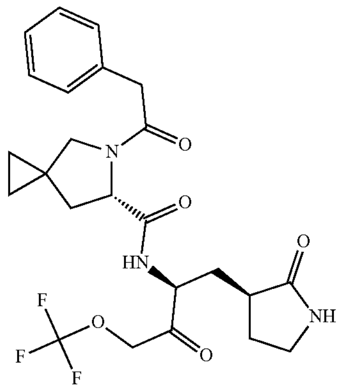 [SMILES: O=C1NCC[C@H]1C[C@H](NC(=O)[C@@H]1CC2(CC2)CN1C(=O)Cc1ccccc1)C(=O)COC(F)(F)F] | (S)-N-((S)-3-oxo-1-((S)-2-oxopyrrolidin-3-yl)-4-(trifluoromethoxy)butan-2-yl)-5-(2-phenylacetyl)-5-azaspiro[2.4]heptane-6-carboxamide | 496.0633 | **** |
| 649 | 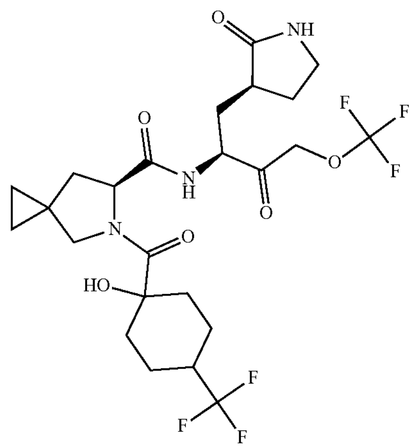 [SMILES: O=C1NCC[C@H]1C[C@H](NC(=O)[C@@H]1CC2(CC2)CN1C(=O)C1(O)CCC(C(F)(F)F)CC1)C(=O)COC(F)(F)F] | (S)-5-(1-hydroxy-4-(trifluoromethyl)cyclohexane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 572.3773 | *** |

TABLE 1-continued

| Compound | Structure | IUPAC | LCMS [M + 1] | EC50, uM (Hela) |
|---|---|---|---|---|
| 651 | 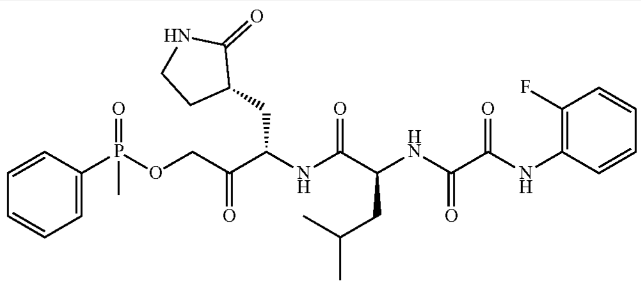 [SMILES: CC(C)C[C@H](NC(=O)C(=O)Nc1ccccc1F)C(=O)N[C@@H](C[C@@H]1CCNC1=O)C(=O)COP(C)(=O)c1ccccc1] | (S)-3-((S)-2-(2-((2-fluorophenyl)amino)-2-oxoacetamido)-4-methylpentanamido)-2-oxo-4-((S)-2-oxopyrrolidin-3-yl)butyl methyl(phenyl)phosphinate | 603.55 | *** |
| 652 | 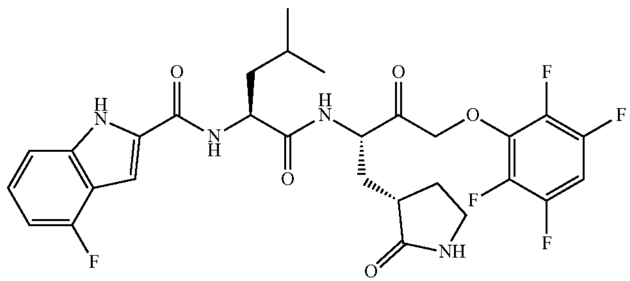 [SMILES: CC(C)C[C@H](NC(=O)c1cc2c(F)cccc2[nH]1)C(=O)N[C@@H](C[C@@H]1CCNC1=O)C(=O)COc1c(F)c(F)cc(F)c1F] | 4-fluoro-N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide | 609.3692 | **** |
| 653 | 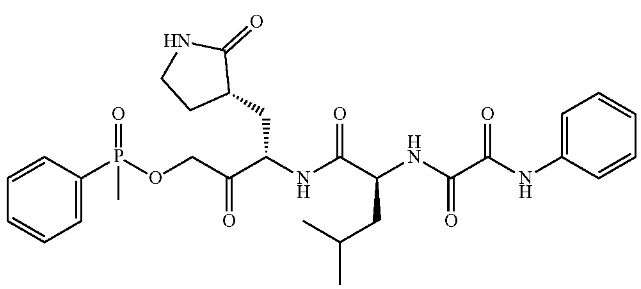 [SMILES: CC(C)C[C@H](NC(=O)C(=O)Nc1ccccc1)C(=O)N[C@@H](C[C@@H]1CCNC1=O)C(=O)COP(C)(=O)c1ccccc1] | (S)-3-((S)-4-methyl-2-(2-oxo-2-(phenylamino)acetamido)pentanamido)-2-oxo-4-((S)-2-oxopyrrolidin-3-yl)butyl methyl(phenyl)phosphinate | 585.4092 | ** |

TABLE 1-continued

| Compound | Structure | IUPAC | LCMS [M + 1] | EC50, uM (Hela) |
|---|---|---|---|---|
| 654 | 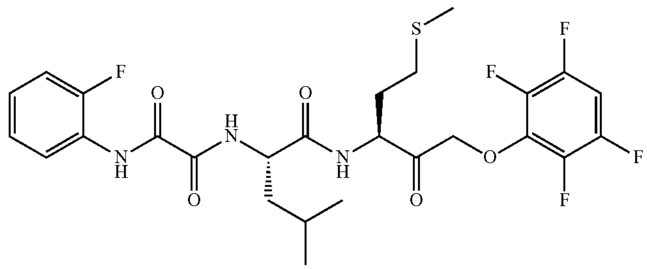 [SMILES: CSCC[C@H](NC(=O)[C@H](CC(C)C)NC(=O)C(=O)Nc1ccccc1F)C(=O)COc1c(F)c(F)cc(F)c1F] | N1-(2-fluorophenyl)-N2-((S)-4-methyl-1-((((S)-5-(methylthio)-2-oxo-1-(2,3,5,6-tetrafluorophenoxy)pentan-3-yl)amino)-1-oxopentan-2-yl)oxalamide | 590.2912 | * |
| 655 | 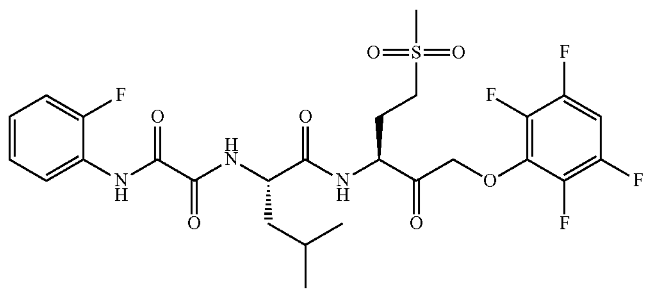 [SMILES: CC(C)C[C@H](NC(=O)C(=O)Nc1ccccc1F)C(=O)N[C@@H](CCS(C)(=O)=O)C(=O)COc1c(F)c(F)cc(F)c1F] | N1-(2-fluorophenyl)-N2-((S)-4-methyl-1-((((S)-5-(methyl sulfonyl)-2-oxo-1-(2,3,5,6-tetrafluorophenoxy)pentan-3-yl)amino)-1-oxopentan-2-yl)oxalamide | 622.2844 | * |
| 656 | 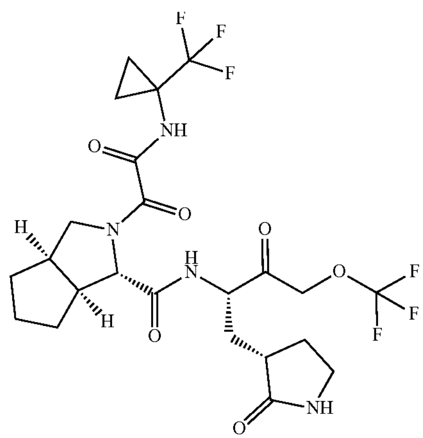 [SMILES: O=C(NC1(C(F)(F)F)CC1)C(=O)N1C[C@@H]2CCC[C@@H]2[C@H]1C(=O)N[C@@H](C[C@@H]1CCNC1=O)C(=O)COC(F)(F)F] | (1S,3aR,6aS)-N-((S)-3-oxo-1-((S)-2-oxopyrrolidin-3-yl)-4-(trifluoromethoxy)butan-2-yl)-2-(2-oxo-2-((1-(trifluoromethyl)cyclopropyl)amino)acetyl)octahydrocyclopenta[c]pyrrole-1-carboxamide | 571.4095 | *** |

TABLE 1-continued

| Compound | Structure | IUPAC | LCMS [M + 1] | EC50, uM (Hela) |
|---|---|---|---|---|
| 657 | 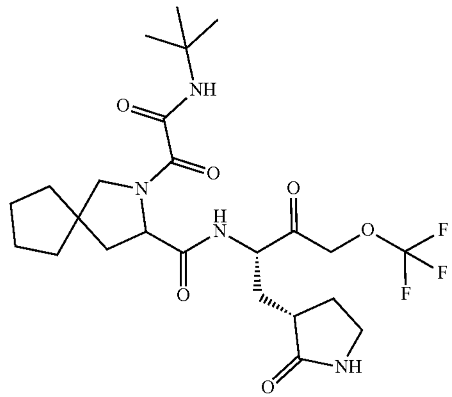 [SMILES: CC(C)(C)NC(=O)C(=O)N1CC2(CCCC2)CC1C(=O)N[C@@H](C[C@@H]1CCNC1=O)C(=O)COC(F)(F)F] | 2-(2-(tert-butylamino)-2-oxoacetyl)-N-((S)-3-oxo-1-((S)-2-oxopyrrolidin-3-yl)-4-(trifluoromethoxy)butan-2-yl)-2-azaspiro[4.4]nonane-3-carboxamide | 533.44 | **** |
| 658 | 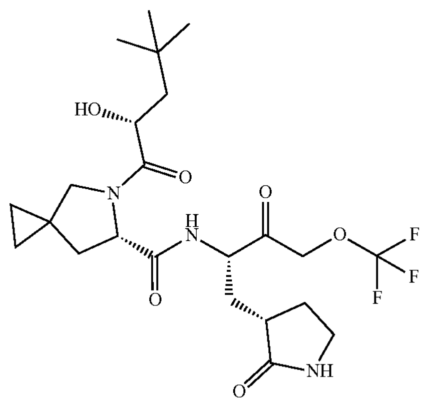 [SMILES: CC(C)(C)C[C@@H](O)C(=O)N1CC2(CC2)C[C@H]1C(=O)N[C@@H](C[C@@H]1CCNC1=O)C(=O)COC(F)(F)F] | (S)-5-((R)-2-hydroxy-4,4-dimethylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 506.4779 | **** |

TABLE 1-continued

| Compound | Structure | IUPAC | LCMS [M + 1] | EC50, uM (Hela) |
|---|---|---|---|---|
| 659 | 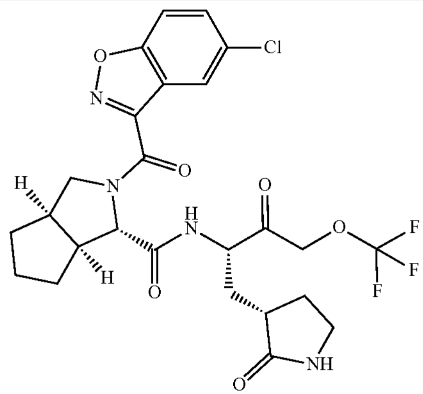 [SMILES: O=C1NCC[C@H]1C[C@H](NC(=O)[C@@H]1[C@H]2CCC[C@H]2CN1C(=O)c1noc2ccc(Cl)cc12)C(=O)COC(F)(F)F] | (1S,3aR,6aS)-2-(5-chlorobenzo[d]isoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 571.3178 | **** |
| 660 | 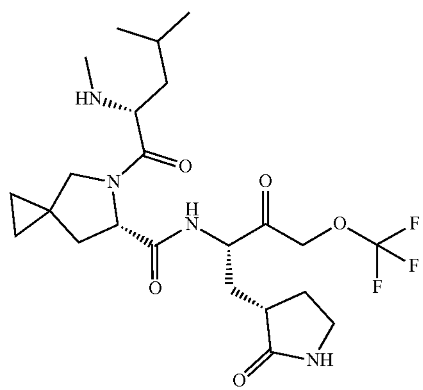 [SMILES: CN[C@H](CC(C)C)C(=O)N1CC2(CC2)C[C@H]1C(=O)N[C@@H](C[C@@H]1CCNC1=O)C(=O)COC(F)(F)F] | (S)-5-(methyl-D-leucyl)-N-((S)-3-oxo-1-((S)-2-oxopyrrolidin-3-yl)-4-(trifluoromethoxy)butan-2-yl)-5-azaspiro[2.4]heptane-6-carboxamide | 505.26 | *** |

TABLE 1-continued

| Compound | Structure | IUPAC | LCMS [M + 1] | EC50, uM (Hela) |
|---|---|---|---|---|
| 661 | 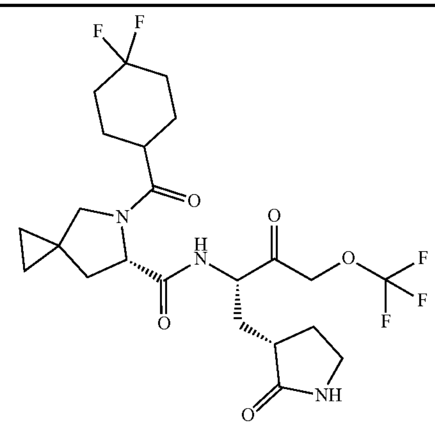 | (S)-5-(4,4-difluorocyclohexane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 524.21 | *** |
| 662 | 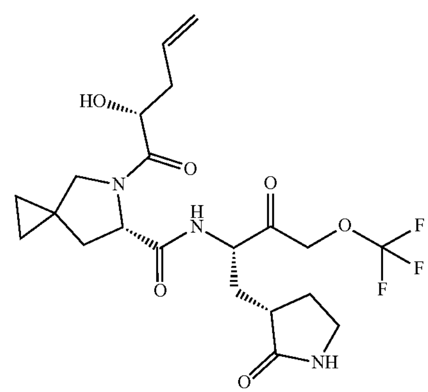 [SMILES: C=CC[C@@H](O)C(=O)N1CC2(CC2)C[C@H]1C(=O)N[C@@H](C[C@@H]1CCNC1=O)C(=O)COC(F)(F)F] | (S)-5-((R)-2-hydroxypent-4-enoyl)-N-((S)-3-oxo-1-((S)-2-oxopyrrolidin-3-yl)-4-(trifluoromethoxy)butan-2-yl)-5-azaspiro[2.4]heptane-6-carboxamide | 476.19 | *** |

TABLE 1-continued

| Compound | Structure | IUPAC | LCMS [M + 1] | EC50, uM (Hela) |
|---|---|---|---|---|
| 663 | 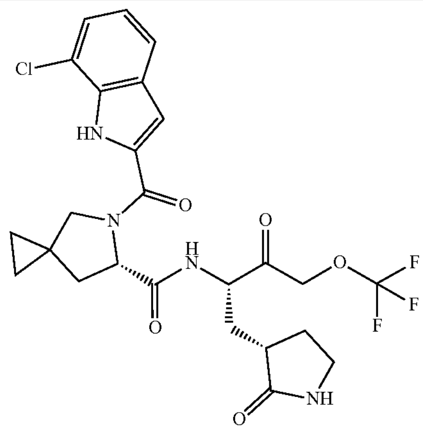 [SMILES: O=C1NCC[C@H]1C[C@H](NC(=O)[C@@H]1CC2(CC2)CN1C(=O)c1cc2cccc(Cl)c2[nH]1)C(=O)COC(F)(F)F] | (S)-5-(7-chloro-1H-indole-2-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 555.3343 | **** |
| 664 | 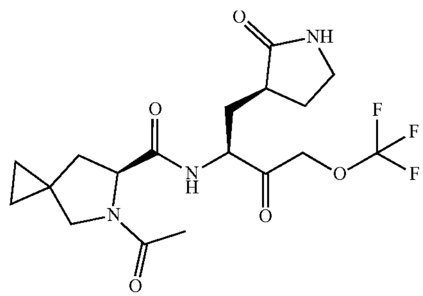 [SMILES: CC(=O)N1CC2(CC2)C[C@H]1C(=O)N[C@@H](C[C@@H]1CCNC1=O)C(=O)COC(F)(F)F] | (S)-5-acetyl-N-((S)-3-oxo-1-((S)-2-oxopyrrolidin-3-yl)-4-(trifluoromethoxy)butan-2-yl)-5-azaspiro[2.4]heptane-6-carboxamide | 420.54 | *** |
| 665 | 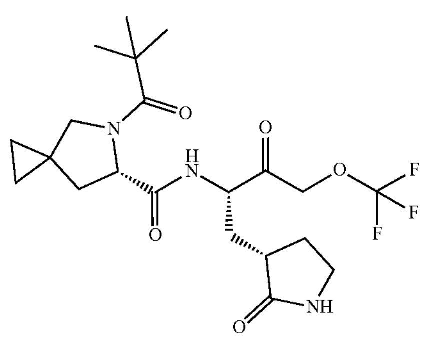 [SMILES: CC(C)(C)C(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-pivaloyl-5-azaspiro[2.4]heptane-6-carboxamide | 462.57 | *** |

| Compound | Structure | IUPAC | LCMS [M + 1] | EC50, uM (Hela) |
|---|---|---|---|---|
| 666 | 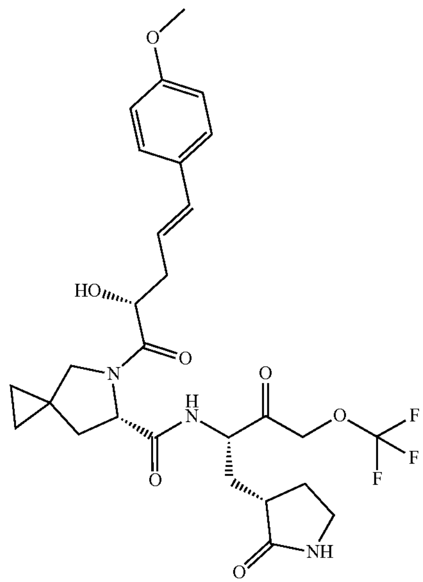 [SMILES: COc1ccc(/C=C/C[C@@H](O)C(=O)N2CC3(CC3)C[C@H]2C(=O)N[C@@H](C[C@@H]2CCNC2=O)C(=O)COC(F)(F)F)cc1] | (S)-5-((R,E)-2-hydroxy-5-(4-methoxyphenyl)pent-4-enoyl)-N-((S)-3-oxo-1-((S)-2-oxopyrrolidin-3-yl)-4-(trifluoromethoxy)butan-2-yl)-5-azaspiro[2.4]heptane-6-carboxamide | 582.3 | *** |

TABLE 1-continued

| Compound | Structure | IUPAC | LCMS [M + 1] | EC50, uM (Hela) |
|---|---|---|---|---|
| 667 | 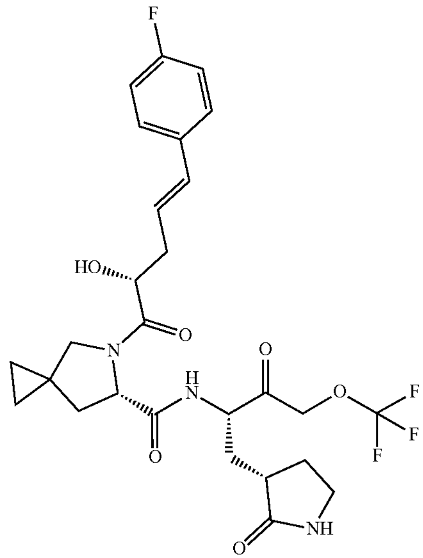 [SMILES: O=C1NCC[C@H]1C[C@H](NC(=O)[C@@H]1CC2(CC2)CN1C(=O)[C@H](O)C/C=C/c1ccc(F)cc1)C(=O)COC(F)(F)F] | (S)-5-((R,E)-5-(4-fluorophenyl)-2-hydroxypent-4-enoyl)-N-((S)-3-oxo-1-((S)-2-oxopyrrolidin-3-yl)-4-(trifluoromethoxy)butan-2-yl)-5-azaspiro[2.4]heptane-6-carboxamide | 570.3 | *** |
| 668 | 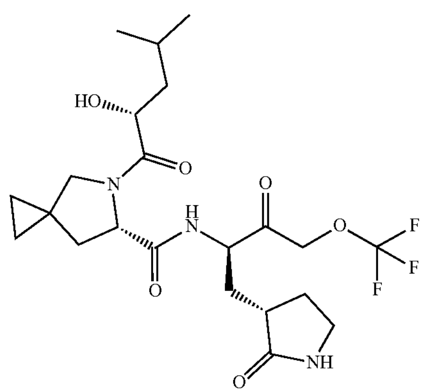 [SMILES: CC(C)C[C@@H](O)C(=O)N1CC2(CC2)C[C@H]1C(=O)N[C@H](C[C@@H]1CCNC1=O)C(=O)COC(F)(F)F] | (S)-5-((R)-2-hydroxy-4-methylpentanoyl)-N-((R)-3-oxo-1-((S)-2-oxopyrrolidin-3-yl)-4-(trifluoromethoxy)butan-2-yl)-5-azaspiro[2.4]heptane-6-carboxamide | 492.3 | *** |

TABLE 1-continued

| Compound | Structure | IUPAC | LCMS [M + 1] | EC50, uM (Hela) |
|---|---|---|---|---|
| 669 | 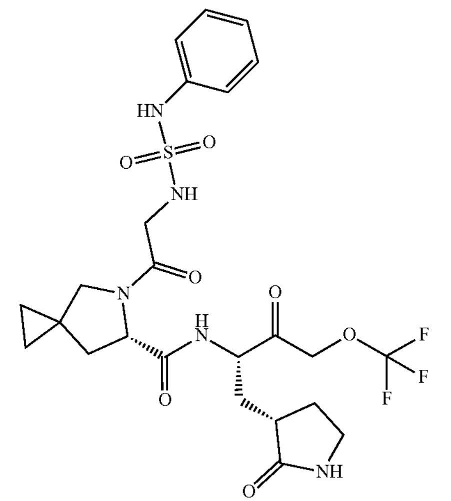 [SMILES: O=C1NCC[C@H]1C[C@H](NC(=O)[C@@H]1CC2(CC2)CN1C(=O)CNS(=O)(=O)Nc1ccccc1)C(=O)COC(F)(F)F] | (S)-N-((S)-3-oxo-1-((S)-2-oxopyrrolidin-3-yl)-4-(trifluoron ethoxy)butan-2-yl)-5-((N-phenyl sulfamoyl)glycyl)-5-azaspiro[2.4]heptane-6-carboxamide | 590.3323 | *** |
| 670 | 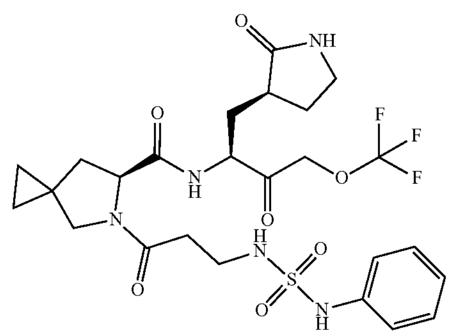 [SMILES: O=C1NCC[C@H]1C[C@H](NC(=O)[C@@H]1CC2(CC2)CN1C(=O)CCNS(=O)(=O)Nc1ccccc1)C(=O)COC(F)(F)F] | (S)-N-((S)-3-oxo-1-((S)-2-oxopyrrolidin-3-yl)-4-(trifluoron ethoxy)butan-2-yl)-5-(3-((N-phenyl sulfamoyl)amino)propanoyl)-5-azaspiro[2.4]heptane-6-carboxamide | 604.3412 | ** |

TABLE 1-continued

| Compound | Structure | IUPAC | LCMS [M + 1] | EC50, uM (Hela) |
|---|---|---|---|---|
| 671 | 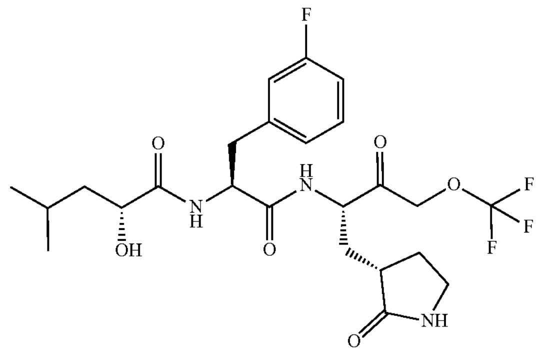 [SMILES: CC(C)C[C@@H](O)C(=O)N[C@@H](Cc1cccc(F)c1)C(=O)N[C@@H](C[C@@H]1CCNC1=O)C(=O)COC(F)(F)F] | (R)-N-((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-2-hydroxy-4-methylpentanamide | 534.3662 | **** |
| 672 | 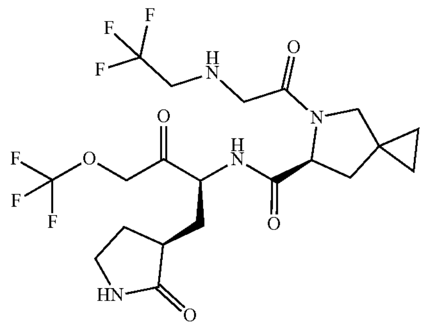 [SMILES: O=C1NCC[C@H]1C[C@H](NC(=O)[C@@H]1CC2(CC2)CN1C(=O)CNCC(F)(F)F)C(=O)COC(F)(F)F] | (S)-N-((S)-3-oxo-1-((S)-2-oxopyrrolidin-3-yl)-4-(trifluorom ethoxy)butan-2-yl)-5-((2,2,2-trifluoroethyl)glycyl)-5-azaspiro[2.4]heptane-6-carboxamide | 517.2 | *** |
| 673 | 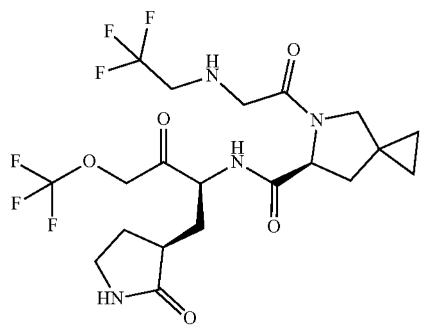 [SMILES: O=C1NCC[C@H]1C[C@H](NC(=O)[C@@H]1CC2(CC2)CN1C(=O)CNCC(F)(F)F)C(=O)COC(F)(F)F] | (S)-N-((S)-3-oxo-1-((S)-2-oxopyrrolidin-3-yl)-4-(trifluorom ethoxy)butan-2-yl)-5-(2-(2,2,2-trifluoroethoxy)acetyl)-5-azaspiro[2.4]heptane-6-carboxamide | 518.3 | *** |

TABLE 1-continued

| Compound | Structure | IUPAC | LCMS [M + 1] | EC50, uM (Hela) |
|---|---|---|---|---|
| 674 | 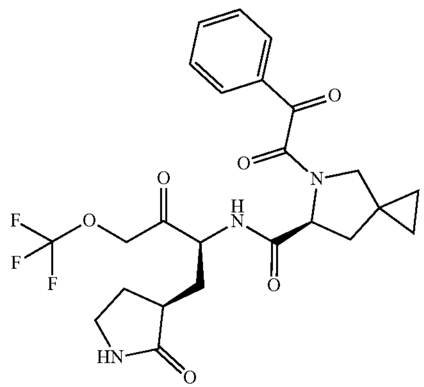 [SMILES: O=C(C(=O)N1CC2(CC2)C[C@H]1C(=O)N[C@@H](C[C@@H]1CCNC1=O)C(=O)COC(F)(F)F)c1ccccc1] | (S)-N-((S)-3-oxo-1-((S)-2-oxopyrrolidin-3-yl)-4-(trifluoron ethoxy)butan-2-yl)-5-(2-oxo-2-phenylacetyl)-5-azaspiro[2.4]heptane-6-carboxamide | 510.2 | *** |
| 675 | 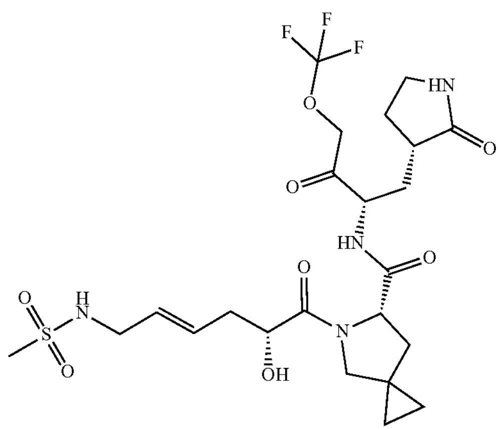 [SMILES: CS(=O)(=O)NC/C=C/C[C@@H](O)C(=O)N1CC2(CC2)C[C@H]1C(=O)N[C@@H](C[C@@H]1CCNC1=O)C(=O)COC(F)(F)F] | (S)-5-((R,E)-2-hydroxy-6-(methylsulfonamido)hex-4-enoyl)-N-((S)-3-oxo-1-((S)-2-oxopyrrolidin-3-yl)-4-(trifluoromethoxy)butan-2-yl)-5-azaspiro[2.4]heptane-6-carboxamide | 583.2 | ** |

TABLE 1-continued

| Compound | Structure | IUPAC | LCMS [M + 1] | EC50, uM (Hela) |
|---|---|---|---|---|
| 676 | 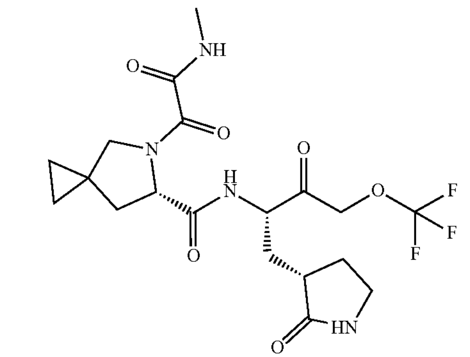 [SMILES: CNC(=O)C(=O)N1CC2(CC2)C[C@H]1C(=O)N[C@@H](C[C@@H]1CCNC1=O)C(=O)COC(F)(F)F] | (S)-5-(2-(methylamino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 463.2584 | *** |
| 677 | 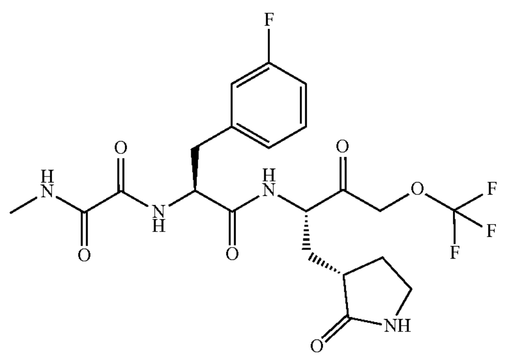 [SMILES: CNC(=O)C(=O)N[C@@H](Cc1cccc(F)c1)C(=O)N[C@@H](C[C@@H]1CCNC1=O)C(=O)COC(F)(F)F] | N1-((S)-3-(3-fluorophenyl)-1-oxo-1-(((S)-3-oxo-1-((S)-2-oxopyrrolidin-3-yl)-4-(trifluoromethoxy)butan-2-yl)amino)propan-2-yl)-N2-methyloxalamide | 505.25 | **** |
| 678 | 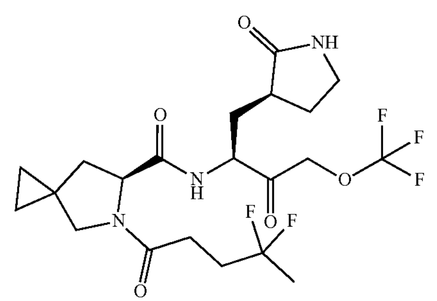 [SMILES: CC(F)(F)CCC(=O)N1CC2(CC2)C[C@H]1C(=O)N[C@@H](C[C@@H]1CCNC1=O)C(=O)COC(F)(F)F] | (S)-5-(4,4-difluoropentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 498.381 | **** |

TABLE 1-continued

| Compound | Structure | IUPAC | LCMS [M + 1] | EC50, uM (Hela) |
|---|---|---|---|---|
| 679 | 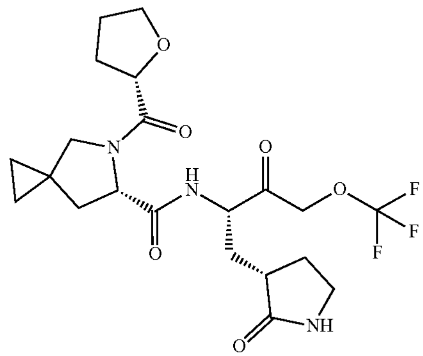 [SMILES: O=C1NCC[C@H]1C[C@H](NC(=O)[C@@H]1CC2(CC2)CN1C(=O)[C@@H]1CCCO1)C(=O)COC(F)(F)F] | (S)-N-((S)-3-oxo-1-((S)-2-oxopyrrolidin-3-yl)-4-(trifluoron ethoxy)butan-2-yl)-5-((S)-tetrahydrofuran-2-carbonyl)-5-azaspiro[2.4]heptane-6-carboxamide | 476.2887 | ** |
| 680 | 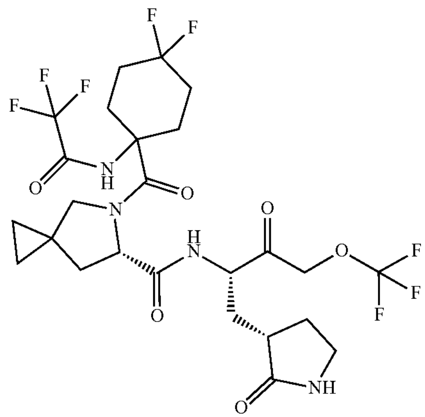 [SMILES: O=C1NCC[C@H]1C[C@H](NC(=O)[C@@H]1CC2(CC2)CN1C(=O)C1(NC(=O)C(F)(F)F)CCC(F)(F)CC1)C(=O)COC(F)(F)F] | (S)-5-(4,4-difluoro-1-(2,2,2-trifluoroacetamido)cyclohexane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 635.2 | ** |

TABLE 1-continued

| Compound | Structure | IUPAC | LCMS [M + 1] | EC50, uM (Hela) |
|---|---|---|---|---|
| 681 | 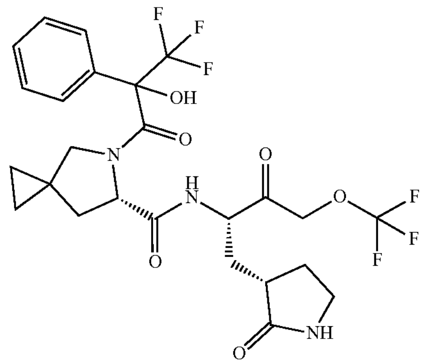 [SMILES: O=C1NCC[C@H]1C[C@H](NC(=O)[C@@H]1CC2(CC2)CN1C(=O)C(O)(c1ccccc1)C(F)(F)F)C(=O)COC(F)(F)F] | (6S)-N-((S)-3-oxo-1-((S)-2-oxopyrrolidin-3-yl)-4-(trifluoromethoxy)butan-2-yl)-5-(3,3,3-trifluoro-2-hydroxy-2-phenyl)propanoyl)-5-azaspiro[2.4]heptane-6-carboxamide | 580.18 | *** |
| 682 | 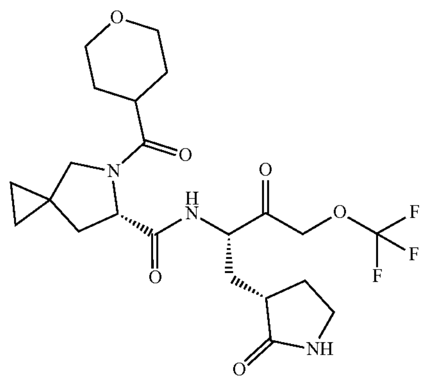 [SMILES: O=C1NCC[C@H]1C[C@H](NC(=O)[C@@H]1CC2(CC2)CN1C(=O)C1CCOCC1)C(=O)COC(F)(F)F] | (S)-N-((S)-3-oxo-1-((S)-2-oxopyrrolidin-3-yl)-4-(trifluorom ethoxy)butan-2-yl)-5-(tetrahydro-2H-pyran-4-carbonyl)-5-azaspiro[2.4]heptane-6-carboxamide | 490.2706 | ** |

TABLE 1-continued

| Compound | Structure | IUPAC | LCMS [M + 1] | EC50, uM (Hela) |
|---|---|---|---|---|
| 683 | 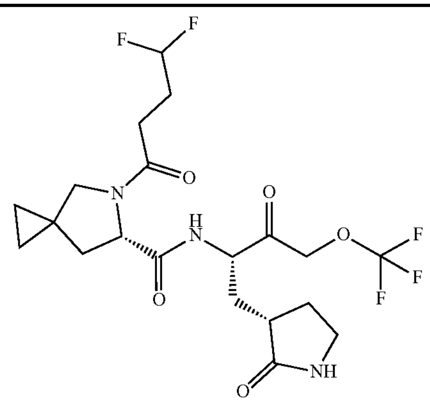 | (S)-5-(4,4-difluorobutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 484.2606 | *** |
| 684 | 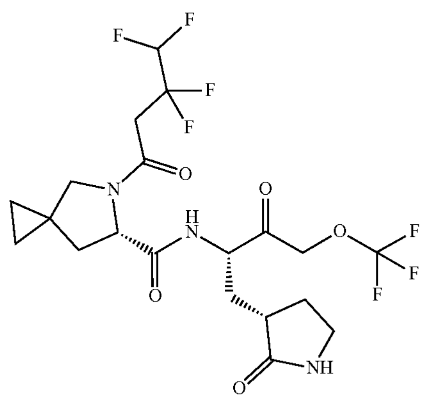 [SMILES: O=C1NCC[C@H]1C[C@H](NC(=O)[C@@H]1CC2(CC2)CN1C(=O)CC(F)(F)C(F)F)C(=O)COC(F)(F)F] | (S)-N-((S)-3-oxo-1-((S)-2-oxopyrrolidin-3-yl)-4-(trifluorom ethoxy)butan-2-yl)-5-(3,3,4,4-tetrafluorobutanoyl)-5-azaspiro[2.4]heptane-6-carboxamide | 520.2473 | *** |

TABLE 1-continued

| Compound | Structure | IUPAC | LCMS [M + 1] | EC50, uM (Hela) |
|---|---|---|---|---|
| 685 | 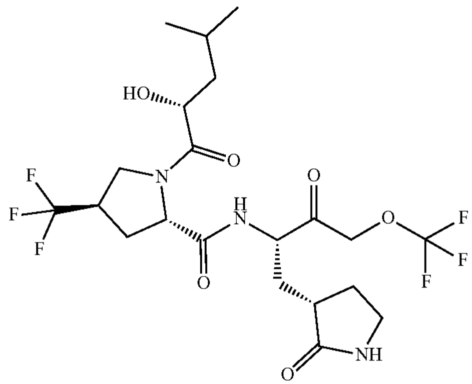 [SMILES: CC(C)C[C@@H](O)C(=O)N1C[C@H](C(F)(F)F)C[C@H]1C(=O)N[C@@H](C[C@@H]1CCNC1=O)C(=O)COC(F)(F)F] | (2S,4R)-1-((R)-2-hydroxy-4-methylpentanoyl)-N-((S)-3-oxo-1-((S)-2-oxopyrrolidin-3-yl)-4-(trifluoromethoxy)butan-2-yl)-4-(trifluoromethyl)pyrrolidine-2-carboxamide | 534.3318 | **** |
| 686 | 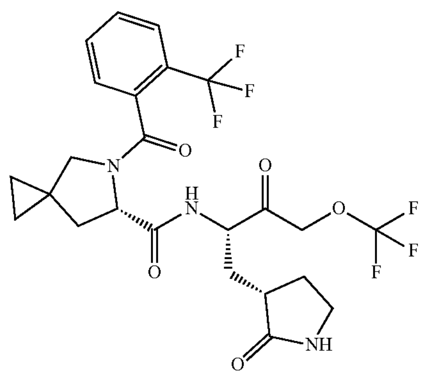 [SMILES: O=C1NCC[C@H]1C[C@H](NC(=O)[C@@H]1CC2(CC2)CN1C(=O)c1ccccc1C(F)(F)F)C(=O)COC(F)(F)F] | (S)-N-((S)-3-oxo-1-((S)-2-oxopyrrolidin-3-yl)-4-(trifluoromethoxy)butan-2-yl)-5-(2-(trifluoromethyl)benzoyl)-5-azaspiro[2.4]heptane-6-carboxamide | 550.2765 | **** |

TABLE 1-continued

| Compound | Structure | IUPAC | LCMS [M + 1] | EC50, uM (Hela) |
|---|---|---|---|---|
| 687 | 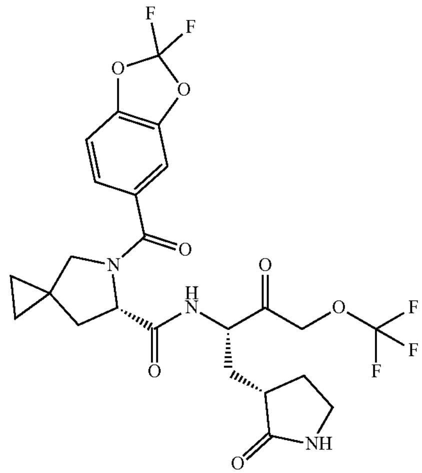 [SMILES: O=C1NCC[C@H]1C[C@H](NC(=O)[C@@H]1CC2(CC2)CN1C(=O)c1ccc2c(c1)OC(F)(F)O2)C(=O)COC(F)(F)F] | (S)-5-(2,2-difluorobenzo[d][1,3]dioxole-5-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 562.2518 | **** |
| 688 | 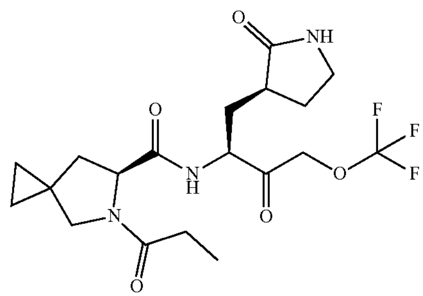 [SMILES: CCC(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-propionyl-5-azaspiro[2.4]heptane-6-carboxamide | 434.18 | *** |
| 689 | 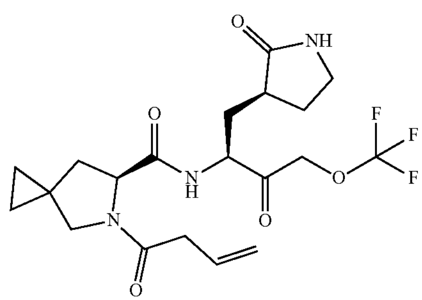 [SMILES: C=CCC(=O)N1CC2(CC2)C[C@H]1C(=O)N[C@@H](C[C@@H]1CCNC1=O)C(=O)COC(F)(F)F] | (S)-5-(but-3-enoyl)-N-((S)-3-oxo-1-((S)-2-oxopyrrolidin-3-yl)-4-(trifluoromethoxy)butan-2-yl)-5-azaspiro[2.4]heptane-6-carboxamide | 446.18 | *** |

TABLE 1-continued

| Compound | Structure | IUPAC | LCMS [M + 1] | EC50, uM (Hela) |
|---|---|---|---|---|
| 690 | 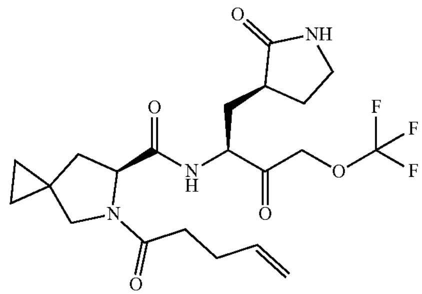 [SMILES: C=CCCC(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluorom ethoxy)butan-2-yl)-5-(pent-4-enoyl)-5-azaspiro[2.4]heptane-6-carboxamide | 460.2 | *** |
| 691 | 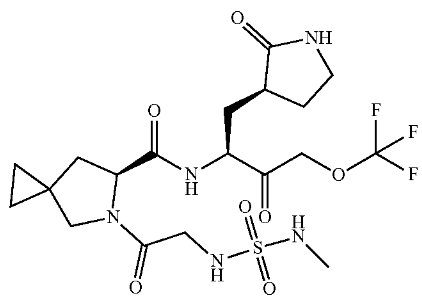 [SMILES: CNS(=O)(=O)NCC(=O)N1CC2(CC2)C[C@H]1C(=O)N[C@@H](C[C@@H]1CCNC1=O)C(=O)COC(F)(F)F] | (S)-5-((N-methylsulfamoyl)glycyl)-N-((S)-3-oxo-1-((S)-2-oxopyrrolidin-3-yl)-4-(trifluoromethoxy)butan-2-yl)-5-azaspiro[2.4]heptane-6-carboxamide | 528.2118 | * |
| 692 | 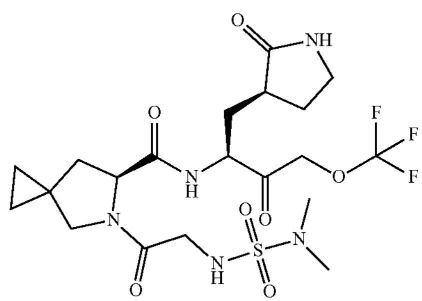 [SMILES: CN(C)S(=O)(=O)NCC(=O)N1CC2(CC2)C[C@H]1C(=O)N[C@@H](C[C@@H]1CCNC1=O)C(=O)COC(F)(F)F] | (S)-5-((N,N-dimethylsulfamoyl)glycyl)-N-((S)-3-oxo-1-((S)-2-oxopyrrolidin-3-yl)-4-(trifluoromethoxy)butan-2-yl)-5-azaspiro[2.4]heptane-6-carboxamide | 542.222 | ** |

TABLE 1-continued

| Compound | Structure | IUPAC | LCMS [M + 1] | EC50, uM (Hela) |
|---|---|---|---|---|
| 693 | 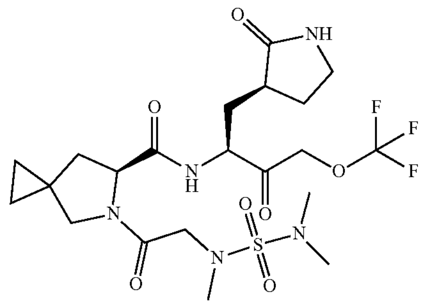 [SMILES: CN(C)S(=O)(=O)N(C)CC(=O)N1CC2(CC2)C[C@H]1C(=O)N[C@@H](C[C@@H]1CCNC1=O)C(=O)COC(F)(F)F] | (S)-5-(N-(N,N-dimethylsulfamoyl)-N-methylglycyl)-N-((S)-3-oxo-1-((S)-2-oxopyrrolidin-3-yl)-4-(trifluoromethoxy)butan-2-yl)-5-azaspiro[2.4]heptane-6-carboxamide | 556.2681 | ** |
| 694 | 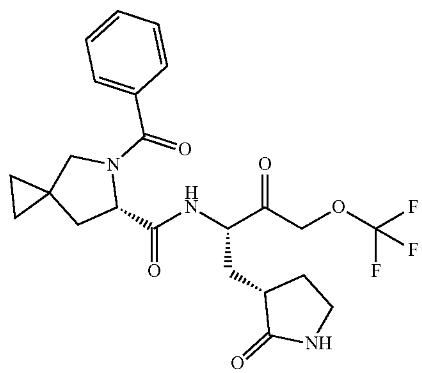 [SMILES: O=C1NCC[C@H]1C[C@H](NC(=O)[C@@H]1CC2(CC2)CN1C(=O)c1ccccc1)C(=O)COC(F)(F)F] | (S)-5-benzoyl-N-((S)-3-oxo-1-((S)-2-oxopyrrolidin-3-yl)-4-(trifluoromethoxy)butan-2-yl)-5-azaspiro[2.4]heptane-6-carboxamide | 482.3445 | *** |

TABLE 1-continued

| Compound | Structure | IUPAC | LCMS [M + 1] | EC50, uM (Hela) |
|---|---|---|---|---|
| 695 | 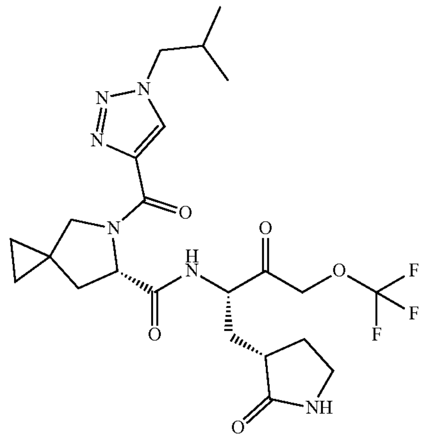 [SMILES: CC(C)Cn1cc(C(=O)N2CC3(CC3)C[C@H]2C(=O)N[C@@H](C[C@@H]2CCNC2=O)C(=O)COC(F)(F)F)nn1] | (S)-5-(1-isobutyl-1H-1,2,3-triazole-4-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 529.2875 | *** |
| 696 | 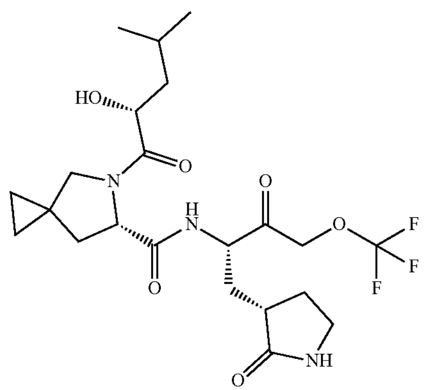 [SMILES: CC(C)C[C@@H](O)C(=O)N1CC2(CC2)C[C@H]1C(=O)N[C@@H](C[C@@H]1CCNC1=O)C(=O)COC(F)(F)F] | (S)-1-((R)-2-hydroxy-4-methylpentanoyl)-N-((S)-3-oxo-1-((S)-2-oxopyrrolidin-3-yl)-4-(trifluoromethoxy)butan-2-yl)pyrrolidine-2-carboxamide | 466.2755 | *** |

TABLE 1-continued

| Compound | Structure | IUPAC | LCMS [M + 1] | EC50, uM (Hela) |
|---|---|---|---|---|
| 697 | 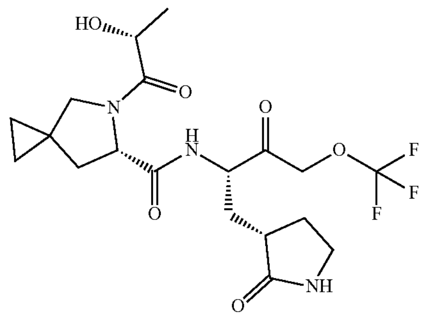 [SMILES: C[C@@H](O)C(=O)N1CC2(CC2)C[C@H]1C(=O)N[C@@H](C[C@@H]1CCNC1=O)C(=O)COC(F)(F)F] | (S)-5-((R)-2-hydroxypropanoyl)-N-((S)-3-oxo-1-((S)-2-oxopyrrolidin-3-yl)-4-(trifluoromethoxy)butan-2-yl)-5-azaspiro[2.4]heptane-6-carboxamide | 450.2 | *** |
| 698 | 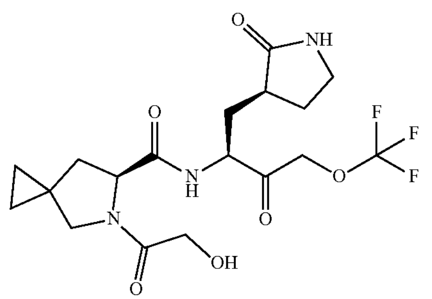 [SMILES: O=C1NCC[C@H]1C[C@H](NC(=O)[C@@H]1CC2(CC2)CN1C(=O)CO)C(=O)COC(F)(F)F] | (S)-5-(2-hydroxy acetyl)-N-((S)-3-oxo-1-((S)-2-oxopyrrolidin-3-yl)-4-(trifluoromethoxy)butan-2-yl)-5-azaspiro[2.4]heptane-6-carboxamide | 436.2 | *** |
| 699 | 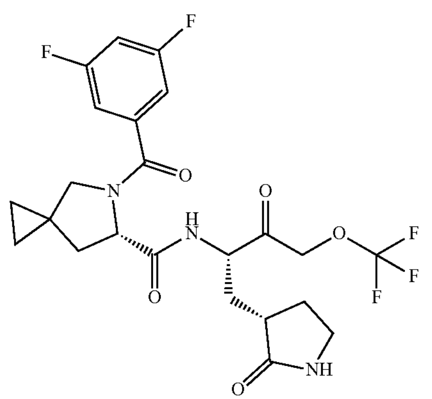 [SMILES: O=C1NCC[C@H]1C[C@H](NC(=O)[C@@H]1CC2(CC2)CN1C(=O)c1cc(F)cc(F)c1)C(=O)COC(F)(F)F] | (S)-5-(3,5-difluorobenzoyl)-N-((S)-3-oxo-1-((S)-2-oxopyrrolidin-3-yl)-4-(trifluoromethoxy)butan-2-yl)-5-azaspiro[2.4]heptane-6-carboxamide | 518.2 | *** |

TABLE 1-continued

| Compound | Structure | IUPAC | LCMS [M + 1] | EC50, uM (Hela) |
|---|---|---|---|---|
| 700 | 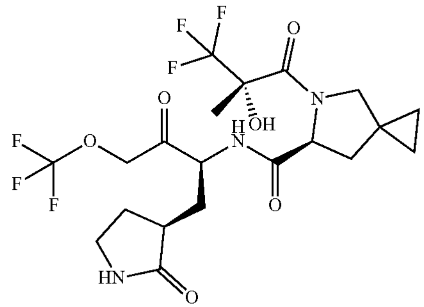 [SMILES: C[C@](O)(C(=O)N1CC2(CC2)C[C@H]1C(=O)N[C@@H](C[C@@H]1CCNC1=O)C(=O)COC(F)(F)F)C(F)(F)F] | (S)-N-((S)-3-oxo-1-((S)-2-oxopyrrolidin-3-yl)-4-(trifluoromethoxy)butan-2-yl)-5-((S)-3,3,3-trifluoro-2-hydroxy-2-methylpropanoyl)-5-azaspiro[2.4]heptane-6-carboxamide | 518.2283 | *** |
| 701 | 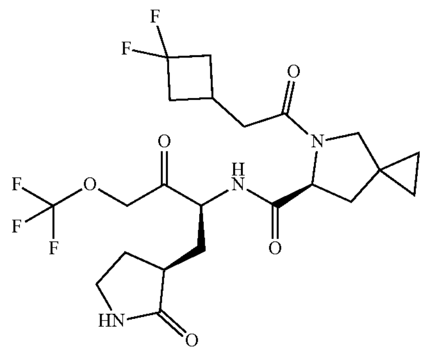 [SMILES: O=C1NCC[C@H]1C[C@H](NC(=O)[C@@H]1CC2(CC2)CN1C(=O)CC1CC(F)(F)C1)C(=O)COC(F)(F)F] | (S)-5-(2-(3,3-difluorocyclobutyl)acetyl)-N-((S)-3-oxo-1-((S)-2-oxopyrrolidin-3-yl)-4-(trifluoromethoxy)butan-2-yl)-5-azaspiro[2.4]heptane-6-carboxamide | 510.2972 | **** |

TABLE 1-continued

| Compound | Structure | IUPAC | LCMS [M + 1] | EC50, uM (Hela) |
|---|---|---|---|---|
| 702 | 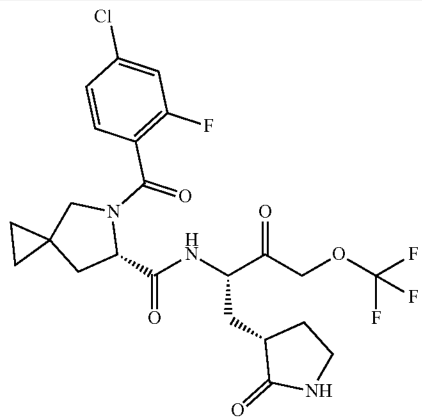 [SMILES: O=C1NCC[C@H]1C[C@H](NC(=O)[C@@H]1CC2(CC2)CN1C(=O)c1ccc(Cl)cc1F)C(=O)COC(F)(F)F] | (S)-5-(4-chloro-2-fluorobenzoyl)-N-((S)-3-oxo-1-((S)-2-oxopyrrolidin-3-yl)-4-(trifluoromethoxy)butan-2-yl)-5-azaspiro[2.4]heptane-6-carboxamide | 524.2314 | *** |
| 703 | 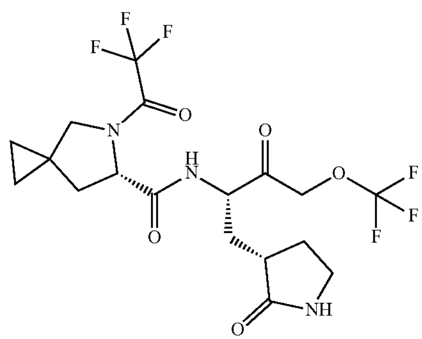 | (S)-N-((S)-3-oxo-1-((S)-2-oxopyrrolidin-3-yl)-4-(trifluorom ethoxy)butan-2-yl)-5-(2,2,2-trifluoroacetyl)-5-azaspiro[2.4]heptane-6-carboxamide | 474.5213 | ** |
| 704 | 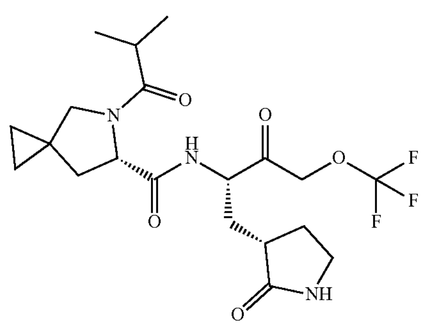 [SMILES: CC(C)C(=O)N1CC2(CC2)C[C@H]1C(=O)N[C@@H](C[C@@H]1CCNC1=O)C(=O)COC(F)(F)F] | (S)-5-isobutyryl-N-((S)-3-oxo-1-((S)-2-oxopyrrolidin-3-yl)-4-(trifluoromethoxy)butan-2-yl)-5-azaspiro[2.4]heptane-6-carboxamide | 448.31 | *** |

TABLE 1-continued

| Compound | Structure | IUPAC | LCMS [M + 1] | EC50, uM (Hela) |
|---|---|---|---|---|
| 705 | 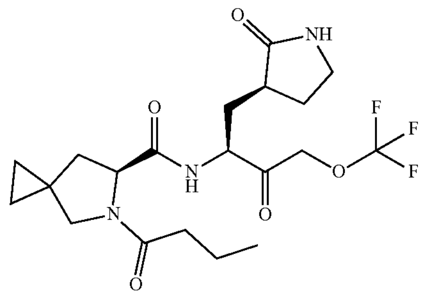 | (S)-5-butyryl-N-((S)-3-oxo-1-((S)-2-oxopyrrolidin-3-yl)-4-(trifluoromethoxy)butan-2-yl)-5-azaspiro[2.4]heptane-6-carboxamide | 448.3 | ** |
| 706 | 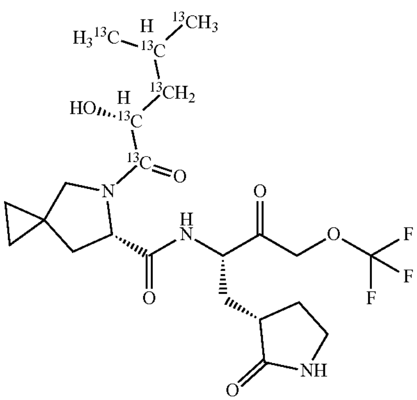 | (S)-5-((R)-2-hydroxy-4-(methyl-13 C)pentanoyl-1,2,3,4,5-13 C5)-N-((S)-3-oxo-1-((S)-2-oxopyrrolidin-3-yl)-4-(trifluoromethoxy)butan-2-yl)-5-azaspiro[2.4]heptane-6-carboxamide | 498.3613 | **** |
| 707 | 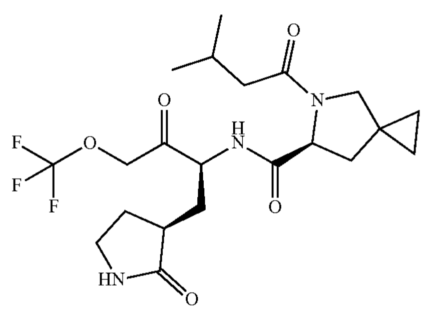 [SMILES: CC(C)CC(=O)N1CC2(CC2)C[C@H]1C(=O)N[C@@H](C[C@@H]1CCNC1=O)C(=O)COC(F)(F)F] | (S)-5-(3-methylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 462.3198 | *** |

TABLE 1-continued

| Compound | Structure | IUPAC | LCMS [M + 1] | EC50, uM (Hela) |
|---|---|---|---|---|
| 708 | 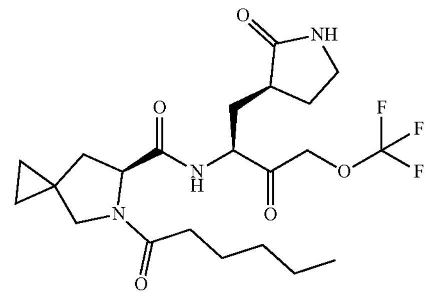 [SMILES: CCCCCC(=O)N1CC2(CC2)C[C@H]1C(=O)N[C@@H](C[C@@H]1CCNC1=O)C(=O)COC(F)(F)F] | (S)-5-hexanoyl-N-((S)-3-oxo-1-((S)-2-oxopyrrolidin-3-yl)-4-(trifluoromethoxy)butan-2-yl)-5-azaspiro[2.4]heptane-6-carboxamide | 476.3055 | *** |
| 709 | 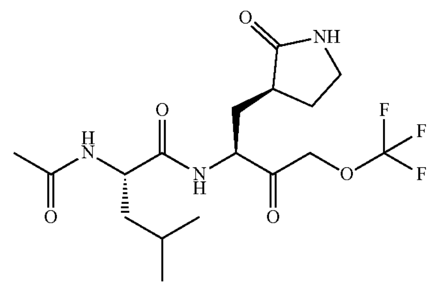 [SMILES: CC(=O)N[C@@H](CC(C)C)C(=O)N[C@@H](C[C@@H]1CCNC1=O)C(=O)COC(F)(F)F] | (S)-2-acetamido-4-methyl-N-((S)-3-oxo-1-((S)-2-oxopyrrolidin-3-yl)-4-(trifluoromethoxy)butan-2-yl)pentanamide | 410.3041 | ** |
| 710 | 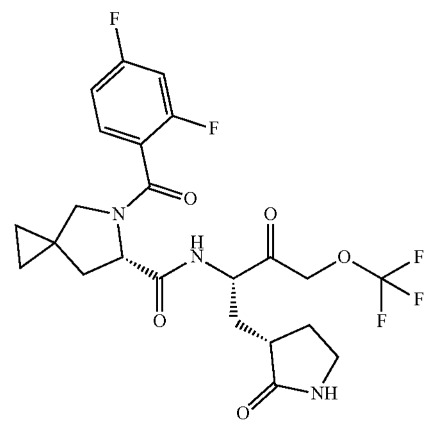 [SMILES: O=C1NCC[C@H]1C[C@H](NC(=O)[C@@H]1CC2(CC2)CN1C(=O)c1ccc(F)cc1F)C(=O)COC(F)(F)F] | (S)-5-(2,4-difluorobenzoyl)-N-((S)-3-oxo-1-((S)-2-oxopyrrolidin-3-yl)-4-(trifluoromethoxy)butan-2-yl)-5-azaspiro[2.4]heptane-6-carboxamide | 518.3 | ** |

TABLE 1-continued

| Compound | Structure | IUPAC | LCMS [M + 1] | EC50, uM (Hela) |
|---|---|---|---|---|
| 711 | 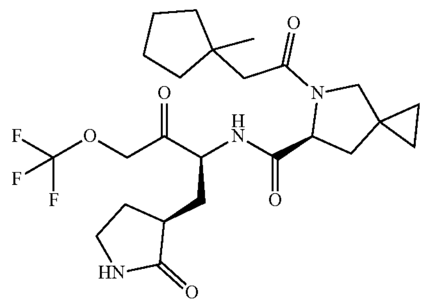 [SMILES: CC1(CC(=O)N2CC3(CC3)C[C@H]2C(=O)N[C@@H](C[C@@H]2CCNC2=O)C(=O)COC(F)(F)F)CCCC1] | (S)-5-(2-(1-methylcyclopentyl)acetyl)-N-((S)-3-oxo-1-((S)-2-oxopyrrolidin-3-yl)-4-(trifluoromethoxy)butan-2-yl)-5-azaspiro[2.4]heptane-6-carboxamide | 502.3266 | **** |
| 712 | 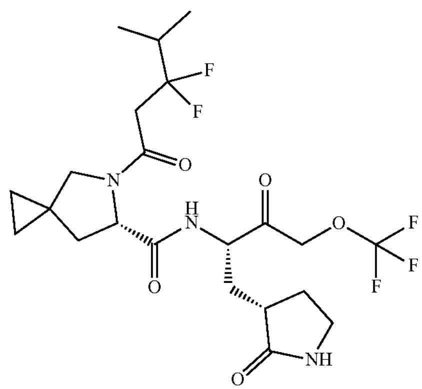 [SMILES: CC(C)C(F)(F)CC(=O)N1CC2(CC2)C[C@H]1C(=O)N[C@@H](C[C@@H]1CCNC1=O)C(=O)COC(F)(F)F] | (S)-5-(3,3-difluoro-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 512.3188 | **** |
| 713 | 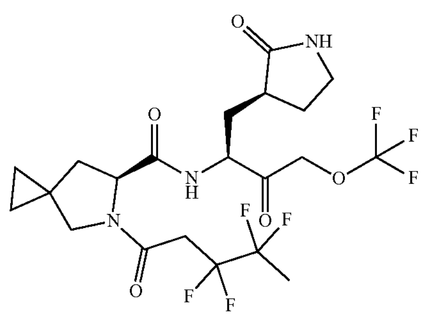 [SMILES: CC(F)(F)C(F)(F)CC(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-(3,3,4,4-tetrafluoropentanoyl)-5-azaspiro[2.4]heptane-6-carboxamide | 534.2938 | *** |

TABLE 1-continued

| Compound | Structure | IUPAC | LCMS [M + 1] | EC50, uM (Hela) |
|---|---|---|---|---|
| 714 | 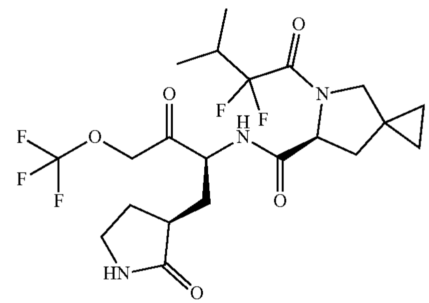 [SMILES: CC(C)C(F)(F)C(=O)N1CC2(CC2)C[C@H]1C(=O)N[C@@H](C[C@@H]1CCNC1=O)C(=O)COC(F)(F)F] | (S)-5-(2,2-difluoro-3-methylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 498.3079 | **** |
| 715 | 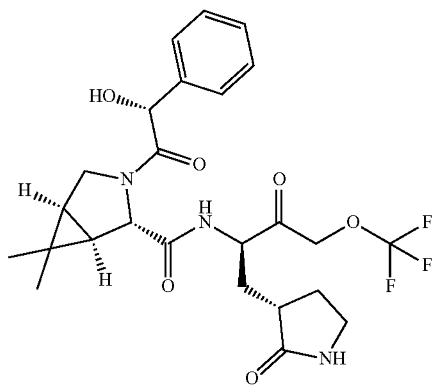 [SMILES: CC1(C)[C@@H]2[C@@H](C(=O)N[C@H](C[C@@H]3CCNC3=O)C(=O)COC(F)(F)F)N(C(=O)[C@H](O)c3ccccc3)C[C@@H]21] | (1R,2S,5S)-3-((R)-2-hydroxy-2-phenylacetyl)-6,6-dimethyl-N-((R)-3-oxo-1-((S)-2-oxopyrrolidin-3-yl)-4-(trifluoromethoxy)butan-2-yl)-3-azabicyclo[3.1.0]hexane-2-carboxamide | 526.21 | *** |

TABLE 1-continued

| Compound | Structure | IUPAC | LCMS [M + 1] | EC50, uM (Hela) |
|---|---|---|---|---|
| 716 | 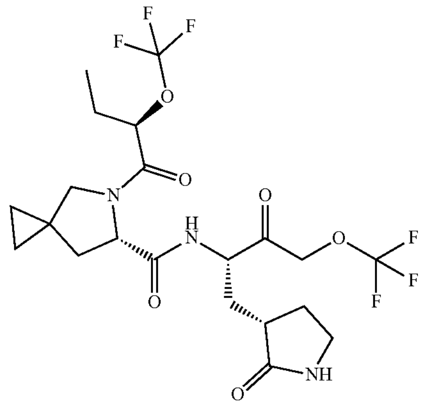 [SMILES: CC[C@@H](OC(F)(F)F)C(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluorom ethoxy)butan-2-yl)-5-((R)-2-(trifluoromethoxy)butanoyl)-5-azaspiro[2.4]heptane-6-carboxamide | 532.18 | *** |
| 717 | 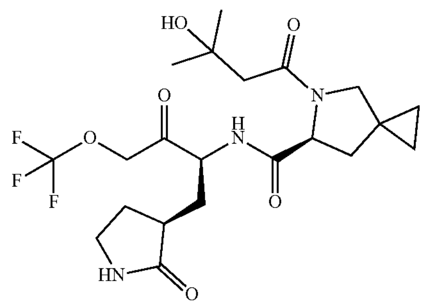 [SMILES: CC(C)(O)CC(=O)N1CC2(CC2)C[C@H]1C(=O)N[C@@H](C[C@@H]1CCNC1=O)C(=O)COC(F)(F)F] | (S)-5-(3-hydroxy-3-methylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 478.3156 | *** |
| 718 | 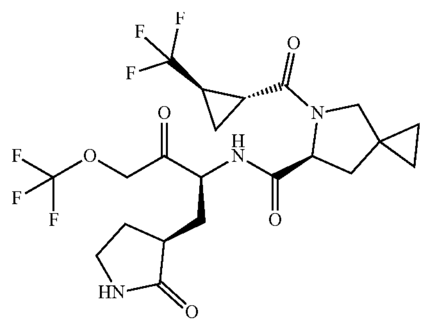 [SMILES: O=C1NCC[C@H]1C[C@H](NC(=O)[C@@H]1CC2(CC2)CN1C(=O)[C@@H]1C[C@H]1C(F)(F)F)C(=O)COC(F)(F)F] | (S)-N-((S)-3-oxo-1-((S)-2-oxopyrrolidin-3-yl)-4-(trifluorom ethoxy)butan-2-yl)-5-((1R,2R)-2-(trifluoromethyl)cyclopropane-1-carbonyl)-5-azaspiro[2.4]heptane-6-carboxamide | 514.2817 | **** |

TABLE 1-continued

| Compound | Structure | IUPAC | LCMS [M + 1] | EC50, uM (Hela) |
|---|---|---|---|---|
| 719 | 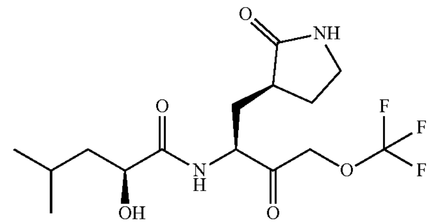 [SMILES: CC(C)C[C@H](O)C(=O)N[C@@H](C[C@@H]1CCNC1=O)C(=O)COC(F)(F)F] | (S)-2-hydroxy-4-methyl-N-((S)-3-oxo-1-((S)-2-oxopyrrolidin-3-yl)-4-(trifluoromethoxy)butan-2-yl)pentanamide | 369.196 | * |
| 720 | 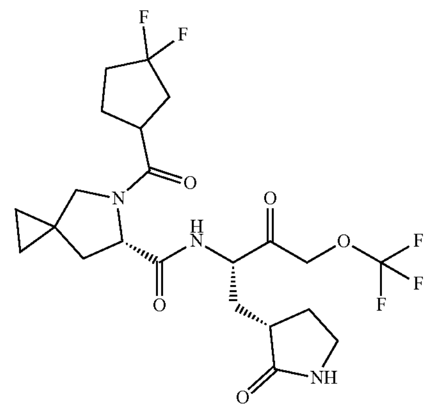 [SMILES: O=C1NCC[C@H]1C[C@H](NC(=O)[C@@H]1CC2(CC2)CN1C(=O)C1CCC(F)(F)C1)C(=O)COC(F)(F)F] | (6S)-5-(3,3-difluorocyclopentane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 510.19 | **** |
| 721 | 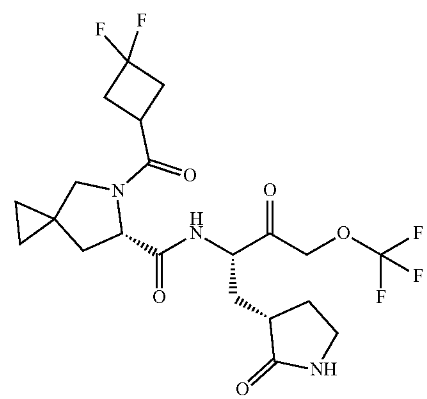 [SMILES: O=C1NCC[C@H]1C[C@H](NC(=O)[C@@H]1CC2(CC2)CN1C(=O)C1CC(F)(F)C1)C(=O)COC(F)(F)F] | (S)-5-(3,3-difluorocyclobutane-1-carbonyl)-N-((S)-3-oxo-1-((S)-2-oxopyrrolidin-3-yl)-4-(trifluoromethoxy)butan-2-yl)-5-azaspiro[2.4]heptane-6-carboxamide | 496.21 | *** |

TABLE 1-continued

| Compound | Structure | IUPAC | LCMS [M + 1] | EC50, uM (Hela) |
|---|---|---|---|---|
| 722 | 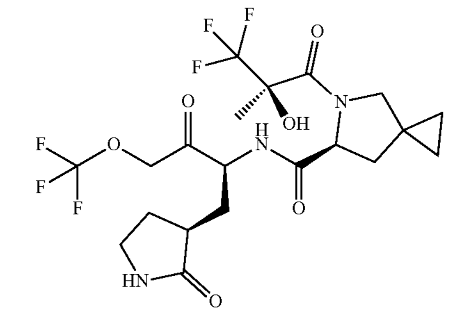 [SMILES: C[C@@](O)(C(=O)N1CC2(CC2)C[C@H]1C(=O)N[C@@H](C[C@@H]1CCNC1=O)C(=O)COC(F)(F)F)C(F)(F)F] | (S)-N-((S)-3-oxo-1-((S)-2-oxopyrrolidin-3-yl)-4-(trifluorom ethoxy)butan-2-yl)-5-((R)-3,3,3-trifluoro-2-hy droxy-2-methylpropanoyl)-5-azaspiro[2.4]heptane-6-carboxamide | 518.1992 | *** |
| 723 | 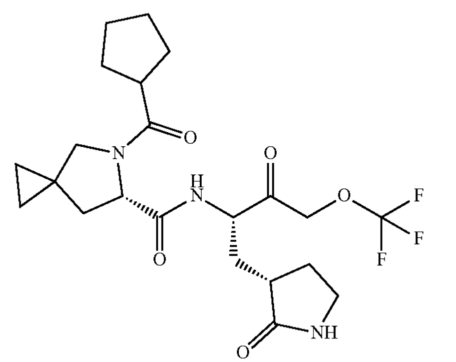 [SMILES: O=C1NCC[C@H]1C[C@H](NC(=O)[C@@H]1CC2(CC2)CN1C(=O)C1CCCC1)C(=O)COC(F)(F)F] | (S)-5-(cyclopentanecarbonyl)-N-((S)-3-oxo-1-((S)-2-oxopyrrolidin-3-yl)-4-(trifluoromethoxy)butan-2-yl)-5-azaspiro[2.4]heptane-6-carboxamide | 474.21 | *** |
| 724 | 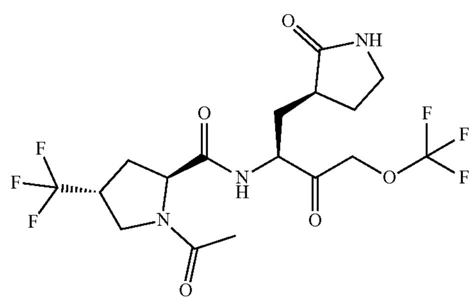 [SMILES: CC(=O)N1C[C@H](C(F)(F)F)C[C@H]1C(=O)N[C@@H](C[C@@H]1CCNC1=O)C(=O)COC(F)(F)F] | (2S,4R)-1-acetyl-N-((S)-3-oxo-1-((S)-2-oxopyrrolidin-3-yl)-4-(trifluoromethoxy)butan-2-yl)-4-(trifluoromethyl)pyrrolidine-2-carboxamide | 462.2227 | *** |

TABLE 1-continued

| Compound | Structure | IUPAC | LCMS [M + 1] | EC50, uM (Hela) |
|---|---|---|---|---|
| 725 | 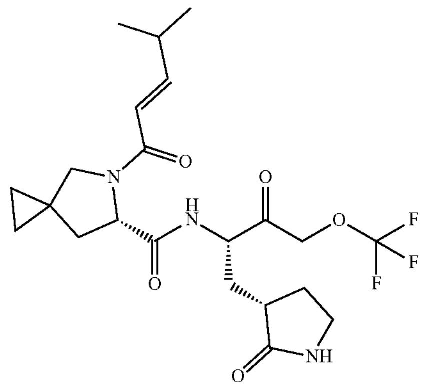 [SMILES: CC(C)/C=C/C(=O)N1CC2(CC2)C[C@H]1C(=O)N[C@@H](C[C@@H]1CCNC1=O)C(=O)COC(F)(F)F] | (S)-5-((E)-4-methylpent-2-enoyl)-N-((S)-3-oxo-1-((S)-2-oxopyrrolidin-3-yl)-4-(trifluoromethoxy)butan-2-yl)-5-azaspiro[2.4]heptane-6-carboxamide | 474.22 | **** |
| 726 | 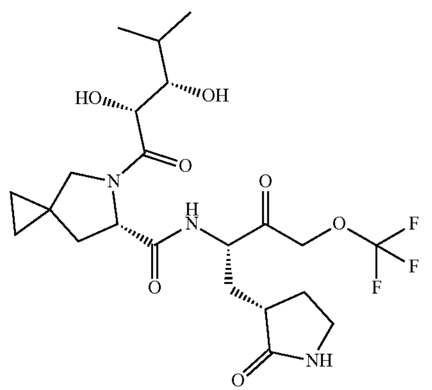 [SMILES: CC(C)[C@H](O)[C@@H](O)C(=O)N1CC2(CC2)C[C@H]1C(=O)N[C@@H](C[C@@H]1CCNC1=O)C(=O)COC(F)(F)F] | (S)-5-((2R,3S)-2,3-dihydroxy-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 508.3475 | ** |

TABLE 1-continued

| Compound | Structure | IUPAC | LCMS [M + 1] | EC50, uM (Hela) |
|---|---|---|---|---|
| 727 | 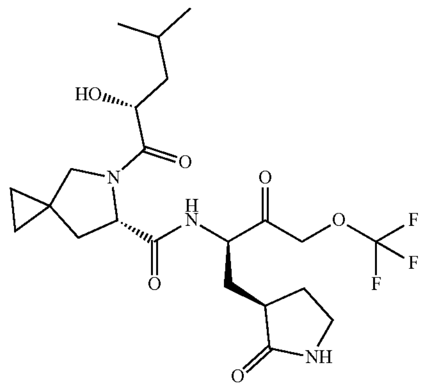 [SMILES: CC(C)C[C@@H](O)C(=O)N1CC2(CC2)C[C@H]1C(=O)N[C@H](C[C@H]1CCNC1=O)C(=O)COC(F)(F)F] | (S)-5-((R)-2-hydroxy-4-methylpentanoyl)-N-((R)-3-oxo-1-((R)-2-oxopyrrolidin-3-yl)-4-(trifluoromethoxy)butan-2-yl)-5-azaspiro[2.4]heptane-6-carboxamide | 492.379 | *** |
| 728 | 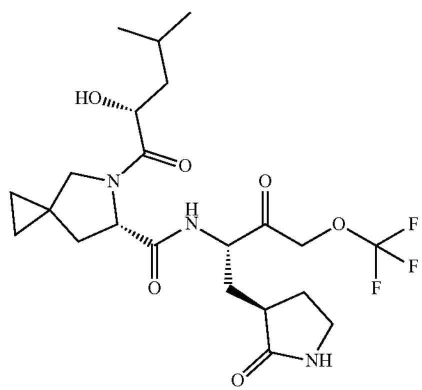 [SMILES: CC(C)C[C@@H](O)C(=O)N1CC2(CC2)C[C@H]1C(=O)N[C@@H](C[C@H]1CCNC1=O)C(=O)COC(F)(F)F] | (S)-5-((R)-2-hydroxy-4-methylpentanoyl)-N-((S)-3-oxo-1-((R)-2-oxopyrrolidin-3-yl)-4-(trifluoromethoxy)butan-2-yl)-5-azaspiro[2.4]heptane-6-carboxamide | 492.3795 | *** |

TABLE 1-continued

| Compound | Structure | IUPAC | LCMS [M + 1] | EC50, uM (Hela) |
|---|---|---|---|---|
| 729 | 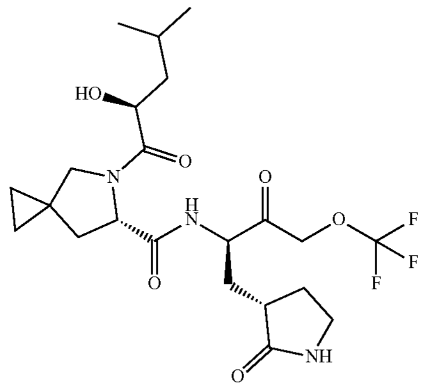 [SMILES: CC(C)C[C@H](O)C(=O)N1CC2(CC2)C[C@H]1C(=O)N[C@H](C[C@@H]1CCNC1=O)C(=O)COC(F)(F)F] | (S)-5-((S)-2-hydroxy-4-methylpentanoyl)-N-((R)-3-oxo-1-((S)-2-oxopyrrolidin-3-yl)-4-(trifluoromethoxy)butan-2-yl)-5-azaspiro[2.4]heptane-6-carboxamide | 492.42 | *** |
| 730 | 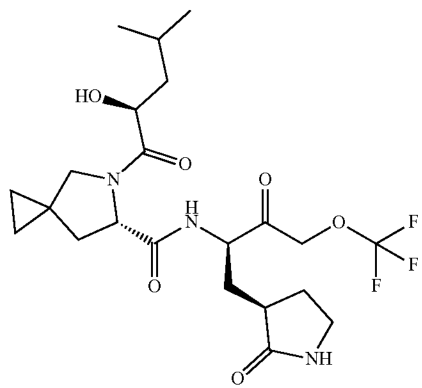 [SMILES: CC(C)C[C@H](O)C(=O)N1CC2(CC2)C[C@H]1C(=O)N[C@H](C[C@H]1CCNC1=O)C(=O)COC(F)(F)F] | (S)-5-((S)-2-hydroxy-4-methylpentanoyl)-N-((R)-3-oxo-1-((R)-2-oxopyrrolidin-3-yl)-4-(trifluoromethoxy)butan-2-yl)-5-azaspiro[2.4]heptane-6-carboxamide | 492.42 | ** |

TABLE 1-continued

| Compound | Structure | IUPAC | LCMS [M + 1] | EC50, uM (Hela) |
|---|---|---|---|---|
| 731 | 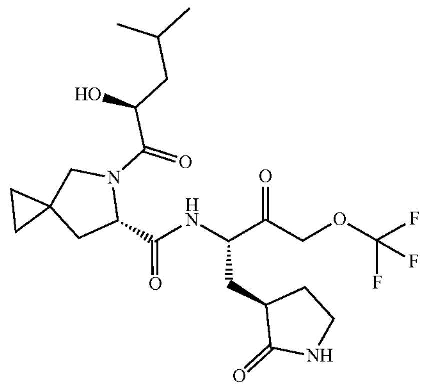 [SMILES: CC(C)C[C@H](O)C(=O)N1CC2(CC2)C[C@H]1C(=O)N[C@@H](C[C@H]1CCNC1=O)C(=O)COC(F)(F)F] | (S)-5-((S)-2-hydroxy-4-methylpentanoyl)-N-((S)-3-oxo-1-((R)-2-oxopyrrolidin-3-yl)-4-(trifluoromethoxy)butan-2-yl)-5-azaspiro[2.4]heptane-6-carboxamide | 492.6 | *** |
| 732 | 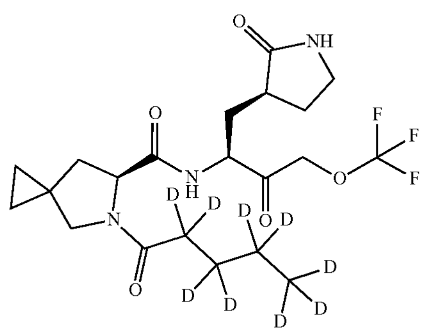 [SMILES: [2H]C([2H])([2H])C([2H])([2H])C([2H])([2H])C([2H])([2H])C(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-(pentanoyl-d9)-5-azaspiro[2.4]heptane-6-carboxamide | 471.27 | **** |
| 733 | 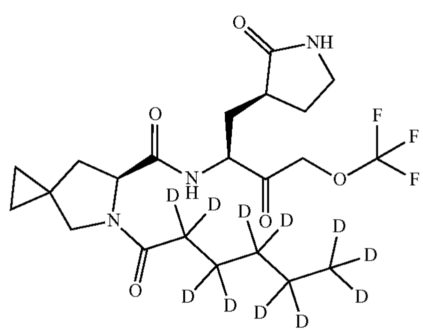 [SMILES: [2H]C([2H])([2H])C([2H])([2H])C([2H])([2H])C([2H])([2H])C([2H])([2H])C(=O)N1CC2(CC2)C[C@H]1C(=O)N[C@@H](C[C@@H]1CCNC1=O)C(=O)COC(F)(F)F] | (S)-5-(hexanoyl-d 11)-N-((S)-3-oxo-1-((S)-2-oxopyrrolidin-3-yl)-4-(trifluoromethoxy)butan-2-yl)-5-azaspiro[2.4]heptane-6-carboxamide | 487.4104 | **** |

TABLE 1-continued

| Compound | Structure | IUPAC | LCMS [M + 1] | EC50, uM (Hela) |
|---|---|---|---|---|
| 734 | 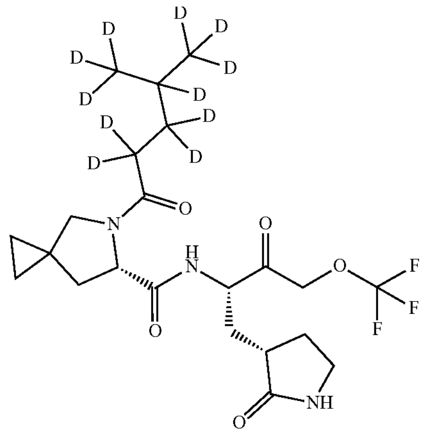 [SMILES: [2H]C([2H])([2H])C([2H])(C([2H])([2H])[2H])C([2H])([2H])C([2H])([2H])C(=O)N1CC2(CC2)C[C@H]1C(=O)N[C@@H](C[C@@H]1CCNC1=O)C(=O)COC(F)(F)F] | (S)-5-(4-(methyl-d3)pentanoyl-2,2,3,3,4,5,5,5-d8)-N-((S)-3-oxo-1-((S)-2-oxopyrrolidin-3-yl)-4-(trifluoromethoxy)butan-2-yl)-5-azaspiro[2.4]heptane-6-carboxamide | 487.4104 | **** |
| 735 | 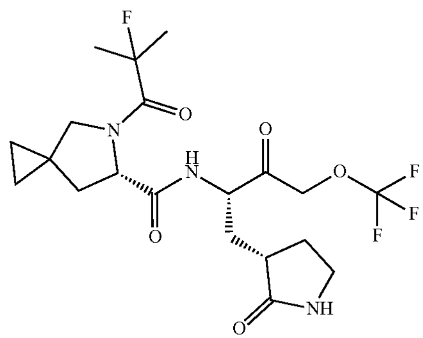 | (S)-5-(2-fluoro-2-methylpropanoyl)-N-((S)-3-oxo-1-((S)-2-oxopyrrolidin-3-yl)-4-(trifluoromethoxy)butan-2-yl)-5-azaspiro[2.4]heptane-6-carboxamide | 466.3025 | **** |

TABLE 1-continued

| Compound | Structure | IUPAC | LCMS [M + 1] | EC50, uM (Hela) |
|---|---|---|---|---|
| 736 | 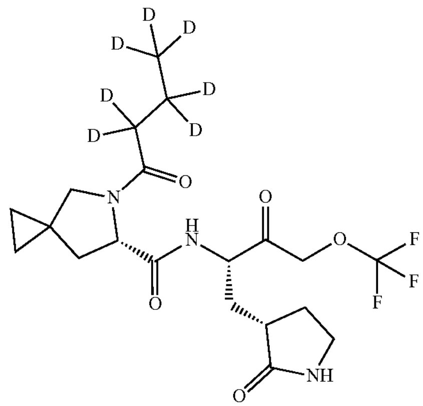 [SMILES: [2H]C([2H])([2H])C([2H])([2H])C([2H])([2H])C(=O)N1CC2(CC2)C[C@H]1C(=O)N[C@@H](C[C@@H]1CCNC1=O)C(=O)COC(F)(F)F] | (S)-5-(butanoyl-d7)-N-((S)-3-oxo-1-((S)-2-oxopyrrolidin-3-yl)-4-(trifluoromethoxy)butan-2-yl)-5-azaspiro[2.4]heptane-6-carboxamide | 455.3319 | **** |
| 737 | 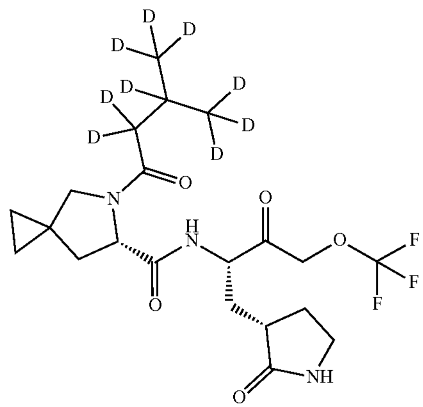 [SMILES: [2H]C([2H])([2H])C([2H])(C([2H])([2H])[2H])C([2H])([2H])C(=O)N1CC2(CC2)C[C@H]1C(=O)N[C@@H](C[C@@H]1CCNC1=O)C(=O)COC(F)(F)F] | (S)-5-(3-(methyl-d3)butanoyl-2,2,3,4,4,4-d6)-N-((S)-3-oxo-1-((S)-2-oxopyrrolidin-3-yl)-4-(trifluoromethoxy)butan-2-yl)-5-azaspiro[2.4]heptane-6-carboxamide | 471.3714 | **** |

TABLE 1-continued

| Compound | Structure | IUPAC | LCMS [M + 1] | EC50, uM (Hela) |
|---|---|---|---|---|
| 738 | 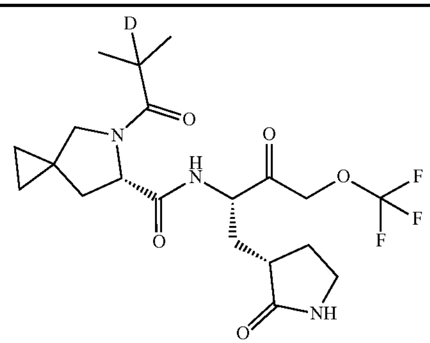 | (S)-5-(2-methylpropanoyl-2-d)-N-((S)-3-oxo-1-((S)-2-oxopyrrolidin-3-yl)-4-(trifluoromethoxy)butan-2-yl)-5-azaspiro[2.4]heptane-6-carboxamide | 449.2852 | *** |
| 739 | 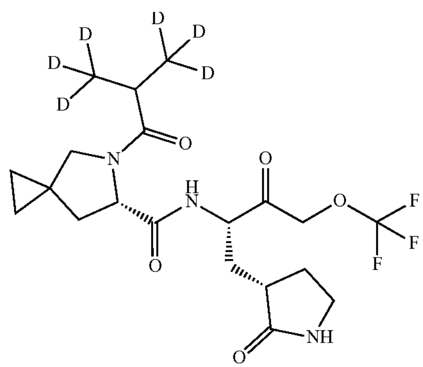 [SMILES: [2H]C([2H])([2H])C(C(=O)N1CC2(CC2)C[C@H]1C(=O)N[C@@H](C[C@@H]1CCNC1=O)C(=O)COC(F)(F)F)C([2H])([2H])[2H]] | (S)-5-(2-(methyl-d3)propanoyl-3,3,3-d3)-N-((S)-3-oxo-1-((S)-2-oxopyrrolidin-3-yl)-4-(trifluoromethoxy)butan-2-yl)-5-azaspiro[2.4]heptane-6-carboxamide | 454.3181 | *** |
| 740 | 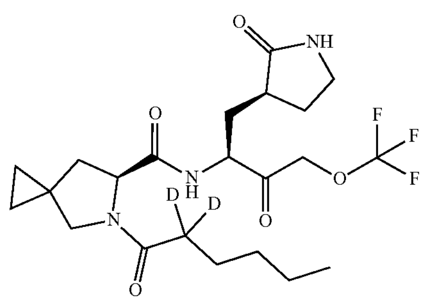 [SMILES: [2H]C([2H])(CCCC)C(=O)N1CC2(CC2)C[C@H]1C(=O)N[C@@H](C[C@@H]1CCNC1=O)C(=O)COC(F)(F)F] | (S)-5-(hexanoyl-2,2-d2)-N-((S)-3-oxo-1-((S)-2-oxopyrrolidin-3-yl)-4-(trifluoromethoxy)butan-2-yl)-5-azaspiro[2.4]heptane-6-carboxamide | 478.3591 | **** |

TABLE 1-continued

| Compound | Structure | IUPAC | LCMS [M + 1] | EC50, uM (Hela) |
|---|---|---|---|---|
| 741 | 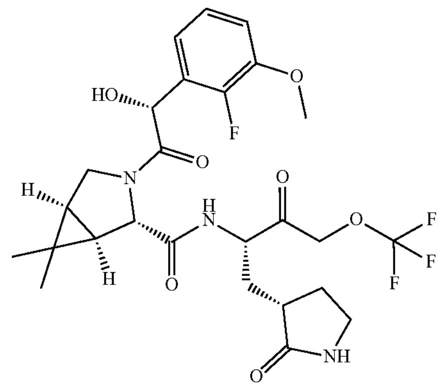 [SMILES: COc1cccc([C@@H](O)C(=O)N2C[C@H]3[C@@H]([C@H]2C(=O)N[C@@H](C[C@@H]2CCNC2=O)C(=O)COC(F)(F)F)C3(C)C)c1F] | (1R,2S,5S)-3-((R)-2-(2-fluoro-3-methoxyphenyl)-2-hydroxyacetyl)-6,6-dimethyl-N-((S)-3-oxo-1-((S)-2-oxopyrrolidin-3-yl)-4-(trifluoromethoxy)butan-2-yl)-3-azabicyclo[3.1.0]hexane-2-carboxamide | 574.37 | **** |
| 742 | 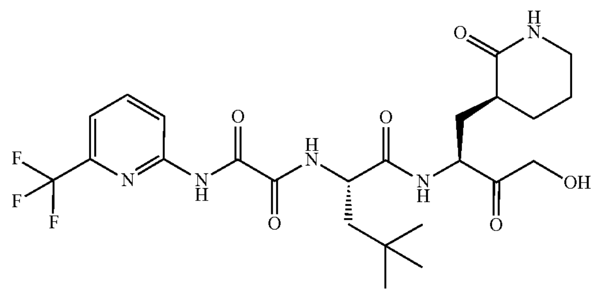 [SMILES: CC(C)(C)C[C@H](NC(=O)C(=O)Nc1cccc(C(F)(F)F)n1)C(=O)N[C@@H](C[C@@H]1CCCNC1=O)C(=O)CO] | N1-((S)-1-(((S)-4-hydroxy-3-oxo-1-((S)-2-oxopiperidin-3-yl)butan-2-yl)amino)-4,4-dimethyl-1-oxopentan-2-yl)-N2-(6-(trifluoromethyl)pyridin-2-yl)oxalamide | 544.36 | ** |

TABLE 1-continued

| Compound | Structure | IUPAC | LCMS [M + 1] | EC50, uM (Hela) |
|---|---|---|---|---|
| 743 | 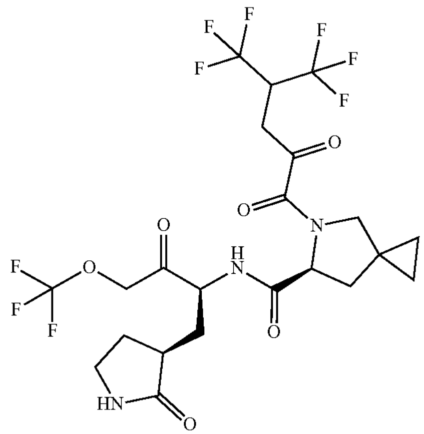 [SMILES: O=C(CC(C(F)(F)F)C(F)(F)F)C(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluoromethoxy)butan-2-yl)-5-(5,5,5-trifluoro-2-oxo-4-(trifluoromethyl)pentanoyl)-5-azaspiro[2.4]heptane-6-carboxamide | 598.15 | **** |
| 744 | 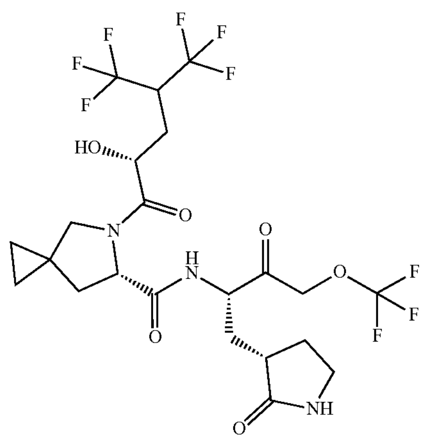 [SMILES: O=C1NCC[C@H]1C[C@H](NC(=O)[C@@H]1CC2(CC2)CN1C(=O)[C@H](O)CC(C(F)(F)F)C(F)(F)F)C(=O)COC(F)(F)F] | (S)-N-((S)-3-oxo-1-((S)-2-oxopyrrolidin-3-yl)-4-(trifluorom ethoxy)butan-2-yl)-5-((R)-5,5,5-trifluoro-2-hydroxy-4-(trifluoromethyl)pentanoyl)-5-azaspiro[2.4]heptane-6-carboxamide | 600.3 | **** |

TABLE 1-continued

| Compound | Structure | IUPAC | LCMS [M + 1] | EC50, uM (Hela) |
|---|---|---|---|---|
| 745 | 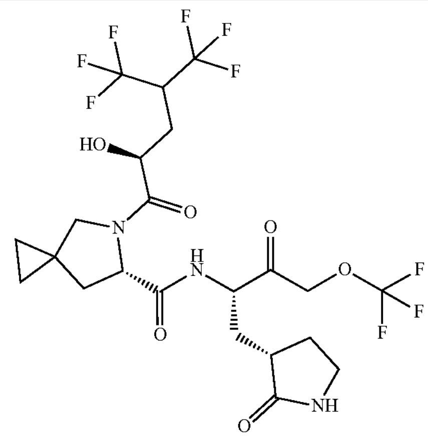 [SMILES: O=C1NCC[C@H]1C[C@H](NC(=O)[C@@H]1CC2(CC2)CN1C(=O)[C@@H](O)CC(C(F)(F)F)C(F)(F)F)C(=O)COC(F)(F)F] | (S)-N-((S)-3-oxo-1-((S)-2-oxopyrrolidin-3-yl)-4-(trifluoromethoxy)butan-2-yl)-5-((S)-5,5,5-trifluoro-2-hydroxy-4-(trifluoromethyl)pentanoyl)-5-azaspiro[2.4]heptane-6-carboxamide | 600.17 | **** |
| 746 | 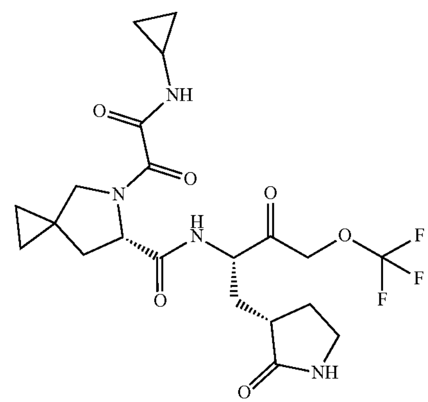 [SMILES: O=C(NC1CC1)C(=O)N1CC2(CC2)C[C@H]1C(=O)N[C@@H](C[C@@H]1CCNC1=O)C(=O)COC(F)(F)F] | (S)-5-(2-(cyclopropylamino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 489.29 | *** |

TABLE 1-continued

| Compound | Structure | IUPAC | LCMS [M + 1] | EC50, uM (Hela) |
|---|---|---|---|---|
| 747 | 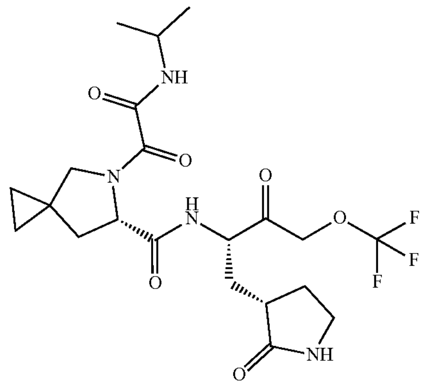 [SMILES: CC(C)NC(=O)C(=O)N1CC2(CC2)C[C@H]1C(=O)N[C@@H](C[C@@H]1CCNC1=O)C(=O)COC(F)(F)F] | (S)-5-(2-(isopropylamino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 491.2 | **** |
| 748 | 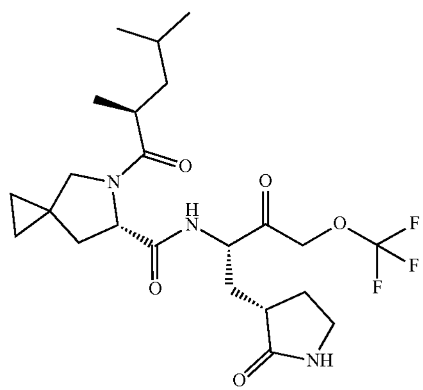 [SMILES: CC(C)C[C@H](C)C(=O)N1CC2(CC2)C[C@H]1C(=O)N[C@@H](C[C@@H]1CCNC1=O)C(=O)COC(F)(F)F] | (S)-5-((S)-2,4-dimethylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 490.3872 | *** |

TABLE 1-continued

| Compound | Structure | IUPAC | LCMS [M + 1] | EC50, uM (Hela) |
|---|---|---|---|---|
| 749 | 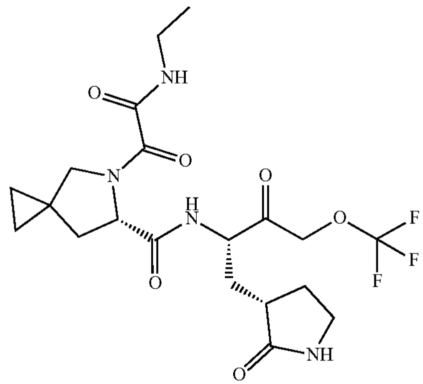 [SMILES: CCNC(=O)C(=O)N1CC2(CC2)C[C@H]1C(=O)N[C@@H](C[C@@H]1CCNC1=O)C(=O)COC(F)(F)F] | (S)-5-(2-(ethylamino)-2-oxoacetyl)-N-((S)-3-oxo-1-((S)-2-oxopyrrolidin-3-yl)-4-(trifluoromethoxy)butan-2-yl)-5-azaspiro[2.4]heptane-6-carboxamide | 477.19 | *** |
| 750 | 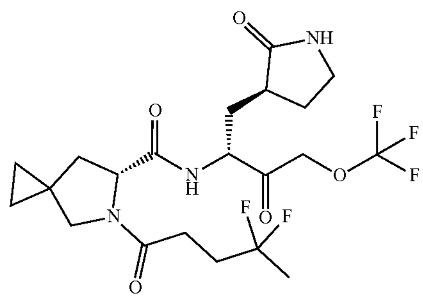 [SMILES: CC(F)(F)CCC(=O)N1CC2(CC2)C[C@@H]1C(=O)N[C@H](C[C@@H]1CCNC1=O)C(=O)COC(F)(F)F] | (R)-5-(4,4-difluoropentanoyl)-N-((R)-3-oxo-1-((S)-2-oxopyrrolidin-3-yl)-4-(trifluoromethoxy)butan-2-yl)-5-azaspiro[2.4]heptane-6-carboxamide | 498.2615 | *** |
| 751 | 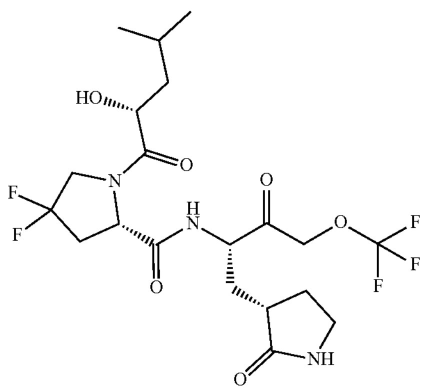 [SMILES: CC(C)C[C@@H](O)C(=O)N1CC(F)(F)C[C@H]1C(=O)N[C@@H](C[C@@H]1CCNC1=O)C(=O)COC(F)(F)F] | (S)-4,4-difluoro-1-((R)-2-hydroxy-4-methylpentanoyl)-N-((S)-3-oxo-1-((S)-2-oxopyrrolidin-3-yl)-4-(trifluoromethoxy)butan-2-yl)pyrrolidine-2-carboxamide | 502.19 | *** |

TABLE 1-continued

| Compound | Structure | IUPAC | LCMS [M + 1] | EC50, uM (Hela) |
|---|---|---|---|---|
| 752 | 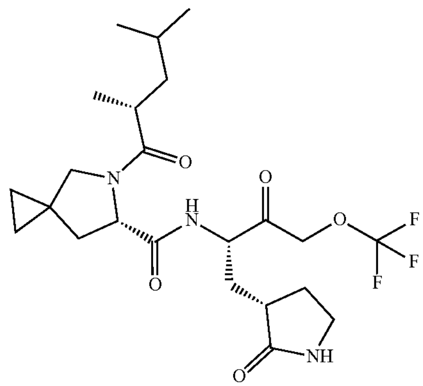 [SMILES: CC(C)C[C@@H](C)C(=O)N1CC2(CC2)C[C@H]1C(=O)N[C@@H](C[C@@H]1CCNC1=O)C(=O)COC(F)(F)F] | (S)-5-((R)-2,4-dimethylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 490.3944 | **** |
| 753 | 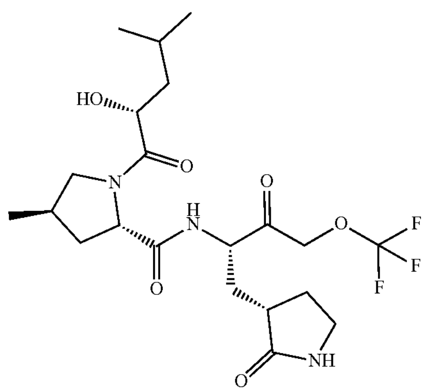 [SMILES: CC(C)C[C@@H](O)C(=O)N1C[C@H](C)C[C@H]1C(=O)N[C@@H](C[C@@H]1CCNC1=O)C(=O)COC(F)(F)F] | (2S,4R)-1-((R)-2-hydroxy-4-methylpentanoyl)-4-methyl-N-((S)-3-oxo-1-((S)-2-oxopyrrolidin-3-yl)-4-(trifluoromethoxy)butan-2-yl)pyrrolidine-2-carboxamide | 480.3395 | **** |

TABLE 1-continued

| Compound | Structure | IUPAC | LCMS [M + 1] | EC50, uM (Hela) |
|---|---|---|---|---|
| 754 | 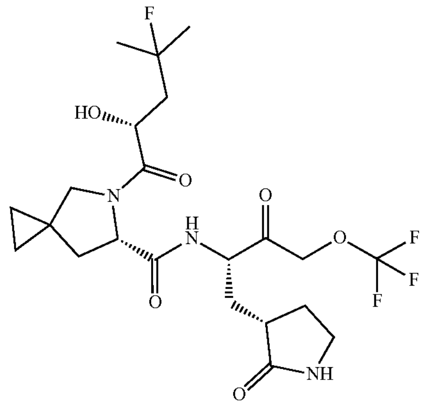 [SMILES: CC(C)(F)C[C@@H](O)C(=O)N1CC2(CC2)C[C@H]1C(=O)N[C@@H](C[C@@H]1CCNC1=O)C(=O)COC(F)(F)F] | (S)-5-((R)-4-fluoro-2-hydroxy-4-methylpentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 510.0742 | *** |
| 755 | 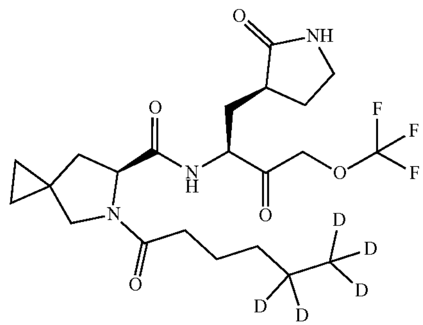 [SMILES: [2H]C([2H])([2H])C([2H])([2H])CCCC(=O)N1CC2(CC2)C[C@H]1C(=O)N[C@@H](C[C@@H]1CCNC1=O)C(=O)COC(F)(F)F] | (S)-5-(hexanoyl-5,5,6,6,6-d5)-N-((S)-3-oxo-1-((S)-2-oxopyrrolidin-3-yl)-4-(trifluoromethoxy)butan-2-yl)-5-azaspiro[2.4]heptane-6-carboxamide | 481.63 | **** |
| 756 | 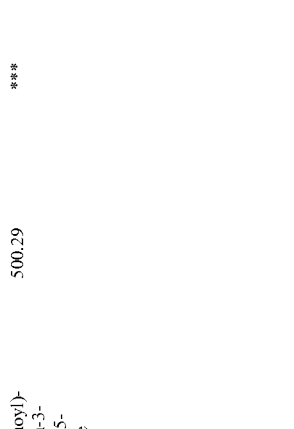 | (6S)-5-(2,2-difluoro-3-hydroxybutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 500.29 | *** |

TABLE 1-continued

| Compound | Structure | IUPAC | LCMS [M + 1] | EC50, uM (Hela) |
|---|---|---|---|---|
| 757 | 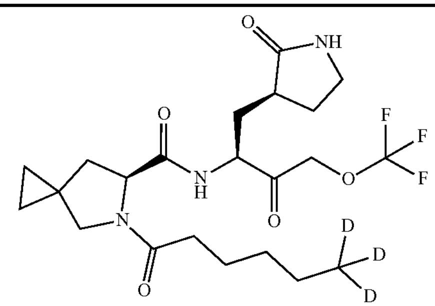 | (S)-5-(hexanoyl-6,6,6-d3)-N-((S)-3-oxo-1-((S)-2-oxopyrrolidin-3-yl)-4-(trifluoromethoxy)butan-2-yl)-5-azaspiro[2.4]heptane-6-carboxamide | 479.25 | **** |
| 758 | 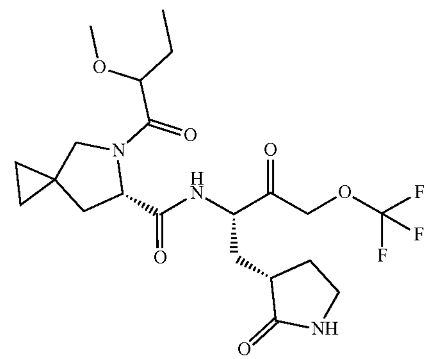 [SMILES: CCC(OC)C(=O)N1CC2(CC2)C[C@H]1C(=O)N[C@@H](C[C@@H]1CCNC1=O)C(=O)COC(F)(F)F] | (6S)-5-(2-methoxybutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 478.21 | ** |
| 759 | 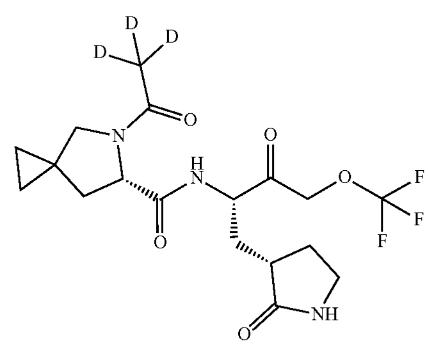 [SMILES: [2H]C([2H])([2H])C(=O)N1CC2(CC2)C[C@H]1C(=O)N[C@@H](C[C@@H]1CCNC1=O)C(=O)COC(F)(F)F] | (S)-5-(acetyl-d3)-N-((S)-3-oxo-1-((S)-2-oxopyrrolidin-3-yl)-4-(trifluoromethoxy)butan-2-yl)-5-azaspiro[2.4]heptane-6-carboxamide | 423.19 | ** |

TABLE 1-continued

| Compound | Structure | IUPAC | LCMS [M + 1] | EC50, uM (Hela) |
|---|---|---|---|---|
| 760 | 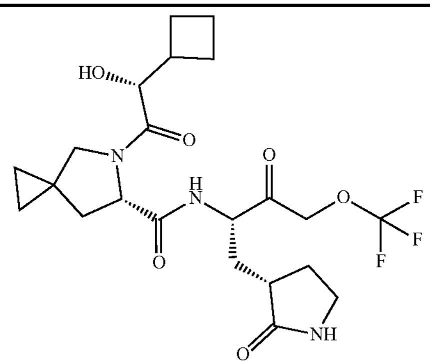 | (S)-5-((R)-2-cyclobutyl-2-hydroxyacetyl)-N-((S)-3-oxo-1-((S)-2-oxopyrrolidin-3-yl)-4-(trifluoromethoxy)butan-2-yl)-5-azaspiro[2.4]heptane-6-carboxamide | 490.21 | *** |
| 761 | 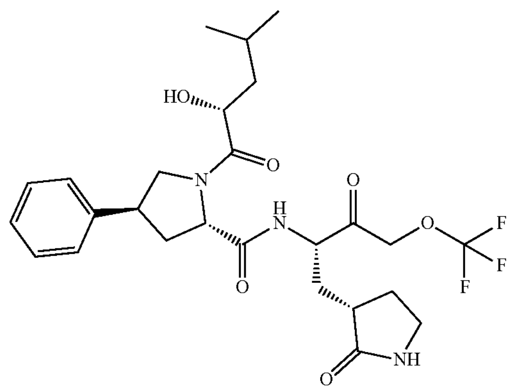 [SMILES: CC(C)C[C@@H](O)C(=O)N1C[C@H](c2ccccc2)C[C@H]1C(=O)N[C@@H](C[C@@H]1CCNC1=O)C(=O)COC(F)(F)F] | (2S,4S)-1-((R)-2-hydroxy-4-methylpentanoyl)-N-((S)-3-oxo-1-((S)-2-oxopyrrolidin-3-yl)butan-2-yl)-4-(trifluoromethoxy)butan-2-yl)-4-phenylpyrrolidine-2-carboxamide | 542.3797 | **** |

TABLE 1-continued

| Compound | Structure | IUPAC | LCMS [M + 1] | EC50, uM (Hela) |
|---|---|---|---|---|
| 762 | 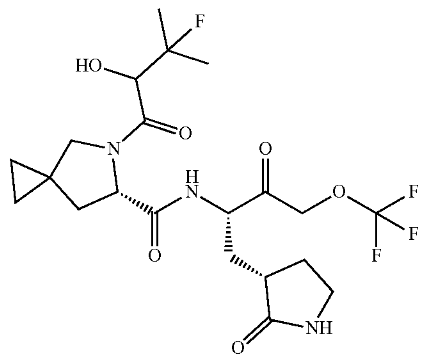 [SMILES: CC(C)(F)C(O)C(=O)N1CC2(CC2)C[C@H]1C(=O)N[C@@H](C[C@@H]1CCNC1=O)C(=O)COC(F)(F)F] | (6S)-5-(3-fluoro-2-hydroxy-3-methylbutanoyl)-N-((S)-3-oxo-1-((S)-2-oxopyrrolidin-3-yl)-4-(trifluoromethoxy)butan-2-yl)-5-azaspiro[2.4]heptane-6-carboxamide | 496.3167 | *** |
| 763 | 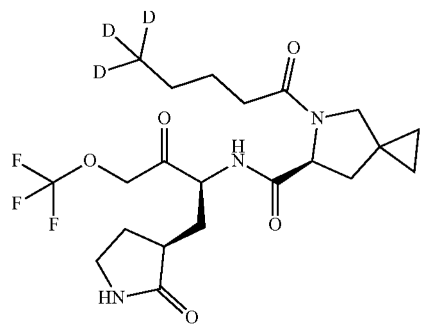 [SMILES: [2H]C([2H])([2H])CCCC(=O)N1CC2(CC2)C[C@H]1C(=O)N[C@@H](C[C@@H]1CCNC1=O)C(=O)COC(F)(F)F] | (S)-N-((S)-3-oxo-1-((S)-2-oxopyrrolidin-3-yl)-4-(trifluorom ethoxy)butan-2-yl)-5-(pentanoyl-5,5,5-d3)-5-azaspiro[2.4]heptane-6-carboxamide | 465.4 | **** |

TABLE 1-continued

| Compound | Structure | IUPAC | LCMS [M + 1] | EC50, uM (Hela) |
|---|---|---|---|---|
| 764 | 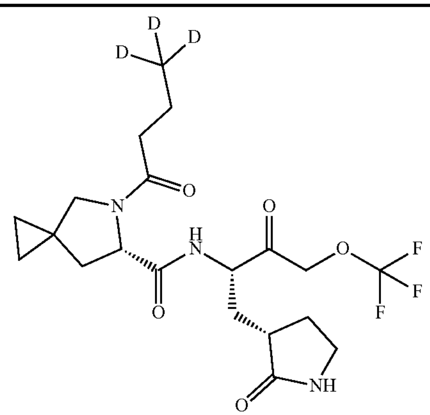 | (S)-5-(butanoyl-4,4,4-d3)-N-((S)-3-oxo-1-((S)-2-oxopyrrolidin-3-yl)-4-(trifluoromethoxy)butan-2-yl)-5-azaspiro[2.4]heptane-6-carboxamide | 451.38 | *** |
| 765 | 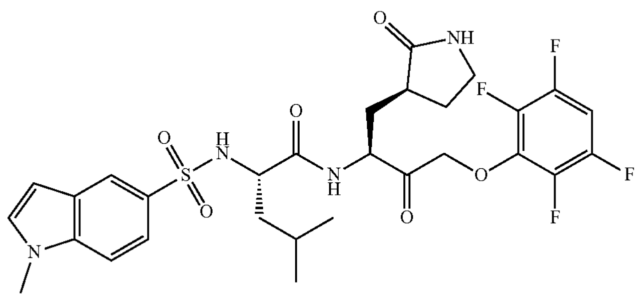 [SMILES: CC(C)C[C@H](NS(=O)(=O)c1ccc2c(ccn2C)c1)C(=O)N[C@@H](C[C@@H]1CCNC1=O)C(=O)COc1c(F)c(F)cc(F)c1F] | (S)-4-methyl-2-((1-methyl-1H-indole)-5-sulfonamido)-N-((S)-3-oxo-1-((S)-2-oxopyrrolidin-3-yl)-4-(2,3,5,6-tetrafluorophenoxy)butan-2-yl)pentanamide | 641.2 | **** |

TABLE 1-continued

| Compound | Structure | IUPAC | LCMS [M + 1] | EC50, uM (Hela) |
|---|---|---|---|---|
| 766 | 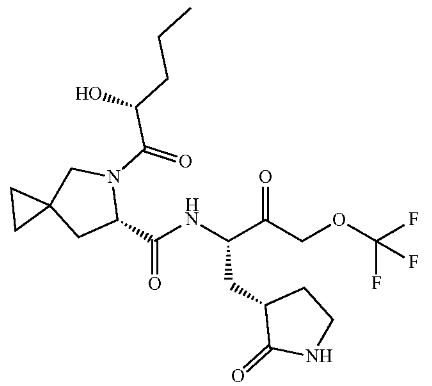 [SMILES: CCC[C@@H](O)C(=O)N1CC2(CC2)C[C@H]1C(=O)N[C@@H](C[C@@H]1CCNC1=O)C(=O)COC(F)(F)F] | (S)-5-((R)-2-hydroxypentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 478.2 | *** |
| 767 | 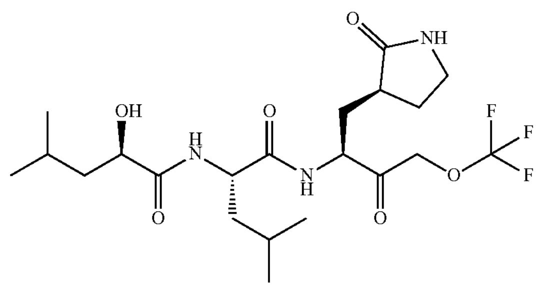 [SMILES: CC(C)C[C@@H](O)C(=O)N[C@@H](CC(C)C)C(=O)N[C@@H](C[C@@H]1CCNC1=O)C(=O)COC(F)(F)F] | (R)-2-hydroxy-4-methyl-N-((S)-4-methyl-1-oxo-1-(((S)-3-oxo-1-((S)-2-oxopyrrolidin-3-yl)-4-(trifluoromethoxy)butan-2-yl)amino)pentan-2-yl)pentanamide | 504.5 (M +Na) | ** |
| 768 | 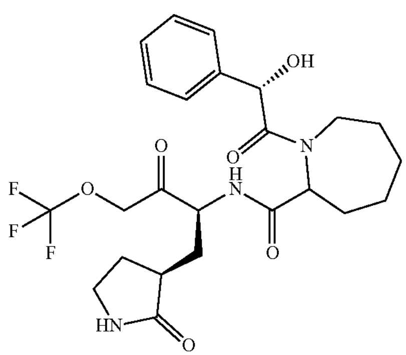 [SMILES: O=C(N[C@@H](C[C@@H]1CCNC1=O)C(=O)COC(F)(F)F)C1CCCCCN1C(=O)[C@@H](O)c1ccccc1] | 1-((S)-2-hydroxy-2-phenylacetyl)-N-((S)-3-oxo-1-((S)-2-oxopyrrolidin-3-yl)-4-(trifluoromethoxy)butan-2-yl)azepane-2-carboxamide | 536.51 (M +Na) | *** |

TABLE 1-continued
| Compound | Structure | IUPAC | LCMS [M + 1] | EC50, uM (Hela) |
|---|---|---|---|---|
| 769 | 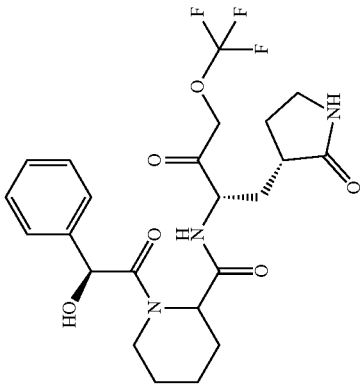 | 1-((S)-2-hydroxy-2-phenylacetyl)-N-((S)-3-oxo-1-((S)-2-oxopyrrolidin-3-yl)-4-(trifluoromethoxy)butan-2-yl)piperidine-2-carboxamide | 522.5 (M+Na) | **** |
| 770 | 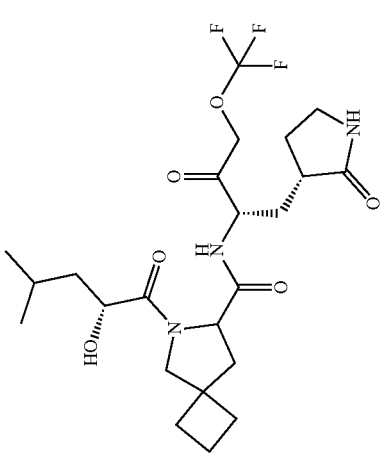 | 6-((R)-2-hydroxy-4-methylpentanoyl)-N-((S)-3-oxo-1-((S)-2-oxopyrrolidin-3-yl)-4-(trifluoromethoxy)butan-2-yl)-6-azaspiro[3.4]octane-7-carboxamide | 528.55 (M+Na) | *** |

TABLE 1-continued

| Compound | Structure | IUPAC | LCMS [M + 1] | EC50, uM (Hela) |
|---|---|---|---|---|
| 771 | 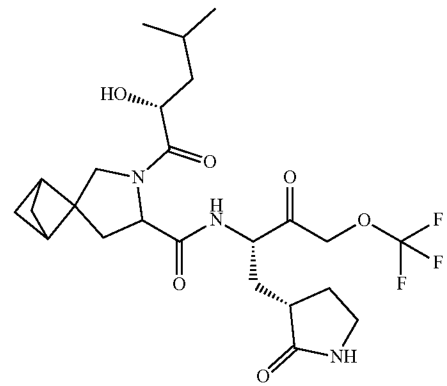 [SMILES: CC(C)C[C@@H](O)C(=O)N1CC2(CC1C(=O)N[C@@H](C[C@@H]1CCNC1=O)C(=O)COC(F)(F)F)C1CC2C1] | (2S)-4-(bicyclo[1.1.1]pentan-2-yl)-1-((R)-2-hydroxy-4-methylpentanoyl)-N-((S)-3-oxo-1-((S)-2-oxopyrrolidin-3-yl)-4-(trifluoromethoxy)butan-2-yl)pyrrolidine-2-carboxamide | | **** |
| 772 | 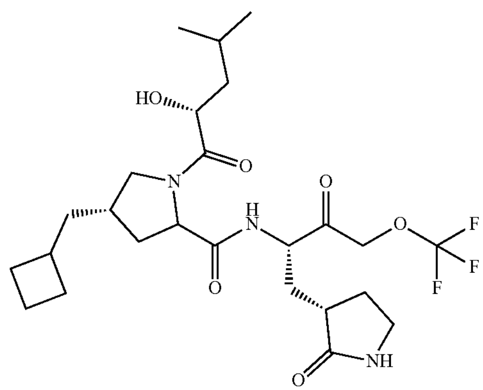 [SMILES: CC(C)C[C@@H](O)C(=O)N1C[C@@H](CC2CCC2)CC1C(=O)N[C@@H](C[C@@H]1CCNC1=O)C(=O)COC(F)(F)F] | (2S,4S)-4-(cyclobutylmethyl)-1-((R)-2-hydroxy-4-methylpentanoyl)-N-((S)-3-oxo-1-((S)-2-oxopyrrolidin-3-yl)-4-(trifluoromethoxy)butan-2-yl)pyrrolidine-2-carboxamide | 534.69 | **** |

TABLE 1-continued

| Compound | Structure | IUPAC | LCMS [M + 1] | EC50, uM (Hela) |
|---|---|---|---|---|
| 773 | 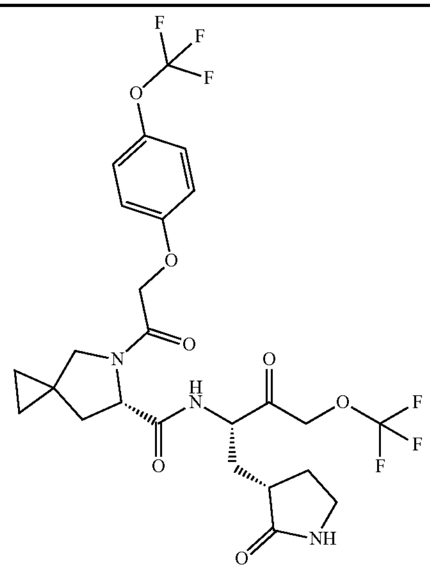 | (S)-N-((S)-3-oxo-1-((S)-2-oxopyrrolidin-3-yl)-4-(trifluoromethoxy)butan-2-yl)-5-(2-(4-(trifluoromethoxy)phenoxy)acetyl)-5-azaspiro[2.4]heptane-6-carboxamide | 595.5 | **** |
| 774 | 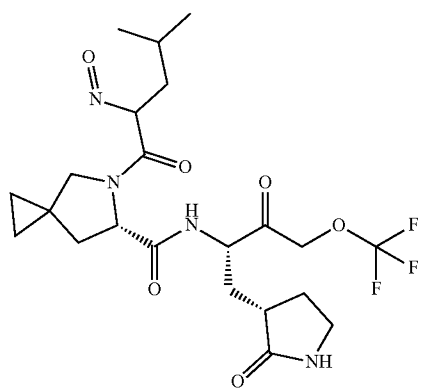 [SMILES: CC(C)CC(N=O)C(=O)N1CC2(CC2)C[C@H]1C(=O)N[C@@H](C[C@@H]1CCNC1=O)C(=O)COC(F)(F)F] | (6S)-5-(4-methyl-2-nitrosopentanoyl)-N-((S)-3-oxo-1-((S)-2-oxopyrrolidin-3-yl)-4-(trifluoromethoxy)butan-2-yl)-5-azaspiro[2.4]heptane-6-carboxamide | 505.48 | |

TABLE 1-continued

| Compound | Structure | IUPAC | LCMS [M + 1] | EC50, uM (Hela) |
|---|---|---|---|---|
| 775 | 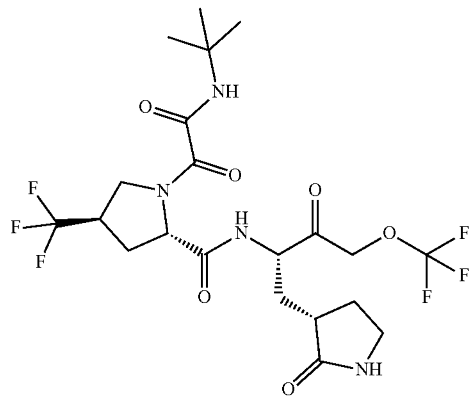 [SMILES: CC(C)(C)NC(=O)C(=O)N1C[C@H](C(F)(F)F)C[C@H]1C(=O)N[C@@H](C[C@@H]1CCNC1=O)C(=O)COC(F)(F)F] | (2S,4R)-1-(2-(tert-butylamino)-2-oxoacetyl)-N-((S)-3-oxo-1-((S)-2-oxopyrrolidin-3-yl)-4-(trifluoromethoxy)butan-2-yl)-4-(trifluoromethyl)pyrrolidine-2-carboxamide | 547.3284 | |
| 776 | 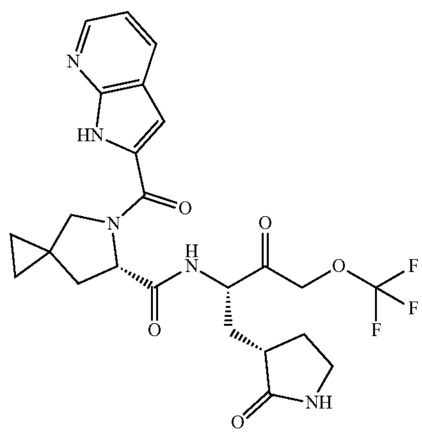 [SMILES: O=C1NCC[C@H]1C[C@H](NC(=O)[C@@H]1CC2(CC2)CN1C(=O)c1cc2cccnc2[nH]1)C(=O)COC(F)(F)F] | (S)-N-((S)-3-oxo-1-((S)-2-oxopyrrolidin-3-yl)-4-(trifluoromethoxy)butan-2-yl)-5-(1H-pyrrolo[2,3-b]pyridine-2-carbonyl)-5-azaspiro[2.4]heptane-6-carboxamide | 522.4 | |

TABLE 1-continued

| Compound | Structure | IUPAC | LCMS [M + 1] | EC50, uM (Hela) |
|---|---|---|---|---|
| 777 | 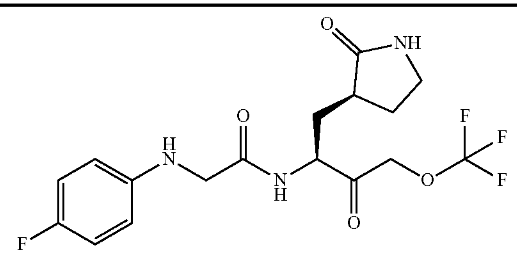 | 2-((4-fluorophenyl)amino)-N-((S)-3-oxo-1-((S)-2-oxopyrrolidin-3-yl)-4-(trifluoromethoxy)butan-2-yl)acetamide | 406.29 | |
| 778 | 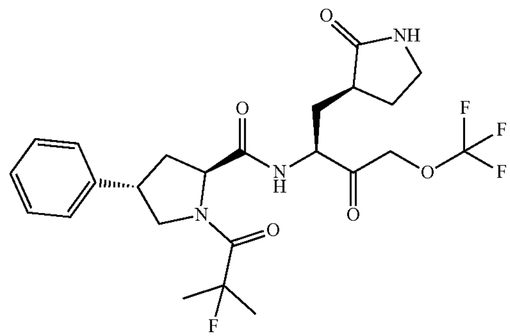 [SMILES: CC(C)(F)C(=O)N1C[C@H](c2ccccc2)C[C@H]1C(=O)N[C@@H](C[C@@H]1CCNC1=O)C(=O)COC(F)(F)F] | (2S,4S)-1-(2-fluoro-2-methylpropanoyl)-N-((S)-3-oxo-1-((S)-2-oxopyrrolidin-3-yl)-4-(trifluoromethoxy)butan-2-yl)-4-phenylpyrrolidine-2-carboxamide | 516.38 | |
| 779 | 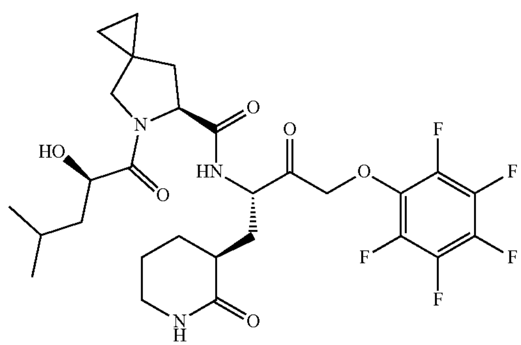 [SMILES: CC(C)C[C@@H](O)C(=O)N1CC2(CC2)C[C@H]1C(=O)N[C@@H](C[C@@H]1CCCNC1=O)C(=O)COc1c(F)c(F)c(F)c(F)c1F] | (S)-5-((R)-2-hydroxy-4-methylpentanoyl)-N-((S)-3-oxo-1-((S)-2-oxopiperidin-3-yl)-4-(perfluorophenoxy)butan-2-yl)-5-azaspiro[2.4]heptane-6-carboxamide | 604.54 | **** |

TABLE 1-continued

| Compound | Structure | IUPAC | LCMS [M + 1] | EC50, uM (Hela) |
|---|---|---|---|---|
| 780 | 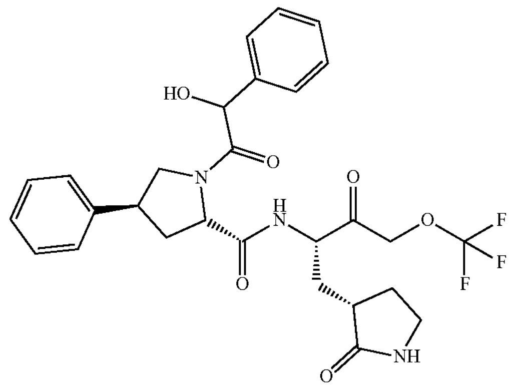 | (2S,4S)-1-((S)-2-hydroxy-2-phenylacetyl)-N-((S)-3-oxo-1-((S)-2-oxopyrrolidin-3-yl)-4-(trifluoromethoxy)butan-2-yl)-4-phenylpyrrolidine-2-carboxamide | 562.3537 | **** |
| 781 | 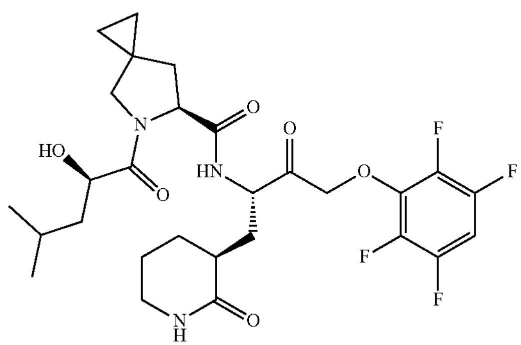 [SMILES: CC(C)C[C@@H](O)C(=O)N1CC2(CC2)C[C@H]1C(=O)N[C@@H](C[C@@H]1CCCNC1=O)C(=O)COc1c(F)c(F)cc(F)c1F] | (S)-5-((R)-2-hydroxy-4-methylpentanoyl)-N-((S)-3-oxo-1-((S)-2-oxopiperidin-3-yl)-4-(2,3,5,6-tetrafluorophenoxy)butan-2-yl)-5-azaspiro[2.4]heptane-6-carboxamide | 586.55 | |
| 782 | 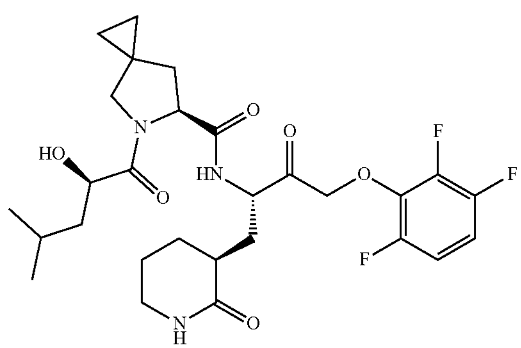 [SMILES: CC(C)C[C@@H](O)C(=O)N1CC2(CC2)C[C@H]1C(=O)N[C@@H](C[C@@H]1CCCNC1=O)C(=O)COc1c(F)ccc(F)c1F] | (S)-5-((R)-2-hydroxy-4-methylpentanoyl)-N-((S)-3-oxo-1-((S)-2-oxopiperidin-3-yl)-4-(2,3,6-trifluorophenoxy)butan-2-yl)-5-azaspiro[2.4]heptane-6-carboxamide | 494.55 | |

TABLE 1-continued

| Compound | Structure | IUPAC | LCMS [M + 1] | EC50, uM (Hela) |
|---|---|---|---|---|
| 783 | 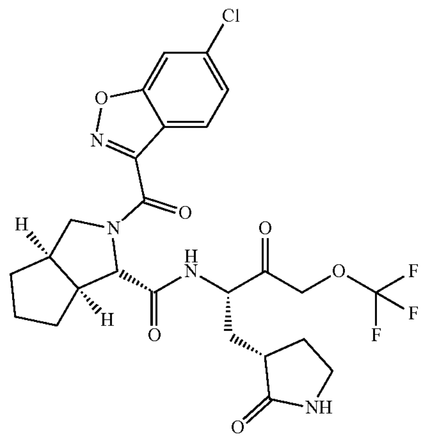 | (1S,3aR,6aS)-2-(6-chlorobenzo[d]isoxazole-3-carbonyl)-N-((S)-3-oxo-1-((S)-2-oxopyrrolidin-3-yl)-4-(trifluoromethoxy)butan-2-yl)octahydrocyclopenta[c]pyrrole-1-carboxamide | 571.2189 | **** |
| 784 | 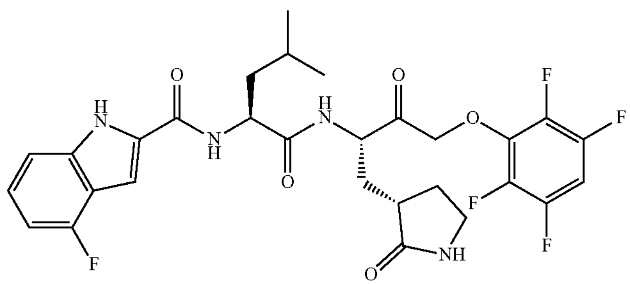 [SMILES: CC(C)C[C@H](NC(=O)c1cc2c(F)cccc2[nH]1)C(=O)N[C@@H](C[C@@H]1CCNC1=O)C(=O)COc1c(F)c(F)cc(F)c1F] | 4-fluoro-N-((S)-4-methyl-1-oxo-1-(((S)-3-oxo-1-((S)-2-oxopyrrolidin-3-yl)-4-(2,3,5,6-tetrafluorophenoxy)butan-2-yl)amino)pentan-2-yl)-1H-indole-2-carboxamide | | **** |

TABLE 1-continued

| Compound | Structure | IUPAC | LCMS [M + 1] | EC50, uM (Hela) |
|---|---|---|---|---|
| 785 | 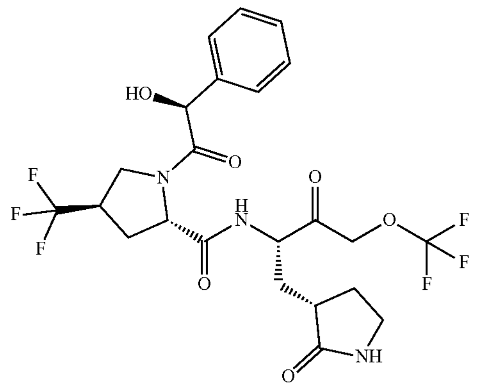 [SMILES: O=C1NCC[C@H]1C[C@H](NC(=O)[C@@H]1C[C@@H](C(F)(F)F)CN1C(=O)[C@@H](O)c1ccccc1)C(=O)COC(F)(F)F] | (2S,4R)-1-((S)-2-hydroxy-2-phenylacetyl)-N-((S)-3-oxo-1-((S)-2-oxopyrrolidin-3-yl)-4-(trifluoromethoxy)butan-2-yl)-4-(trifluoromethyl)pyrrolidine-2-carboxamide | 554.3057 | *** |
| 786 | 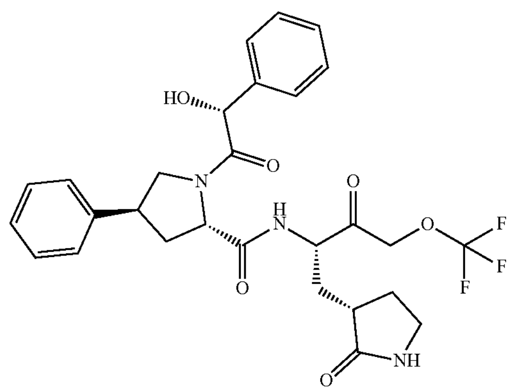 [SMILES: O=C1NCC[C@H]1C[C@H](NC(=O)[C@@H]1C[C@@H](c2ccccc2)CN1C(=O)[C@H](O)c1ccccc1)C(=O)COC(F)(F)F] | (2S,4S)-1-((R)-2-hydroxy-2-phenylacetyl)-N-((S)-3-oxo-1-((S)-2-oxopyrrolidin-3-yl)-4-(trifluoromethoxy)butan-2-yl)-4-phenylpyrrolidine-2-carboxamide | 562.3687 | *** |

TABLE 1-continued

| Compound | Structure | IUPAC | LCMS [M + 1] | EC50, uM (Hela) |
|---|---|---|---|---|
| 787 | 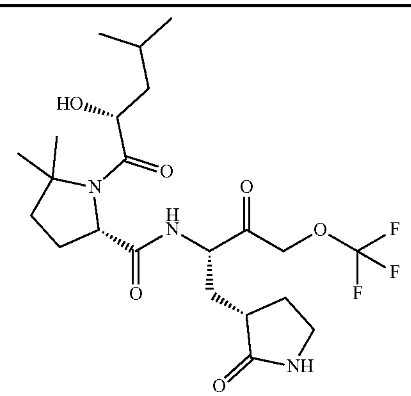 | (S)-1-((R)-2-hydroxy-4-methylpentanoyl)-5,5-dimethyl-N-((S)-3-oxo-1-((S)-2-oxopyrrolidin-3-yl)-4-(trifluoromethoxy)butan-2-yl)pyrrolidine-2-carboxamide | | *** |
| 788 | 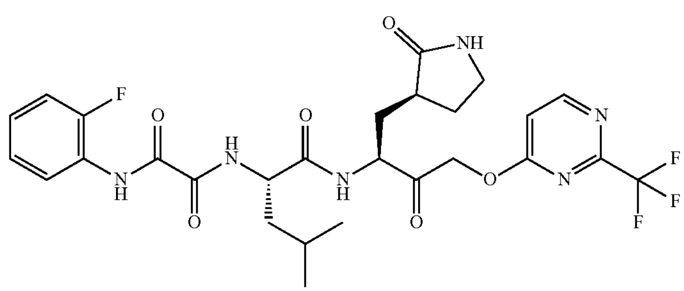 [SMILES: CC(C)C[C@H](NC(=O)C(=O)Nc1ccccc1F)C(=O)N[C@@H](C[C@@H]1CCNC1=O)C(=O)COc1ccnc(C(F)(F)F)n1] | N1-(2-fluorophenyl)-N2*-((S)-4-methyl-1-oxo-1-((S)-3-oxo-1-((S)-2-oxopyrrolidin-3-yl)-4-((2-(trifluoromethyl)pyrimidin-4-yl)oxy)butan-2-yl)amino)pentan-2-yl)oxalamide | | ** |

TABLE 1-continued
| Compound | Structure | IUPAC | LCMS [M + 1] | EC50, uM (Hela) |
|---|---|---|---|---|
| 789 | 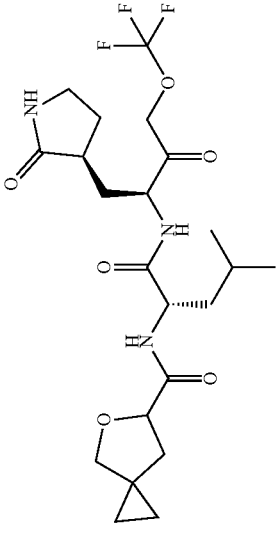 | N-((S)-4-methyl-1-oxo-1-(((S)-3-oxo-1-((S)-2-oxopyrrolidin-3-yl)-4-(trifluoromethoxy)butan-2-yl)amino)pentan-2-yl)-5-oxaspiro[2.4]heptane-6-carboxamide | | **** |
EC50:
<0.05 uM: ****
0.05–<0.2 uM: ***
0.2–<0.5 uM: **
0.5–1.0 uM: *

TABLE 2

| Compound | ¹H NMR Data |
|---|---|
| 5 | (400 MHz, DMSO-$d_6$) δ ppm 11.56 (s, 1H), 8.62 (d, J = 8.0 Hz, 1H), 8.49 (d, J = 7.7 Hz, 1H), 7.63 (s, 2H), 7.61 (s, 1H), 7.59-7.51 (m, 1H), 7.42 (d, J = 8.2 Hz, 1H), 7.26 (s, 1H), 7.18 (t, J = 7.4 Hz, 2H), 7.03 (t, J = 7.0 Hz, 1H), 5.21 (q, J = 18.2 Hz, 2H), 4.65-4.34 (m, 2H), 3.20-3.03 (m, 2H), 2.67 (s, 4H), 2.44 (s, 3H), 2.33(s, 1H), 2.14-1.94 (m, 3H), 1.82-1.54 (m, 10H), 1.48-1.33 (m, 1H), 1.27-1.03 (m, 1H), 1.02-0.82 (m, 3H). |
| 10 | (500 MHz, DMSO-$d_6$) δ ppm 10.66 (s, 1H), 8.92 (d, J = 8.5 Hz, 1H), 8.54 (d, J = 7.9 Hz, 1H), 7.86-7.80 (m, 2H), 7.65 (s, 1H), 7.56 (tt, J = 10.8, 7.2 Hz, 1H), 7.35 (dd, J = 8.6, 7.4 Hz, 2H), 7.19-7.08 (m, 1H), 5.25 (d, J = 17.8 Hz, 1H), 5.17 (d, J = 17.8 Hz, 1H), 4.47 (ddd, J = 11.7, 8.0, 4.0 Hz, 1H), 4.43-4.34 (m, 1H), 3.20-3.07 (m, 2H), 2.29 (m, 1H), 2.14-2.05 (m, 2H), 1.97 (ddd, J = 13.8, 11.3, 4.1Hz, 1H), 1.76 (dd, J = 10.9, 8.8 Hz, 1H), 1.71-1.52 (m, 4H), 0.90 (d, J = 6.2 Hz, 3H), 0.88 (d, J = 6.1 Hz, 3H). |
| 28 | (400 MHz, DMSO-$d_6$) δ ppm 10.23 (s, 1H), 8.98 (d, J = 8.3 Hz, 1H), 8.56 (d, J = 7.9 Hz, 1H), 7.73 (td, J = 7.8, 1.9 Hz, 1H), 7.66 (s, 1H), 7.56 (tt, J = 10.8, 7.3 Hz, 1H), 7.40-7.17 (m, 3H), 5.25 (d, J = 17.7 Hz, 1H), 5.17 (d, J = 17.8 Hz, 1H), 4.47 (ddd, J = 11.6, 7.8, 3.9 Hz, 1H), 4.43-4.32 (m, 1H), 3.20-3.07 (m, 2H), 2.31-2.22 (m, 1H), 2.17-2.04 (m, 1H), 1.97 (ddd, J = 14.2, 11.4, 4.2 Hz, 1H), 1.82-1.72 (m, 1H), 1.71-1.49 (m, 4H), 0.90 (d, J = 6.3 Hz, 3H), 0.88 (d, J = 6.2 Hz, 3H). |
| 32 | (400 MHz, DMSO-$d_6$) δ ppm 10.20 (s, 1H), 9.04 (d, J = 8.2 Hz, 1H), 8.59 (d, J = 7.8 Hz, 1H), 7.91 (d, J = 8.1 Hz, 1H), 7.82-7.72 (m, 2H), 7.67 (s, 1H), 7.57 (tt, J = 10.9, 7.3 Hz, 1H), 7.49 (t, J = 7.8 Hz, 1H), 5.25 (d, J = 17.7 Hz, 1H), 5.17 (d, J = 17.7 Hz, 1H), 4.48 (ddd, J = 11.6, 7.8, 4.0 Hz, 1H), 4.43-4.32 (m, 1H), 3.23-3.07 (m, 2H), 2.32-2.25 (m, 1H), 2.15-2.05 (m, 1H), 1.99 (ddd, J = 13.9, 11.3, 4.1 Hz, 1H), 1.82-1.73 (m, 1H), 1.61 (ddtd, J = 30.2, 13.3, 9.4, 4.2 Hz, 4H), 0.91 (d, J = 6.2 Hz, 3H), 0.89 (d, J = 6.1 Hz, 3H). |
| 81 | (400 MHz, DMSO-$d_6$) δ ppm 8.78 (t, J = 6.1 Hz, 1H), 8.57 (q, J = 7.5 Hz, 2H), 7.65-7.52 (m, 2H), 5.20 (q, J = 15.3 Hz, 2H), 4.45 (s, 1H), 4.32 (s, 1H), 3.31-3.04 (m, 4H), 2.24 (q, J = 6.6 Hz, 4H), 2.11-1.96 (m, 4H), 1.68-1.44 (m, 13H), 0.87 (q, J = 5.8 Hz, 6H). |
| 98 | (400 MHz, DMSO-$d_6$) δ ppm 8.81 (d, J = 5.2 Hz, 1H), 8.61 (d, J = 8.8 Hz, 1H), 8.52 (d, J = 7.6 Hz, 1H), 7.65-7.55 (m, 2H), 5.20 (dd, 2H), 4.47-4.29 (m, 2H), 3.15-3.09 (m, 2H), 2.78-2.50 (m, 1H), 2.26-2.24 (m, 1H), 2.07-1.95 (m, 2H), 1.72-1.50 (m, 5H), 0.89-0.84 (m, 6H), 0.65-0.63 (m, 4H). |
| 99 | (400 MHz, DMSO-$d_6$) δ ppm 8.91 (s, 1H), 8.56 (t, J = 5.1 Hz, 2H), 7.65-7.54 (m, 2H), 5.19 (q, J = 14.7 Hz, 2H), 4.44 (d, J = 7.2 Hz, 1H), 4.30 (t, J = 7.2 Hz, 1H), 3.20-3.07 (m, 2H), 2.30 (q, J = 16.6 Hz, 1H), 2.01 (t, J = 23.6 Hz, 2H), 1.58 (t, J = 27.9 Hz, 5H), 1.28 (s, 4H), 0.87 (q, J = 5.8 Hz, 6H), 0.72 (s, 2H), 0.56 (s, 2H). |
| 100 | (400 MHz, DMSO-$d_6$) δ ppm 8.58 (q, J = 6.8 Hz, 2H), 7.82 (s, 1H), 7.60-7.57 (m, 2H), 5.19 (q, J = 15.1 Hz, 2H), 4.46-4.28 (m, 2H), 3.11 (d, J = 8.3 Hz, 2H), 2.25-2.07 (m, 2H), 1.95 (q, J = 8.3 Hz, 1H), 1.68-1.61 (m, 5H), 1.52 (t, J = 11.9 Hz, 9H), 0.87 (q, J = 5.7 Hz, 6H). |
| 101 | (500 MHz, DMSO-$d_6$) δ ppm 8.75 (d, J = 8.5 Hz, 1H), 8.61 (d, J = 8.5 Hz, 1H), 8.55 (d, J = 7.8 Hz, 1H), 7.65 (s, 1H), 7.57 (tt, J = 10.7, 7.3 Hz, 1H), 5.23 (d, J = 17.8 Hz, 1H), 5.16 (d, J = 17.7 Hz, 1H), 4.45 (ddd, J = 11.5, 7.8, 4.0 Hz, 1H), 4.38-4.30 (m, 1H), 3.89-3.77 (m, 3H), 3.38-3.28 (m, 2H), 3.20-3.13 (m, 1H), 3.13-3.06 (m, 1H), 2.30-2.21 (m, 1H), 2.12-2.03 (m, 1H), 1.96 (ddd, J = 14.5, 11.4, 4.2 Hz, 1H), 1.74-1.45 (m, 9H), 0.88 (d, J = 6.2 Hz, 3H), 0.86 (d, J = 6.1 Hz, 3H). |
| 103 | (400 MHz, DMSO-$d_6$) δ ppm 8.66-8.55 (m, 3H), 7.65-7.54 (m, 2H) 5.19 (t, J = 23.4 Hz, 2H), 4.44-4.32 (m, 2H), 3.32 (s, 3H), 3.23-3.09 (m, 4H), 2.08-1.49 (m, 12H), 0.87 (q, J = 5.9 Hz, 6H). |
| 104 | (400 MHz, DMSO-$d_6$) δ ppm 8.91 (d, J = 7.2 Hz, 1H), 8.67 (d, J = 7.4 Hz, 1H), 7.65-7.55 (m, 2H), 5.22 (d, J = 3.9 Hz, 2H), 4.48-4.28 (m, 2H), 3.47-3.41 (m, 8H), 3.31-3.08 (m, 2H), 2.32-1.47 (m, 11H), 0.89 (q, J = 6.6 Hz, 6H). |
| 124 | (400 MHz, DMSO-$d_6$) δ ppm 9.01 (d, J = 8.5 Hz, 1H), 8.61 (d, J = 8.5 Hz, 1H), 8.50 (d, J = 7.9 Hz, 1H), 7.65 (s, 1H), 7.58 (m, J = 8.3 Hz, 1H), 5.25-5.12 (m, 2H), 4.47-4.43 (m, 1H), 4.35-4.23 (m, J = 7.1 Hz, 2H), 3.15-3.09 (m, 2H), 2.30-2.20 (m, 1H), 2.15-2.02 (m, 5H), 2.00-1.92 (m, 1H), 1.71-1.49 (m, 7H), 0.90-0.83 (m, 6H). |
| 125 | (400 MHz, DMSO-$d_6$) δ ppm 10.25 (s, 1H), 8.91 (d, J = 8.4 Hz, 1H), 8.56 (d, J = 7.6 Hz, 1H), 7.80-7.52 (m, 12H), 7.34-7.25 (m, 4H), 4.84-4.70 (m, 2H), 4.46-4.32 (m, 2H), 3.09 (t, J = 7.8 Hz, 2H), 2.24 (t, J = 4.6 Hz, 1H), 2.04 (q, J = 5.4 Hz, 1H), 1.93-1.87 (m, 1H), 1.70-1.47 (m, 5H), 0.88-0.84 (m, 6H). |
| 126 | (400 MHz, DMSO-$d_6$) δ ppm 8.48 (d, J = 8.0 Hz, 1H), 7.64 (s, 1H), 7.62-7.55 (m, J = 4.3 Hz, 2H), 7.44 (d, J = 7.6 Hz, 1H), 5.28-5.05 (m, 3H), 4.48-4.39 (m, 1H), 3.92-3.98 (m, 1H), 3.90-3.62 (m, 4H), 3.19-3.05 (m, J = 8.3 Hz, 2H), 2.32-2.23 (m, 1H), 2.15-2.03 (m, 2H), 2.00-1.84 (m, 2H), 1.68-1.58 (m, J = 6.3 Hz, 3H), 1.49-1.35 (m, 2H), 0.89-0.84 (m, 6H). |
| 127 | (400 MHz, DMSO-$d_6$) δ ppm 8.48 (d, J = 7.9 Hz, 1H), 7.64 (s, 1H), 7.63-7.53 (m, J = 4.3 Hz, 2H), 7.44 (d, J = 7.6 Hz, 1H), 5.28-5.05 (m, 3H), 4.48-4.39 (m, 1H), 3.92-3.98 (m, 1H), 3.90-3.62 (m, 4H), 3.19-3.05 (m, J = 8.3 Hz, 2H), 2.32-2.23 (m, 1H), 2.15-2.03 (m, 2H), 2.00-1.84 (m, 2H), 1.68-1.58 (m, J = 6.3 Hz, 3H), 1.49-1.35 (m, 2H), 0.89-0.84 (m, 6H). |

TABLE 2-continued

| Compound | ¹H NMR Data |
|---|---|
| 128 | (400 MHz, DMSO-$d_6$) δ ppm 8.51 (d, J = 8.0 Hz, 1H), 7.64 (s, 1H), 7.62-7.53 (m, 1H), 7.37 (d, J = 7.6 Hz, 1H), 7.32-7.25 (m, 3H), 7.17 (d, J = 7.6 Hz, 1H), 5.2-5.17 (m, 2H), 4.42 (m, 1H), 4.03-3.89 (m, 3H), 3.25-3.03 (m, 2H), 2.65-2.62 (m, 2H), 2.24 (m, 1H), 2.08-1.86 (m, 2H), 1.84-1.80 (m, 2H), 1.66-1.59 (m, 3H), 1.49-1.46 (m, 2H), 0.90-0.85 (m, 6H). |
| 133 | (400 MHz, DMSO-$d_6$) δ ppm 8.60 (m, J = 8.4 Hz, 1H), 8.58-8.53 (m, 2H), 7.65 (s, 1H), 7.62-7.53 (m, 2H), 5.25-5.15 (m, 2H), 4.49-4.42 (m, 1H), 4.35-4.28 (m, 2H), 3.73-3.65 (m, 3H), 3.32-3.09 (m, 4H), 2.28-1.92 (m, 3H), 1.86-1.75 (m, 1H), 1.71-1.52 (m, 8H), 1.24 (s, 1H), 0.88 (d, J = 2.4 Hz, 3H), 0.85 (d, J = 2.4 Hz, 3H) |
| 137 | (400 MHz, DMSO-$d_6$) δ ppm 8.47 (d, J = 7.9 Hz, 1H), 7.59 (m, J = 4.6 Hz, 1H), 7.30 (d, J = 7.5 Hz, 1H), 5.18 (q, J = 16.9 Hz, 1H), 4.42 (t, J = 7.7 Hz, 1H), 3.96 (q, J = 7.6 Hz, 1H), 3.80 (d, J = 7.1 Hz, 1H), 3.13 (m, J = 8.7 Hz, 1H), 2.09 (m, J = 9.0 Hz, 1H), 1.39 (m, J = 8.6 Hz, 1H), 0.86 (q, J = 6.4 Hz, 1H). |
| 138 | (400 MHz, DMSO-$d_6$) δ ppm 8.48 (d, J = 7.8 Hz, 1H), 7.63 (s, 1H), 7.60-7.53 (m, 1H), 7.38-7.20 (m, 5H), 5.21 (t, J = 16.6 Hz, 1H), 4.42 (s, 1H), 4.19-4.10 (m, 2H), 3.98-3.96 (m, 1H), 3.18-3.07 (m, 2H), 2.86 (t, J = 6.4 Hz, 1H), 2.24 (t, J = 11.2 Hz, 1H), 2.08 (q, J = 8.9 Hz, 1H), 2.00-1.96 (m, 1H), 1.64-1.35 (m, 6H), 1.25 (d, J = 15.4 Hz, 1H), 0.85 (q, J = 6.5 Hz, 6H). |
| 139 | (400 MHz, DMSO-$d_6$) δ ppm 8.54 (d, J = 7.6 Hz, 1H), 7.63-7.49 (m, 4H), 7.40-7.29 (m, 3H), 6.64 (d, J = 16 Hz, 1H), 6.47-6.40 (m, 1H), 5.28-5.1 (m, 2H), 4.62 (d, J = 5.6 Hz, 2H), 4.46-4.41 (m, 1H), 4.04-3.97 (m, 1H), 3.18-3.06 (m, 2H), 2.32-1.99 (m, 3H), 1.67-1.37 (m, 5H), 0.89-0.85 (m, 6H). |
| 140 | (400 MHz, DMSO-$d_6$) δ ppm 8.75 (d, J = 8.4 Hz, 1H), 8.62 (d, J = 8.8 Hz, 1H), 8.56 (d, J = 7.6 Hz, 1H), 7.65 (s, 1H), 7.62-7.52 (m, 1H), 5.23 (d, J = 18 Hz, 1H), 5.17 (d, J = 18 Hz, 1H), 4.52-4.42 (m, 1H), 4.39-4.31 (m, 2H), 3.91-3.78 (m, 2H), 3.20-3.05 (m, 3H), 2.59-2.52 (m, 1H), 2.23-2.22 (m, 1H), 2.15-1.92 (m, 5H), 1.75-1.42 (m, 9 H), 0.91-0.82 (m, 6H). |
| 143 | (400 MHz, DMSO-$d_6$) δ ppm 10.43 (s, 1H), 9.03 (d, J = 8.2 Hz, 1H), 8.54 (d, J = 7.9 Hz, 1H), 8.05 (d, J = 7.9 Hz, 1H), 7.66-7.53 (m, 2H), 7.41-7.35 (m, 2H), 7.18 (t, J = 7.4 Hz, 1H), 5.21 (q, J = 17.7 Hz, 2H), 4.54-4.35 (m, 4H), 3.33 (s, 3H), 3.19-3.05 (m, 2H), 2.32-2.28 (m, 1H), 2.12-1.92 (m, 2H), 1.78-1.52 (m, 5H), 0.92-0.87 (m, 6H). |
| 144 | (400 MHz, DMSO-$d_6$) δ ppm 8.59 (d, J = 7.8 Hz, 1H), 8.36 (d, J = 7.5 Hz, 1H), 7.62-7.54 (m, 2H), 7.32-7.25 (m, 3H), 7.19 (d, J = 7.0 Hz, 1H), 5.17 (d, J = 7.1 Hz, 2H), 4.43-4.22 (m, 2H), 3.48 (s, 2H), 3.15-3.10 (m, 1H), 3.04-2.95 (m, 1H), 2.29-2.19 (m, 1H), 2.10-1.89 (m, 2H), 1.67-1.51 (m, 3H), 1.51-1.41 (m, 2H), 0.89 (d, J = 6.4 Hz, 3H), 0.81 (d, J = 6.8 Hz, 3H). |
| 145 | (400 MHz, DMSO-$d_6$) δ ppm 8.91 (d, J = 9.2 Hz, 1H), 8.66 (q, J = 11.1 Hz, 2H), 7.64-7.52 (m, 2H), 7.16-7.06 (m, 4H), 5.22 (q, J = 15.0 Hz, 2H), 5.01 (d, J = 4.2 Hz, 1H), 4.46-4.35 (m, 2H), 3.31-3.07 (m, 2H), 2.72-2.66 (m, 2H), 2.18-2.05 (m, 2H), 1.98-1.90 (m, 4H), 1.88-1.52 (m, 6H), 0.89 (q, J = 5.8 Hz, 6H). |
| 146 | (400 MHz, DMSO-$d_6$) δ ppm 8.57 (d, J = 7.7 Hz, 1H), 8.03 (d, J = 8.2 Hz, 1H), 7.63 (s, 1H), 7.59-7.52 (m, 1H), 7.46 (s, 1H), 7.38-7.27 (m, 3H), 6.28 (d, J = 5.3 Hz, 1H), 5.14 (s, 2H), 5.01 (d, J = 5.3 Hz, 1H), 4.44-4.21 (m, 2H), 3.10-2.95 (m, 2H), 2.23-2.15 (d, J = 5.6 Hz, 1H), 2.05-1.89 (m, 2H), 1.69-1.45 (m, 5H), 0.87 (d, J = 6.0 Hz, 3H), 0.80 (d, J = 6.1 Hz, 3H). |
| 147 | (400 MHz, DMSO-$d_6$) δ ppm 8.90 (d, J = 9.1 Hz, 1H), 8.64 (q, J = 15.5 Hz, 2H), 7.65-7.54 (m, 2H), 7.17-7.05 (m, 4H), 5.21 (q, J = 15.0 Hz, 2H), 5.02 (s, 1H), 4.46 (s, 1H), 4.35 (s, 1H), 3.13-3.10 (m, 2H), 2.72-2.66 (m, 2H), 2.26-2.32 (m, 1H), 2.12-2.05 (m, 2H), 1.97-1.92 (m, 4H), 1.73-1.53 (m, 6H), 0.92-0.87 (q, J = 6.2 Hz, 6H). |
| 148 | (400 MHz, DMSO-$d_6$) δ ppm 10.04 (s, 1H), 9.28 (d, J = 8.0 Hz, 1H), 8.58 (d, J = 8.4 Hz, 1H), 8.46 (d, J = 4.0 Hz, 1H), 7.72-7.68 (m, 1H), 7.61-7.47 (m, 3H), 7.30-7.16 (m, 5H), 5.24-5.07 (q, J = 18.0 Hz, 2H), 4.78 (q, J = 1.6 Hz, 1H), 4.43-4.41 (m, 1H), 3.32-3.26 (m, 2H), 3.16-3.04 (m, 2H), 2.18 (s, 1H), 2.01-1.91 (m, 3H), 1.59-1.56 (m, 2H), 1.24 (s, 2H). |
| 149 | (400 MHz, DMSO-$d_6$) δ ppm 9.06-8.94 (m, 1H), 8.69-8.60 (m, 1H), 7.86-7.02 (m, 6H), 5.22 (bs, 2H), 4.50-4.21 (m, 2H), 3.81-3.58 (m, 2H), 3.21-3.12(m, 2H), 2.89-2.66 (m, 2H), 2.33-1.91 (m, 5H), 1.62-1.47 (m, 5H), 1.35-1.30 (m, 6H). |
| 150 | (400 MHz, DMSO-$d_6$) δ ppm 8.52 (d, J = 7.6 Hz, 1H), 7.64-7.55 (m, 3H), 5.57 (s, 1H), 5.19 (q, J = 12.8 Hz, 2H), 4.95 (q, J = 8.0 Hz, 1H), 4.43 (s, 1H), 3.90-3.84 (m, 1H), 3.77 (s, 3H), 3.60-3.56 (m, 1H), 3.16-3.07 (m, 1H), 2.97 (m, 1H), 2.50-2.49 (m, 1H), 2.07 (m, 1H), 1.96-1.90 (m, 2H), 1.65-1.59 (m, 4H), 1.40 (m, 2H), 1.23 (m, 1H), 0.89-0.84 (m, 6H). |
| 151 | (400 MHz, DMSO-$d_6$) δ ppm 8.78 (d, J = 8.4 Hz, 1H), 8.58 (q, J = 8.7 Hz, 2H), 7.65-7.54 (m, 2H), 5.20 (q, J = 15.2 Hz, 2H), 4.45-433 (m, 2H), 3.80 (d, J = 8.0 Hz, 1H), 3.13-3.09 (m, 2H), 2.26 (t, J = 6.1 Hz, 1H), 2.08-1.49 (m, 15H), 0.87 (q, J = 5.6 Hz, 6H). |
| 153 | (500 MHz, DMSO-$d_6$) δ ppm 8.62 (dd, J = 7.4, 5.5 Hz, 1H), 7.89 (d, J = 1.6 Hz, 1H), 7.81 (dd, J = 8.5, 1.7 Hz, 1H), 7.66 (s, 1H), 7.53 (d, J = 8.4 Hz, 1H), 4.99 (d, J = 17.0 Hz, 1H), 4.92 (d, J = 17.0 Hz, 1H), 4.46-4.35 (m, 2H), 3.16 (t, J = 9.1 Hz, 1H), 3.12-3.04 (m, 1H), 2.29-2.22 (m, 1H), 2.12-2.06 (m, 1H), 1.97 (ddd, J = 14.9, 11.3, 4.4 Hz, 1H), 1.82-1.48 (m, 5H), 0.93 (d, J = 5.9 Hz, 3H), 0.88 (d, 3H). |

TABLE 2-continued

| Compound | ¹H NMR Data |
|---|---|
| 154 | (400 MHz, DMSO-$d_6$) δ ppm 8.55 (d, J = 8.0 Hz, 1H), 8.16 (d, J = 7.6 Hz, 1H), 7.87 (dd, J = 8.4, 2.0 Hz, 1H), 7.80-7.79 (m, 1H), 7.62-7.52 (m, 2H), 7.05 (d, J = 8.8 Hz, 1H), 5.18 (q, J = 12.0 Hz, 2H), 4.44-4.39 (m, 1H), 4.29-4.27 (m, 1H), 3.82 (s, 3H), 3.50 (q, J = 15.2 Hz, 2H), 3.11-3.09 (m, 1H), 3.01-2.99 (m, 1H), 2.49 (s, 3H), 2.27-2.21 (m, 1H), 2.1-1.90 (m, 2H), 1.65-1.44 (m, 5H), 0.90 (d, J = 6.4 Hz, 3H), 0.86 (d, J = 6.4 Hz, 3H). |
| 155 | (400 MHz, DMSO-$d_6$) δ ppm 10.0 (s, 1H), 9.29 (d, J = 7.6 Hz, 1H), 8.58 (d, J = 8.0 Hz, 1H), 8.47 (d, J = 4.0 Hz, 1H), 7.62 (s, 1H), 7.50 (d, J = 7.2 Hz, 1H), 7.30-7.16 (m, 5H), 4.98 (d, J = 17.2 Hz, 1H), 4.86 (d, J = 17.2 Hz, 1H), 4.79 (q, J = 6.8Hz& 13.2 Hz, 1H), 4.43-4.37 (m, 1H), 3.31 (s, 2H), 3.16-3.04 (m, 2H), 2.17 (s, 3H), 2.03-1.95 (m, 3H), 1.60-1.56 (m, 2H), 1.22 (s, 1H). |
| 156 | (400 MHz, DMSO-$d_6$) δ ppm 11.3 (s, 1H), 8.86 (d, J = 8.4 Hz, 1H), 8.58 (d, J = 7.8 Hz, 1H), 7.65 (s, 1H), 7.30 (s, 1H), 4.99 (q, J = 15.4 Hz, 1H), 4.57-4.44 (m, 2H), 3.15-3.08 (m, 1H), 2.33-2.30 (m, 1H), 2.10-2.07 (m, 1H), 1.98-1.95 (m, 1H), 1.81-1.79 (m, 1H), 1.68-1.58 (m, 4H), 1.24 (s, 1H), 0.94-0.90 (m, 6H). |
| 157 | (400 MHz, DMSO-$d_6$) δ ppm 11.50 (s, 1H), 8.54 (q, J = 8.4 Hz, 1H), 8.42 (t, J = 6.5 Hz, 1H), 7.64 (d, J = 4.3 Hz, 1H), 7.36 (d, J = 2.2 Hz, 1H), 7.11-6.99 (m, 2H), 6.51 (d, J = 7.7 Hz, 1H), 5.42 (s, 1H), 4.82-4.65 (m, 2H), 4.49-4.44 (m, 2H), 3.88 (s, 3H), 3.13-3.06 (m, 2H), 2.19-2.07 (m, 2H), 1.95-1.73 (m, 1H), 1.68-1.53 (m, 5H), 0.92-0.88 (m, 6H). |
| 158 | (400 MHz, DMSO-$d_6$) δ ppm 11.54 (d, J = 1.7 Hz, 1H), 8.62 (d, J = 7.7 Hz, 1H), 8.44 (d, J = 7.6 Hz, 1H), 7.65 (s, 1H), 7.36 (d, J = 1.6 Hz, 1H), 7.09 (t, J = 7.9 Hz, 1H), 7.01 (d, J = 8.2 Hz, 1H), 6.51 (d, J = 7.6 Hz, 1H), 4.98 (q, J = 14.5 Hz, 1H), 4.45 (m, 1H), 3.88 (s, 1H), 3.12 (m, J = 8.3 Hz, 1H), 2.27 (q, J = 4.6 Hz, 1H), 2.09 (m, 1H), 1.98 (m, 1H), 1.63 (m, 1H), 0.92 (m, 1H). |
| 161 | (400 MHz, DMSO-$d_6$) δ ppm 11.66 (d, J = 8.5 Hz, 1H), 8.99-8.30 (m, 2H), 7.66 (d, J = 6.3 Hz, 1H), 7.47-7.38 (m, 2H), 7.27 (m, 1H), 7.05 (m, 1H), 5.08-4.93 (m, 2H), 4.63-4.33 (m, 2H), 3.29 (m, 1H), 3.22-3.06 (m, 2H), 2.35-2.17 (m, 1H), 2.16-2.07 (m, 1H), 2.04-1.92 (m, 1H), 1.85-1.74 (m, 1H), 1.74-1.51 (m, 3H), 0.86-0.79 (m, 1H), 0.52-0.33 (m, 2H), 0.26-0.18 (m, 1H), 0.16-0.09 (m, 1H). |
| 162 | (400 MHz, DMSO-$d_6$) δ ppm 8.59-8.41 (m, 2H), 7.64 (d, J = 4.4 Hz, 1H), 7.36 (d, J = 1.2 Hz, 1H), 7.11-7.00 (m, 2H), 6.50 (d, J = 7.6 Hz, 2H), 4.54-4.39 (m, 4H), 4.07 (q, J = 9.2 Hz, 2H), 3.88 (s, 3H), 3.16-3.07 (m, 2H), 2.33-1.94 (m, 3H), 1.74-1.54 (m, 5H), 0.95-0.89 (m, 6H). |
| 163 | (400 MHz, DMSO-$d_6$) δ ppm 8.59 (q, J = 7.3 Hz, 1H), 8.51 (d, J = 8.6 Hz, 1H), 7.66 (s, 1H), 4.97 (d, J = 4.4 Hz, 1H), 4.37 (m, J = 5.2 Hz, 1H), 3.57 (d, J = 8.9 Hz, 1H), 3.13 (m, J = 8.7 Hz, 1H), 2.25 (m, J = 4.8 Hz, 1H), 2.08 (m, J = 5.8 Hz, 1H), 1.95 (m, J = 4.6 Hz, 1H), 1.60 (m, J = 13 Hz, 1H), 1.30 (m, J = 10.1 Hz, 1H), 1.09 (m, J = 8.8 Hz, 1H), 0.87 (q, J = 5.9 Hz, 1H). |
| 172 | (400 MHz, DMSO-$d_6$) δ ppm 8.67 (d, J = 8.6 Hz, 1H), 8.53 (d, J = 7.5 Hz, 1H), 7.79 (s, 1H), 7.68 (s, 1H), 4.98 (d, J = 17.0 Hz, 1H), 4.93 (d, J = 17.0 Hz, 1H), 4.39 (ddd, J = 11.3, 7.4, 3.9 Hz, 1H), 4.31 (td, J = 9.0, 3.3 Hz, 1H), 3.21-3.05 (m, 2H), 2.30-2.18 (m, 1H), 2.14-2.03 (m, 1H), 1.96 (ddd, J = 14.7, 11.0, 4.3 Hz, 1H), 1.76 (dd, J = 14.4, 9.3 Hz, 1H), 1.70-1.57 (m, 3H), 1.33 (s, 9H), 0.89 (s, 9H). |
| 174 | (400 MHz, DMSO-$d_6$) δ ppm 8.84 (d, J = 5.4 Hz, 1H), 8.67 (d, J = 8.7 Hz, 1H), 8.55 (d, J = 7.6 Hz, 1H), 7.69 (s, 1H), 5.00 (d, J = 17.1 Hz, 1H), 4.95 (d, J = 17.1 Hz, 1H), 4.42 (tt, J = 7.6, 4.0 Hz, 1H), 4.36-4.28 (m, 1H), 3.15 (tt, J = 17.2, 8.7 Hz, 2H), 2.78 (dd, J = 11.4, 5.2 Hz, 1H), 2.32-2.22 (m, 1H), 2.16-2.03 (m, 1H), 1.96 (ddd, J = 14.9, 11.9, 4.3 Hz, 1H), 1.79-1.60 (m, 3H), 1.59-1.47 (m, 2H), 0.90 (d, J = 5.9 Hz, 3H), 0.86 (d, J = 5.7 Hz, 3H), 0.74-0.60 (m, 4H). |
| 176 | (400 MHz, DMSO-$d_6$) δ ppm 9.36 (d, J = 7.6 Hz, 1H), 8.70 (d, J = 8.2 Hz, 1H), 8.54 (d, J = 7.8 Hz, 1H), 7.67 (s, 1H), 5.01 (d, J = 17.3 Hz, 1H), 4.96 (d, J = 17.1 Hz, 1H), 4.43 (ddd, J = 11.4, 7.7, 4.1 Hz, 1H), 4.39-4.31 (m, 1H), 4.21-4.10 (m, 1H), 3.22-3.04 (m, 2H), 2.93-2.77 (m, 4H), 2.32-2.22 (m, 1H), 2.17-2.03 (m, 1H), 1.95 (ddd, J = 13.8, 11.2, 4.3 Hz, 1H), 1.79 (ddd, J = 14.6, 9.1, 6.3 Hz, 1H), 1.72-1.58 (m, 2H), 1.53 (ddd, J = 13.5, 7.9, 4.8 Hz, 1H), 0.75-0.60 (m, 1H), 0.47-0.29 (m, 2H), 0.22--0.01 (m, 2H). |
| 183 | (500 MHz, DMSO-$d_6$) δ ppm 9.02 (d, J = 7.5 Hz, 1H), 8.78 (d, J = 7.6 Hz, 1H), 8.01 (td, J = 7.7, 1.8 Hz, 1H), 7.74-7.60 (m, 2H), 7.49 (dd, J = 11.2, 8.3 Hz, 1H), 7.44 (td, J = 7.6, 1.1 Hz, 1H), 7.24-7.20 (m, 1H), 5.03 (d, J = 17.0 Hz, 1H), 4.96 (d, J = 17.0 Hz, 1H), 4.58-4.49 (m, 1H), 4.47-4.39 (m, 1H), 3.87-3.79 (m, 2H), 3.29-3.07 (m, 5H), 2.34-2.19 (m, 1H), 2.17-2.08 (m, 1H), 2.03-1.95 (m, 1H), 1.82-1.73 (m, 1H), 1.71-1.54 (m, 6H), 1.30-1.13 (m, 2H).(mixture of compounds) |
| 189 | (400 MHz, DMSO-$d_6$) δ ppm 9.38 (t, J = 6.7 Hz, 1H), 8.86 (d, J = 8.4 Hz, 1H), 8.58 (d, J = 7.6 Hz, 1H), 7.68 (s, 1H), 4.99 (d, J = 17.0 Hz, 1H), 4.94 (d, J = 17.0 Hz, 1H), 4.44-4.37 (m, 1H), 4.36-4.29 (m, 1H), 4.01-3.86 (m, 2H), 3.21-3.05 (m, 2H), 2.31-2.20 (m, 1H), 2.15-2.01 (m, 1H), 1.95 (ddd, J = 13.8, 11.2, 4.2 Hz, 1H), 1.81-1.59 (m, 3H), 1.59-1.46 (m, 2H), 0.89 (d, J = 6.1 Hz, 3H), 0.85 (d, J = 5.9 Hz, 3H). |
| 195 | (400 MHz, DMSO-$d_6$) δ ppm 11.56 (d, J = 3.7 Hz, 1H), 8.56 (q, J = 6.8 Hz, 1H), 8.40 (q, J = 3.9 Hz, 1H), 7.80-7.74 (m, 4H), 7.61-7.51 (m, 7H), 7.33 (s, |

TABLE 2-continued

| Compound | ¹H NMR Data |
|---|---|
| | 1H), 7.12-7.07 (m, 1H), 7.01 (q, J = 4.2 Hz, 1H), 6.51 (q, J = 3.6 Hz, 1H), 4.87-4.73 (m, 2H), 4.44 (q, J = 4.9 Hz, 2H), 3.89 (d, J = 2.6 Hz, 3H), 3.10-3.02 (m, 2H), 2.30-1.85 (m, 3H), 1.65-1.44 (m, 5H), 0.91-0.83 (m, 6H). |
| 196 | 1HNMR (400 MHz, DMSO-$d_6$) δ ppm 9.07-8.94 (m, 1H), 8.75-8.65 (m, 1H), 7.65 (brs, 1H), 7.19-7.03 (m, 3H), 4.41 (brs, 2H), 4.40-4.19 (m, 2H), 3.62-3.51 (m, 3H), 3.17-3.13 (m, 2H), 2.33-1.91 (m, 5H), 1.50-1.34 (m, 5H), 1.26-1.23 (m, 2H), 0.91-0.77 (m, 7H). |
| 201 | (400 MHz, methanol-$d_6$) δ ppm 8.58 (s, 1H), 8.34 (d, J = 1.8 Hz, 1H), 8.02 (dd, J = 8.6, 1.8 Hz, 1H), 7.78 (d, J = 8.6 Hz, 1H), 4.98 (d, J = 17.0 Hz, 1H), 4.92 (d, J = 17.0 Hz, 1H), 4.69-4.57 (m, 2H), 2.68-2.57 (m, 1H), 2.41-2.29 (m, 1H), 2.19-2.06 (m, 1H), 1.97-1.70 (m, 4H), 1.01-0.84 (m, 1H), 0.66-0.47 (m, 2H), 0.33-0.14 (m, 2H). |
| 203 | (400 MHz, DMSO-$d_6$) δ ppm 8.67 (s, 1H), 8.67 (d, J = 7.2 Hz, 1H), 8.62 (dd, J = 4.4, 1.6 Hz, 1H), 8.34 (d, J = 8.4 Hz, 1H), 8.20 (ddd, J = 9.3, 1.6, 0.8 Hz, 1H), 7.66 (s, 1H), 7.36 (dd, J = 9.3, 4.4 Hz, 1H), 5.03 (d, J = 17.1 Hz, 1H), 4.97 (d, J = 17.1 Hz, 1H), 4.62-4.52 (m, 1H), 4.44 (ddd, J = 11.3, 7.6, 4.0 Hz, 1H), 3.21-3.05 (m, 2H), 2.38-2.24 (m, 1H), 2.16-2.04 (m, 1H), 1.85-1.48 (m, 6H), 0.93 (d, J = 6.3 Hz, 3H), 0.91 (d, J = 6.1 Hz, 3H). |
| 205 | (400 MHz, DMSO-$d_6$) δ ppm 9.34 (d, J = 7.6 Hz, 1H), 8.71 (d, J = 8.5 Hz, 1H), 8.53 (d, J = 7.6 Hz, 1H), 7.66 (s, 1H), 4.96 (d, J = 5.8 Hz, 2H), 4.41-4.32 (m, 2H), 4.13 (q, J = 6.9 Hz, 1H), 3.16-3.09 (m, 2H), 2.90-2.79 (m, 4H), 2.30-1.91 (m, 3H), 1.70-1.51 (m, 5H), 0.87 (q, J = 6.3 Hz, 6H). |
| 215 | (400 MHz, DMSO-$d_6$) δ ppm 8.83 (s, 1H), 8.71 (d, J = 8.4 Hz, 1H), 8.63 (d, J = 7.6 Hz, 1H), 7.66 (s, 1H), 7.29 (dd, J = 14.4, 7.6 Hz, 1H), 7.12-7.08 (m, 2H), 7.02 (d, J = 8.4 Hz, 1H), 4.93 (d, J = 4.4 Hz, 2H), 4.54-4.50 (m, 2H), 3.16-3.02 (m, 4H), 2.25-2.22 (m, 1H), 2.08-2.07 (m, 1H), 1.99-1.92 (m, 1H), 1.68-1.61 (m, 2H), 1.25 (s, 3H), 0.67 (dd, J = 19.6, 10.8 Hz, 1H), 0.55 (d, J = 8.0 Hz, 2H). |
| 221 | (400 MHz, DMSO-$d_6$) δ ppm 8.66 (d, J = 5.2 Hz, 1H), 7.79 (d, J = 8.4 Hz, 1H), 7.50 (d, J = 8.8 Hz, 1H), 5.71 (s, 1H), 4.72 (q, J = 16.4 Hz, 2H), 4.53-4.35 (m, 3H), 3.39 (dd, J = 8.8, 4.4 Hz, 2H), 2.45-2.34 (m, 4H), 2.01-1.89 (m, 5H), 1.79-1.62 (m, 5H), 0.98-0.92 (m, 6H). |
| 225 | (400 MHz, DMSO-$d_6$) δ ppm 8.56 (d, J = 7.4 Hz, 1H), 7.72 (d, J = 8.1 Hz, 1H), 7.69 (s, 1H), 4.96 (s, 2H), 4.37 (ddd, J = 11.3, 7.5, 4.0 Hz, 1H), 4.31-4.20 (m, 2H), 3.95-3.85 (m, 1H), 3.81-3.70 (m, 1H), 3.22-3.05 (m, 2H), 2.30-2.18(m, 2H), 2.15-2.02 (m, 2H), 1.94 (ddd, J = 13.7, 11.2, 4.3 Hz, 1H), 1.85-1.72 (m, 3H), 1.70-1.40 (m, 5H), 0.89 (d, J = 6.0 Hz, 3H), 0.85 (d, J = 6.1 Hz, 3H). |
| 226 | (400 MHz, DMSO-$d_6$) δ ppm 9.56 (s, 1H), 8.75 (d, J = 8.7 Hz, 1H), 8.43 (d, J = 7.8 Hz, 1H), 7.67 (s, 1H), 4.97 (d, J = 17.0 Hz, 1H), 4.90 (d, J = 17.0 Hz, 1H), 4.44-4.36 (m, 1H), 4.34-4.26 (m, 1H), 3.20-3.04 (m, 2H), 2.36 (d, J = 2.2 Hz, 6H), 2.30-2.20 (m, 1H), 2.11-2.01 (m, 1H), 1.95 (ddd, J = 14.8, 11.3, 4.1 Hz, 1H), 1.76 (dd, J = 14.4, 9.6 Hz, 1H), 1.70-1.57 (m, 3H), 0.87 (s, 9H). |
| 229 | (400 MHz, DMSO-$d_6$) δ ppm 11.53 (d, J = 1.7 Hz, 1H), 8.60 (d, J = 7.8 Hz, 1H), 8.43 (d, J = 7.6 Hz, 1H), 7.46 (s, 1H), 7.36 (d, J = 1.6 Hz, 1H), 7.09 (t, J = 7.9 Hz, 1H), 7.01 (d, J = 8.2 Hz, 1H), 6.51 (d, J = 7.6 Hz, 1H), 4.97 (q, J = 15.5 Hz, 2H), 4.49-4.46 (m, 2H), 3.88 (s, 3H), 3.09 (s, 2H), 2.21-2.14 (m, 2H), 1.83-1.82 (m, 1H), 1.73-1.68 (m, 4H), 1.58-1.52 (m, 2H), 1.34 (t, J = 9.3 Hz, 1H), 0.91 (q, J = 8.7 Hz, 6H). |
| 235 | (400 MHz, DMSO-$d_6$) δ ppm 8.50 (d, J = 7.6 Hz, 1H), 8.33 (d, J = 7.8 Hz, 1H), 7.66 (s, 1H), 7.03 (q, J = 6.7 Hz, 1H), 6.92 (t, J = 7.6 Hz, 1H), 6.70-6.58 (m, 2H), 5.22 (d, J = 6.4 Hz, 1H), 4.95 (s, 2H), 4.38-4.30 (m, 2H), 4.17 (q, J = 6.6 Hz, 1H), 3.61 (d, J = 5.7 Hz, 1H), 3.26 (d, J = 3.3 Hz, 3H), 3.16-3.08 (m, 2H), 2.21-2.11 (m, 1H), 1.95-1.85 (m, 1H), 1.65-1.54 (m, 3H), 1.48-1.45 (m, 3H), 0.88 (d, J = 6.5 Hz, 3H), 0.78 (d, J = 6.4 Hz, 3H). |
| 236 | (400 MHz, DMSO-$d_6$) δ ppm 8.50 (d, J = 7.6 Hz, 1H), 8.28 (d, J = 7.8 Hz, 1H), 7.63 (s, 1H), 7.05-7.01 (m, 1H), 6.95-6.91 (m, 1H), 6.69-6.58 (m, 2H), 5.19 (d, J = 5.9 Hz, 1H), 4.92 (s, 2H), 4.38-4.34 (m, 1H), 4.26 (q, J = 7.5 Hz, 1H), 4.14 (q, J = 6.2 Hz, 1H), 3.69-3.61 (m, 1H), 3.26 (s, 3H), 3.07 (t, J = 8.7 Hz, 1H), 2.96 (q, J = 8.5 Hz, 1H), 2.31-2.21 (m, 1H), 1.95-1.91 (m, 2H), 1.63-1.42 (m, 5H), 0.81 (q, J = 9.0 Hz, 6H). |
| 244 | (400 MHz, DMSO-$d_6$) δ ppm 9.55 (d, J = 7.1 Hz, 1H), 8.68 (d, J = 8.5 Hz, 1H), 8.53 (d, J = 7.6 Hz, 1H), 7.66 (s, 1H), 4.95-4.85 (m, 3H), 4.68-4.60 (m, 4H), 4.42-4.33 (m, 2H), 3.16-3.10 (m, 2H), 2.29-2.25 (m, 1H), 2.08 (t, J = 3.4 Hz, 1H), 1.97-1.93 (m, 1H), 1.70-1.52 (m, 5H), 0.87 (q, J = 5.9 Hz, 6H). |
| 246 | (400 MHz, DMSO-$d_6$) δ ppm 8.73 (d, J = 8.3 Hz, 1H), 8.65 (d, J = 7.4 Hz, 1H), 8.22 (s, 1H), 7.67 (s, 1H), 6.33 (t, J = 56.8 Hz, 1H), 4.99 (d, J = 17.1 Hz, 1H), 4.94 (d, J = 17.1 Hz, 1H), 4.39 (ddd, J = 11.2, 7.3, 4.0 Hz, 1H), 4.34-4.27 (m, 1H), 3.22-3.04 (m, 2H), 2.32-2.20 (m, 1H), 2.13-2.04 (m, 1H), 1.95 (ddd, J = 15.1, 11.2, 4.3 Hz, 1H), 1.72-1.60 (m, 3H), 1.58-1.45 (m, 2H), 1.36 (s, 6H), 0.89 (d, J = 6.2 Hz, 3H), 0.86 (d, J = 6.0 Hz, 3H). |
| 247 | (400 MHz, DMSO-$d_6$) δ ppm 8.58 (q, J = 7.0 Hz, 1H), 7.79-7.67 (m, 2H), 4.95 (d, J = 6.7 Hz, 2H), 4.37-4.29 (m, 2H), 4.06-4.05 (m, 1H), 3.82 (m, 2H), 3.65 (t, J = 10.3 Hz, 2H), 3.50 (q, J = 7.8 Hz, 1H), 3.32-3.21 (m, 1H), 3.17-3.01 (m, 2H), 2.24 (t, J = 4.5 Hz, 1H), 2.08 (d, J = 7.6 Hz, 1H), 1.95 (d, J = 3.2 Hz, 1H), 1.66-1.54 (m, 5H), 0.90-0.84 (m, 6H). |

TABLE 2-continued

| Compound | ¹H NMR Data |
|---|---|
| 248 | (400 MHz, DMSO-d₆) δ ppm 11.82 (s, 1H), 8.75-8.69 (m, 2H), 8.40 (d, J = 4.2 Hz, 1H), 7.81 (d, J = 8.1 Hz, 1H), 7.66 (d, J = 3.6 Hz, 1H), 7.42 (s, 1H), 7.21 (q, J = 4.2 Hz, 1H), 5.00-4.96 (m, 2H), 4.54-4.44 (m, 2H), 3.16-3.10 (m, 2H), 2.33-1.99 (m, 3H), 1.75-1.58 (m, 5H), 0.96-0.86 (m, 6H). |
| 249 | (400 MHz, DMSO-d₆) δ ppm 12.10 (s, 1H), 8.62 (d, J = 7.7 Hz, 1H), 8.39 (d, J = 8.0 Hz, 1H), 8.30 (s, 1H), 8.26 (d, J = 4.4 Hz, 1H), 8.10 (d, J = 7.2 Hz, 1H), 7.63 (s, 1H), 7.15 (q, J = 4.2 Hz, 1H), 5.04 (d, J = 17.0 Hz, 1H), 4.93 (d, J = 17.0 Hz, 1H), 4.50-4.40 (m, 2H), 3.13 (t, J = 8.7 Hz, 1H), 3.04 (q, J = 8.3 Hz, 1H), 2.26-2.20 (m, 1H), 2.15-1.95 (m, 2H), 1.75-1.50 (m, 5H), 0.95 (d, J = 6.4 Hz, 3H), 0.90 (d, J = 6.4 Hz, 3H). |
| 250 | (400 MHz, DMSO-d₆) δ ppm 8.81 (s, 1H), 8.65 (t, J = 8.8 Hz, 2H), 7.66 (s, 1H), 7.28 (q, J = 4.7 Hz, 2H), 7.07 (t, J = 8.9 Hz, 2H), 4.94-4.91 (m, 2H), 4.51-4.40 (m, 2H), 3.20-3.00 (m, 4H), 2.23-2.21 (m, 1H), 2.10-2.00 (m, 1H), 1.99-1.90 (m, 1H), 1.68-1.59 (m, 2H), 1.24 (s, 3H), 0.67 (d, J = 8.0 Hz, 2H), 0.54 (s, 2H). |
| 253 | (499 MHz, DMSO-d₆) δ ppm 8.88 (d, J = 7.7 Hz, 1H), 8.59 (d, J = 7.7 Hz, 1H), 7.65 (s, 1H), 6.97 (d, J = 1.9 Hz, 1H), 5.00 (d, J = 17.0 Hz, 1H), 4.93 (d, J = 17.0 Hz, 1H), 4.49-4.38 (m, 2H), 3.21-3.13 (m, 1H), 3.13-3.07 (m, 1H), 2.32-2.23 (m, 1H), 2.14-2.04 (m, 1H), 1.97 (ddd, J = 13.9, 11.2, 4.2 Hz, 1H), 1.79 (s, 3H), 1.74 (s, 3H), 1.73-1.60 (m, 4H), 1.55 (ddd, J = 13.0, 8.7, 4.6 Hz, 1H), 0.92 (d, J = 6.5 Hz, 3H), 0.88 (d, J = 6.5 Hz, 3H). |
| 254 | (400 MHz, DMSO-d₆) δ ppm 9.07 (s, 1H), 8.61 (t, J = 7.2, 2H), 7.67 (s, 1H), 4.96 (s, 2H), 4.47-30 (m, 4H), 3.16-3.10 (m, 2H), 2.24-2.22 (m, 1H), 2.09-2.07 (m, 1H), 1.99-1.95 (m, 1H), 1.70-1.49 (m, 5H), 0.89-0.85 (m, 10H). |
| 255 | (400 MHz, DMSO-d₆) δ ppm 8.67-8.65 (m, 1H), 8.17-8.15 (m, 1H), 7.65 (d, J = 6.4 Hz, 1H), 6.85-6.79 (m, 3H), 5.17-5.14 (m, 1H), 4.96 (d, J = 5.2 Hz, 2H), 4.40-4.38 (m, 2H), 3.78 (s, 3H), 3.44-3.40 (m, 1H), 3.18-3.05 (m, 3H), 2.30-2.18 (m, 1H), 2.13-2.01 (m, 1H), 2.00-1.88 (m, 1H), 1.65-1.50 (m, 5H), 0.92-0.80 (m, 6H). |
| 262 | (400 MHz, DMSO-d₆) δ ppm 8.84 (s, 1H), 8.62-8.56 (m, 2H), 7.67 (s, 1H), 4.95 (s, 2H), 4.40-4.31 (m, 2H), 3.42-3.38 (m, 2H), 3.24 (s, 3H), 3.16-3.10 (m, 2H), 2.33-2.24 (m, 1H), 2.09-2.07 (m, 1H), 1.98-1.90 (m, 1H), 1.69-1.48 (m, 5H), 0.89-0.72 (m, 10H). |
| 263 | (400 MHz, DMSO-d₆) δ ppm 11.97 (s, 1H), 9.03 (d, J = 7.6 Hz, 1H), 8.76 (d, J = 7.6 Hz, 1H), 8.49 (d, J = 4.4 Hz, 1H), 8.16 (d, J = 3.2 Hz, 1H), 7.92 (d, J = 8.0 Hz, 1H), 7.63 (s, 1H), 7.26 (q, J = 4.8 Hz, 1H), 5.01 (q, J = 8.0 Hz, 2H), 4.61 (q, J = 7.4 Hz, 1H), 4.42-4.40 (m, 1H), 3.09-3.01 (m, 2H), 2.30-2.28 (m, 1H), 2.01-1.95 (m, 2H), 1.66-1.55 (m, 4H), 1.25-1.17 (m, 1H).0.97-093 (m, 6H). |
| 266 | (499 MHz, DMSO-d₆) δ ppm 9.35 (d, J = 8.3 Hz, 1H), 8.66 (d, J = 8.2 Hz, 1H), 7.61 (s, 1H), 4.99 (s, 2H), 4.51 (d, J = 8.4 Hz, 1H), 4.42 (ddd, J = 11.9, 8.3, 3.7 Hz, 1H), 4.06 (d, J = 5.4 Hz, 1H), 3.82 (dd, J = 10.5, 7.2 Hz, 1H), 3.64 (dd, J = 10.5, 3.0 Hz, 1H), 3.19-3.12 (m, 1H), 3.10-3.02 (m, 1H), 2.72-2.66 (m, 1H), 2.40-2.32 (m, 1H), 2.18-2.10 (m, 1H), 1.96 (ddd, J = 13.8, 11.9, 3.8 Hz, 1H), 1.86-1.74 (m, 2H), 1.73-1.55 (m, 5H), 1.34 (dq, J = 13.7, 7.1 Hz, 1H), 0.99 (s, 9H). |
| 297 | (400 MHz, DMSO-d₆) δ ppm 8.78 (d, J = 7.4 Hz, 0.3H rotamers), 8.63 (d, J = 7.6 Hz, 0.7H rotamers), 7.72 (s, 0.3H rotamers), 7.66 (s, 0.7H rotamers), 5.07 (d, J = 1.3 Hz, 0.7H rotamers), 5.02 (d, J = 17.2 Hz, 1H), 4.95 (d, J = 17.1Hz, 1H), 4.53 (s, 0.3H rotamers), 4.50-4.43 (m, 1H), 4.36 (ddd, J = 11.4, 7.6, 4.0 Hz, 0.7H rotamers), 4.13 (s, 1H), 3.88 (dd, J = 10.7, 5.4 Hz, 0.7H rotamers), 3.81-3.67 (m, 2H), 3.57-3.45 (m, 1.4H rotamers), 3.23-3.07 (m, 2H), 2.29 (ddt, J = 14.9, 9.3, 4.8 Hz, 1H), 2.18-2.04 (m, 2H), 2.03-1.59 (m, 7H), 1.53 (dd, J = 7.6, 5.3 Hz, 0.7H rotamers), 1.43 (d, J = 7.5 Hz, 0.3H rotamers), 1.40-1.35 (m, 0.3H rotamers), 1.30 (d, J = 7.6 Hz, 0.7H rotamers), 1.03 (s, 3H), 0.89 (s, 3H). |
| 299 | (499 MHz, DMSO-d₆) δ ppm 8.68 (d, J = 7.4 Hz, 0.3H), 8.56 (d, J = 7.5 Hz, 0.7H), 7.70 (s, 0.3H), 7.64 (s, 0.7H), 5.10-4.85 (m, 2H), 4.52 (dd, J = 7.9, 5.2 Hz, 1H), 4.49 (d, J = 2.2 Hz, 0.3H), 4.42 (ddd, J = 11.3, 7.5, 3.8 Hz, 0.3H), 4.32 (ddd, J = 11.4, 7.6, 4.0 Hz, 0.7H), 4.27-4.11 (m, 1H), 4.05 (d, J = 3.9 Hz, 0.7H), 3.85-3.79 (m, 1H), 3.79-3.64 (m, 2H), 3.53 (dd, J = 12.1, 8.4 Hz, 0.3H), 3.44-3.34 (m, 1H), 3.21-3.02 (m, 2H), 2.72-2.65 (m, 0.7H), 2.58-2.52 (m, 0.3H), 2.46-2.39 (m, 1H), 2.33-2.17 (m, 1H), 2.16-2.02 (m, 2H), 2.01-1.86 (m, 3H), 1.86-1.73 (m, 3H), 1.72-1.47 (m, 5H), 1.46-1.33 (m, 1H). |
| 303 | (300 MHz, DMSO-d₆) δ ppm 8.53-8.38 (m, 1H), 7.80-7.44 (m, 1H), 5.12-4.85 (m, 2H), 4.84-4.73 (m, 1H), 4.50-4.28 (m, 1H), 4.20-3.97 (m, 1H), 3.88-3.71 (m, 2H), 3.67-3.61 (m, 1H), 3.17-3.07 (m, 2H), 2.29-2.05 (m, 7H), 2.05-1.90 (m, 3H), 1.89-1.43 (m, 2H), 1.00-0.77 (m, 1H), 0.61-0.40 (m, 1H). |
| 304 | (300 MHz, DMSO-d₆) δ ppm 8.42 (d, J = 7.7 Hz, 1H), 7.66 (m, 1H), 5.05-4.83 (m, 2H), 4.81-4.68 (m, 1H), 4.39-4.25 (m, 1H), 4.25-4.06 (m, 1H), |
| 346 | (400 MHz, DMSO-d₆) δ ppm 8.51 (d, J = 7.5 Hz, 0.6H Dias.), 8.41 (d, J = 7.8 Hz, 0.4H Dias.), 7.67 (s, 1H), 5.07-4.82 (m, 2H), 4.70-4.43 (m, 1H), 4.43-4.27 (m, 2H), 4.24-4.13 (m, 1H), 3.62-3.40 (m, 2H), 3.20-3.04 (m, 2H), 2.30-1.89 (m, 4H), 1.82-1.40 (m, 4H), 1.38-1.27 (m, 1H), 0.97-0.89 (m, 9H), 0.70-0.40 (m, 4H). |

TABLE 2-continued

| Compound | ¹H NMR Data |
|---|---|
| 347 | (400 MHz, DMSO-$d_6$) δ ppm 8.68 (d, J = 7.5 Hz, 0.5H, rotamer), 8.61 (d, J = 7.6 Hz, 0.5H, rotamer), 7.78-7.55 (m, 1H), 6.12-5.96 (m, 0.5H, rotamer), 5.15-4.86 (m, 1. 5H, rotamer), 4.76-4.53 (m, 1H), 4.43-4.28 (m, 1H), 4.25-4.09 (m, 2H), 3.88-3.42 (m, 3H), 3.20-3.03 (m, 2H), 2.37-2.22 (m, 1H), 2.20-2.05 (m, 1H), 1.95 (dd, J = 14.4, 10.5 Hz, 1H), 1.73-1.38 (m, 3H), 1.34-1.19 (m, 2H), 1.02 (s, 3H), 0.96-0.79 (m, 12H). |
| 348 | (400 MHz, DMSO-$d_6$) δ ppm 8.64 (d, J = 7.5 Hz, 1H), 8.56 (d, J = 7.6 Hz, 0H), 7.66 (s, 1H), 5.11-4.89 (m, 3H), 4.60 (dd, J = 7.0, 5.5 Hz, 1H), 4.52-4.40 (m, 1H), 4.39-4.16 (m, 3H), 4.14-4.00 (m, 2H), 3.99-3.89 (m, 0.5H), 3.84-3.46 (m, 4H), 3.21-3.07 (m, 2H), 2.76-2.68 (m, 1H), 2.32-2.23 (m, 1H), 2.18-2.06 (m, 1H), 2.01-1.31 (m, 27H), 1.30-1.18 (m, 2H), 1.01-0.90 (m, 17H), 0.89-0.82 (m, 4H). |
| 350 | (400 MHz, DMSO-$d_6$) δ ppm 8.48 (d, J = 7.7 Hz, 1H), 7.67 (s, 1H), 5.12-4.82 (m, 3H), 4.48-4.21 (m, 3H), 3.62 (d, J = 9.8 Hz, 1H), 3.48 (d, J = 9.9 Hz, 1H), 3.21-3.06 (m, 2H), 2.30-2.18 (m, 1H), 2.18-2.06 (m, 2H), 2.06-1.89 (m, 2H), 1.81-1.56 (m, 4H), 1.46-1.27 (m, 6H), 0.67-0.39 (m, 4H). |
| 351 | (500 MHz, DMSO-$d_6$) δ ppm 8.56 (d, J = 7.5 Hz, 1H), 7.66 (s, 1H), 5.26-5.09 (m, 1H), 5.05-4.83 (m, 2H), 4.30 (ddd, J = 11.4, 7.4, 4.0 Hz, 1H), 4.19 (s, 1H), 3.98 (d, J = 11.8 Hz, 1H), 3.92 (dd, J = 11.8, 5.3 Hz, 1H), 3.22-3.07 (m, 2H), 2.34-2.23 (m, 1H), 2.21-2.07 (m, 1H), 2.05-1.94 (m, 2H), 1.69-1.55 (m, 2H), 1.50 (dd, J = 7.7, 5.1 Hz, 1H), 1.29-1.21 (m, 6H), 1.02 (s, 3H), 0.90 (s, 3H).<br>3.91-3.70 (m, 2H), 3.60-3.49 (m, 1H), 3.19-2.99 (m, 2H), 2.30-2.06 (m, 4H), 2.05-1.91 (m, 3H), 1.89-1.69 (m, 3H), 1.69-1.55 (m, 2H), 0.93-0.81 (m, 1H), 0.59-0.49 (m, 1H). |
| 306 | (400 MHz, DMSO-$d_6$) δ ppm 8.92-8.52 (m, 1H), 7.71-7.64 (m, 1H), 5.08-4.98 (m, 2H), 4.63-3.80 (m, 4H), 3.77-3.70 (m, 2H), 3.69-3.44 (m, 5H), 3.16-3.12 (m, 2H), 2.40 (s, 1H), 2.20-2.00 (m, 1H), 2.00-1.85 (m, 1H), 1.80-1.61 (m, 2H), 1.42-1.28 (m, 2H), 1.02 (J = 3.2 Hz, d, 3H), 0.88 (d, J = 6.4 Hz, 3H). |
| 315 | (400 MHz, DMSO-$d_6$) δ ppm 8.68 (d, J = 7.3 Hz, 0.6H), 8.56 (d, J = 7.6 Hz, 0.4H), 7.71 (s, 0.4H), 7.68 (s, 0.6H), 5.07-4.91 (m, 2H), 4.48-4.36 (m, 0.4H), 4.29 (ddd, J = 11.3, 7.3, 4.0 Hz, 0.6H), 4.09 (d, J = 4.1 Hz, 1H), 3.98-3.93 (m, 1.6H), 3.85-3.74 (m, 1H), 3.66 (dd, J = 11.1, 3.7 Hz, 0.6H), 3.54 (dd, J = 12.3, 8.5 Hz, 0.4H), 3.46 (dd, J = 12.3, 4.2 Hz, 0.4H), 3.23-3.04 (m, 2H), 2.64-2.54 (m, 1H), 2.31-2.18 (m, 3H), 2.18-2.02 (m, 3H), 2.01-1.91 (m, 1H), 1.90-1.73 (m, 2H), 1.73-1.47 (m, 5H), 1.47-1.29 (m, 1H). |
| 316 | (400 MHz, DMSO-$d_6$) δ ppm 8.63 (d, J = 7.2 Hz, 1H), 7.95 (d, J = 8.0 Hz, 1H), 7.71 (s, 1H), 5.05-4.90 (m, 2H), 4.43-4.22 (m, 2H), 3.99 (s, 2H), 3.22-3.09 (m, 2H), 2.39-2.33 (m, 2H), 2.31-2.18 (m, 1H), 2.16-2.05 (m, 1H), 2.04-1.86 (m, 3H), 1.71-1.43 (m, 5H), 0.90 (d, J = 6.0 Hz, 3H), 0.86 (d, J = 6.0 Hz, 3H). |
| 318 | (400 MHz, DMSO-$d_6$) δ ppm 8.73 (d, J = 7.3 Hz, 0.6H rotamer), 8.66 (d, J = 7.3 Hz, 0.4H rotamer), 7.70 (s, 1H), 5.09-4.92 (m, 2H), 4.67-4.62 (m, 1H), 4.47-4.29 (m, 1H), 4.19 (s, 1H), 3.99-3.80 (m, 3H), 3.74-3.59 (m, 1H), 3.55-3.42 (m, 1H), 3.22-3.04 (m, 2H), 2.33-2.20 (m, 2H), 2.15-2.03 (m, 2H), 1.99-1.79 (m, 1H), 1.74-1.59 (m, 2H), 1.55-1.50 (m, 1H), 1.42-1.29 (m, 1H), 1.05-0.99 (m, 3H), 0.87 (d, J = 15.7 Hz, 3H). |
| 323 | (400 MHz, DMSO-$d_6$) δ ppm 8.68-8.59 (m, 1H), 7.66-7.65 (m, 1H), 4.98-4.96 (m, 2H), 4.62-3.52 (m, 6H), 3.31-3.10(m, 2H), 2.74-2.70 (m, 1H), 2.50-2.47 (m, 2H), 2.32-2.27 (m, 1H), 2.13-2.09 (m, 1H), 2.11-1.92 (m, 3H), 1.66-1.49 (m, 6H), 1.27-1.24 (m, 2H). |
| 325 | (300 MHz, DMSO-$d_6$) δ ppm 8.792-8.15 (m, 1H), 7.79-7.19 (m, 1H), 5.11-4.82 (m, 2H), 4.81-4.71 (m, 1H), 4.40-4.26 (m, 1H), 4.18-4.03 (m, 1H), 3.88-3.71 (m, 2H), 3.58-3.52 (m, 1H), 3.203-3.07 (m, 2H), 2.27-2.09 (m, 4H), 2.090-1.901 (m, 3H), 1.89-1.79 (m, 2H), 1.80-1.70 (m, 1H), 1.71-1.50 (m, 2H), 0.94-0.81 (m, 1H), 0.60-0.50 (m, 1H) |
| 326 | (300 MHz, DMSO-$d_6$) δ ppm 8.52-8.49(m, 1H), 7.65(m, 1H), 5.08-4.92(m, 2H), 4.91-4.78(m, 1H), 4.73-4.41(m, 1H), 4.10-4.06(m, 2H), 3.95-3.76(m, 3H), 3.61-3.52(m, 1H), 3.15-3.11(m, 3H), 2.50-1.98(m, 8H), 1.97-1.80(m, 3H), 1.75-1.52(m, 2H), 0.98-0.85(m, 1H), 0.67-0.53(m, 2H) |
| 328 | (400 MHz, DMSO-$d_6$) δ ppm 8.76 (d, J = 6.6 Hz, 0.25H rotamer), 7.86 (d, J = 8.2 Hz, 0.75H rotamer), 7.73 (s, 0.25H rotamer), 7.64 (s, 0.75H rotamer), 7.20 (s, 1H), 5.13-4.74 (m, 3H), 4.51-4.34 (m, 2H), 3.65-3.50 (m, 2H), 3.24-3.00 (m, 2H), 2.41-2.18 (m, 2H), 2.18-1.89 (m, 2H), 1.83-1.48 (m, 5H), 1.48-1.38 (m, 1H), 1.17 (s, 9H), 0.97-0.74 (m, 6H), 0.69-0.37 (m, 4H). |
| 329 | (400 MHz, DMSO-$d_6$) δ ppm 7.77 (d, J = 8.6 Hz, 1H), 7.63 (s, 1H), 7.43 (d, J = 7.9 Hz, 1H), 4.93 (d, J = 17.3 Hz, 1H), 4.78 (d, J = 17.2 Hz, 1H), 4.47 (d, J = 9.0 Hz, 2H), 3.67-3.47 (m, 4H), 3.22-2.81 (m, 10H), 2.39-2.19 (m, 3H), 2.14-1.96 (m, 3H), 1.82-1.51 (m, 7H), 1.47-1.34 (m, 2H), 1.06-0.95 (m, 8H), 0.91 (d, J = 6.5 Hz, 3H), 0.89 (d, J = 6.6 Hz, 3H), 0.61 (dd, J = 17.9, 5.6 Hz, 4H). |
| 330 | (400 MHz, DMSO-$d_6$) δ ppm 7.78 (d, J = 8.5 Hz, 1H), 7.64 (s, 1H), 7.48 (d, J = 8.2 Hz, 1H), 4.91 (d, J = 17.3 Hz, 1H), 4.78 (d, J = 17.2 Hz, 1H), 4.52-4.40 (m, 2H), 3.59 (s, 2H), 3.25-2.85 (m, 9H), 2.38-2.21 (m, 3H), 2.04 |

TABLE 2-continued

| Compound | ¹H NMR Data |
|---|---|
| | (dt, J = 25.4, 8.5 Hz, 3H), 1.81-1.48 (m, 14H), 1.47-1.36 (m, 1H), 1.31-0.98 (m, 9H), 0.96-0.74 (m, 9H), 0.68-0.52 (m, 4H), 0.50-0.38 (m, 2H). |
| 333 | (400 MHz, DMSO-d$_6$) δ ppm 8.55 (d, J = 7.6 Hz, 1H), 7.69 (s, 1H), 6.55 (dd, J = 78.6, 73.3 Hz, 1H), 4.96 (d, J = 17.1 Hz, 1H), 4.90 (d, J = 17.0 Hz, 1H), 4.59 (dd, J = 9.8, 3.4 Hz, 1H), 4.43-4.34 (m, 1H), 3.52 (d, J = 9.8 Hz, 1H), 3.48 (d, J = 9.9 Hz, 1H), 3.13 (dtd, J = 18.4, 9.2, 6.9 Hz, 2H), 3.05-2.85 (m, 2H), 2.30-2.19 (m, 2H), 2.18-2.08 (m, 1H), 1.96 (ddd, J = 13.8, 11.4, 4.4 Hz, 1H), 1.77-1.68 (m, 1H), 1.68-1.55 (m, 3H), 1.47 (ddd, J = 13.7, 9.1, 3.4 Hz, 1H), 0.91 (d, J = 6.5 Hz, 3H), 0.90 (d, J = 6.5 Hz, 3H), 0.67-0.47 (m, 4H). |
| 335 | (300 MHz, DMSO-d$_6$) δ ppm 8.77 (m, 1H), 7.77-7.32 (m, 1H), 5.20-4.70 (m, 2H), 4.62-4.06 (m, 2H), 3.97-3.67 (m, 1H), 3.57 (m, 1H), 3.21-3.00 (m, 2H), 2.45-2.25 (m, 1H), 2.20-2.02 (m, 1H), 2.03-1.88 (m, 1H), 1.79-1.18 (m, 7H), 1.09-0.96 (m, 3H), 0.96-0.81 (m, 6H). |
| 336 | (300 MHz, DMSO-d$_6$) δ ppm 8.76 (m, 0.4H), 7.56 (m, 1H), 6.02 (m, 0.6H), 5.02 (m, 1H), 4.25 (m, 1H), 3.98-3.43 (m, 4H), 3.26-2.91 (m, 5H), 2.38 (m, 1H), 2.27-2.04 (m, 1H), 2.03-1.84 (m, 1H), 1.78-1.36 (m, 5H), 1.34-1.13 (m, 2H), 1.02 (m, 3H), 0.94-0.71 (m, 6H). |
| 339 | (400 MHz, DMSO-d$_6$) δ ppm 8.63 (d, J = 7.2 Hz, 1H), 7.66 (s, 1H), 4.54-4.41 (m, 2H), 3.90-3.88 (m, 1H), 3.62-3.40 (m, 2H), 3.21-3.08 (m, 4H), 2.15-2.08 (m, 4H), 1.73-1.62 (m, 5H), 1.33-1.23 (m, 4H), 0.88-0.83 (m, 6H), 0.59-0.53 (m, 4H) |
| 345 | (400 MHz, DMSO-d$_6$) δ ppm 8.73 (d, J = 7.9 Hz, 1H), 7.64 (s, 1H), 5.08-4.96 (m, 2H), 4.76 (d, J = 8.2 Hz, 1H), 4.44-4.33 (m, 1H), 4.23 (s, 1H), 3.84-3.72 (m, 2H), 3.65 (d, J = 10.6 Hz, 1H), 3.20-3.10 (m, 1H), 3.10-3.00 (m, 1H), 2.42-2.28 (m, 1H), 2.19-2.06 (m, 1H), 1.96 (ddd, J = 13.8, 11.7, 3.9 Hz, 1H), 1.67-1.56 (m, 2H), 1.51 (dd, J = 7.7, 5.2 Hz, 1H), 1.29 (d, J = 7.6 Hz, 1H), 1.02 (s, 3H), 0.94-0.83 (m, 13H). |
| 357 | (400 MHz, DMSO-d$_6$) δ ppm 8.85 (d, J = 7.1 Hz, 0.2H), 8.65 (d, J = 7.6 Hz, 0.8H), 7.77 (s, 0.2H), 7.66 (s, 0.8H), 5.25-4.89 (m, 2H), 4.71 (d, J = 6.7 Hz, 0.2H), 4.66 (d, J = 6.9 Hz, 0.8H), 4.50-4.40 (m, 0.2H), 4.35 (ddd, J = 11.4, 7.6, 3.8 Hz, 0.8H), 4.15 (s, 1H), 3.88-3.74 (m, 2H), 3.73-3.47 (m, 2H), 3.23-3.04 (m, 2H), 2.12 (td, J = 11.5, 5.2 Hz, 1H), 1.95 (ddd, J = 14.8, 11.3, 4.1Hz, 1H), 1.85 (hept, J = 5.9 Hz, 1H), 1.68-1.56 (m, 2H), 1.52 (dd, J = 7.6, 5.1Hz, 1H), 1.27 (d, J = 7.6 Hz, 1H), 1.02 (s, 3H), 0.94-0.74 (m, 8H), 0.69 (d, J = 6.6 Hz, 1H). |
| 359 | (400 MHz, DMSO-d$_6$) δ ppm 8.60 (d, J = 7.6 Hz, 1H), 7.66 (s, 1H), 5.10-4.93 (m, 2H), 4.79-4.62 (m, 1H), 4.45-4.27 (m, 1H), 4.09 (d, J = 3.4 Hz, 1H), 3.91-3.70 (m, 2H), 3.64-3.49 (m, 1H), 3.48-3.37 (m, 1H), 3.22-3.04 (m, 1H), 2.51-2.24 (m, 2H), 2.19-2.05 (m, 2H), 2.01-1.70 (m, 3H), 1.69-1.35 (m, 6H), 0.95-0.58 (m, 7H). |
| 363 | (400 MHz, DMSO-d$_6$) δ ppm 8.66 (d, J = 7.2 Hz, 0.3H), 8.56 (d, J = 7.6 Hz, 0.7H), 7.72 (s, 0.3H), 7.66 (s, 0.7H), 5.14-4.87 (m, 2H), 4.68 (d, J = 7.2 Hz, 1H), 4.60 (s, 0.3H), 4.44-4.36 (m, 0.3H), 4.32 (ddd, J = 11.4, 7.5, 3.9 Hz, 0.7H), 4.19-4.09 (m, 0.7H), 4.06 (d, J = 3.5 Hz, 0.7H), 3.93-3.83 (m, 0.3H), 3.84-3.71 (m, 1H), 3.52-3.37 (m, 2H), 3.21-3.04 (m, 2H), 2.45-2.39 (m, 1H), 2.32-2.21 (m, 1H), 2.19-2.04 (m, 1H), 2.04-1.88 (m, 2H), 1.88-1.70 (m, 3H), 1.70-1.46 (m, 5H), 1.46-1.33 (m, 2H), 1.33-1.19 (m, 2H), 0.97-0.70 (m, 6H). |
| 364 | (400 MHz, DMSO-d$_6$) δ ppm 8.37 (d, J = 7.8 Hz, 1H), 7.71 (s, 1H), 7.42-7.21 (m, 5H), 6.09 (s, 1H), 5.11 (d, J = 17.2 Hz, 1H), 4.92 (d, J = 17.1 Hz, 1H), 4.43-4.31 (m, 2H), 3.64 (d, J = 11.3 Hz, 1H), 3.19-3.06 (m, 1H), 2.88 (d, J = 11.3 Hz, 1H), 2.32-2.22 (m, 1H), 2.15 (q, J = 9.0 Hz, 1H), 2.09-1.92 (m, 1H), 1.76 (dd, J = 8.0, 2.5 Hz, 2H), 1.72-1.55 (m, 2H), 1.51 (s, 3H), 0.48-0.32 (m, 2H), 0.31-0.16 (m, 1H), -0.26--0.36 (m, 1H). |
| 366 | (400 MHz, DMSO-d$_6$) δ ppm 8.46 (d, J = 7.5 Hz, 1H), 7.69 (s, 1H), 5.02 (d, J = 17.1 Hz, 1H), 4.93 (d, J = 17.1 Hz, 1H), 4.40-4.27 (m, 2H), 3.54 (d, J = 10.7 Hz, 1H), 3.50 (d, J = 10.6 Hz, 1H), 3.19-3.05 (m, 2H), 3.03-2.91 (m, 2H), 2.47-2.38 (m, 2H), 2.36-2.23 (m, 1H), 2.20-2.10 (m, 1H), 2.03-1.91 (m, 2H), 1.84-1.71 (m, 2H), 1.67-1.56 (m, 2H), 1.15 (s, 3H), 0.93 (s, 3H), 0.64-0.44 (m, 4H). |
| 368 | (500 MHz, DMSO-d$_6$) δ ppm 8.79 (d, J = 7.3 Hz, 0..25H), 8.62 (d, J = 7.6 Hz, 0.75H), 7.73 (s, 0.25H), 7.66 (s, 0.75H), 5.16 (d, J = 7.7 Hz, 0.25H), 5.12-5.04 (m, 0.25H), 5.05-5.00 (m, 1H), 4.97 (d, J = 17.1 Hz, 1H), 4.66 (d, J = 7.3 Hz, 1H), 4.57 (s, 0.25H), 4.49-4.42 (m, 0.25H), 4.37 (ddd, J = 11.4, 7.6, 3.9 Hz, 0.75H), 4.15 (s, 0.75H), 3.99 (td, J = 7.4, 4.5 Hz, 1H), 3.85 (dd, J = 10.7, 5.4 Hz, 1H), 3.67-3.59 (m, 0.25H), 3.59-3.55 (m, 1H), 3.52 (m, 0.25H), 3.06-3.23 (m, 2H), 2.35-2.23 (m, 1H), 2.18-2.08 (m, 1H), 2.01-1.89 (m, 1H), 1.76-1.69 (m, 0.25H), 1.68-1.58 (m, 1.5H), 1.58-1.50 (m, 1.5H), 1.49-1.34 (m, 1.5H), 1.29 (d, J = 7.6 Hz, 0.75H), 1.03 (d, J = 1.9 Hz, 3H), 0.90 (d, J = 2.3 Hz, 3H), 0.86 (t, J = 7.3 Hz, 2.25H), 0.78 (t, J = 7.5 Hz, 0.75H). |
| 369 | (400 MHz, DMSO-d$_6$) δ ppm 8.62 (d, J = 7.6 Hz, 1H), 7.76-7.60 (m, 2H), 5.43 (d, J = 5.4 Hz, 1H), 4.98 (s, 2H), 4.40 (ddd, J = 11.3, 7.4, 3.9 Hz, 1H), 4.32 (td, J = 8.6, 5.6 Hz, 1H), 3.86 (dt, J = 6.7, 4.7 Hz, 1H), 3.21-3.06 (m, 2H), 2.31-2.18 (m, 1H), 2.14-2.03 (m, 1H), 1.96 (ddd, J = 15.0, 11.1, 4.1 Hz, 1H), 1.71-1.38 (m, 7H), 0.97-0.75 (m, 9H). |

TABLE 2-continued

| Compound | ¹H NMR Data |
|---|---|
| 371 | (400 MHz, DMSO-d₆) δ ppm 8.74 (d, J = 7.3 Hz, 0.3H), 8.45 (d, J = 7.7 Hz, 0.7H), 7.75 (s, 0.3H), 7.68 (s, 0.7H), 5.10-4.88 (m, 2H), 4.62 (d, J = 7.0Hz, 0.7H), 4.42-4.28 (m, 1H), 4.08-3.95 (m, 0.7H), 3.61-3.47 (m, 1.7H), 3.23-3.04 (m, 2.3H), 2.31-2.02 (m, 3H), 2.02-1.86 (m, 1H), 1.78-1.53 (m, 4H), 1.53-1.37 (m, 1H), 0.95-0.77 (m, 3H), 0.69-0.37 (m, 4H). |
| 375 | (400 MHz, DMSO-d₆) δ ppm 8.62 (d, J = 7.6 Hz, 1H), 7.63 (t, J = 8.8 Hz, 2H), 5.44 (d, J = 5.6 Hz, 1H), 4.96 (s, 2H), 4.43-4.38 (m, 2H), 3.84 (d, J = 6.0 Hz, 1H), 3.16-3.07 (m, 2H), 2.31-2.19 (m, 1H), 2.15-2.05 (m, 1H), 2.02-1.91 (m, 1H), 1.70-1.43 (m, 6H), 1.23 (s, 1H), 1.02 (s, 3H), 0.83 (t, J = 7.6 Hz, 1H), 0.38(d, J = 6.0 Hz, 1H), 0.22-0.16 (m, 3H). |
| 376 | (400 MHz, DMSO-d₆) δ ppm 8.72 (d, J = 7.2 Hz, 1H), 7.71 (s, 1H), 7.64 (d, J = 8.4Hz, 1H), 5.47(s, 1H), 5.06-4.95 (m, 2H), 4.52-4.29(m, 2H), 3.83 (d, J = 2.4Hz, 1H), 3.16-3.12 (m, 2H), 2.31-2.19 (m, 1H), 2.15-2.05 (m, 1H), 2.02-1.91 (m, 1H), 1.69-1.46 (m, 6H), 1.23 (s, 1H), 0.85 (t, J = 7.6 Hz, 3H), 0.37 (s, 1H), 0.21-0.16 (m, 3H). |
| 377 | (400 MHz, DMSO-d₆) δ ppm 8.66 (d, J = 7.7 Hz, 0.35H rotamer), 8.57 (d, J = 7.6 Hz, 0.65H rotamer), 7.72 (s, 0.35H rotamer), 7.66 (s, 0.65H rotamer), 5.18-4.87 (m, 2H), 4.76-4.51 (m, 1H), 4.48-4.26 (m, 1H), 4.12-3.98 (m, 2H), 3.85-3.73 (m, 1H), 3.58-3.39 (m, 2H), 3.22-3.04 (m, 2H), 2.60-2.53 (m, 1H), 2.20-2.04 (m, 1H), 2.03-1.72 (m, 4H), 1.72-1.33 (m, 8H), 0.95-0.66 (m, 3H). |
| 378 | (400 MHz, DMSO-d₆) δ ppm 8.77 (d, J = 7.3 Hz, 0.25H, rotamer), 8.62 (d, J = 7.6 Hz, 0.75H, rotamer), 7.73 (s, 0.25H, rotamer), 7.66 (s, 0.75H, rotamer), 5.21-4.90 (m, 2H), 4.66 (d, J = 7.4 Hz, 1H), 4.57 (s, 0.25H, rotamer), 4.49-4.40 (m, 0.25H, rotamer), 4.40-4.31 (m, 0.75H, rotamer), 4.13 (s, 0.75H, rotamer), 4.09-3.97 (m, 1H), 3.84 (dd, J = 10.6, 5.4 Hz, 1H), 3.70 (q, J = 6.9 Hz, 0.25H, rotamer), 3.59-3.49 (m, 0.75H, rotamer), 3.23-3.05 (m, 2H), 2.31-2.19 (m, 1H), 2.19-2.04 (m, 1H), 2.02-1.87 (m, 1H), 1.75-1.20 (m, 8H), 1.02 (d, J = 1.9 Hz, 3H), 0.93-0.76 (m, 6H). |
| 384 | (400 MHz, DMSO-d₆) δ ppm 8.68 (d, J = 7.3 Hz, 1H), 8.28 (d, J = 8.2 Hz, 1H), 7.69 (s, 1H), 7.05 (d, J = 7.3 Hz, 1H), 5.05-4.89 (m, 2H), 4.67-4.51 (m, 1H), 4.45-4.32 (m, 2H), 3.21-3.05 (m, 2H), 2.31-2.18 (m, 1H), 2.14-2.03 (m, 1H), 2.02-1.88 (m, 1H), 1.70-1.42 (m, 5H), 0.89 (d, J = 6.1 Hz, 3H), 0.85 (d, J = 6.2 Hz, 3H). |
| 385 | (400 MHz, DMSO-d₆) δ ppm 8.78 (d, J = 7.2 Hz, 0.3H), 8.52 (d, J = 7.5 Hz, 0.7H), 7.75 (s, 0.3H), 7.69 (s, 0.7H), 7.29 (s, 0.3H), 6.68 (d, J = 8.6 Hz, 0.7H), 5.04-4.92 (m, 2H), 4.91-4.83 (m, 1H), 4.48-4.42 (m, 1H), 4.37 (ddd, J = 11.4, 7.5, 3.9 Hz, 1H), 3.65 (d, J = 10.3 Hz, 0.7H), 3.58-3.46 (m, 1.3H), 3.22-3.06 (m, 2H), 2.34-2.25 (m, 1H), 2.21-2.09 (m, 2H), 2.03-1.90 (m, 1H), 1.80-1.72 (m, 1H), 1.72-1.58 (m, 2H), 0.64-0.52 (m, 4H). |
| 387 | (400 MHz, DMSO-d₆) δ ppm 8.52 (d, J = 7.8 Hz, 1H), 7.66 (s, 1H), 6.96-6.79 (m, 1H), 5.09-4.65 (m, 3H), 4.47-4.32 (m, 2H), 3.70 (d, J = 10.3 Hz, 1H), 3.54-3.43 (m, 1H), 3.20-3.03 (m, 2H), 2.32-2.21 (m, 1H), 2.18 (dd, J = 12.6, 8.7 Hz, 1H), 2.15-2.04 (m, 1H), 2.01-1.90 (m, 1H), 1.72 (dd, J = 12.8, 4.8 Hz, 1H), 1.67-1.55 (m, 2H), 0.66-0.42 (m, 4H). |
| 390 | (400 MHz, DMSO-d₆) δ ppm 8.70 (d, J = 7.5 Hz, 0.25H, rotamer), 8.39 (d, J = 7.9 Hz, 0.75H, rotamer), 8.03-7.32 (m, 1H), 6.57-5.81 (m, 1H), 5.22-4.77 (m, 2H), 4.56-4.19 (m, 3H), 4.08-3.72 (m, 0.75H, rotamer), 3.69-3.35 (m, 2.25H, rotamer), 3.28-3.03 (m, 2H), 2.75-2.51 (m, 2H), 2.40-1.89 (m, 3H), 1.85-1.39 (m, 3H), 0.72-0.31 (m, 4H). |
| 393 | (400 MHz, DMSO-d₆) δ ppm 8.66 (d, J = 7.4 Hz, 0.3H), 8.57 (d, J = 7.6 Hz, 0.7H), 7.73 (s, 0.3H), 7.67 (s, 0.7H), 5.21-4.86 (m, 2H), 4.76 (d, J = 7.2 Hz, 0.7H), 4.60 (s, 0.3H), 4.44-4.37 (m, 0.3H), 4.36-4.29 (m, 0.7H), 4.24-4.14 (m, 1H), 4.06 (d, J = 3.4 Hz, 1H), 3.96-3.86 (m, 0.3H), 3.82 (dd, J = 10.5, 8.0 Hz, 0.7H), 3.54-3.48 (m, 0.3H), 3.44-3.38 (m, 0.7H), 3.22-3.06 (m, 2H), 2.72-2.67 (m, 1H), 2.46-2.39 (m, 1H), 2.32-2.24 (m, 1H), 2.18-2.01 (m, 1H), 2.00-1.89 (m, 1H), 1.89-1.72 (m, 2H), 1.72-1.43 (m, 5H), 1.37 (tq, J = 13.6, 6.1 Hz, 2H), 0.91-0.64 (m, 1H), 0.46-0.20 (m, 2H), 0.13--0.10 (m, 2H). |
| 400 | (400 MHz, DMSO-d₆) δ ppm 8.59 (d, J = 7.6 Hz, 0.5H, Dias.), 8.52 (d, J = 7.6 Hz, 0.5H, Dias.), 7.67 (d, J = 3.7 Hz, 1H), 7.44-7.31 (m, 2H), 7.25-7.20 (m, 1H), 5.82 (d, J = 6.9 Hz, 0.5H, Dias.), 5.75 (d, J = 6.7 Hz, 0.5H, Dias.), 5.25 (d, J = 6.8 Hz, 0.5H, Dias.), 5.19 (d, J = 6.6 Hz, 0.5H, Dias.), 5.04 (d, J = 17.0 Hz, 1H), 4.98-4.87 (m, 1H), 4.45 (dd, J = 8.4, 6.0 Hz, 1H), 4.43-4.31 (m, 1H), 3.58 (d, J = 10.1 Hz, 0.5H, Dias.), 3.52-3.24 (m, 0.5H, Dias.), 3.18-3.03 (m, 2H), 2.31-2.27 (m, 1H), 2.19-2.09 (m, 1H), 2.08-2.00 (m, 1H), 1.99-1.91 (m, 0.5H, Dias.), 1.75 (dd, J = 12.6, 6.1 Hz, 0.5H, Dias.), 1.70-1.56 (m, 3H), 1.23 (s, 1H), 0.53 (d, J = 5.4 Hz, 2H), 0.52-0.38 (m, 2H). |
| 402 | (400 MHz, DMSO-d₆) δ ppm 8.60 (s, 0.55H rotamer), 8.53 (s, 0.45H rotamer), 7.69 (s, 0.55H rotamer), 7.66 (s, 0.45H rotamer), 7.51-7.37 (m, 1H), 7.28-7.14 (m, 1H), 7.14-7.01 (m, 1H), 5.71-5.58 (m, 1H), 5.46-5.37 (m, 1H), 5.09-4.86 (m, 2H), 4.52-4.29 (m, 2H), 3.59-3.45 (m, 1H), 3.20-3.05 (m, 3H), 2.31-2.22 (m, 1H), 2.20-2.09 (m, 2H), 2.09-1.89 (m, 2H), 1.82-1.54 (m, 2H), 0.66-0.34 (m, 4H). |
| 403 | (400 MHz, DMSO-d₆) δ ppm 8.53 (s, 1H), 7.68 (s, 1H), 7.44-7.33 (m, 2H), 7.17 (s, 2H), 5.49 (d, 1H), 5.18 (d, 1H), 5.03 (d, 1H), 4.96 (d, 1H), 4.43- |

TABLE 2-continued

| Compound | ¹H NMR Data |
|---|---|
|  | 4.33 (m, 2H), 3.43 (d, 1H), 3.21-3.07 (m, 3H), 2.42-2.20 (m, 1H), 2.20-2.04 (m, 2H), 2.04-1.89 (m, 1H), 1.73-1.50 (m, 3H), 0.62-0.30 (m, 4H). |
| 404 | (400 MHz, DMSO-d₆) δ ppm 8.64 (d, J = 7.6 Hz, 1H), 7.68 (s, 1H), 7.39 (dd, J = 8.7, 5.6 Hz, 2H), 7.18 (t, J = 8.9 Hz, 2H), 5.53 (d, J = 6.6 Hz, 1H), 5.19 (d, J = 6.6 Hz, 1H), 5.07-4.92 (m, 2H), 4.43-4.28 (m, 1H), 4.09 (d, J = 3.6 Hz, 1H), 3.63 (dd, J = 10.7, 7.7 Hz, 1H), 3.23-3.02 (m, 3H), 2.62-2.55 (m, 1H), 2.44-2.36 (m, 1H), 2.36-2.26 (m, 1H), 2.18-2.05 (m, 1H), 2.05-1.86 (m, 1H), 1.80-1.69 (m, 1H), 1.69-1.51 (m, 3H), 1.51-1.30 (m, 3H), 1.08-0.88 (m, 1H). |
| 405 | (400 MHz, DMSO-d₆) δ ppm 8.66-8.51 (m, 1H), 7.76-7.60 (m, 1H), 7.43-7.28 (m, 1H), 7.26-6.98 (m, 3H), 5.82-5.62 (m, 1H), 5.29-5.16 (m, 1H), 5.14-4.82 (m, 2H), 4.53-4.30 (m, 2H), 3.60-3.40 (m, 2H), 3.22-3.01 (m, 2H), 2.31-2.08 (m, 2H), 2.06-1.87 (m, 2H), 1.85-1.52 (m, 3H), 0.62-0.34 (m, 4H). |
| 407 | (400 MHz, DMSO-d₆) δ ppm 8.67 (d, J = 7.6 Hz, 1H), 7.68 (s, 1H), 7.42-7.32 (m, 2H), 7.25-7.13 (m, 2H), 5.55 (d, J = 7.2 Hz, 1H), 5.35 (d, J = 7.0 Hz, 1H), 5.08-4.94 (m, 2H), 4.41 (ddd, J = 11.4, 7.5, 3.9 Hz, 1H), 4.14 (s, 1H), 3.84 (dd, J = 10.5, 5.4 Hz, 1H), 3.21-2.99 (m, 3H), 2.20-2.08 (m, 1H), 2.03-1.87 (m, 1H), 1.72-1.54 (m, 2H), 1.51-1.37 (m, 1H), 1.27 (d, J = 7.5 Hz, 1H), 0.92 (s, 3H), 0.45 (s, 3H). |
| 408 | (400 MHz, DMSO-d₆) δ ppm 8.61 (d, J = 7.6 Hz, 1H), 8.03 (d, J = 8.3 Hz, 1H), 7.67 (s, 1H), 7.42 (td, J = 7.5, 1.8 Hz, 1H), 7.34 (ddt, J = 7.6, 5.3, 3.6 Hz, 1H), 7.21-7.04 (m, 2H), 6.40 (d, J = 5.1 Hz, 1H), 5.22 (d, J = 5.0 Hz, 1H), 5.06-4.85 (m, 2H), 4.44 (ddd, J = 11.4, 7.5, 3.9 Hz, 1H), 4.36 (td, J = 8.8, 5.2 Hz, 1H), 3.12 (t, J = 9.1 Hz, 1H), 2.99 (td, J = 9.1, 7.0 Hz, 1H), 2.32-2.17 (m, 1H), 2.13-2.00 (m, 1H), 1.95 (ddd, J = 13.8, 11.3, 4.2 Hz, 1H), 1.73-1.56 (m, 4H), 1.55-1.45 (m, 1H), 0.91 (d, J = 6.0 Hz, 3H), 0.87 (d, J = 6.0 Hz, 3H). |
| 409 | (400 MHz, DMSO-d₆) δ ppm 8.64 (d, J = 7.6 Hz, 1H), 7.71 (s, 1H), 7.44-7.34 (m, 2H), 7.26-7.17 (m, 2H), 5.56 (d, J = 7.1 Hz, 1H), 5.41 (d, J = 7.1 Hz, 1H), 5.12-4.91 (m, 2H), 4.39 (ddd, J = 11.4, 7.5, 3.9 Hz, 1H), 4.13 (d, J = 3.5 Hz, 1H), 3.76 (dd, J = 10.6, 7.8 Hz, 1H), 3.25-3.09 (m, 2H), 2.99 (dd, J = 10.7, 3.8 Hz, 1H), 2.66-2.56 (m, 1H), 2.49-2.41 (m, 1H), 2.34-2.27 (m, 1H), 2.20-2.08 (m, 1H), 1.97 (ddd, J = 13.8, 11.4, 4.4 Hz, 1H), 1.84-1.71 (m, 1H), 1.71-1.50 (m, 3H), 1.50-1.28 (m, 3H), 0.94-0.82 (m, 1H). |
| 410 | (400 MHz, DMSO-d₆) δ ppm 8.53 (d, J = 7.6 Hz, 1H), 7.69 (s, 1H), 7.42-7.33 (m, 2H), 7.23-7.16 (m, 2H), 5.51 (d, J = 7.0 Hz, 1H), 5.45-5.41 (m, 1H), 5.07-4.99 (m, 1H), 4.92 (d, J = 17.1 Hz, 1H), 4.45-4.35 (m, 2H), 3.47 (d, J = 9.9 Hz, 1H), 3.18-3.10 (m, 2H), 3.04 (d, J = 9.7 Hz, 1H), 2.31-2.23 (m, 1H), 2.15 (dd, J = 12.8, 8.6 Hz, 2H), 2.03-1.92 (m, 1H), 1.71-1.55 (m, 3H), 0.61-0.30 (m, 4H). |
| 413 | (400 MHz, DMSO-d₆) δ ppm 8.69 (d, J = 7.6 Hz, 1H), 7.68 (s, 1H), 7.44-7.13 (m, 5H), 5.38 (d, J = 6.8 Hz, 1H), 5.08 (d, J = 6.9 Hz, 2H), 5.03 (d, J = 8.0 Hz, 2H), 4.44-4.35 (m, 1H), 4.11 (s, 1H), 3.70 (dd, J = 10.5, 5.4 Hz, 1H), 3.23-3.08 (m, 3H), 2.38-2.32 (m, 1H), 2.21-2.05 (m, 1H), 2.05-1.87 (m, 1H), 1.72-1.55 (m, 2H), 1.41 (dd, J = 7.6, 5.3 Hz, 1H), 1.27-1.16 (m, 1H), 0.89 (s, 3H), 0.35 (s, 2H). |
| 414 | (400 MHz, DMSO-d₆) δ ppm 8.60 (d, J = 7.4 Hz, 1H), 7.68 (s, 1H), 7.40-7.19 (m, 5H), 5.43 (d, J = 6.7 Hz, 1H), 5.16 (d, J = 6.8 Hz, 1H), 5.08-4.93 (m, 2H), 4.50-4.31 (m, 1H), 4.10 (d, J = 3.6 Hz, 1H), 3.62 (dd, J = 10.7, 7.7 Hz, 1H), 3.19-3.05 (m, 3H), 2.60-2.54 (m, 1H), 2.45-2.36 (m, 1H), 2.20-2.05 (m, 1H), 2.03-1.88 (m, 1H), 1.80-1.69 (m, 1H), 1.69-1.58 (m, 2H), 1.58-1.47 (m, 1H), 1.47-1.27 (m, 3H), 1.23 (s, 1H), 0.91-0.80 (m, 1H). |
| 415 | (400 MHz, DMSO-d₆) δ ppm 8.59 (d, J = 7.6 Hz, 1H), 7.68 (s, 1H), 7.41-7.35 (m, 2H), 7.35-7.23 (m, 3H), 5.54 (d, J = 6.4 Hz, 1H), 5.23 (d, J = 6.4 Hz, 1H), 5.03-4.92 (m, 2H), 4.48 (dd, J = 8.2, 6.4 Hz, 1H), 4.40-4.30 (m, 1H), 3.51 (d, J = 10.2 Hz, 1H), 3.21 (d, J = 10.2 Hz, 1H), 3.16-3.04 (m, 2H), 2.42-2.28 (m, 1H), 2.24-2.11 (m, 1H), 2.05-1.90 (m, 2H), 1.77 (dd, J = 12.6, 6.4 Hz, 1H), 1.72-1.56 (m, 2H), 0.59-0.40 (m, 4H). |
| 423 | (400 MHz, DMSO-d₆) δ ppm 8.51 (d, J = 7.5 Hz, 0.6H, rotamer), 8.41 (d, J = 7.8 Hz, 0.4H, rotamer), 7.67 (s, 1H), 5.07-4.82 (m, 2H), 4.70-4.43 (m, 1H), 4.43-4.27 (m, 2H), 4.24-4.13 (m, 1H), 3.62-3.40 (m, 2H), 3.20-3.04 (m, 2H), 2.30-1.89 (m, 3H), 1.82-1.40 (m, 5H), 1.38-1.27 (m, 1H), 0.97-0.89 (m, 9H), 0.70-0.40 (m, 4H). |
| 424 | (400 MHz, DMSO-d₆) δ ppm 8.32 (d, J = 7.7 Hz, 1H), 7.69 (s, 1H), 5.00 (d, J = 17.1 Hz, 1H), 4.99 (s, 1H), 4.87 (d, J = 17.1 Hz, 1H), 4.37 (dd, J = 8.4, 6.4 Hz, 1H), 4.30 (ddd, J = 11.5, 7.7, 3.9 Hz, 1H), 3.81 (d, J = 11.1 Hz, 1H), 3.75 (d, J = 11.2 Hz, 1H), 3.20-3.05 (m, 2H), 3.02-2.91 (m, 2H), 2.30-2.21 (m, 1H), 2.18-2.09 (m, 1H), 2.03-1.91 (m, 2H), 1.79-1.36 (m, 10H), 1.15 (d, J = 9.7 Hz, 1H), 0.64-0.45 (m, 4H). |
| 428 | (400 MHz, DMSO-d₆) δ ppm 8.65 (d, J = 7.6 Hz, 0.5H rotamer), 8.53 (d, J = 7.9 Hz, 0.5H rotamer), 7.70 (s, 0.5H rotamer), 7.67 (s, 0.5H rotamer), 5.03 (d, J = 17.3 Hz, 0.5H rotamer), 5.00 (s, 1H), 4.89 (d, J = 17.1 Hz, 0.5H rotamer), 4.79 (dd, J = 8.4, 3.8 Hz, 0.5H rotamer), 4.45 (dd, J = 8.8, 4.3 Hz, 0.5H rotamer), 4.42-4.33 (m, 1H), 3.64 (d, J = 10.8 Hz, 0.5H rotamer), 3.51 (d, J = 11.0 Hz, 0.5H rotamer), 3.45 (d, J = 11.9 Hz, 0.5H rotamer), 3.22-3.07 (m, 2H), 3.00-2.94 (m, 2H), 2.80-2.68 (m, 1.5H rotamer), 2.62 (d, J = |

TABLE 2-continued

| Compound | ¹H NMR Data |
|---|---|
|  | 6.5 Hz, 0.5H rotamer), 2.55 (d, J = 6.6 Hz, 0.5H rotamer), 2.37 (dd, J = 12.7, 8.6 Hz, 1H), 2.28-1.90 (m, 4H), 1.85-1.74 (m, 1H), 1.72-1.57 (m, 4H), 0.91-0.83 (m, 6H), 0.70-0.44 (m, 4H). |
| 429 | (400 MHz, DMSO-d₆) δ ppm 8.38 (d, J = 8.1 Hz, 1H), 7.66 (s, 1H), 5.10-4.95 (m, 1H), 4.82 (d, J = 17.2 Hz, 1H), 4.38-4.21 (m, 2H), 3.56-3.44 (m, 2H), 3.15-3.08 (m, 2H), 2.30-2.16 (m, 4H), 2.16-2.07 (m, 2H), 2.01-1.92 (m, 1H), 1.66-1.55 (m, 3H), 1.40-1.36 (m, 2H), 0.87-0.84 (m, 6H), 0.58-0.45 (m, 4H). |
| 434 | (400 MHz, DMSO-d₆) δ ppm 8.62 (d, J = 7.6 Hz, 1H), 7.84 (J = 8Hz, 1H), 7.67 (s, 1H), 5.00-4.90 (m, 1H), 4.40-4.25 (m, 2H), 3.33-3.30 (m, 2H), 3.29-3.09 (m, 3H), 2.30-2.20 (m, 1H), 2.20-2.10 (m, 1H), 2.00-1.90 (m, 1H), 1.70-1.50 (m, 3H), 1.48-1.40 (m, 2H), 1.23 (d, J = 4 Hz, 1H), 0.93-0.84 (m, 10H). |
| 442 | (300 MHz, CDCl₃) δ ppm 4.95-4.63 (m, 2H), 4.62-4.38 (m, 1H), 4.35 (m, 1H), 4.11-3.58 (m, 2H), 3.53-3.30 (m, 2H), 3.13-2.33 (m, 6H), 2.19-1.39 (m, 4H), 1.29 (m, 2H), 1.15-0.74 (m, 6H). |
| 445 | (400 MHz, DMSO-d₆) δ ppm 8.49 (d, J = 7.7 Hz, 1H), 7.68 (s, 1H), 4.99 (d, J = 17.1 Hz, 1H), 4.90 (d, J = 17.2 Hz, 1H), 4.81 (d, J = 7.4 Hz, 1H), 4.41 (dd, J = 8.5, 5.6 Hz, 1H), 4.38-4.27 (m, 1H), 4.14 (q, J = 7.3 Hz, 1H), 3.61 (d, J = 9.8 Hz, 1H), 3.49 (d, J = 9.9 Hz, 1H), 3.23-3.09 (m, 2H), 2.27 (s, 1H), 2.20-2.13 (m, 1H), 2.08 (dd, J = 12.5, 8.5 Hz, 1H), 2.03-1.89 (m, 1H), 1.85-1.69 (m, 2H), 1.69-1.52 (m, 2H), 1.38 (t, J = 6.8 Hz, 2H), 0.98-0.74 (m, 6H), 0.71-0.44 (m, 4H). |
| 449 | (400 MHz, DMSO-d₆) δ ppm 8.42 (d, J = 7.8 Hz, 1H), 7.65 (m, 1H), 5.03 (m, 1H), 4.92 (m, 1H), 4.38 (m, 2H), 4.10 (m, 1H), 3.36 (m, 1H), 3.14 (m, 2H), 2.37 (m, 1H), 2.28 (m, 1H), 2.14 (m, 1H), 2.05-1.91 (m, 1H), 1.79 (m, 2H), 1.72-1.59 (m, 2H), 1.56-1.43 (m, 1H), 1.40-1.32 (m, 1H), 1.24 (m, 6H), 1.21 (m, 3H), 0.91 (m, 6H), 0.85 (m, 5H), 0.67 (m, 1H). |
| 453 | (400 MHz, DMSO-d₆) δ ppm 8.79-8.63 (m, 1H), 7.70 (d, J = 12.1 Hz, 1H), 7.60-7.31 (m, 4H), 5.05 (d, J = 17.3 Hz, 1H), 4.93 (d, J = 17.2 Hz, 1H), 4.60-4.45 (m, 1H), 4.44-4.30 (m, 1H), 3.79-3.58 (m, 1H), 3.37 (d, J = 9.9 Hz, 1H), 3.22-3.03 (m, 2H), 2.31-2.11 (m, 2H), 2.09-1.88 (m, 2H), 1.83 (dd, J = 12.6, 6.0 Hz, 1H), 1.73-1.52 (m, 2H), 1.32-1.22 (m, 9H), 0.68-0.36 (m, 4H). |
| 454 | (400 MHz, DMSO-d₆) δ ppm 8.61 (d, J = 7.6 Hz, 1H), 7.66 (s, 1H), 5.02 (d, J = 17.2 Hz, 1H), 4.95 (d, J = 17.2 Hz, 1H), 4.56 (d, J = 7.5 Hz, 1H), 4.36 (ddd, J = 11.5, 7.7, 3.9 Hz, 1H), 4.17-4.13 (m, 1H), 3.90-3.83 (m, 1H), 3.48 (d, J = 10.6 Hz, 1H), 3.20-3.05 (m, 2H), 2.36-2.26 (m, 1H), 2.18-2.07 (m, 2H), 1.96 (ddd, J = 15.2, 11.3, 4.3 Hz, 2H), 1.68-1.57 (m, 2H), 1.54 (dd, J = 7.8, 5.2 Hz, 1H), 1.35-1.30 (m, 2H), 1.02 (s, 3H), 0.93 (s, 9H), 0.89 (s, 3H). |
| 460 | (400 MHz, DMSO-d₆) δ ppm 9.09 (d, J = 7.8 Hz, 1H), 8.73 (d, J = 7.7 Hz, 1H), 7.99 (td, J = 7.7, 1.8 Hz, 1H), 7.67 (s, 1H), 7.66-7.57 (m, 1H), 7.53-7.45 (m, 1H), 7.42 (td, J = 8.0, 1.2 Hz, 1H), 7.35-7.31 (m, 2H), 7.30-7.24 (m, 2H), 7.22-7.16 (m, 1H), 7.14 (d, J = 3.0 Hz, 1H), 4.95 (d, J = 17.1 Hz, 1H), 4.85 (d, J = 17.2 Hz, 1H), 4.76-4.67 (m, 1H), 4.42 (ddd, J = 11.3, 7.6, 4.0 Hz, 1H), 3.20-3.02 (m, 4H), 2.29-2.18 (m, 1H), 2.15-2.05 (m, 1H), 2.04-1.93 (m, 1H), 1.71-1.58 (m, 2H). |
| 465 | (400 MHz, DMSO-d₆) δ ppm 11.94 (d, J = 1.2 Hz, 1H), 8.70-8.60 (m, 1H), 7.59-7.30 (m, 2H), 7.27-7.04 (m, 3H), 6.63-6.53 (m, 1H), 5.80-5.67 (m, 1H), 5.01-4.86 (m, 2H), 4.49-4.42 (m, 1H), 4.02-3.89 (m, 1H), 3.03-2.50 (m, 3H), 2.30-1.50 (m, 8H), 0.97 (d, J = 6.0 Hz, 3H), 0.90 (d, J = 3.3 Hz, 3H). |
| 466 | (400 MHz, DMSO-d₆) δ ppm 8.71 (d, J = 8.0 Hz, 1H), 8.64 (d, J = 7.6 Hz, 1H), 7.66 (s, 1H), 7.60 (s, 1H), 7.33 (d, J = 7.2 Hz, 1H), 7.25 (t, J = 8.0 Hz, 1H), 7.08 (d, J = 7.6 Hz, 1H), 4.98 (q, J = 16.8 Hz, 2H), 4.51-4.42 (m, 2H), 3.97 (s, 3H), 3.16-3.09 (m, 2H), 2.28-2.09 (m, 3H), 1.77-1.55 (m, 5H), 0.87 (q, J = 6.4 Hz, 6H). |
| 468 | (600 MHz, CDCl₃) δ ppm 8.38 (s, 1H), 8.31 (d, J = 8.4 Hz, 1H), 5.30 (s, 2H), 4.84 (dd, J = 16.9, 1.6 Hz, 1H), 4.74 (dd, J = 16.7, 1.6 Hz, 1H), 4.69-4.64 (m, 1H), 4.59-4.52 (m, 2H), 4.48-4.44 (m, 1H), 4.32-4.27 (m, 1H), 4.19 (d, J = 12.1 Hz, 1H), 3.93 (s, 1H), 3.39-3.30 (m, 4H), 2.45-2.35 (m, 1H), 2.08-2.00 (m, 1H), 1.96-1.75 (m, 5H), 1.69 (d, J = 1.6 Hz, 1H), 1.62 (t, J = 6.6 Hz, 1H), 1.49 (d, J = 1.6 Hz, 1H), 1.07 (s, 6H). |
| 469 | (499 MHz, DMSO-d₆) δ ppm 8.76 (s, 0.6H rotamer), 8.71 (d, J = 7.4 Hz, 0.4H rotamer), 8.68 (s, 0.6H rotamer), 8.65 (d, J = 7.5 Hz, 0.6H rotamer), 7.66 (s, 0.4H rotamer), 7.65 (s, 0.6H rotamer), 5.07 (d, J = 17.2 Hz, 1H), 5.02 (d, J = 17.4 Hz, 1H), 4.42-4.33 (m, 1H), 3.93 (dd, J = 12.0, 5.4 Hz, 0.6H rotamer), 3.80 (d, J = 12.1 Hz, 1H), 3.59 (dd, J = 12.9, 5.1 Hz, 1H), 3.53 (d, J = 12.8 Hz, 1H), 3.21-3.08 (m, 2H), 2.42-2.33 (m, 0.6H rotamer), 2.32-2.23 (m, 0.6H rotamer), 2.22-2.07 (m, 2H), 2.02-1.90 (m, 1H), 1.73-1.59 (m, 2H), 1.53 (dd, J = 7.6, 5.1 Hz, 0.6H rotamer), 1.48 (d, J = 7.5 Hz, 1H), 1.38 (dd, J = 7.7, 4.9 Hz, 1H), 1.34-1.30 (m, 0.6H rotamer), 1.27 (s, 2H), 1.21 (s, 3H), 1.03 (s, 3H), 1.02-0.99 (m, 1H), 0.88 (s, 3H), 0.70-0.44 (m, 4H). |
| 470 | (499 MHz, DMSO-d₆) δ ppm 8.72 (d, J = 7.5 Hz, 0.4H rotamers), 8.64 (d, J = 7.7 Hz, 0.6H rotamers), 8.42 (d, J = 8.6 Hz, 0.6H rotamers), 8.29 (d, J = 8.5 Hz, 0.4H rotamers), 7.47 (s, 1H), 5.04 (d, J = 17.1 Hz, 1H), 4.99 (d, J = 17.1 Hz, 1H), 4.84 (s, 0.6H rotamers), 4.45-4.34 (m, 1H), 4.25 (s, 0.4H |

TABLE 2-continued

| Compound | ¹H NMR Data |
|---|---|
| | rotamers), 3.94 (dd, J = 12.1, 5.4 Hz, 0.4H rotamers), 3.84 (d, J = 12.0 Hz, 0.4H rotamers), 3.61 (dd, J = 12.8, 5.1 Hz, 0.6H rotamers), 3.56 (d, J = 12.8 Hz, 0.6H rotamers), 3.50-3.40 (m, 1H), 3.17-3.05 (m, 2H), 2.28-2.10 (m, 2H), 1.90-1.83 (m, 1H), 1.78-1.50 (m, 9H), 1.40-1.04 (m, 8H), 1.03 (s, 3H), 0.88 (s, 3H). |
| 471 | (500 MHz, DMSO-d$_6$) δ ppm 8.75 (d, J = 7.4 Hz, 0.4H rotamers), 8.65 (d, J = 7.7 Hz, 0.6H rotamers), 7.86 (s, 0.6H rotamers), 7.80 (s, 0.4H rotamers), 7.67 (s, 0.4H rotamers), 7.65 (s, 0.6H rotamers), 5.12-4.95 (m, 2H), 4.80 (s, 0.6H rotamers), 4.43-4.34 (m, 1H), 4.22 (s, 0.4H rotamers), 3.96 (dd, J = 12.0, 5.5 Hz, 0.4H rotamers), 3.83 (d, J = 12.0 Hz, 0.6H rotamers), 3.61 (dd, J = 12.8, 4.9 Hz, 0.6H rotamers), 3.56 (d, J = 12.8 Hz, 0.4H rotamers), 3.22-3.05 (m, 2H), 2.41-2.33 (m, 0.6H rotamers), 2.32-2.25 (m, 0.4H rotamers), 2.19-2.10 (m, 1H), 2.02-1.92 (m, 1H), 1.72-1.60 (m, 2H), 1.55 (dd, J = 7.7, 5.4 Hz, 0.4H rotamers), 1.48 (d, J = 7.6 Hz, 0.6H rotamers), 1.39 (dd, J = 7.7, 4.8 Hz, 0.6H rotamers), 1.33 (d, J = 7.7 Hz, 0.4H rotamers), 1.30 (s, 3.6H rotamers), 1.25 (s, 5.4H rotamers), 1.04 (s, 3H), 0.90 (s, 1.2H rotamers), 0.89 (s, 1.8H rotamers). |
| 473 | (600 MHz, CDCl$_3$) δ ppm 9.44 (s, 0.7H rotamer), 9.37 (s, 0.3H rotamer), 8.69 (s, 0H), 8.35 (d, J = 6.1 Hz, 1H), 8.03 (d, J = 8.4 Hz, 0H), 7.98 (d, J = 8.0 Hz, 1H), 7.20 (tt, J = 17.2, 7.8 Hz, 3H), 7.09 (dt, J = 14.5, 7.4 Hz, 1H), 6.20-6.02 (m, 1H), 5.12 (s, 1H), 4.79 (t, J = 5.8 Hz, 1H), 4.59 (dt, J = 10.5, 5.6 Hz, 1H), 4.44-4.26 (m, 1H), 3.95 (dd, J = 13.1, 5.5 Hz, 1H), 3.83 (d, J = 13.1 Hz, 1H), 3.42-3.24 (m, 2H), 3.20 (td, J = 9.5, 6.9 Hz, 1H), 2.65 (p, J = 8.3 Hz, 0.6H rotamer), 2.60-2.52 (m, 0.4H rotamer), 2.42 (s, 0.4H rotamer), 2.06 (ddd, J = 15.1, 10.5, 7.8 Hz, 1H), 2.01-1.69 (m, 1H), 1.63 (t, J = 7.3 Hz, 1H), 1.57-1.40 (m, 1H), 1.37-1.22 (m, 2H), 1.10 (d, J = 4.0 Hz, 4H), 0.98 (d, J = 6.4 Hz, 4H). |
| 474 | (600 MHz, CDCl$_3$) δ ppm 8.74 (d, J = 5.7 Hz, 1H), 7.12 (s, 1H), 5.90 (s, 1H), 5.81 (s, 1H), 4.90 (s, 1H), 4.85 (d, J = 16.7 Hz, 1H), 4.76 (d, J = 16.7 Hz, 1H), 4.72 (s, 1H), 4.66-4.59 (m, 1H), 4.53 (s, 1H), 4.50 (dt, J = 10.1, 4.7 Hz, 1H), 4.27 (dd, J = 11.9, 5.6 Hz, 1H), 4.14 (d, J = 11.9 Hz, 1H), 3.96 (s, 1H), 3.51-3.40 (m, 2H), 2.65-2.55 (m, 1H), 2.51-2.41 (m, 2H), 2.12-1.87 (m, 6H), 1.67-1.62 (m, 2H), 1.56 (d, J = 7.6 Hz, 1H), 1.53-1.48 (m, 1H), 1.12 (s, 6H), 1.04-0.97 (m, 4H). |
| 475 | (500 MHz, DMSO-d$_6$) δ ppm 9.44 (s, 0.6H rotamers), 9.40 (s, 0.4H rotamers), 8.78 (d, J = 7.4 Hz, 0.4H rotamers), 8.69 (d, J = 7.3 Hz, 0.6H rotamers), 7.67 (s, 1H), 5.04 (s, 1.2H rotamers), 5.02 (s, 0.8H rotamers), 4.78 (s, 0.6H rotamers), 4.45-4.38 (m, 0.4H rotamers), 4.38-4.32 (m, 0.6H rotamers), 4.26 (s, 0.4H rotamers), 3.94 (dd, J = 11.9, 5.4 Hz, 0.4H rotamers), 3.75 (d, J = 11.9 Hz, 0.4H rotamers), 3.61 (dd, J = 12.9, 5.2 Hz, 0.6H rotamers), 3.55 (d, J = 12.9 Hz, 0.6H rotamers), 3.23-3.08 (m, 2H), 2.40-2.26 (m, 1H), 2.21-2.09 (m, 1H), 2.03-1.90 (m, 1H), 1.73-1.60 (m, 2H), 1.56 (dd, J = 7.7, 5.4 Hz, 0.4H rotamers), 1.51 (d, J = 7.6 Hz, 0.6H rotamers), 1.41 (dd, J = 7.6, 5.1 Hz, 0.6H rotamers), 1.35 (d, J = 7.6 Hz, 0.4H rotamers), 1.32-1.14 (m, 3H), 1.12-1.00 (m, 5H), 0.97-0.85 (m, 4H). |
| 479 | (499 MHz, DMSO-d$_6$) δ ppm 10.18 (s, 0.6H rotamers), 10.07 (s, 0.4H rotamers), 8.60 (d, J = 8.0 Hz, 0.6H rotamers), 8.58 (d, J = 7.9 Hz, 0.4H rotamers), 7.90-7.84 (m, 0.4H rotamers), 7.71-7.64 (m, 0.7H rotamers), 7.65 (s, 0.4H rotamers), 7.59 (s, 0.7H rotamers), 7.35-7.19 (m, 3H), 7.18-7.13 (m, 1H), 5.17 (dd, J = 8.6, 3.0 Hz, 0.7H rotamers), 5.11-4.88 (m, 2.4H rotamers), 4.57 (dd, J = 8.7, 4.4 Hz, 0.4H rotamers), 4.44 (ddd, J = 11.6, 7.9, 3.9 Hz, 0.4H rotamers), 4.35 (ddd, J = 11.6, 7.8, 3.6 Hz, 0..6H rotamers), 3.93 (d, J = 11.6 Hz, 0.4H rotamers), 3.82 (d, J = 11.6 Hz, 0.4H rotamers), 3.62 (d, J = 12.2 Hz, 0.6H rotamers), 3.37 (d, J = 12.2 Hz, 0.6H rotamers), 3.21-3.10 (m, 1H), 3.09-3.03 (m, 1H), 2.94-2.86 (m, 1H), 2.47-2.43 (m, 1H), 2.31-2.21 (m, 2H), 2.19-2.11 (m, 0.4H rotamers), 2.05-1.94 (m, 2H), 1.79 (dd, J = 12.7, 3.1 Hz, 0.6H rotamers), 1.75 (dd, J = 12.7, 4.4 Hz, 0.4H rotamers), 1.70-1.50 (m, 2H), 0.71-0.45 (m, 5H). |
| 480 | (500 MHz, CDCl$_3$) δ ppm 9.46-9.35 (m, 1H), 9.25-9.10 (m, 1H), 8.41-8.32 (m, 1H), 7.97-7.81 (m, 1H), 7.25-7.18 (m, 1H), 7.19-7.13 (m, 2H), 5.80-5.50 (m, 1H), 4.84-4.77 (m, 1H), 4.75-4.69 (m, 1H), 4.65-4.40 (m, 2H), 4.03-3.91 (m, 2H), 3.45-3.31 (m, 4H), 2.57-2.41 (m, 2H), 2.08-1.85 (m, 4H), 1.80-1.69 (m, 2H), 1.68-1.64 (m, 1H), 1.47-1.31 (m, 3H). |
| 483 | (499 MHz, DMSO-d$_6$) δ ppm 8.78-8.67 (m, 1H), 7.81-7.75 (m, 1H), 7.69-7.64 (m, 1H), 5.07-4.90 (m, 2H), 4.70 (d, J = 2.1 Hz, .50H), 4.60 (s, 0.5H), 4.44-4.33 (m, 1H), 4.33-4.28 (m, 1H), 4.05-3.92 (m, 1H), 3.80-3.65 (m, 2H), 3.59-3.52 (m, 1H), 3.20-3.04 (m, 2H), 2.84-2.70 (m, 2H), 2.68-2.64 (m, 1H), 2.61-2.55 (m, 1H), 2.36-2.24 (m, 1H), 2.23-2.08 (m, 1H), 2.02-1.86 (m, 3H), 1.85-1.74 (m, 2H), 1.74-1.38 (m, 9H). |
| 486 | (400 MHz, DMSO-d$_6$) δ ppm 9.44 (s, 0.7H), 9.35 (s, 0.3H), 8.73 (d, J = 7.5 Hz, 0.3H), 8.68 (d, J = 7.8 Hz, 0.7H), 7.68 (s, 0.7H), 7.67 (s, 0.3H), 5.09-4.98 (m, 2H), 4.84 (s, 0.7H), 4.45-4.37 (m, 1H), 4.26 (s, 0.3H), 3.96 (dd, J = 12.2, 5.3 Hz, 0.3H), 3.88 (d, J = 11.9 Hz, 0.3H), 3.62 (dd, J = 13.1, 5.0 Hz, 0.7H), 3.56 (d, J = 12.9 Hz, 0.7H), 3.20-3.07 (m, 2H), 2.35 (d, J = 2.3 Hz, 2H), 2.29 (d, J = 2.2 Hz, 4H), 2.13 (d, J = 6.9 Hz, 1H), 1.99-1.89 (m, 1H), |

TABLE 2-continued

| Compound | ¹H NMR Data |
|---|---|
| | 1.67 (dt, J = 15.0, 8.1 Hz, 2H), 1.54 (s, 1H), 1.49 (d, J = 7.6 Hz, 1H), 1.42-1.36 (m, 1H), 1.06-1.01 (m, 3H), 0.88 (d, J = 2.0 Hz, 3H). |
| 490 | (400 MHz, DMSO-d₆) δ ppm 8.90 (d, J = 7.6 Hz, 1H), 8.62 (d, J = 7.7 Hz, 1H), 7.68 (s, 1H), 7.07-6.89 (m, 1H), 5.13-4.87 (m, 2H), 4.57-4.36 (m, 2H), 3.22-3.05 (m, 2H), 3.05-2.78 (m, 1H), 2.32-2.19 (m, 1H), 2.18-2.04 (m, 1H), 2.04-1.87 (m, 1H), 1.81 (s, 3H), 1.87-1.77 (m, 1H), 1.75 (s, 3H), 1.71-1.60 (m, 1H), 1.60-1.50 (m, 1H), 0.85-0.67 (m, 1H), 0.50-0.32 (m, 2H), 0.25-0.05 (m, 2H). |
| 494 | (499 MHz, DMSO-d₆) δ ppm 8.78 (s, 0.5H), 8.69 (s, 0.5H), 8.64 (d, J = 7.5 Hz, 0.5H), 8.57 (d, J = 7.6 Hz, 0.5H), 7.65 (s, 0.5H), 7.64 (s, 0.5H), 5.11-4.92 (m, 2H), 4.73 (d, J = 2.5 Hz, 0.5H), 4.42-4.29 (m, 1H), 4.12 (d, J = 4.1 Hz, 0.5H), 3.91 (dd, J = 11.8, 7.7 Hz, 1H), 3.67-3.56 (m, 1H), 3.40 (dd, J = 12.7, 4.7 Hz, 1H), 3.19-3.06 (m, 2H), 2.71-2.64 (m, 0.5H), 2.63-2.58 (m, 0.5H), 2.57-2.52 (m, 1H), 2.39-2.31 (m, 0.5H), 2.30-2.21 (m, 0.5H), 2.19-2.06 (m, 1H), 2.03-1.89 (m, 1.5H), 1.87-1.81 (m, 0.5H), 1.81-1.72 (m, 1H), 1.71-1.48 (m, 5H), 1.47-1.35 (m, 1H), 1.28 (s, 1.5H), 1.23 (s, 1.5H), 0.72-0.59 (m, 2H), 0.56 (m, 1H), 0.53-0.45 (m, 1H). |
| 495 | (300 MHz, DMSO-d₆) δ ppm 9.19 (m, 0.6H), 8.10 (m, 1H), 7.74-7.50 (m, 1H), 6.38-6.16 (m, 0.6H), 5.13-4.92 (m, 1H), 4.78-4.29 (m, 1H), 4.10-3.54 (m, 3H), 3.36 (m, 1H), 3.13 (m, 2H), 2.31-1.31 (m, HH), 1.24 (m, 3H), 0.69-0.40 (m, 4H). |
| 500 | (500 MHz, DMSO-d₆) δ ppm 8.74 (d, J = 7.6 Hz, 0.5H), 8.68 (d, J = 7.7 Hz, 0.5H), 7.67 (s, 1H), 7.57-7.26 (m, 1H), 7.25-7.22 (m, 0.5H), 7.22-7.17 (m, 0.5H), 5.07-4.90 (m, 2H), 4.71 (d, J = 2.1 Hz, 0.5H), 4.42-4.32 (m, 1H), 4.30 (d, J = 4.1 Hz, 0.5H), 4.02 (dd, J = 11.4, 7.9 Hz, 0.5H), 3.79-3.67 (m, 1H), 3.54 (dd, J = 12.6, 4.6 Hz, 0.5H), 3.20-3.05 (m, 2H), 2.78-2.70 (m, 0.5H), 2.71-2.65 (m, 0.5H), 2.58-2.52 (m, 0.5H), 2.25-2.32 (m, 0, 5H), 2.23-2.08 (m, 1H), 2.03-1.86 (m, 2H), 1.85-1.73 (m, 1H), 1.73-1.53 (m, 5H), 1.54-1.42 (m, 1H). |
| 502 | (400 MHz, DMSO-d₆) δ ppm 8.58 (s, 1H), 7.87 (s, 0.7H), 7.74 (s, 0.3H), 7.66 (s, 1H), 5.14-4.84 (m, 2H), 4.48-4.27 (m, 1H), 3.82-3.69 (m, 1H), 3.59-3.51 (m, 1H), 3.23 (d, J = 12.0 Hz, 1H), 3.18-3.05 (m, 2H), 2.35-2.19 (m, 1H), 2.20-2.08 (m, 1H), 2.07-1.90 (m, 1H), 1.77-1.55 (m, 3H), 1.30 (s, 4H), 1.27 (s, 5H), 0.68-0.39 (m, 4H).(rotamers) |
| 503 | (500 MHz, DMSO-d₆) δ ppm 8.64 (d, J = 8.0 Hz, 1H), 8.61 (d, J = 7.5 Hz, 1H), 7.80 (d, J = 12.2 Hz, 1H), 7.67 (s, 1H), 5.05-4.94 (m, 2H), 4.42 (ddd, J = 11.3, 7.6, 4.0 Hz, 1H), 4.32 (td, J = 8.4, 5.1 Hz, 1H), 3.21-3.05 (m, 2H), 2.31-2.20 (m, 1H), 2.15-2.04 (m, 1H), 1.95 (ddd, J = 13.8, 11.1, 4.4Hz, 1H), 1.83-1.71 (m, 1H), 1.70-1.61 (m, 2H), 1.55-1.41 (m, 1H), 1.33 (s, 9H), 0.75-0.59 (m, 1H), 0.47-0.28 (m, 2H), 0.20--0.01 (m, 2H). |
| 506 | (500 MHz, DMSO-d₆) δ ppm 9.55 (s, 1H), 8.68 (d, J = 8.5 Hz, 1H), 8.51 (d, J = 7.7 Hz, 1H), 7.66 (s, 1H), 5.05-4.90 (m, 2H), 4.41 (ddd, J = 11.5, 7.7, 3.9 Hz, 1H), 4.31 (td, J = 9.5, 3.8 Hz, 1H), 3.20-3.06 (m, 2H), 2.36 (d, J = 2.2 Hz, 6H), 2.30-2.20 (m, 1H), 2.11-2.03 (m, 1H), 1.95 (ddd, J = 13.8, 11.2, 4.2 Hz, 1H), 1.74-1.58 (m, 3H), 1.57-1.47 (m, 2H), 0.88 (d, J = 6.0 Hz, 3H), 0.84 (d, J = 5.9 Hz, 3H). |
| 508 | (500 MHz, DMSO-d₆) δ ppm 8.62-8.55 (m, 1H), 7.85-7.78 (m, 1H), 7.70-7.64 (m, 1H), 5.17-4.93 (m, 2H), 4.37-4.27 (m, 2H), 4.02-3.85 (m, 1H), 3.65-3.56 (m, 1H), 3.20-3.05 (m, 2H), 2.74-2.57 (m, 1H), 2.34-2.21 (m, 1H), 2.17-2.01 (m, 1H), 2.00-1.84 (m, 1H), 1.73-1.53 (m, 3H), 1.31 (s, 9H), 1.28-1.19 (m, 4H). |
| 509 | (600 MHz, CDCl₃) δ ppm 8.60 (d, J = 6.1 Hz, 1H), 8.10 (d, J = 8.2 Hz, 1H), 7.96 (s, 1H), 6.23 (s, 1H), 4.81-4.65 (m, 2H), 4.62 (ddd, J = 10.4, 6.1, 4.0 Hz, 1H), 4.55-4.46 (m, 1H), 3.44-3.33 (m, 2H), 2.49-2.46 (m, 6H), 2.46-2.40 (m, 2H), 2.10-2.00 (m, 1H), 1.93-1.83 (m, 2H), 1.81-1.69 (m, 2H), 0.79-0.70 (m, 1H), 0.56-0.48 (m, 2H), 0.22-0.11 (m, 2H). |
| 516 | (400 MHz, DMSO-d₆) δ ppm 8.73-8.51 (d, J = 4.8 Hz, 1H), 7.80-7.76 (m, 1H), 5.91-5.61 (m, 2H), 4.91 (s, 1H), 4.19-4.37 (m, 1H), 3.75-3.88 (m, 2H), 3.75-3.88 ( m, 2H), 3.68-3.58 (m, 2H), 3.37-3.39 (m, 2H), 2.63-2.50 (m, 1H), 2.39-2.47 (m, 1H), 1.92-2.09 (m, 3H), 1.54-1.60(m, 1H), 1.37-1.41 (m, 1H), 1.25(s, 2H), 1.0738 (d, J = 6.8 Hz, 6H), 0.95 (d, J = 6 Hz, 6H). |
| 518 | (400 MHz, DMSO-d₆) δ ppm 8.65 (d, J = 7.9 Hz, 0.3H), 8.61 (d, J = 8.0 Hz, .7H), 7.95 (s, 0.7H), 7.81 (s, 0.3H), 7.65 (s, 1H), 5.15 (d, J = 8.7 Hz, 1H), 5.09-4.86 (m, 2H), 4.40 (ddd, J = 11.7, 7.9, 3.6 Hz, 1H), 4.08-3.95 (m, 1H), 3.68 (d, J = 13.0 Hz, 1H), 3.54 (d, J = 12.8 Hz, 1H), 3.23-3.13 (m, 1H), 3.12-3.02 (m, 1H), 2.65-2.55 (m, 1H), 2.47-2.31 (m, 1H), 2.16-2.05 (m, 1H), 2.05-1.94 (m, 1H), 1.76-1.49 (m, 4H), 1.32 (s, 3H), 1.28 (s, 6H). |
| 519 | (400 MHz, DMSO-d₆) δ ppm 9.23 (t, J = 8.8 Hz, 1H) 8 8.48-8.38 (m, 1H), 7.67-7.56 (m, 1H), 6.40-5.70 (m, 1H), 4.99-4.80 (m, 2H), 4.23-3.40 (m, 6H) 3.16-3.08 (m, 1H), 2.67-2.60 (m, 1H), 2.32-1.48 (m, 12H). |
| 520 | (400 MHz, DMSO-d₆) δ ppm 8.66-8.59 (m, 1H), 7.97-7.81 (m, 1H), 7.71-7.62 (m, 1H), 5.21-4.75 (m, 2H), 4.46-4.21 (m, 2H), 3.72-3.55 (m, 2H), 3.20-3.06 (m, 2H), 2.29-2.18 (m, 1H), 2.16-1.91 (m, 3H), 1.72-1.54 (m, 3H), 1.31 (s, 4H), 1.29-1.22 (m, 9H). |
| 523 | (400 MHz, DMSO-d₆) δ ppm 9.15 & 9.26 (d, J = 7.2 Hz, 1H) 8 8.68 & 8.59 (d, J = 8 Hz, 1H), 7.65 (s, 1H), 5.0-4.99 (m, 2H), 4.77-3.64 (m, 4H), 3.44- |

TABLE 2-continued

| Compound | ¹H NMR Data |
|---|---|
| | 3.13 (m, 2H), 3.15-3.10 (m, 2H), 2.84-2.67 (m, 4H), 2.32-2.27 (m, 1H), 1.97-1.89 (m, 1H), 1.76-1.42 ( m, 10H), 1.2 (s, 1H). |
| 525 | (400 MHz, DMSO-$d_6$) δ ppm 9.47 (s, 0.7H), 9.36 (s, 0.3H), 8.66 (d, J = 7.8 Hz, 0.3H), 8.60 (d, J = 7.9 Hz, 0.7H), 7.68 (s, 1H), 5.06-4.94 (m, 2H), 4.74 (d, J = 2.5 Hz, 0.7H), 4.37 (t, J = 7.3 Hz, 1H), 4.15 (d, J = 4.1 Hz, 0.3H), 3.93 (dd, J = 12.0, 7.8 Hz, 0.3H), 3.71 (dd, J = 12.0, 4.2 Hz, 0.3H), 3.62 (dd, J = 12.7, 8.4 Hz, 0.7H), 3.43 (dd, J = 12.9, 4.6 Hz, 0.7H), 3.23-3.01 (m, 2H), 2.61 (d, J = 5.3 Hz, 1H), 2.35 (d, J = 2.2 Hz, 3H), 2.29 (d, J = 2.2 Hz, 4H), 2.12 (dd, J = 12.5, 7.1 Hz, 1H), 2.03-1.82 (m, 2H), 1.82-1.71 (m, 1H), 1.71-1.48 (m, 5H), 1.41 (d, J = 3.6 Hz, 1H). |
| 527 | (400 MHz, DMSO-$d_6$) δ ppm 10.01 (s, 0.6H), 9.93 (s, 0.4H), 8.62 (d, J = 7.8 Hz, 0.4H), 8.58 (d, J = 7.7 Hz, 0.6H), 7.68 (s, 0.4H), 7.59 (s, 0.6H), 7.56 (d, J = 8.0 Hz, 0.4H), 7.40-7.34 (m, 1H), 7.29-7.18 (m, 1H), 7.18-7.08 (m, 2H), 5.22-5.14 (m, 1H), 5.12-4.82 (m, 2H), 4.60-4.52 (m, 0.4H), 4.47-4.37 (m, 0.4H), 4.37-4.29 (m, 0.6H), 3.90 (d, J = 11.6 Hz, 0.4H), 3.83 (d, J = 11.6 Hz, 0.4H), 3.60 (d, J = 12.2 Hz, 0.6H), 3.38 (d, J = 12.1 Hz, 0.6H), 3.01 (t, J = 9.1 Hz, 1H), 2.88-2.75 (m, 1H), 2.30-2.22 (m, 2H), 2.20 (s, 3H), 2.06-1.89 (m, 2H), 1.88-1.71 (m, 1H), 1.69-1.60 (m, 1H), 1.60-1.47 (m, 1H), 0.70-0.44 (m, 4H). |
| 553 | (300 MHz, DMSO-$d_6$) δ ppm 8.68 (m = 7.6 Hz, 1H), 8.00-7.56 (m, 2H), 5.24-4.70 (m, 2H), 4.48-4.28 (m, 1H), 4.01-3.45 (m, 2H), 3.13 (m, 2H), 2.42-1.46 (m, 7H), 1.34-1.26 (m, 9H), 1.25 (m, 1H), 0.99-0.46 (m, 4H). |
| 554 | (400 MHz, DMSO-$d_6$) δ ppm 8.65 (m, 1H), 8.37 (m, 1H), 7.82-7.45 (m, 1H), 6.55-5.99 (m, 1H), 5.09-4.93 (m, 1H), 4.36 (m, 0.6H), 4.22 (m, 0.6H), 3.93-3.79 (m, 1H), 3.67-3.52 (m, 1H), 3.23-3.04 (m, 2H), 2.76-2.54 (m, 2H), 2.30 (m, 1H), 2.20-2.07 (m, 1H), 2.05-1.49 (m, 8H), 1.49-1.28 (m, 7H), 1.23 (m, 2H). |
| 557 | (400 MHz, DMSO-$d_6$) δ ppm 8.79 (d, J = 7.8 Hz, 0.5H rotamer), 8.67 (s, 0.5H rotamer), 8.06-7.96 (m, 1H), 7.91-7.78 (m, 1H), 7.77-7.70 (m, 1H), 7.69-7.59 (m, 1H), 7.53-7.45 (m, 1H), 5.15-4.83 (m, 3H), 4.51-4.18 (m, 1H), 4.10 (dd, J = 11.4, 8.0 Hz, 0.25H rotamer), 3.93-3.77 (m, 1.5H rotamer), 3.70-3.55 (m, 0.25H rotamer), 3.22-2.82 (m, 2H), 2.04-1.41 (m, 13H). |
| 564 | (400 MHz, DMSO-$d_6$) δ ppm 9.58 (s, 1H), 8.96 (d, J = 8.7 Hz, 1H), 8.47 (d, J = 7.8 Hz, 1H), 7.76-7.59 (m, 1H), 5.76 (t, J = 56.7 Hz, 1H), 5.06-4.87 (m, 2H), 4.50-4.28 (m, 2H), 3.20-3.06 (m, 2H), 2.38 (d, J = 2.3 Hz, 6H), 2.33-2.20 (m, 1H), 2.14-2.03 (m, 1H), 2.02-1.83 (m, 3H), 1.71-1.51 (m, 2H), 0.95 (s, 3H), 0.91 (s, 4H). |
| 573 | (300 MHz, DMSO-$d_6$) δ ppm 9.54 (m, 1H), 8.55 (m, 2H), 7.65 (m, 1H), 4.95 (m, 2H), 4.48-4.24 (m, 2H), 3.21-3.03 (m, 2H), 2.36 (m, 6H), 2.27 (m, 1H), 2.09 (m, 1H), 2.02-1.43 (m, 11H), 1.09 (s, 3H). |
| 575 | (300 MHz, DMSO-$d_6$) δ ppm 9.34-9.04 (m, 2H), 7.91 (m, 1H), 7.69-7.32 (m, 1H), 7.31-6.96 (m, 2H), 6.95-6.76 (m, 1H), 5.43 (m, 0.5H), 5.10-4.32 (m, 3H), 3.86-3.69 (m, 4H), 3.47 (m, 1H), 3.19-3.05 (m, 1H), 2.41 (m, 1H), 2.31-1.78 (m, 4H), 1.77-1.21 (m, 2H), 0.75-0.40 (m, 4H). |
| 576 | (400 MHz, DMSO-$d_6$) δ ppm 10.20 (s, 0.6H), 10.15 (s, 0.4H), 8.68-8.57 (m, 1H), 8.02 (d, J = 8.2 Hz, 0.4H), 7.86-7.59 (m, 3.6H), 7.49-7.41 (m, 1H), 5.21 (dd, J = 8.6, 2.8 Hz, 0.6H), 5.09-4.86 (m, 2H), 4.59 (dd, J = 8.7, 4.3 Hz, 0.4H), 4.47-4.40 (m, 0.4H), 4.39-4.31 (m, 1H), 3.98 (d, J = 11.7 Hz, 0.4H), 3.86 (d, J = 11.7 Hz, 0.4H), 3.64 (d, J = 12.3 Hz, 0.6H), 3.22-3.11 (m, 1H), 3.10-3.03 (m, 1H), 2.92-2.80 (m, 1H), 2.31-2.19 (m, 1H), 2.19-2.10 (m, 0.4H), 2.07-1.93 (m, 1.6H), 1.84-1.70 (m, 1H), 1.72-1.48 (m, 2H), 0.71-0.46 (m, 4H). |
| 577 | (400 MHz, DMSO-$d_6$) δ ppm 8.98-8.91 (m, 1H), 8.72-8.40 (m, 2H), 7.72-7.66 (m, 1H), 5.09-4.92 (m, 2H), 4.52-4.33 (m, 2H), 3.22-3.07 (m, 2H), 2.30-2.15 (m, 1H), 2.15-2.04 (m, 1H), 2.04-1.91 (m, 1H), 1.91-1.77 (m, 1H), 1.70-1.59 (m, 2H), 1.60-1.48 (m, 1H), 1.30 (d, J = 1.9 Hz, 3H), 1.02 (d, J = 2.2 Hz, 3H), 0.79-0.64 (m, 2H), 0.63-0.53 (m, 2H), 0.46-0.37 (m, 1H), 0.25-0.13 (m, 3H). |
| 578 | (400 MHz, DMSO-$d_6$) δ ppm 8.92-8.79 (m, 1H), 8.67-8.49 (m, 2H), 7.75-7.60 (m, 1H), 5.08-4.89 (m, 2H), 4.56-4.31 (m, 2H), 3.24-3.04 (m, 2H), 2.87-2.76 (m, 1H), 2.32-2.16 (m, 1H), 2.15-2.03 (m, 1H), 2.03-1.78 (m, 2H), 1.73-1.58 (m, 2H), 1.58-1.47 (m, 1H), 1.01 (d, J = 2.2 Hz, 3H), 0.72-0.58 (m, 4H), 0.50-0.36 (m, 1H), 0.24-0.13 (m, 3H). |
| 592 | (400 MHz, DMSO-$d_6$) δ ppm 9.09-9.04 (m, 1H), 8.63 (d, J = 10 Hz, 1H), 7.72 (d, J = 13.6 Hz, 1H), 5.56-5.49 (m, 1H), 5.11-4.92 (m, 2H), 4.51 (s, 1H), 4.53-4.47 (m, 1H), 3.20-3.05 (m, 2H), 2.21-1.83 (m, 5H), 1.70-1.58 (m, 2H), 1.38 (s, 9H), 1.24-1.13 (m, 1H), 0.90-0.86 (m, 6H) |
| 606 | (400 MHz, DMSO-$d_6$) δ ppm 10.15 (s, 0.4H, rotamer), 10.11 (s, 0.4H, rotamer), 8.64 (d, J = 7.8 Hz, 0.6H, rotamer), 8.57 (d, J = 8.0 Hz, 0.4H, rotamer), 8.10 (dd, J = 8.2, 1.6 Hz, 0.4H, rotamer), 7.94 (dd, J = 8.1, 1.6 Hz, 0.6H, rotamer), 7.65 (d, J = 16.7 Hz, 1H), 7.56 (td, J = 7.8, 1.5 Hz, 1H), 7.40 (td, J = 7.8, 1.5 Hz, 0.4H, rotamer), 7.33 (td, J = 7.8, 1.5 Hz, 0.6H, rotamer), 7.27-7.19 (m, 1H), 5.23 (dd, J = 8.6, 2.9 Hz, 1H), 5.14-4.85 (m, 2H), 4.48-4.31 (m, 1H), 3.93 (d, 11.7 Hz, 1H), 3.86 (d, 11.7 Hz, 1H), 3.64 (d, J = 12.3 Hz, 1H), 3.37 (d, J = 12.3 Hz, 1H), 3.21-3.03 (m, 1H), 2.92 (q, 1H), 2.37-2.21 (m, 1H), 2.08-1.92 (m, 2H), 1.84-1.70 (m, 1H), 1.70-1.48 (m, 2H), 0.73-0.39 (m, 4H). |

TABLE 2-continued

| Compound | ¹H NMR Data |
|---|---|
| 608 | (400 MHz, DMSO-$d_6$) δ ppm 11.51 (s, 1H), 8.82 (d, 0.4H rotamer), 8.71 (d, J = 7.6 Hz, 0.6H rotamer), 7.68 (s, 0.6H rotamer), 7.55 (s, 0.4H rotamer), 7.18-6.98 (m, 2H), 6.95 (s, 0.6H rotamer), 6.80 (s, 0.4H rotamer), 6.55-6.38 (m, 1H), 5.06-4.90 (m, 1H), 4.45-4.31 (m, 1H), 4.23-4.10 (m, 1H), 3.88 (s, 3H), 3.85-3.73 (m, 3H), 3.18-3.09 (m, 1H), 2.93-2.75 (m, 2H), 2.42-2.29 (m, 1H), 2.19-2.05 (m, 1H), 2.05-1.75 (m, 3H), 1.74-1.55 (m, 4H), 1.55-1.33 (m, 3H). |
| 609 | (400 MHz, DMSO-$d_6$) δ ppm 8.79 (d, J = 7.6 Hz, 0.5H rotamer), 8.69 (d, J = 7.9 Hz, 0.5H rotamer), 8.14 (d, J = 1.6 Hz, 0.5H rotamer), 8.09 (d, J = 1.6 Hz, 0.5H rotamer), 8.05-7.92 (m, 1H), 7.67 (d, J = 10.1 Hz, 1H), 7.60-7.51 (m, 1H), 5.15-4.79 (m, 2H), 4.48-4.21 (m, 1H), 4.14-3.98 (m, 1H), 3.90-3.56 (m, 2H), 3.21-2.83 (m, 2H), 2.61-2.56 (m, 2H), 2.19-1.88 (m, 3H), 1.88-1.42 (m, 8H). |
| 612 | (400 MHz, DMSO-$d_6$) δ ppm 8.62 (m, 1H), 7.95-7.54 (m, 2H), 5.14-4.91 (m, 2H), 4.36 (m, 1H), 3.25-3.03 (m, 2H), 2.61 (m, 2H), 2.39-2.22 (m, 1H), 2.13 (m, 1H), 2.04-1.71 (m, 3H), 1.71-1.50 (m, 5H), 1.42 (m, 1H), 1.28 (m, 9H). |
| 614 | (400 MHz, DMSO-$d_6$) δ ppm 8.81-8.67 (m, 1H), 8.01-7.87 (m, 1H), 7.77-7.58 (m, 3H), 5.15-4.79 (m, 2H), 4.52-4.05 (m, 2H), 3.92-3.57 (m, 2H), 3.21-3.04 (m, 2H), 2.92-2.70 (m, 2H), 2.31-2.09 (m, 1H), 2.07-1.39 (m, 10H). |
| 616 | (400 MHz, DMSO-$d_6$) δ ppm 8.74 (d, J = 7.8 Hz, 1H), 7.75-7.39 (m, 6H), 5.12-4.89 (m, 2H), 4.62-4.47 (m, 1H), 4.47-4.28 (m, 1H), 3.43-3.34 (m, 2H), 3.22-3.03 (m, 2H), 2.46-2.25 (m, 1H), 2.22-2.06 (m, 2H), 2.03-1.92 (m, 1H), 1.76-1.53 (m, 3H), 0.57-0.34 (m, 4H). |
| 620 | (401 MHz, DMSO-$d_6$) δ ppm 8.70 (d, J = 7.6 Hz, 1H), 7.58 (s, 1H), 7.36-7.29 (m, 6H), 5.05-4.95 (m, 4H), 4.39 (t, J = 3.6 Hz, 1H), 4.20 (s, 2H), 4.09 (m, J = 8.8 Hz, 1H), 3.85-3.79 (m, 2H), 3.14-3.05 (m, 2H), 2.36-2.32 (m, 1H), 2.26-2.19 (m, 1H), 1.99-1.91 (m, 1H), 1.64-1.45 (m, 3H), 1.29 (d, J = 3.6 Hz, 1H), 1.02-0.85 (m, 15H). |
| 623 | (400 MHz, DMSO-$d_6$) δ ppm 8.67 (d, J = 7.5 Hz, 1H), 7.67 (s, 1H), 4.99 (d, J = 17.4 Hz, 1H), 4.94 (d, J = 17.0 Hz, 1H), 4.48 (dd, J = 8.5, 5.7 Hz, 1H), 4.33 (ddd, J = 11.4, 7.5, 3.7 Hz, 1H), 3.66-3.56 (m, 2H), 3.21-3.05 (m, 2H), 2.30-2.21 (m, 1H), 2.18-2.07 (m, 2H), 2.06-1.85 (m, 4H), 1.74 (dd, J = 12.8, 5.8 Hz, 1H), 1.70-1.58 (m, 2H), 0.94 (d, J = 5.7 Hz, 3H), 0.92 (d, J = 5.4 Hz, 3H), 0.72-0.48 (m, 4H). |
| 624 | (400 MHz, DMSO-$d_6$) δ ppm 8.38 (d, J = 8.1 Hz, 1H), 7.67 (s, 1H), 5.01 (d, J = 17.1 Hz, 1H), 4.81 (d, J = 17.2 Hz, 1H), 4.44-4.31 (m, 2H), 3.56 (d, J = 9.6 Hz, 1H), 3.41 (d, J = 9.8 Hz, 1H), 3.20-3.05 (m, 2H), 2.41-2.30 (m, 2H), 2.28-2.18 (m, 1H), 2.18-2.07 (m, 2H), 1.97 (ddd, J = 14.1, 11.8, 4.0 Hz, 1H), 1.89-1.76 (m, 3H), 1.73-1.57 (m, 2H), 1.33 (d, J = 1.5 Hz, 3H), 1.28 (d, J = 1.5 Hz, 3H), 0.66-0.52 (m, 4H). |
| 625 | (400 MHz, DMSO-$d_6$) δ ppm 8.49 (d, J = 7.4 Hz, 1H), 7.67 (s, 1H), 5.01 (d, J = 17.0 Hz, 1H), 4.91 (d, J = 17.1 Hz, 1H), 4.34 (t, J = 7.6 Hz, 1H), 4.27-4.19 (m, 1H), 3.68 (d, J = 10.1 Hz, 1H), 3.54 (d, J = 9.9 Hz, 1H), 3.12 (dq, J = 16.8, 9.3 Hz, 2H), 2.31-2.23 (m, 1H), 2.15 (d, J = 7.7 Hz, 1H), 1.99 (ddd, J = 15.1, 11.7, 4.4 Hz, 1H), 1.91-1.80 (m, 1H), 1.74 (dd, J = 12.5, 7.3 Hz, 1H), 1.69-1.49 (m, 4H), 1.36 (dd, J = 14.0, 5.1 Hz, 1H), 1.15 (s, 3H), 1.10 (s, 3H), 0.85 (d, J = 6.6 Hz, 3H), 0.79 (d, J = 6.7 Hz, 3H), 0.59-0.46 (m, 4H). |
| 626 | (400 MHz, DMSO-$d_6$) δ ppm 8.77 (d, J = 6.5 Hz, 0.25H rotamer), 7.94 (d, J = 8.0 Hz, 0.75H rotamer), 7.75 (s, 0.25H rotamer), 7.65 (s, 0.25H rotamer), 5.17-4.98 (m, 0.5H rotamer), 5.00-4.78 (m, 1.5H rotamer), 4.46-4.32 (m, 2H), 3.59 (d, 1H), 3.52 (d, J = 9.4 Hz, 1H), 3.20-3.02 (m, 3H), 2.41-2.20 (m, 5H), 2.16-2.05 (m, 1H), 2.04-1.93 (m, 1H), 1.79-1.57 (m, 4H), 1.54-1.41 (m, 1H), 1.05-0.96 (m, 3H), 0.95-0.84 (m, 5H), 0.68-0.37 (m, 4H). |
| 631 | (400 MHz, DMSO-$d_6$) δ ppm 8.55-7.75 (m, 1H), 7.29-7.27 (m, 1H), 5.21-4.82 (m, 3H), 4.60-4.35 (m, 2H), 3.65-3.48 (m, 2H), 3.21-3.04 (m, 2H), 2.61-2.50 (m, 1H), 2.38-2.12 (m, 3H), 2.07-1.89 (m, 1H), 1.81-1.47 (m, 6H), 1.26-1.04 (m, 6H), 0.96-0.81 (m, 6H), 0.67-0.45 (m, 4H). |
| 632 | (400 MHz, CDCl$_3$) δ ppm 7.46 (d, J = 7.6 Hz, 1H), 7.32-7.29 (m, 5H), 5.40 (s, 1H), 4.84-4.81 (m, 1H), 4.73-4.70 (m, 3H), 4.67-4.65 (m, 1H), 3.69-3.67 (m, 2H), 3.54 (s, 2H), 3.33-3.28 (m, 2H), 2.36-2.31 (m, 3H), 2.10-2.00 (m, 1H), 1.93-1.75 (m, 5H), 1.45-1.35 (m, 1H), 0.94 (d, J = 6.8 Hz 3H), 0.87 (d, J = 6.8 Hz 3H), 0.67-0.58 (m, 4H). |
| 633 | (400 MHz, CDCl$_3$) δ ppm 8.33 (d, J = 7.7 Hz, 1H), 7.70 (s, 1H), 5.01 (d, J = 17.2 Hz, 1H), 4.88 (d, J = 17.1 Hz, 1H), 4.38 (dd, J = 8.4, 6.2 Hz, 1H), 4.29 (ddd, J = 11.4, 7.6, 3.8 Hz, 1H), 3.83 (d, J = 11.2 Hz, 1H), 3.73 (d, J = 11.1 Hz, 1H), 3.21-3.07 (m, 2H), 2.30-2.21 (m, 1H), 2.19-2.09 (m, 1H), 2.03-1.93 (m, 2H), 1.88-1.72 (m, 2H), 1.72-1.57 (m, 3H), 1.55-1.41 (m, 4H), 1.18-1.08 (m, 2H), 0.87 (s, 3H), 0.83 (s, 3H), 0.64-0.46 (m, 4H). |
| 636 | (400 MHz, CDCl$_3$) δ ppm 8.58 (d, J = 7.6 Hz, 0.40H rotamer), 8.51 (d, J = 7.0 Hz, 0.60H rotamer), 7.77-7.64 (m, 1H), 5.08-4.81 (m, 3H), 4.62 (d, J = 7.1 Hz, 1H), 4.54-4.30 (m, 2H), 3.76 (d, J = 13.3 Hz, 1H), 3.27-3.07 (m, 3H), 2.29-2.19 (m, 1H), 2.18-2.05 (m, 2H), 2.04-1.85 (m, 1H), 1.85-1.44 (m, 6H), 1.43-1.12 (m, 4H), 0.97-0.73 (m, 6H). |

TABLE 2-continued

| Compound | ¹H NMR Data |
|---|---|
| 637 | (400 MHz, CDCl₃) δ ppm 8.48 (d, J = 7.6 Hz, 1H), 7.68 (s, 1H), 5.07 (d, J = 17.4 Hz, 1H), 4.92 (d, J = 17.4 Hz, 1H), 4.37-4.26 (m, 2H), 4.15 (dd, J = 12.1, 5.7 Hz, 1H), 3.73-3.64 (m, 1H), 3.19-3.06 (m, 2H), 3.04-2.90 (m, 2H), 2.31-2.17 (m, 1H), 2.15-2.03 (m, 1H), 2.02-1.86 (m, 2H), 1.83-1.68 (m, 2H), 1.68-1.55 (m, 2H), 1.49-1.17 (m, 5H), 0.88 (d, J = 6.4 Hz, 3H), 0.87 (d, J = 6.3 Hz, 3H), 0.83 (s, 9H). |
| 639 | (400 MHz, CDCl₃) δ ppm 8.55 (d, J = 7.3 Hz, , 0.40H rotamer), 8.45 (d, J = 7.5 Hz, 0.60H rotamer), 7.73 (s, 0.40H rotamer), 7.67 (s, 0.60H rotamer), 5.23-4.82 (m, 3H), 4.44-4.26 (m, 2H), 4.11 (td, J = 8.3, 4.8 Hz, 0H), 4.02-3.70 (m, 2H), 3.47-3.23 (m, 1H), 3.26-3.03 (m, 2H), 2.45-2.20 (m, 1H), 2.19-2.03 (m, 2H), 1.95 (dtd, J = 15.0, 11.0, 4.2 Hz, 1H), 1.83 (d, J = 9.3 Hz, 2H), 1.77-1.50 (m, 5H), 1.50-1.12 (m, 5H), 1.06-0.70 (m, 6H). |
| 643 | (400 MHz, CDCl₃) δ ppm 8.09 (d, J = 8.3 Hz, 1H), 7.63 (s, 1H), 6.82 (d, J = 7.4 Hz, 1H), 4.99 (d, J = 17.1 Hz, 1H), 4.83 (d, J = 17.3 Hz, 1H), 4.46-4.32 (m, 2H), 4.19-4.10(m, 1H), 4.07-3.93 (m, 1H), 3.53 (d, J = 9.7 Hz, 1H), 3.49 (d, J = 10.1 Hz, 1H), 3.25-3.05 (m, 2H), 3.03-2.86 (m, 2H), 2.24 (dd, J = 12.5, 8.6 Hz, 1H), 2.19-2.05 (m, 1H), 2.04-1.94 (m, 1H), 1.81-1.53 (m, 4H), 1.34 (s, 9H), 0.88 (d, J = 6.1 Hz, 3H), 0.86 (d, J = 6.3 Hz, 3H), 0.65-0.47 (m, 4H). |
| 646 | (400 MHz, CDCl₃) δ ppm 8.64 (d, J = 7.3 Hz, 1H), 7.66 (s, 1H), 5.03 (d, J = 17.0 Hz, 1H), 4.94 (d, J = 17.0 Hz, 1H), 4.46 (dd, J = 8.2, 6.6 Hz, 1H), 4.22 (ddd, J = 11.3, 7.3, 3.9 Hz, 1H), 3.69 (d, J = 11.0 Hz, 1H), 3.65 (d, J = 11.1 Hz, 1H), 3.31 (s, 3H), 3.17 (s, 3H), 3.16-3.05 (m, 2H), 3.03-2.91 (m, 2H), 2.31-2.23 (m, 1H), 2.18-2.08 (m, 1H), 2.04-1.71 (m, 9H), 1.67-1.54 (m, 2H), 0.71-0.45 (m, 4H). |
| 663 | (400 MHz, CDCl₃) δ ppm 11.62 (s, 0.25H rotamer), 11.36 (s, 0.75H rotamer), 8.77 (d, J = 7.2 Hz, 0.25H rotamer), 8.69 (d, J = 7.6 Hz, 0.75H rotamer), 7.72-7.65 (m, 1H), 7.62 (d, J = 8.0 Hz, 1H), 7.33-7.23 (m, 1H), 7.13-7.00 (m, 2H), 5.07 (d, J = 17.2 Hz, 1H), 4.95 (d, J = 17.2 Hz, 1H), 4.71-4.61 (m, 1H), 4.45-4.35 (m, 1H), 3.93 (d, J = 10.0 Hz, 1H), 3.79 (d, J = 10.0 Hz, 1H), 3.14 (p, J = 8.8 Hz, 2H), 2.42-2.25 (m, 1H), 2.40-2.27 (m, 0H), 2.26-2.09 (m, 2H), 2.09-1.92 (m, 1H), 1.92-1.76 (m, 1H), 1.71-1.54 (m, 2H), 0.74-0.44 (m, 4H). |
| 664 | (400 MHz, CDCl₃) δ ppm 8.46 (d, J = 7.8 Hz, 1H), 7.69 (s, 1H), 5.07-5.01 (m, 1H), 4.84 (d, J = 17.4 Hz, 1H), 4.37-4.32 (m, 1H), 3.53 (d, J = 9.6 Hz, 1H), 3.48-3.41 (m, 1H), 3.37 (d, J = 10.0 Hz, 1H), 3.20-3.08 (m, 3H), 2.23 (dd, J = 12.6, 8.8 Hz, 2H), 2.12 (h, J = 7.4 Hz, 1H), 1.95 (s, 2H), 1.74-1.58 (m, 3H), 1.58-1.42 (m, 1H), 0.62-0.41 (m, 4H). |
| 665 | (400 MHz, CDCl₃) δ ppm 8.52-8.38 (m, 1H), 7.68 (s, 1H), 5.08-4.79 (m, 2H), 4.44-4.32 (m, 1H), 4.29-4.20 (m, 1H), 3.60-3.49 (m, 1H), 3.22-3.07 (m, 3H), 2.28-2.20 (m, 1H), 2.18-2.09 (m, 1H), 2.04-1.88 (m, 2H), 1.77-1.55 (m, 3H), 1.15 (s, 9H), 0.61-0.44 (m, 4H). |
| 671 | (400 MHz, CDCl₃) δ ppm 8.63 (d, J = 7.6 Hz, 1H), 7.89 (d, J = 8.1 Hz, 1H), 7.69 (s, 1H), 7.36-7.27 (m, 1H), 7.10 (dd, J = 9.1, 3.2 Hz, 2H), 7.07-6.99 (m, 1H), 5.38 (d, J = 6.0 Hz, 1H), 4.96-4.81 (m, 2H), 4.57-4.50 (m, 1H), 4.46-4.34 (m, 1H), 3.87-3.77 (m, 1H), 3.20-3.05 (m, 3H), 2.97-2.91 (m, 1H), 2.25-2.16 (m, 1H), 2.13-2.04 (m, 1H), 2.04-1.91 (m, 1H), 1.69-1.60 (m, 3H), 1.31-1.25 (m, 2H), 0.82 (d, J = 6.6 Hz, 6H). |
| 676 | (400 MHz, CDCl₃) δ ppm 8.69 (q, J = 4.8 Hz, 0.6H rotamers), 8.58 (d, J = 7.8 Hz, 1H), 8.52 (q, J = 5.0 Hz, 0.4H rotamers), 7.68 (s, 0.4H rotamers), 7.65 (s, 0.6H rotamers), 5.14 (dd, J = 8.7, 3.0 Hz, 0.6H rotamers), 5.09-4.86 (m, 2H), 4.48 (dd, J = 8.5, 4.8 Hz, 0.4H rotamers), 4.43-4.29 (m, 1H), 3.81 (d, J = 11.6 Hz, 0.4H rotamers), 3.74 (d, J = 11.5 Hz, 0.4H rotamers), 3.54 (d, J = 12.1 Hz, 0.6H rotamers), 3.27 (d, J = 12.1 Hz, 0.6H rotamers), 3.23-3.05 (m, 2H), 2.64 (d, J = 4.8 Hz, 1H), 2.58 (d, J = 4.7 Hz, 2H), 2.40 (dd, J = 12.6, 8.8 Hz, 0.4H rotamers), 2.31-2.22 (m, 1H), 2.20-2.07 (m, 1.4H), 2.04-1.91 (m, 1H), 1.77-1.67 (m, 1H), 1.67-1.54 (m, 2.2H), 0.67-0.42 (m, 4H). |
| 678 | (400 MHz, CDCl₃) δ ppm 8.38 (d, J = 8.2 Hz, 1H), 7.68 (s, 1H), 5.01 (d, J = 17.2 Hz, 1H), 4.81 (d, J = 17.3 Hz, 1H), 4.44-4.32 (m, 2H), 3.57 (d, J = 9.7 Hz, 1H), 3.39 (d, J = 9.7 Hz, 1H), 3.21-3.06 (m, 2H), 2.46-2.39 (m, 1H), 2.30-1.90 (m, 7H), 1.70-1.52 (m, 6H), 0.67-0.44 (m, 4H). |
| 683 | (400 MHz, CDCl₃) δ ppm 8.39 (d, J = 8.2 Hz, 1H), 7.67 (s, 1H), 6.11 (t, J = 4.4 Hz, 1H), 5.08-4.91 (m, 1H), 4.81 (d, J = 17.3 Hz, 1H), 4.65-4.26 (m, 2H), 3.60-3.41 (m, 1H), 3.41-3.34 (m, 1H), 3.23-3.02 (m, 2H), 2.47-2.35 (m, 2H), 2.35-1.85 (m, 6H), 1.84-1.47 (m, 3H), 0.67-0.34 (m, 4H). |
| 685 | (400 MHz, CDCl₃) δ ppm 8.80 (d, J = 7.2 Hz, 0.3H), 8.70 (d, J = 7.7 Hz, 0.7H), 7.76 (s, 03H), 7.68 (s, 0.7H), 5.22 (d, J = 7.3 Hz, 0.3H), 5.12-5.05 (m, 1.3H), 5.05-5.00 (m, 1H), 4.99-4.93 (m, 0.3H), 4.48-4.40 (m, 1H), 4.35 (ddd, J = 11.4, 7.5, 3.9 Hz, 0.7H), 4.22-4.14 (m, 0.7H), 3.99 (dd, J = 10.9, 7.9 Hz, 0.7H), 3.97-3.91 (m, 0.5H), 3.77 (d, J = 11.0, 6.4 Hz, 0.7H), 3.62 (d, J = 8.2 Hz, 0.5H), 3.19-3.09 (m, 2H), 2.35-2.21 (m, 2H), 2.16-1.86 (m, 3H), 1.83-1.68 (m, 1.5H), 1.67-1.57 (m, 1.7H), 1.49-1.39 (m, 1.3H), 1.35-1.23 (m, 2H), 0.92-0.87 (m, 4.3H), 0.87-0.80 (m, 1.7H) |
| 687 | (400 MHz, CDCl₃) δ ppm 8.71 (d, J = 7.4 Hz, 1H), 7.74 (s, 1H), 7.67 (s, 1H), 7.53-7.45 (m, 2H), 5.03 (d, J = 17.2 Hz, 1H), 4.92 (d, J = 17.1 Hz, 1H), 4.64-4.44 (m, 1H), 4.45-4.34 (m, 1H), 3.76-3.56 (m, 1H), 3.20-3.06 |

TABLE 2-continued

| Compound | ¹H NMR Data |
|---|---|
| | (m, 2H), 2.31-2.22 (m, 1H), 2.22-2.13 (m, 1H), 2.07-1.95 (m, 3H), 1.90-1.79 (m, 1H), 1.75-1.59 (m, 2H), 0.69-0.39 (m, 4H). |
| 688 | (400 MHz, CDCl₃) δ ppm 8.72 (d, J = 7.5 Hz, 0.2H rotamer), 8.39 (d, J = 8.1 Hz, 0.8H rotamer), 7.71 (s, 0.2H rotamer), 7.67 (s, 0.8H rotamer), 5.03 (d, J = 17.3 Hz, 1H), 4.82 (d, J = 17.2 Hz, 1H), 4.42-4.32 (m, 1H), 3.99-3.67 (m, 1H), 3.54-3.41 (m, 2H), 3.22-3.02 (m, 2H), 2.28-2.05 (m, 5H), 2.03-1.89 (m, 1H), 1.74-1.41 (m, 3H), 0.96 (t, J = 7.3 Hz, 3H), 0.62-0.45 (m, 4H). |
| 701 | (400 MHz, CDCl₃) δ ppm 8.40 (d, J = 8.1 Hz, 1H), 7.68 (s, 1H), 4.99 (d, J = 17.2 Hz, 1H), 4.82 (d, J = 17.2 Hz, 1H), 4.43-4.30 (m, 2H), 3.51 (d, J = 9.7 Hz, 1H), 3.21-3.06 (m, 3H), 2.75-2.56 (m, 3H), 2.42-2.07 (m, 7H), 2.02-1.92 (m, 1H), 1.80-1.56 (m, 3H), 0.66-0.44 (m, 4H). |
| 704 | (400 MHz, CDCl₃) δ ppm 8.44 (d, J = 7.9 Hz, 1H), 7.69 (s, 1H), 5.01 (d, J = 17.2 Hz, 1H), 4.86 (d, J = 17.3 Hz, 1H), 4.61-4.30 (m, 2H), 3.60-3.45 (m, 2H), 3.24-3.09 (m, 2H), 2.67-2.57 (m, 1H), 2.29-2.06 (m, 3H), 2.06-1.91 (m, 1H), 1.82-1.51 (m, 3H), 1.06-0.96 (m, 6H), 0.69-0.48 (m, 4H). |
| 708 | (400 MHz, CDCl₃) δ ppm 8.41 (d, J = 8.0 Hz, 1H), 7.68 (s, 1H), 5.03 (d, J = 17.2 Hz, 1H), 4.84 (d, J = 17.3 Hz, 1H), 4.43-4.27 (m, 2H), 3.56-3.37 (m, 2H), 3.21-3.09 (m, 2H), 2.29-2.19 (m, 4H), 2.04-1.92 (m, 1H), 1.69-1.61 (m, 2H), 1.49 (t, J = 7.4 Hz, 2H), 1.32-1.21 (m, 6H), 0.89-0.84 (m, 3H), 0.68-0.35 (m, 4H). |
| 712 | (400 MHz, CDCl₃) δ ppm 8.52 (d, J = 7.6 Hz, 1H), 7.70 (s, 1H), 5.14-4.80 (m, 2H), 4.70-4.42 (m, 1H), 4.42-4.25 (m, 2H), 3.65-3.40 (m, 2H), 3.22-2.86 (m, 4H), 2.31-2.04 (m, 3H), 2.04-1.90 (m, 1H), 1.81-1.50 (m, 3H), 0.96 (d, J = 6.8 Hz, 6H), 0.70-0.34 (m, 4H). |
| 714 | (400 MHz, CDCl₃) δ ppm 8.72 (d, J = 7.5 Hz, 1H), 7.72 (s, 0.2H rotamer), 7.68 (s, 0.8H rotamer), 5.13-4.88 (m, 2H), 4.52 (dd, J = 8.5, 5.6 Hz, 1H), 4.46-4.18 (m, 1H), 3.63 (s, 2H), 3.25-3.05 (m, 2H), 2.48-2.37 (m, 1H), 2.35-2.20 (m, 1H), 2.20-2.06 (m, 2H), 2.06-1.88 (m, 1H), 1.82-1.48 (m, 3H), 1.09-0.86 (m, 6H), 0.75-0.34 (m, 4H). |
| 718 | (400 MHz, CDCl₃) δ ppm 8.52 (d, J = 7.9 Hz, 1H), 7.75-7.61 (m, 1H), 5.07-4.94 (m, 1H), 4.82 (dd, J = 17.2, 1.7 Hz, 1H), 4.52-4.25 (m, 2H), 3.77-3.58 (m, 2H), 3.22-3.04 (m, 2H), 2.31-2.02 (m, 4H), 2.02-1.88 (m, 1H), 1.84-1.52 (m, 3H), 1.33-1.09 (m, 3H), 0.69-0.39 (m, 4H). |
| 725 | (400 MHz, CDCl₃) δ ppm 8.44 (d, J = 8.0 Hz, 1H), 7.65 (s, 1H), 6.74-6.58 (m, 1H), 6.09 (d, J = 15.1, 1.5 Hz, 1H), 5.13-4.79 (m, 2H), 4.56-4.28 (m, 2H), 3.97-3.68 (m, 1H), 3.68-3.42 (m, 2H), 3.27-3.03 (m, 2H), 2.27-2.05 (m, 2H), 2.03-1.89 (m, 1H), 1.79-1.43 (m, 3H), 1.07-0.89 (m, 7H), 0.67-0.37 (m, 4H). |
| 735 | (400 MHz, CDCl₃) δ ppm 8.73-8.44 (m, 1H), 7.79-7.57 (m, 1H), 5.12-4.72 (m, 2H), 4.53-4.36 (m, 1H), 4.36-4.19 (m, 1H), 3.79-3.51 (m, 2H), 3.27-3.03 (m, 3H), 2.31-2.19 (m, 1H), 2.19-1.88 (m, 3H), 1.75-1.58 (m, 3H), 1.61-1.42 (m, 5H), 0.71-0.37 (m, 4H). |
| 752 | (400 MHz, CDCl₃) δ ppm 8.44 (d, J = 7.8 Hz, 1H), 7.68 (s, 1H), 5.09-4.81 (m, 2H), 4.37-4.23 (m, 2H), 3.51 (s, 2H), 3.18-3.07 (m, 2H), 2.60-2.50 (m, 1H), 2.31-2.07 (m, 3H), 2.07-1.85 (m, 1H), 1.74-1.56 (m, 3H), 1.56-1.44 (m, 1H), 1.44-1.34 (m, 1H), 1.16-1.03 (m, 1H), 0.98 (d, J = 6.6 Hz, 3H), 0.91-0.72 (m, 6H), 0.69-0.40 (m, 4H). |
| 754 | (400 MHz, CDCl₃) δ ppm 8.68 (d, J = 7.2 Hz, 0.25H rotamer), 8.43 (d, J = 7.8 Hz, 0.75H rotamer), 7.80-7.62 (m, 1H), 5.34 (d, J = 7.8 Hz, 0.25H rotamer), 5.11-4.95 (m, 1H), 4.90 (d, J = 17.3 Hz, 1H), 4.83 (d, J = 7.4 Hz, 0.75H rotamer), 4.49-4.18 (m, 3H), 3.67-3.41 (m, 2H), 3.25-3.04 (m, 2H), 2.31-2.05 (m, 3H), 2.05-1.87 (m, 2H), 1.86-1.51 (m, 4H), 1.48-1.17 (m, 6H), 0.68-0.30 (m, 4H). |
| 779 | (400 MHz, CDCl₃) δ ppm 8.67 (d, J = 7.0 Hz, 0.2H rotamer), 8.42 (d, J = 7.9 Hz, 0.8H rotamer), 7.57 (s, 0.2H rotamer), 7.49 (s, 0.8H rotamer), 5.36-5.00 (m, 2H), 4.93-4.66 (m, 1H), 4.49-4.08 (m, 2H), 3.57-3.45 (m, 1H), 3.15-3.07 (m, 2H), 2.29-2.12 (m, 3H), 1.95-1.84 (m, 1H), 1.84-1.47 (m, 6H), 1.47-1.18 (m, 4H), 1.03-0.73 (m, 6H), 0.73-0.33 (m, 4H). |
| 780 | (400 MHz, CDCl₃) δ ppm 8.91 (d, J = 7.5 Hz, 0.15H rotamer), 8.66 (d, J = 7.8 Hz, 0.85H rotamer), 7.75 (s, 0.15H rotamer), 7.66 (s, 0.85H rotamer), 7.53-7.11 (m, 10H), 5.72-5.55 (m, 1H), 5.29 (d, J = 6.9 Hz, 1H), 5.02 (d, J = 1.3 Hz, 2H), 4.61-4.47 (m, 1H), 4.47-4.34 (m, 1H), 3.80-3.59 (m, 2H), 3.59-3.42 (m, 1H), 3.23-3.03 (m, 2H), 2.41-2.30 (m, 1H), 2.30-2.20 (m, 1H), 2.20-2.08 (m, 2H), 2.07-1.90 (m, 1H), 1.71-1.56 (m, 2H). |
| 781 | (400 MHz, CDCl₃) δ ppm 8.44 (d, J = 7.8 Hz, 1H), 7.67-7.40 (m, 2H), 5.37-5.05 (m, 2H), 4.89-4.64 (m, 1H), 4.53-4.05 (m, 2H), 3.15-3.06 (m, 3H), 2.28-2.13 (m, 3H), 2.00-1.50 (m, 7H), 1.50-1.20 (m, 4H), 1.07-0.76 (m, 6H), 0.75-0.41 (m, 4H). |
| 782 | (400 MHz, CDCl₃) δ ppm 8.66 (d, J = 7.0 Hz, 0.3H rotamer), 8.44 (d, J = 7.9 Hz, 0.7H rotamer), 7.57 (s, 0.3H rotamer), 7.50 (s, 0.7H rotamer), 7.30-7.07 (m, 2H), 5.23-5.14 (m, 1H), 5.08 (d, J = 18.0 Hz, 1H), 4.88-4.78 (m, 1H), 4.48-4.08 (m, 2H), 3.58-3.41 (m, 1H), 3.15-3.04 (m, 2H), 2.30-2.08 (m, 2H), 2.00-1.83 (m, 2H), 1.83-1.67 (m, 3H), 1.67-1.48 (m, 3H), 1.48-1.11 (m, 4H), 1.03-0.74 (m, 6H), 0.73-0.34 (m, 4H). |
| 783 | (400 MHz, CDCl₃) δ ppm 8.79 (d, J = 7.6 Hz, 0.5H rotamer), 8.69 (d, J = 7.9 Hz, 0.5H rotamer), 8.14 (d, J = 1.6 Hz, 0.5H rotamer), 8.09 (d, J = 1.6 Hz, 0.5H rotamer), 8.05-7.92 (m, 1H), 7.67 (d, J = 10.1 Hz, 1H), 7.60-7.51 |

TABLE 2-continued

| Compound | $^1$H NMR Data |
|---|---|
| | (m, 1H), 5.15-4.79 (m, 2H), 4.48-4.21 (m, 1H), 4.14-3.98 (m, 1H), 3.90-3.56 (m, 2H), 3.21-2.83 (m, 2H), 2.61-2.56 (m, 2H), 2.19-1.88 (m, 3H), 1.88-1.42 (m, 8H). |
| 785 | (400 MHz, CDCl$_3$) δ ppm 8.92-8.69 (m, 1H), 7.98-7.63 (m, 1H), 7.49-7.22 (m, 5H), 5.82-5.66 (m, 1H), 5.37-5.25 (m, 1H), 5.12-4.95 (m, 2H), 4.58-4.32 (m, 2H), 3.93-3.72 (m, 1H), 3.61-3.46 (m, 1H), 3.21-3.03 (m, 2H), 3.03-2.84 (m, 1H), 2.30-1.87 (m, 5H), 1.71-1.51 (m, 2H). |
| 786 | (400 MHz, CDCl$_3$) δ ppm 8.80-8.59 (m, 1H), 7.69 (s, 1H), 7.44-7.15 (m, 8H), 7.15-7.03 (m, 2H), 5.51 (d, J = 6.5 Hz, 1H), 5.30 (d, J = 6.5 Hz, 1H), 5.14-4.92 (m, 2H), 4.51-4.30 (m, 2H), 4.11 (dd, J = 10.1, 7.5 Hz, 1H), 3.58-3.38 (m, 1H), 3.19-3.02 (m, 3H), 2.44-2.34 (m, 1H), 2.25-2.14 (m, 2H), 2.14-2.06 (m, 1H), 2.06-1.91 (m, 1H), 1.74-1.53 (m, 2H). |
| 787 | (400 MHz, CDCl$_3$) δ ppm 8.63-8.50 (m, 2H), 8.04 (s, 1H), 5.36 (d, J = 17.5 Hz, 0H), 5.18 (d, J = 17.6 Hz, 1H), 4.78-4.66 (m, 1H), 4.61 (dd, J = 10.5, 4.9 Hz, 1H), 4.40-4.16 (m, 1H), 3.27-3.20 (m, 1H), 2.65-2.53 (m, 1H), 2.63-2.44 (m, 2H), 2.32-2.24 (m, 1H), 2.21-2.08 (m, 1H), 2.08-1.98 (m, 1H), 1.97-1.62 (m, 6H), 1.60-1.49 (m, 2H), 1.47 (s, 3H), 1.37 (s, 3H), 1.01-0.74 (m, 6H). |

We claim:

1. A compound, which is (S)-5-((R)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide, or a pharmaceutically acceptable salt thereof.

2. A compound, which is (S)-5-((R)-2-hydroxy-4-methylpentanoyl)-N—((S)-3-oxo-1-((S)-2-oxopyrrolidin-3-yl)-4-(trifluoromethoxy)butan-2-yl)-5-azaspiro[2.4]heptane-6-carboxamide.

3. A pharmaceutical composition comprising a compound or pharmaceutically acceptable salt thereof according to claim 1 and a pharmaceutically acceptable carrier.

4. A pharmaceutical composition comprising a compound according to claim 2 and a pharmaceutically acceptable carrier.

* * * * *

UNITED STATES PATENT AND TRADEMARK OFFICE
CERTIFICATE OF CORRECTION

PATENT NO. : 11,708,348 B2  
APPLICATION NO. : 17/837814  
DATED : July 25, 2023  
INVENTOR(S) : Chatterjee et al.

Page 1 of 1

It is certified that error appears in the above-identified patent and that said Letters Patent is hereby corrected as shown below:

On the Title Page

Item (72) Inventors: please replace with the following list of inventors:
(72) Inventors: Arnab K. Chatterjee, San Diego, CA (US);
Jian Jeffrey Chen, San Diego, CA (US);
Elshan Nakath, La Jolla, CA (US);
Alireza Rahimi, La Jolla, CA (US);
Anil Kumar Gupta, San Diego, CA (US);
Gennadii Grabovyi, La Jolla, CA (US);
Katy Wilson, La Jolla, CA (US);
Sourav Ghorai, La Jolla, CA (US);
Armen Nazarian, La Jolla, CA (US);
James Pedroarena, La Jolla, CA (US);
Wrickban Mazumdar, La Jolla, CA (US);
Frank Weiss, La Jolla, CA (US);
Lirui Song, San Diego, CA (US);
Malina A. Bakowski, La Jolla, CA (US);
Laura Riva, San Diego, CA (US);
Karen Wolff, Encinitas, CA (US);
Case W. McNamara, San Marcos, CA (US);
Thomas F. Rogers, Del Mar, CA (US);
Jacqueline Malvin, San Diego, CA (US);
Shuangwei Li, San Diego, CA (US);
Sean Joseph, San Diego, CA (US);
Ashley Woods, San Diego, CA (US);
Yuyin Liu, San Diego, CA (US);
Neechi Okwor, Del Mar, CA (US);
Dongdong Liu, Fremont, CA (US)

Signed and Sealed this  
Seventeenth Day of December, 2024

Derrick Brent  
*Acting Director of the United States Patent and Trademark Office*